United States Patent
Wang et al.

(10) Patent No.: US 9,670,499 B2
(45) Date of Patent: Jun. 6, 2017

(54) YIELD TRAITS FOR MAIZE

(71) Applicant: Syngenta Participations AG, Basel (CH)

(72) Inventors: Daolong Wang, Research Triangle Park, NC (US); Librardo Andres Gutierrez-Rojas, Santiago (CL); Xi Chen, Beijing (CN); Joseph Dallas Clarke, V, Research Triangle Park, NC (US); Michael G. Muszynski, Johnston, IA (US); Paul Altendorf, Research Triangle Park, NC (US); Sarah Alissa Forrester, Research Triangle Park, NC (US); Mary Lynn Senior, Research Triangle Park, NC (US); Venkata Krishna Kishore, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 568 days.

(21) Appl. No.: 14/193,208

(22) Filed: Feb. 28, 2014

(65) Prior Publication Data

US 2014/0182010 A1 Jun. 26, 2014

Related U.S. Application Data

(63) Continuation of application No. 12/904,450, filed on Oct. 14, 2010, now abandoned.

(60) Provisional application No. 61/256,623, filed on Oct. 30, 2009.

(51) Int. Cl.
| | | |
|---|---|---|
| C12N 15/82 | (2006.01) | |
| A01H 1/02 | (2006.01) | |
| A01H 1/04 | (2006.01) | |
| A01H 5/10 | (2006.01) | |
| C12Q 1/68 | (2006.01) | |

(52) U.S. Cl.
CPC .......... *C12N 15/8261* (2013.01); *A01H 1/02* (2013.01); *A01H 1/04* (2013.01); *A01H 5/10* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

PUBLICATIONS

Bomblies et al. (Development 130, pp. 2385-2395 (2003)).*
Bomblies et al. (Genetics 172: pp. 519-531 (Jan. 2006)).*
Frascaroli et al., Genetics, 2007, p. 625-644.
Tao et al., Plant Science, 2004, p. 743-751.
S.-X. Xu et al., Hereditas, 2004, 141, p. 207-215.
Genbank, NM_001112090 and NP_001105560 (2 pgs).
NM_001112090 aligned to AY523572 (3 pgs).
Bradbury et al., "TASSEL: Software for Association Mapping of Complex Traits in Diverse Samples," Bioinformatics, 2007, pp. 2633-2635, vol. 23.
Evanno et al., "Detecting the number of Clusters of Individuals Using the Software STRUCTURE: a Simulation Study," Molecular Ecology, 2005, pp. 2611-2620, vol. 14.
Hardy & Vekemans, "SPAGeDi: A Versatile Computer Program to Analyze Spatial Genetic Structure at the Individual or Population Levels," Molecular Ecology Notes, 2002, pp. 618-620, vol. 2.
Liu & Muse, "PowerMarker: An Integrated Analysis Environment for Genetic Marker Analysis," Bioinformatics, 2005, pp. 2128-2129, vol. 21.
Patterson et al., "Population Structure and Eigenanalysis," PLoS Genetics, 2006, p. e190, vol. 2.
Price et al., "Principal Components Analysis Corrects for Stratification in Genome-wide Association Studies," Nature Genetics, 2006, pp. 904-909, vol. 38.
Pritchard et al., "Inference of Population Structure Using Multilocus Genotype Data," Genetics, 2000, pp. 945-959, vol. 155.
Stich et al., "A New Test for Family-based Association Mapping with Inbred Lines from Plant Breeding Programs," Theoretical and Applied Genetics, 2006, pp. 1121-1130, vol. 113.
Zhang et al., Genetic Epidemiol., 2001, pp. 370-375, vol. 21.

* cited by examiner

*Primary Examiner* — Brent Page
*Assistant Examiner* — Jared Shapiro
(74) *Attorney, Agent, or Firm* — Kevin Markham

(57) ABSTRACT

Methods for introgressing an allele of interest of a locus associated with a yield trait into *Zea mays* germplasm are provided. In some embodiments, the methods include providing a *Zea mays* plant that contains an allele of interest of a locus associated with a yield trait, wherein the locus associated with the yield trait is identifiable by PCR amplification of a *Zea mays* nucleic acid with a pair of oligonucleotides primers as disclosed herein, and introgressing the allele of interest into *Zea mays* germplasm that lacks the allele. Also provided are methods for identifying *Zea mays* plants that contain at least one allele associated with improved yield, improved maize plants, elite *Zea mays* plants, biomass produced from improved *Zea mays* plants, isolated and purified genetic markers, and compositions that include an amplification primer pair capable of amplifying a *Zea mays* nucleic acid to generate a *Zea mays* marker amplicon.

9 Claims, No Drawings

```
                        SEQUENCE LISTING

<160> NUMBER OF SEQ ID NOS: 382

<210> SEQ ID NO 1
<211> LENGTH: 3908
<212> TYPE: DNA
<213> ORGANISM: Zea mays
<220> FEATURE:
<221> NAME/KEY: misc_feature
<222> LOCATION: (1)..(3908)
<223> OTHER INFORMATION: n is a, c, g, or t
<220> FEATURE:
<221> NAME/KEY: misc_feature
<222> LOCATION: (1333)..(1333)
<223> OTHER INFORMATION: y is c or t

<400> SEQUENCE: 1
taggataata gcccagtttc atttggattt tgaatttact tgcgggccat catcgattgg      60
tggctggatc taatggcacg cacgtcaccc ccaccggatg catgccacag atctgtgcat     120
gtgctcacca tgctgaggga ggtcaggatt ggtgcctgca cgcatggggt tcctacgccc     180
agaccaaaag gatctggttg ctatctttcg cccatacacg gatgctcttc ttcagatctg     240
gttaagcggg caatgattgc attgcggggg caccagcacc agaaacaaac tgtaggaggt     300
tgctgcggtg gtccctgtgg ggtctactg ctttaggatt attttctggg atctgttttt     360
tttccagccc gagtatgcat gccgtcgagg ttcaggttcc tcctctctta gcaaagtttt     420
atgaagcttc tttttggctt ctggttgctg cctgcacaac tttatcaagc taccaaacgt     480
actagttgta ctgcttcctt tggattatag aggagttact aaataaactg tgttgggtgt     540
gcatattctc aaggctgtgg tcttaggaat tgctttcagt tatgcaagag atacttactt     600
ggcatacaac tactggcgct ccgaatgccc tgccaccccc ctggcctgat agattctttg     660
atctggacct tatatggtta gtttattcag tgttgctgca ctgtctctct acatgtttcc     720
tgaaacatca gtagattgtg gaatagcagt gtgatggtgt agctttatgg ttacagctaa     780
ctcagctgtt ggtgagatag ctccttgcag ttgcagatan caatgtgctt ccttcagctg     840
tttcttccat ctagtgtact tgtncaagtt cttccatgan atgataaatg tgtattttnt     900
nttnacttca ctgtttatct aactctgctg ngtnantttn cantngnttt ttcagtagca     960
accaccaccc anggnggacg tgcacgaacc tttggngcgc cgtaagagga ananggtttt    1020
ggtggactac ttggtgaagt tccgatngat cctcgtgatc ttcgtggtcc ttcctatttn    1080
```

```
aactctgatc tacttcaaca tcttcctggg cgacatgtgg tccgccatga agtcggagaa   1140
gaagcgccag aagcagcacg acgagaacgt gcagaaggtc gtgaagcggc tcaagcagag   1200
gaacccgaag aagganggtc ttgtttgnac ggccaggaag ccctggatcg ctgttggcat   1260
gcgcaacgtg gactacaagc gtgcgaggca tttcgaggtc ganctttctt cnttcaggaa   1320
catccttgag atygacaaag agaggatggt tgccaaggtc gagcccctng tnaacatggg   1380
tcagataacc agagctacct gcccaatgaa ccttgccctt gcggtcgtcg ccgagctcga   1440
cgacctcact gttggtgggc tgatcaacgg ttacggcatc gagggagct ctcacctcta    1500
tggccttttc tcngacacgg ttgtcgcgat ggaggttgtt ctcgcagatg gccgggtcgt   1560
nagagccacc aaggacaacg agtactctga ccttttctat ggnattccct ggtcccaggg   1620
aacactgggg ttccttgtct ctgcngagat caagctgatc cccatcaagg agtacatgaa   1680
gctcacctac actccagtca agggggtct aaaggagatc gcgcaggcct acgcggattc    1740
tttcgcnccg agggacggtg acccggcaaa ggtccctgac tttgttgaag ggatggtgta   1800
cacagagagc gagggtgtca tgatgacggg cgtgtacgct tcnaaagaag aggcgaagaa   1860
gaagggcaac aagatcaact gcgtggggtg gtggtttaag ccctggttct accagcacgc   1920
tcagacggcg ctgaagaggg gngagtttgt ggagtacatc ccgacgaggg agtactacca   1980
ccggcacacc cggtgcctgt actgggaggg aagctgatc ctgcccttcn gcgaccagtt    2040
ctggttcagg ttcctgctgg gctggctgat gccaccgaag gtgtcccngc tgaaggcgac   2100
ccagggcgag gctatnanga actacnccac gacaaccatg tgatccagna catgctggtg   2160
ccgctgtaca aggttgggga ngcgctggan ttcgtgcacc gcgngatgga ggtacaatgg   2220
ctggctggtg ctggtgctgg tgcngcttgc tttatnagta gttnactgga tatactaata   2280
ataatngaaa ttcttttggg taggtgtatc ctctntggct gtgccctcac cggcngtacn   2340
gctgccggtg aaganatngt gtacccggag cctgggttcn agcaccagna cangnagggc   2400
gacacgagct acgcncagat gttcacggac gtgggcgtgt actacgcccc cggggcntgc   2460
tgaggggga gnagttnaac ggcgcgnagg ctgtgcacag gctggagcag tggctgatng    2520
agaaccacan ctnccngccg cngtncgcgg tgtnggancg gaacgagaan gacttntggn   2580
gcatgttngn cgngtncnct ncgancacng ccnccaaaan tncggggngn gggcncgttn   2640
atgangngtn ctacnantnc nanaangggn cnanacggan aaggangngc nggnggnggn   2700
ggnggccnac nggnccngcc tncncggncn ggnggcctaa anctngnggt ngttttgctt   2760
ncccnttta attnaacntn anggangtng ngngntntna antcntngta ntnactntta    2820
aanctngngg tcgntcggtc ggtngtcant cngtntgtng ntgantccan cntnttttt    2880
attttaatat tntntaangg aatcntctcag attgattcgg gacttgctat gnctntnctn   2940
tttgcctatt tgttatgttt tttttnaaa gttctccagg cgctgctnct gcgtcttgca    3000
aggagccngg agctgntgac tancagcagc ancagctngg aacggtggga ggcagcacca   3060
ccatggcacc atgtggctga gctgggctgg caggcacagt gagaaaaaga aagacaccag   3120
ccatctactc cccagtcccc ccacaagagc aaaagcaaag aaagatgcat gtgcatgtgc   3180
agtgcagcaa ctctgccatg ctgtcatgtg ggacggcacg gcaccagct gcactgcact    3240
gcaccgcccc acagttatat tgtttactgc tgctgtgccc actccttgta tatttgcatc   3300
actgcctgct tctggaatca ggaaaggaga tcaccacttc actcaagaag gcaccctccc   3360
ttgccactcc ttttccttga gatgacgatg acgacgatga agaagcagca gcagctcctc   3420
```

-continued

| | | | | |
|---|---|---|---|---|
| ctcctcctttt | ctctcatgtt | tctcgttgct | gtgacagcag | ccgctgttgc tgccgatcca | 3480 |
| catccacagc | aggtggtact | acgcctactc | tcctcttctc | ctcggcatca tccaaactga | 3540 |
| atcagattga | agaatcatca | ggtcattaac | atgttcagtg | tgtgtccagc aggtgcaggt | 3600 |
| gcagcagcag | cagcaagcac | agatgaggat | taacagggcc | accagatccc ttcttcctca | 3660 |
| gccgccgccg | aaactaggta | ctactgaaaa | ctgtagacaa | caagatacaa gatctcattt | 3720 |
| cattgacgcc | tgtttctcac | gcaatacaga | ctgcccgtcc | acctgctccg tgcgctgcgg | 3780 |
| caacaactgg | aagaaccaga | tgtgcaacaa | gatgtgcaac | gtctgctgca acaagtgcag | 3840 |
| ctgcgtgccg | ccggggaccg | gccaggacac | ccgccacctc | tgcccctgct acgacaccat | 3900 |
| gctcaatc | | | | | 3908 |

<210> SEQ ID NO 2
<211> LENGTH: 4049
<212> TYPE: DNA
<213> ORGANISM: Zea mays
<220> FEATURE:
<221> NAME/KEY: misc_feature
<222> LOCATION: (1)..(4049)
<223> OTHER INFORMATION: n is a, c, g, or t
<220> FEATURE:
<221> NAME/KEY: misc_feature
<222> LOCATION: (2420)..(2420)
<223> OTHER INFORMATION: s is c or g

<400> SEQUENCE: 2

| | | | | | |
|---|---|---|---|---|---|
| gacacatcca | cgacacgaac | gccgcgacga | gactgggcaa | tgcaagtggt gtgggagtat | 60 |
| ttatcancct | ngccgtgncn | ttttatgttc | cagcacgtaa | tgtagggngc gtagaatcta | 120 |
| ganatcanat | cgcgaggggc | gagnggagcg | acnacgacng | ngcntgcanc tttnacagga | 180 |
| ctagtcgttt | tcacgtcgta | gcagagcacg | ctcgcttgga | gcagccgaca aacaccaagc | 240 |
| gctantanct | aggactacag | tgcagtgcgt | ctcnaagtcc | acgggcctcg cattgcattg | 300 |
| naaaaaaaaa | naaaaaaanc | anttgccgct | ntntaanagg | atccangcan ggcanggngg | 360 |
| cnggncanca | ncanggagtc | aaggagcncn | agttaggtng | gcaaccctcg agagtcgaga | 420 |
| gcatggatcc | caacgacgcc | ttctcggcgg | cgcacccgtt | ccgtgggac ctgggcccgc | 480 |
| cggccccgc | cgcgcccgcg | cctccgcccc | caccgccgcc | cgcgccgcag ctgctgcccc | 540 |
| acgcgccgct | gctgagcgcg | cngngctgga | ngncntggng | ncngctncng cgncgcngnc | 600 |
| ncgnggcnan | ctcntcgngt | ncncngccan | gntcngncng | acggagcgcg agctcgacga | 660 |
| catgatggcc | gcgctcgcgg | ggctgttccg | ctgggacgtg | ctcctcggcg agcgcttcgg | 720 |
| cctccgcgcc | gcgctgcggg | ccgagcgcgg | gcgngtcatg | tccctcggcg gccgcttcca | 780 |
| caccgggagc | acnttggacg | ncgcgtcaca | agaaggtata | canagcatgg tcgtcaaatt | 840 |
| gtttgcctct | gtggtcgtgc | aacctgtgag | atgtgntcgt | gcatgcatgc ggacagtgcc | 900 |
| catgnttcag | tcatgttgag | ttgagttctg | nttgcnggcc | tgtgangtta tntgttcttg | 960 |
| ttcaatcata | tcgcangnca | ntgctgtcng | acagagcgnga | cgccncggcc agnggcggct | 1020 |
| tngcggaagg | cgaggccggc | aggaggatgg | tgacgncngn | caagnanaag gnaaganagg | 1080 |
| ngtngncgcg | aggaagggca | agaaggcgag | gaggaagaag | gagctgaggc cgttggacgt | 1140 |
| gctggacgac | gagaacgacn | gagacgaggn | cggnggcggc | gncggngggt cagantngac | 1200 |
| ggagtcttcc | gctggcggct | ccggcggcgg | ggagaggcag | cgggagcacc ccttcgtggt | 1260 |
| cacagagccc | ggcgaggtgg | ccaggggccaa | gaagaacggg | cttgactacc tcttccantg | 1320 |
| tacgagcagt | gccgcgtctt | cctgctgcag | gtgcagtccc | ttgctaagct gggcggccac | 1380 |

```
aagtccccta cnaaggtacg cacacttatn attaatttag cagggcaacg tttttatatt    1440
acatantata aatccattng gtggtgcata cggatagcta gattgaatna cgataaacaa    1500
acaaaaactn tagngttaaa aaacgtaatg taatgaanca anttttttngg tcgntgacan   1560
gctnggnact gtntataatt tgctctaaaa catgtgttat atattctcag acanagttgg    1620
agtcacacaa gttaagggtc agaactctat taataattta atangaagac gtaattctca    1680
actttgttng tngtgaaacg gtttaagggt tgactaaant tatatataaa aanctaacat    1740
ttatgatntt aaataagnac attgttagaa taataatnaa gtatatntat ctcantagta    1800
ntctagntgg tatataatta ccaatactat ttgctatagt aaattngatc naagttagtc    1860
tngttcaact ttcacaaatc ctagaaanan gatactattc antntaataa catcatagtc    1920
atagtaaaaa agatctagtg gcatgcaaaa ggcccttcac atcacctaga aggaagaagn    1980
aaatcctttg cagtggaatt ctattatatt ttgtgtaccg taagtacgtc tacagtagca    2040
catgtgcaaa agatggtcta tatagtacgc cgtagtagtc tgtagncaag tacttctacg    2100
tacgtgtact caagtatatt tttgctacag ccgcacacgc acgtagatga cctggaaaaa    2160
ngcgcgacgt gtcagtcatc ggtaggctgc caaagcctgt gcagntngtg ttgtcttgtc    2220
cggncggccc caggcctcan atacanatag gcatgcatgg acnggacgca cccctctcc    2280
tctcggagtc cgtggcctgt gtgctgttgc caccggtttc gcgcgtacca gtacgagcca    2340
tgtgagctcg cttttggcag tttggccggc gtacgagtag tcgcgactcg cgtgctcgcc    2400
cgcagtgaaa tgaatgcacs ctggcctgtc cggattccag ggctgattgg atatgatgat    2460
agcttccctg acctggacgg ctgcatcgat gcgctgctcc tgcgtccgcg ccaggcgcac    2520
ccgaccacac cggcngtttc angncaccgg aaccnangac cgtggntgat gaacctttt    2580
tttttngntn gcngcaggtn accaaccagg tgttccggta cgccaanaag tgcggcgcga    2640
gctacatcaa caagcccaag atgcggcact acgtgcactg ctacgcgctg cactgcctgg    2700
acgaggangc ctccaacgcg ctgcgccggg cgtacaaggc ccgtggcgag aacgtcggtg    2760
cctggaggca ggcctgctac gcgccgctcg tcgagatcgc cgcgcgccac ggcttcgaca    2820
tcgacgccgt cttcnccgcg caccccgcgcc tcaccatctg gtacgtgccc accaggttgc    2880
gccagctctg ccaccaggca cgggggagcc acgcccacgc cgccgccggc ctcccccgc    2940
ccccgatntt ctagctgcgt cgtcgatgtg tgcctgcacc ggcgcggcgc cgtacgtctc    3000
acatcgcagt tcaggctgtt ccatggcgcc atcgaaaagt ggaaggcggn cttcgtctgc    3060
ctctcatgtt gtcgctttgt tcgttgcgtt gtggttagtc agaagtgggc ttagatttag    3120
aatggggacg tcacttgttc ggccgagcgg gccgggaaac aatttactgt ttnatgggcc    3180
acttgttagt ttgttacctc gcggcnttac taagttgtat tgtatccctc gtgatanttg    3240
tcccccatcc tccaaaaaaa aaacccgacg gtgtaccgnt cctgtgntga tatatnctna    3300
gagtaaaaat acattttcnt tacttcaact tatatgacgt tatatgttaa ctcggtccat    3360
aaacttttaa agtgtgtcag tctggtcntt aattgttgtt ccggtcttag ttaggtcgaa    3420
acgcgncntg gttgacatat gaacccccnc attttngcct angtatcnat ttnatntntc    3480
tttctnggtt ntctntcncn gnacangngg aaaanagagn caaaananat acncatgntc    3540
ncatgtnggg ggtccatatg tcaatcacaa ccngttngga tctaactgag acccaaacaa    3600
caattaaata tnggattgac anactttaaa agtttgttaa ccagnatgac ataggcgac    3660
aagtttcaga actgtaaatg tattttacnc tatatcctaa ttatgcngta acantagcac    3720
```

```
catttttttt tgcnccttnt attcgctcta attgtngaan ggttggnaat gactaanatg    3780
tctntttgac tttctnataa ggttgtctnc tnatacancn ctcttagctc attcgtgatt    3840
ttctttggtt cattctaata gtcaagttgt aggaaatgaa aactatctct ttgaccctat    3900
tctctctttt acnatcatcc ctctctccat gttctctctt ttttcaacct ttccttggtc    3960
accttaccta atttgaaagc tataaaantt ccattggtgc aagantactg atgttaggtt    4020
agtccgcnta tnantgttgc gacttatcc                                     4049
```

<210> SEQ ID NO 3
<211> LENGTH: 4050
<212> TYPE: DNA
<213> ORGANISM: Zea mays
<220> FEATURE:
<221> NAME/KEY: misc_feature
<222> LOCATION: (1)..(4050)
<223> OTHER INFORMATION: n is a, c, g, or t
<220> FEATURE:
<221> NAME/KEY: misc_feature
<222> LOCATION: (2709)..(2706)
<223> OTHER INFORMATION: k is g or t

<400> SEQUENCE: 3

```
gacacatcca cgacacgaac gccgcgacga gactgggcaa tgcaagtggt gtgggagtat      60
ttatcancct ngccgtgncn ttttatgttc cagcacgtaa tgtagggngc gtagaatcta     120
ganatcanat cgcgaggggc gagnggagcg acnacgacng ngcntgcanc tttnacagga     180
ctagtcgttt tcacgtcgta gcagagcacg ctcgcttgga gcagccgaca aacaccaagc     240
gctantanct aggactacag tgcagtgcgt ctcnaagtcc acgggcctcg cattgcattg     300
naaaaaaaaa naaaaaaanc anttgccgct ntntaanagg atccangcan ggcanggngg     360
cnggncanca ncanggagtc aaggagcncn agttaggtng gcaaccctcg agagtcgaga     420
gcatggatcc caacgacgcc ttctcggcgg cgcacccgtt ccggtgggac ctgggcccgc     480
cggcccccgc cgcgcccgcg cctccgcccc caccgccgcc cgcgccgcag ctgctgcccc     540
acgcgccgct gctgagcgcg cngngctgga ngncntgnng ncngctncng cgncgcngnc     600
ncgnggcnan ctcntcgngt ncncngccan gntcngncg acggagcgcg agctcgacga      660
catgatggcc gcgctcgcgg ggctgttccg ctgggacgtg ctcctcggcg agcgcttcgg     720
cctccgcgcc gcgctgcggg ccgagcgcgg gcgngtcatg tccctcggcg gccgcttcca     780
caccgggagc acnttggacg ncgcgtcaca agaaggtata canagcatgg tcgtcaaatt     840
gtttgcctct gtggtcgtgc aacctgtgag atgtgntcgt gcatgcatgc ggacagtgcc     900
catgnttcag tcatgttgag ttgagttctg nttgcnggcc tgtgangtta tntgttcttg     960
ttcaatcata tcgcangnca ntgctgtcng acgagcgnga cgcncggcc agnggcggct    1020 tngcggaagg cgaggccggc aggaggatgg tgacgncngn caagnanaag gnaaganagg    1080
ngtngncgcg aggaagggca agaaggcgag gaggaagaag gagctgaggc cgttggacgt    1140
gctggacgac gagaacgacn gagacgaggn cggnggcggc gncggnnggt cagantngac    1200
ggagtcttcc gctggcggct ccggcggcgg ggagaggcag cgggagcacc ccttcgtggt    1260
cacagagccc ggcgaggtgg ccaggccaa gaagaacggg cttgactacc tcttccantg    1320
tacgagcagt gccgcgtctt cctgctgcag gtgcagtccc ttgctaagct gggcggccac    1380
aagtccccta cnaaggtacg cacacttatn attaatttag cagggcaacg tttttatatt    1440
acatantata aatccattng gtggtgcata cggatagcta gattgaatna cgataaacaa    1500
acaaaaactn tagngttaaa aaacgtaatg taatgaanca antttttngg tcgntgacan    1560
```

```
gctnggnact gtntataatt tgctctaaaa catgtgttat atattctcag acanagttgg    1620
agtcacacaa gttaagggtc agaactctat taataattta atangaagac gtaattctca    1680
actttgttng tngtgaaacg gtttaagggt tgactaaant tatatataaa aanctaacat    1740
ttatgatntt aaataagnac attgttagaa taataatnaa gtatatntat ctcantagta    1800
ntctagntgg tatataatta ccaatactat ttgctatagt aaattngatc naagttagtc    1860
tngttcaact ttcacaaatc ctagaaanan gatactattc antntaataa catcatagtc    1920
atagtaaaaa agatctagtg gcatgcaaaa ggcccttcac atcacctaga aggaagaagn    1980
aaatcctttg cagtggaatt ctattatatt ttgtgtaccg taagtacgtc tacagtagca    2040
catgtgcaaa agatggtcta tatagtacgc cgtagtagtc tgtagncaag tacttctacg    2100
tacgtgtact caagtatatt tttgctacag ccgcacacgc acgtagatga cctggaaaaa    2160
ngcgcgacgt gtcagtcatc ggtaggctgc caaagcctgt gcagntngtg ttgtcttgtc    2220
cggncggccc caggcctcan atacanatag gcatgcatgg acnggacgca cccccctctcc   2280 tctcggagtc cgtggcctgt gtgctgttgc caccggtttc gcgcgtacca gtacgagcca    2340
tgtgagctcg cttttggcag tttggccggc gtacgagtag tcgcgactcg cgtgctcgcc    2400
cgcagtgaaa tgaatgcacg nctggcctgt ccggattcca gggctgattg gatatgatga    2460
tagcttccct gacctggacg gctgcatcga tgcgctgctc ctgcgtccgc gccaggcgca    2520
cccgaccaca ccggcngttt cangncaccg gaaccnanga ccgtggntga tgaacctttt    2580 tttttttngnt ngcngcaggt naccaaccag gtgttccggt acgccaanaa gtgcggcgcg    2640
agctacatca acaagcccaa gatgcggcac tacgtgcact gctacgcgct gcactgcctg    2700
gacgaggakg cctccaacgc gctcgcccgg gcgtacaagg cccgtggcga aacgtcggt    2760 gcctggaggc aggcctgcta cgcgccgctc gtcgagatcg ccgcgcgcca cggcttcgac    2820
atcgacgccg tcttcnccgc gcacccgcgc ctcaccatct ggtacgtgcc caccaggttg    2880
cgccagctct gccaccaggc acgggggagc cacgcccacg ccgccgccgg cctccccccg    2940
cccccgatnt tctagctgcg tcgtcgatgt gtgcctgcac cggcgcggcg ccgtacgtct    3000
cacatcgcag ttcaggctgt tccatggcgc catcgaaaag tggaaggcgg ncttcgtctg    3060
cctctcatgt tgtcgctttg ttcgttgcgt tgtggttagt cagaagtggg cttagattta    3120
gaatggggac gtcacttgtt cggccgagcg ggccgggaaa caatttactg tttnatgggc    3180
cacttgttag tttgttacct cgcggcntta ctaagttgta ttgtatccct cgtgatantt    3240
gtcccccatc ctccaaaaaa aaacccgac ggtgtaccgn tcctgtgntg atatatnctn    3300
agagtaaaaa tacattttcn ttacttcaac ttatatgacg ttatatgtta actcggtcca    3360 taaacttta aagtgtgtca gtctggtcnt taattgttgt tccggtctta gttaggtcga    3420
aacgcgncnt ggttgacata tgaacccccn cattttngcc tangtatcna tttnatntnt    3480 ctttctngg tntctntcnc ngnacangng gaaaanagag ncaaaanana tacncatgnt    3540
cncatgtngg gggtccatat gtcaatcaca accngttngg atctaactga gacccaaaca    3600
acaattaaat atnggattga canacttttaa aagtttgtta accagnatga catagggcga    3660
caagtttcag aactgtaaat gtattttacn ctatatccta attatgcngt aacantagca    3720 ccatttttt ttgcncccttn tattcgctct aattgtngaa nggttggnaa tgactaanat    3780
gtctntttga ctttctnata aggttgtctn ctnatacanc nctcttagct cattcgtgat    3840
tttctttggt tcattctaat agtcaagttg taggaaatga aaactatctc tttgaccccta    3900
```

```
ttctctctttt tacnatcatc cctctctcca tgttctctct tttttcaacc tttccttggt   3960
caccttacct aatttgaaag ctataaaant tccattggtg caagantact gatgttaggt   4020
tagtccgcnt atnantgttg cgacttatcc                                    4050

<210> SEQ ID NO 4
<211> LENGTH: 4050
<212> TYPE: DNA
<213> ORGANISM: Zea mays
<220> FEATURE:
<221> NAME/KEY: misc_feature
<222> LOCATION: (1)..(4050)
<223> OTHER INFORMATION: n is a, c, g, or t
<220> FEATURE:
<221> NAME/KEY: misc_feature
<222> LOCATION: (368)..(368)
<223> OTHER INFORMATION: k is g or t

<400> SEQUENCE: 4
gacacatcca cgacacgaac gccgcgacga gactgggcaa tgcaagtggt gtgggagtat     60
ttatcancct ngccgtgncn ttttatgttc cagcacgtaa tgtaggngc gtagaatcta    120 ganatcanat cgcgaggggc gagnggagcg acnacgacng ngcntgcanc tttnacagga    180
ctagtcgttt tcacgtcgta gcagagcacg ctcgcttgga gcagccgaca aacaccaagc    240
gctantanct aggactacag tgcagtgcgt ctcnaagtcc acgggcctcg cattgcattg    300
naaaaaaaaa naaaaaaanc anttgccgct ntntaaagg atccangcan ggcanggngg    360
cnggncakca ncanggagtc aaggagcncn agttaggtng gcaaccctcg agagtcgaga    420
gcatggatcc caacgacgcc ttctcggcgg cgcacccgtt ccggtgggac ctgggcccgc    480 cggccccgc cgcgcccgcg cctccgcccc caccgccgcc cgcgccgcag ctgctgcccc    540
acgcgccgct gctgagcgcg cngngctgga ngcntggng ncngctncng cgncgcngnc    600
ncgnggcnan ctcntcgngt ncncngccan gntcngncng acggagcgcg agctcgacga    660
catgatggcc gcgctcgcgg ggctgttccg ctgggacgtg ctcctcggcg agcgcttcgg    720
cctccgcgcc gcgctgcggg ccgagcgcgg gcgngtcatg tccctcggcg ccgcttcca    780 caccgggagc acnttggacg ncgcgtcaca agaaggtata canagcatgg tcgtcaaatt    840
gtttgcctct gtggtcgtgc aacctgtgag atgtgntcgt gcatgcatgc ggacagtgcc    900
catgnttcag tcatgttgag ttgagttctg nttgcnggcc tgtgangtta tntgttcttg    960
ttcaatcata tcgcangnca ntgctgtcng acgagcgnga cgccncggcc agnggcggct   1020
tngcggaagg cgaggccggc aggaggatgg tgacgncgn caagnanaag gnaaganagg   1080
ngtngncgcg aggaagggca agaaggcgag gaggaagaag gagctgaggc cgttggacgt   1140
gctggacgac gagaacgacn gagacgaggn cggnggcggc gncggnggt cagantngac   1200 ggagtcttcc gctggcggct ccggcggcgg ggagaggcag cgggagcacc ccttcgtggt   1260
cacagagccc ggcgaggtgg ccagggccaa gaagaacggg cttgactacc tcttccantg   1320
tacgagcagt gccgcgtctt cctgctgcag gtgcagtccc ttgctaagct gggcggccac   1380
aagtccccta cnaaggtacg cacacttatn attaatttag cagggcaacg ttttatatt    1440 acatantata aatccattng gtggtgcata cggatagcta gattgaatna cgataaacaa   1500
acaaaaactn tagngttaaa aaacgtaatg taatgaanca antttttngg tcgntgacan   1560
gctnggnact gtntataatt tgctctaaaa catgtgttat atattctcag acanagttgg   1620
agtcacacaa gttaagggtc agaactctat taataattta atangaagac gtaattctca   1680
actttgttng tngtgaaacg gtttaagggt tgactaaant tatatataaa aanctaacat   1740
```

```
ttatgatntt aaataagnac attgttagaa taataatnaa gtatatntat ctcantagta    1800
ntctagntgg tatataatta ccaatactat ttgctatagt aaattngatc naagttagtc    1860
tngttcaact ttcacaaatc ctagaaanan gatactattc antntaataa catcatagtc    1920
atagtaaaaa agatctagtg gcatgcaaaa ggcccttcac atcacctaga aggaagaagn    1980
aaatcctttg cagtggaatt ctattatatt ttgtgtaccg taagtacgtc tacagtagca    2040
catgtgcaaa agatggtcta tatagtacgc cgtagtagtc tgtagncaag tacttctacg    2100
tacgtgtact caagtatatt tttgctacag ccgcacacgc acgtagatga cctggaaaaa    2160
ngcgcgacgt gtcagtcatc ggtaggctgc caaagcctgt gcagntngtg ttgtcttgtc    2220
cggncggccc caggcctcan atacanatag gcatgcatgg acnggacgca ccccctctcc    2280
tctcggagtc cgtggcctgt gtgctgttgc accggtttc gcgcgtacca gtacgagcca    2340
tgtgagctcg cttttggcag tttggccggc gtacgagtag tcgcgactcg cgtgctcgcc    2400
cgcagtgaaa tgaatgcacg nctgcctgt ccggattcca gggctgattg gatatgatga    2460
tagcttccct gacctggacg gctgcatcga tgcgctgctc ctgcgtccgc gccaggcgca    2520
cccgaccaca ccggcngttt cangncaccg gaaccnanga ccgtggntga tgaacctttt    2580 tttttttngnt ngcngcaggt naccaaccag gtgttccggt acgccaanaa gtgcggcgcg    2640
agctacatca acaagcccaa gatgcggcac tacgtgcact gctacgcgct gcactgcctg    2700
gacgaggang cctccaacgc gctgcgccgg gcgtacaagg cccgtggcga aacgtcggt    2760 gcctggaggc aggcctgcta cgcgccgctc gtcgagatcg ccgcgcgcca cggcttcgac    2820
atcgacgccg tcttcnccgc gcacccgcgc ctcaccatct ggtacgtgcc caccaggttg    2880
cgccagctct gccaccaggc acgggggagc cacgcccacg ccgccgccgg cctccccccg    2940
cccccgatnt tctagctgcg tcgtcgatgt gtgcctgcac cggcgcggcg ccgtacgtct    3000
cacatcgcag ttcaggctgt tccatggcgc catcgaaaag tggaaggcgg ncttcgtctg    3060
cctctcatgt tgtcgctttg ttcgttgcgt tgtggttagt cagaagtggg cttagattta    3120
gaatggggac gtcacttgtt cggccgagcg ggccgggaaa caatttactg tttnatgggc    3180
cacttgttag tttgttacct cgcggcntta ctaagttgta ttgtatccct cgtgatantt    3240
gtcccccatc ctccaaaaaa aaaacccgac ggtgtaccgn tcctgtgntg atatatnctn    3300
agagtaaaaa tacattttcn ttacttcaac ttatatgacg ttatatgtta actcggtcca    3360 taaacttta aagtgtgtca gtctggtcnt taattgttgt tccggtctta gttaggtcga    3420
aacgcgncnt ggttgacata tgaaccccn catttttngcc tangtatcna tttnatntnt    3480
ctttctnggt tntctntcnc ngnacangng gaaaanagag ncaaaanana tacncatgnt    3540
cncatgtngg gggtccatat gtcaatcaca accngttngg atctaactga gacccaaaca    3600
acaattaaat atnggattga canactttaa aagtttgtta accagnatga catagggcga    3660
caagtttcag aactgtaaat gtattttacn ctatatccta attatgcngt aacantagca    3720
ccattttttt ttgcnccttn tattcgctct aattgtngaa nggttggnaa tgactaanat    3780
gtctntttga ctttctnata aggttgtctn ctnatacanc nctcttagct cattcgtgat    3840
tttctttggt tcattctaat agtcaagttg taggaaatga aaactatctc tttgacccta    3900
ttctctcttt tacnatcatc cctctctcca tgttctctct tttttcaacc tttccttggt    3960
caccttacct aatttgaaag ctataaaant tccattggtg caagantact gatgttaggt    4020
tagtccgcnt atnantgttg cgacttatcc                                     4050
```

<210> SEQ ID NO 5
<211> LENGTH: 4421
<212> TYPE: DNA
<213> ORGANISM: Zea mays
<220> FEATURE:
<221> NAME/KEY: misc_feature
<222> LOCATION: (1)..(4421)
<223> OTHER INFORMATION: n is a, c, g, or t
<220> FEATURE:
<221> NAME/KEY: misc_feature
<222> LOCATION: (4038)..(4038)
<223> OTHER INFORMATION: r is a or g

<400> SEQUENCE: 5

| | | | | | |
|---|---|---|---|---|---|
| cggcatgatg | cacaggtcat | ttatgtgttc | ttcgttctaa | ttatccactt | ttaactagtg | 60 |
| ttgatcacat | gtaatgaata | ggagaggcca | caaaccattg | agattatcta | tatcctcttt | 120 |
| attacatttt | ngagtattac | atgcataatg | aagatcatgc | cacgagtaat | ataantacaa | 180 |
| gctaaaagca | tatagagaac | atgatttatc | acaaggtttg | gntataccac | aaagtagtgt | 240 |
| ttncgtttca | gttntcgagt | gaccacaaag | gcctttagag | tcttttttaaa | ccccccctct | 300 |
| ttctcaagcg | accaaaaaaa | tcaagccatg | atctctacta | gaacaaatgg | gtaatacaaa | 360 |
| cttttctaggc | acccttttaca | aacacaaatc | aggagtgtcg | cnagacaaca | cctagccaac | 420 |
| taggattcaa | agaccccaaa | agtaataaaa | tggaaaagaa | atcaccgatg | ggtgccacaa | 480 |
| gtgctcaaga | gatggatctt | actctttgaa | atcaagatct | agtgaagagc | tcactccaat | 540 |
| ctcactcaca | agacgaaaat | ctagcaaggg | cgtgaggaag | tatgagagag | tgtaaagaga | 600 |
| gcttgctttt | tgtttcaaag | tggttttgtg | aattgaaang | ngctgacccc | ngaaaacaag | 660 |
| agggtgagag | aaataaatcc | ccttgtctta | gctagagagc | cattgctgan | caggaagggt | 720 |
| tccctctcna | atttcaacta | gggaggcttg | gaatttnctg | aggtggataa | gagaaanctc | 780 |
| ngtgcatcca | tagtcaaaga | gatttgaccc | aagggcaccc | cacctcaaat | ttcgagggtt | 840 |
| cagaatttcc | aaaggagagg | aagataccat | aaagcaaaac | ttcgaagttt | agaggtgtta | 900 |
| ctcaaatttt | tccaaggggg | ggtttgaaat | tttccaaggg | gagagaattt | tttggggaaa | 960 |
| gaggaacatc | agcagaaagc | caaggttcaa | agttaaggcg | gtgtccagaa | ttttttgtgg | 1020 |
| tgttgaaaac | aggacgaata | aaagaaagag | aatacttgct | cttttagagg | ttttttaaga | 1080 |
| gacctttttta | gagtattatt | gggaatgtta | ggagttaatg | agtataatgt | tttgagcata | 1140 |
| ttttgacacc | tacaagtaat | ttttttctata | tccttcttta | tgatatacta | tacttgaaag | 1200 |
| aagattgaat | taaaactaaa | atctctctct | caagttgaat | tgttgtgcca | catctttcac | 1260 |
| taatttataa | ttaaagggtc | tcatattttt | tgtacttttt | tataattata | tttaattgta | 1320 |
| aatctcataa | aatattgtta | gctcgtgtca | tcaaatcact | aaaatccata | aataggattg | 1380 |
| atgcacttag | ctctttaaaa | tgaaaaaggt | acaaaaatat | aaaaaaaatc | gtgaaccccc | 1440 |
| caatcaattt | ctaattgcat | tgtgaaaact | tcgacaacaa | aaatataaga | taccaccaaa | 1500 |
| ataaaatagt | atcaaacaat | atcatcctct | atttcaaact | tctttatgca | agcagcgtca | 1560 |
| ttcacaattt | cgcgtcctct | attttacaca | ctgtactgna | gacaacctta | acatctatgt | 1620 |
| tggntgtatc | acatattttt | gttgtagaaa | atttccaaag | nacatttaaa | cttgatnaaa | 1680 |
| atattttggg | ggtttaacga | tattttttta | ttattctaga | actaaatata | tttttaaagc | 1740 |
| ttatagatat | attttcgcgg | gctctaaata | cttttttctc | nggncccnat | ctatttctaa | 1800 |
| tattttttgaa | ctttttatat | acnttcaatg | ttttaaataa | acttttttccg | attttcttag | 1860 |
| taaaaagttg | aaaccatcct | aaaataaaaa | ctatttctan | ccatggnaga | gagctaattt | 1920 |

```
aagcggcttt aagatttgaa gaagaaattg ccttatttta gagttcattc aagnangaaa   1980
aaatggagtn ctagttgagg gaaaacacca cagattccnc agccttngcc tgttcnccac   2040
ctttcctcca aaatttgacc cacacgcggn gncgcccgag ccccgagcg accacatcct    2100 ccgcggccgc ggcgacgccc gaggcctgca anacctaac cactcaggtt ctgccggcna    2160
ccgccaccac caccncngtc caccacnang ctgacagcca ctcccctacc ccatcagctc   2220
ctggccacct tcctcctcgt cctggcgtcg gcnacccaac ctgcagtccc tgcctccacc   2280
gaccgcgcag cgcttctcgc cttccgcgcg tccctgtcgc cgccctcccg cgccgcncta   2340
tcctcgtgga gcgccccgct ctcgccatcc tggctcggcg tgtcgctcca ccccgccacg   2400
gcgccagccc cttcggtcac cactccctcc gtngccgaac tctcgctccg ggcctcaac    2460 ctcacgggcg tgatccccgc ggcgccgctc gcgctcctcc gacgtctccg gacgctcgac   2520
ctctccgcca acgcgctttc gggagagctt ccctgctccc tcccgcgctc gctcctcgcg   2580
ctcgacctct cccgcaacgc gctctcgggg gctgtcccca cctgcctgcc gtcctcgctc   2640
cccgcgctcc gcaccctcaa cctctccgcc aacttcctcc gcctcccgct ctccccgcgt   2700
ctctccttcc ccgcgcgcct cgctgccctt gatctctccc gcaacgccat ctccggcgcc   2760
gtcccgccgc ggatcgtcgc cgaccccgac aactccgctc tcctcctcct cgacctctcc   2820
cacaaccgct tctccggcga gatccccgcc ngtatcgcag ccgtacggag cctgcagggg   2880 cttttttctcg cggacaacca gntntccggg gacattcctc cggggatagg gaacctgacc   2940
tatttgcagg tgctggatt tgtcgaataac cgattgtccg gttcagtgcc tgccggactt   3000
gcaggctgct tccagcttct gtacctgcag cttgggggta accagctctc tggggcactc   3060
cgtccggagc tcgacgcact agctagtctc aaggttcnan anttgngaat aacaagatat   3120
ctggggagat tcccctgccg ctggctgggt gcaggtcttt ggaggtggtg gacttgtcag   3180
gnaatgagat ctccggtgag ctcagcagtg ctgtagcgaa atggctgagc ntgaagttct   3240
tntcacnggc tggtaaccag ctctccggcc accnacctga cnggatgttc tcgttccccc   3300
tgctccagtg gcttgatttg tctagtaata agtttgtggg tttcatccca gatgggggt    3360 tcaatgtcag tgaagtgctt aacggtggag gtggtcaggg gactccatca gagngtgtgc   3420 ttccaccca attgtttgtg tcagcttctg tggacacggt gtcatggcag ttggatttgg    3480
ggtntnantt caggcaacta ctggtataga cctgtctggg aatgagctct gtggggagat   3540
accanaaggg ttggttgaca tgaagggntt ggagtatttg aacctntcct gtaattactt   3600
ggctgggcag atccctgcgg ggcttgggg catgggagg ttgcatacgc ttgacttctc     3660
acataatggg ctgtcagggg aggtgcctcc tggaattgca gccatgacag tgcttgaggt   3720
gcttaacctc tcctacaata gcctgtctgg gcctttgcca acaacgaagt tcccaggagc   3780
attagctgga aacccaggaa tttgcagtgg gaaagggtgc tctgagaatg caaggactcc   3840
ngaagggana atgaaggta gcaatcaccg cggttggntt ggtggctggc atggagagaa    3900
tggatgggtn tctcttggtg cattttgtat cagcacaatg actagcttct atgtatcatt   3960
agcaacctta ctatgctcct ctaatgcaag aaacttcgtg tttcggcctg tgagggttga   4020
atattaacaa gaggggarat tgcaaaatca ggttgttttg aagttcgagc gactctggtc   4080
tgcagctgat taacaagaaa tatgagcata tgagatggat atcttcagcc aagaggaagt   4140
gctgtctctt ntaatgatca atcaagctct cttgattgtt tcctaatatt cttgatcttg   4200
ggatgtgtag atctagttct aatnttccta ctgttataga atgcaatcac ctgctggtgc   4260
```

```
ttggttgtag ccctggcgtg tttggaggat tggacaccaa ggatgcacat aanttgaagn    4320
gctngtactg tgaaccactt cagatgtaaa tntnttcttt ggtttttagt tctgatctng    4380
tttaaaactg gacatgtatt tagtgttgtt gagctacctt t                        4421

<210> SEQ ID NO 6
<211> LENGTH: 4421
<212> TYPE: DNA
<213> ORGANISM: Zea mays
<220> FEATURE:
<221> NAME/KEY: misc_feature
<222> LOCATION: (1)..(4421)
<223> OTHER INFORMATION: n is a, c, g, or t
<220> FEATURE:
<221> NAME/KEY: misc_feature
<222> LOCATION: (4038)..(4038)
<223> OTHER INFORMATION: r is a or g

<400> SEQUENCE: 6
cggcatgatg cacaggtcat ttatgtgttc ttcgttctaa ttatccactt ttaactagtg      60
ttgatcacat gtaatgaata ggagaggcca caaaccattg agattatcta tatcctcttt    120
attacatttt ngagtattac atgcataatg aagatcatgc cacgagtaat ataantacaa    180
gctaaaagca tatagagaac atgatttatc acaaggtttg gntataccac aaagtagtgt    240
ttncgtttca gttntcgagt gaccacaaag gcctttagag tctttttaaa cccccctct     300 ttctcaagcg accaaaaaaa tcaagccatg atctctacta gaacaaatgg gtaatacaaa    360 cttttctaggc acccttttaca aacacaaatc aggagtgtcg cnagacaaca cctagccaac   420
taggattcaa agaccccaaa agtaataaaa tggaaaagaa atcaccgatg ggtgccacaa    480
gtgctcaaga gatggatctt actctttgaa atcaagatct agtgaagagc tcactccaat    540
ctcactcaca agacgaaaat ctagcaaggg cgtgaggaag tatgagagag tgtaaagaga    600
gcttgctttt tgtttcaaag tggttttgtg aattgaaang ngctgacccc ngaaaacaag    660
agggtgagag aaataaatcc ccttgtctta gctagagagc cattgctgan caggaagggt    720
tccctctcna atttcaacta gggaggcttg gaatttnctg aggtggataa gagaaanctc    780
ngtgcatcca tagtcaaaga gatttgaccc aagggcaccc cacctcaaat ttcgagggtt    840
cagaatttcc aaaggagagg aagataccat aaagcaaaac ttcgaagttt agaggtgtta    900
ctcaaatttt tccaaagggg ggtttgaaat tttccaaggg gagagaattt tttggggaaa    960
gaggaacatc agcagaaagc caaggttcaa agttaaggcg gtgtccagaa ttttttgtgg   1020
tgttgaaaac aggacgaata aaagaaagag aatacttgct cttttagagg ttttttaaga   1080 gacctttta gagtattatt gggaatgtta ggagttaatg agtataatgt tttgagcata   1140
ttttgacacc tacaagtaat tttttctata tccttcttta tgatatacta tacttgaaag   1200
aagattgaat taaaactaaa atctctctct caagttgaat tgttgtgcca catctttcac   1260
taatttataa ttaaagggtc tcatattttt tgtacttttt tataattata tttaattgta   1320
aatctcataa aatattgtta gctcgtgtca tcaaatcact aaaatccata aataggattg   1380
atgcacttag ctctttaaaa tgaaaaaggt acaaaaatat aaaaaaaatc gtgaacccc    1440 caatcaattt ctaattgcat tgtgaaaact tcgacaacaa aaatataaga taccaccaaa   1500
ataaaatagt atcaaacaat atcatcctct atttcaaact tctttatgca agcagcgtca   1560
ttcacaattt cgcgtcctct attttacaca ctgtactgna gacaaccttta acatctatgt   1620 tggntgtatc acatatttttt gttgtagaaa atttccaaag nacatttaaa cttgatnaaa   1680
atattttggg ggtttaacga tatttttttta ttattctaga actaaatata ttttttaaagc   1740
```

```
ttatagatat attttcgcgg gctctaaata cttttttctc nggncccnat ctatttctaa   1800
tatttttgaa cttttttatat acnttcaatg ttttaaataa actttttccg attttcttag   1860
taaaaagttg aaaccatcct aaaataaaaa ctatttctan ccatggnaga gagctaattt   1920
aagcggcttt aagatttgaa gaagaaattg ccttattta gagttcattc aagnangaaa    1980
aaatggagtn ctagttgagg gaaaacacca cagattccnc agccttngcc tgttcnccac   2040
ctttcctcca aaatttgacc cacacgcggn gncgcccgag gccccgagcg accacatcct   2100
ccgcggccgc ggcgacgccc gaggcctgca anaccctaac cactcaggtt ctgccggcna   2160
ccgccaccac caccncngtc caccacnang ctgacagcca ctcccctacc ccatcagctc   2220
ctggccacct tcctcctcgt cctggcgtcg gcnacccaac ctgcagtccc tgcctccacc   2280
gaccgcgcag cgcttctcgc cttccgcgcg tccctgtcgc cgccctcccg cgccgcncta   2340
tcctcgtgga gcggcccgct ctcgccatcc tggctcggcg tgtcgctcca ccccgccacg   2400
gcgccagccc cttcggtcac cactccctcc gtngccgaac tctcgctccg gggcctcaac   2460
ctcacgggcg tgatccccgc ggcgccgctc gcgctcctcc gacgtctccg gacgctcgac   2520
ctctccgcca acgcgctttc gggagagctt ccctgctccc tccgcgctc gctcctcgcg    2580
ctcgacctct cccgcaacgc gctctcgggg gctgtcccca cctgcctgcc gtcctcgctc   2640
cccgcgctcc gcaccctcaa cctctccgcc aacttcctcc gcctcccgct ctcccgcgt    2700
ctctccttcc ccgcgcgcct cgctgcccct tgatctctccc gcaacgccat ctccggcgcc   2760
gtcccgccgc ggatcgtcgc cgaccccgac aactccgctc tcctcctcct cgacctctcc   2820
cacaaccgct tctccggcga gatccccgcc ngtatcgcag ccgtacggag cctgcagggg   2880
cttttttctcg cggacaacca gntntccggg gacattcctc cggggatagg gaacctgacc   2940
tatttgcagg tgctggattt gtcgaataac cgattgtccg gttcagtgcc tgccggactt   3000
gcaggctgct tccagcttct gtacctgcag cttggggta accagctctc tggggcactc     3060
cgtccggagc tcgacgcact agctagtctc aaggttcnan anttgngaat aacaagatat   3120
ctggggagat tcccctgccg ctggctgggt gcaggtctt ggaggtggtg gacttgtcag    3180
gnaatgagat ctccggtgag ctcagcagtg ctgtagcgaa atggctgagc ntgaagttct   3240
tntcacnggc tggtaaccag ctctccggcc accnacctga cnggatgttc tcgttccccc   3300
tgctccagtg gcttgatttg tctagtaata agtttgtggg tttcatccca gatggggggt   3360
tcaatgtcag tgaagtgctt aacggtggag gtggtcaggg gactccatca gagngtgtgc   3420
ttccacccca attgtttgtg tcagcttctg tggacacggt gtcatggcag ttggatttgg   3480
ggtntnantt caggcaacta ctggtataga cctgtctggg aatgagctct gtgggagat    3540
accanaaggg ttggttgaca tgaagggntt ggagtatttg aacctntcct gtaattactt   3600
ggctgggcag atccctgcgg ggcttggggg catgggagg ttgcatacgc ttgacttctc     3660
acataatggg ctgtcagggg aggtgcctcc tggaattgca gccatgacag tgcttgaggt   3720
gcttaacctc tcctacaata gcctgtctgg gcctttgcca acaacgaagt tcccaggagc   3780
attagctgga aacccaggaa tttgcagtgg gaaaggtgc tctgagaatg caaggactcc     3840
ngaagggana atggaaggta gcaatcaccg cggttggntt ggtggctggc atggagaaa     3900
tggatgggtn tctcttggtg cattttgtat cagcacaatg actagcttct atgtatcatt   3960
agcaacctta ctatgctcct ctaatgcaag aaacttcgtg tttcggcctg tgagggttga   4020
atattaacaa gaggggarat tgcaaaatca ggttgttttg aagttcgagc gactctggtc   4080
```

```
tgcagctgat taacaagaaa tatgagcata tgagatggat atcttcagcc aagaggaagt    4140
gctgtctctt ntaatgatca atcaagctct cttgattgtt tcctaatatt cttgatcttg    4200
ggatgtgtag atctagttct aatnttccta ctgttataga atgcaatcac ctgctggtgc    4260
ttggttgtag ccctggcgtg tttgaggat tggacaccaa ggatgcacat aanttgaagn    4320
gctngtactg tgaaccactt cagatgtaaa tntnttcttt ggttttagt tctgatctng    4380 tttaaaactg gacatgtatt tagtgttgtt gagctacctt t                       4421
```

<210> SEQ ID NO 7
<211> LENGTH: 4421
<212> TYPE: DNA
<213> ORGANISM: Zea mays
<220> FEATURE:
<221> NAME/KEY: misc_feature
<222> LOCATION: (1)..(4421)
<223> OTHER INFORMATION: n is a, c, g, or t
<220> FEATURE:
<221> NAME/KEY: misc_feature
<222> LOCATION: (402)..(402)
<223> OTHER INFORMATION: y is c or t

<400> SEQUENCE: 7

```
cggcatgatg cacaggtcat ttatgtgttc ttcgttctaa ttatccactt ttaactagtg      60
ttgatcacat gtaatgaata ggagaggcca caaaccattg agattatcta tatcctctttt    120 attacattt ngagtattac atgcataatg aagatcatgc cacgagtaat ataantacaa      180
gctaaaagca tatagagaac atgatttatc acaaggtttg gntataccac aaagtagtgt     240
ttncgtttca gttntcgagt gaccacaaag gcctttagag tcttttttaaa cccccctct    300 ttctcaagcg accaaaaaaa tcaagccatg atctctacta gaacaaatgg gtaatacaaa    360 cttttctaggc ccccttttaca aacacaaatc aggagtgtcg cyagacaaca cctagccaac   420
taggattcaa agacccccaaa agtaataaaa tggaaaagaa atcaccgatg ggtgccacaa    480
gtgctcaaga gatggatctt actctttgaa atcaagatct agtgaagagc tcactccaat    540
ctcactcaca agacgaaaat ctagcaaggg cgtgaggaag tatgagagag tgtaaagaga    600
gcttgctttt tgtttcaaag tggttttgtg aattgaaang ngctgacccc ngaaaacaag   660
agggtgagag aaataaatcc ccttgtctta gctagagagc cattgctgan caggaagggt    720
tccctctcna atttcaacta gggaggcttg gaatttnctg aggtggataa agaaaanctc    780
ngtgcatcca tagtcaaaga gatttgaccc aagggcaccc cacctcaaat ttcgagggtt    840
cagaatttcc aaaggagagg aagataccat aaagcaaaac ttcgaagttt agaggtgtta    900
ctcaaatttt tccaaggggg ggtttgaaat tttccaaggg gagagaattt tttggggaaa    960
gaggaacatc agcagaaagc caaggttcaa agttaaggcg gtgtccagaa tttttgtgg    1020 tgttgaaaac aggacgaata aaagaaagag aatacttgct cttttagagg ttttttaaga   1080 gacctttttta gagtattatt gggaatgtta ggagttaatg agtataatgt tttgagcata   1140
ttttgacacc tacaagtaat ttttctata tccttctta tgatatacta tacttgaaag     1200
aagattgaat taaaactaaa atctctctct caagttgaat tgttgtgcca catctttcac    1260
taatttataa ttaaagggtc tcatatttt tgtactttt tataattata tttaattgta      1320
aatctcataa aatattgtta gctcgtgtca tcaaatcact aaaatccata aataggattg    1380
atgcacttag ctcttttaaaa tgaaaaaggt acaaaaatat aaaaaaaatc gtgaacccccc  1440 caatcaattt ctaattgcat tgtgaaaact tcgacaacaa aaatataaga taccaccaaa    1500
ataaaatagt atcaaacaat atcatcctct atttcaaact tctttatgca agcagcgtca   1560
```

```
ttcacaattt cgcgtcctct attttacaca ctgtactgna gacaaccttt acatctatgt    1620
tggntgtatc acatattttt gttgtagaaa atttccaaag nacatttaaa cttgataaaa    1680
atattttggg ggtttaacga tattttttta ttattctaga actaaatata tttttaaagc    1740
ttatagatat attttcgcgg gctctaaata cttttttctc nggncccnat ctatttctaa    1800 tattttgaa cttttatat acnttcaatg ttttaaataa acttttttccg attttcttag     1860 taaaagttg aaaccatcct aaaataaaaa ctatttctan ccatggnaga gagctaattt     1920
aagcggcttt aagatttgaa gaagaaattg ccttattta gagttcattc aagnangaaa     1980
aaatggagtn ctagttgagg gaaaacacca cagattccnc agccttngcc tgttcnccac    2040
ctttcctcca aaatttgacc cacacgcggn gncgcccgag gccccgagcg accacatcct    2100
ccgcggccgc ggcgacgccc gaggcctgca anaccctaac cactcaggtt ctgccggcna    2160
ccgccaccac caccncngtc caccacnang ctgacagcca ctccctaccc ccatcagctc    2220
ctggccacct tcctcctcgt cctggcgtcg gcnacccaac ctgcagtccc tgcctccacc    2280
gaccgcgcag cgcttctcgc cttccgcgcg tccctgtcgc cgccctcccg cgccgcncta    2340
tcctcgtgga gcggcccgct ctcgccatcc tggctcggcg tgtcgctcca ccccgccacg    2400
gcgccagccc cttcggtcac cactccctcc gtngccgaac tctcgctccg gggcctcaac    2460
ctcacgggcg tgatccccgc ggcgccgctc gcgctcctcc gacgtctccg gacgctcgac    2520
ctctccgcca acgcgctttc gggagagctt ccctgctccc tcccgcgctc gctcctcgcg    2580
ctcgacctct cccgcaacgc gctctcgggg gctgtcccca cctgcctgcc gtcctcgctc    2640
cccgcgctcc gcaccctcaa cctctccgcc aacttcctcc gcctcccgct ctccccgcgt    2700
ctctccttcc ccgcgcgcct cgctgccctt gatctctccc gcaacgccat ctccggcgcc    2760
gtcccgccgc ggatcgtcgc cgaccccgac aactccgctc tcctcctcct cgacctctcc    2820
cacaaccgct tctccggcga gatccccgcc ngtatcgcag ccgtacggag cctgcagggg    2880
ctttttctcg cggacaacca gntntccggg gacattcctc cggggatagg gaacctgacc    2940
tatttgcagg tgctggattt gtcgaataac cgattgtccg gttcagtgcc tgccggactt    3000
gcaggctgct tccagcttct gtacctgcag cttgggggta accagctctc tggggcactc    3060
cgtccggagc tcgacgcact agctagtctc aaggttcnan anttgngaat aacaagatat    3120
ctggggagat tcccctgccg ctggctgggt gcaggtcttt ggaggtggtg gacttgtcag    3180
gnaatgagat ctccggtgag ctcagcagtg ctgtagcgaa atggctgagc ntgaagttct    3240
tntcacnggc tggtaaccag ctctccggcc accnacctga cnggatgttc tcgttccccc    3300
tgctccagtg gcttgatttg tctagtaata agtttgtggg tttcatccca gatgggggt     3360 tcaatgtcag tgaagtgctt aacggtggag gtggtcaggg gactccatca gagngtgtgc    3420 ttccaccca attgtttgtg tcagcttctg tggacacggt gtcatggcag ttggatttgg     3480
ggtntnantt caggcaacta ctggtataga cctgtctggg aatgagctct gtgggagat     3540 accanaaggg ttggttgaca tgaagggntt ggagtatttg aacctntcct gtaattactt    3600
ggctgggcag atccctgcgg ggcttggggg catgggagg ttgcatacgc ttgacttctc      3660
acataatggg ctgtcagggg aggtgcctcc tggaattgca gccatgacag tgcttgaggt    3720
gcttaaccct cctacaata gcctgtctgg gcctttgcca acaacgaagt tcccaggagc      3780
attagctgga aacccaggaa tttgcagtgg gaaagggtgc tctgagaatg caaggactcc    3840
ngaagggana atggaaggta gcaatcaccg cggttggntt ggtggctggc atggagagaa    3900
```

-continued

```
tggatgggtn tctcttggtg cattttgtat cagcacaatg actagcttct atgtatcatt     3960 agcaaccttactatgctcct ctaatgcaag aaacttcgtg tttcggcctg tgagggttga      4020
atattaacaa gagggganat tgcaaaatca ggttgttttg aagttcgagc gactctggtc     4080
tgcagctgat taacaagaaa tatgagcata tgagatggat atcttcagcc aagaggaagt     4140
gctgtctctt ntaatgatca atcaagctct cttgattgtt tcctaatatt cttgatcttg     4200
ggatgtgtag atctagttct aatnttccta ctgttataga atgcaatcac ctgctggtgc     4260
ttggttgtag ccctggcgtg tttggaggat tggacaccaa ggatgcacat aanttgaagn    4320
gctngtactg tgaaccactt cagatgtaaa tntnttcttt ggtttttagt tctgatctng     4380
tttaaaactg gacatgtatt tagtgttgtt gagctacctt t                        4421
```

<210> SEQ ID NO 8
<211> LENGTH: 4422
<212> TYPE: DNA
<213> ORGANISM: Zea mays
<220> FEATURE:
<221> NAME/KEY: misc_feature
<222> LOCATION: (1)..(4422)
<223> OTHER INFORMATION: n is a, c, g, or t
<220> FEATURE:
<221> NAME/KEY: misc_feature
<222> LOCATION: (3050)..(3050)
<223> OTHER INFORMATION: k is g or t

<400> SEQUENCE: 8

```
gagctagctt aatatggaag ccacactcac tcaccaagtc atggatgaga ggagagagtg      60
tggagagcca cacgcgcgcg cgcgctcgct cgcctcgcct cgcctggcct ggccgggccg     120
ggccggggcg gggcgaaggg cgcgggcgca cgacatgcgc gtgaatggtc cgccgaaatc     180
cggcccctcg ccttgcgagg gcgcgactac cttttgccgt ttgattttttggtttcttgg     240 ctgttacgct tatcctaacc gatcgctaca aaatctcaac tgattgcgag attttcgtgg     300
gcggataagc acgggggtc gcggactcga ccctataaaa ggagcccggc agccagcctc     360
caaatcatcc cagatcccag ttcgctttcg cctctcttca tagctgagcc gccttttagt    420
tcccttcgtc ccgaccgcag aggtgcatct gcgatcagga gagcaggtct ccggaaccct    480
tcgtcttcta gatcctgcac cgggagaggg cgaataaggt ttttgggaag cgtcttcgcg     540
cgactgctcg tgatctgctg acctcgtcaa cccatctgat cctggcgcgc gccaacaatc     600
agtaagtcta atcagtacgc atcatctgat ttggctttta tttcagttct tctgatttgg     660
tcatgattta tattcggaat ttaatttgga atttgtctaa ttattcaaca ggtgcaatct    720
ccggcctcta ctcactccag atctattctt cgcttcgcct gcaggcagca gtagcaccgt     780
tcaagttcaa ccaacgcggc caacgcacct gttgaagttg aaccatgcat gaacccgcga    840
cgtgtttatc ctccattatc cacggtgagc tctgaaatcc acgttgactc acatacatac    900
acggtacgcg cgtcagggat ttcactcgga ggcaagaatc gaaaagaaa aaggaagcca     960 cgcgtacgac gtgcaacggg gacacacatc cacacggacg ccgcgacggg actgcacagt    1020
ggcaatggca acgcaggtgc agtggtggtg gtgttggagt gtttattatt gcctcaccgt    1080
gtgcttcttt ttttatgttc cagagcaagc acgtaatgta gtagggggcgt agaatctaga   1140 ctatcaaatc gcgaggggcg acgacggtgc tcggtgcagt gcagctttgt acaggaacag    1200
gactagtcgt tttcacgtcg taacagagca cgctcccgcg tcgatagatc gctacgagca   1260
gtcgacagac acggcagcat aaatgcgcgc gcaaaagcta gtagtaggac taggcctaca   1320
gtgcagtgcg tccccgagat tcattcgtca agttcaggtc gaccggccgg ccttgccctt   1380
```

```
gcattggaaa acagttaccg ctatataaca aacagccgcg gcgcacggcg agccaagccc     1440
gtcaaggcac gaggactgca ggagcagaaa gttggcaacc ctttgagttc ctcactcaca     1500
cgcgcgcgag ccgagagagc atggatccca acgacgcctt ctcggcggcg cacccgttcc     1560
ggtgggacct cggcccgccg gcgcacgccg cgcccgcgcc cgcgcctccg cctccgccgc     1620
tagcaccgct gctgctgccg cctcacgcgc gcgggagct ggaggacctg gtggccggct      1680
acggcgtgcg cccgtccacg gtggcgcgga tctcggagct cgggttcacg gcgagcacgc     1740
tcctcggcat gacggagcgc gagctggacg acatgatggc cgcgctcgcg gggctgttcc     1800
gctgggacgt gctcctcggc gagcgcttcg gcctccgcgc cgcgctgcgc gccgagcgcg     1860
gccgcgtcat gtccctcggc gcccgctgct ccacgccgg gagcaccttg gatgccgcgt      1920
cacaagaagg tacggcgtat aggagtatgt actcgtgtca cacacataca nacncttgta     1980
tatagtgctc agttttcttc tgtagttctg tactagttct gtgtgtttnc ngnatgtgat     2040
gatgtggtcg cnggtngatg gtcgtgtgca tcgtgcctgc gttantnatg catgcatgca     2100
tgcggacagt gtccatgcat cagtctttgt tngactagag tcacgngctc tgctctgctc     2160
gcctgtgatg ttacttgntc ttgttcnatc ataccgcaaa ctcgcagcgn tgtccgacga     2220
gcngangccg cggccagcgg cggcggcatg gcngcggaag gcgaggcngg caggaggatg     2280
gtgangacga ccgccggcaa gaagggcaag aaaggggtcg ttggcacgag gaagggcaag     2340
aaggcgagga ggaagaagga gctgatgagg ccgctgaacg tgctggacga cgagaacgac     2400
ggggacgagt acggcggcgg gtcggagtcg acngagtcgt ccgcgggagg ctccggggag     2460
agncagcggg agcacccgtt cgtggtcacc gagcccggcg aggtggcgag ggccaagaag     2520
aacgggctcg actacctctt ccacctgtac gagcagtgcc gcgtcttcct gctccaggtg     2580
cagtccatcg ctaagctggg cggccacaaa tcccctacca aggtacgcgc gcgcacacac     2640
ttagggcggg ggaggggtta gggacccctt ccctatatgg atggggagaa ccgaacaagc     2700
cttaggggtg ttnggttaca ccccgntaaa ntttagctca tgtcccatcg aangtttaaa     2760
cctccnttcc ggatatnaaa tgtngtcnga ttatnaaact aatttgtcag ccgaagatta     2820
aaagangaga cgaatctagt cnagttgatt gggtctatat ttcatactcc tatttaaaag     2880
tcaaacgctt gatgtgaccc gagctaaact ttagcaggag caaccaaaca ccccccttatt    2940 catttagcag agtaacattt ttnatataca aanggcagan gttttctgta tacgaacnct     3000
gtcgtgaatg tnccaatctt tttaggtcgt tgacaagcta taacaatatk atggtanana     3060
aaatatantg gcacgcaaag cgccaaagcc cgctntcatt acctaggact aggaggaagg     3120
aagcagcaaa ccctttgtag tgnaattcta tatntcctgc gccgttnagt ctatgctant     3180
acatgtacta catcaccata gtatatgcgg tcctcaattc aagtactcgt aatgatcgtg     3240
tagcacttgt acatacntac tgcttaaagt atattttgct tgagacgcac ccgcactcgt     3300
ggataangcg agtgacgtgt catcagtcgt cggtgncaaa gcctggggtg gctttgtgtc     3360
gtcttgtccg gccctagggt cagacgggca tgcatggcat cgacactctc tcggagtccg     3420
tggctgtgtg ctgttgttgc nccngttctcg cgcgtaccag tacgactgta cgagccacgt    3480
gggctcgatt tgtgncagtt tggtggccgg cgtacgagta gtctcgtgct cgcccccngt     3540
cttcagacgg tgtgcgtcga agtgaaatga atgcacggtc tggcctggac ggattccagg     3600
gtgattggat atgatgatag cttggtgacc tactgacctg acccggaggg ccncatcgat     3660
gcgctcctgc gtcngcntct gcgccaggct agcccacnca gatcnagacc gagaccgaga     3720
```

| | |
|---|---|
| ccggccggcc actggccagg cncgcnagct tgttcgatcc gtgagcagct gctgctgntg | 3780 |
| ctgctgcntg cgcacttgtg cgcgacgcga cncgacacgn cncgancagc gagctgctct | 3840 |
| gcactgcact gcacgtctgc acgggaacca accaaccatg gntgatnagc gacatntncg | 3900 |
| cgtggcgcgc gcgatcgtgc tcgtgcttgc tngcttgcag gtgaccaacc aggtgttccg | 3960 |
| gtacgcgaac aagtgcgggg cnagctacat caacaagccc aagntgcggc actacgtgca | 4020 |
| ctgctacgcg ctgcacngcc tggacgagga ggcctccnac gcgctgcgcc gggcgtacaa | 4080 |
| gtcccgcggc gagaacgtgg gcgccnggag gcaggcctgc tacgcgccnc tcgtcganat | 4140 |
| cgccncgcgc cacggcttcg acatngacgc cgtcttcncc gcgcacccgc ncctcgccgt | 4200 |
| ctggtacgtn cccaccaggc tgcnccagct ngccaccagg cgcgggggag ccacgcccac | 4260 |
| gcccacgctg ccgccggact cccnccgccc ccnatgttct agcgtgcgtc gtcgatgtgt | 4320 |
| gcctgcaccg tcgccgtacg tctcacagnc nttttntttt tagagtgtga accaccangg | 4380 |
| aaaattggat tccctctcat atgatgttgc cacttctcag tt | 4422 |

<210> SEQ ID NO 9
<211> LENGTH: 4422
<212> TYPE: DNA
<213> ORGANISM: Zea mays
<221> NAME/KEY: misc_feature
<222> LOCATION: (1)..(4422)
<223> OTHER INFORMATION: n is a, c, g, or t
<220> FEATURE:
<221> NAME/KEY: misc_feature
<222> LOCATION: (2146)..(2146)
<223> OTHER INFORMATION: y is c or t

<400> SEQUENCE: 9

| | |
|---|---|
| gagctagctt aatatggaag ccacactcac tcaccaagtc atggatgaga ggagagagtg | 60 |
| tggagagcca cacgcgcgcg cgcgctcgct cgcctcgcct cgcctggcct ggccgggccg | 120 |
| ggccggggcg gggcgaaggg cgcgggcgca cgacatgcgc gtgaatggtc cgccgaaatc | 180 |
| cggcccctcg ccttgcgagg gcgcgactac cttttgccgt ttgattttt ggtttcttgg | 240 |
| ctgttacgct tatcctaacc gatcgctaca aaatctcaac tgattgcgag attttcgtgg | 300 |
| gcggataagc acgggggtc gcggactcga ccctataaaa ggagcccggc agccagcctc | 360 |
| caaatcatcc cagatcccag ttcgcttcg cctctcttca tagctgagcc gccttttagt | 420 |
| tcccttcgtc ccgaccgcag aggtgcatct gcgatcagga gagcaggtct ccggaaccct | 480 |
| tcgtcttcta gatcctgcac cgggagaggg cgaataaggt ttttgggaag cgtcttcgcg | 540 |
| cgactgctcg tgatcgctg acctcgtcaa cccatctgat cctggcgcgc gccaacaatc | 600 |
| agtaagtcta atcagtacgc atcatctgat ttggcttta tttcagttct tctgatttgg | 660 |
| tcatgattta tattcggaat ttaatttgga atttgtctaa ttattcaaca ggtgcaatct | 720 |
| ccggcctcta ctcactccag atctattctt cgcttcgcct gcaggcagca gtagcaccgt | 780 |
| tcaagttcaa ccaacgcggc caacgcacct gttgaagttg aaccatgcat gaacccgcga | 840 |
| cgtgtttatc ctccattatc cacggtgagc tctgaaatcc acgttgactc acatacatac | 900 |
| acggtacgcg cgtcagggat ttcactcgga ggcaagaatc gaaaagaaa aaggaagcca | 960 |
| cgcgtacgac gtgcaacggg gacacacatc cacacgacg ccgcgacggg actgcacagt | 1020 |
| ggcaatggca acgcaggtgc agtggtggtg tgttggagt gtttattatt gcctcaccgt | 1080 |
| gtgcttcttt tttatgttc cagagcaagc acgtaatgta gtaggggcgt agaatctaga | 1140 |
| ctatcaaatc gcgaggggcg acgacggtgc tcggtgcagt gcagctttgt acaggaacag | 1200 |

```
gactagtcgt tttcacgtcg taacagagca cgctcccgcg tcgatagatc gctacgagca    1260
gtcgacagac acggcagcat aaatgcgcgc gcaaaagcta gtagtaggac taggcctaca    1320
gtgcagtgcg tccccgagat tcattcgtca agttcaggtc gaccggccgg ccttgccctt    1380
gcattggaaa acagttaccg ctatataaca aacagccgcg gcgcacggcg agccaagccc    1440
gtcaaggcac gaggactgca ggagcagaaa gttggcaacc ctttgagttc ctcactcaca    1500
cgcgcgcgag ccgagagagc atggatccca acgacgcctt ctcggcggcg cacccgttcc    1560
ggtgggacct cggcccgccg gcgcacgccg cgcccgcgcc cgcgcctccg cctccgccgc    1620
tagcaccgct gctgctgccg cctcacgcgc gcgggagct ggaggacctg gtggccggct     1680
acggcgtgcg cccgtccacg gtggcgcgga tctcggagct cgggttcacg gcgagcacgc    1740
tcctcggcat gacggagcgc gagctggacg acatgatggc cgcgctcgcg gggctgttcc    1800
gctgggacgt gctcctcggc gagcgcttcg gcctccgcgc cgcgctgcgc gccgagcgcg    1860
gccgcgtcat gtccctcggc gcccgctgct ccacgccgg gagcaccttg gatgccgcgt     1920
cacaagaagg tacggcgtat aggagtatgt actcgtgtca cacacataca nacncttgta    1980
tatagtgctc agtttttcttc tgtagttctg tactagttct gtgtgttttnc ngnatgtgat   2040
gatgtggtcg cnggtngatg gtcgtgtgca tcgtgcctgc gttantnatg catgcatgca    2100
tgcggacagt gtccatgcat cagtctttgt tngactagag tcacgygctc tgctctgctc    2160
gcctgtgatg ttacttgntc ttgttcnatc ataccgcaaa ctcgcagcgn tgtccgacga    2220
gcngangccg cggccagcgg cggcggcatg gcngcggaag gcgaggcngg caggaggatg    2280
gtgangacga ccgccggcaa gaagggcaag aaaggggtcg ttggcacgag gaagggcaag    2340
aaggcgagga ggaagaagga gctgatgagg ccgctgaacg tgctggacga cgagaacgac    2400
ggggacgagt acggcggcgg gtcggagtcg acngagtcgt ccgcgggagg ctccggggag    2460
agncagcggg agcacccgtt cgtggtcacc gagcccggcg aggtggcgag ggccaagaag    2520
aacgggctcg actacctctt ccacctgtac gagcagtgcc gcgtcttcct gctccaggtg    2580
cagtccatcg ctaagctggg cggccacaaa tcccctacca aggtacgcgc gcgcacacac    2640
ttagggcggg ggaggggtta gggaccccctt ccctatatgg atggggagaa ccgaacaagc   2700
cttaggggtg ttnggttaca ccccgntaaa ntttagctca tgtcccatcg aangtttaaa   2760
cctccnttcc ggatatnaaa tgtngtcnga ttatnaaact aatttgtcag ccgaagatta    2820
aaagangaga cgaatctagt cnagttgatt gggtctatat ttcatactcc tatttaaaag    2880
tcaaacgctt gatgtgaccc gagctaaact ttagcaggag caaccaaaca ccccttatt     2940
catttagcag agtaacattt ttnatataca aanggcagan gttttctgta tacgaacnct    3000
gtcgtgaatg tnccaatctt tttaggtcgt tgacaagcta taacaatatn atggtanana   3060
aaatatantg gcacgcaaag cgccaaagcc cgctntcatt acctaggact aggaggaagg    3120
aagcagcaaa cccctttgtag tgnaattcta tatntcctgc gccgttnagt ctatgctant   3180
acatgtacta catcaccata gtatatgcgg tcctcaattc aagtactcgt aatgatcgtg    3240
tagcacttgt acatacntac tgcttaaagt atattttgct tgagacgcac ccgcactcgt    3300
ggataangcg agtgacgtgt catcagtcgt cggtgncaaa gctggggtg gctttgtgtc     3360
gtcttgtccg gccctagggt cagacgggca tgcatggcat cgacactctc tcggagtccg    3420
tggctgtgtg ctgttgttgc nccngttttcg cgcgtaccag tacgactgta cgagccacgt   3480
gggctcgatt tgtgncagtt tggtggccgg cgtacgagta gtctcgtgct cgcccccngt    3540
cttcagacgg tgtgcgtcga agtgaaatga atgcacggtc tggcctggac ggattccagg    3600
```

```
gtgattggat atgatgatag cttggtgacc tactgacctg acccggangg ccncatcgat    3660
gcgctcctgc gtcngcntct gcgccaggct agcccacnca gatcnagacc gagaccgaga    3720
ccggccggcc actggccagg cncgcnagct tgttcgatcc gtgagcagct gctgctgntg    3780
ctgctgcntg cgcacttgtg cgcgacgcga cncgacacgn cncgancagc gagctgctct    3840
gcactgcact gcacgtctgc acgggaacca accaaccatg gntgatnagc gacatntncg    3900
cgtggcgcgc gcgatcgtgc tcgtgcttgc tngcttgcag gtgaccaacc aggtgttccg    3960
gtacgcgaac aagtgcgggg cnagctacat caacaagccc aagntgcggc actacgtgca    4020
ctgctacgcg ctgcacngcc tggacgagga ggcctccnac gcgctgcgcc gggcgtacaa    4080
gtcccgcggc gagaacgtgg gcgccnggag gcaggcctgc tacgcgccnc tcgtcganat    4140
cgccncgcgc cacggcttcg acatngacgc cgtcttcncc gcgcacccgc ncctcgccgt    4200
ctggtacgtn cccaccaggc tgcnccagct ngccaccagg cgcggggag ccacgcccac     4260 gcccacgctg ccgccggact cccnccgccc ccnatgttct agcgtgcgtc gtcgatgtgt    4320
gcctgcaccg tcgccgtacg tctcacagnc nttttttnttt tagagtgtga accaccangg   4380
aaaattggat tccctctcat atgatgttgc cacttctcag tt                      4422
```

<210> SEQ ID NO 10
<211> LENGTH: 561
<212> TYPE: DNA
<213> ORGANISM: Zea mays
<220> FEATURE:
<221> NAME/KEY: misc_feature
<222> LOCATION: (1)..(561)
<223> OTHER INFORMATION: n is a, c, g, or t
<220> FEATURE:
<221> NAME/KEY: misc_feature
<222> LOCATION: (408)..(408)
<223> OTHER INFORMATION: r is a or g

<400> SEQUENCE: 10

```
naatnaatan atgagataaa nantntntag agatanttaa gtcatcccac tgcaggtatn     60
ctcncaacaa tagcaagtac tcaattcata ttnaaatcca ccctgtngaa ttccatggat    120
ggtggcattg tnctttctat caaccaaagc agatcactcn tggnacggag tgagntcgat    180
cttgaatggc ttctttccct tggtaactcg cttcacatga tggagaaaag gggggganaaa   240 caaagggtaa atttactgat atttggcttg aatatantga aggatatcaa acttacagca    300
attgcaatta attcctccaa cagctcttcc agattgcgca anggctaaga atgaaaangg    360
tgcaaanaaa tagtatgtgg gttatatgat aaacatnatc aatgctargt aacgtggaaa    420
agnctgcacg gaatgnactg gattatacc attgagttgg gccatcgcat ggtgcattca    480
aggggtcatc atgtacctgt gngattatgc aataagatcc gtttaatgtt gagcataaca    540
gcagattatg ttaatatacc a                                              561
```

<210> SEQ ID NO 11
<211> LENGTH: 538
<212> TYPE: DNA
<213> ORGANISM: Zea mays
<220> FEATURE:
<221> NAME/KEY: misc_feature
<222> LOCATION: (1)..(538)
<223> OTHER INFORMATION: n is a, c, g, or t
<220> FEATURE:
<221> NAME/KEY: misc_feature
<222> LOCATION: (160)..(160)
<223> OTHER INFORMATION: s is c or g

<400> SEQUENCE: 11

```
cgtcgtagng ttgttgtggt gcgcgcagcg cggcgcgttg acgggcagca tcaggtagtt    60
nggncccagc ctgtagcgct gcgtgtcggc gtaggcgaac acccggcact gcagcatctt   120
gtcgtccgag tagtagatcc ctggcaccac cagccccggs ccgaacgcca gctgctcgtt   180
ctcgttgaag aagttgtcca cgttccngtc cagcacccag cctccccacg ggncngagcg   240
gnagcaggtc ctccggccac gtcttggtgt cgtccagcgg gtcgaagtcg tactgctcct   300
ccgtgtcngg ntccatcacc tgcacgtaca gcgtccactc cgggaagctc cccgccgcga   360
tggagtcgta caggtcctgc gtngcgtggc tgtggttccg tccccgacc agcgccgcnt    420 cctcgtncgt caggatgcac cgcacgncgc acgtcggctt ccagtggaac ttnacgtact   480
gcgccttccc cgccgcgctc acgaacgncg nccntncngn gngngnccna ngnanacg     538
```

<210> SEQ ID NO 12
<211> LENGTH: 538
<212> TYPE: DNA
<213> ORGANISM: Zea mays
<220> FEATURE:
<221> NAME/KEY: misc_feature
<222> LOCATION: (1)..(538)
<223> OTHER INFORMATION: n is a, c, g, or t
<220> FEATURE:
<221> NAME/KEY: misc_feature
<222> LOCATION: (311)..(311)
<223> OTHER INFORMATION: s is c or g

<400> SEQUENCE: 12

```
cgtcgtagng ttgttgtggt gcgcgcagcg cggcgcgttg acgggcagca tcaggtagtt    60
nggncccagc ctgtagcgct gcgtgtcggc gtaggcgaac acccggcact gcagcatctt   120
gtcgtccgag tagtagatcc ctggcaccac cagccccggn ccgaacgcca gctgctcgtt   180
ctcgttgaag aagttgtcca cgttccngtc cagcacccag cctccccacg ggncngagcg   240
gnagcaggtc ctccggccac gtcttggtgt cgtccagcgg gtcgaagtcg tactgctcct   300
ccgtgtcngg stccatcacc tgcacgtaca gcgtccactc cgggaagctc cccgccgcga   360
tggagtcgta caggtcctgc gtngcgtggc tgtggttccg tccccgacc agcgccgcnt    420 cctcgtncgt caggatgcac cgcacgncgc acgtcggctt ccagtggaac ttnacgtact   480
gcgccttccc cgccgcgctc acgaacgncg nccntncngn gngngnccna ngnanacg     538
```

<210> SEQ ID NO 13
<211> LENGTH: 875
<212> TYPE: DNA
<213> ORGANISM: Zea mays
<220> FEATURE:
<221> NAME/KEY: misc_feature
<222> LOCATION: (1)..(875)
<223> OTHER INFORMATION: n is a, c, g, or t
<220> FEATURE:
<221> NAME/KEY: misc_feature
<222> LOCATION: (338)..(338)
<223> OTHER INFORMATION: y is c or t

<400> SEQUENCE: 13

```
gatgttataa gtggatcaan gaggtgctgc ttgcgattat gactgtaaat gcaaatatat    60
acatagatct gaaaaccatg gaaaaaatat taatacatac accaaaaaac agtacagatt   120
atcaaaaagc tgatcaaaca tnacatagag acacatgaaa ccccaatgaa tcaagccaaa   180
taaaaatata ggnccggcat ttgtccacaa acttaatcca aancattgat ttacaaatc    240 atactaatca caggagacaa agctaagaaa atgaaccatc caagcaaacg gaatgaaaaa   300
```

-continued

| | |
|---|---|
| tagaagactt ccctagcaat aacagaagta cataactyga agaccaaact gcatcatggt | 360 |
| tttctagtac attcatccag ttccatatct atgactgatg aagacagtgg agctggaagg | 420 |
| ggcagcacat aatgcaggnt ctacctagaa cccttcngga cgaactaatc aagtaattgc | 480 |
| aaactgacgg ctttaaagaa cggatttgca aattaaaata aaaatgataa ctgcagtaaa | 540 |
| ctgatgttta agagcaacct tatatagtac aagtaaatgc atccccgaac tcaactgaag | 600 |
| cttatgaaat ttaactagca ctacaagctt gttactgccg cagcctggct aacaacagtt | 660 |
| catcagatcg aatagactac accancatgc cagattaaag gtaaacgatn aatcttcttt | 720 |
| gcagncaaga taaccaaacg ctaaccctca ccttattgaa ctcaatctgc ggcgtccagt | 780 |
| agtgaagcag accgaagaag tagtcgaaca tctcgacgga tgaggagaac tctttngncc | 840 |
| ccagcttcac tggcttgcgc tccgcctcca ctgtc | 875 |

<210> SEQ ID NO 14
<211> LENGTH: 8191
<212> TYPE: DNA
<213> ORGANISM: Zea mays
<220> FEATURE:
<221> NAME/KEY: misc_feature
<222> LOCATION: (1)..(8191)
<223> OTHER INFORMATION: n is a, c, g, or t
<220> FEATURE:
<221> NAME/KEY: misc_feature
<222> LOCATION: (5356)..(5356)
<223> OTHER INFORMATION: y is c or t

<400> SEQUENCE: 14

| | |
|---|---|
| acgttgttgg agagaaagta gatataagga gatgaaatct tttagagaag cctgtaaagg | 60 |
| acggatatag aggatgtata tagaggacgt tgctggagac agtctaaaga gctatttta | 120 |
| gagaagagtt gctgtaacgt cggagtaggt ctgtaggtgg acaagagcgg gcctagtggt | 180 |
| ttaaaaaaac aacagaggct aggacataga caatcctgtc gtgtccagct caccggatct | 240 |
| cccccacgca agacacacgg acgaaaggaa aaaaataat agaagaaact gggacgaccc | 300 |
| tttttctgtc cgtccgtggt cccttcaatc tctctgcgca atcaaactgc ggtggccaac | 360 |
| cccggaagcg gcggcgggca aagcgcgcga cgcagagaag cgtaacttca ggccgccggt | 420 |
| cgctctacgc atcctgctcc ccgttctcgt cggagatcca ccggggcagc cttcttcc | 480 |
| ccttcctcaa tcaagtcggt gagtaatccg agctcgattg cgtgggtgga ttgccttatc | 540 |
| tcacccaatc attcaaccag atccaatttc gcgcgcgggt cgggctcgcc ttctcctcca | 600 |
| gtctccacct ccaccagcgc tcgaggtcga cggacgctac tcgcagcagt tcttctttgc | 660 |
| ggtgcggccg agaagaagct aaggctcagg catgagcttc cgggaccagg agagtggcgg | 720 |
| ggaggatggg ggcaggacgt cctccgcctc cgacctgcgg aagccgctca tcaacaccgg | 780 |
| gagctggtac cgcatgccgc cggcgggtgg cgtgatgggc tcgcggcaat ctagcctcat | 840 |
| ggagcgattg ggctcctctg cgttctctct ccgcgacgtc gctatctcgg cgacgctctg | 900 |
| cacgctcatt gtcgcgctag gtcccatcca gttcggtttc acatgtggct actcctcacc | 960 |
| cacgcaggac gccatcattg ctgaccttgg cctctccctc tctgaggtga accctgttc | 1020 |
| ttttatcatt cgttctttct ttcttttaa tgcttaccct tgcttgcttg ctctttcttg | 1080 |
| gcggatgcat gcagttctcc ctcttcggtt cattatctaa tgtaggggcg atggtaggcg | 1140 |
| ccatctccag tggcaactt gcagagtata tcggccgcaa gggggtgaga ctaccacctt | 1200 |
| actttgtctt tgctagatca tgaatcgcaa tgcaatacga ctgacttaat cattgtttaa | 1260 |

```
gtgtgcatag catccatact ataggagg cttcgctgct ttgctaattg gaaccttgaa       1320
agatatgcct gtgatgattt ttcagaccga tggactgatt gaattatttg tttggccttg    1380
tagtctctca tgatcgctgc gatttcaaac ataattgggt ggctcgcgat atcatttgca    1440
aaagtaagtt caactaccat ccttttttcca tgcttctgct gctgatttcc tttgttcgtc   1500
aatatatgat aataacctgt gagtgttttt tttacttctg ttgcggtgca tattcaggat    1560
tcctctttct tgtttatggg tcggctgcta gaaggatttg gagttggtgt aatatcgtat    1620
acagtatgcc tcccctttct cctccctctt agtaaaaaca aattactcta gtggcatttt    1680
catgttcatc cgtcttccag ctgttaaaga ttacaatcct ttggtatttt tttaatcgaa    1740
aattctggtt ttcacaatta aagtcttaac aagtccatac aaacaaaaat ctgaagtccc    1800
gacatatttc aaacaaaaca atatgttcta gtggaaaatg taagcgtagt aaggcatata    1860
gcttggaatg atgaaacaaa attaaataac aagtcgacta aaaaagtgc agagtttgta     1920
gctcttaaat acaatgctac tttcttaggt tacattatct caacaacaat aaagtatttt    1980
agtcataatc aagtttgggt aggctagagt tgaaacccaa cggaaacagt cgaggttcag    2040
acacatggat agctattttt cgtgtgctcc tattcaaggc taaatatttg ggtatattcc    2100
atccctgcat cttcctatgt caactcggtc tttccctgcc tctatttata ttcttatgga    2160
cttatggtgc cttaagatct cactagcact ggtgcctctg gaggtctccg ttggacatgt    2220
ccaaactatc tcaactagcg ttgaaaagtt tttcttcttt ccataataca taattgaata    2280
ttaataatac tagacaagaa aactcataaa ccaaggtcac tgacccttgt tcagaataat    2340
agggtataat tatttcattg tcaaatgaga ctactagcac ttagaagtga ctgaaatcct    2400
atgtcgaata ctgttgtaga attgactttc tatatgcaag ttgtactata taaagcacca    2460
ttttccacgg tttgcaccgt cgtcgtggtc ccccacattt aaatggcaaa aggctaaaat    2520
tatgtacaaa tgaggattcg aaccatggtt gttggctcta aacccacact cacactcact    2580
tagccaacaa aacaaacatg tctttatgtt ttatactcta tactcaagca taaatgaaaa    2640
ccgtacaaaa atggcacttt actagttttc caaatgtttg tattttaaca ttttaaaatg    2700
gaagaacttg tcttctagtt ttcctattta caaaaaaaat tggctttatg acactccact    2760
agaatacaca ttgttctgag ttatacagca cactgtggct attgtacatt tgtactatag    2820
taactttact ttatgacata ggggagggggt gttgtggcgt ntgagtnaga cagggagagt   2880
ancataaagg nccaaaatat taaaattaca gtaccacaat ttggctattt tgtcaagggt    2940
ttgttggtac tgctcctgac agacgtagac tcctgnttag tgaaggtgtg gttgatttat    3000
ctgcctttag tctcccangc ttaaatnatt ttaggttatt gtactctttt gtgtcatgct    3060
atttccttgc ttttantaca tctgagccct tcaaaaaaca tgtgaggcta ctttatcntt    3120
tctatgcgtt caccattctt agaattacga ggacaacaan ggttacatgc ctccnantta    3180
tgaagaagga acatcctcng aggaggantg agaatgaaac tcaaacagtt tcacaanagg    3240
tatntggttt ccatttgctt acaggtnatg gganagaaac aataacttat ccttttctaa    3300
tgatgatgca gcacaacatc attnactgcc nttgacaaga actatctnac nccattttt    3360
accagtnaga cagatgatna taacnatgan gacttcngtg agtaactnat ttnttaanag   3420
atatgcagta aatgatgtca ccgaactatg aaattgatag tntgtgtgct acttataatt   3480
aagtatagca taattatctt catcctctat ctagtccact aagtcttgtc aatccactta   3540
gcaaattcat ggngaacaat tagtcctatc ttcaaacatt tgattctccc acttatttct   3600
gaanttgttt gttgctctct aattcactnt gtcaggtcag caaccccaaa accgaagnct   3660
```

```
agcttttat gatcaatagc ggaatttgat nctctacata tcaagctaaa tacacggagc    3720
agaactgacg tgcatgactn tntctntntg tgngnnnaan ancngngcan gagnngcatn    3780 aganantnt ancngacaaa ntnanggntn angncnttgg gngnnganan anccncngcn     3840
ngnanatant ntnggctncc ttnanaactn agtgggnctc cananaaaan cntgtgngna    3900
ntntnancnc nccntgtnaa tntnataaac ccgaccgttn gnccnctaag nnntntntaa    3960
tngncngttg caccagttgc cccantggct ngttgcacca gtggnaaatt nangngtncn    4020
anatataatg tnatngctga ttataaaant tctgcanagc actgaaagca aatatcatcc    4080
caggtcaggg aagtatgctg atgtttatta ttttaacgtt aacatttact cctattctaa    4140
caaagtagtt cagttttgaa atggttggcc ggtttaagct ggaactagaa tttattgcaa    4200
gtaccatgta gggattgagc tggaaagttg ttctccagtc cggtttatat tgcagaaatc    4260
gctcctcaag atcagagggg agctcttggt tctgtcaatc agctctccgt cacgattggt    4320
atattgcttg cctatttgtt tggcatgttt gttccctgga gaattcttgc tgttctaggc    4380
attttaccct gttcaatcct gattcctgga ctgttctttg tccctgaatc cccaaggtgg    4440
ttggcaaaaa tggggaagat ggaggatttt gaatattcat tgcaagttct gcgaggattt    4500
cagacagata tcacagcaga agtaaatgaa ataaaggtaa tcaatagtgg aaactccagt    4560
ttagttaaaa tagagataga gatatacagt ttttttcttg gacatgcagg agagctgtgt    4620
acttacaaac atacccacac aacacactca gtccaacatt ttagttttag gaagataaac    4680
acgccaatac ataataaaac tcgatcatga cctaaactca actaatagat gaagggacat    4740
aagataagaa atacttcaag ctgctggcat gggagatgcc ccatcaaaaa cacaccagtt    4800
acgatgagtc ggtgacacca aaggtccag gcaccaagag acatatatac ttcgtcaatc    4860
ttgctcccag tggtatacnc tggtgcanct gccantgcat ngctctctag tagcnanaag    4920
ctgtngtagn atctcttaaa tttttgcagn ataatgtgcc ataggagntg ngaattacat    4980
aattatcttc cttttttttac acagagntca ttagcatcat cnaggaggag gacaaccata    5040
aggttcgctg atatcaaaca gaagagatac agtgttcccc ttgtggttgg tgacttgcta    5100
tttgtttctc tgtttacata tngatgttta aacttttgta gttttgctaa ttggcttgtt    5160
tttagatagg aatcggtctc cttgtcctgc agcagctaag tggtgtcaat ggcatnctat    5220
tttatgctgc gagcatcttc aaagctgctg gtacattctt caaaacanga tcaatctctg    5280
atgcnantna nantnantgc nttngcttgc ntattcntga acttgtncng gaaatgaaag    5340
naccttgntt tggttygatt cngcntngca ngagacactg tgacnatgan tcanttacta    5400
tgtaaaaaan gangaagant ntagaaccta ggnttcatca aagtctgata tcttncctga    5460
antncttncc tcaacaggta tnncaaacag taatctagca acatttggtt taggggctgt    5520
tcaggtacat ttgttttaaa gttgttacat cccttgtttc tcagacaaat tttaggcaga    5580
tgtgggcttg gcactgcata cttaatggga tcttgtcgtt tcaggtgatt gctactggag    5640
tgacaacctg gttgactgac aaagctggtc gaaggcttct tctcattgtt agtttccaac    5700
tttccatcac aattgtttat cggacatgct tttccagttt tgttaattga gctgtctttt    5760
cagatttcca ccacaggaat ggtcattact cttgttattg tttctgtgtc atttttttgtg    5820 aaggtaatgt cacttaaaag tttaatagta gcatgctatt gtttgcagca cactcctatt    5880
gaaataatca tattgcttag agtctatcga cattgtcatt cctttctgaa atactcttgc    5940
ttcacttctg gagcaggaca acatagctgc tggttcgcac ttatactctg taatgagtat    6000
```

```
gctttcactg gctggacttg tggttagttc cactactatt acagattgtt tgccgccctt    6060
gttgagataa gcttgtttaa tgccttgtct tttgctattc caggcatttg tgattgcatt    6120
ttctcttggc ttgggagcga ttccgtggat cattatgtct gaggtatagt ttgttcttgc    6180
tttttatatt atacagagct tttaattcgc taatgtgtct ttgctatctt atctttatgt    6240
aattattatg agtgccactt agcacttttg ctctaagtcc ccagctctga atttcacgca    6300
ctctgagaca ctgcaacccc aaatccacaa cctctcagca taggggttgt ttggataccc    6360
accccacccc cccttttttc ttcttttttc tgtcttggtc tatttttttg gcagcttgta    6420
ctgggtctac tttagacctc tatctccttt tcttaatat ataagatgcg cagttctcct    6480
gcgcgttcga taaaaaagct atagcttntt taaaatcgca tgggtctcta gccagaggac    6540
atccatgcct acctcaaata actgaaatta cctcatccag tagctattaa tttaaccgcg    6600
aatgatagtg agcaacttat ctagtctagt tgcctagact agataagttc agtgaaatac    6660
ctagaggtac tgcatctgca aacttgcggg gagatttatg cacttacatt gtgtttcctt    6720
tcagatcctt cctgttaaca tcaagagcct tgctggaagt gttgcgaccc tggcgaactg    6780
gctgacagca tgggccatta caatgacggc aagcctgatg ttgaactgga gcagtggagg    6840
tctcttcctt tcttttttcca ttctctccct cccttcaaga acgtgtttcc cattgcgacg    6900
ttggatctaa ccgtgtgtct tggtttgacc aggaaccttt gctatctacg ccgtcgtgtc    6960
taccatggcc ctcattttcg tgtgcttgtg ggtgcctgag accaagggaa gaacgctaga    7020
ggaaatcgcc ttctcattcc gctgacacgt cgtcatgatc taggtatggg aagccacacc    7080
acaccatgtg tcattgagtc atgccgcggt gcgttcagtt catgaatccc gcagggaaaa    7140
atcaccactc cgatgccgga gcactggtgg gcgaagaacc acccatgcca tttacaatat    7200
gacgacgact cttgcggcca ttctgttgct tggatgtacc accatcttca gtgttcatac    7260
caatgtacat tgtacaatat gacgacgacg ccatagcaga aaggcaagtg ggtttatgtt    7320
tgtacgatgg actagtagca gaaagcactc gaaccctgt acgggttgcg gaggagagca    7380
atttatttgc tgtattttcc tggttcaata ccggacacgt tagaattttg aaaaataaaa    7440
atctgagcaa atttatcaac ggtgctgcca gctccatgcg tttgcctgca tgcggtcatg    7500
aagtagaaga cattggagcc taaatatcta ggaacggttt tgatttagga aaaaaaaag    7560 ggaaggaatt ttattctgaa acctaggggc atggttgtgc agcggcaaac ttgactgctg    7620
aaggggctga tcggaattag gtaccttgtg gttttgaagc gttgtttgaa atcggcgtca    7680
gcctcgcccc accagcctct tctaatcgtc tgaaacgggg gctgcaagat ctccgtggac    7740
ctcggccgcc gcgtctgcct gcccatgcgg cattagcgcc ttcatgcgac gtcggaggat    7800
caggaaaccg tggcatgtga aaggatcat ttccatggac ctcaacgcg gacgccggat    7860 ggcaggggca tcatctgatg atcatccgcc tgccgcgtgc gccgccggag atcaggaagc    7920
cgtgcccagt caacactctg caggccacca gcccaccaat ttgggcaccc ggttgtggca    7980
gagcgagcga atgcgaagca cggtcgactt cactaaccct gctgcgactg tgagaaaaaa    8040
aaggcccttt tggcctaacc caatgcctag tttgctcggc ccatctgctg gatattttgt    8100 ttctttttc cttttgcgaa aaagttggta catttgttg aactcaaacc gtgaagacgc    8160
aaatccttaa attttttatt ggttcacgcc a                                  8191
```

<210> SEQ ID NO 15
<211> LENGTH: 8191
<212> TYPE: DNA
<213> ORGANISM: Zea mays

<220> FEATURE:
<221> NAME/KEY: misc_feature
<222> LOCATION: (1)..(8191)
<223> OTHER INFORMATION: n is a, c, g, or t
<220> FEATURE:
<221> NAME/KEY: misc_feature
<222> LOCATION: (5371)..(5371)
<223> OTHER INFORMATION: k is g or t

<400> SEQUENCE: 15

| | | | | | |
|---|---|---|---|---|---|
| acgttgttgg | agagaaagta | gatataagga | gatgaaatct | tttagagaag | cctgtaaagg | 60 |
| acggatatag | aggatgtata | tagaggacgt | tgctggagac | agtctaaaga | gctattttta | 120 |
| gagaagagtt | gctgtaacgt | cggagtaggt | ctgtaggtgg | acaagagcgg | gcctagtggt | 180 |
| ttaaaaaaac | aacagaggct | aggacataga | caatcctgtc | gtgtccagct | caccggatct | 240 |
| cccccacgca | agacacacgg | acgaaaggaa | aaaaataat | agaagaaact | gggacgaccc | 300 |
| tttttctgtc | cgtccgtggt | cccttcaatc | tctctgcgca | atcaaactgc | ggtggccaac | 360 |
| cccggaagcg | gcggcgggca | aagcgcgcga | cgcagagaag | cgtaacttca | ggccgccggt | 420 |
| cgctctacgc | atcctgctcc | ccgttctcgt | cggagatcca | ccggggcagc | ctttctttcc | 480 |
| ccttcctcaa | tcaagtcggt | gagtaatccg | agctcgattg | cgtgggtgga | ttgccttatc | 540 |
| tcacccaatc | attcaaccag | atccaatttc | gcgcgcgggt | cgggctcgcc | ttctcctcca | 600 |
| gtctccacct | ccaccagcgc | tcgaggtcga | cggacgctac | tcgcagcagt | tcttctttgc | 660 |
| ggtgcggccg | agaagaagct | aaggctcagg | catgagcttc | cgggaccagg | agagtggcgg | 720 |
| ggaggatggg | ggcaggacgt | cctccgcctc | cgacctgcgg | aagccgctca | tcaacaccgg | 780 |
| gagctggtac | cgcatgccgc | cggcgggtgg | cgtgatgggc | tcgcggcaat | ctagcctcat | 840 |
| ggagcgattg | ggctcctctg | cgttctctct | ccgcgacgtc | gctatctcgg | cgacgctctg | 900 |
| cacgctcatt | gtcgcgctag | gtcccatcca | gttcggtttc | acatgtggct | actcctcacc | 960 |
| cacgcaggac | gccatcattg | ctgaccttgg | cctctccctc | tctgaggtga | cccctgttc | 1020 |
| ttttatcatt | cgttctttct | ttcttttaa | tgcttaccct | tgcttgcttg | ctctttcttg | 1080 |
| gcggatgcat | gcagttctcc | ctcttcggtt | cattatctaa | tgtagggcg | atggtaggcg | 1140 |
| ccatctccag | tgggcaactt | gcagagtata | tcggccgcaa | gggggtgaga | ctaccacctt | 1200 |
| actttgtctt | tgctagatca | tgaatcgcaa | tgcaatacga | ctgacttaat | cattgtttaa | 1260 |
| gtgtgcatag | catccatact | atataggagg | cttcgctgct | ttgctaattg | gaaccttgaa | 1320 |
| agatatgcct | gtgatgattt | ttcagaccga | tggactgatt | gaattatttg | tttggccttg | 1380 |
| tagtctctca | tgatcgctgc | gatttcaaac | ataattgggt | ggctcgcgat | atcatttgca | 1440 |
| aaagtaagtt | caactaccat | ccttttttcca | tgcttctgct | gctgatttcc | tttgttcgtc | 1500 |
| aatatatgat | aataacctgt | gagtgttttt | tttacttctg | ttgcggtgca | tattcaggat | 1560 |
| tcctctttct | tgtttatggg | tcggctgcta | gaaggatttg | gagttggtgt | aatatcgtat | 1620 |
| acagtatgcc | tccccttct | cctccctctt | agtaaaaaca | aattactcta | gtggcatttt | 1680 |
| catgttcatc | cgtcttccag | ctgttaaaga | ttacaatcct | ttggtatttt | tttaatcgaa | 1740 |
| aattctggtt | ttcacaatta | aagtcttaac | aagtccatac | aaacaaaaat | ctgaagtccc | 1800 |
| gacatatttc | aaacaaaaca | atatgttcta | gtggaaaatg | taagcgtagt | aaggcatata | 1860 |
| gcttggaatg | atgaaacaaa | attaaataac | aagtcgacta | aaaaagtgc | agagtttgta | 1920 |
| gctcttaaat | acaatgctac | tttcttaggt | tacattatct | caacaacaat | aaagtatttt | 1980 |
| agtcataatc | aagtttgggt | aggctagagt | tgaaacccaa | cggaaacagt | cgaggttcag | 2040 |

```
acacatggat agctatttttt cgtgtgctcc tattcaaggc taaatatttg ggtatattcc    2100
atccctgcat cttcctatgt caactcggtc tttccctgcc tctatttata ttcttatgga    2160
cttatggtgc cttaagatct cactagcact ggtgcctctg gaggtctccg ttggacatgt    2220
ccaaactatc tcaactagcg ttgaaaagtt tttcttcttt ccataataca taattgaata    2280
ttaataatac tagacaagaa aactcataaa ccaaggtcac tgacccttgt tcagaataat    2340
agggtataat tatttcattg tcaaatgaga ctactagcac ttagaagtga ctgaaatcct    2400
atgtcgaata ctgttgtaga attgactttc tatatgcaag ttgtactata taaagcacca    2460
ttttccacgg tttgcaccgt cgtcgtggtc ccccacattt aaatggcaaa aggctaaaat    2520
tatgtacaaa tgaggattcg aaccatggtt gttggctcta aacccacact cacactcact    2580
tagccaacaa aacaaacatg tctttatgtt ttatactcta tactcaagca taaatgaaaa    2640
ccgtacaaaa atggcacttt actagttttc caaatgtttg tattttaaca ttttaaaatg    2700
gaagaacttg tcttctagtt ttcctattta caaaaaaaat tggctttatg acactccact    2760
agaatacaca ttgttctgag ttatacagca cactgtggct attgtacatt tgtactatag    2820
taactttact ttatgacata ggggaggggt gttgtggcgt ntgagtnaga cagggagagt    2880
ancataaagg nccaaaatat taaaattaca gtaccacaat ttggctattt tgtcaagggt    2940
ttgttggtac tgctcctgac agacgtagac tcctgnttag tgaaggtgtg gttgatttat    3000
ctgcctttag tctcccangc ttaaatnatt ttaggttatt gtactctttt gtgtcatgct    3060
atttccttgc ttttantaca tctgagccct tcaaaaaaca tgtgaggcta ctttatcntt    3120
tctatgcgtt caccattctt agaattacga ggacaacaan ggttacatgc ctccnantta    3180
tgaagaagga acatcctcng aggaggantg agaatgaaac tcaaacagtt tcacaanagg    3240
tatntggttt ccatttgctt acaggtnatg gganagaaac aataacttat ccttttctaa    3300
tgatgatgca gcacaacatc attnactgcc nttgacaaga actatctnac nccattttt    3360
accagtnaga cagatgatna taacnatgan gacttcngtg agtaactnat ttnttaanag    3420
atatgcagta aatgatgtca ccgaactatg aaattgatag tntgtgtgct acttataatt    3480
aagtatagca taattatctt catcctctat ctagtccact aagtcttgtc aatccactta    3540
gcaaattcat ggngaacaat tagtcctatc ttcaaacatt tgattctccc acttatttct    3600
gaantttgttt gttgctctct aattcactnt gtcaggtcag caaccccaaa accgaagnct    3660
agcttttttat gatcaatagc ggaatttgat nctctacata tcaagctaaa tacacggagc    3720
agaactgacg tgcatgactn tntctntntg tgngnnnaan ancngngcan gagnngcatn    3780
agananatnt ancngacaaa ntnanggntn angncnntgg gngnnganan anccncngcn    3840
ngnanatant ntnggctncc ttnanaactn agtgggnctc cananaaaan cntgtgngna    3900
ntntnancnc nccntgtnaa tntnataaac ccgaccgttn gnccnctaag nnntntntaa    3960
tngncngttg caccagttgc cccantggct ngttgcacca gtggnaaatt nangngtncn    4020
anatataatg tnatngctga ttataaaant tctgcanagc actgaaagca aatatcatcc    4080
caggtcaggg aagtatgctg atgtttatta ttttaacgtt aacatttact cctattctaa    4140
caaagtagtt cagttttgaa atggttggcc ggtttaagct ggaactagaa tttattgcaa    4200
gtaccatgta gggattgagc tggaaagttg ttctccagtc cggtttatat tgcagaaatc    4260
gctcctcaag atcagagggg agctcttggt tctgtcaatc agctctccgt cacgattggt    4320
atattgcttg cctatttgtt tggcatgttt gttccctgga gaattcttgc tgttctaggc    4380
attttaccct gttcaatcct gattcctgga ctgttctttg tccctgaatc cccaaggtgg    4440
```

```
ttggcaaaaa tggggaagat ggaggatttt gaatattcat tgcaagttct gcgaggattt    4500
cagacagata tcacagcaga agtaaatgaa ataaaggtaa tcaatagtgg aaactccagt    4560
ttagttaaaa tagagataga gatatacagt ttttttcttg gacatgcagg agagctgtgt    4620
acttacaaac atacccacac aacacactca gtccaacatt ttagttttag gaagataaac    4680
acgccaatac ataataaaac tcgatcatga cctaaactca actaatagat gaagggacat    4740
aagataagaa atacttcaag ctgctggcat gggagatgcc ccatcaaaaa cacaccagtt    4800
acgatgagtc ggtgacacca aaaggtccag gcaccaagag acatatatac ttcgtcaatc    4860
ttgctcccag tggtatacnc tggtgcanct gccantgcat ngctctctag tagcnanaag    4920
ctgtngtagn atctcttaaa tttttgcagn ataatgtgcc ataggagntg ngaattacat    4980
aattatcttc ctttttttac acagagntca ttagcatcat cnaggaggag gacaaccata    5040
aggttcgctg atatcaaaca gaagagatac agtgttcccc ttgtggttgg tgacttgcta    5100
tttgtttctc tgtttacata tngatgttta aacttttgta gttttgctaa ttggcttgtt    5160
tttagatagg aatcggtctc cttgtcctgc agcagctaag tggtgtcaat ggcatnctat    5220
tttatgctgc gagcatcttc aaagctgctg gtacattctt caaaacanga tcaatctctg    5280
atgcnantna nantnantgc nttngcttgc ntattcntga acttgtncng gaaatgaaag    5340
naccttgntt tggttngatt cngcntngca kgagacactg tgacnatgan tcanttacta    5400
tgtaaaaaan gangaagant ntagaaccta ggnttcatca aagtctgata tcttncctga    5460
antncttncc tcaacaggta tnncaaacag taatctagca acatttggtt tagggggctgt    5520
tcaggtacat ttgttttaaa gttgttacat cccttgtttc tcagacaaat tttaggcaga    5580
tgtgggcttg gcactgcata cttaatggga tcttgtcgtt tcaggtgatt gctactggag    5640
tgacaacctg gttgactgac aaagctggtc gaaggcttct tctcattgtt agtttccaac    5700
tttccatcac aattgtttat cggacatgct tttccagttt tgttaattga gctgtctttt    5760
cagatttcca ccacaggaat ggtcattact cttgttattg tttctgtgtc attttttgtg    5820
aaggtaatgt cacttaaaag tttaatagta gcatgctatt gtttgcagca cactcctatt    5880
gaaataatca tattgcttag agtctatcga cattgtcatt cctttctgaa atactcttgc    5940
ttcacttctg gagcaggaca acatagctgc tggttcgcac ttatactctg taatgagtat    6000
gctttcactg gctggacttg tggttagttc cactactatt acagattgtt tgccgcccett    6060
gttgagataa gcttgtttaa tgccttgtct tttgctattc caggcatttg tgattgcatt    6120
ttctcttggc ttgggagcga ttccgtggat cattatgtct gaggtatagt ttgttcttgc    6180
tttttatatt atacagagct tttaattcgc taatgtgtct ttgctatctt atctttatgt    6240
aattattatg agtgccactt agcacttttg ctctaagtcc ccagctctga atttcacgca    6300
ctctgagaca ctgcaacccc aaatccacaa cctctcagca tagggttgt ttggataccc    6360
accccacccc cccttttttc ttcttttttc tgtcttggtc tattttttg gcagcttgta    6420
ctgggtctac tttagacctc tatctccttt ttcttaatat ataagatgcg cagttctcct    6480
gcgcgttcga taaaaagct atagcttntt taaaatcgca tgggtctcta gccagaggac    6540
atccatgcct acctcaaata actgaaatta cctcatccag tagctattaa tttaaccgcg    6600
aatgatagtg agcaacttat ctagtctagt tgcctagact agataagttc agtgaaatac    6660
ctagaggtac tgcatctgca aacttgcggg gagatttatg cacttacatt gtgtttcctt    6720
tcagatcctt cctgttaaca tcaagagcct tgctggaagt gttgcgaccc tggcgaactg    6780
```

```
gctgacagca tgggccatta caatgacggc aagcctgatg ttgaactgga gcagtggagg    6840
tctcttcctt tcttttttcca ttctctccct cccttcaaga acgtgtttcc cattgcgacg    6900
ttggatctaa ccgtgtgtct tggtttgacc aggaaccttt gctatctacg ccgtcgtgtc    6960
taccatggcc ctcattttcg tgtgcttgtg ggtgcctgag accaagggaa gaacgctaga    7020
ggaaatcgcc ttctcattcc gctgacacgt cgtcatgatc taggtatggg aagccacacc    7080
acaccatgtg tcattgagtc atgccgcggt gcgttcagtt catgaatccc gcagggaaaa    7140
atcaccactc cgatgccgga gcactggtgg gcgaagaacc acccatgcca tttacaatat    7200
gacgacgact cttgcggcca ttctgttgct tggatgtacc accatcttca gtgttcatac    7260
caatgtacat tgtacaatat gacgacgacg ccatagcaga aaggcaagtg ggtttatgtt    7320
tgtacgatgg actagtagca gaaagcactc gaaccctgt acgggttgcg gaggagagca     7380
atttatttgc tgtattttcc tggttcaata ccggacacgt tagaattttg aaaaataaaa    7440
atctgagcaa atttatcaac ggtgctgcca gctccatgcg tttgcctgca tgcggtcatg    7500
aagtagaaga cattggagcc taaatatcta ggaacggttt tgatttagga aaaaaaaaag   7560
ggaaggaatt ttattctgaa acctaggggc atggttgtgc agcggcaaac ttgactgctg    7620
aaggggctga tcggaattag gtaccttgtg gttttgaagc gttgtttgaa atcggcgtca    7680
gcctcgcccc accagcctct tctaatcgtc tgaaacgggg gctgcaagat ctccgtggac    7740
ctcggccgcc gcgtctgcct gcccatgcgg cattagcgcc ttcatgcgac gtcggaggat    7800
caggaaaccg tggcatgtga gaaggatcat ttccatggac ctcaacggcg gacgccggat    7860 ggcagggggca tcatctgatg atcatccgcc tgccgcgtgc gccgccggag atcaggaagc    7920
cgtgcccagt caacactctg caggccacca gcccaccaat ttgggcaccc ggttgtggca    7980
gagcgagcga atgcgaagca cggtcgactt cactaaccct gctgcgactg tgagaaaaaa    8040
aaggcccttt tggcctaacc caatgcctag tttgctcggc ccatctgctg gatattttgt    8100
ttcttttttc cttttgcgaa aaagttggta cattttgttg aactcaaacc gtgaagacgc    8160
aaatccttaa atttttttatt ggttcacgcc a                                  8191
```

<210> SEQ ID NO 16
<211> LENGTH: 1843
<212> TYPE: DNA
<213> ORGANISM: Zea mays
<220> FEATURE:
<221> NAME/KEY: misc_feature
<222> LOCATION: (563)..(1185)
<223> OTHER INFORMATION: k is g or t
<220> FEATURE:
<221> NAME/KEY: misc_feature
<222> LOCATION: (1587)..(1587)
<223> OTHER INFORMATION: y is c or t

<400> SEQUENCE: 16

```
agcattgtca tgctccttgc ctatgtagcc tacctttttct tccaactgaa aacccaccgc      60
caactatttg aaccccaacc ccaagaggtg tgtattgtaa tttgttgctg atcagtaacc     120
agcaggaact gctaacatag aaccagcttg ctaatttggg tatgtgggtc caaccaaatg     180
attttgtagg ttgaaagatg atggtgatga ttcggtctct caagacgagg cagtactggg     240
atttttccag tgcaatgatt tggctgggag tcatgaccct gatgacagca ctcctatcag     300
agtttgttgt gagcacaatt gaggtatgca ccactgagta caatgccatg tttatgttac    360
ccatttcagt cagcacatac actgtagtaa gttgtagtac agctaatggt tttatgacag    420
aatcttgtta acacttwaca ggcagcatcg gaatcttggg agctatctgt cagtttcatt    480
```

```
agcgtcatct tgattccaat agttggtaat gcagcagagc atgctggtgc agtgatattt       540
gcgtttaaaa acaatctggt agkgaaatcg aggaggtctt acacactcat cacgatgtta       600
tggtagcaga tactaacata acattgttgg ctgaaacagg acatcaccct cggagtatct       660
ttggggtccg ctacgcagat ttccatgttt gtggtgtgta ttaacttaaa tgtagagata       720
gttccatgtg ctttttttg catcggtaaa ctttaatggt ggaagcgaaa tgtgctaggt        780
gccattgagt gtccttgtag catggatcat gggagtcccg atggatcttg atttcaactt       840
gcttgagact ggttgtttgt ttcttgcaat attagtaacg gccttcacgc tccaggtatt       900
cttttgcacc ctcctcgatc cggcttgaac ataatcgata acacgcatgg attttttcat       960
tgacagaaca tccatgaatc ttgagtggtt agttgtatgt gctgattttg tttattaaga     1020
aaagaaatgt ccacttgtgc ggttcggctg tgtccttgtt tctaaggatg cggggccata     1080
ggagttctgt caatatcgtg gttttagcgg taaagagtga ctgttctatg cgttttgca      1140 ggatggatca tcacattatc tgaagggact gctgcttgtg ttttkctaca ttgtcatctc     1200
cttatgcttt ttcgttttga gacagcatgg aagtatggat ttctagtctt aacaaccttc     1260
attcaaaaaa aaacctatag atgcattatt ggttgacatt ttctaaataa tctcaataac     1320
atgttactga tgctagatgg aagcaacgat gatcagctgg gtgtagcaag caagccatgg     1380
aggatttagg gcgcctgagc tggcagtagt ttctcaacaa gtagcgtgga ctttggtttg     1440
cacgattttg catggaacac tggaggggag acccgtgaag tttgactaaa gtatgtagac     1500
tgcgggaaga tgctgttcag ctgatgtgtg aatgtaagta catacaaaga ctatagatga     1560
aaactgatgt tgcgtgagag actatytgtg tgtgtttttc ttgttctttc caccaagcaa     1620
tggctagaat tcggttgagc tgttgaaatt gtctcctgta taaatcagtg acatgtcata     1680
ctattttcca actggactta acagagcctt tatccttcta attggttacc cgcatggtca     1740
taatctggat catcatcgtg cgttaacttt gtctaaatgt ttgtttggtt gcctgcaagt     1800
ggagggcatg gactgtatga actaatgcaa ataagttat ttt                        1843
```

<210> SEQ ID NO 17
<211> LENGTH: 616
<212> TYPE: DNA
<213> ORGANISM: Zea mays
<220> FEATURE:
<221> NAME/KEY: misc_feature
<222> LOCATION: (1)..(616)
<223> OTHER INFORMATION: k is g or t
<220> FEATURE:
<221> NAME/KEY: misc_feature
<222> LOCATION: (1)..(616)
<223> OTHER INFORMATION: m is a or c
<220> FEATURE:
<221> NAME/KEY: misc_feature
<222> LOCATION: (1)..(616)
<223> OTHER INFORMATION: n is a, c, g, or t
<220> FEATURE:
<221> NAME/KEY: misc_feature
<222> LOCATION: (1)..(616)
<223> OTHER INFORMATION: r is a or g
<220> FEATURE:
<221> NAME/KEY: misc_feature
<222> LOCATION: (1)..(616)
<223> OTHER INFORMATION: v is a, c, or g
<220> FEATURE:
<221> NAME/KEY: misc_feature
<222> LOCATION: (1)..(616)
<223> OTHER INFORMATION: y is c or t

<400> SEQUENCE: 17

```
natttaactc ttttcaagaa gattgynaga tcccatgggg tatggcgagg atgatctccc    60
tctagtatcg ttacagtctg tttccaaagg taratttaya tarccagcta ckttatctgc   120
cktttggyca agtaactggc ttatccaaaa vattttgytg ctgcaaccag gatactatgg   180
agagtgtggt aaaagaggag ggtacatgga gattactggc ttcagtrctc cagtaagaga   240
gcagatctac aagatagctt cagtgaacyt rtgctccaat atcactggtc aaatccttgc   300
gagcctcgtc atgaatcyac caaaggtctg ccatatggaa ttctttaaat tmcgccctgg   360
ttggaattag gaaatgccaa atcgtccrgt taaaratcrt tgctttattc tccaggytgg   420
rgacgaatca tatgcttcct acaaggcaga gaargatgga atccttgagt ctttagctcg   480
tcgtgcaaag gttmgcctgg ttgcatttcc actacwctct tgaktgtctt ctwtaaaaat   540
attcaagatt tttcttttgt tcgttttaca ggcgttggag gatgcattca acaagcttga   600
gggattttca tgtaac                                                   616
```

<210> SEQ ID NO 18
<211> LENGTH: 616
<212> TYPE: DNA
<213> ORGANISM: Zea mays
<220> FEATURE:
<221> NAME/KEY: misc_feature
<222> LOCATION: (1)..(616)
<223> OTHER INFORMATION: k is g or t
<220> FEATURE:
<221> NAME/KEY: misc_feature
<222> LOCATION: (1)..(616)
<223> OTHER INFORMATION: m is a or c
<220> FEATURE:
<221> NAME/KEY: misc_feature
<222> LOCATION: (1)..(616)
<223> OTHER INFORMATION: n is a, c, g, or t
<220> FEATURE:
<221> NAME/KEY: misc_feature
<222> LOCATION: (1)..(616)
<223> OTHER INFORMATION: r is a or g
<220> FEATURE:
<221> NAME/KEY: misc_feature
<222> LOCATION: (1)..(616)
<223> OTHER INFORMATION: v is a, c, or g
<220> FEATURE:
<221> NAME/KEY: misc_feature
<222> LOCATION: (1)..(616)
<223> OTHER INFORMATION: y is c or t

<400> SEQUENCE: 18

```
natttaactc ttttcaagaa gattgynaga tcccatgggg tatggcgagg atgatctccc    60
tctagtatcg ttacagtctg tttccaaagg taratttaya tarccagcta ckttatctgc   120
cktttggyca agtaactggc ttatccaaaa vattttgytg ctgcaaccag gatactatgg   180
agagtgtggt aaaagaggag ggtacatgga gattactggc ttcagtrctc cagtaagaga   240
gcagatctac aagatagctt cagtgaacyt rtgctccaat atcactggtc aaatccttgc   300
gagcctcgtc atgaatcyac caaaggtctg ccatatggaa ttctttaaat tmcgccctgg   360
ttggaattag gaaatgccaa atcgtccrgt taaaratcrt tgctttattc tccaggytgg   420
rgacgaatca tatgcttcct acaaggcaga gaargatgga atccttgagt ctttagctcg   480
tcgtgcaaag gttmgcctgg ttgcatttcc actacwctct tgaktgtctt ctwtaaaaat   540
attcaagatt tttcttttgt tcgttttaca ggcgttggag gatgcattca acaagcttga   600
gggattttca tgtaac                                                   616
```

<210> SEQ ID NO 19
<211> LENGTH: 616

```
<212> TYPE: DNA
<213> ORGANISM: Zea mays
<220> FEATURE:
<221> NAME/KEY: misc_feature
<222> LOCATION: (1)..(616)
<223> OTHER INFORMATION: k is g or t
<220> FEATURE:
<221> NAME/KEY: misc_feature
<222> LOCATION: (1)..(616)
<223> OTHER INFORMATION: m is a or c
<220> FEATURE:
<221> NAME/KEY: misc_feature
<222> LOCATION: (1)..(616)
<223> OTHER INFORMATION: n is a, c, g, or t
<220> FEATURE:
<221> NAME/KEY: misc_feature
<222> LOCATION: (1)..(616)
<223> OTHER INFORMATION: r is a or g
<220> FEATURE:
<221> NAME/KEY: misc_feature
<222> LOCATION: (1)..(616)
<223> OTHER INFORMATION: v is a, c, or g
<220> FEATURE:
<221> NAME/KEY: misc_feature
<222> LOCATION: (1)..(616)
<223> OTHER INFORMATION: y is c or t

<400> SEQUENCE: 19
natttaactc ttttcaagaa gattgynaga tcccatgggg tatggcgagg atgatctccc      60
tctagtatcg ttacagtctg tttccaaagg taratttaya tarccagcta cktttatctgc   120 cktttggyca agtaactggc ttatccaaaa vattttgytg ctgcaaccag gatactatgg    180
agagtgtggt aaaagaggag ggtacatgga gattactggc ttcagtrctc cagtaagaga   240
gcagatctac aagatagctt cagtgaacyt rtgctccaat atcactggtc aaatccttgc   300
gagcctcgtc atgaatcyac caaaggtctg ccatatggaa ttctttaaat tmcgccctgg   360
ttggaattag gaaatgccaa atcgtccrgt taaaratcrt tgctttattc tccaggytgg   420
rgacgaatca tatgcttcct acaaggcaga gaargatgga atccttgagt ctttagctcg   480
tcgtgcaaag gttmgcctgg ttgcatttcc actacwctct tgaktgtctt ctwtaaaaat   540
attcaagatt tttcttttgt tcgttttaca ggcgttggag gatgcattca acaagcttga   600
gggattttca tgtaac                                                    616

<210> SEQ ID NO 20
<211> LENGTH: 5615
<212> TYPE: DNA
<213> ORGANISM: Zea mays
<220> FEATURE:
<221> NAME/KEY: misc_feature
<222> LOCATION: (1)..(5615)
<223> OTHER INFORMATION: n is a, c, g, or t
<220> FEATURE:
<221> NAME/KEY: misc_feature
<222> LOCATION: (2458)..(2458)
<223> OTHER INFORMATION: w is a or t

<400> SEQUENCE: 20
atacatatca tcttttgaca ggatataata tgtgaaacaa aaaaagtcac ctacgtgcgg     60
tgtgggtagg ggcggtacgt aatggatcac gattcatttg agtccttaat aaattttagt   120
ataatattaa acaaaaatag ggctcgatct taatatggct cgatcctaaa attttatagc   180
gtaaaattga gaacccagta ccatcatagg tgtgggacat gtacatagaa caagatcagt   240
ggatactttg gttgttactg tgtaactgtg ttacagcacc cttatatgcg aggttccacg   300
ggagccattg atttcgtcat agagaggcac acattgacct aggacgatgc gattgtactt   360
```

```
gcacgaggag taaattgacc atcaacgggg aataacataa taataagaaa agaaacaca      420
tctactatag aatggaacaa aaagaaacac gacgcgtccc aatatataca ttgactgcga     480
tcaaggtagc ccatttatac agcgccaaca aggagtagaa ttcacggtag gtacgtacac    540
gtacacgtac ggaatgtacg tatgtagtat ttcaacttgt ttttattaca gtggctttaa    600
tttgtgcatc ctggagaatc tcaaagttac caatcttaaa atttgcttaa cttttaacaa    660
tgtgtaccag ggagggcttg agcaccgcag ccctatgcta tgcacctgcg ctcccaatac    720
tagtcggagt agactagtag gagtagattt tctgtctctc tcacacactc tctatgcctg    780
cgtgtttgac tgcacctcag ccagcctaga tgctaggcta ctcacgctgg accatcctcc    840
tatagtccta gctatagccc cccctccatg ataaaagcta cctacgcttg cgttactgtg    900
ctctactgcg ccactgtgtg gtaatttggc aacagtaaaa tcagagatca tacgagggtt    960
tttcttttag ctagggcttg tccgggagcc acgggatcga ggtcagttag aattcctcgt   1020
tatttactcc ctccagtttc ctattagttg tcgttttgga taaggttcga gtcaaattta   1080
taaaatttta actacaaata actattttat tatttagttt tggaacctaa tatttatatg   1140
catcaatttg tcataaaaag tacttttata aaagtataaa tgtattaaga gttcatttgt   1200
attttaacaa aaaacattgg tcaaagttat attttgaaga ccgtgtcgtt gtcctaaacg   1260
acaactaata ggaaaccgga gggagtaaaa ttcaatagtg tgagatttta accctgatc    1320
aatccactcc attactttta cttaaacaa gggtttatag agaaagaggg aaaagaacac    1380
taagggctag tttganaact ntactttcca antgattcta tttttttaaa gagaaaata    1440
aactaatttc ttttagaaaa ataaaaatct cttgagaaaa taggctgcaa aactagctct   1500
aaataaataa ttaactaaac aaatgaaaag aaggcggcta aaagaaagga aacaaaggc   1560
agccttattt tcccccttct ctctccttcc cctgccttct gctactatat agctccccct   1620
caccttccgt tctagagaga gagaagggag aggcgaggga gctcaccagg agagagggc   1680
ctgtgtgagc attgagcaaa gcaaacgaag cagtacatac atctctcgct cgcagaggcc   1740
cggccggccg gctccatgca acaagggacg acgagcggtg gcggtgggcg atgatgatga   1800
tgatggcggg ggagcacgtg ctggccgctc tggccaccct gcttctggcc tcgctcctga   1860
ccctggtgct gaaccacttc ctgcccttgc ttctgaaccc caaggccccc aggggaagct   1920
tcgggtggcc gctcctcggc gagacgctca ggttcctcac gccgcacgcc tccaacacgc   1980
tgggcggctt cctcgaggat cactgctcca ggtacactgt gatactagtg ccgtttgccg   2040
cgcgcgccgg ccgccccggc ggcccttttt nccccntnt nttttacctt tttccaccgt    2100
ccgtgcccgt gttccatgca cacggncggc ncctagctgn ctagccaacc ggcnggccat   2160
atgagatgga nggatggatn gatngatgga tggatggatg gatcgatcga tcggtcttgn   2220
taccgtgcna ttaagtatcn cgccattatt tcatgtgaca gcaaanggtg acncgctgcc   2280
cgcnggncgc tgtcatgtct aagctagcag caggcagcnt tttntntttc tcttcgtgtc   2340
atgcatcttt cacggttttg ttcttgggtc gttccgagan cgggacgaca gtagtctgat   2400
ctgatctgag agagnagtaa aaaaanaaag gagaaagtaa acaacngcgc tcgacgawag   2460
attttactta catgcatgcn tgcatgnatn tnctnctngc tanctagcta gctaatggca   2520
gcatgnattg ttgatatgca ggtatgggcg ggtgttcaag tcccacctgt tctgcacccc   2580
gacggtggtg tcctgcgacc aggacctcaa ccacttcatc ctgcagaacg aggagcggct   2640
gttccagtgc agctacccga ggccgatcca tggcnectgg gcaagtcctc catgctcgtc   2700
gtcctgggcg aggaccacaa gcgcctcagg aacctngccc tcgccctcgt cacctccacc   2760
```

```
aagctcaagc ccagctacct aggcgacatc gagaagatcg cgctgcacgt cgtcggcgca    2820
tggcgacggc acggcggcag cggcggcgtc agggtcgtcg cattctgcga ggaggcaaga    2880
aaggttcgtc atgttgcctc tgcatcaatn tttttgccat ggagantctg tttgacttac    2940
caggatcgtt tgttttcntt ttcctttcct atttcctntg ggccgnccgc gcgtgtacgt    3000
cctntgctct gtcnttgaga aaagcacagt tngcattcag tgtgatagtg aagcaggtgc    3060
tggggctgnc gccagaggan ccggtcactg caaggatnct naggacttcc tggcnttcat    3120
gaagggnctc atctccttcc ccctctacat cccagggacc ccatatncca agnctgtccg    3180
ngtaatcatc ncnccangtg tctttagtag cacatgccat ncttgcttgn ttgcttgcgt    3240
tcgtaaagan catccatgat ccatctnttc attngntatg cntacaatac atacatagac    3300
acacactatn cntacatnta cataaccgtg gntacgtttn ttttgttgcn tanatcccaa    3360
cggcancgag agagaggata tccagcactg tgaagggcat catcaagnag cggaggagcn    3420
ctgggtcatg naacaagcag ggcgacttcc ttgacgtgct gctgtcaagc nacgagctat    3480
ctgacgagga gaaagtgagc tttgtgctgg actccctgct gggagggtat gagaccacct    3540
cgctcctcat ctcaatatca ctggtgaaag cacagcacag cacaggcaca nttttttttt    3600
ggtgctggtt tgggcatcat caataaaatta tnagctatcc atgaacatgc agagggagca    3660
cgacagcatn agatccaaca aaggcaagga ggagtgcttg acttcagaag actacaagaa    3720
gatggaatat accnaacaag tgagatagat gaccattcat tcaatcaata tatacatnat    3780
gctagtagta ttaganatgg aagtagtaaa tatgataaat ttttttattc tgtgctgtaa    3840
gtatgctgca gtangtggan tagaaatgtt gttgtcattc atgcccttna ccacctnctt    3900
gatncaggtn atcancgagg cgntgagngn ggcncatntc angttngtcc nccggangnc    3960
gngaangacg tcananacna nggngatgna gnagngancc nccncccntc ntgctcctgn    4020
atcgagagac tttcgcngca gattccatct gtgctcatca catgacagtg gatcaggcag    4080
aggggatggc cgcgccttta agcctgattt ttngcgattg ttttatgccc agaataacct    4140
cctatagctt ttgctaaacg aagatgctca aaaagcaagt ggctctgcct ntgctctgtt    4200
gcananatct gattccatct ggctggaagg tcctaccggt cttcactgcc gttcatctga    4260 accctcact  ncatggagac gcgcagcagt ttcagccctg taggtgggag gtacgctgcg    4320
ncccttctca ggagctcaga ctccttcctc attactactg ttctgcactt gcatctaac     4380 tataacggca atgatccaat catccatgtt ccatgaatag tgaaggttac ctttgtgata    4440
atatatatat ggtgctactt aatcaaaact gaatgaaata ataggaatca aaggcagaga    4500
acctatcaaa caagcttatc aggggctttt gctcttaggg aatcttcttt aaagtgtgca    4560
ctctaactaa ttgctacctt tagttagtgt gtgtccatct gtgacatagt tactctcaac    4620
tgttctggta tgttcagatg gcaagcatgc tgcctnatgt agtgcttgtt ggttgttaat    4680
ggtcctaacc atgattccgt tcgttgaaag ccagccctct gggctttgnt ncgnttttn    4740 ttcttcttca atgatgttca tggtctcatt aattttgtgt gactcatctg attgatgtat    4800
accagggcac aagccaaggg acaagcaaga ggtttacacc gttcggtggt ggccccggc    4860 tctgcccagg atcagagctc gctaaagtgg agnctgcttn cttcctccat caccttgtcc    4920
tcaattatag gtaaataaac aaaggacggt gttattagtc ctaactgagt tggtggattt    4980
ttggcaaacc aaagcacggt acacctgaac atcatgcaaa attctaacca aacctaagga    5040
aatcttgtgg caggacagac agtgttaatc cacatgctag gaagtaatgg caacaaggtt    5100
```

| | |
|---|---|
| atgacagcac tgttaaatgg aaaatatatt atgaggaaaa aatgaacaag gactcacaat | 5160 |
| atcgagattg atagtgtcca actagtaaga aaaactatag caagtgatgg caacaaggtt | 5220 |
| acgataacaa ctggcctctc taatttatgt ttttgtcaac agggaccaca ggtctcaaaa | 5280 |
| taaatgttta actaattttg gatccaggac tgtagagcat atatatcaga agataccata | 5340 |
| cagtacaaat atgggcagct ttaggttttc gacaagtagg ctatgcaagt tgagtgttat | 5400 |
| catacaagat atagaattct gaaatatgac caaaccgcca aaatgttgcc catgataatc | 5460 |
| ttaagccaac tgaatgttta gtaataaggc gtttctttca ctgttattgt ttctttcaga | 5520 |
| gtaagtaaaa ctacttaggg gcttgtttgg gaccaagtga aacaaagaga attgaggggg | 5580 |
| ctataatccc ttgttattca aaattgaata gcaag | 5615 |

<210> SEQ ID NO 21
<211> LENGTH: 5615
<212> TYPE: DNA
<213> ORGANISM: Zea mays
<220> FEATURE:
<221> NAME/KEY: misc_feature
<222> LOCATION: (1)..(5615)
<223> OTHER INFORMATION: n is a, c, g, or t
<220> FEATURE:
<221> NAME/KEY: misc_feature
<222> LOCATION: (4037)..(4037)
<223> OTHER INFORMATION: k is g or t

<400> SEQUENCE: 21

| | |
|---|---|
| atacatatca tcttttgaca ggatataata tgtgaaacaa aaaaagtcac ctacgtgcgg | 60 |
| tgtgggtagg ggcggtacgt aatggatcac gattcatttg agtccttaat aaattttagt | 120 |
| ataatattaa acaaaaatag ggctcgatct taatatggct cgatcctaaa attttatagc | 180 |
| gtaaaattga gaacccagta ccatcatagg tgtgggacat gtacatagaa caagatcagt | 240 |
| ggatactttg gttgttactg tgtaactgtg ttacagcacc cttatatgcg aggttccacg | 300 |
| ggagccattg atttcgtcat agagaggcac acattgacct aggacgatgc gattgtactt | 360 |
| gcacgaggag taaattgacc atcaacgggg aataacataa taataagaaa agaaacaca | 420 |
| tctactatag aatggaacaa aaagaaacac gacgcgtccc aatatataca ttgactgcga | 480 |
| tcaaggtagc ccatttatac agcgccaaca aggagtagaa ttcacggtag gtacgtacac | 540 |
| gtacacgtac ggaatgtacg tatgtagtat ttcaacttgt ttttattaca gtggctttaa | 600 |
| tttgtgcatc ctggagaatc tcaaagttac caatcttaaa atttgcttaa cttttaacaa | 660 |
| tgtgtaccag ggagggcttg agcaccgcag ccctatgcta tgcacctgcg ctcccaatac | 720 |
| tagtcggagt agactagtag gagtagattt tctgtctctc tcacacactc tctatgcctg | 780 |
| cgtgtttgac tgcacctcag ccagcctaga tgctaggcta ctcacgctgg accatcctcc | 840 |
| tatagtccta gctatagccc cccctccatg ataaaagcta cctacgcttg cgttactgtg | 900 |
| ctctactgcg ccactgtgtg gtaatttggc aacagtaaaa tcagagatca tacgagggtt | 960 |
| tttcttttag ctagggcttg tccgggagcc acgggatcga ggtcagttag aattcctcgt | 1020 |
| tatttactcc ctccagtttc ctattagttg tcgttttgga taaggttcga gtcaaattta | 1080 |
| taaaatttta actacaaata actattttat tatttagttt tggaacctaa tatttatatg | 1140 |
| catcaatttg tcataaaaag tacttttata aaagtataaa tgtattaaga gttcattgt | 1200 |
| attttaacaa aaaacattgg tcaaagttat attttgaaga ccgtgtcgtt gtcctaaacg | 1260 |
| acaactaata ggaaaccgga gggagtaaaa ttcaatagtg tgagatttta accctgatc | 1320 |
| aatccactcc attactttta ctttaaacaa gggtttatag agaaagaggg aaaagaacac | 1380 |

```
taagggctag tttganaact ntactttcca antgattcta ttttttttaaa gagaaaaata   1440
aactaatttc ttttagaaaa ataaaaatct cttgagaaaa taggctgcaa aactagctct   1500
aaataaataa ttaactaaac aaatgaaaag aaggcggcta aaagaaagga aacaaaaggc   1560
agccttattt tccccttct ctctccttcc cctgccttct gctactatat agctcccct    1620
caccttccgt tctagagaga gagaagggag aggcgaggga gctcaccagg agagaggggc   1680
ctgtgtgagc attgagcaaa gcaaacgaag cagtacatac atctctcgct cgcagaggcc   1740
cggccggccg gctccatgca acaagggacg acgagcggtg gcggtgggcg atgatgatga   1800
tgatggcggg ggagcacgtg ctggccgctc tggccaccct gcttctggcc tcgctcctga   1860
ccctggtgct gaaccacttc ctgcccttgc ttctgaaccc caaggccccc aggggaagct   1920
tcgggtggcc gctcctcggc gagacgctca ggttcctcac gccgcacgcc tccaacacgc   1980
tgggcggctt cctcgaggat cactgctcca ggtacactgt gatactagtg ccgtttgccg   2040
cgcgcgccgg ccgcccggc ggcctttttt nccccntnt nttttacctt tttccaccgt    2100
ccgtgcccgt gttccatgca cacggncggc nctagctgn ctagccaacc ggcnggccat    2160
atgagatgga nggatggatn gatngatgga tggatggatg gatcgatcga tcggtcttgn   2220
taccgtgcna ttaagtatcn cgccattatt tcatgtgaca gcaaanggtg acncgctgcc   2280
cgcnggncgc tgtcatgtct aagctagcag caggcagcnt tttntntttc tcttcgtgtc   2340
atgcatcttt cacggttttg ttcttgggtc gttccgagan cgggacgaca gtagtctgat   2400
ctgatctgag agagnagtaa aaaaanaaag gagaaagtaa acaacngcgc tcgacganag   2460
attttactta catgcatgcn tgcatgnatn tnctnctngc tanctagcta gctaatggca   2520
gcatgnattg ttgatatgca ggtatgggcg ggtgttcaag tcccacctgt tctgcacccc   2580
gacggtggtg tcctgcgacc aggacctcaa ccacttcatc ctgcagaacg aggagcggct   2640
gttccagtgc agctacccga ggccgatcca tggcnectgg gcaagtcctc catgctcgtc   2700
gtcctgggcg aggaccacaa gcgcctcagg aacctngccc tcgccctcgt cacctccacc   2760
aagctcaagc ccagctacct aggcgacatc gagaagatcg cgctgcacgt cgtcggcgca   2820
tggcgacggc acggcggcag cggcggcgtc agggtcgtcg cattctgcga ggaggcaaga   2880
aaggttcgtc atgttgcctc tgcatcaatn tttttgccat ggagantctg tttgacttac   2940
caggatcgtt tgtttctctt tcctttcct atttcctntg ggccgnccgc gcgtgtacgt    3000
cctntgctct gtcnttgaga aaagcacagt tngcattcag tgtgatagtg aagcaggtgc   3060
tggggctgnc gccagaggan ccggtcactg caaggatnct naggacttcc tggcnttcat   3120
gaagggnctc atctccttcc ccctctacat cccagggacc ccatatncca agnctgtccg   3180
ngtaatcatc ncnccangtg tctttagtag cacatgccat ncttgcttgn ttgcttgcgt   3240
tcgtaaagan catccatgat ccatctnttc attngntatg cntacaatac atacatagac   3300
acacactatn cntacatnta cataaccgtg gntacgtttn ttttgttgcn tanatcccaa   3360
cggcancgag agagaggata tccagcactg tgaagggcat catcaagnag cggaggagcn   3420
ctgggtcatg naacaagcag ggcgacttcc ttgacgtgct gctgtcaagc nacgagctat   3480
ctgacgagga gaaagtgagc tttgtgctgg actccctgct gggagggtat gagaccacct   3540
cgctcctcat ctcaatatca ctggtgaaag cacagcacag cacaggcaca ntttttttt    3600
ggtgctggtt tggcatcat caataaatta tnagctatcc atgaacatgc agagggagca   3660
cgacagcatn agatccaaca aaggcaagga ggagtgcttg acttcagaag actacaagaa   3720
```

```
gatggaatat accnaacaag tgagatagat gaccattcat tcaatcaata tatacatnat    3780
gctagtagta ttaganatgg aagtagtaaa tatgataaat tttttatttc tgtgctgtaa    3840
gtatgctgca gtangtggan tagaaatgtt gttgtcattc atgcccttna ccacctnctt    3900
gatncaggtn atcancgagg cgntgagngn ggcncatntc angttngtcc nccggangnc    3960
gngaangacg tcananacna nggngatgna gnagngacc nccncntc ntgctcctgn       4020 atcgagagac tttcgckgca gattccatct gtgctcatca catgacagtg gatcaggcag    4080
aggggatggc cgcgcccttta agcctgattt ttngcgattg ttttatgccc agaataaccct  4140 cctatagctt ttgctaaacg aagatgctca aaaagcaagt ggctctgcct ntgctctgtt    4200
gcananatct gattccatct ggctggaagg tcctaccggt cttcactgcc gttcatctga    4260
acccctcact ncatggagac gcgcagcagt ttcagccctg taggtgggag gtacgctgcg    4320 nccccttctca ggagctcaga ctccttcctc attactactg ttctgcactt gccatctaac   4380
tataacggca atgatccaat catccatgtt ccatgaatag tgaaggttac ctttgtgata    4440
atatatatat ggtgctactt aatcaaaact gaatgaaata ataggaatca aaggcagaga    4500
acctatcaaa caagcttatc aggggctttt gctcttaggg aatcttcttt aaagtgtgca    4560
ctctaactaa ttgctaccttt tagttagtgt gtgtccatct gtgacatagt tactctcaac   4620
tgttctggta tgttcagatg gcaagcatgc tgcctnatgt agtgcttgtt ggttgttaat    4680
ggtcctaacc atgattccgt tcgttgaaag ccagccctct gggctttgnt ncgnttttttn  4740 ttcttcttca atgatgttca tggtctcatt aattttgtgt gactcatctg attgatgtat    4800
accagggcac aagccaaggg acaagcaaga ggtttacacc gttcggtggt ggccccccggc   4860 tctgcccagg atcagagctc gctaaagtgg agnctgcttn cttcctccat caccttgtcc    4920
tcaattatag gtaaataaac aaaggacggt gttattagtc ctaactgagt tggtggattt    4980
ttggcaaacc aaagcacggt acacctgaac atcatgcaaa attctaacca aacctaagga    5040
aatcttgtgg caggacagac agtgttaatc cacatgctag gaagtaatgg caacaaggtt    5100
atgacagcac tgttaaatgg aaaatatatt atgaggaaaa aatgaacaag gactcacaat    5160
atcgagattg atagtgtcca actagtaaga aaaactatag caagtgatgg caacaaggtt    5220
acgataacaa ctggcctctc taatttatgt ttttgtcaac agggaccaca ggtctcaaaa    5280 taaatgtttta actaattttg gatccaggac tgtagagcat atatatcaga agataccata   5340
cagtacaaat atgggcagct ttaggttttc gacaagtagg ctatgcaagt tgagtgttat    5400
catacaagat atagaattct gaaatatgac caaaccgcca aaatgttgcc catgataatc    5460
ttaagccaac tgaatgttta gtaataaggc gtttctttca ctgttattgt ttctttcaga    5520
gtaagtaaaa ctacttaggg gcttgtttgg gaccaagtga aacaaagaga attgaggggg    5580
ctataatccc ttgttattca aaattgaata gcaag                              5615
```

<210> SEQ ID NO 22
<211> LENGTH: 5836
<212> TYPE: DNA
<213> ORGANISM: Zea mays
<220> FEATURE:
<221> NAME/KEY: misc_feature
<222> LOCATION: (1)..(5836)
<223> OTHER INFORMATION: n is a, c, g, or t
<220> FEATURE:
<221> NAME/KEY: misc_feature
<222> LOCATION: (849)..(849)
<223> OTHER INFORMATION: y is c or t

<400> SEQUENCE: 22

```
catggaccat gcccctagct tagctaggcc acccacacac aaactaccaa acaaaaactt      60
aacaacctat ccctctctct gcactagctt tcgtattttt gttttctga tgggagatgt     120 gtgagtacca aacaaaacgt tgacaggcta gtaggccagg agagatacac ctagaagcta    180 gtcccttag ctagctctcc gctcgtgtgc atcatatatt cagatatata gatagatgca     240
tggccgtagt gtggttgttg tgcgctgcat cgatcgtctg atgaaaacgt tggttgccgc    300 ctattttgg aagcaacaaa aatccgtgtg ccgcgcgcag acgactgcag agtcgacaca     360
tatattatac gcgcgcgcac gtacgggact agcagctgcc agctagggag agtagtatgt    420
agtcagagat acacgaacga agacgaagaa gacgacgacg acctactaat aataatcaca    480
atctacataa aacacgagac cacagccctc aaaatgcaac gnaaaattga actgcctcct    540
ccctctcagc ntcttgtgct ctcggtcaaa acgctacgat ngccttggtc gtcggcgacc    600
cgctggaccc tgatcggnag gcccttgggg aagtcgacga aagggtagac gaaggcctgg    660
tccggctccg ccagctccca ccggaagttg agcaccaggt ggtgcaggaa gatggccatc    720
tccagcttgg ccagctccga cccggcgcac agccgcggcc cgccgccgta cggcatgaag    780
ctgcttggcg cgttgntntc tgcagctagn aacagcagcg gcngcaaaaa aaaaaaatat    840
taaacacayg cgatngncat gcgagagagc gcatgatcga tgagagaata tantagatna   900
tccntgagga gaaaggagc gcgctttnga cgggctnatc gtctcntcag tgatcagtag     960
tggaangagn tcnatngcca ctgacatgtg acantcacag cgangccgat cgcctgaacc   1020
tagtacntac gtgccttgcg tcgcgtcgtc acctcaatca ccttaacact aangtatcca   1080
aacaaagcct ngcctgagca aaaaattatt tccccatcna cggntgcgan ggatnagaaa   1140
angacgcgtc ggcgacggan ggaaggattn cgagagcaga gcatttccga ncacccgccc   1200
aacgtggcgt tcgttttcag tgctctngna gctggagtag tccctcgcgt tcggcacgaa   1260
cccagncgcg ctcccgcctc ccgnaggccg aagctggnaa ctaggacgtc tctttcgacc   1320
ccgagancac gcgaaagatc gcgcgccgaa acattcccct tcgcgcgcat cagctccatg   1380
ccgccctctc acatcaataa tggagggcaa gcgagcggca tagctgtcgt gctttggcng   1440
ggtactcttc actcttcact cttgngangg ntggcgtgnc acatgnatgc ntctcangcc   1500
gcanattcta gcgacacaag ccgtgaacgt ttttagangc ggattttctc tcgtactgtc   1560
atgctcgcgc ggatactttc ctctgggtcc ntcggcganc gacgttnatc cacatctant   1620
gntcagttaa tcngtnttca tgctgacttc attttttttn tnanananan ttgnggggn    1680 gggnaggggg naggncnctn acnttccntc tccaaggntt gaaccggcng ggncctcgna   1740
cagcgacgag tccaggtgca ccgccgctag aaccggcagg attttccacc cccgcggtat   1800
gtcgtaccct tcattttgat gagagcgaga gcgagagaca acatgcaacg caattaagca   1860
attaagcaga gagaaacgnt cantgcaccg gccgtctgca tgtgctgtgc gtgaccgatt   1920
tcaggaatcg cgtgcttaaa gnttnggtnt taaaanaagg ggtcgtacca ttgtagtgna   1980
catctcgnat gaccttccgg tgcaggaanc tgaccacgtt gccgagccgc aatgtctcgt   2040
ttataacctg cacgaacacc agnaaaaaaa taaagaaatc tgttnataaa agaaanaaag   2100
aaagaagaan ctccatccat tntgnagcta gctgcctagc tgacgaggca ttcgacatct   2160
aacagttggt tttaggtctn gcgacggaat tctgttttgt ttatttagac atganatgag   2220 accccctgagc ancgngatac ggcacagana ccttcctgtc gncaggtgct acacaagaac  2280
aacaatgngt acttctcact tctcagcata tgtggattgt tgcgagacga tgatgggggc   2340
```

```
agccagcact ctaatggagt gtttggtttg aggaattatg tagtccatca tcttctcact    2400
cctcactttt ttgtttggtt tgtgaattgg agtgagttaa tccatcacca cctcattcct    2460
catagttagt tgtttagtaa taatatgtgc aatgaaggca tcccaccaaa tttgaggaat    2520
ggacccatga tacaccactt cattttggat agagtgattc atcaaaccaa acncctcata    2580
aaactctgct gggagatgat gagagcaaga gcaagcagac gccatgcgct ccaaaagtag    2640
gcatccaatt attctgcgcg gacagagagc ctcgggtctc cgttcgtaca tgacatttct    2700
agagagaggg agttgcagtt gctatcctgt accacgcaac cagacgaggc ggtttgtgct    2760
ggtacgagtt ggacgggagc aggccagata gcgagcaagg ggatctcgcg ctaccacagt    2820
accactgcag tggaaggaac gaacagaaca aattaaaggg ggggtgggcg cttacacact    2880
gcgtgaaaac catttccttg tagtcttccc agctcaattt ggacgccccc cttagccttt    2940
gtctcctagc aatcaggaga tgctcctcct gcaagtcata tgccggtgta aactattatt    3000
tatctctata tataataata ataattccat gttttttttgt tttgttttgt tttgaccaac    3060
atcgacctag ctagctcact gtgcaaagtt tgaaaacgga ccagtgaaca aaagcaggtg    3120
ctctaaaact aactgattgt tggttcggat ttgtacccgg agttcttgca cggccttagg    3180
gcacccttcg aggaagaaga tggcgagggc gagcgccatg gacgaagtct cgtgccccgc    3240
gaagagcagg ctcagcaaga ggtccaggat ctgttccttg gacaggttgg attgcttcag    3300
ggcccatcca agaaggtcgt cctcctccac gcttgatttc tccctgctca tcttctcaag    3360
cctgtcctcc atcttcctct ctatcactcc aagtatggac gcgcgcgact tgagcgcctt    3420
ccagtaggcc gtgcccggga agttgagcgg cgctgacacg acgcccttca tgaaggtgat    3480
gtactccagc cgcagccgct ccgtctcctc ctcgccgggg tccatgctca ttatgttctt    3540
cgccatcagg ttaaacgtga actgcactcg tcatccggcc ggccgcgcgc ccatcaccgg    3600
ttgttatccc ggccggggca ccggttgtta gcggcgatcc tttgcatgga ttcagccaca    3660
tatatagata gaactgatct gatgtggcac gtacgtacta cgcgtggaga caaattgaag    3720
ggtcagaaga aggatggtga tgagtaccgt accttcttgg cttcgtgctg ggcggagaag    3780
gtgccgtcgg agggcggcca cgagcggagg accagcaggg tgtggcgctc cacctcgggg    3840
agcagcacgg cgcggaggcg gacggagctg aggaagttga gcgagatagc gcgcatctcg    3900
cggtgcgcgt cgcccacgag caccagcatg gaccacttgc ccaggatgcc gccgatgctg    3960
cgcgggtagc tgcactcgaa cagccgcccc tcgttctgca ggatgtagcg gttcagcccc    4020
gcgtccgccg acaccaccgt ccgctccccg aacaggctcg accggtatat cttcccgtac    4080
ctgcatgcac gcatggacgt cgccgcgtta gcaagcaagc tctcggtctc agagctaatt    4140
ctgattccat cgatgtcgcg ccatgcatga taggtgcgcg ctgctcgctg caccgtgcat    4200
gcatgtcgtc tgctgtctgc acagaggtag agacagcggc ggcggcgacg caccgtgcga    4260
catgccgctc catgaagcgg cccacggagg tggccgggtg ggcgcggagg tagccgaaag    4320
tttcgccgac caagggccat ccgcgggcgc ccggggggcag gttgggccgc ttcttcttct    4380
gacggcgcca cnggtgggtg ccgtggcatt tnggcgacgg tggtggtgta cnaggcgagg    4440
agggccagca ggatgaaggg aaggaagaag aggagctcgc tggttatgga ggccatcatg    4500
gcgcccatga gctcctgctg atcagaggtc tagctttctt caaatttatt tcctgcctgc    4560
tgcctctctg cctgatcact cgcccgcttc gttggttttt atgtgtggag agagaggacg    4620
gatgggttga agagagaaag caggagaggg aatgaatgaa gcgcctttat ctctggattt    4680
ctctctccct ctctctcagc aagtgcaagc tttgcgcaag gaaaaaaaaa actagtaaga    4740
```

-continued

```
agctaggcnc cccacttcgt ccccncttct gagctctntg gtgctcttat aggtttttn    4800 gagaggtagc tgtggggtcc tttaatttag gnccattcc aaacttctaa aactancaan    4860
ttntaacaac taaaatttat gagaggtata naacantcca ctaangancn gttaattgtn    4920
agctatattc ttaaatagtt attactantt gttagctacc tcnactcant taaaaccgta   4980
ccagctaata tgtggtgcta accaaantgc tcttggngtt tctacttatt atattagcta   5040
atggttanct agcnaattta gctatcaact tattagtcaa tnaataatta gctctagaaa   5100
tttaaaacaa aaactnctat gtttgattgc gctagagcta ctaataatta ntgacgacat   5160
ctaaatagtc tanctaatag ntaaactatt atctagtttt agcaaattag ctaatagtta   5220
gctagctatt tgttanccaa ctaatttcac tatatttttt ttagcaaact aactattagc   5280
tatagngcat tnaaatgagc tttaataaaa aaattaattt tagtcgncac aaggagtagg   5340
ttagggncat tcattaaaac atccaatgtt tagtangtnt catataagat gtttgaatga    5400
ctattacgag tattaaatat agttaaatta taaaactaaa tacatagtag gtttattaga    5460
ttcatattac accgtttagt gcatatctgc atatctgtat aattaaattt tanaattaga    5520
ttttatttaa tacttataac taacatcaac atttgatntg atatagatta aaaattagga    5580
acgtgccacg cacgatttgg ctcgtcgaca gtcagcatcc aacccgatgg ggcgatggtt    5640
gctgcaggtt gagaatcatt gctcgagcca atcaaatatg ctggtcaggt tgaatctgtt    5700
aacagcttat aatcagggta cggtgtaata aaaatacaag aaagctnagt tcacagaatt    5760
tgctttggac cacccattat ctctaagttt actccttata tatataccat caaaaaataa    5820
gtttgcttgc ctatat                                                    5836
```

<210> SEQ ID NO 23
<211> LENGTH: 5836
<212> TYPE: DNA
<213> ORGANISM: Zea mays
<220> FEATURE:
<221> NAME/KEY: misc_feature
<222> LOCATION: (1)..(5836)
<223> OTHER INFORMATION: n is a, c, g, or t
<220> FEATURE:
<221> NAME/KEY: misc_feature
<222> LOCATION: (966)..(966)
<223> OTHER INFORMATION: r is a or g

<400> SEQUENCE: 23

```
catggaccat gcccctagct tagctaggcc acccacacac aaactaccaa acaaaaactt     60
aacaacctat ccctctctct gcactagctt tcgtattttt gttttctga tgggagatgt    120 gtgagtacca acaaaacgt tgacaggcta gtaggccagg agagatacac ctagaagcta    180
gtccctttag ctagctctcc gctcgtgtgc atcatatatt cagatatata gatagatgca    240
tggccgtagt gtggttgttg tgcgctgcat cgatcgtctg atgaaaacgt tggttgccgc    300 ctattttgg aagcaacaaa atccgtgtg ccgcgcgcag acgactgcag agtcgacaca    360
tatattatac gcgcgcgcac gtacgggact agcagctgcc agctagggag agtagtatgt    420
agtcagagat acacgaacga agacgaagaa gacgacgacg acctactaat aataatcaca    480
atctacataa aacacgagac cacagccctc aaaatgcaac gnaaaattga actgcctcct    540
ccctctcagc ntcttgtgct ctcggtcaaa acgctacgat ngccttggtc gtcggcgacc    600
cgctggaccc tgatcggnag gcccttgggg aagtcgacga aagggtagac gaaggcctgg    660
tccggctccg ccagctccca ccggaagttg agcaccaggt ggtgcaggaa gatggccatc    720
```

```
tccagcttgg ccagctccga cccggcgcac agccgcggcc cgccgccgta cggcatgaag    780
ctgcttggcg cgttgntntc tgcagctagn aacagcagcg gcngcaaaaa aaaaaaatat    840
taaacacang cgatngncat gcgagagagc gcatgatcga tgagagaata tantagatna    900
tccntgagga gaaaaggagc gcgctttnga cgggctnatc gtctcntcag tgatcagtag    960
tggaargagn tcnatngcca ctgacatgtg acantcacag cgangccgat cgcctgaacc   1020
tagtacntac gtgccttgcg tcgcgtcgtc acctcaatca ccttaacact aangtatcca   1080
aacaaagcct ngcctgagca aaaaattatt tccccatcna cggntgcgan ggatnagaaa   1140
angacgcgtc ggcgacggan ggaaggattn cgagagcaga gcatttccga ncacccgccc   1200
aacgtggcgt tcgttttcag tgctctngna gctggagtag tccctcgcgt tcggcacgaa   1260
cccagncgcg ctcccgcctc ccgnaggccg aagctggnaa ctaggacgtc tctttcgacc   1320
ccgagancac gcgaaagatc gcgcgccgaa acattcccttt tcgcgcgcat cagctccatg   1380
ccgccctctc acatcaataa tggagggcaa gcgagcggca tagctgtcgt gctttggcng   1440
ggtactcttc actcttcact cttgngangg ntggcgtgnc acatgnatgc ntctcangcc   1500
gcanattcta gcgacacaag ccgtgaacgt ttttagangc ggattttctc tcgtactgtc   1560
atgctcgcgc ggatactttc ctctgggtcc ntcggcganc gacgttnatc cacatctant   1620
gntcagttaa tcngtnttca tgctgacttc atttttttn tnanananan ttgnggggn    1680
gggnagggg naggcncctn acnttccntc tccaaggntt gaaccggcng ggncctcgna    1740
cagcgacgag tccaggtgca ccgccgctag aaccggcagg attttccacc cccgcggtat   1800
gtcgtaccct tcattttgat gagagcgaga gcgagagaca acatgcaacg caattaagca   1860
attaagcaga gagaaacgnt cantgcaccg gccgtctgca tgtgctgtgc gtgaccgatt   1920
tcaggaatcg cgtgcttaaa gnttnggtnt taaaanaagg ggtcgtacca ttgtagtgna   1980
catctcgnat gaccttccgg tgcaggaanc tgaccacgtt gccgagccgc aatgtctcgt   2040
ttataacctg cacgaacacc agnaaaaaaa taaagaaatc tgttnataaa agaaanaaag   2100
aaagaagaan ctccatccat tntgnagcta gctgcctagc tgacgaggca ttcgacatct   2160
aacagttggt tttaggtctn gcgacggaat tctgttttgt ttatttagac atganatgag   2220
accccctgagc ancgngatac ggcacagana ccttcctgtc gncaggtgct acacaagaac   2280
aacaatgngt acttctcact tctcagcata tgtggattgt tgcgagacga tgatgggggc   2340
agccagcact ctaatggagt gtttggtttg aggaattatg tagtccatca tcttctcact   2400
cctcactttt ttgtttggtt tgtgaattgg agtgagttaa tccatcacca cctcattcct   2460
catagttagt tgtttagtaa taatatgtgc aatgaaggca tcccaccaaa tttgaggaat   2520
ggacccatga tacaccactt cattttggat agagtgattc atcaaaccaa acncctcata   2580
aaactctgct gggagatgat gagagcaaga gcaagcagac gccatgcgct ccaaaagtag   2640
gcatccaatt attctgcgcg gacagagagc ctcgggtctc cgttcgtaca tgacatttct   2700
agagagaggg agttgcagtt gctatcctgt accacgcaac cagacgaggc ggtttgtgct   2760
ggtacgagtt ggacgggagc aggccagata gcgagcaagg ggatctcgcg ctaccacagt   2820
accactgcag tggaaggaac gaacagaaca aattaagggg ggggtgggcg cttacacact   2880
gcgtgaaaac catttccttg tagtcttccc agctcaattt ggacgccccc cttagccttt   2940
gtctcctagc aatcaggaga tgctcctcct gcaagtcata tgccggtgta aactattatt   3000
tatctctata tataataata ataattccat gttttttgt tttgttttgt tttgaccaac    3060
atcgacctag ctagctcact gtgcaaagtt tgaaaacgga ccagtgaaca aaagcaggtg    3120
```

```
ctctaaaact aactgattgt tggttcggat ttgtacccgg agttcttgca cggccttagg    3180
gcacccttcg aggaagaaga tggcgagggc gagcgccatg gacgaagtct cgtgccccgc    3240
gaagagcagg ctcagcaaga ggtccaggat ctgttccttg gacaggttgg attgcttcag    3300
ggcccatcca agaaggtcgt cctcctccac gcttgatttc tccctgctca tcttctcaag    3360
cctgtcctcc atcttcctct ctatcactcc aagtatggac gcgcgcgact tgagcgcctt    3420
ccagtaggcc gtgcccggga agttgagcgg cgctgacacg acgcccttca tgaaggtgat    3480
gtactccagc cgcagccgct ccgtctcctc ctcgccgggg tccatgctca ttatgttctt    3540
cgccatcagg ttaaacgtga actgcactcg tcatccggcc ggccgcgcgc ccatcaccgg    3600
ttgttatccc ggccggggca ccggttgtta gcggcgatcc tttgcataga ttcagccaca    3660
tatatagata gaactgatct gatgtggcac gtacgtacta cgcgtggaga caaattgaag    3720
ggtcagaaga aggatggtga tgagtaccgt accttcttgg cttcgtgctg ggcggagaag    3780
gtgccgtcgg agggcggcca cgagcggagg accagcaggg tgtggcgctc cacctcgggg    3840
agcagcacgg cgcggaggcg gacggagctg aggaagttga gcgagatagc gcgcatctcg    3900
cggtgcgcgt cgcccacgag caccagcatg gaccacttgc ccaggatgcc gccgatgctg    3960
cgcgggtagc tgcactcgaa cagccgcccc tcgttctgca ggatgtagcg gttcagcccc    4020
gcgtccgccg acaccaccgt ccgctccccg aacaggctcg accggtatat cttcccgtac    4080
ctgcatgcac gcatggacgt cgccgcgtta gcaagcaagc tctcggtctc agagctaatt    4140
ctgattccat cgatgtcgcg ccatgcatga taggtgcgcg ctgctcgctg caccgtgcat    4200
gcatgtcgtc tgctgtctgc acagaggtag agacagcggc ggcggcgacg caccgtgcga    4260
catgccgctc catgaagcgg cccacggagg tggccgggtg ggcgcggagg tagccgaaag    4320
tttcgccgac caagggccat ccgcgggcgc ccggggggcag gttgggccgc ttcttcttct    4380
gacggcgcca cnggtgggtg ccgtggcatt tnggcgacgg tggtggtgta cnaggcgagg    4440
agggccagca ggatgaaggg aaggaagaag aggagctcgc tggttatgga ggccatcatg    4500
gcgcccatga gctcctgctg atcagaggtc tagctttctt caaatttatt tcctgcctgc    4560
tgcctctctg cctgatcact cgcccgcttc gttggttttt atgtgtggag agagaggacg    4620
gatgggttgg agagagaaag caggagaggg aatgaatgaa gcgcctttat ctctggattt    4680
ctctctccct ctctctcagc aagtgcaagc tttgcgcaag gaaaaaaaaa actagtaaga    4740
agctaggcnc cccacttcgt ccccncttct gagctctntg gtgctcttat aggttttttn    4800
gagaggtagc tgtggggtcc tttaatttag gnectattcc aaacttctaa aactancaan    4860
ttntaacaac taaaatttat gagaggtata naacantcca ctaangancn gttaattgtn    4920
agctatattc ttaaatagtt attactantt gttagctacc tcnactcant taaaaccgta    4980
ccagctaata tgtggtgcta accaaantgc tcttggngtt tctacttatt atattagcta    5040
atggttanct agcnaattta gctatcaact tattagtcaa tnaataatta gctctagaaa    5100
tttaaaacaa aaactnctat gtttgattgc gctagagcta ctaataatta ntgacgacat    5160
ctaaatagtc tanctaatag ntaaactatt atctagtttt agcaaattag ctaatagtta    5220
gctagctatt tgttanccaa ctaatttcac tatattttt ttagcaaact aactattagc    5280
tatagngcat tnaaatgagc tttaataaaa aaattaattt tagtcgncac aaggagtagg    5340
ttagggncat tcattaaaac atccaatgtt tagtangtnt catataagat gtttgaatga    5400
ctattacgag tattaaatat agttaaatta taaaactaaa tacatagtag gtttattaga    5460
```

| | | | | |
|---|---|---|---|---|
| ttcatattac | accgtttagt | gcatatctgc | atatctgtat | aattaaattt tanaattaga | 5520 |
| ttttatttaa | tacttataac | taacatcaac | atttgatntg | atatagatta aaaattagga | 5580 |
| acgtgccacg | cacgatttgg | ctcgtcgaca | gtcagcatcc | aacccgatgg ggcgatggtt | 5640 |
| gctgcaggtt | gagaatcatt | gctcgagcca | atcaaatatg | ctggtcaggt tgaatctgtt | 5700 |
| aacagcttat | aatcagggta | cggtgtaata | aaaatacaag | aaagctnagt tcacagaatt | 5760 |
| tgctttggac | cacccattat | ctctaagttt | actccttata | tatataccat caaaaaataa | 5820 |
| gtttgcttgc | ctatat | | | | 5836 |

<210> SEQ ID NO 24
<211> LENGTH: 6154
<212> TYPE: DNA
<213> ORGANISM: Zea mays
<220> FEATURE:
<221> NAME/KEY: misc_feature
<222> LOCATION: (1)..(6154)
<223> OTHER INFORMATION: n is a, c, g, or t
<220> FEATURE:
<221> NAME/KEY: misc_feature
<222> LOCATION: (1032)..(1032)
<223> OTHER INFORMATION: s is c or g

<400> SEQUENCE: 24

| | | | | | |
|---|---|---|---|---|---|
| gaacggccgc | ctcaagacgc | tggacgtcac | cagtaaccac | ctcaccggca | ccataccgcc | 60 |
| ggacctctgc | gccggacgga | acctgnagct | gctcgtgctc | atggacaacg | gcttcttcgg | 120 |
| cagcatcccc | gagtcgctcg | gcgactgcaa | gacgctcacg | cgcgtncgcc | tcggcaagaa | 180 |
| cttcctgacc | ggccccgtcc | cggccgggct | cttcganctt | ccccaggcga | acatgctcga | 240 |
| gctcaccgac | aacatgctca | cnggngagct | cccggacgtg | atcgcnggag | acaagatcgg | 300 |
| catgctcatg | ctggggaaca | atcgcatcgg | agggcgcatc | cccgcngcna | tcggcaacct | 360 |
| ncccgcgctg | cagacgctgt | ccctggagtc | gaacaacttc | tctggcccgc | tgccnccgga | 420 |
| gatcggnagg | ctcaggaacc | tcaccaggct | caacgccagc | ggcaacgcgc | tcacgggagg | 480 |
| catcccgagg | gagctcatgg | gctgcgcctc | cctgggcgcc | gtcgacctca | gccggaacgg | 540 |
| cctcaccggc | gagntaccgg | acaccgtgac | gtcgctcaag | atcctgtgca | cgctcaacgt | 600 |
| gtcgaggaac | aggctgtcgg | gcgagctgcn | ggcggcgatg | gncaacatga | cgagcctgac | 660 |
| gacgctggac | gtgtcntaca | accagctgtc | gggccccgtg | ccgatgcagg | gccagttcct | 720 |
| ggtnttnacg | agagctcgtt | cgtgggcaac | ccggggngtg | gcagcgcgtg | cccccatcg | 780 |
| tccngcggcg | cncggtcncc | cttctcgctg | cgccggtggg | actcgaagaa | gctgctggtg | 840 |
| tggctggtcg | tnctcctcac | cctgctggtc | ctggcggtcc | tgggcgcgcg | gaaggcgcac | 900 |
| gaggcgtggc | gcgaggcggc | gcggcngcgg | tcggggcct | ggaagatgac | ggcgttccag | 960 |
| aagctggact | tctcggcgga | cgacgtggtg | gagtgtctca | aggaggacaa | catcatcggc | 1020 |
| aagggcggcg | csgggatcgt | gtaccacggc | gtgacncgcg | gcggcgcgga | gctggcgatc | 1080 |
| aagcggctgg | tggggagagg | gtgnggcgac | cacgaccgcg | ggttcaccgc | agaggtcacc | 1140 |
| acgctgggcc | gcatccggca | ccgcaacatc | gtgcgcctgc | tcggcttcgt | ctccaaccgg | 1200 |
| gaggccaacc | tgctgctgta | cgagtacatg | cccaacgggt | cgctaggcga | gatgctgcac | 1260 |
| gncggcaang | gccacctngg | gtgggaggcc | cgggcgcgcg | tngcggcgga | ggcggcgcgc | 1320 |
| gggctctgnt | acctgcacca | cgactgcgcg | cccggatca | tncaccgcga | cgtcaagtcc | 1380 |
| aacaacatcc | tcctcgactc | cgccttcgag | gcgcacgtcg | cggactttgg | cctcgccaag | 1440 |
| ttcctcggcg | gcggcggcgc | cacgtccgag | tgcatgtctg | ccatcgccgg | ctcctacggc | 1500 |

-continued

```
tacatcgccc caggtnacaa aactctcgcc gcatagcanc atancangtg tttgtactcc    1560
ttttaataat attttttttc actggctcgc atgcagagta cgcgtacacc cttcgcgtgg    1620
acgagaagag tgacgtgtac agcttcggcg tggtgctgct ggagctcatc acggggcggc    1680
gccccgtggg cagcttcggc gacggcgtgg acatcgtgca ctgggtgcgc aaggtgaccg    1740
cggacgccgc cgccgcggan gagcccgtcc tgctggtggc ggaccgtcgg ctggcgccgg    1800
agccggtgcc gctgctggcg gacctctaca gggtggccat ggcgtgcgtg gaggaggcca    1860
gcacggcccg gcccaccatg cgcgaggtcg tgcacatgct ctccacctcc gccncggccc    1920
agcccgacgt cccnacgcc ttgtgcaagg gtcgtcgatt aatttgcctt atatatgacg    1980
attatgtata tgatccgggc ngggttagcg cctgtgatct atttagcggc tgccttttng    2040
gcgtcactcn tctcgtgtgt gatgatggct gnatggatgt gtaaaacaaa taaccagcan    2100
gtggctactc gtgaatgaaa gttgcngttc ttattctcat gcatatatnt tagcaancac    2160
aaagtgagat ggcatatatt ccctttccct ggcgtttgtt gctttgnang tnttggcttc    2220
tcgcggaagg tctttctgct gttcntgaac gacaggtgtc tgttcatagt atagaggctt    2280
ctatgnggaa agatgcttca tgctgcgaaa gttgaaaatg gcagatgcac attgcgtatc    2340
cccacagggc aggncacttt gcgcatggcc agttgcccta gtactaacac aatccatgga    2400
gcaaggaaca ttactgccct tggcctccaa gctgcttcct taatcatcaa ggatgaatta    2460
gnaaaaaaaa ggataaacgg accgccatga ccagagcnag tgagggagcc acttcacctg    2520
ccgactgcaa tcgacggccc acccgtcagc cagagagaaa cagtccaccg nggttggatt    2580
ggacgacgag atctcaacgt ggggcggtcc gagccgggcg cacgcgcaca cgcgcttctc    2640
aactcccacc aatattaccc tccatatatc accgacaggt gggacatcaa ccaagccggt    2700
acccaacaac agcacagaaa accccacagg tcatagacag cggagctccc tccagtctcc    2760
atccaataac acgagctaac caccgcccaa ccgaaaccgg gccccaccgg tctcccgtc    2820 gccacgtacg cggccggagc gccctataca agcgccacgt cgatcgccga ctcgccgtcg    2880
ccgcgtcccc cacggctctt ccttcatcct ccggcgagct ataaatccct cccgccgacg    2940 ccaccccat ggcatcccgc ggttcccctt cctcctactc ctccccgagg accccgacgt    3000
cgtcgaaggc taaccctggg cccgcgccct ccgccccgcc gctgtacccg acgctctcca    3060
tggccgacct cgcgcccgtc gagatagggc ccgcctcgtc gccgacggcc tcggatgact    3120
acaacgcgcc tccgccgtct gaggacgtcc tcctccgggt ccccggcgcg cggctccacc    3180
tcgtcgaccc cagccgcagc caccccgctgg ccgccggcga cctctccctc ctccgcatcc    3240
gctccggcga cacctccctg gccgccatcg cgctgctggg cccggtccag tggccgctcg    3300
cgcgcgacgt ggccgccgtc aagctggatc cctgccacta cgccttctcc ctcaccgtgc    3360
cggcctccgc cgacgacccc agccccgacc cgctccacta cggcctcacg ctctcccgcc    3420
ccgatgtgcg cctcgacggc gtcctcgctg cctacaccag cttctccgtg cacgccgtgg    3480
tcggcgccgg gcagctggag gccagggtgc gcgacgaggc cgaggccgcc gcgtactgga    3540
cggccgtcgc gcccaacgtg gaggcgtacg gaggcgcggt ggccaggacc atcgccacgg    3600
gcgccgagca cctcgccaag gggatactgt ggtgcgggga ggtcacggtg gagaggctcc    3660
gttggggcaa tgaggtcctc aagaggagga tgcagcctgg cgacgccaac gccgaggtca    3720
gccccgagat gctcaggcga atcaaaaggt attggccgtt tccgctatt ctcttttgt    3780 tcctagtaat atacattgga aataaaaatt actaaggtcg gttattctaa tgatatgtgg    3840
```

| | |
|---|---|
| attgaagtgt attagaatga agatttaaat cgactcaata ccactcaatg cacatgtatt | 3900 |
| aacggtgaaa caaacaagtc ttagtcttat ttggttatta tcaattcatg tgatgggtag | 3960 |
| agatggcaaa tttgtgatag attatgatag attttgactg gttatggatt taaaccgact | 4020 |
| caatgtcatc caatctacat ggattgccgt ctaaacaaac atgccctgaa gatgtaatct | 4080 |
| actaatgttt gcttcataca acattcagtt atggtgttgt gccttgactc tttgttttg | 4140 |
| ccaattgcca tctagaagag ctgaaggggc tccctatttc taaaacattt ctttagcgat | 4200 |
| gtccactgat attgacagag gagtatgcac tctgtgatcg atttcagaga tggactgaac | 4260 |
| tggattggac tgatgccatg ccacatagcc atagatatat gcagatgtca acttataatg | 4320 |
| agactgttcg ctgaggtctg aggcgtcgtt ttctgaactt gtgattgctt ggctgagtag | 4380 |
| tatatgtttg gtgttaagag attgttcaga tgtctatgct accatagcct gatatatgtc | 4440 |
| ttcgtaacct ttttgtgtct gtgtgtggac atttctgttg ccaataacat cgcattgttt | 4500 |
| ctgcctctag acgtcgaatt tacgtatggt ttgcctgact gtattgactc atttttttgcc | 4560 |
| tgactgtatt gactcatttt tgggtatatt ggttttacgt tttttttggta atacacaagc | 4620 |
| tttaaactac tatttaaacg attttggaca tagataggtt tggcatattc tgtgtgagtc | 4680 |
| tgagatatag gaaattcagg caaatatctg agttgcttaa caacgtcctt gcttacggtt | 4740 |
| gctggcaggg ctaagagggt gagccaaata tctgagaaag tggcgactgg gattttgtcc | 4800 |
| ggagtggtga aggtcactgg ttacttcaca agctctctgg ccaactcgaa agctggcaag | 4860 |
| aagttcttca acatgttgcc tggagagatc gttcttgctt cgcttgacgg atttggtacg | 4920 |
| ttgctgttac taacacttgt atcgtataag gccaagtgcc cgtgtggcat tactcgtctg | 4980 |
| tcatttcact ctagcggcat tgttagatat aatattaatt gagatgtgcc cctctgccag | 5040 |
| ccttgcataa gtcaacagac aactgtctgt ctgtgtatgt tgtagtagtt tctgtgttaa | 5100 |
| tagagatgcc ttggatgccc tttatagagt ctcgtattgt ttttttgtttt attgagatga | 5160 |
| taacttctgt agttgtggct ttacgaggaa atttagatag tgtttggttc cggagccact | 5220 |
| cgaggtagaa tggttccgtc ccgagagcgg ctccgtcctg gagattttga ggagtcagat | 5280 |
| gatttaacaa ttgagcatga cttttccattt ttagaatcac tccattctat atatgaaatc | 5340 |
| aatccaaaca acagtaaatt aagagcggag cgacctgttg gtttcagtac agccacaaca | 5400 |
| aaagtgctga tgatctatat aagtcaagtc aagtcgtcaa agattctga acatttgcga | 5460 |
| cttccattcc accccatgct ctgtgaatag gtggctgaat gctttgcact ctgcttgcca | 5520 |
| ccgtggttta tgcacccaac ttacgctgac atgtatgtct tccttcgttg tcgccgacgc | 5580 |
| cataaacagg gaagatctgc gacgccgtgg aggtggccgg aaagaacgtt ttgtccacgt | 5640 |
| cgtcaactgt gacgaccggg ctagtatctc acaggtacgg agacaaagcc gccgccgcaa | 5700 |
| cgaacgaagg gctggacgcc gccgggcacg ccatcgggac ggcatgggcc gtgttcaaga | 5760 |
| tccggcaggc cttgaacccc aagagcgtcc tcaaacccac ggcgctggcc acgtccacca | 5820 |
| tcagggccaa cgttgccgag cttcgcgcga tgcacggcag cagcaagtag ctcgcgcctg | 5880 |
| ccgtccctgt ttcgtaaaaa ctctattatc tcgctctgtc acgaccaacg atgcactcgc | 5940 |
| tgcttccagc agcagcgttg gctgttgcct gttggcctgt aaattcgtgt ggctgaaact | 6000 |
| gggaaagccg ggaactgaaa ggcttaccgc ttccgctttg ttagtgatgc tggtgatgtt | 6060 |
| ctaagagctt ttaccactgc tgtgctgctg cgttggcttg aactgtcacg agttgttcgg | 6120 |
| ttttggcctc tgaagtctga accaagtaaa aaaa | 6154 |

```
<210> SEQ ID NO 25
<211> LENGTH: 6154
<212> TYPE: DNA
<213> ORGANISM: Zea mays
<220> FEATURE:
<221> NAME/KEY: misc_feature
<222> LOCATION: (1)..(6154)
<223> OTHER INFORMATION: n is a, c, g, or t
<220> FEATURE:
<221> NAME/KEY: misc_feature
<222> LOCATION: (286)..(286)
<223> OTHER INFORMATION: y is c or t

<400> SEQUENCE: 25
```

| | | | | | |
|---|---|---|---|---|---|
| gaacggccgc | ctcaagacgc | tggacgtcac | cagtaaccac | ctcaccggca | ccataccgcc       60 |
| ggacctctgc | gccggacgga | acctgnagct | gctcgtgctc | atggacaacg | gcttcttcgg      120 |
| cagcatcccc | gagtcgctcg | gcgactgcaa | gacgctcacg | cgcgtncgcc | tcggcaagaa      180 |
| cttcctgacc | ggccccgtcc | cggccgggct | cttcganctt | ccccaggcga | acatgctcga      240 |
| gctcaccgac | aacatgctca | cnggngagct | cccggacgtg | atcgcyggag | acaagatcgg      300 |
| catgctcatg | ctggggaaca | atcgcatcgg | agggcgcatc | cccgcngcna | tcggcaaccct    360 |
| ncccgcgctg | cagacgctgt | ccctggagtc | gaacaacttc | tctggcccgc | tgccnccgga      420 |
| gatcggnagg | ctcaggaacc | tcaccaggct | caacgccagc | ggcaacgcgc | tcacgggagg      480 |
| catcccgagg | gagctcatgg | gctgcgcctc | cctgggcgcc | gtcgacctca | gccggaacgg      540 |
| cctcaccggc | gagntaccgg | acaccgtgac | gtcgctcaag | atcctgtgca | cgctcaacgt      600 |
| gtcgaggaac | aggctgtcgg | gcgagctgcn | ggcggcgatg | gncaacatga | cgagcctgac      660 |
| gacgctggac | gtgtcntaca | accagctgtc | gggccccgtg | ccgatgcagg | gccagttcct      720 |
| ggtntttacg | agagctcgtt | cgtgggcaac | ccggggntgt | gcagcgcgtg | cccccccatcg     780 |
| tccngcggcg | cncggtcncc | cttctcgctg | cgccggtggg | actcgaagaa | gctgctggtg      840 |
| tggctggtcg | tnctcctcac | cctgctggtc | ctggcggtcc | tgggcgcgcg | gaaggcgcac      900 |
| gaggcgtggc | gcgaggcggc | gcggcngcgg | tcggggggcct | ggaagatgac | ggcgttccag     960 |
| aagctggact | tctcggcgga | cgacgtggtg | gagtgtctca | aggaggacaa | catcatcggc     1020 |
| aagggcggcg | cngggatcgt | gtaccacggc | gtgacncgcg | gcggcgcgga | gctggcgatc     1080 |
| aagcggctgg | tggggagagg | gtgnggcgac | cacgaccgcg | ggttcaccgc | agaggtcacc     1140 |
| acgctgggcc | gcatccggca | ccgcaacatc | gtgcgcctgc | tcggcttcgt | ctccaaccgg     1200 |
| gaggccaacc | tgctgctgta | cgagtacatg | cccaacgggt | cgctaggcga | gatgctgcac     1260 |
| gncggcaang | gccacctngg | gtgggaggcc | cgggcgcgcg | tngcggcgga | ggcggcgcgc     1320 |
| gggctctgnt | acctgcacca | cgactgcgcg | ccccggatca | tncaccgcga | cgtcaagtcc     1380 |
| aacaacatcc | tcctcgactc | cgccttcgag | gcgcacgtcg | cggactttgg | cctcgccaag     1440 |
| ttcctcggcg | gcggcggcgc | cacgtccgag | tgcatgtctg | ccatcgccgg | ctcctacggc     1500 |
| tacatcgccc | caggtnacaa | aactctcgcc | gcatagcanc | atancangtg | tttgtactcc     1560 |
| ttttaataat | atttttttc  | actggctcgc | atgcagagta | cgcgtacacc | cttcgcgtgg     1620 |
| acgagaagag | tgacgtgtac | agcttcggcg | tggtgctgct | ggagctcatc | acggggcggc     1680 |
| gccccgtggg | cagcttcggc | gacggcgtgg | acatcgtgca | ctgggtgcgc | aaggtgaccg     1740 |
| cggacgccgc | cgccgcggan | gagcccgtcc | tgctggtggc | ggaccgtcgg | ctggcgccgg     1800 |
| agccggtgcc | gctgctggcg | gacctctaca | gggtggccat | ggcgtgcgtg | gaggaggcca     1860 |
| gcacggcccg | gcccaccatg | cgcgaggtcg | tgcacatgct | ctccacctcc | gccncggccc     1920 |

-continued

```
agcccgacgt ccccnacgcc ttgtgcaagg gtcgtcgatt aatttgcctt atatatgacg   1980
attatgtata tgatccgggc ngggttagcg cctgtgatct atttagcggc tgccttttng   2040
gcgtcactcn tctcgtgtgt gatgatggct gnatggatgt gtaaaacaaa taaccagcan   2100
gtggctactc gtgaatgaaa gttgcngttc ttattctcat gcatatatnt tagcaancac   2160
aaagtgagat ggcatatatt ccctttccct ggcgtttgtt gctttgnang tnttggcttc   2220
tcgcggaagg tctttctgct gttcntgaac gacaggtgtc tgttcatagt atagaggctt   2280
ctatgnggaa agatgcttca tgctgcgaaa gttgaaaatg gcagatgcac attgcgtatc   2340
cccacagggc aggncacttt gcgcatggcc agttgcccta gtactaacac aatccatgga   2400
gcaaggaaca ttactgccct tggcctccaa gctgcttcct taatcatcaa ggatgaatta   2460
gnaaaaaaaa ggataaacgg accgccatga ccagagcnag tgagggagcc acttcacctg   2520
ccgactgcaa tcgacggccc acccgtcagc cagagagaaa cagtccaccg nggttggatt   2580
ggacgacgag atctcaacgt ggggcggtcc gagccgggcg cacgcgcaca cgcgcttctc   2640
aactcccacc aatattaccc tccatatatc accgacaggt gggacatcaa ccaagccggt   2700
acccaacaac agcacagaaa accccacagg tcatagacag cggagctccc tccagtctcc   2760
atccaataac acgagctaac caccgcccaa ccgaaaccgg gccccaccgg tctcccgtc    2820
gccacgtacg cggccggagc gccctataca agcgccacgt cgatcgccga ctcgccgtcg   2880
ccgcgtcccc cacggctctt ccttcatcct ccggcgagct ataaatccct cccgccgacg   2940
ccaccccccat ggcatcccgc ggttccccctt cctcctactc ctccccgagg accccgacgt  3000
cgtcgaaggc taaccctttgg cccgcgccct ccgcccgcc gctgtacccg acgtctccca   3060
tggccgacct cgcgcccgtc gagataggggc ccgcctcgtc gccgacggcc tcggatgact  3120
acaacgcgcg tccgccgtct gaggacgtcc tcctccgggt ccccggcgcg cggctccacc   3180
tcgtcgaccg cagccgcagc caccgctggg ccgccggcga cctctccctc ctccgcatcc   3240
gctccggcga cacctccctg gccgccatcg cgctgctggg cccggtccag tggccgctcg   3300
cgcgcgacgt ggccgccgtc aagctggatc cctgccacta cgccttctcc ctcaccgtgc   3360
cggcctccgc cgacgacccc agcccgaccc cgctccacta cggcctcacg ctctcccgcc   3420
ccgatgtgcg cctcgacggc gtcctcgctg cctacaccag cttctccgtg cacgccgtgg   3480
tcggcgccgg gcagctggag gccagggtgc gcgacgaggc cgaggccgcc gcgtactgga   3540
cggccgtcgc gcccaacgtg gaggcgtacg gaggcgcggt ggccaggacc atcgccacgg   3600
gcgccgagca cctcgccaag gggatactgt ggtgcgggga ggtcacggtg gagaggctcc   3660
gttgggggcaa tgaggtcctc aagaggagga tgcagcctgg cgacgccaac gccgaggtca  3720
gccccgagat gctcaggcga atcaaaaggt attggccgtt tccgctattt ctctttttgt   3780
tcctagtaat atacattgga aataaaaatt actaaggtcg gttattctaa tgatatgtgg   3840
attgaagtgt attagaatga agatttaaat cgactcaata ccactcaatg cacatgtatt   3900
aacggtgaaa caaacaagtc ttagtcttat ttggttatta tcaattcatg tgatgggtag   3960
agatggcaaa tttgtgatag attatgatag attttgactg gttatggatt taaaccgact   4020
caatgtcatc caatctacat ggattgccgt ctaaacaaac atgccctgaa gatgtaatct   4080
actaatgttt gcttcataca acattcagtt atggtgttgt gccttgactc tttgttttg    4140
ccaattgcca tctagaagag ctgaagggc tccctatttc taaaacattt ctttagcgat    4200
gtccactgat attgacagag gagtatgcac tctgtgatcg atttcagaga tggactgaac   4260
tggattggac tgatgccatg ccacatagcc atagatatat gcagatgtca acttataatg   4320
```

```
agactgttcg ctgaggtctg aggcgtcgtt ttctgaactt gtgattgctt ggctgagtag   4380
tatatgtttg gtgttaagag attgttcaga tgtctatgct accatagcct gatatatgtc   4440
ttcgtaacct ttttgtgtct gtgtgtggac atttctgttg ccataacat cgcattgttt    4500 ctgcctctag acgtcgaatt tacgtatggt ttgcctgact gtattgactc attttttgcc   4560
tgactgtatt gactcatttt tgggtatatt ggttttacgt ttttttggta atacacaagc   4620
tttaaactac tatttaaacg attttggaca tagataggtt tggcatattc tgtgtgagtc   4680
tgagatatag gaaattcagg caaatatctg agttgcttaa caacgtcctt gcttacggtt   4740
gctggcaggg ctaagagggt gagccaaata tctgagaaag tggcgactgg gattttgtcc   4800
ggagtggtga aggtcactgg ttacttcaca agctctctgg ccaactcgaa agctggcaag   4860
aagttcttca acatgttgcc tggagagatc gttcttgctt cgcttgacgg atttggtacg   4920
ttgctgttac taacacttgt atcgtataag gccaagtgcc cgtgtggcat tactcgtctg   4980
tcatttcact ctagcggcat tgttagatat aatattaatt gagatgtgcc cctctgccag   5040
ccttgcataa gtcaacagac aactgtctgt ctgtgtatgt tgtagtagtt tctgtgttaa   5100
tagagatgcc ttgatgccc tttatagagt ctcgtattgt ttttgtttt attgagatga     5160 taacttctgt agttgtggct ttacgaggaa atttagatag tgtttggttc cggagccact   5220
cgaggtagaa tggttccgtc ccgagagcgg ctccgtcctg gagattttga ggagtcagat   5280
gatttaacaa ttgagcatga ctttccattt ttagaatcac tccattctat atatgaaatc   5340
aatccaaaca acagtaaatt aagagcgag cgacctgttg gtttcagtac agccacaaca   5400
aaagtgctga tgatctatat aagtcaagtc aagtcgtcaa agatttctga acatttgcga   5460
cttccattcc accccatgct ctgtgaatag gtggctgaat gctttgcact ctgcttgcca   5520
ccgtggttta tgcacccaac ttacgctgac atgtatgtct tccttcgttg tcgccgacgc   5580
cataaacagg gaagatctgc gacgccgtgg aggtggccgg aaagaacgtt ttgtccacgt   5640
cgtcaactgt gacgaccggg ctagtatctc acaggtacgg agacaaagcc gccgccgcaa   5700
cgaacgaagg gctggacgcc gccgggcacg ccatcgggac ggcatgggcc gtgttcaaga   5760
tccggcaggc cttgaacccc aagagcgtcc tcaaacccac ggcgctggcc acgtccacca   5820
tcagggccaa cgttgccgag cttcgcgcga tgcacggcag cagcaagtag ctcgcgcctg   5880
ccgtccctgt ttcgtaaaaa ctctattatc tcgctctgtc acgaccaacg atgcactcgc   5940
tgcttccagc agcagcgttg gctgttgcct gttggcctgt aaattcgtgt ggctgaaact   6000
gggaaagccg ggaactgaaa ggcttaccgc ttccgctttg ttagtgatgc tggtgatgtt   6060
ctaagagctt ttaccactgc tgtgctgctg cgttggcttg aactgtcacg agttgttcgg   6120
ttttggcctc tgaagtctga accaagtaaa aaaa                               6154
```

<210> SEQ ID NO 26
<211> LENGTH: 6154
<212> TYPE: DNA
<213> ORGANISM: Zea mays
<220> FEATURE:
<221> NAME/KEY: misc_feature
<222> LOCATION: (1)..(6154)
<223> OTHER INFORMATION: n is a, c, g, or t
<220> FEATURE:
<221> NAME/KEY: misc_feature
<222> LOCATION: (346)..(346)
<223> OTHER INFORMATION: m is a or c

<400> SEQUENCE: 26

```
gaacggccgc ctcaagacgc tggacgtcac cagtaaccac ctcaccggca ccataccgcc    60
ggacctctgc gccggacgga acctgnagct gctcgtgctc atggacaacg gcttcttcgg   120
cagcatcccc gagtcgctcg gcgactgcaa gacgctcacg cgcgtncgcc tcggcaagaa   180
cttcctgacc ggccccgtcc cggccgggct cttcganctt ccccaggcga acatgctcga   240
gctcaccgac aacatgctca cnggngagct cccggacgtg atcgcnggag acaagatcgg   300
catgctcatg ctggggaaca atcgcatcgg agggcgcatc cccgcmgcna tcggcaacct   360
ncccgcgctg cagacgctgt ccctggagtc gaacaacttc tctggcccgc tgccnccgga   420
gatcggnagg ctcaggaacc tcaccaggct caacgccagc ggcaacgcgc tcacgggagg   480
catcccgagg gagctcatgg gctgcgcctc cctgggcgcc gtcgacctca gccggaacgg   540
cctcaccggc gagntaccgg acaccgtgac gtcgctcaag atcctgtgca cgctcaacgt   600
gtcgaggaac aggctgtcgg gcgagctgcn ggcggcgatg gncaacatga cgagcctgac   660
gacgctggac gtgtcntaca accagctgtc ggggccccgtg ccgatgcagg gccagttcct   720
ggtnttnacg agagctcgtt cgtgggcaac ccggggntgt gcagcgcgtg cccccccatcg   780 tccngcggcg cncggtcncc cttctcgctg cgccggtggg actcgaagaa gctgctggtg   840
tggctggtcg tnctcctcac cctgctggtc ctggcggtcc tgggcgcgcg gaaggcgcac   900
gaggcgtggc gcgaggcggc gcggcngcgg tcggggccct ggaagatgac ggcgttccag   960
aagctggact tctcgcggga cgacgtggtg gagtgtctca aggaggacaa catcatcggc  1020
aagggcggcg cnggatcgt gtaccacggc gtgacncgcg gcggcgcgga gctggcgatc  1080
aagcggctgg tggggagagg gtgnggcgac cacgaccgcg ggttcaccgc agaggtcacc  1140
acgctgggcc gcatccggca ccgcaacatc gtgcgcctgc tcggcttcgt ctccaaccgg  1200
gaggccaacc tgctgctgta cgagtacatg cccaacgggt cgctaggcga gatgctgcac  1260
gncggcaang gccacctngg gtgggaggcc cgggcgcgcg tngcggcgga ggcggcgcgc  1320
gggctctgnt acctgcacca cgactgcgcg ccccggatca tncaccgcga cgtcaagtcc  1380
aacaacatcc tcctcgactc cgccttcgag gcgcacgtcg cggactttgg cctcgccaag  1440
ttcctcggcg gcggcggcgc cacgtccgag tgcatgtctg ccatcgccgg ctcctacggc  1500
tacatcgccc caggtnacaa aactctcgcc gcatagcanc atancangtg tttgtactcc  1560 tttaataat attttttttc actggctcgc atgcagagta cgcgtacacc cttcgcgtgg  1620
acgagaagag tgacgtgtac agcttcggcg tggtgctgct ggagctcatc acggggcggc  1680
gccccgtggg cagcttcggc gacggcgtgg acatcgtgca ctgggtgcgc aaggtgaccg  1740
cggacgccgc cgccgcggan gagcccgtcc tgctggtggc ggaccgtcgg ctggcgccgg  1800
agccggtgcc gctgctggcg gacctctaca gggtggccat ggcgtgcgtg gaggaggcca  1860
gcacggcccg gcccaccatg cgcgaggtcg tgcacatgct ctccacctcc gccncggccc  1920
agcccgacgt cccnacgcc ttgtgcaagg gtcgtcgatt aatttgcctt atatatgacg  1980
attatgtata tgatccgggc ngggttagcg cctgtgatct atttagcggc tgccttttng  2040
gcgtcactcn tctcgtgtgt gatgatggct gnatggatgt gtaaaacaaa taaccagcan  2100
gtggctactc gtgaatgaaa gttgcngttc ttattctcat gcatatatnt tagcaancac  2160
aaagtgagat ggcatatatt cccttttccct ggcgtttgtt gctttgnang tnttggcttc  2220
tcgcggaagg tctttctgct gttcntgaac gacaggtgtc tgttcatagt atagaggctt  2280
ctatgnggaa agatgcttca tgctgcgaaa gttgaaaatg gcagatgcac attgcgtatc  2340
cccacagggc aggncacttt gcgcatggcc agttgcccta gtactaacac aatccatgga  2400
```

```
gcaaggaaca ttactgccct tggcctccaa gctgcttcct taatcatcaa ggatgaatta    2460
gnaaaaaaaa ggataaacgg accgccatga ccagagcnag tgagggagcc acttcacctg    2520
ccgactgcaa tcgacggccc acccgtcagc cagagagaaa cagtccaccg nggttggatt    2580
ggacgacgag atctcaacgt ggggcggtcc gagccgggcg cacgcgcaca cgcgcttctc    2640
aactcccacc aatattaccc tccatatatc accgacaggt gggacatcaa ccaagccggt    2700
acccaacaac agcacagaaa accccacagg tcatagacag cggagctccc tccagtctcc    2760
atccaataac acgagctaac caccgcccaa ccgaaaccgg ccccaccgg tctcccgtc      2820 gccacgtacg cggccggagc gccctataca agcgccacgt cgatcgccga ctcgccgtcg    2880
ccgcgtcccc cacggctctt ccttcatcct ccggcgagct ataaatccct cccgccgacg    2940
ccacccccat ggcatcccgc ggttccccctt cctcctactc ctccccgagg accccgacgt    3000
cgtcgaaggc taaccctggg cccgcgccct ccgccccgcc gctgtacccg acgctctcca    3060
tggccgacct cgcgcccgtc gagatagggc ccgcctcgtc gccgacggcc tcggatgact    3120
acaacgcgcc tccgccgtct gaggacgtcc tcctccgggt ccccggcgcg cggctccacc    3180
tcgtcgaccg cagccgcagc cacccgctgg ccgccggcga cctctccctc ctccgcatcc    3240
gctccggcga cacctccctg gccgccatcg cgctgctggg cccggtccag tggccgctcg    3300
cgcgcgacgt ggccgccgtc aagctggatc cctgccacta cgccttctcc ctcaccgtgc    3360
cggcctccgc cgacgacccc agccccgacc cgctccacta cggcctcacg ctctcccgcc    3420
ccgatgtgcg cctcgacggc gtcctcgctg cctacaccag cttctccgtg cacgccgtgg    3480
tcggcgccgg gcagctggag gccagggtgc gcgacgaggc cgaggccgcc gcgtactgga    3540
cggccgtcgc gcccaacgtg gaggcgtacg gaggcgcggt ggccaggacc atcgccacgg    3600
gcgccgagca cctcgccaag gggatactgt ggtgcgggga ggtcacggtg gagaggctcc    3660 gttgggcaa tgaggtcctc aagaggagga tgcagcctgg cgacgccaac gccgaggtca    3720
gccccgagat gctcaggcga atcaaaaggt attggccgtt tccgctattt ctcttttgt    3780 tcctagtaat atacattgga aataaaaatt actaaggtcg ttattctaa tgatatgtgg    3840 attgaagtgt attagaatga agatttaaat cgactcaata ccactcaatg cacatgtatt    3900
aacggtgaaa caaacaagtc ttagtcttat ttggttatta tcaattcatg tgatgggtag    3960
agatggcaaa tttgtgatag attatgatag atttttgactg gttatggatt taaaccgact    4020
caatgtcatc caatctacat ggattgccgt ctaaacaaac atgccctgaa gatgtaatct    4080
actaatgttt gcttcataca acattcagtt atggtgttgt gccttgactc tttgtttttg    4140
ccaattgcca tctagaagag ctgaaggggc tccctatttc taaaacattt ctttagcgat    4200
gtccactgat attgacagag gagtatgcac tctgtgatcg atttcagaga tggactgaac    4260
tggattggac tgatgccatg ccacatagcc atagatatat gcagatgtca acttataatg    4320
agactgttcg ctgaggtctg aggcgtcgtt ttctgaactt tgattgcttt ggctgagtag    4380
tatatgtttg gtgttaagag attgttcaga tgtctatgct accatagcct gatatatgtc    4440
ttcgtaacct ttttgtgtct gtgtgtggac atttctgttg ccataacat cgcattgttt       4500 ctgcctctag acgtcgaatt tacgtatggt ttgcctgact gtattgactc attttttgcc    4560
tgactgtatt gactcatttt tgggtatatt ggttttacgt ttttttggta atacacaagc    4620
tttaaactac tatttaaacg attttggaca tagataggtt tggcatattc tgtgtgagtc    4680
tgagatatag gaaattcagg caaatatctg agttgcttaa caacgtcctt gcttacggtt    4740
```

| | |
|---|---|
| gctggcaggg ctaagagggt gagccaaata tctgagaaag tggcgactgg gattttgtcc | 4800 |
| ggagtggtga aggtcactgg ttacttcaca agctctctgg ccaactcgaa agctggcaag | 4860 |
| aagttcttca acatgttgcc tggagagatc gttcttgctt cgcttgacgg atttggtacg | 4920 |
| ttgctgttac taacacttgt atcgtataag gccaagtgcc cgtgtggcat tactcgtctg | 4980 |
| tcatttcact ctagcggcat tgttagatat aatattaatt gagatgtgcc cctctgccag | 5040 |
| ccttgcataa gtcaacagac aactgtctgt ctgtgtatgt tgtagtagtt tctgtgttaa | 5100 |
| tagagatgcc ttggatgccc tttatagagt ctcgtattgt ttttttgtttt attgagatga | 5160 |
| taacttctgt agttgtggct ttacgaggaa atttagatag tgtttggttc cggagccact | 5220 |
| cgaggtagaa tggttccgtc ccgagagcgg ctccgtcctg gagattttga ggagtcagat | 5280 |
| gatttaacaa ttgagcatga ctttccattt ttagaatcac tccattctat atatgaaatc | 5340 |
| aatccaaaca acagtaaatt aagagcggag cgacctgttg gtttcagtac agccacaaca | 5400 |
| aaagtgctga tgatctatat aagtcaagtc aagtcgtcaa agattctga acatttgcga | 5460 |
| cttccattcc accccatgct ctgtgaatag gtggctgaat gctttgcact ctgcttgcca | 5520 |
| ccgtggttta tgcacccaac ttacgctgac atgtatgtct tccttcgttg tcgccgacgc | 5580 |
| cataaacagg gaagatctgc gacgccgtgg aggtggccgg aaagaacgtt ttgtccacgt | 5640 |
| cgtcaactgt gacgaccggg ctagtatctc acaggtacgg agacaaagcc gccgccgcaa | 5700 |
| cgaacgaagg gctggacgcc gccgggcacg ccatcgggac ggcatgggcc gtgttcaaga | 5760 |
| tccggcaggc cttgaacccc aagagcgtcc tcaaacccac ggcgctggcc acgtccacca | 5820 |
| tcagggccaa cgttgccgag cttcgcgcga tgcacggcag cagcaagtag ctcgcgcctg | 5880 |
| ccgtccctgt ttcgtaaaaa ctctattatc tcgctctgtc acgaccaacg atgcactcgc | 5940 |
| tgcttccagc agcagcgttg gctgttgcct gttggcctgt aaattcgtgt ggctgaaact | 6000 |
| gggaaagccg ggaactgaaa ggcttaccgc ttccgctttg ttagtgatgc tggtgatgtt | 6060 |
| ctaagagctt ttaccactgc tgtgctgctg cgttggcttg aactgtcacg agttgttcgg | 6120 |
| ttttggcctc tgaagtctga accaagtaaa aaaa | 6154 |

<210> SEQ ID NO 27
<211> LENGTH: 8516
<212> TYPE: DNA
<213> ORGANISM: Zea mays
<220> FEATURE:
<221> NAME/KEY: misc_feature
<222> LOCATION: (1)..(8516)
<223> OTHER INFORMATION: n is a, c, g, or t
<220> FEATURE:
<221> NAME/KEY: misc_feature
<222> LOCATION: (6968)..(6968)
<223> OTHER INFORMATION: w is a or t

<400> SEQUENCE: 27

| | |
|---|---|
| accaaaacac cccccttta gttatataag caaccaaaca aatgtcttat atgagctcaa | 60 |
| tccggtgcta cttactcatc atggctggcc tcggacaacc tggcagcgct ggcaaccaac | 120 |
| cagacgtgtc atcatgccta caccatcgtc tcatataaag acagggcaag gcatacggtg | 180 |
| cgaagatatg gaagaagatg aggggcatgt ttcatttgct gcgtccgagt ttattattta | 240 |
| caagatgcac caacaatccc caagccaaga gttgccgcgg ctttgctcgc ccagcttatt | 300 |
| gcactgttcg cactactcca ctagatacat atattaataa catcggaaga gctagctact | 360 |
| ggaaccgatg cgaccgcacc aaaccatttc tcgtcgtcca tggcaacatc cggcaccacc | 420 |
| agcccttctt cctcatgttc ttgtccctcc gacggctcaa gtcaaggtcg ggcgcgcgcc | 480 |

| | |
|---|---|
| tcaaactaag tctcaactct caagacgatg actaacctgt aaccttgcac gccatgcgta | 540 |
| aggccaaagt tagtctctat atgacggtgc cgtccttgat ggttgcgttt ttcaggacta | 600 |
| ccacgatccc agaccggatg tagtatcctt cgtccggccg gtcggcttct tggacgccct | 660 |
| ggcagagaac acacgatgca agtagagtca attaggagcg tgttcttgg tggtggtcat | 720 |
| ttcttctttt gggagataga aatatttcgg ctcctcagaa acttaatatg ttcctccccc | 780 |
| atttgctcac ctctttgttt gttatggaga cgttccttcc aaccctggca ttcatgtcga | 840 |
| tgatgcagtt gctgcaacgc atcaatagaa gggcttatta aaccatcgtg ttatgacaca | 900 |
| caatactttt cttttttgtt ccttcttcca tcaaggttca agccaagcgc tcaccttatc | 960 |
| ttcgtgttct cccctacgcc aatgggcacc ttgccctctg ccagtagcct tgagatctcg | 1020 |
| tcttcggtct catacaaatc cgcacccatc atcatggtat tctgcaaagc accgttcgcg | 1080 |
| tcagtgtctg cgggcgctca atacagatac aagactgagc agtcatcgac gatgaacaag | 1140 |
| caagcgaacc ttgagctcgc atccagagtt taggcgtgag cgaacaccaa caatagagtg | 1200 |
| ctcgatggca cactcacgca agaagcagcc gtgtgaaatg atcgcgtctt taatctgcac | 1260 |
| acgttgaatc caaaggtcaa ataggcacaa gctcatacta cagtttacag gtcacaggca | 1320 |
| ccattcattc catgcatagg aagcgcgtac cctgcactta tccgacttcg ttggtggcaa | 1380 |
| gtaccgaggg gaagtgaaga atggtgtttt cggatcgtaa aactcgaact ttggaggctg | 1440 |
| cgacggggca tacgagatga aaactgtatt agtctggatg gaaatctatc atttcaagat | 1500 |
| attttcagtc taaatgcact ggacagttaa gagcacatta gaccttggaa agagaaaaca | 1560 |
| gaatatacct gctcgcagag ggccatgttt gcatcaaaga aagatctgat tgttccaatg | 1620 |
| tcctcccagt agtcagtgaa acatatgcc tgacaaacga agtcacatga actgcctgtg | 1680 |
| catttggtgc gatactgctc taccctaata gagattggac tcgtgcaaag ctgactgggc | 1740 |
| ccgtgattta ccgaataatg gaagtgaatc acaaaggaaa ctgttttacc tgtacattgt | 1800 |
| gctcatgcaa agccttgggc agaatttcag aaccaaagtc atgcagttca gcataccgtg | 1860 |
| acctataaga atgctccagt tagaatgcag actatgggga actgtatgga ccacaaagaa | 1920 |
| aaaaaaactc ttactttaga aggtctaaca aaacatctct cttaaaaacg taaactccca | 1980 |
| ttgaagcgat atagggatat tcagctgggg aatcaatggc gaaattgagg aagctggtat | 2040 |
| ccactttctg caacaagcag aagcaacaac gtacatttca gatagtgcta gttttgtaaa | 2100 |
| gtaagttatt cttggaaggt tccaatatat atctgagtcc ctgaggtaag atgatggcta | 2160 |
| accatttctt ccaaggcagc acccttggt ttctcagaga actgaattac acggcctgaa | 2220 |
| ctatcgaact taactaatcc atagtcagat gctcgacttc caaaacaaag aaaaaatcag | 2280 |
| catgtgcacc ggttttctga tgacaagtgc tgaaaaaaaa tcagaaacct gatgtaatga | 2340 |
| catacctctc tccaacagga gcgcatgata aagttatgtc tgcattgtca tcgacatgtt | 2400 |
| tctgaaaata gtagatgtca gggcatcatc agacagttaa actaaagaac atatacacat | 2460 |
| acaatacaat atacaggagc ggatcaccaa cctgcacaag ctccatgtaa tccatacgat | 2520 |
| agagttgatc tcctgacaaa atcaaaatgt gttctatagc tttatgcttg taataatcct | 2580 |
| gaaaaagtac acacaacata agatgcattg ttccaggaat caaataagt caggcaacat | 2640 |
| gtaccatcag ccactagaca taattattac ctcaagtacc cagataaatt ttctaacggc | 2700 |
| gtctgctgtg ccctggaacc aaccagcagc ctccccaggc atttgtgttg cagccagcac | 2760 |
| ctatttgttg ccaaatttat atcagtaaat gcatgttcta cgctttaatg agataaagaa | 2820 |

```
atttaaccaa gctccgagat gggaatcgtg anaataatat ttgnaagctc tctgagtaan    2880
caatcaaant tgaggtgact tacctcaaca gatccntcag tgaagttgat ccccccacca    2940
agataggtac gatgaatgtg acggttaaga gaagctgagt tgaactgagt cataacaaat    3000
atcttgttta tgccactgtt gaaacagttg ntcatgggga tatnaataag cctgtaacat    3060
cctccaatag gaacctaagt aatgcaacaa aaggaaagaa acaagattca gaccactgat    3120
tnaatgcaac aaaaggatgg agatggacaa agtagtggaa ggnatcatnt gcggtggggc    3180
cctgctaata attaataatt nanaatttaa acatacngaa acctcgctac tgnaggaatt    3240
atggtttaac tacctttata caaatnaatt taccatgtga atatttctag nanagccaca    3300 nactttggt gccttctgca gtagaggtgt atctacttga aataaaataa agctggagat    3360
tgctagagat ctctagatcn tgtctactta ataagaccga agatgattat naaatcggta    3420
cttcttgcaa catgaagccn ataaagtcaa agtgtgccat ctnacancan gggtggccct    3480
tgtgcttgtg agagggaaaa gctgantccc ggtaccacca cccaaaatga cggcagcgac    3540
ttcattagga tcagcataat tcctccgaaa ggatgttcgg acgacctgta agttttgca    3600 tccagaaatt gataattata gcagctaaca tcaagtcaaa taaaaaata caagggctg    3660 tgatgaaaca ccgacactat tatcgacagg atgagactta caagagtgtc tgggccagca    3720
tctgatgtga gcacacactg cgtgctgctc acagcacccc ttgcactgaa acacatcctc    3780
ctcagtgcct tgttgcgcct gatgctgcag cagttgatcc tcatcctctc actcccataa    3840
cctccactgc ctctcctcac tgggctcata cacgctttc cctctagggg aagcacgctg    3900
ctgaactgca tagctgaagc acacctgcac gatcacaacc attaaccacc aggcagtcct    3960
ggaaatctat ttcactatgt actgaatcaa gatgcagggc aagactatat aaaaaaactg    4020
attttcttgc ctagttcctg acaaatcccc gcatcaatca agggaaaagg gagccatact    4080
tttgcggaat ccttactgcc gtaaggaggg atcatcaacg tactcgcgga ataacggact    4140
ggataataaa ggattaaagg gtggtggtgc aatggtgtac acnacacaag ngagatttcg    4200
aaagcnaagg atggaagcac acatcagact gaggaaagct ataaaaagga ccttctgcct    4260
tcttttcggg agttagacat gtgaatcaca acagctcant cccagttgng ttggatcttt    4320
tcttccttgt acactctgaa cccatataga agcaaagtgt antngggaaaa ctttgcgata    4380 gaaaantact ccacgatcca aggatgaaaa gcaaccagga gaagaacatg aggttgaata    4440
acgtcataac gaatagtcac aaccccaaat tagcaacccg gcccacctaa aatcaagtgc    4500
anctaaccaa aacgtatgca ggacagattc ataccagaaa tgggaggaga ttgcagaaag    4560
tgcttcggaa ncaagtggaa gcgtggagcc actcgacgcg aggaggggn gnggaaangg    4620 cagcagcact tttggagttg tttaaggaca acaatgatga acggggatg tccacaagtc    4680 aaatacaagt aataaaacca agagcgcagg atccaagaac gaaacggagg acccattttt    4740
gttgttgggt tgggagacga acacacgaaa agaganagag ataggtngaa gaacacgtcg    4800 actnccgtt ccacccgcga gnaccnagag acgtactaca nccgtctcgg naacggcaan    4860
caagaacgaa atcttgcgga gagccggaga ctgtataaga actcaaagta ctatttgctg    4920
caccatcaat tcaggcaaaa tataantgga aacagaaaaa aaaatcgag agaaatccng    4980 cnggagcagg antacnatcc tagccnacgn cnccgtnctc tggagagttn gtaananctc    5040
cccctccttc tccctcgcct cgccngaggg ctgancccctt attcacggnc ncacnccaca    5100
cactacccgg cacccacccn cctnatccac cgccctccn gccgccggcn ccaaantcct    5160
acncaggtna nangcacaan taanaacntc gngngcatac nccncggca aaacccaacg    5220
```

```
aangaaggaa atgttccang gaaccnaang cgcgcccnca ncancagcat tcgntnaggg    5280
gcancgncnc aggcnaangc gtccntngna ccgcccatgc gttccaggaa cnacnagngc    5340
acccgggcgc cgntnantca naggcntntn tnccttggac gcanaaatgc gnanacnacg    5400
cgnaggcngc ntcgacggca cgccacgaa ggagacaaga gtaacgaaga tggatgggtt    5460
ggnttaccta gggacggatg gatcgattgc gntgggagcc ggagcgatgc gatggacgag    5520
agagaatggg tggccgcgac ggtgcgagac ggtggcgatg tggcgcgggc ggcggccta    5580 aaagcggggc gaggccgttg cgttggaatg gagtggagtg gggaggagga aggcgagcga    5640
ggcaaatgga aatgagaatg ggaatggacg gacgaacggt ggagaaggcg tggccgcggc    5700
ctcgcttggc gctactacgc cgcgtgtgcc ctgctccccg tgccgcgcct gcncttgccc    5760
atgtggggga ggagcccggc gcacggtaaa cnaccangag ngtngntaac agacgccact    5820
ctatctcctc ctncntccac cgcgccaccg ctcgccgggt cggtcccgtc cgtttctgtg    5880
ttttcccgga tcaaaacgcc tcgtcgtcgc ttgcattatt ggctccatct gacgtgacgt    5940
gacttganat ggagattttt ttttgccctc ntccttaagg agaagaaaa aagnaaatn    6000 tttttttggcg gtttcattga caacaaaacg gaaaatnaaa ataaaaaaan tggntgtggc    6060
cactccttag aatgncgtgt canctttta aagtcttgga gcnactgaa atacantttt    6120 gacggnttac gaatgaaatg gngccaagtg caatccatag tgaatgggaa accgatccta    6180
aaacaagaag cctaaaacga gctcaaacga cngctaagcc tgagatngag ggtgagagga    6240
gtcttccgcc aaaaacatga gcatccaacg gctgcgaggn aantcatcgt cgaacggacg    6300
gttctaaatc gaagggctca atcgccancc actagcagta gctancacgg tggaggagcg    6360
gacaaaactg tgcangtncc cnccctggg ccctggccgc aagagcaagt ggcccgtgcc    6420
tgtaacaatt ctcccgtggg atgtcaggca gaggcatgca taggcngtag gngtgtggcc    6480
tgtggcctgt gggagtggga cacacagccg gggcaactga cggttggaat cgcgcnccac    6540
ggcagcgaac gtacctgctc cgcacgtcat gggccccgcg ccgaggatct tttggtngtn    6600
ctcgccacgc gcgggcccac gtgncggcg gatctgcgcc gggtgatcgg acctcttgtc    6660
cgggcccggg cgtcctcccc tcctgcgtgg tgnggtgggc cangnggacc tctccggcct    6720
gtcctgtccc ncgcgcgtca cacgtcagag cctgccactg nccactgctg ggcctggact    6780
nttccttgaa tgtctcgagg aaagggaatc aagtctggcc catgtaaaag gtgtgcatgc    6840
atgcccnctg ccatccaacn agctgtgtgt ngcacgtgcc gatnccntac tatgtactag    6900
cagcgncagc ngcagccagn agcgtcgttt aggctttggc cgtggttggc tgngaattgg    6960
gatnattwtt ggtaatagca tgtcatcact ggctccntnt ttttntnttt agccattaga    7020
ttgatgacga tgagcgcggg cggccagggc cggattgaag ccgagctta cggagcacgg    7080 gtcatggatg gctccagatc aacaggtgct acggaccgtc gatgggatc tggcacccgg    7140 ctaccgctt aattttgtcc gcttgcgtca ttaaacgccc atctcgtcgt gcaaagcaaa    7200
ccaatcgctt gacgacgcac ggatccgacg tcgccgtggg cccggatcgg acctccgtcc    7260
gcaactcacg cagccttgca aacctgcccg ctcgctgggt gctggccgct ccagagtcca    7320
gaccccatca atcatgatac acagcggtgt gggtgcgcgg gcatcgccgt cccgtccgga    7380
ctcgggagcg acccccatgcg cgcgtggcac ccgcagcccg cgcaccacgt ggtgtctgct    7440
ctgctctctc tgctgctact gtggcctgtg ggtcgggtac gtactgtact gtacgttgcc    7500
gcgacgcgac cgcctcggtc cgaccgtcgt ctggttggtt cgatggcgtc tccttttcct    7560
```

```
gctgctacga ctatgctcgc gcggccggcc gccggtgcga cgctgcgtgt ccgatcgagg      7620
catggccgca gcgttcggcc tgatgtttgt ttatttaggg cgcaaaacaa actagctact      7680
gacaccttac aggccagctt ggactggcat gggggcagca cgacagcaca ccaggaggcg      7740
aggcaggcag agaatgagaa tgccacttcc cttctcctcc tgcaggctgc agcataccga      7800
taagataaaa taaaactagg gtctaggatc tgttgttatt aagtcctgtt ttctaagcac      7860
tctcctagtt acttgtgcta gttaattata gtcattaaag accttgagca gctcaacagg      7920
tgtgtgcggc tgccaaggct cctatctgat tagctaagct ctaatgagct gttatgtaat      7980
caatgtgact catctcctct tttctatata atcaaagcaa tgatgctga ggttagcacc      8040 tccggaaaaa ccactctgtt tacctctaac atttggtatc agagcttagg ttagacacct      8100
gagagtctca aggccgactc ctctcttctc tactcatgtc gacctctgct gagcgcgctg      8160
ccaggctcaa ggccaaggga accagcgaag gagagctggg cgacttttcc agcagggctg      8220
cacgcctgaa ggctgcagag gaagcagcgg ctgcagcaga ggcagcggca aggacggcgc      8280
aggagctgcg ggccgaaatc gccaccgaga agggagaaga tgaggaggac tgggaagagg      8340
agacagagag gaacaggcgc atgaggactc caccgcgaga taggaggcgc tcgcagtcac      8400
cactacggga ccgaaggcgc tgccgtggcg gcgctcgcta cgagtcgccg caaggaaggg      8460
tggtgtaccg cgactccggc agcggcacgt cgtggccaat gctggacaag acgaac         8516
```

<210> SEQ ID NO 28
<211> LENGTH: 8516
<212> TYPE: DNA
<213> ORGANISM: Zea mays
<220> FEATURE:
<221> NAME/KEY: misc_feature
<222> LOCATION: (1)..(8516)
<223> OTHER INFORMATION: n is a, c, g, or t
<220> FEATURE:
<221> NAME/KEY: misc_feature
<222> LOCATION: (6083)..(6083)
<223> OTHER INFORMATION: y is c or t

<400> SEQUENCE: 28

```
accaaaacac ccccccttta gttatataag caaccaaaca aatgtcttat atgagctcaa        60
tccggtgcta cttactcatc atggctggcc tcggacaacc tggcagcgct ggcaaccaac       120
cagacgtgtc atcatgccta caccatcgtc tcatataaag acagggcaag gcatacggtg       180
cgaagatatg gaagaagatg aggggcatgt ttcatttgct gcgtccgagt ttattattta       240
caagatgcac caacaatccc caagccaaga gttgccgcgg ctttgctcgc ccagcttatt       300
gcactgttcg cactactcca ctagatacat atattaataa catcggaaga gctagctact       360
ggaaccgatg cgaccgcacc aaaccatttc tcgtcgtcca tggcaacatc cggcaccacc       420
agcccttctt cctcatgttc ttgtccctcc gacggctcaa gtcaaggtcg ggcgcgcgcc       480
tcaaactaag tctcaactct caagacgatg actaacctgt aaccttgcac gccatgcgta       540
aggccaaagt tagtctctat atgacggtgc cgtccttgat ggttgcgttt ttcaggacta       600
ccacgatccc agaccggatg tagtatcctt cgtccggccg gtcggcttct tggacgccct       660
ggcagagaac acacgatgca agtagagtca attaggagcg tgttcttgg tggtggtcat       720 ttcttctttt gggagataga aatatttcgg ctcctcagaa acttaatatg ttcctccccc       780
atttgctcac ctctttgttt gttatggaga cgttccttcc aaccctggca ttcatgtcga       840
tgatgcagtt gctgcaacgc atcaatagaa gggcttatta aaccatcgtg ttatgacaca       900
caatactttt cttttttgtt ccttcttcca tcaaggttca agccaagcgc tcaccttatc       960
```

```
ttcgtgttct cccctacgcc aatgggcacc ttgccctctg ccagtagcct tgagatctcg    1020
tcttcggtct catacaaatc cgcacccatc atcatggtat tctgcaaagc accgttcgcg    1080
tcagtgtctg cgggcgctca atacagatac aagactgagc agtcatcgac gatgaacaag    1140
caagcgaacc ttgagctcgc atccagagtt taggcgtgag cgaacaccaa caatagagtg    1200
ctcgatggca cactcacgca agaagcagcc gtgtgaaatg atcgcgtctt taatctgcac    1260
acgttgaatc caaaggtcaa ataggcacaa gctcatacta cagtttacag gtcacaggca    1320
ccattcattc catgcatagg aagcgcgtac cctgcactta tccgacttcg ttggtggcaa    1380
gtaccgaggg gaagtgaaga atggtgtttt cggatcgtaa aactcgaact ttggaggctg    1440
cgacggggca tacgagatga aaactgtatt agtctggatg gaaatctatc atttcaagat    1500
attttcagtc taaatgcact ggacagttaa gagcacatta gaccttggaa agagaaaaca    1560
gaatatacct gctcgcagag ggccatgttt gcatcaaaga aagatctgat tgttccaatg    1620
tcctcccagt agtcagtgaa acatatgcc tgacaaacga agtcacatga actgcctgtg     1680
catttggtgc gatactgctc taccctaata gagattggac tcgtgcaaag ctgactgggc    1740
ccgtgattta ccgaataatg gaagtgaatc acaaaggaaa ctgttttacc tgtacattgt    1800
gctcatgcaa agccttgggc agaatttcag aaccaaagtc atgcagttca gcataccgtg    1860
acctataaga atgctccagt tagaatgcag actatgggga actgtatgga ccacaaagaa    1920 aaaaaactc ttactttaga aggtctaaca aaacatctct cttaaaaacg taaactccca     1980
ttgaagcgat atagggatat tcagctgggg aatcaatggc gaaattgagg aagctggtat    2040
ccactttctg caacaagcag aagcaacaac gtacatttca gatagtgcta gttttgtaaa    2100
gtaagttatt cttggaaggt tccaatatat atctgagtcc ctgaggtaag atgatggcta    2160
accatttctt ccaaggcagc acccctttggt ttctcagaga actgaattac acggcctgaa   2220
ctatcgaact taactaatcc atagtcagat gctcgacttc caaaacaaag aaaaaatcag    2280
catgtgcacc ggttttctga tgacaagtgc tgaaaaaaaa tcagaaacct gatgtaatga    2340
catacctctc tccaacagga gcgcatgata aagttatgtc tgcattgtca tcgacatgtt    2400
tctgaaaata gtagatgtca gggcatcatc agacagttaa actaaagaac atatacacat    2460
acaatacaat atacaggagc ggatcaccaa cctgcacaag ctccatgtaa tccatacgat    2520
agagttgatc tcctgacaaa atcaaaatgt gttctatagc tttatgcttg taataatcct    2580
gaaaaagtac acacaacata agatgcattg ttccaggaat caaaataagt caggcaacat    2640
gtaccatcag ccactagaca taattattac ctcaagtacc cagataaatt ttctaacggc    2700
gtctgctgtg ccctggaacc aaccagcagc ctccccaggc atttgtgttg cagccagcac    2760
ctatttgttg ccaaatttat atcagtaaat gcatgttcta cgctttaatg agataaagaa    2820
atttaaccaa gctccgagat gggaatcgtg anaataatat ttgnaagctc tctgagtaan    2880
caatcaaant tgaggtgact tacctcaaca gatccntcag tgaagttgat cccccccacca   2940 agataggtac gatgaatgtg acggttaaga gaagctgagt tgaactgagt cataacaaat    3000
atcttgttta tgccactgtt gaaacagttg ntcatgggga tatnaataag cctgtaacat    3060
cctccaatag gaacctaagt aatgcaacaa aaggaaagaa acaagattca gaccactgat    3120
tnaatgcaac aaaaggatgg agatggacaa agtagtggaa ggnatcatnt gcggtggggc    3180
cctgctaata attaataatt nanaatttaa acatacngaa acctcgctac tgnaggaatt    3240
atggtttaac taccttttata caaatnaatt taccatgtga atatttctag nanagccaca   3300
```

```
nactttggt  gccttctgca  gtagaggtgt  atctacttga  aataaaataa  agctggagat   3360
tgctagagat  ctctagatcn  tgtctactta  ataagaccga  agatgattat  naaatcggta   3420
cttcttgcaa  catgaagccn  ataaagtcaa  agtgtgccat  ctnacancan  gggtggccct   3480
tgtgcttgtg  agagggaaaa  gctgantccc  ggtaccacca  cccaaaatga  cggcagcgac   3540
ttcattagga  tcagcataat  tcctccgaaa  ggatgttcgg  acgacctgta  agtttttgca   3600
tccagaaatt  gataattata  gcagctaaca  tcaagtcaaa  taaaaaaata  caaagggctg   3660
tgatgaaaca  ccgacactat  tatcgacagg  atgagactta  caagagtgtc  tgggccagca   3720
tctgatgtga  gcacacactg  cgtgctgctc  acagcacccc  ttgcactgaa  acacatcctc   3780
ctcagtgcct  tgttgcgcct  gatgctgcag  cagttgatcc  tcatcctctc  actcccataa   3840
cctccactgc  ctctcctcac  tgggctcata  acgcttttc   cctctagggg  aagcacgctg   3900
ctgaactgca  tagctgaagc  acacctgcac  gatcacaacc  attaaccacc  aggcagtcct   3960
ggaaatctat  ttcactatgt  actgaatcaa  gatgcagggc  aagactatat  aaaaaaactg   4020
attttcttgc  ctagttcctg  acaaatcccc  gcatcaatca  agggaaaagg  gagccatact   4080
tttgcggaat  ccttactgcc  gtaaggaggg  atcatcaacg  tactcgcgga  ataacggact   4140
ggataataaa  ggattaaagg  gtggtggtgc  aatggtgtac  acnacacaag  ngagatttcg   4200
aaagcnaagg  atggaagcac  acatcagact  gaggaaagct  ataaaaagga  ccttctgcct   4260
tcttttcggg  agttagacat  gtgaatcaca  acagctcant  cccagttgng  ttggatcttt   4320
tcttccttgt  acactctgaa  cccatataga  agcaaagtgt  antggaaaa   ctttgcgata   4380
gaaaantact  ccacgatcca  aggatgaaaa  gcaaccagga  gaagaacatg  aggttgaata   4440
acgtcataac  gaatagtcac  aaccccaaat  tagcaacccg  gcccacctaa  aatcaagtgc   4500
anctaaccaa  aacgtatgca  ggacagattc  ataccgaaaa  tgggaggaga  ttgcagaaag   4560
tgcttcggaa  ncaagtggaa  gcgtggagcc  actcgacgcg  aggagggggn  gnggaaangg   4620
cagcagcact  tttggagttg  tttaaggaca  acaatgatga  acggggatg   tccacaagtc   4680
aaatacaagt  aataaaacca  agagcgcagg  atccaagaac  gaaacggagg  acccattttt   4740
gttgttgggt  tgggagacga  acacacgaaa  agaganagag  ataggtngaa  gaacacgtcg   4800
actnccgtt   ccacccgcga  gnaccnagag  acgtactaca  nccgtctcgg  naacggcaan   4860
caagaacgaa  atcttgcgga  gagccggaga  ctgtataaga  actcaaagta  ctatttgctg   4920
caccatcaat  tcaggcaaaa  tataantgga  aacagaaaaa  aaaaatcgag  agaaatccng   4980
cnggagcagg  antacnatcc  tagccnacgn  cnccgtnctc  tggagagttn  gtaananctc   5040
cccctccttc  tccctcgcct  cgccngaggg  ctganccctt  attcacggnc  ncacnccaca   5100
cactacccgg  cacccacccn  cctnatccac  cgccctccn   gccgccggcn  ccaaantcct   5160
acncaggtna  nangcacaan  taanaacntc  gngngcatac  nccncggca   aaacccaacg   5220
aangaaggaa  atgttccang  gaaccnaang  cgcgcccnca  ncancagcat  tcgntnaggg   5280
gcancgncnc  aggcnaangc  gtccntngna  ccgcccatgc  gttccaggaa  cnacnagngc   5340
acccgggcgc  cgntnantca  naggcntntn  tnccttggac  gcanaaatgc  gnanacnacg   5400
cgnaggcngc  ntcgacggca  cgccnacgaa  ggagacaaga  gtaacgaaga  tggatgggtt   5460
ggnttaccta  gggacggatg  gatcgattgc  gntgggagcc  ggagcgatgc  gatggacgag   5520
agagaatggg  tggccgcgac  ggtgcgagac  ggtggcgatg  tggcgcgggc  ggcggcctat   5580
aaagcggggc  gaggccgttg  cgttggaatg  gagtggagtg  gggaggagga  aggcgagcga   5640
ggcaaatgga  aatgagaatg  ggaatggacg  gacgaacggt  ggagaaggcg  tggccgcggc   5700
```

```
ctcgcttggc gctactacgc cgcgtgtgcc ctgctcccg tgccgcgcct gcncttgccc    5760
atgtggggga ggagcccggc gcacggtaaa cnaccangag ngtngntaac agacgccact    5820
ctatctcctc ctncntccac cgcgccaccg ctcgccgggt cggtcccgtc cgtttctgtg    5880
ttttcccgga tcaaaacgcc tcgtcgtcgc ttgcattatt ggctccatct gacgtgacgt    5940
gacttganat ggagattttt ttttgccctc ntccttaagg agaaagaaaa aaagnaaatn    6000
tttttttggcg gtttcattga caacaaaacg gaaaatnaaa ataaaaaaan tggntgtggc    6060
cactccttag aatgncgtgt caycttttta aagtcttgga gcncactgaa atacantttt    6120
gacggnttac gaatgaaatg ngccaagtg caatccatag tgaatgggaa accgatccta    6180
aaacaagaag cctaaaacga gctcaaacga cngctaagcc tgagatngag ggtgagagga    6240
gtcttccgcc aaaaacatga gcatccaacg gctgcgaggn aantcatcgt cgaacggacg    6300
gttctaaatc gaagggctca atcgccancc actagcagta gctancacgg tggaggagcg    6360
gacaaaactg tgcangtncc cnccccctggg ccctggccgc aagagcaagt ggcccgtgcc    6420
tgtaacaatt ctcccgtggg atgtcaggca gaggcatgca taggcngtag gngtgtggcc    6480
tgtggcctgt gggagtggga cacacagccg gggcaactga cggttggaat cgcgcnccac    6540
ggcagcgaac gtacctgctc cgcacgtcat gggccccgcg ccgaggatct tttggtngtn    6600
ctcgccacgc gcgggcccac gtgncggcg gatctgcgcc gggtgatcgg acctcttgtc    6660
cgggcccggg cgtcctcccc tcctgcgtgg tgnggtgggc cangnggacc tctccggcct    6720
gtcctgtccc ncgcgcgtca cacgtcagag cctgccactg nccactgctg ggcctggact    6780
nttccttgaa tgtctcgagg aaagggaatc aagtctggcc catgtaaaag gtgtgcatgc    6840
atgcccnctg ccatccaacn agctgtgtgt ngcacgtgcc gatnccntac tatgtactag    6900
cagcgncagc ngcagccagn agcgtcgttt aggctttggc cgtggttggc tgngaattgg    6960
gatnattntt ggtaatagca tgtcatcact ggctccntnt ttttntnttt agccattaga    7020
ttgatgacga tgagcgcggg cggccagggc cggattgaag ccgagcttta cggagcacgg    7080
gtcatggatg gctccagatc aacaggtgct acgaccgtc gatggggatc tggcaccccgg    7140
ctacccgctt aattttgtcc gcttgcgtca ttaaacgccc atctcgtcgt gcaaagcaaa    7200
ccaatcgctt gacgacgcac ggatccgacg tcgccgtggg cccggatcgg acctccgtcc    7260
gcaactcacg cagccttgca aacctgcccg ctcgctgggt gctggccgct ccagagtcca    7320
gaccccatca atcatgatac acagcggtgt gggtgcgcgg gcatcgccgt cccgtccgga    7380
ctcgggagcg accccatgcg cgcgtggcac ccgcagcccg cgcaccacgt ggtgtctgct    7440
ctgctctctc tgctgctact gtggcctgtg ggtcgggtac gtactgtact gtacgttgcc    7500
gcgacgcgac cgcctcggtc cgaccgtcgt ctggttggtt cgatgccgtc tccttttcct    7560
gctgctacga ctatgctcgc gcggccggcc gccggtgcga cgctgcgtgt ccgatcgagg    7620
catggccgca gcgttcggcc tgatgtttgt ttatttaggg cgcaaaacaa actagctact    7680
gacaccttac aggccagctt ggactggcat gggggcagca cgacagcaca ccaggaggcg    7740
aggcaggcag agaatgagaa tgccacttcc cttctcctcc tgcaggctgc agcataccga    7800
taagataaaa taaaactagg gtctaggatc tgttgttatt aagtcctgtt ttctaagcac    7860
tctcctagtt acttgtgcta gttaattata gtcattaaag accttgagca gctcaacagg    7920
tgtgtgcggc tgccaaggct cctatctgat tagctaagct ctaatgagct gttatgtaat    7980
caatgtgact catctcctct tttctatata atcaaagcaa tgatggctga ggttagcacc    8040
```

```
tccggaaaaa ccactctgtt tacctctaac atttggtatc agagcttagg ttagacacct    8100
gagagtctca aggccgactc ctctcttctc tactcatgtc gacctctgct gagcgcgctg    8160
ccaggctcaa ggccaaggga accagcgaag gagagctggg cgacttttcc agcagggctg    8220
cacgcctgaa ggctgcagag gaagcagcgg ctgcagcaga ggcagcggca aggacggcgc    8280
aggagctgcg ggccgaaatc gccaccgaga agggagaaga tgaggaggac tgggaagagg    8340
agacagagag gaacaggcgc atgaggactc caccgcgaga taggaggcgc tcgcagtcac    8400
cactacggga ccgaaggcgc tgccgtggcg gcgctcgcta cgagtcgccg caaggaaggg    8460
tggtgtaccg cgactccggc agcggcacgt cgtggccaat gctggacaag acgaac       8516
```

<210> SEQ ID NO 29
<211> LENGTH: 2722
<212> TYPE: DNA
<213> ORGANISM: Zea mays
<220> FEATURE:
<221> NAME/KEY: misc_feature
<222> LOCATION: (1)..(2722)
<223> OTHER INFORMATION: n is a, c, g, or t
<220> FEATURE:
<221> NAME/KEY: misc_feature
<222> LOCATION: (1729)..(1729)
<223> OTHER INFORMATION: r is a or g

<400> SEQUENCE: 29

```
aggagcatgg gagttgataa acacttacat tatcaaagac acttggaaga aggtgcatta      60
tattcgattg tgtagtgcta accggaaact ggcanatgac acanactttt ctgctatctg     120
gcatagtgcg atgcatgtac aataagtcat tatagaggca ctttaatttt gggacgactt     180
gtctaaatgc atagacaaaa atgcacatat tttaacacag agggtattga tgtcctttat     240
tctagtcgac atgaaattc taggagatca gatcaaaatg tttttggacc atactctatt     300
tntatttgat ttttaactaa aattaattaa ggtatcaaac aaatcatgaa aaaccaatt     360 gaatcgtacg tgatccatta ccatccctac ctacacccga gatattttga acgtgtcaca    420
agaaaatttc cagatgtta gtttcacaac tagattaaat gtgtttgtaa aatcaggtg      480 aaatatttct tatccacatc gattttttta gccaaactaa ttccaactaa caattacacc    540
aatttgaagt atctatgtag aaaaacaaaa tggcttacaa tttgaagtaa agatngtatt    600
tatgaagagt atngaggana aggtgtggna aagtagatnt tcncgagggt ataatatagc    660
aaaattggtt gttgtttact acntcgatcg atcaatccac atagtagnat ggattccatt    720
ccacgtgaac ttcgaaattc tatatttgtt gttcaaatgc tacatcttct gacgtacact    780
tttcgtctta aattataagt cncgctgtag ttttttttag agtcgaagta tcttaagctt    840
gaccaagttt gtacaataaa ataacaatat ttataatatc aaataaatat tgttatattt    900
ggtagtatat gatgttacaa ttctttagtt tttatacaat tttaattaaa tttaagactt    960 gttgatttt tttcaaata ttgaaatgcc ctgtaatccg gaacaaagga agtagcaaga    1020
ngtgattgtn agctagcacn tgcatagtgt actcccatca gcccacgaaa gactatngtn   1080
gtnaaaaaaa aaagattccn atgtgggtag cagtaagaac acacatctga attaaagtac   1140
tagttgctgc nagcnggcta tattttgccn gtaattgata ncttnattta tgtacatatg   1200
attaagnggg cgcacntaga aatcagcaat tcagcacagc aatgacncgc tacgatgagt   1260
agctagctag aantaatctg ccgacgncgn tggcatanca taccatcgat tacatcagtc   1320
catanaggct aaaccactng accacgctgc tgtcagcgta ggcatagtca ggaacataga   1380
gcaggtngtc gtcccccagg tgatngccgc cgccgccgcc gcctcctccg ggctgctggc   1440
```

```
aggtgcngtn ganaacgatg agctcgggct cccgctgcag acggcacggg ccatgacgtn   1500
tccgccgtca ccggagaccg cgtggttgcc cgcggatctg aaacgcgtca gctcctcctc   1560
ggcgagcacc agcttgtcct tcagcctcat cacctgccag ccgtgcatgt gcccacgaaa   1620
tgcatgctna gtattatata tatatactgc aagtctgcaa cgccgtcnat gatccatggc   1680
gcatggngng aacagagaag aggattggag cacaggcaaa gagtnagarg taggnggcgg   1740
catgtacctc gttctcaagg tggcatttgt ggaggatggc ggcgtcgtgt gcctgcttga   1800
gcttggcgaa ctcctcctcg agcagcttgc tcttgtggcg ngcgcggcgg ttctggaacc   1860
agacggcgac ctgcttgggg tcgagcccga gctcggnggc caggtgcacc ttccggccgg   1920
tctccagctt ccgctcctcc cggaagctca gctccagcat ctctacctgc tcgtcggtca   1980
gccgccgctt cttgtggtcc cctcctccgt ccagctcgcc nccgcngccg ccgcacctcg   2040
ctgctcgacg cctcctgcgc cncgctcncg gtctctcctc ctgcgcagtg cctgcaaacc   2100
gcacagaata cacatcaatt gccattcatg tagcaggtgc atgtcctgca ggtagcnggt   2160
aggcnggtac tgatgatgag ctgcgcagtt gcagagacga agtacctaca gctacacaac   2220
tgtgagaaag agaatgtacg actactncgc accgttggcg ttgggcacca ggaggaggga   2280
tgaggagngt ccacgtaggc gggaggaaag agcccgtcgt attgttccat ccttcgcctg   2340
cgcgcgctcc cggccgggcg ggcgcggatc agctgctgca acgcctttct ctctccttgt   2400
caagcgtgac cactgngtca ggttatctgg agaggaccan ggatagagaa agagagngag   2460
gngaggctgc tggggagagg accaaggaca gagaaagaga gggaggctgg ggagaggaga   2520
cgtgctgtgc gaggaggagc tgcaggagga gtggatcaag gagcgaggac cacagggcaa   2580
ggcaccagct ggggtggtna agtaagctgg gggtgcgggt ctcgagagag acctaggnat   2640
atatngggct agcaaaggcn cnacgccgga aggcgttggg ggtcgccggg cggctgggcc   2700
ggccgggtcc gggggggtggt gc                                           2722
```

<210> SEQ ID NO 30
<211> LENGTH: 2722
<212> TYPE: DNA
<213> ORGANISM: Zea mays
<220> FEATURE:
<221> NAME/KEY: misc_feature
<222> LOCATION: (1)..(2722)
<223> OTHER INFORMATION: n is a, c, g, or t
<220> FEATURE:
<221> NAME/KEY: misc_feature
<222> LOCATION: (1668)..(1668)
<223> OTHER INFORMATION: m is a or c

<400> SEQUENCE: 30

```
aggagcatgg gagttgataa acacttacat tatcaaagac acttggaaga aggtgcatta    60
tattcgattg tgtagtgcta accggaaact ggcanatgac acanactttt ctgctatctg   120
gcatagtgcg atgcatgtac aataagtcat tatagaggca cttaattttt gggacgactt   180
gtctaaatgc atagacaaaa atgcacatat tttaacacag agggtattga tgtcctttat   240
tctagtcgac atgaaattc taggagatca gatcaaaatg ttttggacc atactctatt    300 tntatttgat tttaactaa aattaattaa ggtatcaaac aaatcatgaa aaaccaatt    360 gaatcgtacg tgatccatta ccatccctac ctacacccga gatattttga acgtgtcaca   420
agaaaatttc cagatgttta gtttcacaac tagattaaat gtgtttgtaa gaatcaggtg   480
aaatatttct tatccacatc gatttttta gccaaactaa ttccaactaa caattacacc   540
```

-continued

| | |
|---|---|
| aatttgaagt atctatgtag aaaaacaaaa tggcttacaa tttgaagtaa agatngtatt | 600 |
| tatgaagagt atngaggana aggtgtggna aagtagatnt tcncgagggt ataatatagc | 660 |
| aaaattggtt gttgtttact acntcgatcg atcaatccac atagtagnat ggattccatt | 720 |
| ccacgtgaac ttcgaaattc tatatttgtt gttcaaatgc tacatcttct gacgtacact | 780 |
| tttcgtctta aattataagt cncgctgtag tttttttttag agtcgaagta tcttaagctt | 840 |
| gaccaagttt gtacaataaa ataacaatat ttataatatc aaataaatat tgttatattt | 900 |
| ggtagtatat gatgttacaa ttctttagtt tttatacaat tttaattaaa tttaagactt | 960 |
| gttgattttt ttttcaaata ttgaaatgcc ctgtaatccg gaacaaagga agtagcaaga | 1020 |
| ngtgattgtn agctagcacn tgcatagtgt actcccatca gcccacgaaa gactatngtn | 1080 |
| gtnaaaaaaa aaagattccn atgtgggtag cagtaagaac acacatctga attaaagtac | 1140 |
| tagttgctgc nagcnggcta tattttgccn gtaattgata ncttnattta tgtacatatg | 1200 |
| attaagnggg cgcacntaga aatcagcaat tcagcacagc aatgacncgc tacgatgagt | 1260 |
| agctagctag aantaatctg ccgacgncgn tggcatanca taccatcgat tacatcagtc | 1320 |
| catanaggct aaaccactng accacgctgc tgtcagcgta ggcatagtca ggaacataga | 1380 |
| gcaggtngtg gtcccccagg tgatngccgc cgccgccgcc gcctcctccg ggctgctggc | 1440 |
| aggtgcngtn ganaacgatg agctcgggct cccgctgcag acggcacggg ccatgacgtn | 1500 |
| tccgccgtca ccggagaccg cgtggttgcc cgcggatctg aaacgcgtca gctcctcctc | 1560 |
| ggcgagcacc agcttgtcct tcagcctcat cacctgccag ccgtgcatgt gcccacgaaa | 1620 |
| tgcatgctna gtattatata tatatactgc aagtctgcaa cgccgtcmat gatccatggc | 1680 |
| gcatggngng aacagagaag aggattggag cacaggcaaa gagtnagang taggnggcgg | 1740 |
| catgtacctc gttctcaagg tggcatttgt ggaggatggc ggcgtcgtgt gcctgcttga | 1800 |
| gcttggcgaa ctcctcctcg agcagcttgc tcttgtggcg ngcgcggcgg ttctggaacc | 1860 |
| agacggcgac ctgcttgggg tcgagcccga gctcggnggc caggtgcacc ttccggccgg | 1920 |
| tctccagctt ccgctcctcc cggaagctca gctccagcat ctctacctgc tcgtcggtca | 1980 |
| gccgccgctt cttgtggtcc cctcctccgt ccagctcgcc nccgcngccg ccgcacctcg | 2040 |
| ctgctcgacg cctcctgcgc cncgctcncg gtctctcctc ctgcgcagtg cctgcaaacc | 2100 |
| gcacagaata cacatcaatt gccattcatg tagcaggtgc atgtcctgca ggtagcnggt | 2160 |
| aggcnggtac tgatgatgag ctgcgcagtt gcagagacga agtacctaca gctacacaac | 2220 |
| tgtgagaaag agaatgtacg actactncgc accgttggcg ttgggcacca ggaggaggga | 2280 |
| tgaggagngt ccacgtaggc gggaggaaag agcccgtcgt attgttccat ccttcgcctg | 2340 |
| cgcgcgctcc cggccgggcg ggcgcggatc agctgctgca acgcctttct ctctccttgt | 2400 |
| caagcgtgac cactgngtca ggttatctgg agaggaccan ggatagagaa agagagngag | 2460 |
| gngaggctgc tggggagagg accaaggaca gagaaagaga gggaggctgg ggagaggaga | 2520 |
| cgtgctgtgc gaggaggagc tgcaggagga gtggatcaag gagcgaggac cacagggcaa | 2580 |
| ggcaccagct ggggtggtna agtaagctgg gggtgcgggt ctcgagagag acctaggnat | 2640 |
| atatngggct agcaaaggcn cnacgccgga aggcgttggg ggtcgccggg cggctgggcc | 2700 |
| ggccgggtcc gggggtggt gc | 2722 |

<210> SEQ ID NO 31
<211> LENGTH: 8821
<212> TYPE: DNA
<213> ORGANISM: Zea mays

<220> FEATURE:
<221> NAME/KEY: misc_feature
<222> LOCATION: (1)..(8821)
<223> OTHER INFORMATION: n is a, c, g, or t
<220> FEATURE:
<221> NAME/KEY: misc_feature
<222> LOCATION: (5516)..(5516)
<223> OTHER INFORMATION: r is a or g

<400> SEQUENCE: 31

```
taatcatccg ataaatatga gttgagggat tgaatattga tccttgttat gttatttgga    60
acgattcaga cttgtgaaca acttatgtta ctcaaagttc tattatgaat tcataaatat   120
ggtgtgcatg attttatgtg atgtgttgtg aattgaatta tgtgtgtgta tgagacgtgg   180
gcaaatatat gtatttgtga atgtatggaa tatggttgaa tatgtatgcg ttataattga   240
gctagattga ctaatttggt tggatatgta tgtgtatggg atatagttga atatgtgtgt   300
gtatgggatg tggataaata catgtatttg tgaatttatg tgatgaggat tggatatgta   360
tgactggacc acgaaaatca gagcaactaa tttccctggg cggagcatag ccgacgaaaa   420
ctagatggac taattcgttt gtcggcaaaa atcagatagt ttttgtcatt taatctggta   480
gacccaagta tcgacaaaaa tatatattat caatgacaat tacttaattt cataaacaat   540
ataatttta taagtgaaca tatcatgtgt attcatgcta actaacttgt ccaaccatac   600
atccagacat ttaaaggcat ccgacattta atgacatccg atttgcatcc aacgcacact   660
ggcagtggta tgtctttttt ggcaaaattt acgttggatc actattcact agatactcat   720
gctaacctgt ccaaccatac agtttttatg taaaatgtac tcacctatga tatgtgttgc   780
acatgtttta gcacgggggt gtgcatttaa ccgatgaggt ggcatttaat aaaaaaccaa   840
taccatcaat tgtacaggtc atcttcagag gtacccactg gttcaggttc tggagactcc   900
tacaaaagta ggatgtacat caacaaatta tcgatgtgtg tcaagctcta gaaatggtgg   960
cgatggaaat ctttgcgttt catggatgac gatcaaatgc aagacttgag tgtgcctagt  1020
gttttttcata gccatgttat ttggtttcgt cgagttagtt ttattttta aagaactgtt  1080
cattaagtca atatttgata tgtaatggct gtacgcatct gatgcgaaaa gccggaactc  1140
ttgtttccat tataaaaaaa agcatttaac cgatgaaaat nancaagaga ctactgntgn  1200
atgcagaata tataaattgg tanagataaa tggangccaa tgttngntgt gtgtgagtgt  1260
gaggatngga tgagagatcc tagnggaata tatatatgtg cggtgaaata ttccggtccg  1320
gcggcagcta gcgcagtgca ttgagtgccc gatcggtacg cgctcgatcg gagacgaggg  1380
ccgagcgcga cgcgccggcg caagagggct cgcggtgacg cgcagcggtt tgtccccgcc  1440
aacaacgggc caaacgcgcc gtgtcgtccg caccaaatcc cacgtagcga tcgtcatttt  1500
ccgtacgtcc ccccctgtat atcctactac tacatactat tcctacggct acggagtacg  1560
cgcaacaccc atggtccggt gggtggatat actacgccgt gcaacagggt atcgatcgcg  1620
tcggcgtcgc tgccggcagg acatgcgttc gaccggcggc cagccgggcg cgcctgctgc  1680
atgcatggga catgggtggc tgcagaaagg attcgattcg tgcgggtgac gcagggcgtc  1740
cacatacgta agcatcacca ccctcgagcg cacgcacggc acgatccgta accgcctgcg  1800
aatgcgaatc ctaactaacg gacggtgaag cgaaatccaa cggacgcgca acgagctggg  1860
gtggggccac ggcctagcca cgtttcgcca gtgccgcggc tttctcagag caactccaat  1920
agttatgtaa attttagctc tctaaatcac atatttaaga aattgctaaa tgactttgg   1980
agtaaaaaaa tatgagttct ccaatagttc tctaaatata ggttgtaatt ttgttttgta  2040
```

-continued

```
tctatccaca taaaaaataa gtcacaaaaa ctatataatg cagtcaacat ttttgtttag    2100
ggagttgtta aatggttgcc aaatgtagag agaaaatgag gttagataac aagttgttaa    2160
atttagaaag ttcatttaga gaactgttgg aaaatagttt tcatgttaac tacctaaatt    2220
attgatttag aaagttttta gagaactact ggagttgctc tcacccgccc gcgcgcctcc    2280
tcccttctcc gtccgtggca acggaagccc ccctataacc gcggccgccg ctgcaactgc    2340
atgcacggca cgaacctccc ttctttctca aattctctct ccgcctccct gctccgatgc    2400
cgcggtgacg cgtggtgcat gcgtgcgcgc gcgccttttc ccctgcctgg atccccgtc     2460 ctctctcgat cggttccagt taacactcgc agcctcgttc tcgagtctcg actctcgact    2520
tgagtcgcca gtggccacgc gcgccgggac acgggcgcgc tttctcgctg ccgcgccaaa    2580
gcaggaaaca gagcaacggc caggaaggac tcacgcgcga ggcgaaaagc gaagcgggtg    2640
ggagaagcgt gggcgcctgg gctagtgctc ccgcagcgag cgatctacgg tagagttccg    2700
gccgggcgcg cggagagga ggaggtcggg gggaggatcc gatggccggg aacgagtgga     2760
tcaatgggta cctggaggcg atcctcgaca gccacacctc gtcgcggggt gccggcggcg    2820
gcggcggcgg nggggacccc aggtcgccga cgaaggcggc gagccccgc ggcgcgcaca     2880 tgaacttcaa cccctcncac tacttcgtcg aggaggtggt caaggcgtc gacgagagcg     2940 acctccaccg gacgtggatc aaggtcgtcg ccacccgcaa cgcccgcgag cgcagcacca    3000
ggctcgagaa catgtgctgg cggatctggc acctcgcgcg caagaagaag caggtcaggg    3060
tttcgcgccc gcctctttct cggttaaatt ctctcgctgc atgttctgtt ttttttattt    3120
ttacattctc gctcgtctct gaattagatg attttcaagt gttctctgtt tgctggacgg    3180
attaatgaag cgcacactgc acagcgagta gaatatctta taaatatttt aattgttccc    3240
tttatgaact tgtttctggt tgatgtttta atgtttatgc ccgatgatgg tagatcagac    3300
atgcatggtt ggttgtggtg ctttctgaat tcagaaccgc acgcttaact ggatgtcacg    3360
tctaaaaaga agcttactag ttgattgcag tgtttcactg ttgttcgtat aaaggtatct    3420
cattcagtcg ttctagcatg tactacctgt caggacggat acggtatact cgcggattta    3480
gtttgctttc tcctcgcctt tttttgaatt gaaataaact ggtcacagcc tggatttacg    3540
gttttgtcca tggcaacaga gaattccaca tattcacgct gagattctcg ccctctgctg    3600 atgcttctg aattgtgtta tgagcagctg gagctggagg gcatccagag aatctcggca    3660
agaaggaagg aacaggagca ggtgcgtcgt gaggcgacgg aggacctggc cgaggatctg    3720
tcagaaggcg agaagggaga caccatcggc gagcttgcgc cggttgagac gaccaagaag    3780
aagttccaga ggaacttctc tgaccttacc gtctgntctg acgacaataa ggagaagaag    3840
ctttacattg tgctcatcag cgtctaccca cttgcacatt gttttgttct atgttgtgct    3900
aaattggtaa accatatata tatatatata tatatcgtaa tgaaatgtct ctagcctttt    3960
ttatggctat agttttttt attctatcgt ctaataaaat ccatggaaag cttttgccgt     4020
cgtttctaaa aaaagcctc tagccttagt tttctttgca ctttgcacat cgtaggagta    4080
gaaattttgg tatttttttn tataaaaata atttacagtt aaacntctng attttcaca     4140 agntgtttct ttnttgactg cctttttgan tgcagntgca tggtcttgtt cgtggagaaa    4200
acatggaact aggtcgtgat tctgatacag gtggccaggt naacatcatt ggtcngttac    4260
ttggnagaag ttccttatgn cgagtcaagt ttttcatgg ttgagngnga ttnatctttg     4320
aatctcacan gtnaaatatg tggncgaact tgcaagagcg atgtcaatga tgnctggagt    4380
gtacagggtg gacctcttca ctcgtcaagt gtcatctcct gacgtggact ggagctacgg    4440
```

```
tgagccaacc gagatgttat gcgccggttc caatgatgga gagggatgg gtgagagtgg    4500
cggagcctac attgtgcgca taccgtgtgg gccgcgggat aaatacctca agaaggaagc    4560
gttgtggcct tacctccaag agtttgtnga tggagccctt gcgcatatcc tgaacatgtc    4620
caaggctctg ggagagcagg ttggaaatgg gaggccagta ctgccttacg tgatacatgg    4680
gcactatgcc gatgctggag atgttgctgc tctcctttct ggtgcgctga atgtgccaat    4740
ggtgctcact ggccactcac ttgggaggaa caagctggan canctgctga agcaagggcg    4800
catgtccaag gaggagatcg attcgacata caagatcatg aggcgtatcg agggtgagga    4860
gctgccctg gatgcgtcag agcttgtaat cacgagcaca aggcaggaga ttgatgagca    4920
gtggggattg tacgatggat ttgatgtcaa gcttgagaaa gtgctgaggg cacgggcgag    4980
gcgcggggtt agctgccatg gtcgttacat gcctaggatg gtggtaagta taaaaatctc    5040
tgttatccat gccaagtagt aagtgctgtt caacataaat aattaaaatc cattaatcca    5100
tatatgtatt gattagagaa ctttgttggc aggtgattcc tccgggaatg gatttcagca    5160
atgttgtagt tcatgaagac attgatgggg atggtgacgt caaagatgat atcgttggtt    5220
tggagggtgc ctcacccaag tcaatgcccc caatttgggc cgaagttggt gcttgatccc    5280
aaattccttt gcagacctac aacaactgtc ttcacaagtg tcgtaaatct taaggtcgct    5340
gcatgacaac tttgtcgcag gtgatgcggt tcctgaccaa ccctacaag ccgatgatcc     5400
tggcgttatc aagaccagac ccgaagaaga acatcactac cctcgtcaaa gcgtttggag    5460
agtgtcgtcc actcagggaa cttgcaaacc ttgtaagaaa caccgaagtg cactcrtata    5520
atttcattgc tactaatgtt tataatttgt atgnccaaat aactagtgct accatgacca    5580
caatgcagga atactttct tatctctagc acacctacat gaaaccttct gatcctgaac     5640
aatgcagtag ctgcatgtat taccatgtga tgaagttttc ttctgtttca gactctgatc    5700
atgggtaaca gagatgacat cgacgacatg tctgctggca atgccagtgt cctcaccaca    5760
gttctgaagc tgattgacaa gtatgatctg tacggaagcg tggcgttccc taagcatcac    5820
aatcaggctg acgtcccgga natctatcgc ctcgcggcca aaatgaaggt ctgctgcata    5880
ccacgaccct tcattgagct tgacaagtc acactcaacc ataactgatt gctccctgca     5940
gggngtcttc atcaaccctg ctctcgttga gccgtttggt ctcaccctga tcgaggtcag    6000
cttnttctct agttctntaa ccagctgttg ccttttttt ntaaaaaaaa tacattacat     6060
tgcactnaaa antntgtggc tttcaggctg nggcacacgg actcccgata gtcgctacca    6120
agaatggtgg tccggtcgac attacaaatg tgagaaacca tattttgaac attcaatttg    6180
tgaaaaaaca tctgcaattc acttgtgaaa acagcggata attatttgcg tgcatcatac    6240
tggcaggcat taaacaacgg actgctcgtt gacccacacg accagaacgc catcgctgat    6300
gcactgctga agcttgtggc agacaagaac ctgtggcagg aatgccggag aaacgggctg    6360
cgcaacatcc acctctactc atggccgag cactgccgca cttacctcac cagggtggcc     6420
gggtgccggt aaggaaccc gaggtggctg aaggacacac cagcagatgc cggagccgat     6480
gaggaggagt tcctggagga ttccatggac gctcaggacc tgtcactccg tctgtccatc    6540
gacggtgaga agagctcgct gaacactaac gatccactgt ggttcgaccc ccaggatcaa    6600
gtgcagaaga tcatgaacaa catcaagcag tcgtcagcgc ttcctccgtc catgtcctca    6660
gtcgcagccg agggcacagg cagcaccatg aacaaatacc cactcctgcg ccggcgccgg    6720
cgcttgttcg tcatagctgt ggactgctac caggacgatg gccgtgctag caagaagatg    6780
```

```
ctgcaggtga tccaggaagt tttcagagca gtccgatcgg actcccagat gttcaagatc    6840
tcagggttca cgctgtcgac tgccatgccg ttgtccgaga cactccagct tctgcagctc    6900
ggcaagatcc cagcgaccga cttcgacgcc ctcatctgtg gcagcggcag cgaggtgtac    6960
tatcctggca cggcgaactg catggacgct gaaggaaagc tgcgcccaga tcaggactat    7020
ctgatgcaca tcagccaccg ctggtcccat gacggcgcga ggcagaccat agcgaagctc    7080
atgggcgctc aggacggttc aggcgacgct gtcgagcagg acgtggcgtc cagtaatgca    7140
cactgtgtcg cgttcctcat caaagacccc caaaaggtta gggaattctt taataacacg    7200
tgtgcatcct taattcctcc agttaaaacc agttgctgta tgaatctgaa ttatgttttc    7260
ctgcttaagg tgaaaacggt cgatgagatg agggagcggc tgaggatgcg tggtctccgc    7320
tgccacatca tgtactgcag gaactcgaca aggcttcagg ttgtccctct gctngcatca    7380
aggtcacagg cactcaggta agaacataca gnatctatct aacctgaaaa gctctcgtgg    7440
aaatntctga taacaaaagt tgcgaatgtg atctgtctg tnataacaan aanaaaaaat     7500
tcaatttcag gtatctttcc gtgcgctggg gcgtatctgt ggggaacatg tatctgatca    7560
ccggggaaca tggcgacacc gatctagagg agatgctntc cgggctacac aagaccgtga    7620
tcgtccgtgg cgtcaccgan aagggttcgg aagcnctggt gaggagccca ggaagctaca    7680
agagggacga tgtcgtcccg tctgagaccc ccttggctgc gtacacgact ggtganctga    7740
aggccgacga gatnatgcgg gctctgaagc aagtctccaa gacttccagc ggcatgtgaa    7800
tttgatgctt nttttacatt ttgtcctttt cttcactgct atataaaata agttgtgaac    7860
agtaccgngg gtgtgtatat atatattgca gtgacaaata aaacaggaca ctgctaacta    7920
tactggtgaa tatacgactg tcaagattgt atgctaagta ctccatttct caatgtatca    7980
atgtatatag aagttaacgt gcatgaggag ataatgatga ctcagaagtt actaacgatt    8040
aattcagttt tagttccggt caatccagtt tggttttaag tttcggttat tttgccaggc    8100
atatccacat ctcacaatga tgccattgcc cgttcattgc gatgtccata attgtttatg    8160
tatggacgta tggtgagcac tttgaatcta caaatgagga agacgacgac acaatgttct    8220
tgtaaacggt attgcaggtc tggttgctga ttcaaggcag tctcgttgtt gatcacgtgg    8280
aaccaggtta tcctccaata caagcacaaa tcgcatacnt gtgggctgcc ggataacatc    8340
tcggttgcag gcctgggttt ctctttgata tcattacgga tggctcgtga atgttgtcat    8400
ccatatcata atcgtataac acatatgcat atataaatta tcgagatatt ccatgtcccc    8460
gttgcaacgc acgagcactg acctagtaat caataaaaga gagaaaaaga tacttacatt    8520
attttctctc tctctcaaat acgaaaggag agtaagaatt aacagagtgt ttggtttaag    8580
taatgagata ttccattatt ttctcacttc gcatttttta gttatataat aaaatgagtt    8640
gattcattat cgtctcattc tttacaatta attagttagt attaatatta aaataacaa     8700
atttatagaa tagacctatg atgtaccgtc ttattttata ttaaataatt tttgaaacca    8760
aacatccttt taaaaattaa ttatgttact ctgttttttt tttcagaatt actatagatc    8820
c                                                                   8821
```

<210> SEQ ID NO 32
<211> LENGTH: 2370
<212> TYPE: DNA
<213> ORGANISM: Zea mays
<220> FEATURE:
<221> NAME/KEY: misc_feature
<222> LOCATION: (1)..(2370)
<223> OTHER INFORMATION: n is a, c, g, or t
<220> FEATURE:
<221> NAME/KEY: misc_feature
<222> LOCATION: (1255)..(1255)
<223> OTHER INFORMATION: r is a or g

<400> SEQUENCE: 32

| | | | | | |
|---|---|---|---|---|---|
| gtgtatcttc | gaaatgacga | gctgagcagc | gagtgccatg | gcaagggag | cttgctagag | 60 |
| ttcaccagna | ttcgncctga | agagctcagn | cggatgccna | gcaagnagct | gtgcaacttc | 120 |
| actcgggtgt | acatggggag | cacngagtan | accttcaata | agaatggatc | natgatattt | 180 |
| ctggatttgt | catttaatca | nctngactcn | gagatcccaa | aggagcttgg | gaacatgtac | 240 |
| tacctcatga | tcntgaatct | tgggcacaac | ttnctgtctg | gcgtcatccc | accagaacta | 300 |
| gctggtgcca | agaagcttgc | ggtnctngac | ctgtcacaca | accagttnaa | gggcctattc | 360 |
| ccaactcntt | ctcnacgttg | tccttgtcgg | agatcaacct | ttcaaataat | cagctgaatg | 420 |
| gntcaattcc | agagctgggt | tcgctgttca | cattcccgan | gatttcatat | gagaanaact | 480 |
| ctggtctttg | tggcttccca | ctgttgccat | gngggcacaa | tgctggctca | agttcttcag | 540 |
| ntgnccancg | atcccaccgg | acccaggctt | cnctcgcagg | tagtgttgct | atgggactct | 600 |
| tgttctcgnt | gttctgtata | gttggtattg | tcatcatagc | cattgagtgc | aagaagcgga | 660 |
| agcagatcaa | tgaagaggca | agtacctcnc | gtgacatata | cattgatagc | cggtcacatt | 720 |
| ctgggacaat | gaattccaat | tggagactct | ctggtactaa | tgcnctcagc | gtcaacctcg | 780 |
| ctgcatttga | gaagcgnctg | cagaagctna | cttttaatga | tcttattgtg | gcaacgaatg | 840 |
| gcttccacaa | tgatagccaa | atcgggtctg | gtggttttgg | ggatgtctat | aaggcccagc | 900 |
| tcaaggatgg | aaaggttgtt | gcaatcaaga | agcttataca | tgtgagtggc | caaggtgacc | 960 |
| gngagtttac | agcagaaatg | gagaccatng | ggaggatcaa | acaccgnaat | cttgttccgc | 1020 |
| tccttggcta | ctgcaagtgt | ggcgaggagc | ggctgttggt | ttatgattac | atgagntttg | 1080 |
| gcagcttgga | agacgtgttg | catgaccgan | aaaagatcgg | gatcaagcta | aattgggcag | 1140 |
| caaggaaaaa | gatcgccatt | ggggctgcaa | gggnattggc | atacctccac | cacaactgta | 1200 |
| tnccgcacat | cancaccgag | acatgnagtc | nagcaatgtg | cttatcgatg | agcarttaga | 1260 |
| ggcangggta | tccgatttcg | gtatggcaag | gatgatgagc | gtggtggata | cccacctgag | 1320 |
| cgtgtccact | ctcgcnggca | ctccaggcta | cgtgccgcca | gagtactacc | agagcttcag | 1380 |
| atgcactacc | aagggcgatg | tgtatagcta | tggcgttgta | ttgctcgagc | tgctcactgg | 1440 |
| gaaaccgcct | acagattcaa | ccgacttcgg | cgaggacaac | aatctngtag | gatgggtcaa | 1500 |
| acancactca | aagtcgaagc | tggcngatct | gtttgaccct | gtactactgg | tggaggatcc | 1560 |
| ngccttggag | ctcgagctac | tagagcacct | gaaantcgcn | tgtgcgtgct | tggatgancg | 1620 |
| nccatccaag | cgcccgacga | tgctnaaagt | catggcgatg | ntcaaggaga | tgcaggccag | 1680 |
| ttcggctgtg | gntngaagac | ctcagcatgc | acggtcgccg | tggatgatgc | gtgttttggc | 1740 |
| gacgtggaga | tgacgaccct | gaaagnagac | aaggaggaga | angactagag | cnaggcccac | 1800 |
| cgacacgcga | gaagctgccc | nggtnctgcn | anggncgagc | ggcagctaca | cggtcagtca | 1860 |
| gatctcagat | gcaaaaaana | aaanaaaaaa | acgcccgtag | gaatcagttg | gtcaggacac | 1920 |
| cattcgaagc | atcttcttga | gcttagcatt | cccttctgac | ggtacaagac | agaagttttt | 1980 |
| tntcccttgt | agcttcgcaa | agctgaagat | gttatgtacc | tatgggaatg | ggagtaggtn | 2040 |
| attttctttt | nttttttttn | ttntancntt | aatnatntnt | nctngncnca | cttttngtaa | 2100 |
| nagcngngna | ngnananana | taaanggngg | ttttcntng | gncnaancca | tntttcgttt | 2160 |

| | |
|---|---|
| cattccttgt tgtcaaatt taaaatttta ccttgcttt gaccaacgat gttgcaaatc | 2220 |
| ataaccang aatgtagata gaanacatgg ttgcaggtgc agcaagcatg atggaaatgg | 2280 |
| ngcgtccaaa tctgagatgc aggcagtgtg aggcaccaag ggatgagggg gaggaagtgc | 2340 |
| aagagtacac tggactggtc aagcaagatg | 2370 |

<210> SEQ ID NO 33
<211> LENGTH: 2370
<212> TYPE: DNA
<213> ORGANISM: Zea mays
<220> FEATURE:
<221> NAME/KEY: misc_feature
<222> LOCATION: (1)..(2370)
<223> OTHER INFORMATION: n is a, c, g, or t
<220> FEATURE:
<221> NAME/KEY: misc_feature
<222> LOCATION: (1366)..(1366)
<223> OTHER INFORMATION: s is c or g

<400> SEQUENCE: 33

| | |
|---|---|
| gtgtatcttc gaaatgacga gctgagcagc gagtgccatg gcaaggggag cttgctagag | 60 |
| ttcaccagna ttcgncctga agagctcagn cggatgccna gcaagnagct gtgcaacttc | 120 |
| actcgggtgt acatggggag cacngagtan accttcaata agaatggatc natgatattt | 180 |
| ctggatttgt catttaatca nctngactcn gagatcccaa aggagcttgg gaacatgtac | 240 |
| tacctcatga tcntgaatct tgggcacaac ttnctgtctg gcgtcatccc accagaacta | 300 |
| gctggtgcca agaagcttgc ggtnctngac ctgtcacaca accagttnaa gggcctattc | 360 |
| ccaactcntt ctcnacgttg tccttgtcgg agatcaacct ttcaaataat cagctgaatg | 420 |
| gntcaattcc agagctgggt tcgctgttca cattcccgan gatttcatat gagaanaact | 480 |
| ctggtctttg tggcttccca ctgttgccat gngggcacaa tgctggctca agttcttcag | 540 |
| ntgnccancg atcccaccgg acccaggctt cnctcgcagg tagtgttgct atgggactct | 600 |
| tgttctcgnt gttctgtata gttggtattg tcatcatagc cattgagtgc aagaagcgga | 660 |
| agcagatcaa tgaagaggca agtacctcnc gtgacatata cattgatagc cggtcacatt | 720 |
| ctgggacaat gaattccaat tggagactct ctggtactaa tgcnctcagc gtcaacctcg | 780 |
| ctgcatttga aagcgnctg cagaagctna cttttaatga tcttattgtg caacgaatg | 840 |
| gcttccacaa tgatagccaa atcgggtctg gtggttttgg ggatgtctat aaggcccagc | 900 |
| tcaaggatgg aaaggttgtt gcaatcaaga agcttataca tgtgagtggc caaggtgacc | 960 |
| gngagtttac agcagaaatg gagaccatng ggaggatcaa acaccgnaat cttgttccgc | 1020 |
| tccttggcta ctgcaagtgt ggcgaggagc ggctgttggt ttatgattac atgagntttg | 1080 |
| gcagcttgga agacgtgttg catgaccgan aaagatcgg gatcaagcta aattgggcag | 1140 |
| caaggaaaaa gatcgccatt ggggctgcaa gggnattggc atacctccac cacaactgta | 1200 |
| tnccgcacat cancaccgag acatgnagtc nagcaatgtg cttatcgatg agcanttaga | 1260 |
| ggcangggta tccgatttcg gtatggcaag gatgatgagc gtggtggata cccacctgag | 1320 |
| cgtgtccact ctcgcsggca ctccaggcta cgtgccgcca gagtactacc agagcttcag | 1380 |
| atgcactacc aagggcgatg tgtatagcta tggcgttgta ttgctcgagc tgctcactgg | 1440 |
| gaaaccgcct acagattcaa ccgacttcgg cgaggacaac aatctngtag gatgggtcaa | 1500 |
| acancactca aagtcgaagc tggcngatct gtttgaccct gtactactgg tggaggatcc | 1560 |
| ngccttggag ctcgagctac tagagcacct gaaantcgcn tgtgcgtgct tggatgancg | 1620 |
| nccatccaag cgcccgacga tgctnaaagt catggcgatg ntcaaggaga tgcaggccag | 1680 |

```
ttcggctgtg gntngaagac ctcagcatgc acggtcgccg tggatgatgc gtgttttggc    1740
gacgtggaga tgacgaccct gaaagnagac aaggaggaga angactagag cnaggcccac    1800
cgacacgcga gaagctgccc nggtnctgcn anggncgagc ggcagctaca cggtcagtca    1860
gatctcagat gcaaaaaana aaanaaaaaa acgcccgtag gaatcagttg gtcaggacac    1920
cattcgaagc atcttcttga gcttagcatt cccttctgac ggtacaagac agaagttttt    1980
tntcccttgt agcttcgcaa agctgaagat gttatgtacc tatgggaatg ggagtaggtn    2040
attttctttt nttttttttn ttntancntt aatnatntnt nctngncnca cttttngtaa    2100
nagcngngna ngnananana taaanggngg tttttcntng gncnaancca tntttcgttt    2160
cattccttgt ttgtcaaatt taaaatttta ccttgctttt gaccaacgat gttgcaaatc    2220 ataccang aatgtagata gaanacatgg ttgcaggtgc agcaagcatg atggaaatgg    2280
ngcgtccaaa tctgagatgc aggcagtgtg aggcaccaag ggatgagggg gaggaagtgc    2340
aagagtacac tggactggtc aagcaagatg                                     2370
```

<210> SEQ ID NO 34
<211> LENGTH: 2370
<212> TYPE: DNA
<213> ORGANISM: Zea mays
<220> FEATURE:
<221> NAME/KEY: misc_feature
<222> LOCATION: (1)..(2370)
<223> OTHER INFORMATION: n is a, c, g, or t
<220> FEATURE:
<221> NAME/KEY: misc_feature
<222> LOCATION: (1486)..(1486)
<223> OTHER INFORMATION: y is c or t

<400> SEQUENCE: 34

```
gtgtatcttc gaaatgacga gctgagcagc gagtgccatg gcaaggggag cttgctagag      60
ttcaccagna ttcgncctga agagctcagn cggatgccna gcaagnagct gtgcaacttc     120
actcgggtgt acatggggag cacngagtan accttcaata agaatggatc natgatattt     180
ctggatttgt catttaatca nctngactcn gagatcccaa aggagcttgg gaacatgtac     240
tacctcatga tcntgaatct tgggcacaac ttnctgtctg gcgtcatccc accagaacta     300
gctggtgcca agaagcttgc ggtnctngac ctgtcacaca accagttnaa gggcctattc     360
ccaactcntt ctcnacgttg tccttgtcgg agatcaacct ttcaaataat cagctgaatg     420
gntcaattcc agagctgggt tcgctgttca cattcccgan gatttcatat gagaanaact     480
ctggtctttg tggcttccca ctgttgccat gngggcacaa tgctggctca agttcttcag     540
ntgnccancg atcccaccgg acccaggctt cnctcgcagg tagtgttgct atgggactct     600
tgttctcgnt gttctgtata gttggtattg tcatcatagc cattgagtgc aagaagcgga     660
agcagatcaa tgaagaggca agtacctcnc gtgacatata cattgatagc cggtcacatt     720
ctgggacaat gaattccaat tggagactct ctggtactaa tgcnctcagc gtcaacctcg     780
ctgcatttga gaagcgnctg cagaagctna ctttttaatga tcttattgtg gcaacgaatg     840
gcttccacaa tgatagccaa atcgggtctg gtggttttgg ggatgtctat aaggcccagc     900
tcaaggatgg aaaggttgtt gcaatcaaga agcttataca tgtgagtggc caaggtgacc     960
gngagtttac agcagaaatg gagaccatng ggaggatcaa acaccgnaat cttgttccgc    1020
tccttggcta ctgcaagtgt ggcgaggagc ggctgttggt ttatgattac atgagntttg    1080
gcagcttgga agacgtgttg catgaccgan aaaagatcgg gatcaagcta aattgggcag    1140
```

```
caaggaaaaa gatcgccatt ggggctgcaa gggnattggc atacctccac cacaactgta      1200
tnccgcacat cancaccgag acatgnagtc nagcaatgtg cttatcgatg agcanttaga      1260
ggcangggta tccgatttcg gtatggcaag gatgatgagc gtggtggata cccacctgag      1320
cgtgtccact ctcgcnggca ctccaggcta cgtgccgcca gagtactacc agagcttcag      1380
atgcactacc aagggcgatg tgtatagcta tggcgttgta ttgctcgagc tgctcactgg      1440
gaaaccgcct acagattcaa ccgacttcgg cgaggacaac aatctygtag gatgggtcaa      1500
acancactca aagtcgaagc tggcngatct gttttgaccct gtactactgg tggaggatcc      1560
ngccttggag ctcgagctac tagagcacct gaaantcgcn tgtgcgtgct ggatgancg       1620 nccatccaag cgcccgacga tgctnaaagt catggcgatg ntcaaggaga tgcaggccag      1680
ttcggctgtg gntngaagac ctcagcatgc acggtcgccg tggatgatgc gtgttttggc      1740
gacgtggaga tgacgaccct gaaagnagac aaggaggaga angactagag cnaggcccac      1800
cgacacgcga gaagctgccc nggtnctgcn anggncgagc ggcagctaca cggtcagtca      1860
gatctcagat gcaaaaaana aaanaaaaaa acgcccgtag gaatcagttg gtcaggacac      1920
cattcgaagc atcttcttga gcttagcatt cccttctgac ggtacaagac agaagttttt      1980
tntcccttgt agcttcgcaa agctgaagat gttatgtacc tatgggaatg ggagtaggtn      2040
attttctttt ntttttttn ttntancntt aatnatntnt nctngncnca cttttngtaa       2100
nagcngngna ngnananana taaanggngg tttttcntng gncnaancca tntttcgttt      2160
cattccttgt ttgtcaaatt taaaatttta ccttgctttt gaccaacgat gttgcaaatc      2220 ataccnang aatgtagata gaanacatgg ttgcaggtgc agcaagcatg atggaaatgg       2280
ngcgtccaaa tctgagatgc aggcagtgtg aggcaccaag ggatgagggg gaggaagtgc      2340
aagagtacac tggactggtc aagcaagatg                                       2370

<210> SEQ ID NO 35
<211> LENGTH: 2599
<212> TYPE: DNA
<213> ORGANISM: Zea mays
<220> FEATURE:
<221> NAME/KEY: misc_feature
<222> LOCATION: (1)..(2599)
<223> OTHER INFORMATION: n is a, c, g, or t
<220> FEATURE:
<221> NAME/KEY: misc_feature
<222> LOCATION: (1742)..(1742)
<223> OTHER INFORMATION: y is c or t

<400> SEQUENCE: 35
ctcaccgagt aagcccctat ctctctctct ctcttttcag ccttttttnat taatttgcct      60 tatcttcttc antcangagt gtttttatgt tctctttgtc gttcgttcct gtgcnggcag     120
atcgcgatat acaccggccc caccggtaag tcacggncgt cgtcagttng ntnccacncg     180 gccgntttt tccaagccta acgctngctt ctgctgctgt tctgctctgc tgcatggcgc      240
gtgtgcagtg ggcggccncc tcaacgcgac gtgnggcaac nccacnganc tcatcatcgc     300
gctcttcgcg ctcatggngg gccagatnga ggtcgtcaag tgctccctcc tcggctccnt      360
cctctccaac ctgctgctcg tgctcggcac gtccctcttc tgcggcggcg tcntcaacct     420
cggctccnac cagccntang acngggtgcg tgcgtacaaa caacnaanan cgtcntcnac     480
ctcttctcca cactgcanga gcgccntcga tcntaataat gtgtatataa ngcngcncgn     540
tatnaatata ttattatata tatgcagacn caagcggacg tcagcacggg cctcctcatc     600
ctcggcgtgc tgngccagtc gctgccgctc ngctgcgcta ngcggtgggc gccggcgagc     660
```

```
actccgtcgc cgcgnccacc acggtgctcg acctctcccg cgcctgcagc gtcgtcatgc    720
tgctngccta cgtcgcctac ctcttcttcc agctcaagac gcacgcgcag ctgttcgagc    780
cgcaggaggt ggacgacggc tgcgaggcgg aagaggacga gcaggccgtc atcggcttcg    840
ccagcggntc ttctggctng ccttcaacac cgtgctcatc gccatcctgt ccgagtacgt    900
ngtcggcacn atcgaggtac agccgtacnt acagtacagt acagtncagt acatgcngtt    960
tatntttnta ctnctacnca tcntcnttcn attcgtnccc tctgttcttg ttaattaatn   1020
annnntnnnn acngccagcc tacctccaan tcctggggtt tgtccgtcag cttcatcagc   1080
atcatacttc tncccatcgt ggggaacgcc gcggagcacg ccggagcaat cattttttgct   1140 ctcaagaaca agctggtact gtacctagcc ttcacacacc canacccngn ccngantatn   1200
ccncntgtct cantgncang tntgntcana nccncntgcn tgnanttnaa attanctcnc   1260
ncngaanccn ganacacagg acattaccct cggagtagcg ttggggtcgg cgacccagat   1320
ctccatgttt gtggtgggta ttgcaattta aaactgacgc gtacagattt cattcgctta   1380
aactattnaa ctaccgaatc atgctggaat aatcgtacga ctatgcttcn gtatacgcca   1440
aacgagacag gtgccgctga gtgtcattgt agcttggatc gcgggtattc aaatggatct   1500
tgacttcaag ctcatagaga ccggctctct cttcgtctca gtnatagtga cagcattcac   1560
ccnccagnta cacacacaca catacatana nacacactac ancatactct ccnttctnat   1620
cangatgnac ntcnantnat natcactncn gcctngcngn gnttngtcac ncctnagggg   1680
atcnttntgn tgntgtnant gtnatnggng cntnttntnt nttngncnac naangnctnt   1740
nycananana gngnatnaca cnctctgtct tcggttgttc tgattttttgc cggcntgtgc   1800 tgccattctc gtccatcatc atttcnatga taggtaacaa caanggcgnt gggctgtcgc   1860
tgccaactgg nactttgagt gcncnagctg cntgatnggt gagcctgcag aaccttgttt   1920
ttcnttgttc atcnatccac tagtaggttn tagtagttta aaaaaggata ataggtacgg   1980
tgtttggttt cganctctga tggcananat gatacgaaag caactcctgt ngtntnatca   2040
tgcaaaatgc atgccccccgt nctatagaat catcctgacc ttattgggac agctggtgng   2100
ttcatcatct gatctgatga ntagctnatg tgtcgtattc atagnttaag tatatatagg   2160
tcctngtata taatttttgcc gcggnggtca catgtcntgc atggaactta cttaaatgtg   2220
tntcgatnta tttgnatctc tctgggccga atgcttgttc tcccacacag acacagcaan   2280
aactattttt cagtcagcng cttctnctna cctgtntcaa ataaaaaaat gtgcnagtcg   2340
tttaaactca actgatagg atggtgaggt ttgaccgntc natanatata tccatttcac   2400
gttctggcca gcagatgact gctntatatc tctgcagtcc tgtcagattt attctgtnat   2460
tatcngaaan caccttatgt ntttgntgtg tagccaatat gctatattca tcatggattt   2520
aagtatgtgt gtgtctccta atctgtacnt ttagcaatga aatatatgtc caactttttc   2580
attaatgtgt tgtggccca                                                2599
```

<210> SEQ ID NO 36
<211> LENGTH: 2598
<212> TYPE: DNA
<213> ORGANISM: Zea mays
<220> FEATURE:
<221> NAME/KEY: misc_feature
<222> LOCATION: (1)..(2598)
<223> OTHER INFORMATION: n is a, c, g, or t
<220> FEATURE:
<221> NAME/KEY: misc_feature
<222> LOCATION: (2457)..(2457)

<223> OTHER INFORMATION: m is a or c

<400> SEQUENCE: 36

```
ctcaccgagt aagcccctat ctctctctct ctcttttcag ccttttttnat taatttgcct    60
tatcttcttc antcangagt gttttttatgt tctctttgtc gttcgttcct gtgcnggcag   120
atcgcgatat acaccggccc caccggtaag tcacggncgt cgtcagttng ntnccacncg   180
gccgntttt tccaagccta acgctngctt ctgctgctgt tctgctctgc tgcatggcgc   240
gtgtgcagtg ggcggccncc tcaacgcgac gtgnggcaac nccacnganc tcatcatcgc   300
gctcttcgcg ctcatggngg gccagatnga ggtcgtcaag tgctccctcc tcggctccnt   360
cctctccaac ctgctgctcg tgctcggcac gtccctcttc tgcggcggcg tcntcaacct   420
cggctccnac cagccntang acngggtgcg tgcgtacaaa caacnaanan cgtcntcnac   480
ctcttctcca cactgcanga gcgccntcga tcntaataat gtgtatataa ngcngcncgn   540
tatnaatata ttattatata tatgcagacn caagcggacg tcagcacggg cctcctcatc   600
ctcggcgtgc tgngccagtc gctgccgctc ngctgcgcta ngcggtgggc gccggcgagc   660
actccgtcgc cgcgnccacc acggtgctcg acctctcccg cgcctgcagc gtcgtcatgc   720
tgctngccta cgtcgcctac ctcttcttcc agctcaagac gcacgcgcag ctgttcgagc   780
cgcaggaggt ggacgacggc tgcgaggcgg aagaggacga gcaggccgtc atcggcttcg   840
ccagcggntc ttctggctng ccttcaacac cgtgctcatc gccatcctgt ccgagtacgt   900
ngtcggcacn atcgaggtac agccgtacnt acagtacagt acagtncagt acatgcngtt   960
tatntttnta ctnctacnca tcntcnttcn attcgtncccc tctgttcttg ttaattaatn  1020
annnntnnnn acngccagcc tacctccaan tcctggggtt tgtccgtcag cttcatcagc  1080
atcatacttc tncccatcgt ggggaacgcc gcggagcacg ccggagcaat cattttttgct  1140
ctcaagaaca agctggtact gtacctagcc ttcacacacc canacccngn ccngantatn  1200
ccncntgtct cantgncang tntgntcana nccncntgcn tgnanttnaa attanctcnc  1260
ncngaanccn ganacacagg acattaccct cggagtagcg ttggggtcgg cgacccagat  1320
ctccatgttt gtggtgggta ttgcaattta aaactgacgc gtacagattt cattcgctta  1380
aactattnaa ctaccgaatc atgctggaat aatcgtacga ctatgcttcn gtatacgcca  1440
aacgagacag gtgccgctga gtgtcattgt agcttggatc gcgggtattc aaatggatct  1500
tgacttcaag ctcatagaga ccggctctct cttcgtctca gtnatagtga cagcattcac  1560
ccnccagnta cacacacaca catacatana nacacactac ancatactct ccnttctnat  1620
cangatgnac ntcnantnat natcactncn gcctngcngn gnttngtcac ncctnagggg  1680
atcnttntgn tgntgtnant gtnatnggng cntntttntnt nttngncnac naangnctnt  1740
ncanananag ngnatnacac nctctgtctt cggttgttct gatttttgcc ggcntgtgct  1800
gccattctcg tccatcatca tttcnatgat aggtaacaac aanggcgntg ggctgtcgct  1860
gccaactggn actttgagtg cncnagctgc ntgatnggtg agcctgcaga accttgtttt  1920
tcnttgttca tcnatccact agtaggttnt agtagtttaa aaaggataa taggtacggt  1980
gtttggtttc ganctctgat ggcananatg atacgaaagc aactcctgtn gtntnatcat  2040
gcaaaatgca tgcccccgtn ctatagaatc atcctgacct tattgggaca gctggtgngt  2100
tcatcatctg atctgatgan tagctnatgt gtcgtattca tagnttaagt atatataggt  2160
cctngtatat aattttgccg cggnggtcac atgtcntgca tggaacttac ttaaatgtgt  2220
ntcgatntat ttgnatctct ctgggccgaa tgcttgttct cccacacaga cacagcaana  2280
```

```
actattttc agtcagcngc ttctnctnac ctgtntcaaa taaaaaaatg tgcnagtcgt    2340
ttaaactcaa ctgataggga tggtgaggtt tgaccgntcn atanatatat ccatttcacg    2400
ttctggccag cagatgactg ctntatatct ctgcagtcct gtcagattta ttctgtmatt    2460
atcngaaanc accttatgtn tttgntgtgt agccaatatg ctatattcat catggattta    2520
agtatgtgtg tgtctcctaa tctgtacntt tagcaatgaa atatatgtcc aacttttca    2580 ttaatgtgtt gtggccca                                                  2598
```

<210> SEQ ID NO 37
<211> LENGTH: 2599
<212> TYPE: DNA
<213> ORGANISM: Zea mays
<220> FEATURE:
<221> NAME/KEY: misc_feature
<222> LOCATION: (1)..(2599)
<223> OTHER INFORMATION: n is a, c, g, or t
<220> FEATURE:
<221> NAME/KEY: misc_feature
<222> LOCATION: (631)..(631)
<223> OTHER INFORMATION: w is a or t

<400> SEQUENCE: 37

```
ctcaccgagt aagcccctat ctctctctct ctcttttcag cctttttnat taatttgcct      60
tatcttcttc antcangagt gttttatgt tctctttgtc gttcgttcct gtgcnggcag     120
atcgcgatat acaccggccc caccggtaag tcacggncgt cgtcagttng ntnccacncg     180 gccgntttt tccaagccta acgctngctt ctgctgctgt tctgctctgc tgcatggcgc     240
gtgtgcagtg ggcggccncc tcaacgcgac gtgnggcaac nccacnganc tcatcatcgc     300
gctcttcgcg ctcatggngg gccagatnga ggtcgtcaag tgctccctcc tcggctccnt     360
cctctccaac ctgctgctcg tgctcggcac gtccctcttc tgcggcggcg tcntcaacct     420
cggctccnac cagccntang acngggtgcg tgcgtacaaa caacnaanan cgtcntcnac     480
ctcttctcca cactgcanga gcgccntcga tcntaataat gtgtatataa ngcngcncgn     540
tatnaatata ttattatata tatgcagacn caagcggacg tcagcacggg cctcctcatc     600
ctcggcgtgc tgngccagtc gctgccgctc wngctgcgct angcggtggg cgccggcgag     660
cactccgtcg ccgcgnccac cacggtgctc gacctctccc gcgcctgcag cgtcgtcatg     720
ctgctngcct acgtcgccta cctcttcttc cagctcaaga cgcacgcgca gctgttcgag     780
ccgcaggagg tggacgacgg ctgcgaggcg gaagaggacg agcaggccgt catcggcttc     840
gccagcggnt cttctggctn gccttcaaca ccgtgctcat cgccatcctg tccgagtacg     900
tngtcggcac natcgaggta cagccgtacn tacagtacag tacagtncag tacatgcngt     960 ttatnttnt actnctacnc atcntcnttc nattcgtncc ctctgttctt gttaattaat    1020
nannnntnnn nacngccagc ctacctccaa ntcctggggt ttgtccgtca gcttcatcag    1080
catcatactt ctncccatcg tggggaacgc cgcggagcac gccggagcaa tcattttgc    1140 tctcaagaac aagctggtac tgtacctagc cttcacacac ccanaccng nccngantat    1200 nccncntgtc tcantgncan gtntgntcan anccncntgc ntgnanttna aattanctcn    1260
cncngaancc nganacacag gacattaccc tcggagtagc gttggggtcg gcgacccaga    1320
tctccatgtt tgtggtgggt attgcaattt aaaactgacg cgtacagatt tcattcgctt    1380
aaactattna actaccgaat catgctggaa taatcgtacg actatgcttc ngtatacgcc    1440
aaacgagaca ggtgccgctg agtgtcattg tagcttggat cgcgggtatt caaatggatc    1500
```

```
ttgacttcaa gctcatagag accggctctc tcttcgtctc agtnatagtg acagcattca      1560
cccnccagnt acacacacac acatacatan anacacacta cancatactc tccnttctna      1620
tcangatgna cntcnantna tnatcactnc ngcctngcng ngnttngtca cnccctnaggg     1680 gatcnttntg ntgntgtnan tgtnatnggn gcntnttntn tnttngncna cnaangnctn      1740
tncananana gngnatnaca cnctctgtct tcggttgttc tgattttgc cggcntgtgc       1800 tgccattctc gtccatcatc atttcnatga taggtaacaa caanggcgnt gggcgtcgc       1860 tgccaactgg nactttgagt gcncnagctg cntgatnggt gagcctgcag aaccttgttt     1920
ttcnttgttc atcnatccac tagtaggttn tagtagttta aaaaaggata ataggtacgg      1980
tgtttggttt cganctctga tggcananat gatacgaaag caactcctgt ngtntnatca      2040
tgcaaaatgc atgcccccgt nctatagaat catcctgacc ttattgggac agctggtgng     2100
ttcatcatct gatctgatga ntagctnatg tgtcgtattc atagnttaag tatatatagg     2160
tcctngtata taattttgcc gcggnggtca catgtcntgc atggaactta cttaaatgtg    2220
tntcgatnta tttgnatctc tctgggccga atgcttgttc tcccacacag acacagcaan     2280 aactatttt cagtcagcng cttctnctna cctgtntcaa ataaaaaat gtgcnagtcg     2340 tttaaactca actgataggg atggtgaggt ttgaccgntc natanatata tccatttcac      2400
gttctggcca gcagatgact gctntatatc tctgcagtcc tgtcagattt attctgtnat      2460
tatcngaaan caccttatgt ntttgntgtg tagccaatat gctatattca tcatggattt     2520
aagtatgtgt gtgtctccta atctgtacnt ttagcaatga aatatatgtc caactttttc      2580
attaatgtgt tgtggccca                                                  2599

<210> SEQ ID NO 38
<211> LENGTH: 4251
<212> TYPE: DNA
<213> ORGANISM: Zea mays
<220> FEATURE:
<221> NAME/KEY: misc_feature
<222> LOCATION: (1)..(4251)
<223> OTHER INFORMATION: n is a, c, g, or t
<220> FEATURE:
<221> NAME/KEY: misc_feature
<222> LOCATION: (945)..(945)
<223> OTHER INFORMATION: r is a or g

<400> SEQUENCE: 38
ttttggacgc ctattaggac gacagggatg tatttgacng ncnaataatg tttngnagan       60
ctatatnata cctanatagg cacanaaaan ancnaacggc aactcnatac taancaagtn      120
cttttgttcn gttanttcta atttcantgn attatggtgn acnggatcag nttnaatnaa      180
ttttgncttg tgctatatat ttanacggat tcaatanaca cccaatctac tacatgnatn      240
aacgntnaaa cgaataagac gacgtgnaaa ttttgctctc aacgtgnatt tttaaaactc      300
tgggggttgg gcagatgaaa cgagaatata cgacgaggnt ancttnttt tttaccataa       360 cgtaaataat gaccttgaca tacatcagtg cngtgatcaa tctatataca gattaattaa      420
tagccgctag ctgggantta ttcacattat tgtcccaaga anctaaaaca tgcatgcatg     480
catgatgcat ggnatcatca tcagttgaag atgtcctggc cggggagag cagcctcttg     540 gggtcgtact tgttcttcat ctccacgaag cgattccact tggcggcgcc gaagtggcgg     600
acccagtcac tgcggtccgt gtgccgcgcc aggtaggtct tgtactggat cccggcgagg     660
tcgcagaagc gcaggatcct cctgttctgc tcctgcagcc tcgccaggtc gttgggcgcc     720
accgacgaga agagcagcga caccgcgtag aacacgtcct cngacggcgt cgccgccgac     780
```

```
atgccgtcgt cccacctgaa aaaccaaacc ccagaaagac nggtcnagtc gtcagaggcc      840
ggccggggcg tgcctagcta gctagctagc cgatcgattc aacacgtaca tggatttgtt      900
gaggggtag acgatgagcg ggccgacgat gtcggtgccc tgcargatgc ccttgaanac       960
gccgcggtcg aagtcggcga tgcgcgagcg cggcacgaac atgttgagcc acgggtgcgg     1020
cacccgccac agccccagct tgttgagcgc cacctcctcg ccgtgcaccc ggtcaaggaa     1080
cgccgngtag gncacgtcgc gctggaacgc gaaccntcc acgtagctca gcgtgcccag      1140
cacggacgcg agctcctggt ccaccgccgc cgccgccgcc gtggcgttgt cgtagttgag     1200
cgtggcctcg atgctgtaca cggtggtggc gttccgctcc ccggcgagcg cgacgatccg     1260
ggcgacgtcg gcgtcggtga agaaccccgt gttcgccagg tcggtcgcca ggctctggtt     1320
cacgaacacc gaccctttcca cgtagctcat cgggccgaac gacgcgccgc cgccgccggg    1380
ccgcggggcg gtcagccgct cctggtcggc gctgaacgcc gcgaagtcgg tgtacacgag     1440
ccgcacccac cgcgcccgcg ccggcgccgg ctccaccgcg atccgggccc gggtgatcac     1500
tccgaactgc cccagcccgc ccaggacggc gtcgaacagg tccgcgttca gctgcttgga     1560
gcacgtcacc atctccccat ggcctgcgtt cgatcaccac aaagtcaacn ccccagcant    1620
ntaantctat tagccgaaac gaacaaaggc acaatgtcaa cgcancagcg ctgcgagagc     1680
cagcatgcat gctgatttat gactagttat taaagacgtc gccgcccctc gccggccggg    1740
cgggcggccg gccggtgcag cgcggacatt aaccaccatg caccactaat aatactanaa     1800
ataaataaat atatgattcg cantgtaggt aacgaatttc aatccggctg attgaacacg     1860
gtgttgcccc gtggnaagca acagaagtcg atgcaggtgt antgncncgt aaaaaaaaaa     1920
caagcttttg cttgcttgct ggtgtggttg tgcaagggag ggaaaagtag tngtaggtgc     1980
acacgtaccg gtgataacgt ccatctccag cacgttagat atctgtgggc cgtggcggaa     2040
cgcctggccg ctgatgcctg cgttggacag cgtgccgccg acggtgaggt agaggtagtc     2100
ggtccaggag cgcggcgcca cgccgcgcgc cagngacgcg cgcancacgt cgatccacac     2160
ctgctcgccg ccggcgtcca cgtagcggcc gtccgcggac acgttgatgc gcggcggcgc     2220
ggcggcgtcg cccagggacg ccatgttgac gacgacgccg ccggggggcga aggcctggcc    2280
catgagggag tggccgcncg cggaacgnga tggtgtaggg ccaccccggg gtggagttgg     2340
ccgcgctcag cagcgccacc aggtcgncng tggacnangg gtacaggacc gccgccngga     2400
gcgccgacgt gatgttgccn aantccgtcn aggccgcngc cgtcgcgttg ctgtcggtcc     2460
ggagcttgcc gtccaaggcc agcgcggcga ggnagnctgg ccaggggacgg ccgcgatcnt    2520
ctccgagcgc angcgtgcct gccgctagtg catgagagca ggcgatcagc ncggccagca    2580
gcaggtaata aaccaccgcc nttagcgacg tcgtcgttca cggagagag agagagagag      2640
agctatacnt tatgtgtgag tgtttggtaa ctaggtgatt gcnccccgta tatatatagg     2700
anggatacgg cggcacatac gtgtaggtgt antgcgatta catacttctt caattacgta    2760
ctcgaacaca gagatgagct gctttccaag gaaaaaaaaa nattctgcat cccgtctagt    2820
tttattctgt ttgaccacag aaaaatatgc gcacaagtaa ggtgcctagt taccaacttn   2880
accatcctnc aagaatntac agangangna naaactatta tatatatngt cctgcctant   2940
aattaccccc tgttgccatg caatgcaata tancgtattt atacatttaa aaanctgtaa   3000
tnataaatat aagcgatcaa ttcttgagaa tgnaatagtt ttcncacnaa atagtngtac   3060
aaatttggta gctagctata ggtgtgtgtt gaccatatca atcgtttgnt tatgaaataa   3120
```

```
aanangccgt cttttatgtt atnacttaat gtntgtgtgt gcctnctcaa aatngtctct     3180
actagacaga cagctgtacn gcattacgta caggacgacg aaggaaagca ggctgtaatt     3240
ttggtactng tacgancgnc ccagctggtt ggtcgacttc caaaatacac naagctgatg     3300
aaggtttaat caagctagcc acgattatta ttctggccat attatttgat ttgctaccag     3360
aacaanctgc caaacttctc atattttgct atcaaaaang tcgctagcct ngggatctta     3420
tananatnta tatatagaga gagatttctt gtcgctttat ctcaccttaa cagccatgaa     3480
tnaatatagg attgattaag caaatggcaa cattttggaa acaaacaatc gtccctagct     3540
tgattgggac aattatattt ttgttcggta agtcgcgtca acatacgtta ctactacact     3600
acnacnanan tngtntnaga ngncntntng ntagntntna natntnggnt nttntntntt     3660
tttttntntn tntnaanaan anantngtna ncacacngta cntntttntn ttntntnttt     3720
ncncnccagc tccacgaaca acacgtacgg acttcggaat tcgccgnatg ctgntnatag     3780
aacaaattag cacgcatgac ttacacatgn gtattctaat tttgagtcaa tgactantat     3840
tctntccngt accagtngtn atacatagca gccgttgttt cagctagcta gtaggtagaa     3900
tttctacgca cgaccacact gtaattttgg ttggtgatac gaaaatgaca tcccatccaa     3960
ataatccata tatagatcat actttaagtt acagttttt ttccaatata tgactcgagc     4020
atgcgcagcc tcctctcgtc gtcggagtct cgagatcgga tgccgccaat ttttatgttt     4080
tggccgcttg ccgcttgcag tgactccagg cagcgcatac agacgcgcgc gtgacggcgg     4140
tgaaaccgac gatgcgtctg catcgcgacc gatttttttt ctatttagc cctttccgtg     4200 ttttattttc acaaataggt tcttttatt tgaatttaga atatggacct t              4251
```

<210> SEQ ID NO 39
<211> LENGTH: 4251
<212> TYPE: DNA
<213> ORGANISM: Zea mays
<220> FEATURE:
<221> NAME/KEY: misc_feature
<222> LOCATION: (1)..(4251)
<223> OTHER INFORMATION: n is a, c, g, or t
<220> FEATURE:
<221> NAME/KEY: misc_feature
<222> LOCATION: (2378)..(2378)
<223> OTHER INFORMATION: y is c or t

<400> SEQUENCE: 39

```
ttttggacgc ctattaggac gacagggatg tatttgacng ncnaataatg tttngnagan      60
ctatatnata cctanatagg cacanaaaan ancnaacggc aactcnatac taancaagtn     120
cttttgttcn gttanttcta atttcantgn attatggtgn acnggatcag nttnaatnaa     180
ttttgncttg tgctatatat ttanacggat tcaatanaca cccaatctac tacatgnatn     240
aacgntnaaa cgaataagac gacgtgnaaa ttttgctctc aacgtgnatt tttaaaactc     300
tgggggttgg gcagatgaaa cgagaatata cgacgaggnt ancttntttt tttaccataa     360
cgtaaataat gaccttgaca tacatcagtg cngtgatcaa tctatataca gattaattaa     420
tagccgctag ctgggantta ttcacattat tgtcccaaga anctaaaaca tgcatgcatg     480
catgatgcat ggnatcatca tcagttgaag atgtcctggc cgggggagag cagcctcttg     540
gggtcgtact tgttcttcat ctccacgaag cgattccact tggcggcgcc gaagtggcgg     600
acccagtcac tgcggtccgt gtgccgcgcc aggtaggtct tgtactggat cccggcgagg     660
tcgcagaagc gcaggatcct cctgttctgc tcctgcagcc tcgccaggtc gttgggcgcc     720
accgacgaga agagcagcga caccgcgtag aacacgtcct cngacggcgt cgccgccgac     780
```

-continued

```
atgccgtcgt cccacctgaa aaaccaaacc ccagaaagac nggtcnagtc gtcagaggcc      840
ggccggggcg tgcctagcta gctagctagc cgatcgattc aacacgtaca tggatttgtt      900
gaggggtag acgatgagcg ggccgacgat gtcggtgccc tgcangatgc ccttgaanac       960
gccgcggtcg aagtcggcga tgcgcgagcg cggcacgaac atgttgagcc acgggtgcgg     1020
cacccgccac agccccagct tgttgagcgc cacctcctcg ccgtgcaccc ggtcaaggaa     1080
cgccgngtag gncacgtcgc gctggaacgc gaacccntcc acgtagctca gcgtgcccag     1140
cacggacgcg agctcctggt ccaccgccgc cgccgccgcc gtggcgttgt cgtagttgag     1200
cgtggcctcg atgctgtaca cggtggtggc gttccgctcc ccggcgagcg cgacgatccg     1260
ggcgacgtcg gcgtcggtga agaaccccgt gttcgccagg tcggtcgcca ggctctggtt     1320
cacgaacacc gaccccttcca cgtagctcat cgggccgaac gacgcgccgc cgccgccggg   1380
ccgcggggcg gtcagccgct cctggtcggc gctgaacgcc gcgaagtcgg tgtacacgag     1440
ccgcacccac cgcgcccgcg ccggcgccgg ctccaccgcg atccgggccc gggtgatcac     1500
tccgaactgc cccagcccgc ccaggacggc gtcgaacagg tccgcgttca gctgcttgga     1560
gcacgtcacc atctccccat ggcctgcgtt cgatcaccac aaagtcaacn ccccagcant     1620
ntaantctat tagccgaaac gaacaaaggc acaatgtcaa cgcancagcg ctgcgagagc     1680
cagcatgcat gctgatttat gactagttat taaagacgtc gccgcccctc gccggccggg     1740
cgggcggccg gccggtgcag cgcggacatt aaccaccatg caccactaat aatactanaa    1800
ataaataaat atatgattcg cantgtaggt aacgaatttc aatccggctg attgaacacg    1860
gtgttgcccc gtggnaagca acagaagtcg atgcaggtgt antgncncgt aaaaaaaaaa    1920
caagcttttg cttgcttgct ggtgtggttg tgcaagggag ggaaaagtag tngtaggtgc    1980
acacgtaccg gtgataacgt ccatctccag cacgttagat atctgtgggc cgtggcggaa    2040
cgcctggccg ctgatgcctg cgttggacag cgtgccgccg acggtgaggt agaggtagtc    2100
ggtccaggag cgcggcgcca cgccgcgcgc cagngacgcg cgcancacgt cgatccacac    2160
ctgctcgccg ccggcgtcca cgtagcggcc gtccgcggac acgttgatgc gcggcggcgc    2220
ggcggcgtcg cccagggacg ccatgttgac gacgacgccc ccggggggcga aggcctggcc   2280
catgagggag tggccgccncg cggaacgnga tggtgtaggg ccaccccggg gtggagttgg    2340
ccgcgctcag cagcgccacc aggtcgncng tggacnaygg gtacaggacc gccgccngga    2400
gcgccgacgt gatgttgccn aantccgtcn aggccgcngc cgtcgcgttg ctgtcggtcc    2460
ggagcttgcc gtccaaggcc agcgcggcga ggnagnctgg ccaggacgg ccgcgatcnt     2520
ctccgagcgc angcgtgcct gccgctagtg catgagagca ggcgatcagc ncggccagca    2580
gcaggtaata aaccaccgcc nttagcgacg tcgtcgttca cggagagag agagagagag     2640
agctatacnt tatgtgtgag tgtttggtaa ctaggtgatt gcnccccgta tatatatagg    2700
anggatacgg cggcacatac gtgtaggtgt antgcgatta catacttctt caattacgta    2760
ctcgaacaca gagatgagct gctttccaag gaaaaaaaaa nattctgcat cccgtctagt    2820
tttattctgt ttgaccacag aaaaatatgc gcacaagtaa ggtgcctagt taccaacttn    2880
accatcctnc aagaatntac agangangna naaactatta tatatatngt cctgcctant    2940
aattacccc tgttgccatg caatgcaata tancgtattt atacatttaa aanctgtaa     3000
tnataaatat aagcgatcaa ttcttgagaa tgnaatagtt ttcncacnaa atagtngtac    3060
aaatttggta gctagctata ggtgtgtgtt gaccatatca atcgtttgnt tatgaaataa    3120
```

```
aanangccgt cttttatgtt atnacttaat gtntgtgtgt gcctnctcaa aatngtctct    3180
actagacaga cagctgtacn gcattacgta caggacgacg aaggaaagca ggctgtaatt    3240
ttggtactng tacgancgnc ccagctggtt ggtcgacttc caaaatacac naagctgatg    3300
aaggtttaat caagctagcc acgattatta ttctggccat attatttgat ttgctaccag    3360
aacaanctgc caaacttctc atattttgct atcaaaaang tcgctagcct ngggatctta    3420
tananatnta tatatagaga gagatttctt gtcgctttat ctcaccttaa cagccatgaa    3480
tnaatatagg attgattaag caaatggcaa cattttggaa acaaacaatc gtccctagct    3540
tgattgggac aattatattt ttgttcggta agtcgcgtca acatacgtta ctactacact    3600
acnacnanan tngtntnaga ngncntntng ntagntntna natntnggnt nttntntntt    3660
tttttntntn tntnaanaan anantngtna ncacacngta cntntttntn ttntntnttt    3720
ncncnccagc tccacgaaca acacgtacgg acttcggaat tcgccgnatg ctgntnatag    3780
aacaaattag cacgcatgac ttacacatgn gtattctaat tttgagtcaa tgactantat    3840
tctntccngt accagtngtn atacatagca gccgttgttt cagctagcta gtaggtagaa    3900
tttctacgca cgaccacact gtaattttgg ttggtgatac gaaaatgaca tcccatccaa    3960
ataatccata tatagatcat actttaagtt acagttttt ttccaatata tgactcgagc    4020
atgcgcagcc tcctctcgtc gtcggagtct cgagatcgga tgccgccaat ttttatgttt    4080
tggccgcttg ccgcttgcag tgactccagg cagcgcatac agacgcgcgc gtgacggcgg    4140
tgaaaccgac gatgcgtctg catcgcgacc gatttttttt ctatttagc cctttcgtg    4200 ttttattttc acaaataggt tctttttatt tgaatttaga atatggacct t             4251
```

<210> SEQ ID NO 40
<211> LENGTH: 4251
<212> TYPE: DNA
<213> ORGANISM: Zea mays
<220> FEATURE:
<221> NAME/KEY: misc_feature
<222> LOCATION: (1)..(4251)
<223> OTHER INFORMATION: n is a, c, g, or t
<220> FEATURE:
<221> NAME/KEY: misc_feature
<222> LOCATION: (3860)..(3860)
<223> OTHER INFORMATION: w is a or t

<400> SEQUENCE: 40

```
ttttggacgc ctattaggac gacagggatg tatttgacng ncnaataatg tttngnagan      60
ctatatnata cctanatagg cacanaaaan ancnaacggc aactcnatac taancaagtn     120
cttttgttcn gttanttcta atttcantgn attatggtgn acnggatcag nttnaatnaa     180
ttttgncttg tgctatatat ttanacggat tcaatanaca cccaatctac tacatgnatn     240
aacgntnaaa cgaataagac gacgtgnaaa ttttgctctc aacgtgnatt tttaaaactc     300
tgggggttgg gcagatgaaa cgagaatata cgacgaggnt ancttnttt tttaccataa      360 cgtaaataat gaccttgaca tacatcagtg cngtgatcaa tctatataca gattaattaa     420
tagccgctag ctgggantta ttcacattat tgtcccaaga anctaaaaca tgcatgcatg     480
catgatgcat ggnatcatca tcagttgaag atgtcctggc cggggagag cagcctcttg      540 gggtcgtact tgttcttcat ctccacgaag cgattccact tggcggcgcc gaagtggcgg     600
acccagtcac tgcggtccgt gtgccgcgca aggtaggtct tgtactggat cccggcgagg     660
tcgcagaagc gcaggatcct cctgttctgc tcctgcagcc tcgccaggtc gttgggcgcc     720
accgacgaga agagcagcga caccgcgtag aacacgtcct cngacggcgt cgccgccgac     780
```

-continued

```
atgccgtcgt cccacctgaa aaaccaaacc ccagaaagac nggtcnagtc gtcagaggcc      840
ggccggggcg tgcctagcta gctagctagc cgatcgattc aacacgtaca tggatttgtt      900
gaggggtag acgatgagcg ggccgacgat gtcggtgccc tgcangatgc ccttgaanac       960
gccgcggtcg aagtcggcga tgcgcgagcg cggcacgaac atgttgagcc acgggtgcgg     1020
cacccgccac agccccagct tgttgagcgc cacctcctcg ccgtgcaccc ggtcaaggaa     1080
cgccgngtag gncacgtcgc gctggaacgc gaaccntcc acgtagctca gcgtgcccag      1140
cacggacgcg agctcctggt ccaccgccgc cgccgccgcc gtggcgttgt cgtagttgag     1200
cgtggcctcg atgctgtaca cggtggtggc gttccgctcc ccggcgagcg cgacgatccg     1260
ggcgacgtcg gcgtcggtga agaacccgt gttcgccagg tcggtcgcca ggctctggtt      1320
cacgaacacc gacccttcca cgtagctcat cgggccgaac gacgcgccgc cgccgccggg     1380
ccgcggggcg gtcagccgct cctggtcggc gctgaacgcc gcgaagtcgg tgtacacgag     1440
ccgcacccac cgcgcccgcg ccggcgccgg ctccaccgcg atccgggccc gggtgatcac     1500
tccgaactgc cccagcccgc ccaggacggc gtcgaacagg tccgcgttca gctgcttgga     1560
gcacgtcacc atctccccat ggcctgcgtt cgatcaccac aaagtcaacn ccccagcant     1620
ntaantctat tagccgaaac gaacaaaggc acaatgtcaa cgcancagcg ctgcgagagc     1680
cagcatgcat gctgatttat gactagttat taaagacgtc gccgcccctc gccggccggg     1740
cgggcggccg gccggtgcag cgcggacatt aaccaccatg caccactaat aatactanaa     1800
ataaataaat atatgattcg cantgtaggt aacgaatttc aatccggctg attgaacacg     1860
gtgttgcccc gtggnaagca acagaagtcg atgcaggtgt antgncncgt aaaaaaaaaa     1920
caagcttttg cttgcttgct ggtgtggttg tgcaagggag ggaaaagtag tngtaggtgc     1980
acacgtaccg gtgataacgt ccatctccag cacgttagat atctgtgggc cgtggcggaa     2040
cgcctggccg ctgatgcctg cgttggacag cgtgccgccg acggtgaggt agaggtagtc     2100
ggtccaggag cgcggcgcca cgccgcgcgc cagngacgcg cgcancacgt cgatccacac     2160
ctgctcgccg ccggcgtcca cgtagcggcc gtccgcggac acgttgatgc gcggcggcgc     2220
ggcggcgtcg cccagggacg ccatgttgac gacgacgccg ccggggggcga aggcctggcc     2280
catgagggag tggccgccncg cggaacgnga tggtgtaggg ccaccccggg gtggagttgg     2340
ccgcgctcag cagcgccacc aggtcgncng tggacnangg gtacaggacc gccgccngga     2400
gcgccgacgt gatgttgccn aantccgtcn aggccgcngc cgtcgcgttg ctgtcggtcc     2460
ggagcttgcc gtccaaggcc agcgcggcga ggnagnctgg ccaggacgg ccgcgatcnt      2520
ctccgagcgc angcgtgcct gccgctagtg catgagagca ggcgatcagc ncggccagca     2580
gcaggtaata aaccaccgcc nttagcgacg tcgtcgttca cggagagag agagagagag      2640
agctatacnt tatgtgtgag tgtttggtaa ctaggtgatt gcnccccgta tatatagg       2700
anggatacgg cggcacatac gtgtaggtgt antgcgatta catacttctt caattacgta     2760
ctcgaacaca gagatgagct gctttccaag gaaaaaaaaa nattctgcat cccgtctagt     2820
tttattctgt ttgaccacag aaaaatatgc gcacaagtaa ggtgcctagt taccaacttn     2880
accatcctnc aagaatntac agangangna naaactatta tatatatngt cctgcctant     2940
aattacccc tgttgccatg caatgcaata tancgtattt atacatttaa aaanctgtaa      3000
tnataaatat aagcgatcaa ttcttgagaa tgnaatagtt ttcncacnaa atagtngtac     3060
aaatttggta gctagctata ggtgtgtgtt gaccatatca atcgtttgnt tatgaaataa     3120
```

| | |
|---|---|
| aanangccgt cttttatgtt atnacttaat gtntgtgtgt gcctnctcaa aatngtctct | 3180 |
| actagacaga cagctgtacn gcattacgta caggacgacg aaggaaagca ggctgtaatt | 3240 |
| ttggtactng tacgancgnc ccagctggtt ggtcgacttc caaaatacac naagctgatg | 3300 |
| aaggtttaat caagctagcc acgattatta ttctggccat attatttgat ttgctaccag | 3360 |
| aacaanctgc caaacttctc atattttgct atcaaaaang tcgctagcct ngggatctta | 3420 |
| tananatnta tatatagaga gagatttctt gtcgctttat ctcaccttaa cagccatgaa | 3480 |
| tnaatatagg attgattaag caaatggcaa cattttggaa acaaacaatc gtccctagct | 3540 |
| tgattgggac aattatattt ttgttcggta agtcgcgtca acatacgtta ctactacact | 3600 |
| acnacnanan tngtntnaga ngncntntng ntagntntna natntnggnt nttntntntt | 3660 |
| tttttntntn tntnaanaan anantngtna ncacacngta cntntttntn ttntntnttt | 3720 |
| ncncnccagc tccacgaaca acacgtacgg acttcggaat tcgccgnatg ctgntnatag | 3780 |
| aacaaattag cacgcatgac ttacacatgn gtattctaat tttgagtcaa tgactantat | 3840 |
| tctntccngt accagtngtw atacatagca gccgttgttt cagctagcta gtaggtagaa | 3900 |
| tttctacgca cgaccacact gtaattttgg ttggtgatac gaaaatgaca tcccatccaa | 3960 |
| ataatccata tatagatcat actttaagtt acagttttt ttccaatata tgactcgagc | 4020 |
| atgcgcagcc tcctctcgtc gtcggagtct cgagatcgga tgccgccaat ttttatgttt | 4080 |
| tggccgcttg ccgcttgcag tgactccagg cagcgcatac agacgcgcgc gtgacggcgg | 4140 |
| tgaaaccgac gatgcgtctg catcgcgacc gattttttt ctattttagc ccttttcgtg | 4200 |
| ttttattttc acaaataggt tcttttatt tgaatttaga atatggacct t | 4251 |

<210> SEQ ID NO 41
<211> LENGTH: 4251
<212> TYPE: DNA
<213> ORGANISM: Zea mays
<220> FEATURE:
<221> NAME/KEY: misc_feature
<222> LOCATION: (1)..(4251)
<223> OTHER INFORMATION: n is a, c, g, or t
<220> FEATURE:
<221> NAME/KEY: misc_feature
<222> LOCATION: (2519)..(2519)
<223> OTHER INFORMATION: k is g or t

<400> SEQUENCE: 41

| | |
|---|---|
| ttttggacgc ctattaggac gacagggatg tatttgacng ncnaataatg tttngnagan | 60 |
| ctatatnata cctanatagg cacanaaaan ancnaacggc aactcnatac taancaagtn | 120 |
| cttttgttcn gttanttcta atttcantgn attatggtgn acnggatcag nttnaatnaa | 180 |
| ttttgncttg tgctatatat ttanacggat tcaatanaca cccaatctac tacatgnatn | 240 |
| aacgntnaaa cgaataagac gacgtgnaaa ttttgctctc aacgtgnatt tttaaaactc | 300 |
| tgggggttgg gcagatgaaa cgagaatata cgacgaggnt ancttnttt tttaccataa | 360 |
| cgtaaataat gaccttgaca tacatcagtg cngtgatcaa tctatataca gattaattaa | 420 |
| tagccgctag ctgggantta ttcacattat tgtcccaaga anctaaaaca tgcatgcatg | 480 |
| catgatgcat ggnatcatca tcagttgaag atgtcctggc cggggagag cagcctcttg | 540 |
| gggtcgtact tgttcttcat ctccacgaag cgattccact tggcggcgcc gaagtggcgg | 600 |
| acccagtcac tgcggtccgt gtgccgcgcg aggtaggtct tgtactggat cccggcgagg | 660 |
| tcgcagaagc gcaggatcct cctgttctgc tcctgcagcc tcgccaggtc gttgggcgcc | 720 |
| accgacgaga agagcagcga caccgcgtag aacacgtcct cngacggcgt cgccgccgac | 780 |

```
atgccgtcgt cccacctgaa aaaccaaacc ccagaaagac nggtcnagtc gtcagaggcc      840
ggccggggcg tgcctagcta gctagctagc cgatcgattc aacacgtaca tggatttgtt      900
gaggggtag acgatgagcg ggccgacgat gtcggtgccc tgcangatgc ccttgaanac       960
gccgcggtcg aagtcggcga tgcgcgagcg cggcacgaac atgttgagcc acgggtgcgg     1020
cacccgccac agccccagct tgttgagcgc cacctcctcg ccgtgcaccc ggtcaaggaa     1080
cgccgngtag gncacgtcgc gctggaacgc gaacccntcc acgtagctca gcgtgcccag     1140
cacggacgcg agctcctggt ccaccgccgc cgccgccgcc gtggcgttgt cgtagttgag     1200
cgtggcctcg atgctgtaca cggtggtggc gttccgctcc ccggcgagcg cgacgatccg     1260
ggcgacgtcg gcgtcggtga agaacccgt gttcgccagg tcggtcgcca ggctctggtt      1320
cacgaacacc gacccttcca cgtagctcat cgggccgaac gacgcgccgc cgccgccggg     1380
ccgcggggcg gtcagccgct cctggtcggc gctgaacgcc gcgaagtcgg tgtacacgag     1440
ccgcacccac cgcgcccgcg ccggcgccgg ctccaccgcg atccgggccc gggtgatcac     1500
tccgaactgc cccagcccgc ccaggacggc gtcgaacagg tccgcgttca gctgcttgga     1560
gcacgtcacc atctccccat ggcctgcgtt cgatcaccac aaagtcaacn ccccagcant     1620
ntaantctat tagccgaaac gaacaaaggc acaatgtcaa cgcancagcg ctgcgagagc     1680
cagcatgcat gctgatttat gactagttat taaagacgtc gccgcccctc gccggccggg     1740
cgggcggccg gccggtgcag cgcggacatt aaccaccatg caccactaat aatactanaa     1800
ataaataaat atatgattcg cantgtaggt aacgaatttc aatccggctg attgaacacg     1860
gtgttgcccc gtggnaagca acagaagtcg atgcaggtgt antgncncgt aaaaaaaaaa     1920
caagcttttg cttgcttgct ggtgtggttg tgcaagggag ggaaaagtag tngtaggtgc     1980
acacgtaccg gtgataacgt ccatctccag cacgttagat atctgtgggc cgtggcggaa     2040
cgcctggccg ctgatgcctg cgttggacag cgtgccgccg acggtgaggt agaggtagtc     2100
ggtccaggag cgcggcgcca cgccgcgcgc cagngacgcg cgcancacgt cgatccacac     2160
ctgctcgccg ccggcgtcca cgtagcggcc gtccgcggac acgttgatgc gcggcggcgc     2220
ggcggcgtcg cccagggacg ccatgttgac gacgacgccc ccggggggcga aggcctggcc     2280
catgagggag tggccgcncg cggaacgnga tggtgtaggg ccaccccggg gtggagttgg     2340
ccgcgctcag cagcgccacc aggtcgncng tggacnangg gtacaggacc gccgccngga     2400
gcgccgacgt gatgttgccn aantccgtcn aggccgcngc cgtcgcgttg ctgtcggtcc     2460
ggagcttgcc gtccaaggcc agcgcggcga ggnagnctgg ccaggacgg ccgcgatckt      2520
ctccgagcgc angcgtgcct gccgctagtg catgagagca ggcgatcagc ncggccagca     2580
gcaggtaata aaccaccgcc nttagcgacg tcgtcgttca cggagagag agagagagag      2640
agctatacnt tatgtgtgag tgtttggtaa ctaggtgatt gcncccgta tatatagg        2700
anggatacgg cggcacatac gtgtaggtgt antgcgatta catacttctt caattacgta     2760
ctcgaacaca gagatgagct gctttccaag gaaaaaaaaa nattctgcat cccgtctagt     2820
tttattctgt ttgaccacag aaaaatatgc gcacaagtaa ggtgcctagt taccaacttn     2880
accatcctnc aagaatntac agangangna naaactatta tatatatngt cctgcctant     2940
aattacccccc tgttgccatg caatgcaata tancgtatt atacattttaa aaanctgtaa   3000
tnataaatat aagcgatcaa ttcttgagaa tgnaatagtt ttcncacnaa atagtngtac     3060
aaatttggta gctagctata ggtgtgtgtt gaccatatca atcgtttgnt tatgaaataa     3120
```

```
aanangccgt cttttatgtt atnacttaat gtntgtgtgt gcctnctcaa aatngtctct   3180
actagacaga cagctgtacn gcattacgta caggacgacg aaggaaagca ggctgtaatt   3240
ttggtactng tacgancgnc ccagctggtt ggtcgacttc caaaatacac naagctgatg   3300
aaggtttaat caagctagcc acgattatta ttctggccat attatttgat ttgctaccag   3360
aacaanctgc caaacttctc atattttgct atcaaaaang tcgctagcct ngggatctta   3420
tananatnta tatatagaga gagatttctt gtcgctttat ctcaccttaa cagccatgaa   3480
tnaatatagg attgattaag caaatggcaa cattttggaa acaaacaatc gtccctagct   3540
tgattgggac aattatattt ttgttcggta agtcgcgtca acatacgtta ctactacact   3600
acnacnanan tngtntnaga ngncntntng ntagntntna natntnggnt nttntntntt   3660
tttttntntn tntnaanaan anantngtna ncacacngta cntntttntn ttntntnttt   3720
ncncnccagc tccacgaaca acacgtacgg acttcggaat tcgccgnatg ctgntnatag   3780
aacaaattag cacgcatgac ttacacatgn gtattctaat tttgagtcaa tgactantat   3840
tctntccngt accagtngtn atacatagca gccgttgttt cagctagcta gtaggtagaa   3900
tttctacgca cgaccacact gtaattttgg ttggtgatac gaaaatgaca tcccatccaa   3960
ataatccata tatagatcat actttaagtt acagttttt tccaatata tgactcgagc   4020 atgcgcagcc tcctctcgtc gtcggagtct cgagatcgga tgccgccaat ttttatgttt   4080
tggccgcttg ccgcttgcag tgactccagg cagcgcatac agacgcgcgc gtgacggcgg   4140
tgaaaccgac gatgcgtctg catcgcgacc gatttttttt ctatttagc ccttttcgtg   4200 ttttattttc acaaataggt tcttttttatt tgaatttaga atatggacct t   4251
```

<210> SEQ ID NO 42
<211> LENGTH: 5149
<212> TYPE: DNA
<213> ORGANISM: Zea mays
<220> FEATURE:
<221> NAME/KEY: misc_feature
<222> LOCATION: (1)..(5149)
<223> OTHER INFORMATION: n is a, c, g, or t
<220> FEATURE:
<221> NAME/KEY: misc_feature
<222> LOCATION: (903)..(903)
<223> OTHER INFORMATION: r is a or g

<400> SEQUENCE: 42

```
tgcgtttgca ggtgtccgta tagtcgaccg ttgcgctggt agtcgtgact ccgctggtgc     60
accagacagt ccggtggcac accagacagt ccggtgaatt atagcggagt ggcgcttgag    120
aagcccgagg gtggctagtt cagagttgta cggtcctggt gcaccggaca ttgtccggtg    180
gcacaccgga cagtccggtg cgccagacca gggtactctt cggtttcttt tgctcctttc    240
ttttgaaccc taactttgac attttattgg tttgtattga acctttatgt acctgtagaa    300
tatataatct agagcaaact agttagtcca attatttgtg ttgggcattc aaccaccaaa    360
attatttata ggaaaatgtt aagccctatt tcccctttca gcatgcnanc cctngancccc    420 ntaatnggct ncnacncnat acacgaccca acagcccaac agacggtntc gcagcaccaa    480
aacagaatct naacntgant tntttcgacn attcccnttg actccggatn aattttaant    540
ggncagttgg gttggnagnt tatntcctta tctttgcatt catataaaac ccaacctaac    600
cgaagttcgg atgcatcctg gtcgtctatt ttagtgcata ctggtcctag agtccaaggt    660
ggagacgaag ttgagtcaga cttggatttc tcttgntgtg aacgtcctag cttctcctcc    720
ctgacatctt ggtatttccc aagtccttga tggtactctc caaggttcct agagattttg    780
```

```
ttgtcgtgca tgtgctcgtg ttgttggccc atgcattatt tgtataggag tgatgtcttc    840
atcatcctcc ctcattcgaa ttggagttgt cttcgactca ggcgatggcc aaggggatgg    900
ccraacaacc ctaagatgta caaggcatgt aggcccaaaa acatgtgtca ttgatttctg    960
gtagattctg gtcatcatct tgttatgacg attctcatca actccgagta tattttacg    1020
tgggactagt tgggttggaa agcttatcac cttagcttcc caacagtatc tagaacgtca   1080
aaaatggagt atgtagcctg agcgtccgtt ttcgtgagnc nctcttgcag ncgaaccgaa   1140
tttgcnaata aacnggactt caantcccct tgagcttgag attctatgat ngattgagcc   1200
ttgaccatat ngttnacatc catgtactca tgaagtaatg tcgagccaca aatgggttat   1260
gttggncatg cttatnctga ntggatatcc atcctaacat caggctaaat gggtcgacta   1320
taangcagtc gtgctcgagc cgctcgatgg ccttgcacac aagctcatgc atggtccatg   1380
atgggcctcg tgtcggccta ggcacggttt tgtngaaatc cctataatga gtagcatttg   1440
ttgctgccaa ataaaccaac tttaagatgg gatacgatgc tcgataaggc atgaggtttc   1500
agtatcataa cagtttactn gtagtnacgc cnacaaatct catctagaac tctttgtgct   1560
ttgataacat acatatatat gcgttttttgt gctttgaaaa cccnttcgaa ttaaaaaana   1620
tcataattat tgttatttttt tttatcgtaa tattgtttag cacataatat actttntatt   1680
tgagttttca tttattttaa aaataaaata aataggaaga tcggtcaaac gtgacagaaa   1740
aagtcaaatg aattataatt taggatgaag gtgcaggcaa tgccttatat ccagnggacc   1800
acggagaaaa caatacactg cactgtagtt tgacggaaa cagaggcagg caccagtatt   1860
taccatagat atttttctt tataagaagt atcnattttg ccacgttcat atttggctcc   1920
cctcatcccc tgtacagaac cgatcacagc agccatggca gancacgcga ttaacaaccc   1980
cacatttgta catgaaccaa ccggagntaa ctaaacaatc ctgtatggtt acngctgtag   2040
ctagtacctc taccttacac taaacgcgcc taataattag tataagcagc tggattacgt   2100
tacgagtcgg ccgcgagcgc cggcgagccg ggcggcctga agatgccctg ccccgccgcc   2160
aggatggccc gcgggtcgaa ctcggccttg agcctcgcga accggtccca cctcgcggcg   2220
ccgaagtgct ccgcccactc gtgccgcgcc ttgtggcccg gcaggtactg cttggcgccg   2280
atgcccgcgc ccgcgcagaa gtcgaggatc cgctggttct gccgcgccag cgcctccagg   2340
ctctccggcg cgcccggcag cgccgaccgc aggaacgcca ccaggtagaa cacctcctcg   2400
tccggggtca ccgccgagct cctcgggtcc cacctgcgcg cacgaagcag cccgtcngcc   2460
acacggccca gtccagatct canagctgca gtcgctaatc gacgcgaaaa gggtttggna   2520
nactgcacga tactagtaca gaatagagta cgggaaaaaa taaataaaaa agcagcggtt   2580
tttagcagga tcgtctggtg attctgatac gtctttttttt ttaggttggt tgtgtatgcg   2640
ctgaagctga aagcaacaaa caaattggtg ccgtctaggc gtctacccgg cccactgacc   2700
ccaatgcaaa caaagtacta aaaggcgagc aggtctcagc taaggaattc cgattctgac   2760
cgctccgagc tcgttgcgcc ctgtaaagct ctcgtcgcgg cgccggttta aaatggcag   2820
gtcggcgtca ccggccgcag ttgcgtggcg tccattgcaa cagaatagan taggccctgt   2880
cgcgcgagtg cgcggtttgt ccncggccat tctatcnatn ggggctccag attcggctcg   2940
cgcagttggg caaataataa tccgctgcta cngatgggct ggctggtgat ttgcgtgcgt   3000
ggcgccaata atgggcggca caagtccatc gcaatcgcaa cacntgacac atgagcgagc   3060
cggcacctgc gctgcgcgtg cggtgccgac tgcngtccgc gtgtgggcgg cgcatgtgag   3120
```

```
ggagggtgct gtccgcctgt ccccgtgtcc cgngcgncgc atgtggatgg aatggaatgg    3180
aaggttggtt ggttggttgg aagcgcgggg cggggcggg  gacggcgagg gcgacgcgcc    3240
gcgcctccgc gtgcgtggcg gcagatcgat gancgcgcgc ggcctttggc ttgtggtccg    3300
tgtgtgcctt tgtgnttgac gacttacttg tgcttgttca tggggtagat gaggangggg    3360
ccgccggcgc cggcgccggc ggtgcggccc cccagcacgc cacggaagac gccgcggtcg    3420
aagtcggcga tgcnggacgc cggcacgaag aggttgagcc acgggtgcgg cacctcccac    3480
atccccttgg cgcgcagctt cagctccgcc ttgtgcacgc ggtccaggaa gtccacgtac    3540
ggcaggtccg tagtgaacac cgtgccaggg aggaagttca gctcgcccag nagcgtatcc    3600
acgtcctgaa cgnaganaag aagaaaaata ttagcacaca cagtacactg nctgctactg    3660
ttatatcata cggcctctta cagctagtaa ctgaaaaagc aaggctccga gtccgagtac    3720
ntacctggtc naccgaccct gcggtttcgt cgtcgtagtt cttggtgacc tcgaggcagt    3780
agaggacgcn ggaatggtgc ttgagcgagg tgagcttcac ggggttctgc ggcgagaaga    3840
aggaggacct ccagttgttg atgaggccct nggcggcgac gacgaagccc tccacgtagt    3900
cgaaccggcg tccgccgccg ccgccgctgc cgagggagat gaggcgctcc tggtccgccg    3960
tgaactcgct gaagttggag tagagcgccc ggatccaccg aacctgcaag gcaaccacca    4020
ccaccnccnc cacccatgca ttcccgcccg tcaattctta gctgctatac taagattaca    4080
ggccgattaa ttagcagagg aacaaaatct tgcgaaagat cccacgagct aaacaaaaag    4140
aaaaaggcgg actcgatgac gacgncncgg cggcngcggc taatcgttga gcaggggcac    4200
cggcgtggac catgcacctg accggatgac gcgtacgtat tgtcggact  ggccnggctg    4260
gcccgggcgg ctggggngcc cctgcttata gntagaccna cggntactac agtggcgatt    4320
atcnagacgt acacgtacta cgcggcgtg  ganttttcg  gacgctacac atgtggcagc    4380
cgtttnatta gcggncggca gagnaggcgc tttcctcaac ggatcagcag cgcgctcgct    4440
cgccacttgc atggccggcc ggtgtgctgg gtcggtcatt agttggaaag cgaggccggt    4500
gacacacgcc acgggaggag atgcactgcc cgccccgccc tgtgttcctt tcccggtgcc    4560
acacgatcga gacacgactc acgggaggga aattaaaggn tatctaatng ntgcaggtgg    4620
tgatccatca gggcgcgcgc ctgaagggag gtccagacac gacagagagc agaagggagc    4680
gaggagaacg cagttgtggg ctgcctaagc tgtttactta ccctcttggg agcacgctcc    4740
agggcgatgc gcgcccgcgt gatgatgccg aactggccca gcccgcccag gacgccgaag    4800
aacaggtccg ggttctccgt ctccgagcag gtcaccacct ctcccttccc tgccaacgca    4860
cagcgcacgt gtgtcagtca gtnggttcat tcgtcgncgg cncgccagag acagcgcctt    4920
gcatctacga ctcgtcggcc ggctcgatcg cctagctagc tgctacgcta cctgtgacga    4980
cgtcgagctc gtagacattg ctgatctgng gcccgtggtg gaacgcctgc ccgctgatgc    5040
cggcgttgga gagggtgccg cccacggaca ggtacaggta gtccgtccac gaccgcggcg    5100
ccagcccgcc gtgggacagc gtccagttga gcacgtccac ccacagctc                5149
```

<210> SEQ ID NO 43
<211> LENGTH: 2142
<212> TYPE: DNA
<213> ORGANISM: Zea mays
<220> FEATURE:
<221> NAME/KEY: misc_feature
<222> LOCATION: (1)..(2142)
<223> OTHER INFORMATION: n is a, c, g, or t
<220> FEATURE:
<221> NAME/KEY: misc_feature
<222> LOCATION: (1795)..(1795)
<223> OTHER INFORMATION: r is a or g

<400> SEQUENCE: 43

```
tgattgacaa ttattgcttc gcccgacccg aggctagcgc acagtccntc ntgtgggcct      60
ggctgtgtgg tttccgtcct gatgctgatg cctgaaggga cctgcgtgcg tgtgcgtgcg     120
tgcnggtggg accccaacac gtcggtggcg ctgccggagg gcgaggtctt ctacctggtg     180
gcgctgctgc ggttctgccg gagcggcggg ccggcggtgg acgagctggt ggcgcagaac     240
ggngccatcc tccgcgcctg ccgcgccaac ggctacgact acaaggccta cttcccgagc     300
taccgcggcg aggccgactg ggcgcgccac ttcggcgccg ccaggtggag gcgcttcgtg     360
gaccgcaagg cccggtacga cccgctggcg atcctcgcgc cggggccana agatcttccc     420
tcgngtnccg gcgtccgtcg ccgtgtagag caagggggg aggaccagcc agctgccagc     480
caagacagga ggaggaggag gagggaggc tgatggatcg ccgctgctgt tgccggtaat     540
gatggcgatt acgctgctga tcctggtgat gatgatggac gatcgaggaa gccgcagggc     600
cgggcaatga tggcgatagg gccaccgtta ggtgtgcatc cggggcnca aattaaaggg     660
attgctgtgt ggagatctgc acgagttttt gctccatgca tgcttgccgt tcgtgtccgc     720
gtgtccctct cccccttgtt attattcctt cgcccgccga ggccgagcga gcgggtggtg     780
gcgncgacgc tggatttgtc tgctctgctn tgctccgccg ccgtgccac cccggtggcg     840
tgcgcccgca agctgttcnt tngcgcntnt gnccgncgtt ntcnccgtng tngcttncnc     900
ccctcgccgt cctggtcccc ccgcccgccc ggcaccccac gtggcacacc agcccgatcc     960
aaacgccgcg accgcgacgc gcggggccgt tggttcgcgt tcccgttccg tagnagcttg    1020
nccgcagnac acgacgaccg cgaacaaagc gcggccaaaa ccgacggacg ggtctcgccg    1080
ccgccgccgc ggacgcgncn cggacagga ggaatatcac tctggggcca tccgcgcggg    1140
accagagaac tggtcgggtc gatgtcgatc gatatcggca ctctgtgctg gctggcgang    1200
nggaccgagc ggcagggacg tgacggttgn tgccgcccga gcgcgacggc gaccgtcntt    1260
cgtctctggg ncggggcggc gcgggcggcg ttttcgtttg gaaantttgt ggacttctac    1320
ttgtattgta tataaaaaan caacgatcgg cgnacgtata caaccagtct tccttteect    1380
gtcgtgccca gtcgcattcc gtgatgcgag ccggatngcg acggaagcgg ctcnacgagc    1440
gtcgtccctg ctgcaccctg ctngcatccg tcgcgacaga tgggcgctgc ttcnaggaca    1500
ggatgatngn ttncacgccg gcctcgatct ngcccagctg tgtgggttca tcaggacggc    1560
ccagcttgct tgnctggcac gtgcggccac ccatcgggcg agatgagatc catcaaaccg    1620
ancacctcat cggtgcncta cggaacggaa cagatttttc gctgtcgact ggtccgaaac    1680
gagcggcga cctcgaccga ccgaccctct ccccttccc cctcccccgc cgcccgccg      1740
acccatcgct gttgcgctac aggctgctgg caacgacgct gtcgaggccg atgcrcagca    1800
ccggtgatga cccggagcag aaagggcgtt agctggctgg ttaatgtatc aagctgcaga    1860
ganacttatc cccgggatt aggtacgcga gggcgacact cctggataga tttacctcgt    1920
ctccatgcct cgcaggaatt ctaatgantn tttttctcna ttgtttatca ggacctgccc    1980
tgccaggata ccagccggag agctttcagg cgacaaaagc cgcggcgagg ggatcagcgn    2040
ggatctgccg ggccaccgcc accgccgccg cccccgcgttt tatactggag ggtgggtgtg    2100
ctccaagtgg tgcctttctg acaacgcgat ctaggctatg ag                       2142
```

<210> SEQ ID NO 44

<211> LENGTH: 2142
<212> TYPE: DNA
<213> ORGANISM: Zea mays
<220> FEATURE:
<221> NAME/KEY: misc_feature
<222> LOCATION: (1)..(2142)
<223> OTHER INFORMATION: n is a, c, g, or t
<220> FEATURE:
<221> NAME/KEY: misc_feature
<222> LOCATION: (2040)..(2040)
<223> OTHER INFORMATION: r is a or g

<400> SEQUENCE: 44

```
tgattgacaa ttattgcttc gcccgacccg aggctagcgc acagtccntc ntgtgggcct      60
ggctgtgtgg tttccgtcct gatgctgatg cctgaaggga cctgcgtgcg tgtgcgtgcg     120
tgcnggtggg accccaacac gtcggtggcg ctgccgnagg gcgaggtctt ctacctggtg     180
gcgctgctgc ggttctgccg gagcggcggg ccggcggtgg acgagctggt ggcgcagaac     240
ggngccatcc tccgcgcctg ccgcgccaac ggctacgact acaaggccta cttcccgagc     300
taccgcggcg aggccgactg ggcgcgccac ttcggcgccg ccaggtggag gcgcttcgtg     360
gaccgcaagg cccggtacga cccgctggcg atcctcgcgc gggggccana agatcttccc     420
tcgngtnccg gcgtccgtcg ccgtgtagag caagggggg aggaccagcc agctgccagc     480
caagacagga ggaggaggag gaggggaggc tgatggatcg ccgctgctgt tgccggtaat     540
gatggcgatt acgctgctga tcctggtgat gatgatggac gatcgaggaa gccgcagggc     600
cgggcaatga tggcgatagg gccaccgtta ggtgtgcatc cggggcnca aattaaaggg      660
attgctgtgt ggagatctgc acgagttttt gctccatgca tgcttgccgt tcgtgtccgc     720
gtgtccctct cccccttgtt attattcctt cgcccgccga ggccgagcga gcgggtggtg     780
gcgncgacgc tggatttgtc tgctctgctn tgctccgccg ccgtgccac cccggtggcg      840
tgcgcccgca agctgttcnt tngcgcntnt gnccgncgtt ntcnccgtng tngcttncnc     900
ccctcgccgt cctggtcccc ccgcccgccc ggcaccccac gtggcacacc agcccgatcc     960
aaacgccgcg accgcgacgc gcggggccgt tggttcgcgt tcccgttccg tagnagcttg    1020
nccgcagnac acgacgaccg cgaacaaagc gcggccaaaa ccgacggacg ggtctcgccg    1080
ccgccgccgc ggacgcgncn cggacagga ggaatatcac tctggggcca tccgcgcggg     1140
accagagaac tggtcgggtc gatgtcgatc gatatcggca ctctgtgctg gctggcgang    1200
nggaccgagc ggcagggacg tgacggttgn tgccgcccga gcgcgacggc gaccgtcntt    1260
cgtctctggg ncggggcggc gcgggcggcg ttttcgtttg gaaantttgt ggacttctac    1320
ttgtattgta tataaaaaan caacgatcgg cgnacgtata caaccagtct tccttttccct   1380
gtcgtgccca gtcgcattcc gtgatgcgag ccggatngcg acggaagcgg ctcnacgagc    1440
gtcgtccctg ctgcaccctg ctngcatccg tcgcgacaga tgggcgctgc ttcnaggaca    1500
ggatgatngn ttncacgccg gcctcgatct ngcccagctg tgtgggttca tcaggacggc    1560
ccagcttgct tgnctggcac gtgcggccac ccatcgggcg agatgagatc catcaanccg    1620
ancacctcat cggtgcncta cggaacggaa cagatttttc gctgtcgact ggtccgaaac    1680
gagccggcga cctcgaccga ccgaccctct ccccttccc cctccccgc cgcccgccg       1740
acccatcgct gttgcgctac aggctgctgg caacgacgct gtcgaggccg atgcncagca    1800
ccggtgatga cccggagcag aaagggcgtt agctggctgg ttaatgtatc aagctgcaga    1860
ganacttatc cccgggggatt aggtacgcga gggcgacact cctggataga tttacctcgt   1920
ctccatgcct cgcaggaatt ctaatgantn ttttctcna ttgtttatca ggacctgccc     1980
```

```
tgccaggata ccagccggag agctttcagg cgacaaaagc cgcggcgagg ggatcagcgr     2040
ggatctgccg ggccaccgcc accgccgccg ccccgcgttt tatactggag ggtgggtgtg     2100
ctccaagtgg tgcctttctg acaacgcgat ctaggctatg ag                       2142
```

<210> SEQ ID NO 45
<211> LENGTH: 3709
<212> TYPE: DNA
<213> ORGANISM: Zea mays
<220> FEATURE:
<221> NAME/KEY: misc_feature
<222> LOCATION: (1)..(3709)
<223> OTHER INFORMATION: n is a, c, g, or t
<220> FEATURE:
<221> NAME/KEY: misc_feature
<222> LOCATION: (3597)..(3597)
<223> OTHER INFORMATION: w is a or t

<400> SEQUENCE: 45

```
ccactacggg ataaaaaagc ctcttggtat ccataatgcc tggcctaata caaatatttg       60
aggttaattt agttttgagt actgcccata atggggcaat atcttaatat aatgtatcaa      120
ttatttgata tatgttatga atcttatga acgttcttga tactgcacta tgggagtttg      180
cttctgacaa aagtgcccag atgtgcagac acttttgaag catgaattga caactatgtt      240
ttctttcatt tcatttgaat agcctatttc aggatatttg aaggtcgagt agctaaactg      300
aaacaaatag agaatatgct ctgtttggtt taatgagttt tgtgtacagt tgtcctattt      360
ttataaagtc gatagtttct aaatattgca tcgtgttccc cagttttgtg cttgttactt      420
ctcagtgctt gcatttgcat cctgcaaacg acaaccgacc attgacaccc agctaacgta      480
gaacacctga gggctggggt ccagactcat caagggcaaa tgacactgct attacttatg      540
aacaaccaat gcgtaacaca tacatagtat caactgatat natntcaagg acttgnctga      600
tcttancagg catctaagat gctcntngcn tcccattntn atantnaatg cataaagnaa      660
atgttttcat aaaangatna atngtaagat tgatgagatt cttcagaaca ccttttgnaa      720
ncantttttt acttggatca aatccnaaca atantttttt ttgctttgna atttatgtat      780
ttgctaagtc aaagcaaact ctatatntgt ttcttatttg tttcattacc ttagcaggaa      840
caaggacatc tagtaaatcc tgtttgtggc agctactttc ctgtaattga gccaccatca      900
cgnaaaggca ggcatttctt ccggctgctc ctctagaaat gcctcatcca ggtggatact      960
cttgtgttgc ggctttggct gagcaccanc caccaagcat ggatttctct tacatggctg     1020
gcagtagcac atacccagtc tttgacatga tccgccgacc ntgcaacatg tctagtggaa     1080
gcttgtgcag cgtcgagaac agttcactag cacctggag cgggatggca ccaaattgca     1140
gcagaggagt ggtaagagag gagggagagt gctcaaccga ccactggtcg gagggtgcgg     1200
aggcgggaac aagctatgcc ggatcggaca tcatggtgga tgcaggggcc atgcaaccgc     1260
tgcctttcgc tgagaatttc accatggctc caagccactt cngccggag agcatcgagg     1320 agcagatgat gttttccatg gccgtgtcac tagcagaagg tcatcatggt aggacgcaag     1380
cgcaaggtct ggcatggttg taagttgtat aacactaatt ttgacgcctt gatccctgcc     1440
cctttctgtt ggttcgacct gcttcccctg cacctctgct ttttgccac tttgtttagc     1500 ttttgctcc ttttttttt cttttcttc tttttgcat gtgttgcttc atggcttgat     1560
atagatcttg ctatagtcct ccattgtcat tgcttatatg tatgtaaaat ggaatatgtg     1620
gaaataggaa agaaaatggg tcgaaagttc ttttgccggt aggatgcgca gtgtgttttc     1680
```

```
gcattgcaaa gcattccaag attttgcaaa gttgacctgg aacaggcatt ctagctattc      1740
tctccgttga catgttcttg gggtgtaaag atgtttgntt ctatgggnaa aacaactaga      1800
ctctggaccg gngaggttaa tttcanacat gtttcgatct atttgtgaat tcttctgatc      1860
tgttgtagaa ctactttcag ctgtagtgta tgacttgtca ggcagaggca ggcaacagca      1920
acaccaatat tatccagccn taccacaagt atgttttnt taaaaggggg ctcaagtaca       1980
ggtattttgg catggagcat gtcgatggag gatggacaga ctgaggacaa tgtacagaga     2040
tttgttgcgt tgcacacgat tccgcattcc gaancgtgag gttgacaaaa ggagagagga    2100
tctcttcttg gagaggaagc atcctgtttc ttaacagcag ttagcaggtg aggtgagaaa    2160
ccttggatgc cnacaccaat atgcaaagct ggccggactg aaacacggga attccaagtt    2220
tcgtgggaat attgtatgat tttgtcttat tttccgcnaa acttacgcga agcgaaggcc    2280
aacnatggct tnaaatgcgt tttggggta agaaatgaat gcagcttgtg gcttgaaatg    2340
aggncatgag ccancgtgtg ggaagggcaa gggcttgcag ttaggatggt agggcttgaa   2400
atggtaatga attacgatct aaatantttt ttcataattt atttaagctt ttaattaatt    2460
tnagtttaaa aataaatana aatagacctc ggtcataatt cgattcgatc cttaaatttt    2520
gtagtgtaaa atttagagct cattaccacc tctatttgta gttgcncgtg tggacaacta    2580
ggtgttgaaa attaggttcg ggatctagct cggagcatca naagtatctc taaaattagg    2640
ttcgggatct agctcggagc atcacaagta tctctcccac atagccgata gtaatataca    2700
aatatattcc atataaaatc atattagctt aattgatcta cgcataaatt acaattatta    2760
gtatggaatt caattccaag gatcngaacg gggctaagaa antaaaaaat ttanatttac    2820
ttaaaaatac ataatacata tgtcaaantn aaataaaaag ttcacaatgc ataaaaaaca    2880
aaaattacat atctaataca aataaaattt aattttgtgg tacagatcat gaatatgctc    2940
cattaaatta ttttggagtt gatcatatat cgagcttgct tggattgcgg cctcacgttg    3000
aaagctcatt ggtgcttcga ggggtgacgg ttggtgttgc aacagagaac tcaagttgtt    3060
gggggattgg atccctaggc tctaggggga ccatgagtca gagggagaat ggagagaggc    3120
ccgcctaggt aaatctgccc ctagatgacc ctgcgcgctg agcctaggga tcggacgagg    3180
cgaagccagg caagggtcg gacgaactgc tagggaacca ctcaagtagg ttccgcgtgt    3240
ggccaacgag ttcctctcgt catcaatacc acacacgttg cattaattgt gctcccacac    3300
atggcctatg agccctaggc ctgagtccca ctcatgacct acgggcccta ggggtcctag    3360
gcntgagccc tttgatgccc tangaagcac gcaagacaac nanaaagcta gaggtcnggc    3420
tacnaagacc aatggtcgtc atgggaagag gtggataaga ggagtaataa tgaagntcag    3480
gctctcgtca ccngcacgct cccctagcag ccttaaaaga agcangaccn gagatttaca    3540
tgaggatgga tatcaacaca cantaangct tttancgggg gctaaccaac ccattcwacc    3600
cnagcacgac natcccttcc gagagaatat atntgtaatc anggtcancc cgaaaaagng    3660
naaaagagag aagataaacg agaagagggg gcccaaaccg agagcaaac                3709
```

<210> SEQ ID NO 46
<211> LENGTH: 3709
<212> TYPE: DNA
<213> ORGANISM: Zea mays
<220> FEATURE:
<221> NAME/KEY: misc_feature
<222> LOCATION: (1)..(3709)
<223> OTHER INFORMATION: n is a, c, g, or t
<220> FEATURE:
<221> NAME/KEY: misc_feature
<222> LOCATION: (3611)..(3611)
<223> OTHER INFORMATION: r is a or g

<400> SEQUENCE: 46

| | | | | | |
|---|---|---|---|---|---|
| ccactacggg | ataaaaaagc | ctcttggtat | ccataatgcc | tggcctaata | caaatatttg | 60 |
| aggttaattt | agttttgagt | actgcccata | atggggcaat | atcttaatat | aatgtatcaa | 120 |
| ttatttgata | tatgttatga | aatcttatga | acgttcttga | tactgcacta | tgggagtttg | 180 |
| cttctgacaa | aagtgcccag | atgtgcagac | acttttgaag | catgaattga | caactatgtt | 240 |
| ttctttcatt | tcatttgaat | agcctatttc | aggatatttg | aaggtcgagt | agctaaactg | 300 |
| aaacaaatag | agaatatgct | ctgtttggtt | taatgagttt | tgtgtacagt | tgtcctattt | 360 |
| ttataaagtc | gatagtttct | aaatattgca | tcgtgttccc | cagttttgtg | cttgttactt | 420 |
| ctcagtgctt | gcatttgcat | cctgcaaacg | acaaccgacc | attgacaccc | agctaacgta | 480 |
| gaacacctga | gggctggggt | ccagactcat | caagggcaaa | tgacactgct | attacttatg | 540 |
| aacaaccaat | gcgtaacaca | tacatagtat | caactgatat | natntcaagg | acttgnctga | 600 |
| tcttancagg | catctaagat | gctcntngcn | tcccattntn | atantnaatg | cataaagnaa | 660 |
| atgttttcat | aaaangatna | atngtaagat | tgatgagatt | cttcagaaca | ccttttgnaa | 720 |
| ncantttttt | acttggatca | aatccnaaca | atantttttt | ttgctttgna | atttatgtat | 780 |
| ttgctaagtc | aaagcaaact | ctatatntgt | ttcttatttg | tttcattacc | ttagcaggaa | 840 |
| caaggacatc | tagtaaatcc | tgtttgtggc | agctactttc | ctgtaattga | gccaccatca | 900 |
| cgnaaaggca | ggcatttctt | ccggctgctc | tctagaaat | gcctcatcca | ggtggatact | 960 |
| cttgtgttgc | ggctttggct | gagcaccanc | caccaagcat | ggatttctct | tacatggctg | 1020 |
| gcagtagcac | atacccagtc | tttgacatga | tccgccgacc | ntgcaacatg | tctagtggaa | 1080 |
| gcttgtgcag | cgtcgagaac | agttcactag | acacctggag | cgggatggca | ccaaattgca | 1140 |
| gcagaggagt | ggtaagagag | gagggagagt | gctcaaccga | ccactggtcg | gagggtgcgg | 1200 |
| aggcgggaac | aagctatgcc | ggatcggaca | tcatggtgga | tgcaggggcc | atgcaaccgc | 1260 |
| tgccttcgc | tgagaatttc | accatggctc | caagccactt | cngcccggag | agcatcgagg | 1320 |
| agcagatgat | gttttccatg | gccgtgtcac | tagcagaagg | tcatcatggt | aggacgcaag | 1380 |
| cgcaaggtct | ggcatggttg | taagttgtat | aacactaatt | ttgacgcctt | gatccctgcc | 1440 |
| cctttctgtt | ggttcgacct | gcttcccctg | cacctctgct | ttttgccac | tttgtttagc | 1500 |
| tttttgctcc | tttttttttt | cttttctttc | tttttgcat | gtgttgcttc | atggcttgat | 1560 |
| atagatcttg | ctatagtcct | ccattgtcat | tgcttatatg | tatgtaaaat | ggaatatgtg | 1620 |
| gaaataggaa | agaaaatggg | tcgaaagttc | ttttgccggt | aggatgcgca | gtgtgttttc | 1680 |
| gcattgcaaa | gcattccaag | attttgcaaa | gttgacctgg | aacaggcatt | ctagctattc | 1740 |
| tctccgttga | catgttcttg | gggtgtaaag | atgtttgntt | ctatgggnaa | aacaactaga | 1800 |
| ctctggaccg | gngaggttaa | tttcanacat | gtttcgatct | atttgtgaat | tcttctgatc | 1860 |
| tgttgtagaa | ctactttcag | ctgtagtgta | tgacttgtca | ggcagaggca | ggcaacagca | 1920 |
| acaccaatat | tatccagccn | taccacaagt | atgttttnt | taaaaggggg | ctcaagtaca | 1980 |
| ggtattttgg | catggagcat | gtcgatggag | gatggacaga | ctgaggacaa | tgtacagaga | 2040 |
| tttgttgcgt | tgcacacgat | tccgcattcc | gaancgtgag | gttgacaaaa | ggagagagga | 2100 |
| tctcttcttg | gagaggaagc | atcctgtttc | ttaacagcag | ttagcaggtg | aggtgagaaa | 2160 |
| ccttggatgc | cnacaccaat | atgcaaagct | ggccggactg | aaacacggga | attccaagtt | 2220 |

```
tcgtgggaat attgtatgat tttgtcttat tttccgcnaa acttacgcga agcgaaggcc      2280
aacnatggct tnaaatgcgt tttgggggta agaaatgaat gcagcttgtg gcttgaaatg      2340
aggncatgag ccancgtgtg ggaagggcaa gggcttgcag ttaggatggt agggcttgaa      2400
atggtaatga attacgatct aaatantttt ttcataattt atttaagctt ttaattaatt      2460
tnagtttaaa aataaatana aatagacctc ggtcataatt cgattcgatc cttaaatttt      2520
gtagtgtaaa atttagagct cattaccacc tctatttgta gttgcncgtg tggacaacta      2580
ggtgttgaaa attaggttcg ggatctagct cggagcatca naagtatctc taaaattagg      2640
ttcgggatct agctcggagc atcacaagta tctctcccac atagccgata gtaatataca      2700
aatatattcc atataaaatc atattagctt aattgatcta cgcataaatt acaattatta      2760
gtatggaatt caattccaag gatcngaacg gggctaagaa antaaaaaat ttanatttac      2820
ttaaaaatac ataatacata tgtcaaantn aaataaaaag ttcacaatgc ataaaaaaca      2880
aaaattacat atctaataca aataaaattt aattttgtgg tacagatcat gaatatgctc      2940
cattaaatta ttttggagtt gatcatatat cgagcttgct tggattgcgg cctcacgttg      3000
aaagctcatt ggtgcttcga ggggtgacgg ttggtgttgc aacagagaac tcaagttgtt      3060
gggggattgg atccctaggc tctaggggga ccatgagtca gagggagaat ggagagaggc      3120
ccgcctaggt aaatctgccc ctagatgacc ctgcgcgctg agcctaggga tcggacgagg      3180
cgaagccagg caagggtcg gacgaactgc taggaaccaa ctcaagtagg ttccgcgtgt        3240
ggccaacgag ttcctctcgt catcaatacc acacgttg cattaattgt gctcccacac        3300
atggcctatg agcccctaggc ctgagtccca ctcatgacct acgggcccta ggggtcctag     3360
gcntgagccc tttgatgccc tangaagcac gcaagacaac nanaaagcta gaggtcnggc      3420
tacnaagacc aatggtcgtc atgggaagag gtggataaga ggagtaataa tgaagntcag      3480
gctctcgtca ccngcacgct cccctagcag ccttaaaaga agcangaccn gagatttaca      3540
tgaggatgga tatcaacaca cantaangct tttancgggg gctaaccaac ccattcnacc      3600
cnagcacgac ratcccttcc gagagaatat atntgtaatc anggtcancc cgaaaaagng     3660
naaaagagag aagataaacg agaagagggg gcccaaaccg agagcaaac                 3709
```

<210> SEQ ID NO 47
<211> LENGTH: 2242
<212> TYPE: DNA
<213> ORGANISM: Zea mays
<220> FEATURE:
<221> NAME/KEY: misc_feature
<222> LOCATION: (1)..(2242)
<223> OTHER INFORMATION: n is a, c, g, or t
<220> FEATURE:
<221> NAME/KEY: misc_feature
<222> LOCATION: (131)..(131)
<223> OTHER INFORMATION: s is c or g

<400> SEQUENCE: 47

```
gacccatgac tcctttagca aacttatgat gtgctgcaga ccatacagtg ccaatgcaaa        60
anatgaacac ctcaangaaa cacagggtac ttgtactgag aagatgtata aagcagctgc       120
ggccaaaaga sagggagagg aggaggagga gctcttcttg cccacatccc tttgtcaaga      180
agaatctctg atgcttgctt gtttccatgt gacagggaag cttggtactt actgctctct      240
ttacaaaaaa anaaaacaaa acaaaacaaa caaaccccca ctgcagaat agaatngaat       300 agaatagaat agcctttgtt tccctcccc caaaaagcta aagttctcat catgcttaaa        360
accgtcttaa atagcagtgc ttagaagaag atagggnggc cacctccccc tagttacacc      420
```

```
cagcatccca gcgcanaccc accagnccac cccacgatgc acctctgtc tgttcctctt      480 cctccatgca atgcaagtat gcaacgcaac gcatcttctg tttgctngcc gccgctccca      540
acacgtcgct atcgccggcc tcttcgggtt cggangctnc acgcctcggc atgcgcgctc      600
cngacgtcat gctcgtcccg gcgatcgtcc tgacttgccg gttcctctgc aggatttgaa      660
ancgggttag aagctgaagc tgaagcnagc agggactgag acagcagcac agtctttgtt      720
tcggcaggtg atgcactgaa accgttnagg ctttcctgta gtttaccatc atgatgaacc      780
gtgggtgtgg tgctgtgctg tgctttgttt tgttttgntn ctttcatgga tgtagactaa      840
tgatttcang aatgatangt gcatctacgt tgctcactgg gggaatagga cttgtgtgnt      900
tgcttttgnt gaaagattat agcatatcat cataggggaa tgtgggagtg gtgagggaaa      960
aagagccgca nggcatcttt tgctcatatg cgtcgtctcc ctttgttttt tcttccctct     1020
ccctgcgttt tatccgttat catttatttt atattattat gaaaaagtat tgntntntnt     1080
tctttntttc ctgantatat cctacgtgaa aatatccaac aaaacatggt aaatgggagc     1140
atatggcaag acaaaatgat nacaacagac gcactncaaa acattcacct tagacttgca     1200
taccancgca gtcagaaact ggtgaaacaa gaacattccc ttcattccgt aacgcaagct     1260
tancaaanaa acaagccatg acnanaaaaa acgncangng tnggaattnt gctagtncaa     1320
ntntgaaggn tncngcattn ggcctcatat cgtangtagn aaagaagccn tttttttnaaa     1380 atcctaaagc ttctngtttc aagaaaccag tgcattgggt acngggngg ggggncaact      1440 caaacaccaa aaccaaagct tgnagcgcag taagctgtac gtagatcaaa gtacctgttg     1500
tggataggat cagggccatt gggcaccctt ctnttnctgt cctggaaggg atcatgagcc     1560
ttgaaatcct ccagggtcct cagccctccg gcgcctccgc ccagcatcat cctcctcccg     1620
ccgatcgccg ccggnggagc cgcttttcctg acgccgtcca cgacgaacga caccagaagg     1680
agcgctccga acaagatggc caatgccgcn ggcgccgccc gcctcacgga cacggccgac     1740
cttctcatga cacccaccga ccagtcgtcc gtcgccgcgc agcgcancgt cgtcttcttc     1800
ttccgtagag cggcctcctc ctcctcctct cctggcgagc gacaacgctg gtcttctaag     1860
agctnttctc atggcanggg gtggcgctaa gtgtgatgca acggctgcgg ctgcgcaacg     1920
tgactgcnta tnataatgtg gggaagaagt agcggcagga tttgtgtcag tcgctgtcgc     1980
gcgggtattc ctgcttcttg ttctgttctg gccttctttc gctttggccc gattctgctg     2040
tgctnntgaa ggatgccctg ccccctaatgg aggggagggg ggggcagcan anagtagaat     2100
caaagcaagc tgagccacgc tgcgctttgc ttttttgagcc atgttgtttt cctcctgcct     2160 ttccctttt tttancccc ntgtttttc ttcttctcgt gaagagaaga agggtaaaag        2220
acggtggata aataataaaa aa                                               2242
```

<210> SEQ ID NO 48
<211> LENGTH: 2514
<212> TYPE: DNA
<213> ORGANISM: Zea mays
<220> FEATURE:
<221> NAME/KEY: misc_feature
<222> LOCATION: (1)..(2514)
<223> OTHER INFORMATION: n is a, c, g, or t
<220> FEATURE:
<221> NAME/KEY: misc_feature
<222> LOCATION: (2273)..(2273)
<223> OTHER INFORMATION: w is a or t

<400> SEQUENCE: 48

| | | | | | |
|---|---|---|---|---|---|
| ccaaccggca | atgccagcac | aacacatgga | tcctacaaaa | atctcgggca | natggcatcg | 60 |
| cggcgctgtn | caaccggngg | gtgtgcccgg | cccggcgagc | cgcttgcttt | tattgtattt | 120 |
| atatttatac | gagccccatg | ggcgcttgcc | tcagtcgttt | gcccntttgg | tccctctccc | 180 |
| tcccccntcc | gccctgcact | ctccaagctc | aacaaggaag | aagaggggc | cttcaccaca | 240 |
| ccactcgatt | cctctttaga | gcacgactta | cgaagngtgc | ccaggccntc | gccgccgacc | 300 |
| agcaaaaggg | ctggaaagcc | accctctttt | tgtgctgtgn | gtgcaactcg | gctcctgccc | 360 |
| tgccatcttg | cttttccaaga | cccctgcgcc | cccagnccca | taattagtta | ggattaggat | 420 |
| caccaccatt | tccnaatcct | ngcaganctg | ccgaagcgcn | gatcacagat | gaagaggcaa | 480 |
| tccaagaggc | ccaccgccag | ccgcgaatcc | ccagaaacag | gtattgccgc | cgccttgcct | 540 |
| gtgagatgag | atctcctttg | tctcgtgtac | ttgttgcgtc | cgtgatgtcc | gtgacagaat | 600 |
| accaantgga | gtatactcgt | agttagtgaa | tagaaaagta | cgtatgcgtg | cttttgacat | 660 |
| ctgatcagtg | ttgcttctgc | ctgcattcca | ttttttnttt | ggttagcttg | ctgccacaaa | 720 |
| gctgcagaaa | gaacgggtct | cccccttca | ttttggggaa | tcctccagta | gctaaccgca | 780 |
| cgcgcgaatt | gcaggggaga | agcagaagct | ggcgttcgcg | gaggaagagg | ccccgccggc | 840 |
| gcggaaggtg | gagcccgacg | acgaggccga | gatggacgag | gacgaggacg | agctgggccc | 900 |
| gggcctgggc | ggcgggcgcg | cggcgcggtc | gccgtgcggg | ctcggggaga | agaagcggcg | 960 |
| cctggcgctg | gagcaggtgc | gcgcgctgga | gcgctgcttc | gagacggaca | caagctgga | 1020 |
| cccggaccgc | aaggcccgca | tcgcgcgcga | cctcgcgctg | cagccgcgcc | aggtcgccgt | 1080 |
| ctggttccag | aaccgccgcg | cccgctgaaa | gaccaagacg | ctcgagcgcg | acttcgcggc | 1140 |
| gctgcgcgcg | cgccacgacg | ccctccgcgc | cgactgcgac | gcgctccgcc | gcgacaagga | 1200 |
| cgccctcgcc | gccgaggtaa | ttaaccgact | gctcttgctc | tgtcatgtca | tgtcatgtca | 1260 |
| ccgccggtca | tggtcagcan | ccgtctacgt | actctccgcg | tcttgtccgg | tgccacttcc | 1320 |
| aacctgccgt | cactcactga | tgtcgttttg | gcgcgcgcgc | gcgcccgctc | ggcgcttctt | 1380 |
| atcagataag | ggagctgagg | cagaagctgc | tgcccaagcc | ggaagccacg | gtgaagctgg | 1440 |
| aggcgacgac | gggcaatgac | acggcggagg | agcgccgcca | ggcgacggcc | ggcgcgccgc | 1500 |
| ccgcgggggc | ctgcaaggac | ggctcctcgg | acagcgactc | cagcgtggtc | ttcagcgacg | 1560 |
| tcgaggcgtc | gccctactcc | ggcggcgcgg | cgttngagcc | gccggncttg | gccgggctcg | 1620 |
| gcgcgccgtt | cctggacacg | tcggtggcgc | cgacgggctg | ctcgtctccc | cccgttttcg | 1680 |
| tcgagaccaa | gtggcagcag | cacggggccga | cacagtaccc | gttcccattc | gactcgtaca | 1740 |
| aggcctgcgc | cggctatggc | ttcacggagg | natggcncgc | nagctcggac | ctcatcggcn | 1800 |
| gcgacgcgg | cgcggcgggg | ttcttctccg | aggatnacgc | ctccnctcaa | cttcaactgg | 1860 |
| tgcccgagtg | gcatccaggg | ctgggagtga | ngggnttttt | gatctgcncg | gctagtgtaa | 1920 |
| aaaaaccgat | gttacggtgg | catttgtaca | tgcnttgatg | catgnaactg | gagtctagtg | 1980 |
| ncctggcctg | gcgagntgng | tgtggccaaa | gctagaggac | atccagcgca | aaaggcggga | 2040 |
| acaggagcag | tagtagcctg | tnacaataac | ggaataactt | gagccaggct | agtaaaaaaa | 2100 |
| aganagagga | tgtaaatgta | gtacaaggta | aaaagaggtt | ntgtcgnanc | actacgcacg | 2160 |
| gcactatcac | tnggatgcaa | catgcaatgc | ancaaatcgg | cnacnagagc | gtntnaaggg | 2220 |
| gaaaggggaa | antggtaagc | aggctgcaat | ttacggtgcc | ggatgagata | cgwcaaantc | 2280 |
| taatcaaaat | aaatgttntt | tgactcgttt | acatttgaaa | ttaacgtctt | cagaanaana | 2340 |
| attttagtgt | tangntaaaa | ccgaagccga | gcgacgaagg | ctatactaca | agagccctgc | 2400 |

```
ggagcggttt gcttttccn tttttnttnc tnttnccttt tcctnccnct ncttcnttcn    2460
ccttntaaaa aanaaaanaa aacggaggga gggcttaaaa ggggagcacg gaag         2514
```

<210> SEQ ID NO 49
<211> LENGTH: 2514
<212> TYPE: DNA
<213> ORGANISM: Zea mays
<220> FEATURE:
<221> NAME/KEY: misc_feature
<222> LOCATION: (1)..(2514)
<223> OTHER INFORMATION: n is a, c, g, or t
<220> FEATURE:
<221> NAME/KEY: misc_feature
<222> LOCATION: (187)..(187)
<223> OTHER INFORMATION: s is c or g

<400> SEQUENCE: 49

```
ccaaccggca atgccagcac aacacatgga tcctacaaaa atctcgggca natggcatcg      60
cggcgctgtn caaccggngg gtgtgcccgg cccggcgagc cgcttgcttt tattgtattt     120
atatttatac gagccccatg ggcgcttgcc tcagtcgttt gcccntttgg tccctctccc     180 tccccstcc gccctgcact ctccaagctc aacaaggaag aagaggggc cttcaccaca       240 ccactcgatt cctctttaga gcacgactta cgaagngtgc ccaggccntc gccgccgacc     300
agcaaaaggg ctggaaagcc acccctcttt tgtgctgtgn gtgcaactcg gctcctgccc     360
tgccatcttg ctttccaaga cccctgcgcc cccagnccca taattagtta ggattaggat     420
caccaccatt tccnaatcct ngcaganctg ccgaagcgcn gatcacagat gaagaggcaa     480
tccaagaggc ccaccgccag ccgcgaatcc ccagaaacag gtattgccgc cgccttgcct     540
gtgagatgag atctcctttg tctcgtgtac ttgttgcgtc cgtgatgtcc gtgacagaat     600
accaantgga gtatactcgt agttagtgaa tagaaaagta cgtatgcgtg cttttgacat     660
ctgatcagtg ttgcttctgc ctgcattcca ttttttnttt ggttagcttg ctgccacaaa     720
gctgcagaaa gaacgggtct ccccccttca ttttgggaa tcctccagta gctaaccgca     780
cgcgcgaatt gcaggggaga agcagaagct ggcgttcgcg gaggaagagg ccccgccggc     840
gcggaaggtg gagcccgacg acgaggccga gatggacgag gacgaggacg agctgggccc     900
gggcctgggc ggcgggcgcg cggcgcggtc gccgtgcggg ctcggggaga agaagcggcg     960
cctggcgctg gagcaggtgc gcgcgctgga gcgctgcttc gagacggaca acaagctgga    1020
cccggaccgc aaggcccgca tcgcgcgcga cctcgcgctg cagccgcgcc aggtcgccgt    1080
ctggttccag aaccgccgcg cccgctgaa gaccaagacg ctcgagcgcg acttcgcggc    1140
gctgcgcgcg cgccacgacg ccctccgcgc cgactgcgac gcgctccgcc gcgacaagga    1200
cgccctcgcc gccgaggtaa ttaaccgact gctcttgctc tgtcatgtca tgtcatgtca    1260
ccgccggtca tggtcagcan ccgtctacgt actctccgcg tcttgtccgg tgccacttcc    1320
aacctgccgt cactcactga tgtcgttttg gcgcgcgcgc gcgcccgctc ggcgcttctt    1380
atcagataag ggagctgagg cagaagctgc tgcccaagcc ggaagccacg gtgaagctgg    1440
aggcgacgac gggcaatgac acggcggagg agcgccgcca ggcgacggcc ggcgcgccgc    1500 ccgcggggc ctgcaaggac ggctcctcgg acagcgactc cagcgtggtc ttcagcgacg    1560
tcgaggcgtc gccctactcc ggcggcgcgg cgttngagcc gccggncttg gccgggctcg    1620
gcgcgccgtt cctggacacg tcggtggcgc cgacgggctg ctcgtctccc cccgttttcg    1680
tcgagaccaa gtggcagcag cacgggccga cacagtaccc gttcccattc gactcgtaca    1740
```

```
aggcctgcgc cggctatggc ttcacggagg natggcncgc nagctcggac ctcatcggcn   1800
gcgacggcgg cgcggcgggg ttcttctccg aggatnacgc ctccnctcaa cttcaactgg   1860
tgcccgagtg gcatccaggg ctgggagtga ngggnttttt gatctgcncg gctagtgtaa   1920
aaaaaccgat gttacggtgg catttgtaca tgcnttgatg catgnaactg gagtctagtg   1980
ncctggcctg gcgagntgng tgtggccaaa gctagaggac atccagcgca aaaggcggga   2040
acaggagcag tagtagcctg tnacaataac ggataacttt gagccaggct agtaaaaaaa   2100
aganagagga tgtaaatgta gtacaaggta aaaagaggtt ntgtcgnanc actacgcacg   2160
gcactatcac tnggatgcaa catgcaatgc ancaaatcgg cnacnagagc gtntnaaggg   2220
gaaaggggaa antggtaagc aggctgcaat ttacggtgcc ggatgagata cgncaaantc   2280
taatcaaaat aaatgttntt tgactcgttt acatttgaaa ttaacgtctt cagaanaana   2340
attttagtgt tangntaaaa ccgaagccga gcgacgaagg ctatactaca agagccctgc   2400
ggagcggttt gcttttttccn tttttnttnc tnttnccttt tcctnccnct ncttcnttcn   2460
ccttntaaaa aanaaaanaa aacggaggga gggcttaaaa ggggagcacg gaag         2514

<210> SEQ ID NO 50
<211> LENGTH: 3908
<212> TYPE: DNA
<213> ORGANISM: Zea mays
<220> FEATURE:
<221> NAME/KEY: misc_feature
<222> LOCATION: (1)..(3908)
<223> OTHER INFORMATION: n is a, c, g, or t
<220> FEATURE:
<221> NAME/KEY: misc_feature
<222> LOCATION: (1603)..(1603)
<223> OTHER INFORMATION: m is a or c

<400> SEQUENCE: 50
taggataata gcccagtttc atttggattt tgaatttact tgcgggccat catcgattgg     60
tggctggatc taatggcacg cacgtcaccc ccaccggatg catgccacag atctgtgcat    120
gtgctcacca tgctgaggga ggtcaggatt ggtgcctgca cgcatgggt tcctacgccc     180 agaccaaaag gatctggttg ctatctttcg cccatacacg gatgctcttc ttcagatctg    240
gttaagcggg caatgattgc attgcggggg caccagcacc agaaacaaac tgtaggaggt    300
tgctgcggtg gtccctgtgg ggttctactg ctttaggatt attttctggg atctgttttt    360
tttccagccc gagtatgcat gccgtcgagg ttcaggttcc tcctctctta gcaaagtttt    420
atgaagcttc ttttggcctt ctggttgctg cctgcacaac tttatcaagc taccaaacgt    480
actagttgta ctgcttcctt tggattatag aggagttact aaataaactg tgttgggtgt    540
gcatattctc aaggctgtgg tcttaggaat tgctttcagt tatgcaagag atacttactt    600
ggcatacaac tactggcgct ccgaatgccc tgccacccc ctggcctgat agattctttg      660
atctggacct tatatggtta gtttattcag tgttgctgca ctgtctctct acatgtttcc    720
tgaaacatca gtagattgtg gaatagcagt gtgatggtgt agctttatgg ttacagctaa    780
ctcagctgtt ggtgagatag ctccttgcag ttgcagatan caatgtgctt ccttcagctg    840
tttcttccat ctagtgtact tgtncaagtt cttccatgan atgataaatg tgtattttnt    900
nttnacttca ctgtttatct aactctgctg ngtnantttn cantngnttt ttcagtagca    960
accaccaccc anggnggacg tgcacgaacc tttgggncgc cgtaagagga ananggtttt   1020
ggtggactac ttggtgaagt tccgatngat cctcgtgatc ttcgtggtcc ttcctatttn   1080
aactctgatc tacttcaaca tcttcctggg cgacatgtgg tccgccatga agtcggagaa   1140
```

```
gaagcgccag aagcagcacg acgagaacgt gcagaaggtc gtgaagcggc tcaagcagag    1200
gaacccgaag aaggangqtc ttgtttgnac ggccaggaag ccctggatcg ctgttggcat    1260
gcgcaacgtg gactacaagc gtgcgaggca tttcgaggtc ganctttctt cnttcaggaa    1320
catccttgag atcgacaaag agaggatggt tgccaaggtc gagcccctng tnaacatggg    1380
tcagataacc agagctacct gcccaatgaa ccttgccctt gcggtcgtcg ccgagctcga    1440
cgacctcact gttggtgggc tgatcaacgg ttacggcatc gaggggagct ctcacctcta    1500
tggccttttc tcngacacgg ttgtcgcgat ggaggttgtt ctcgcagatg gccgggtcgt    1560
nagagccacc aaggacaacg agtactctga ccttttctat ggmattccct ggtcccaggg    1620
aacactgggg ttccttgtct ctgcngagat caagctgatc cccatcaagg agtacatgaa    1680
gctcacctac actccagtca aggggggtct aaaggagatc gcgcaggcct acgcggattc    1740
tttcgcnccg agggacggtg acccggcaaa ggtccctgac tttgttgaag ggatggtgta    1800
cacagagagc gagggtgtca tgatgacggg cgtgtacgct tcnaaagaag aggcgaagaa    1860
gaagggcaac aagatcaact gcgtggggtg gtggtttaag ccctggttct accagcacgc    1920
tcagacggcg ctgaagaggg gngagtttgt ggagtacatc ccgacgaggg agtactacca    1980
ccggcacacc cggtgcctgt actgggaggg gaagctgatc ctgcccttcn gcgaccagtt    2040
ctggttcagg ttcctgctgg gctggctgat gccaccgaag gtgtcccngc tgaaggcgac    2100
ccagggcgag gctatnanga actacnccac gacaaccatg tgatccagna catgctggtg    2160
ccgctgtaca aggttgggga ngcgctggan ttcgtgcacc gcgngatgga ggtacaatgg    2220
ctggctggtg ctggtgctgg tgcngcttgc tttatnagta gttnactgga tatactaata    2280
ataatngaaa ttcttttttgg taggtgtatc ctctntggct gtgccctcac cggcngtacn    2340
gctgccggtg aaganatngt gtacccggag cctgggttcn agcaccagna cangnagggc    2400
gacacgagct acgcncagat gttcacggac gtgggcgtgt actacgcccc cggggcntgc    2460
tgagggggga gnagttnaac ggcgcgnagg ctgtgcacag gctggagcag tggctgatng    2520
agaaccacan ctnccngccg cngtncgcgg tgtnggannct gaacgagaan gacttntggn    2580
gcatgttngn cgngtncnct ncgancacng ccnccaaaan tncggggngn gggcncgttn    2640
atgangngtn ctacnantnc nanaangggn cnanacggan aaggangngc ngggnggnggn    2700 ggnggccnac nggnccngcc tncncggncn ggnggcctaa anctngnggt ngttttgctt    2760 ncccnttta attnaacntn anggangtng ngngtntna antcntngta ntnactnta     2820 aanctngngg tcgntcggtc ggtngtcant cngtntgtng ntgantccan cntntttttt    2880
attttaatat tntntaangg aatctntcag attgattcgg gacttgctat gnctntnctn    2940
tttgcctatt tgttatgttt ttttttnaaa gttctccagg cgctgctnct gcgtcttgca    3000
aggagccngg agctgntgac tancagcagc ancagctngg aacggtggga ggcagcacca    3060
ccatggcacc atgtggctga ctggggctgg caggcacagt gagaaaaaga aagacaccag    3120
ccatctactc cccagtcccc ccacaagagc aaaagcaaag aaagatgcat gtgcatgtgc    3180
agtgcagcaa ctctgccatg ctgtcatgtg ggacggcacg ggcaccagct gcactgcact    3240
gcaccgcccc acagttatat tgtttactgc tgctgtgccc actccttgta tatttgcatc    3300
actgcctgct tctggaatca ggaaaggaga tcaccacttc actcaagaag gcaccctccc    3360
ttgccactcc ttttccttga gatgacgatg acgacgatga agaagcagca gcagctcctc    3420
ctcctccttt ctctcatgtt tctcgttgct gtgacagcag ccgctgttgc tgccgatcca    3480
```

| | |
|---|---|
| catccacagc aggtggtact acgcctactc tcctcttctc ctcggcatca tccaaactga | 3540 |
| atcagattga agaatcatca ggtcattaac atgttcagtg tgtgtccagc aggtgcaggt | 3600 |
| gcagcagcag cagcaagcac agatgaggat taacagggcc accagatccc ttcttcctca | 3660 |
| gccgccgccg aaactaggta ctactgaaaa ctgtagacaa caagatacaa gatctcattt | 3720 |
| cattgacgcc tgtttctcac gcaatacaga ctgcccgtcc acctgctccg tgcgctgcgg | 3780 |
| caacaactgg aagaaccaga tgtgcaacaa gatgtgcaac gtctgctgca acaagtgcag | 3840 |
| ctgcgtgccg ccggggaccg gccaggacac ccgccacctc tgcccctgct acgacaccat | 3900 |
| gctcaatc | 3908 |

<210> SEQ ID NO 51
<211> LENGTH: 3908
<212> TYPE: DNA
<213> ORGANISM: Zea mays
<220> FEATURE:
<221> NAME/KEY: misc_feature
<222> LOCATION: (1)..(3908)
<223> OTHER INFORMATION: n is a, c, g, or t
<220> FEATURE:
<221> NAME/KEY: misc_feature
<222> LOCATION: (2859)..(2859)
<223> OTHER INFORMATION: y is c or t

<400> SEQUENCE: 51

| | |
|---|---|
| taggataata gcccagtttc atttggattt tgaatttact tgcgggccat catcgattgg | 60 |
| tggctggatc taatggcacg cacgtcaccc ccaccggatg catgccacag atctgtgcat | 120 |
| gtgctcacca tgctgaggga ggtcaggatt ggtgcctgca cgcatggggt tcctacgccc | 180 |
| agaccaaaag gatctggttg ctatctttcg cccatacacg gatgctcttc ttcagatctg | 240 |
| gttaagcggg caatgattgc attgcggggg caccagcacc agaaacaaac tgtaggaggt | 300 |
| tgctgcggtg gtccctgtgg ggttctactg ctttaggatt attttctggg atctgttttt | 360 |
| tttccagccc gagtatgcat gccgtcgagg ttcaggttcc tcctctctta gcaaagtttt | 420 |
| atgaagcttc tttttggctt ctggttgctg cctgcacaac tttatcaagc taccaaacgt | 480 |
| actagttgta ctgcttcctt tggattatag aggagttact aaataaactg tgtttgggtgt | 540 |
| gcatattctc aaggctgtgg tcttaggaat tgctttcagt tatgcaagag atacttactt | 600 |
| ggcatacaac tactggcgct ccgaatgccc tgccaccccc ctggcctgat agattctttg | 660 |
| atctggacct tatatggtta gtttattcag tgttgctgca ctgtctctct acatgtttcc | 720 |
| tgaaacatca gtagattgtg gaatagcagt gtgatggtgt agctttatgg ttacagctaa | 780 |
| ctcagctgtt ggtgagatag ctccttgcag ttgcagatan caatgtgctt ccttcagctg | 840 |
| tttcttccat ctagtgtact tgtncaagtt cttccatgan atgataaatg tgtatttnt | 900 |
| nttnacttca ctgtttatct aactctgctg ngtnantttn cantngnttt ttcagtagca | 960 |
| accaccaccc anggnggacg tgcacgaacc tttggngcgc cgtaagagga ananggtttt | 1020 |
| ggtggactac ttggtgaagt tccgatngat cctcgtgatc ttcgtggtcc ttcctatttn | 1080 |
| aactctgatc tacttcaaca tcttcctggg cgacatgtgg tccgccatga agtcggagaa | 1140 |
| gaagcgccag aagcagcacg acgagaacgt gcagaaggtc gtgaagcggc tcaagcagag | 1200 |
| gaacccgaag aaggangtc ttgtttgnac ggccaggaag ccctggatcg ctgttggcat | 1260 |
| gcgcaacgtg gactacaagc gtgcgaggca tttcgaggtc ganctttctt cnttcaggaa | 1320 |
| catccttgag atcgacaaag agaggatggt tgccaaggtc gagcccctng tnaacatggg | 1380 |
| tcagataacc agagctacct gcccaatgaa ccttgcccct gcggtcgtcg ccgagctcga | 1440 |

```
cgacctcact gttggtgggc tgatcaacgg ttacggcatc gagggagct  ctcacctcta   1500
tggccttttc tcngacacgg ttgtcgcgat ggaggttgtt ctcgcagatg gccgggtcgt   1560
nagagccacc aaggacaacg agtactctga ccttttctat ggnattccct ggtcccaggg   1620
aacactgggg ttccttgtct ctgcngagat caagctgatc cccatcaagg agtacatgaa   1680
gctcacctac actccagtca aggggggtct aaaggagatc gcgcaggcct acgcggattc   1740
tttcgcnccg agggacggtg acccggcaaa ggtccctgac tttgttgaag ggatggtgta   1800
cacagagagc gagggtgtca tgatgacggg cgtgtacgct tcnaaagaag aggcgaagaa   1860
gaagggcaac aagatcaact gcgtgggtg  gtggtttaag ccctggttct accagcacgc   1920
tcagacggcg ctgaagaggg gngagtttgt ggagtacatc ccgacgaggg agtactacca   1980
ccggcacacc cggtgcctgt actgggaggg gaagctgatc ctgcccttcn gcgaccagtt   2040
ctggttcagg ttcctgctgg gctggctgat gccaccgaag gtgtcccngc tgaaggcgac   2100
ccagggcgag gctatnanga actacnccac gacaaccatg tgatccagna catgctggtg   2160
ccgctgtaca aggttgggga ngcgctggan ttcgtgcacc gcgngatgga ggtacaatgg   2220
ctggctggtg ctggtgctgg tgcngcttgc tttatnagta gttnactgga tatactaata   2280
ataatngaaa ttcttttgg  taggtgtatc ctctntggct gtgccctcac cggcngtacn   2340
gctgccggtg aaganatngt gtacccggag cctgggttcn agcaccagna cangnagggc   2400
gacacgagct acgcncagat gttcacggac gtgggcgtgt actacgcccc cggggcntgc   2460
tgagggggga gnagttnaac ggcgcgnagg ctgtgcacag gctggagcag tggctgatng   2520
agaaccacan ctnccngccg cngtncgcgg tgtngganct gaacgagaan gacttntggn   2580
gcatgttngn cgngtncnct ncgancacng ccnccaaaan tncggggngn gggcncgttn   2640
atgangngtn ctacnantnc nanaangggn cnanacggan aaggangngc nggnggnggn   2700
ggnggccnac nggnccngcc tncncggncn ggnggcctaa anctngnggt ngttttgctt   2760
ncccntttta attnaacntn anggangtng ngngntntna antcntngta ntnactnttta  2820
aanctngngg tcgntcggtc ggtngtcant cngtntgtyg ntgantccan cntntttttt  2880
attttaatat tntntaangg aatctntcag attgattcgg gacttgctat gnctntnctn  2940
tttgcctatt tgttatgttt tttttnaaa  gttctccagg cgctgctnct gcgtcttgca   3000
aggagccngg agctgntgac tancagcagc ancagctngg aacggtggga ggcagcacca   3060
ccatggcacc atgtggctga gctgggctgg caggcacagt gagaaaaaga aagacaccag   3120
ccatctactc cccagtcccc ccacaagagc aaaagcaaag aaagatgcat gtgcatgtgc   3180
agtgcagcaa ctctgccatg ctgtcatgtg ggacggcacg ggcaccagct gcactgcact   3240
gcaccgcccc acagtatat  tgtttactgc tgctgtgccc actccttgta tatttgcatc   3300
actgcctgct tctggaatca ggaaaggaga tcaccacttc actcaagaag gcaccctccc   3360
ttgccactcc ttttccttga gatgacgatg acgacgatga agaagcagca gcagctcctc   3420
ctcctccttt ctctcatgtt tctcgttgct gtgacagcag ccgctgttgc tgccgatcca   3480
catccacagc aggtggtact acgcctactc tcctcttctc ctcggcatca tccaaactga   3540
atcagattga agaatcatca ggtcattaac atgttcagtt tgtgtccagc aggtgcaggt   3600
gcagcagcag cagcaagcac agatgaggat taacagggcc accagatccc ttcttcctca   3660
gccgccgccg aaactaggta ctactgaaaa ctgtagacaa caagatacaa gatctcattt   3720
cattgacgcc tgtttctcac gcaatacaga ctgcccgtcc acctgctccg tgcgctgcgg   3780
```

```
caacaactgg aagaaccaga tgtgcaacaa gatgtgcaac gtctgctgca acaagtgcag      3840
ctgcgtgccg ccggggaccg gccaggacac ccgccacctc tgcccctgct acgacaccat      3900
gctcaatc                                                               3908
```

<210> SEQ ID NO 52
<211> LENGTH: 17
<212> TYPE: DNA
<213> ORGANISM: Zea mays

<400> SEQUENCE: 52

```
gcgtgcgagg catttcg                                                     17
```

<210> SEQ ID NO 53
<211> LENGTH: 19
<212> TYPE: DNA
<213> ORGANISM: Zea mays

<400> SEQUENCE: 53

```
gctcgacctt ggcaaccat                                                   19
```

<210> SEQ ID NO 54
<211> LENGTH: 86
<212> TYPE: DNA
<213> ORGANISM: Zea mays
<220> FEATURE:
<221> NAME/KEY: misc_feature
<222> LOCATION: (25)..(34)
<223> OTHER INFORMATION: n is a, c, g, or t
<220> FEATURE:
<221> NAME/KEY: misc_feature
<222> LOCATION: (55)..(55)
<223> OTHER INFORMATION: y is c or t

<400> SEQUENCE: 54

```
gcgtgcgagg catttcgagg tcganctttc ttcnttcagg aacatccttg agatygacaa      60
agagaggatg gttgccaagg tcgagc                                           86
```

<210> SEQ ID NO 55
<211> LENGTH: 16
<212> TYPE: DNA
<213> ORGANISM: Zea mays

<400> SEQUENCE: 55

```
ctctttgtca atctca                                                      16
```

<210> SEQ ID NO 56
<211> LENGTH: 18
<212> TYPE: DNA
<213> ORGANISM: Zea mays

<400> SEQUENCE: 56

```
ctctctttgt cgatctca                                                    18
```

<210> SEQ ID NO 57
<211> LENGTH: 18
<212> TYPE: DNA
<213> ORGANISM: Zea mays

<400> SEQUENCE: 57

```
ctcgcccgca gtgaaatg                                                    18
```

<210> SEQ ID NO 58
<211> LENGTH: 24

```
<212> TYPE: DNA
<213> ORGANISM: Zea mays

<400> SEQUENCE: 58
catatccaat cagccctgga atcc                                          24

<210> SEQ ID NO 59
<211> LENGTH: 61
<212> TYPE: DNA
<213> ORGANISM: Zea mays
<220> FEATURE:
<221> NAME/KEY: misc_feature
<222> LOCATION: (26)..(26)
<223> OTHER INFORMATION: s is c or g

<400> SEQUENCE: 59
ctcgcccgca gtgaaatgaa tgcacsctgg cctgtccgga ttccagggct gattggatat    60
g                                                                   61

<210> SEQ ID NO 60
<211> LENGTH: 14
<212> TYPE: DNA
<213> ORGANISM: Zea mays

<400> SEQUENCE: 60
ccaggccgtg catt                                                     14

<210> SEQ ID NO 61
<211> LENGTH: 14
<212> TYPE: DNA
<213> ORGANISM: Zea mays

<400> SEQUENCE: 61
ccagggcgtg catt                                                     14

<210> SEQ ID NO 62
<211> LENGTH: 19
<212> TYPE: DNA
<213> ORGANISM: Zea mays

<400> SEQUENCE: 62
ggcactacgt gcactgcta                                                19

<210> SEQ ID NO 63
<211> LENGTH: 16
<212> TYPE: DNA
<213> ORGANISM: Zea mays

<400> SEQUENCE: 63
cgccacgggc cttgta                                                   16

<210> SEQ ID NO 64
<211> LENGTH: 84
<212> TYPE: DNA
<213> ORGANISM: Zea mays
<220> FEATURE:
<221> NAME/KEY: misc_feature
<222> LOCATION: (44)..(44)
<223> OTHER INFORMATION: k is g or t

<400> SEQUENCE: 64
ggcactacgt gcactgctac gcgctgcact gcctggacga ggakgcctcc aacgcgctgc    60
gccgggcgta caaggcccgt ggcg                                          84
```

```
<210> SEQ ID NO 65
<211> LENGTH: 14
<212> TYPE: DNA
<213> ORGANISM: Zea mays

<400> SEQUENCE: 65
acgaggatgc ctcc                                                           14

<210> SEQ ID NO 66
<211> LENGTH: 13
<212> TYPE: DNA
<213> ORGANISM: Zea mays

<400> SEQUENCE: 66
cgaggaggcc tcc                                                            13

<210> SEQ ID NO 67
<211> LENGTH: 24
<212> TYPE: DNA
<213> ORGANISM: Zea mays

<400> SEQUENCE: 67
gttgccgcta tataacagga tcca                                                24

<210> SEQ ID NO 68
<211> LENGTH: 22
<212> TYPE: DNA
<213> ORGANISM: Zea mays

<400> SEQUENCE: 68
acctaactcg tgctccttga ct                                                  22

<210> SEQ ID NO 69
<211> LENGTH: 79
<212> TYPE: DNA
<213> ORGANISM: Zea mays
<220> FEATURE:
<221> NAME/KEY: misc_feature
<222> LOCATION: (25)..(55)
<223> OTHER INFORMATION: n is a, c, g, or t
<220> FEATURE:
<221> NAME/KEY: misc_feature
<222> LOCATION: (49)..(49)
<223> OTHER INFORMATION: k is g or t

<400> SEQUENCE: 69
gttgccgcta tataacagga tccangcang gcanggnggc nggnaacakc ancanggagt         60
caaggagcac gagttaggt                                                      79

<210> SEQ ID NO 70
<211> LENGTH: 15
<212> TYPE: DNA
<213> ORGANISM: Zea mays

<400> SEQUENCE: 70
caggcaacag caaca                                                          15

<210> SEQ ID NO 71
<211> LENGTH: 15
<212> TYPE: DNA
<213> ORGANISM: Zea mays

<400> SEQUENCE: 71
caggcaacat caaca                                                          15
```

```
<210> SEQ ID NO 72
<211> LENGTH: 25
<212> TYPE: DNA
<213> ORGANISM: Zea mays

<400> SEQUENCE: 72
ggcctgtgag ggttgaatat taaca                                     25

<210> SEQ ID NO 73
<211> LENGTH: 22
<212> TYPE: DNA
<213> ORGANISM: Zea mays

<400> SEQUENCE: 73
cgctcgaact tcaaaacaac ct                                        22

<210> SEQ ID NO 74
<211> LENGTH: 67
<212> TYPE: DNA
<213> ORGANISM: Zea mays
<220> FEATURE:
<221> NAME/KEY: misc_feature
<222> LOCATION: (34)..(34)
<223> OTHER INFORMATION: r is a or g

<400> SEQUENCE: 74
ggcctgtgag ggttgaatat taacaagagg ggarattgca aaatcaggtt gttttgaagt 60
tcgagcg                                                          67

<210> SEQ ID NO 75
<211> LENGTH: 14
<212> TYPE: DNA
<213> ORGANISM: Zea mays

<400> SEQUENCE: 75
tttgcaattt cccc                                                  14

<210> SEQ ID NO 76
<211> LENGTH: 16
<212> TYPE: DNA
<213> ORGANISM: Zea mays

<400> SEQUENCE: 76
attttgcaat ctcccc                                                16

<210> SEQ ID NO 77
<211> LENGTH: 25
<212> TYPE: DNA
<213> ORGANISM: Zea mays

<400> SEQUENCE: 77
ggcctgtgag ggttgaatat taaca                                      25

<210> SEQ ID NO 78
<211> LENGTH: 22
<212> TYPE: DNA
<213> ORGANISM: Zea mays

<400> SEQUENCE: 78
cgctcgaact tcaaaacaac ct                                         22

<210> SEQ ID NO 79
```

```
<211> LENGTH: 67
<212> TYPE: DNA
<213> ORGANISM: Zea mays
<220> FEATURE:
<221> NAME/KEY: misc_feature
<222> LOCATION: (34)..(34)
<223> OTHER INFORMATION: r is a or g

<400> SEQUENCE: 79
ggcctgtgag ggttgaatat taacaagagg ggarattgca aaatcaggtt gttttgaagt      60
tcgagcg                                                               67

<210> SEQ ID NO 80
<211> LENGTH: 15
<212> TYPE: DNA
<213> ORGANISM: Zea mays

<400> SEQUENCE: 80
ttttgcaatc tcccc                                                      15

<210> SEQ ID NO 81
<211> LENGTH: 15
<212> TYPE: DNA
<213> ORGANISM: Zea mays

<400> SEQUENCE: 81
ttttgcaatt tcccc                                                      15

<210> SEQ ID NO 82
<211> LENGTH: 25
<212> TYPE: DNA
<213> ORGANISM: Zea mays

<400> SEQUENCE: 82
ggcacccttt acaaacacaa atcag                                           25

<210> SEQ ID NO 83
<211> LENGTH: 25
<212> TYPE: DNA
<213> ORGANISM: Zea mays

<400> SEQUENCE: 83
cccatcggtg atttcttttc cattt                                           25

<210> SEQ ID NO 84
<211> LENGTH: 105
<212> TYPE: DNA
<213> ORGANISM: Zea mays
<220> FEATURE:
<221> NAME/KEY: misc_feature
<222> LOCATION: (35)..(35)
<223> OTHER INFORMATION: y is c or t

<400> SEQUENCE: 84
ggcacccttt acaaacacaa atcaggagtg tcgcyagaca cacctagcc aactaggatt      60 caaagacccc aaaagtaata aaatggaaaa gaaatcaccg atggg                    105

<210> SEQ ID NO 85
<211> LENGTH: 17
<212> TYPE: DNA
<213> ORGANISM: Zea mays

<400> SEQUENCE: 85
ctaggtgttg tctagcg                                                    17
```

```
<210> SEQ ID NO 86
<211> LENGTH: 17
<212> TYPE: DNA
<213> ORGANISM: Zea mays

<400> SEQUENCE: 86
ctaggtgttg tctggcg                                                    17

<210> SEQ ID NO 87
<211> LENGTH: 25
<212> TYPE: DNA
<213> ORGANISM: Zea mays

<400> SEQUENCE: 87
acaactgtcg tgaatgtacc aatct                                           25

<210> SEQ ID NO 88
<211> LENGTH: 25
<212> TYPE: DNA
<213> ORGANISM: Zea mays

<400> SEQUENCE: 88
gctttgcgtg ccactatatt ttctt                                           25

<210> SEQ ID NO 89
<211> LENGTH: 87
<212> TYPE: DNA
<213> ORGANISM: Zea mays
<220> FEATURE:
<221> NAME/KEY: misc_feature
<222> LOCATION: (56)..(56)
<223> OTHER INFORMATION: k is g or t

<400> SEQUENCE: 89
acaactgtcg tgaatgtacc aatctttta ggtcgttgac aagctataac aatatkatgg       60
taaagaaaat atagtggcac gcaaagc                                         87

<210> SEQ ID NO 90
<211> LENGTH: 20
<212> TYPE: DNA
<213> ORGANISM: Zea mays

<400> SEQUENCE: 90
aagctataac aatagaatgg                                                 20

<210> SEQ ID NO 91
<211> LENGTH: 21
<212> TYPE: DNA
<213> ORGANISM: Zea mays

<400> SEQUENCE: 91
caagctataa caatataatg g                                               21

<210> SEQ ID NO 92
<211> LENGTH: 24
<212> TYPE: DNA
<213> ORGANISM: Zea mays

<400> SEQUENCE: 92
agtgtccatg catcagtctt tgtt                                            24

<210> SEQ ID NO 93
```

```
<211> LENGTH: 19
<212> TYPE: DNA
<213> ORGANISM: Zea mays

<400> SEQUENCE: 93
gctgcgagtt tgcggtatg                                                   19

<210> SEQ ID NO 94
<211> LENGTH: 101
<212> TYPE: DNA
<213> ORGANISM: Zea mays
<220> FEATURE:
<221> NAME/KEY: misc_feature
<222> LOCATION: (25)..(80)
<223> OTHER INFORMATION: n is a, c, g, or t
<220> FEATURE:
<221> NAME/KEY: misc_feature
<222> LOCATION: (39)..(39)
<223> OTHER INFORMATION: y is c or t

<400> SEQUENCE: 94
agtgtccatg catcagtctt tgttngacta gagtcacgyg ctctgctctg ctcgcctgtg     60
atgttacttg ntcttgttcn atcataccgc aaactcgcag c                        101

<210> SEQ ID NO 95
<211> LENGTH: 14
<212> TYPE: DNA
<213> ORGANISM: Zea mays

<400> SEQUENCE: 95
cagagcgcgt gact                                                        14

<210> SEQ ID NO 96
<211> LENGTH: 16
<212> TYPE: DNA
<213> ORGANISM: Zea mays

<400> SEQUENCE: 96
agcagagcac gtgact                                                      16

<210> SEQ ID NO 97
<211> LENGTH: 22
<212> TYPE: DNA
<213> ORGANISM: Zea mays

<400> SEQUENCE: 97
tccaacagct cttccagatt gc                                               22

<210> SEQ ID NO 98
<211> LENGTH: 19
<212> TYPE: DNA
<213> ORGANISM: Zea mays

<400> SEQUENCE: 98
cgatggccca actcaatgg                                                   19

<210> SEQ ID NO 99
<211> LENGTH: 152
<212> TYPE: DNA
<213> ORGANISM: Zea mays
<220> FEATURE:
<221> NAME/KEY: misc_feature
<222> LOCATION: (27)..(121)
<223> OTHER INFORMATION: n is a, c, g, or t
<220> FEATURE:
<221> NAME/KEY: misc_feature
```

<222> LOCATION: (93)..(93)
<223> OTHER INFORMATION: r is a or g

<400> SEQUENCE: 99
tccaacagct cttccagatt gcgcaaggc taagaatgaa aanggtgcaa anaaatagta    60
tgtgggttat atgataaaca tnatcaatgc targtaacgt ggaaaagnct gcacggaatg   120
nactggatta tacccattga gttgggccat cg                                152

<210> SEQ ID NO 100
<211> LENGTH: 17
<212> TYPE: DNA
<213> ORGANISM: Zea mays

<400> SEQUENCE: 100
ccacgttacc tagcatt                                                  17

<210> SEQ ID NO 101
<211> LENGTH: 20
<212> TYPE: DNA
<213> ORGANISM: Zea mays

<400> SEQUENCE: 101
tttccacgtt acttagcatt                                               20

<210> SEQ ID NO 102
<211> LENGTH: 24
<212> TYPE: DNA
<213> ORGANISM: Zea mays

<400> SEQUENCE: 102
gcatcttgtc gtccgagtag taga                                          24

<210> SEQ ID NO 103
<211> LENGTH: 22
<212> TYPE: DNA
<213> ORGANISM: Zea mays

<400> SEQUENCE: 103
acgtggacaa cttcttcaac ga                                            22

<210> SEQ ID NO 104
<211> LENGTH: 90
<212> TYPE: DNA
<213> ORGANISM: Zea mays
<220> FEATURE:
<221> NAME/KEY: misc_feature
<222> LOCATION: (47)..(47)
<223> OTHER INFORMATION: s is c or g

<400> SEQUENCE: 104
gcatcttgtc gtccgagtag tagatccctg gcaccaccag ccccggsccg aacgccagct    60
gctcgttctc gttgaagaag ttgtccacgt                                    90

<210> SEQ ID NO 105
<211> LENGTH: 13
<212> TYPE: DNA
<213> ORGANISM: Zea mays

<400> SEQUENCE: 105
cccggcccga acg                                                      13

<210> SEQ ID NO 106

```
<211> LENGTH: 13
<212> TYPE: DNA
<213> ORGANISM: Zea mays

<400> SEQUENCE: 106
cccgggccga acg                                                         13

<210> SEQ ID NO 107
<211> LENGTH: 19
<212> TYPE: DNA
<213> ORGANISM: Zea mays

<400> SEQUENCE: 107
gcgggtcgaa gtcgtactg                                                   19

<210> SEQ ID NO 108
<211> LENGTH: 18
<212> TYPE: DNA
<213> ORGANISM: Zea mays

<400> SEQUENCE: 108
ggagtggacg ctgtacgt                                                    18

<210> SEQ ID NO 109
<211> LENGTH: 65
<212> TYPE: DNA
<213> ORGANISM: Zea mays
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(35)
<223> OTHER INFORMATION: s is c or g

<400> SEQUENCE: 109
gcgggtcgaa gtcgtactgc tcctccgtgt cnggstccat cacctgcacg tacagcgtcc      60
actcc                                                                  65

<210> SEQ ID NO 110
<211> LENGTH: 14
<212> TYPE: DNA
<213> ORGANISM: Zea mays

<400> SEQUENCE: 110
caggtgatgg agcc                                                        14

<210> SEQ ID NO 111
<211> LENGTH: 14
<212> TYPE: DNA
<213> ORGANISM: Zea mays

<400> SEQUENCE: 111
caggtgatgg accc                                                        14

<210> SEQ ID NO 112
<211> LENGTH: 29
<212> TYPE: DNA
<213> ORGANISM: Zea mays

<400> SEQUENCE: 112
agaagacttc cctagcaata acagaagta                                        29
```

-continued

<210> SEQ ID NO 113
<211> LENGTH: 28
<212> TYPE: DNA
<213> ORGANISM: Zea mays

<400> SEQUENCE: 113
ggaactggat gaatgtacta gaaaacca                                          28

<210> SEQ ID NO 114
<211> LENGTH: 83
<212> TYPE: DNA
<213> ORGANISM: Zea mays
<220> FEATURE:
<221> NAME/KEY: misc_feature
<222> LOCATION: (37)..(37)
<223> OTHER INFORMATION: y is c or t

<400> SEQUENCE: 114
agaagacttc cctagcaata acagaagtac ataactygaa gaccaaactg catcatggtt       60
ttctagtaca ttcatccagt tcc                                              83

<210> SEQ ID NO 115
<211> LENGTH: 17
<212> TYPE: DNA
<213> ORGANISM: Zea mays

<400> SEQUENCE: 115
ttggtcttca agttatg                                                     17

<210> SEQ ID NO 116
<211> LENGTH: 18
<212> TYPE: DNA
<213> ORGANISM: Zea mays

<400> SEQUENCE: 116
tttggtcttc gagttatg                                                    18

<210> SEQ ID NO 117
<211> LENGTH: 25
<212> TYPE: DNA
<213> ORGANISM: Zea mays

<400> SEQUENCE: 117
gcgtattctt gaacttgtcc aggaa                                            25

<210> SEQ ID NO 118
<211> LENGTH: 25
<212> TYPE: DNA
<213> ORGANISM: Zea mays

<400> SEQUENCE: 118
cagactttga tgaagcctag gttct                                            25

<210> SEQ ID NO 119
<211> LENGTH: 140
<212> TYPE: DNA
<213> ORGANISM: Zea mays
<220> FEATURE:
<221> NAME/KEY: misc_feature
<222> LOCATION: (33)..(113)
<223> OTHER INFORMATION: n is a, c, g, or t
<220> FEATURE:
<221> NAME/KEY: misc_feature
<222> LOCATION: (58)..(58)
<223> OTHER INFORMATION: s is c or g -continued

```
<400> SEQUENCE: 119
gcgtattctt gaacttgtcc aggaaatgaa agnaccttgn tttggttyga ttcngcntng    60
cangagacac tgtgacnatg antcanttac tatgtaaaaa angangaaga ntntagaacc   120
taggcttcat caaagtctga                                               140

<210> SEQ ID NO 120
<211> LENGTH: 17
<212> TYPE: DNA
<213> ORGANISM: Zea mays

<400> SEQUENCE: 120
aagcatgaat caaacca                                                   17

<210> SEQ ID NO 121
<211> LENGTH: 19
<212> TYPE: DNA
<213> ORGANISM: Zea mays

<400> SEQUENCE: 121
caaagcatga atcgaacca                                                 19

<210> SEQ ID NO 122
<211> LENGTH: 25
<212> TYPE: DNA
<213> ORGANISM: Zea mays

<400> SEQUENCE: 122
gcgtattctt gaacttgtcc aggaa                                          25

<210> SEQ ID NO 123
<211> LENGTH: 25
<212> TYPE: DNA
<213> ORGANISM: Zea mays

<400> SEQUENCE: 123
cagactttga tgaagcctag gttct                                          25

<210> SEQ ID NO 124
<211> LENGTH: 139
<212> TYPE: DNA
<213> ORGANISM: Zea mays
<220> FEATURE:
<221> NAME/KEY: misc_feature
<222> LOCATION: (33)..(113)
<223> OTHER INFORMATION: n is a, c, g, or t
<220> FEATURE:
<221> NAME/KEY: misc_feature
<222> LOCATION: (58)..(58)
<223> OTHER INFORMATION: s is c or g

<400> SEQUENCE: 124
gcgtattctt gaacttgtcc aggaaatgaa agnaccttgn tttggttnga ttcngcntng    60
cakgagacac tgtgacnatg antcanttac tatgtaaaaa angangaaga ntntagaacc   120
taggcttcat caaagtctg                                                139

<210> SEQ ID NO 125
<211> LENGTH: 16
<212> TYPE: DNA
<213> ORGANISM: Zea mays

<400> SEQUENCE: 125
cagtgtctca atgcaa                                                    16
```

<210> SEQ ID NO 126
<211> LENGTH: 17
<212> TYPE: DNA
<213> ORGANISM: Zea mays

<400> SEQUENCE: 126
acagtgtctc catgcaa                                                  17

<210> SEQ ID NO 127
<211> LENGTH: 25
<212> TYPE: DNA
<213> ORGANISM: Zea mays

<400> SEQUENCE: 127
agatgaaaac tgatgttgcg tgaga                                         25

<210> SEQ ID NO 128
<211> LENGTH: 23
<212> TYPE: DNA
<213> ORGANISM: Zea mays

<400> SEQUENCE: 128
ccattgcttg gtggaaagaa caa                                           23

<210> SEQ ID NO 129
<211> LENGTH: 69
<212> TYPE: DNA
<213> ORGANISM: Zea mays
<220> FEATURE:
<221> NAME/KEY: misc_feature
<222> LOCATION: (32)..(32)
<223> OTHER INFORMATION: y is c or t

<400> SEQUENCE: 129
agatgaaaac tgatgttgcg tgagagacta tytgtgtgtg tttttcttgt tctttccacc   60
aagcaatgg                                                           69

<210> SEQ ID NO 130
<211> LENGTH: 15
<212> TYPE: DNA
<213> ORGANISM: Zea mays

<400> SEQUENCE: 130
cacacacaaa tagtc                                                    15

<210> SEQ ID NO 131
<211> LENGTH: 16
<212> TYPE: DNA
<213> ORGANISM: Zea mays

<400> SEQUENCE: 131
acacacacag atagtc                                                   16

<210> SEQ ID NO 132
<211> LENGTH: 23
<212> TYPE: DNA
<213> ORGANISM: Zea mays

<400> SEQUENCE: 132
ccctggttgg aattaggaaa tgc                                           23

<210> SEQ ID NO 133

```
<211> LENGTH: 25
<212> TYPE: DNA
<213> ORGANISM: Zea mays

<400> SEQUENCE: 133
gccttgtagg aagcatatga ttcgt                                        25

<210> SEQ ID NO 134
<211> LENGTH: 93
<212> TYPE: DNA
<213> ORGANISM: Zea mays
<220> FEATURE:
<221> NAME/KEY: misc_feature
<222> LOCATION: (34)..(67)
<223> OTHER INFORMATION: r is a or g
<220> FEATURE:
<221> NAME/KEY: misc_feature
<222> LOCATION: (63)..(63)
<223> OTHER INFORMATION: y is c or t

<400> SEQUENCE: 134
ccctggttgg aattaggaaa tgccaaatcg tccrgttaaa ratcrttgct ttattctcca   60
ggytggrgac gaatcatatg cttcctacaa ggc                               93

<210> SEQ ID NO 135
<211> LENGTH: 17
<212> TYPE: DNA
<213> ORGANISM: Zea mays

<400> SEQUENCE: 135
caaatcgtcc agttaaa                                                 17

<210> SEQ ID NO 136
<211> LENGTH: 17
<212> TYPE: DNA
<213> ORGANISM: Zea mays

<400> SEQUENCE: 136
caaatcgtcc ggttaaa                                                 17

<210> SEQ ID NO 137
<211> LENGTH: 25
<212> TYPE: DNA
<213> ORGANISM: Zea mays

<400> SEQUENCE: 137
tcatatgctt cctacaaggc agaga                                        25

<210> SEQ ID NO 138
<211> LENGTH: 25
<212> TYPE: DNA
<213> ORGANISM: Zea mays

<400> SEQUENCE: 138
aacgcctgta aaacgaacaa aagaa                                        25

<210> SEQ ID NO 139
<211> LENGTH: 149
<212> TYPE: DNA
<213> ORGANISM: Zea mays
<220> FEATURE:
<221> NAME/KEY: misc_feature
<222> LOCATION: (34)..(67)
<223> OTHER INFORMATION: r is a or g
<220> FEATURE:
<221> NAME/KEY: misc_feature
```

```
<222> LOCATION: (63)..(63)
<223> OTHER INFORMATION: y is c or t

<400> SEQUENCE: 139
tcatatgctt cctacaaggc agagaargat ggaatccttg agtctttagc tcgtcgtgca    60
aaggttmgcc tggttgcatt tccactacwc tcttgaktgt cttctwtaaa aatattcaag   120
atttttcttt tgttcgtttt acaggcgtt                                    149

<210> SEQ ID NO 140
<211> LENGTH: 14
<212> TYPE: DNA
<213> ORGANISM: Zea mays

<400> SEQUENCE: 140
ccaggctaac cttt                                                     14

<210> SEQ ID NO 141
<211> LENGTH: 13
<212> TYPE: DNA
<213> ORGANISM: Zea mays

<400> SEQUENCE: 141
caggcgaacc ttt                                                      13

<210> SEQ ID NO 142
<211> LENGTH: 26
<212> TYPE: DNA
<213> ORGANISM: Zea mays

<400> SEQUENCE: 142
ctccctctag tatcgttaca gtctgt                                        26

<210> SEQ ID NO 143
<211> LENGTH: 24
<212> TYPE: DNA
<213> ORGANISM: Zea mays

<400> SEQUENCE: 143
actctccata gtatcctggt tgca                                          24

<210> SEQ ID NO 144
<211> LENGTH: 130
<212> TYPE: DNA
<213> ORGANISM: Zea mays
<220> FEATURE:
<221> NAME/KEY: misc_feature
<222> LOCATION: (38)..(48)
<223> OTHER INFORMATION: r is a or g
<220> FEATURE:
<221> NAME/KEY: misc_feature
<222> LOCATION: (44)..(103)
<223> OTHER INFORMATION: y is c or t
<220> FEATURE:
<221> NAME/KEY: misc_feature
<222> LOCATION: (57)..(67)
<223> OTHER INFORMATION: k is g or t
<220> FEATURE:
<221> NAME/KEY: misc_feature
<222> LOCATION: (96)..(96)
<223> OTHER INFORMATION: v is a, c, or g

<400> SEQUENCE: 144
ctccctctag tatcgttaca gtctgtttcc aaaggtarat ttayatarcc agctacktta    60
tctgcckttt ggycaagtaa ctggcttatc caaaavattt tgytgctgca accaggatac   120
```
tatggagagt                                                                    130

<210> SEQ ID NO 145
<211> LENGTH: 17
<212> TYPE: DNA
<213> ORGANISM: Zea mays

<400> SEQUENCE: 145
ccagctactt tatctgc                                                             17

<210> SEQ ID NO 146
<211> LENGTH: 16
<212> TYPE: DNA
<213> ORGANISM: Zea mays

<400> SEQUENCE: 146
cagctacgtt atctgc                                                              16

<210> SEQ ID NO 147
<211> LENGTH: 25
<212> TYPE: DNA
<213> ORGANISM: Zea mays

<400> SEQUENCE: 147
acgacagtag tctgatctga tctga                                                    25

<210> SEQ ID NO 148
<211> LENGTH: 21
<212> TYPE: DNA
<213> ORGANISM: Zea mays

<400> SEQUENCE: 148
caatgcatgc tgccattagc t                                                        21

<210> SEQ ID NO 149
<211> LENGTH: 146
<212> TYPE: DNA
<213> ORGANISM: Zea mays
<220> FEATURE:
<221> NAME/KEY: misc_feature
<222> LOCATION: (31)..(119)
<223> OTHER INFORMATION: n is a, c, g, or t
<220> FEATURE:
<221> NAME/KEY: misc_feature
<222> LOCATION: (74)..(74)
<223> OTHER INFORMATION: w is a or t

<400> SEQUENCE: 149
acgacagtag tctgatctga tctgagagag nagtaaaaaa anaaaggaga aagtaaacaa             60
cngcgctcga cgawagattt tacttacatg catgcntgca tgnatntnct nctngctanc            120
tagctagcta atggcagcat gcattg                                                 146

<210> SEQ ID NO 150
<211> LENGTH: 15
<212> TYPE: DNA
<213> ORGANISM: Zea mays

<400> SEQUENCE: 150
ctcgacgata gattt                                                               15

<210> SEQ ID NO 151
<211> LENGTH: 15
<212> TYPE: DNA
<213> ORGANISM: Zea mays

<400> SEQUENCE: 151
ctcgacgaaa gattt                                              15

<210> SEQ ID NO 152
<211> LENGTH: 18
<212> TYPE: DNA
<213> ORGANISM: Zea mays

<400> SEQUENCE: 152
gtcctgctcc tgcatcga                                           18

<210> SEQ ID NO 153
<211> LENGTH: 23
<212> TYPE: DNA
<213> ORGANISM: Zea mays

<400> SEQUENCE: 153
gcctgatcca ctgtcatgtg atg                                     23

<210> SEQ ID NO 154
<211> LENGTH: 71
<212> TYPE: DNA
<213> ORGANISM: Zea mays
<220> FEATURE:
<221> NAME/KEY: misc_feature
<222> LOCATION: (30)..(30)
<223> OTHER INFORMATION: k is g or t

<400> SEQUENCE: 154
gtcctgctcc tgcatcgaga gactttcgck gcagattcca tctgtgctca tcacatgaca    60
gtggatcagg c                                                  71

<210> SEQ ID NO 155
<211> LENGTH: 16
<212> TYPE: DNA
<213> ORGANISM: Zea mays

<400> SEQUENCE: 155
actttcgctg cagatt                                             16

<210> SEQ ID NO 156
<211> LENGTH: 15
<212> TYPE: DNA
<213> ORGANISM: Zea mays

<400> SEQUENCE: 156
ctttcgcggc agatt                                              15

<210> SEQ ID NO 157
<211> LENGTH: 15
<212> TYPE: DNA
<213> ORGANISM: Zea mays

<400> SEQUENCE: 157
gctgcttggc gcgtt                                              15

<210> SEQ ID NO 158
<211> LENGTH: 20
<212> TYPE: DNA
<213> ORGANISM: Zea mays

<400> SEQUENCE: 158
cgcgctcctt ttctcctcaa                                              20

<210> SEQ ID NO 159
<211> LENGTH: 144
<212> TYPE: DNA
<213> ORGANISM: Zea mays
<220> FEATURE:
<221> NAME/KEY: misc_feature
<222> LOCATION: (17)..(125)
<223> OTHER INFORMATION: n is a, c, g, or t
<220> FEATURE:
<221> NAME/KEY: misc_feature
<222> LOCATION: (70)..(70)
<223> OTHER INFORMATION: y is c or t

<400> SEQUENCE: 159
gctgcttggc gcgttgntnt ctgcagctag naacagcagc ggcngcaaaa aaaaaaata    60 ttaaacacay gcgatngnca tgcgagagag cgcatgatcg atgagagaat atantagatn  120
atccntgagg agaaaggag cgcg                                          144

<210> SEQ ID NO 160
<211> LENGTH: 14
<212> TYPE: DNA
<213> ORGANISM: Zea mays

<400> SEQUENCE: 160
tcgcgtgtgt ttaa                                                    14

<210> SEQ ID NO 161
<211> LENGTH: 16
<212> TYPE: DNA
<213> ORGANISM: Zea mays

<400> SEQUENCE: 161
catcgcatgt gtttaa                                                  16

<210> SEQ ID NO 162
<211> LENGTH: 19
<212> TYPE: DNA
<213> ORGANISM: Zea mays

<400> SEQUENCE: 162
gagaaaagga gcgcgctttt                                              19

<210> SEQ ID NO 163
<211> LENGTH: 21
<212> TYPE: DNA
<213> ORGANISM: Zea mays

<400> SEQUENCE: 163
gtactaggtt caggcgatcg g                                            21

<210> SEQ ID NO 164
<211> LENGTH: 118
<212> TYPE: DNA
<213> ORGANISM: Zea mays
<220> FEATURE:
<221> NAME/KEY: misc_feature
<222> LOCATION: (20)..(96)
<223> OTHER INFORMATION: n is a, c, g, or t
<220> FEATURE:
<221> NAME/KEY: misc_feature
<222> LOCATION: (58)..(58)
<223> OTHER INFORMATION: r is a or g

<400> SEQUENCE: 164
gagaaaagga gcgcgctttn gacgggctna tcgtctcntc agtgatcagt agtggaarga    60
gntcnatngc cactgacatg tgacantcac agcgangccg atcgcctgaa cctagtac    118

<210> SEQ ID NO 165
<211> LENGTH: 17
<212> TYPE: DNA
<213> ORGANISM: Zea mays

<400> SEQUENCE: 165
atcagtagtg gaaagag    17

<210> SEQ ID NO 166
<211> LENGTH: 17
<212> TYPE: DNA
<213> ORGANISM: Zea mays

<400> SEQUENCE: 166
atcagtagtg gaaggag    17

<210> SEQ ID NO 167
<211> LENGTH: 24
<212> TYPE: DNA
<213> ORGANISM: Zea mays

<400> SEQUENCE: 167
tgtctcaagg aggacaacat catc    24

<210> SEQ ID NO 168
<211> LENGTH: 17
<212> TYPE: DNA
<213> ORGANISM: Zea mays

<400> SEQUENCE: 168
cccaccagcc gcttgat    17

<210> SEQ ID NO 169
<211> LENGTH: 101
<212> TYPE: DNA
<213> ORGANISM: Zea mays
<220> FEATURE:
<221> NAME/KEY: misc_feature
<222> LOCATION: (39)..(39)
<223> OTHER INFORMATION: s is c or g
<220> FEATURE:
<221> NAME/KEY: misc_feature
<222> LOCATION: (63)..(63)
<223> OTHER INFORMATION: n is a, c, g, or t

<400> SEQUENCE: 169
tgtctcaagg aggacaacat catcggcaag ggcggcgcsg ggatcgtgta ccacggcgtg    60
acncgcggcg gcgcggagct ggcgatcaag cggctggtgg g    101

<210> SEQ ID NO 170
<211> LENGTH: 14
<212> TYPE: DNA
<213> ORGANISM: Zea mays

<400> SEQUENCE: 170
acgatcccgg cgcc    14

<210> SEQ ID NO 171
<211> LENGTH: 17
<212> TYPE: DNA

<213> ORGANISM: Zea mays

<400> SEQUENCE: 171
tacacgatcc ccgcgcc                                                        17

<210> SEQ ID NO 172
<211> LENGTH: 15
<212> TYPE: DNA
<213> ORGANISM: Zea mays

<400> SEQUENCE: 172
ccggccgggc tcttc                                                          15

<210> SEQ ID NO 173
<211> LENGTH: 20
<212> TYPE: DNA
<213> ORGANISM: Zea mays

<400> SEQUENCE: 173
ttgttcccca gcatgagcat                                                     20

<210> SEQ ID NO 174
<211> LENGTH: 122
<212> TYPE: DNA
<213> ORGANISM: Zea mays
<220> FEATURE:
<221> NAME/KEY: misc_feature
<222> LOCATION: (18)..(66)
<223> OTHER INFORMATION: n is a, c, g, or t
<220> FEATURE:
<221> NAME/KEY: misc_feature
<222> LOCATION: (87)..(87)
<223> OTHER INFORMATION: y is c or t

<400> SEQUENCE: 174
ccggccgggc tcttcganct tccccaggcg aacatgctcg agctcaccga caacatgctc         60
acnggngagc tcccggacgt gatcgcygga gacaagatcg gcatgctcat gctggggaac        120
aa                                                                       122

<210> SEQ ID NO 175
<211> LENGTH: 15
<212> TYPE: DNA
<213> ORGANISM: Zea mays

<400> SEQUENCE: 175
ttgtctccgg cgatc                                                          15

<210> SEQ ID NO 176
<211> LENGTH: 16
<212> TYPE: DNA
<213> ORGANISM: Zea mays

<400> SEQUENCE: 176
cttgtctcca gcgatc                                                         16

<210> SEQ ID NO 177
<211> LENGTH: 21
<212> TYPE: DNA
<213> ORGANISM: Zea mays

<400> SEQUENCE: 177
gacaagatcg gcatgctcat g                                                   21

```
<210> SEQ ID NO 178
<211> LENGTH: 17
<212> TYPE: DNA
<213> ORGANISM: Zea mays

<400> SEQUENCE: 178
cagggacagc gtctgca                                                    17

<210> SEQ ID NO 179
<211> LENGTH: 96
<212> TYPE: DNA
<213> ORGANISM: Zea mays
<220> FEATURE:
<221> NAME/KEY: misc_feature
<222> LOCATION: (57)..(57)
<223> OTHER INFORMATION: m is a or c
<220> FEATURE:
<221> NAME/KEY: misc_feature
<222> LOCATION: (60)..(72)
<223> OTHER INFORMATION: n is a, c, g, or t

<400> SEQUENCE: 179
gacaagatcg gcatgctcat gctggggaac aatcgcatcg gagggcgcat ccccgcmgcn    60
atcggcaacc tnccgcgct gcagacgctg tccctg                              96

<210> SEQ ID NO 180
<211> LENGTH: 14
<212> TYPE: DNA
<213> ORGANISM: Zea mays

<400> SEQUENCE: 180
cgcatccccg ccgc                                                       14

<210> SEQ ID NO 181
<211> LENGTH: 14
<212> TYPE: DNA
<213> ORGANISM: Zea mays

<400> SEQUENCE: 181
cgcatccccg cagc                                                       14

<210> SEQ ID NO 182
<211> LENGTH: 17
<212> TYPE: DNA
<213> ORGANISM: Zea mays

<400> SEQUENCE: 182
aggctttggc cgtggtt                                                    17

<210> SEQ ID NO 183
<211> LENGTH: 24
<212> TYPE: DNA
<213> ORGANISM: Zea mays

<400> SEQUENCE: 183
cgctcatcgt catcaatcta atgg                                            24

<210> SEQ ID NO 184
<211> LENGTH: 106
<212> TYPE: DNA
<213> ORGANISM: Zea mays
<220> FEATURE:
<221> NAME/KEY: misc_feature
<222> LOCATION: (23)..(77)
<223> OTHER INFORMATION: n is a, c, g, or t
<220> FEATURE:
```

```
<221> NAME/KEY: misc_feature
<222> LOCATION: (38)..(38)
<223> OTHER INFORMATION: w is a or t

<400> SEQUENCE: 184
aggctttggc cgtggttggc tgngaattgg gatnattwtt ggtaatagca tgtcatcact        60
ggctccntnt ttttntnttt agccattaga ttgatgacga tgagcg                     106

<210> SEQ ID NO 185
<211> LENGTH: 16
<212> TYPE: DNA
<213> ORGANISM: Zea mays

<400> SEQUENCE: 185
tgctattacc aaaaat                                                       16

<210> SEQ ID NO 186
<211> LENGTH: 18
<212> TYPE: DNA
<213> ORGANISM: Zea mays

<400> SEQUENCE: 186
catgctatta ccaataat                                                     18

<210> SEQ ID NO 187
<211> LENGTH: 24
<212> TYPE: DNA
<213> ORGANISM: Zea mays

<400> SEQUENCE: 187
ttggcggttt cattgacaac aaaa                                              24

<210> SEQ ID NO 188
<211> LENGTH: 24
<212> TYPE: DNA
<213> ORGANISM: Zea mays

<400> SEQUENCE: 188
cattcactat ggattgcact tggc                                              24

<210> SEQ ID NO 189
<211> LENGTH: 162
<212> TYPE: DNA
<213> ORGANISM: Zea mays
<220> FEATURE:
<221> NAME/KEY: misc_feature
<222> LOCATION: (33)..(138)
<223> OTHER INFORMATION: n is a, c, g, or t
<220> FEATURE:
<221> NAME/KEY: misc_feature
<222> LOCATION: (79)..(79)
<223> OTHER INFORMATION: y is c or t

<400> SEQUENCE: 189
ttggcggttt cattgacaac aaaacggaaa atnaaaataa aaaaantggn tgtggccact        60
ccttagaatg ncgtgtcayc tttttaaagt cttggagcnc actgaaatac anttttgacg      120
gnttacgaat gaaatgggnc caagtgcaat ccatagtgaa tg                         162

<210> SEQ ID NO 190
<211> LENGTH: 22
<212> TYPE: DNA
<213> ORGANISM: Zea mays

<400> SEQUENCE: 190
```

```
caagacttta aaaaggtgac ac                                              22

<210> SEQ ID NO 191
<211> LENGTH: 22
<212> TYPE: DNA
<213> ORGANISM: Zea mays

<400> SEQUENCE: 191
caagacttta aaaagatgac ac                                              22

<210> SEQ ID NO 192
<211> LENGTH: 22
<212> TYPE: DNA
<213> ORGANISM: Zea mays

<400> SEQUENCE: 192
gagaagagga ttggagcaca gg                                              22

<210> SEQ ID NO 193
<211> LENGTH: 22
<212> TYPE: DNA
<213> ORGANISM: Zea mays

<400> SEQUENCE: 193
acaaatgcca ccttgagaac ga                                              22

<210> SEQ ID NO 194
<211> LENGTH: 76
<212> TYPE: DNA
<213> ORGANISM: Zea mays
<220> FEATURE:
<221> NAME/KEY: misc_feature
<222> LOCATION: (31)..(41)
<223> OTHER INFORMATION: n is a, c, g, or t
<220> FEATURE:
<221> NAME/KEY: misc_feature
<222> LOCATION: (35)..(35)
<223> OTHER INFORMATION: r is a or g

<400> SEQUENCE: 194
gagaagagga ttggagcaca ggcaaagagt nagargtagg nggcggcatg tacctcgttc     60
tcaaggtggc atttgt                                                     76

<210> SEQ ID NO 195
<211> LENGTH: 19
<212> TYPE: DNA
<213> ORGANISM: Zea mays

<400> SEQUENCE: 195
aaagagtgag aggtaggat                                                  19

<210> SEQ ID NO 196
<211> LENGTH: 20
<212> TYPE: DNA
<213> ORGANISM: Zea mays

<400> SEQUENCE: 196
caaagagtga gaagtaggat                                                 20

<210> SEQ ID NO 197
<211> LENGTH: 18
<212> TYPE: DNA
<213> ORGANISM: Zea mays
```

-continued

```
<400> SEQUENCE: 197
gcccacgaaa tgcatgct                                                   18

<210> SEQ ID NO 198
<211> LENGTH: 24
<212> TYPE: DNA
<213> ORGANISM: Zea mays

<400> SEQUENCE: 198
gctccaatcc tcttctctgt tcat                                            24

<210> SEQ ID NO 199
<211> LENGTH: 102
<212> TYPE: DNA
<213> ORGANISM: Zea mays
<220> FEATURE:
<221> NAME/KEY: misc_feature
<222> LOCATION: (19)..(77)
<223> OTHER INFORMATION: n is a, c, g, or t
<220> FEATURE:
<221> NAME/KEY: misc_feature
<222> LOCATION: (58)..(58)
<223> OTHER INFORMATION: m is a or c

<400> SEQUENCE: 199
gcccacgaaa tgcatgctna gtattatata tatatactgc aagtctgcaa cgccgtcmat     60
gatccatggc gcatggngat gaacagagaa gaggattgga gc                       102

<210> SEQ ID NO 200
<211> LENGTH: 13
<212> TYPE: DNA
<213> ORGANISM: Zea mays

<400> SEQUENCE: 200
ccgtccatga tcc                                                        13

<210> SEQ ID NO 201
<211> LENGTH: 13
<212> TYPE: DNA
<213> ORGANISM: Zea mays

<400> SEQUENCE: 201
ccgtcaatga tcc                                                        13

<210> SEQ ID NO 202
<211> LENGTH: 24
<212> TYPE: DNA
<213> ORGANISM: Zea mays

<400> SEQUENCE: 202
tcagggaact tgcaaacctt gtaa                                            24

<210> SEQ ID NO 203
<211> LENGTH: 25
<212> TYPE: DNA
<213> ORGANISM: Zea mays

<400> SEQUENCE: 203
cattgtggtc atggtagcac tagtt                                           25

<210> SEQ ID NO 204
<211> LENGTH: 113
<212> TYPE: DNA
<213> ORGANISM: Zea mays
```

```
<220> FEATURE:
<221> NAME/KEY: misc_feature
<222> LOCATION: (44)..(44)
<223> OTHER INFORMATION: r is a or g
<220> FEATURE:
<221> NAME/KEY: misc_feature
<222> LOCATION: (82)..(82)
<223> OTHER INFORMATION: n is a, c, g, or t

<400> SEQUENCE: 204
tcagggaact tgcaaacctt gtaagaaaca ccgaagtgca ctcrtataat ttcattgcta    60
ctaatgttta taatttgtat gnccaaataa ctagtgctac catgaccaca atg          113

<210> SEQ ID NO 205
<211> LENGTH: 16
<212> TYPE: DNA
<213> ORGANISM: Zea mays

<400> SEQUENCE: 205
agtgcactca tataat                                                   16

<210> SEQ ID NO 206
<211> LENGTH: 17
<212> TYPE: DNA
<213> ORGANISM: Zea mays

<400> SEQUENCE: 206
aagtgcactc gtataat                                                  17

<210> SEQ ID NO 207
<211> LENGTH: 23
<212> TYPE: DNA
<213> ORGANISM: Zea mays

<400> SEQUENCE: 207
ccgagacatg aagtcaagca atg                                           23

<210> SEQ ID NO 208
<211> LENGTH: 22
<212> TYPE: DNA
<213> ORGANISM: Zea mays

<400> SEQUENCE: 208
tgccataccg aaatcggata cc                                            22

<210> SEQ ID NO 209
<211> LENGTH: 73
<212> TYPE: DNA
<213> ORGANISM: Zea mays
<220> FEATURE:
<221> NAME/KEY: misc_feature
<222> LOCATION: (40)..(40)
<223> OTHER INFORMATION: r is a or g
<220> FEATURE:
<221> NAME/KEY: misc_feature
<222> LOCATION: (50)..(50)
<223> OTHER INFORMATION: n is a, c, g, or t

<400> SEQUENCE: 209
ccgagacatg aagtcaagca atgtgcttat cgatgagcar ttagaggcan gggtatccga   60
tttcggtatg gca                                                      73

<210> SEQ ID NO 210
<211> LENGTH: 17
<212> TYPE: DNA
```

```
<213> ORGANISM: Zea mays

<400> SEQUENCE: 210
atcgatgagc agttaga                                                    17

<210> SEQ ID NO 211
<211> LENGTH: 16
<212> TYPE: DNA
<213> ORGANISM: Zea mays

<400> SEQUENCE: 211
tcgatgagca attaga                                                     16

<210> SEQ ID NO 212
<211> LENGTH: 21
<212> TYPE: DNA
<213> ORGANISM: Zea mays

<400> SEQUENCE: 212
atgatgagcg tggtggatac c                                               21

<210> SEQ ID NO 213
<211> LENGTH: 18
<212> TYPE: DNA
<213> ORGANISM: Zea mays

<400> SEQUENCE: 213
gtactctggc ggcacgta                                                   18

<210> SEQ ID NO 214
<211> LENGTH: 75
<212> TYPE: DNA
<213> ORGANISM: Zea mays
<220> FEATURE:
<221> NAME/KEY: misc_feature
<222> LOCATION: (45)..(45)
<223> OTHER INFORMATION: s is c or g

<400> SEQUENCE: 214
atgatgagcg tggtggatac ccacctgagc gtgtccactc tcgcsggcac tccaggctac     60
gtgccgccag agtac                                                      75

<210> SEQ ID NO 215
<211> LENGTH: 14
<212> TYPE: DNA
<213> ORGANISM: Zea mays

<400> SEQUENCE: 215
ctctcgccgg cact                                                       14

<210> SEQ ID NO 216
<211> LENGTH: 14
<212> TYPE: DNA
<213> ORGANISM: Zea mays

<400> SEQUENCE: 216
ctctcgcggg cact                                                       14

<210> SEQ ID NO 217
<211> LENGTH: 18
<212> TYPE: DNA
<213> ORGANISM: Zea mays

<400> SEQUENCE: 217
```
cgacttcggc gaggacaa                                                    18

<210> SEQ ID NO 218
<211> LENGTH: 25
<212> TYPE: DNA
<213> ORGANISM: Zea mays

<400> SEQUENCE: 218
ccagtagtac agggtcaaac agatc                                            25

<210> SEQ ID NO 219
<211> LENGTH: 89
<212> TYPE: DNA
<213> ORGANISM: Zea mays
<220> FEATURE:
<221> NAME/KEY: misc_feature
<222> LOCATION: (25)..(25)
<223> OTHER INFORMATION: y is c or t
<221> NAME/KEY: misc_feature
<222> LOCATION: (43)..(64)
<223> OTHER INFORMATION: n is a, c, g, or t

<400> SEQUENCE: 219
cgacttcggc gaggacaaca atctygtagg atgggtcaaa cancactcaa agtcgaagct      60
ggcngatctg tttgaccctg tactactgg                                        89

<210> SEQ ID NO 220
<211> LENGTH: 15
<212> TYPE: DNA
<213> ORGANISM: Zea mays

<400> SEQUENCE: 220
catcctacaa gattg                                                       15

<210> SEQ ID NO 221
<211> LENGTH: 16
<212> TYPE: DNA
<213> ORGANISM: Zea mays

<400> SEQUENCE: 221
ccatcctacg agattg                                                      16

<210> SEQ ID NO 222
<211> LENGTH: 20
<212> TYPE: DNA
<213> ORGANISM: Zea mays

<400> SEQUENCE: 222
aggcaacctg caagtacgtt                                                  20

<210> SEQ ID NO 223
<211> LENGTH: 25
<212> TYPE: DNA
<213> ORGANISM: Zea mays

<400> SEQUENCE: 223
ggcaaaaatc agaacaaccg aagac                                            25

<210> SEQ ID NO 224
<211> LENGTH: 77
<212> TYPE: DNA
<213> ORGANISM: Zea mays
<220> FEATURE:
<221> NAME/KEY: misc_feature

```
<222> LOCATION: (22)..(48)
<223> OTHER INFORMATION: n is a, c, g, or t
<220> FEATURE:
<220> FEATURE:
<221> NAME/KEY: misc_feature
<222> LOCATION: (28)..(28)
<223> OTHER INFORMATION: y is c or t

<400> SEQUENCE: 224
aggcaacctg caagtacgtt gnctntnyca nananagngn atnacacnct ctgtcttcgg      60
ttgttctgat ttttgcc                                                    77

<210> SEQ ID NO 225
<211> LENGTH: 16
<212> TYPE: DNA
<213> ORGANISM: Zea mays

<400> SEQUENCE: 225
ctgttctgtg aaagga                                                     16

<210> SEQ ID NO 226
<211> LENGTH: 17
<212> TYPE: DNA
<213> ORGANISM: Zea mays

<400> SEQUENCE: 226
tctgttctgt ggaagga                                                    17

<210> SEQ ID NO 227
<211> LENGTH: 20
<212> TYPE: DNA
<213> ORGANISM: Zea mays

<400> SEQUENCE: 227
gttctggcca gcagatgact                                                 20

<210> SEQ ID NO 228
<211> LENGTH: 30
<212> TYPE: DNA
<213> ORGANISM: Zea mays

<400> SEQUENCE: 228
agacacacac atacttaaat ccatgatgaa                                      30

<210> SEQ ID NO 229
<211> LENGTH: 136
<212> TYPE: DNA
<213> ORGANISM: Zea mays
<220> FEATURE:
<221> NAME/KEY: misc_feature
<222> LOCATION: (24)..(86)
<223> OTHER INFORMATION: n is a, c, g, or t
<220> FEATURE:
<220> FEATURE:
<221> NAME/KEY: misc_feature
<222> LOCATION: (58)..(58)
<223> OTHER INFORMATION: m is a or c

<400> SEQUENCE: 229
gttctggcca gcagatgact gctntatatc tctgcagtcc tgtcagattt attctgtmat      60
tatcngaaan caccttatgt ntttgntgtg tagccaatat gctatattca tcatggattt     120
aagtatgtgt gtgtct                                                    136

<210> SEQ ID NO 230
```

```
<211> LENGTH: 20
<212> TYPE: DNA
<213> ORGANISM: Zea mays

<400> SEQUENCE: 230
atttattctg tcattatcgg                                          20

<210> SEQ ID NO 231
<211> LENGTH: 23
<212> TYPE: DNA
<213> ORGANISM: Zea mays

<400> SEQUENCE: 231
cagatttatt ctgtaattat cgg                                      23

<210> SEQ ID NO 232
<211> LENGTH: 16
<212> TYPE: DNA
<213> ORGANISM: Zea mays

<400> SEQUENCE: 232
tgctgtgcca gtcgct                                              16

<210> SEQ ID NO 233
<211> LENGTH: 15
<212> TYPE: DNA
<213> ORGANISM: Zea mays

<400> SEQUENCE: 233
cggcgacgga gtgct                                               15

<210> SEQ ID NO 234
<211> LENGTH: 66
<212> TYPE: DNA
<213> ORGANISM: Zea mays
<220> FEATURE:
<221> NAME/KEY: misc_feature
<222> LOCATION: (24)..(24)
<223> OTHER INFORMATION: w is a or t
<220> FEATURE:
<221> NAME/KEY: misc_feature
<222> LOCATION: (25)..(35)
<223> OTHER INFORMATION: n is a, c, g, or t

<400> SEQUENCE: 234
tgctgtgcca gtcgctgccg ctcwngctgc gctangcggt gggcgccggc gagcactccg  60
tcgccg                                                            66

<210> SEQ ID NO 235
<211> LENGTH: 14
<212> TYPE: DNA
<213> ORGANISM: Zea mays

<400> SEQUENCE: 235
ccgctcttgc tgcg                                                14

<210> SEQ ID NO 236
<211> LENGTH: 14
<212> TYPE: DNA
<213> ORGANISM: Zea mays

<400> SEQUENCE: 236
ccgctcatgc tgcg                                                14
```

```
<210> SEQ ID NO 237
<211> LENGTH: 15
<212> TYPE: DNA
<213> ORGANISM: Zea mays

<400> SEQUENCE: 237
gcgggccgac gatgt                                                    15

<210> SEQ ID NO 238
<211> LENGTH: 17
<212> TYPE: DNA
<213> ORGANISM: Zea mays

<400> SEQUENCE: 238
cgcatcgccg acttcga                                                  17

<210> SEQ ID NO 239
<211> LENGTH: 67
<212> TYPE: DNA
<213> ORGANISM: Zea mays
<220> FEATURE:
<221> NAME/KEY: misc_feature
<222> LOCATION: (28)..(28)
<223> OTHER INFORMATION: r is a or g
<220> FEATURE:
<221> NAME/KEY: misc_feature
<222> LOCATION: (41)..(41)
<223> OTHER INFORMATION: n is a, c, g, or t

<400> SEQUENCE: 239
gcgggccgac gatgtcggtg ccctgcarga tgcccttgaa nacgccgcgg tcgaagtcgg   60
cgatgcg                                                             67

<210> SEQ ID NO 240
<211> LENGTH: 14
<212> TYPE: DNA
<213> ORGANISM: Zea mays

<400> SEQUENCE: 240
ctgcaggatg ccct                                                     14

<210> SEQ ID NO 241
<211> LENGTH: 15
<212> TYPE: DNA
<213> ORGANISM: Zea mays

<400> SEQUENCE: 241
cctgcaagat gccct                                                    15

<210> SEQ ID NO 242
<211> LENGTH: 16
<212> TYPE: DNA
<213> ORGANISM: Zea mays

<400> SEQUENCE: 242
tcagcagcgc caccag                                                   16

<210> SEQ ID NO 243
<211> LENGTH: 19
<212> TYPE: DNA
<213> ORGANISM: Zea mays

<400> SEQUENCE: 243
cggacttcgg caacatcac                                                19
```

<210> SEQ ID NO 244
<211> LENGTH: 81
<212> TYPE: DNA
<213> ORGANISM: Zea mays
<220> FEATURE:
<221> NAME/KEY: misc_feature
<222> LOCATION: (21)..(51)
<223> OTHER INFORMATION: n is a, c, g, or t
<220> FEATURE:
<220> FEATURE:
<221> NAME/KEY: misc_feature
<222> LOCATION: (32)..(32)
<223> OTHER INFORMATION: y is c or t

<400> SEQUENCE: 244
tcagcagcgc caccaggtcg ncngtggacn ayggggtacag gaccgccgcc nggagcgccg    60
acgtgatgtt gccgaagtcc g                                              81

<210> SEQ ID NO 245
<211> LENGTH: 15
<212> TYPE: DNA
<213> ORGANISM: Zea mays

<400> SEQUENCE: 245
ctgtacccat cgtcc                                                     15

<210> SEQ ID NO 246
<211> LENGTH: 16
<212> TYPE: DNA
<213> ORGANISM: Zea mays

<400> SEQUENCE: 246
cctgtacccg tcgtcc                                                    16

<210> SEQ ID NO 247
<211> LENGTH: 26
<212> TYPE: DNA
<213> ORGANISM: Zea mays

<400> SEQUENCE: 247
aaattagcac gcatgactta cacatg                                         26

<210> SEQ ID NO 248
<211> LENGTH: 18
<212> TYPE: DNA
<213> ORGANISM: Zea mays

<400> SEQUENCE: 248
gctgaaacaa cggctgct                                                  18

<210> SEQ ID NO 249
<211> LENGTH: 101
<212> TYPE: DNA
<213> ORGANISM: Zea mays
<220> FEATURE:
<221> NAME/KEY: misc_feature
<222> LOCATION: (27)..(74)
<223> OTHER INFORMATION: n is a, c, g, or t
<220> FEATURE:
<220> FEATURE:
<221> NAME/KEY: misc_feature
<222> LOCATION: (77)..(77)
<223> OTHER INFORMATION: w is a or t

<400> SEQUENCE: 249
aaattagcac gcatgactta cacatgngta ttctaatttt gagtcaatga ctantattct    60

```
ntccngtacc agtngtwata catagcagcc gttgtttcag c                         101
```

<210> SEQ ID NO 250
<211> LENGTH: 20
<212> TYPE: DNA
<213> ORGANISM: Zea mays

<400> SEQUENCE: 250

```
cagtaccagt agttatacat                                                  20
```

<210> SEQ ID NO 251
<211> LENGTH: 20
<212> TYPE: DNA
<213> ORGANISM: Zea mays

<400> SEQUENCE: 251

```
cagtaccagt agtaatacat                                                  20
```

<210> SEQ ID NO 252
<211> LENGTH: 17
<212> TYPE: DNA
<213> ORGANISM: Zea mays

<400> SEQUENCE: 252

```
cggagcttgc cgtccaa                                                     17
```

<210> SEQ ID NO 253
<211> LENGTH: 20
<212> TYPE: DNA
<213> ORGANISM: Zea mays

<400> SEQUENCE: 253

```
cgcctgctct catgcactag                                                  20
```

<210> SEQ ID NO 254
<211> LENGTH: 105
<212> TYPE: DNA
<213> ORGANISM: Zea mays
<221> NAME/KEY: misc_feature
<222> LOCATION: (34)..(73)
<223> OTHER INFORMATION: n is a, c, g, or t
<220> FEATURE:
<220> FEATURE:
<221> NAME/KEY: misc_feature
<222> LOCATION: (60)..(60)
<223> OTHER INFORMATION: k is g or t

<400> SEQUENCE: 254

```
cggagcttgc cgtccaaggc cagcgcggcg aggnagnctg gccagggacg gccgcgatck     60
tctccgagcg cangcgtgcc tgccgctagt gcatgagagc aggcg                    105
```

<210> SEQ ID NO 255
<211> LENGTH: 16
<212> TYPE: DNA
<213> ORGANISM: Zea mays

<400> SEQUENCE: 255

```
ccgcgatctt ctccga                                                      16
```

<210> SEQ ID NO 256
<211> LENGTH: 15
<212> TYPE: DNA
<213> ORGANISM: Zea mays

<400> SEQUENCE: 256
cgcgatcgtc tccga                                            15

<210> SEQ ID NO 257
<211> LENGTH: 25
<212> TYPE: DNA
<213> ORGANISM: Zea mays

<400> SEQUENCE: 257
cctcattcga attggagttg tcttc                                 25

<210> SEQ ID NO 258
<211> LENGTH: 20
<212> TYPE: DNA
<213> ORGANISM: Zea mays

<400> SEQUENCE: 258
tttgggccta catgccttgt                                       20

<210> SEQ ID NO 259
<211> LENGTH: 90
<212> TYPE: DNA
<213> ORGANISM: Zea mays
<220> FEATURE:
<221> NAME/KEY: misc_feature
<222> LOCATION: (54)..(54)
<223> OTHER INFORMATION: r is a or g

<400> SEQUENCE: 259
cctcattcga attggagttg tcttcgactc aggcgatggc caaggggatg gccraacaac    60
cctaagatgt acaaggcatg taggcccaaa                                    90

<210> SEQ ID NO 260
<211> LENGTH: 13
<212> TYPE: DNA
<213> ORGANISM: Zea mays

<400> SEQUENCE: 260
atggccgaac aac                                              13

<210> SEQ ID NO 261
<211> LENGTH: 13
<212> TYPE: DNA
<213> ORGANISM: Zea mays

<400> SEQUENCE: 261
atggccaaac aac                                              13

<210> SEQ ID NO 262
<211> LENGTH: 16
<212> TYPE: DNA
<213> ORGANISM: Zea mays

<400> SEQUENCE: 262
aggctgctgg caacga                                           16

<210> SEQ ID NO 263
<211> LENGTH: 20
<212> TYPE: DNA
<213> ORGANISM: Zea mays

<400> SEQUENCE: 263
tttctgctcc gggtcatcac                                       20

-continued

<210> SEQ ID NO 264
<211> LENGTH: 63
<212> TYPE: DNA
<213> ORGANISM: Zea mays
<221> NAME/KEY: misc_feature
<222> LOCATION: (35)..(35)
<223> OTHER INFORMATION: r is a or g

<400> SEQUENCE: 264
aggctgctgg caacgacgct gtcgaggccg atgcrcagca ccggtgatga cccggagcag    60
aaa    63

<210> SEQ ID NO 265
<211> LENGTH: 14
<212> TYPE: DNA
<213> ORGANISM: Zea mays

<400> SEQUENCE: 265
ccgatgcgca gcac    14

<210> SEQ ID NO 266
<211> LENGTH: 14
<212> TYPE: DNA
<213> ORGANISM: Zea mays

<400> SEQUENCE: 266
ccgatgcaca gcac    14

<210> SEQ ID NO 267
<211> LENGTH: 22
<212> TYPE: DNA
<213> ORGANISM: Zea mays

<400> SEQUENCE: 267
ggagagcttt caggcgacaa aa    22

<210> SEQ ID NO 268
<211> LENGTH: 23
<212> TYPE: DNA
<213> ORGANISM: Zea mays

<400> SEQUENCE: 268
cacccaccct ccagtataaa acg    23

<210> SEQ ID NO 269
<211> LENGTH: 101
<212> TYPE: DNA
<213> ORGANISM: Zea mays
<220> FEATURE:
<221> NAME/KEY: misc_feature
<222> LOCATION: (44)..(44)
<223> OTHER INFORMATION: r is a or g

<400> SEQUENCE: 269
ggagagcttt caggcgacaa aagccgcggc gaggggatca gcgrggatct gccgggccac    60
cgccaccgcc gccgccccgc gttttatact ggagggtggg t    101

<210> SEQ ID NO 270
<211> LENGTH: 15
<212> TYPE: DNA
<213> ORGANISM: Zea mays

<400> SEQUENCE: 270

-continued

```
agatccccgc tgatc                                                    15

<210> SEQ ID NO 271
<211> LENGTH: 16
<212> TYPE: DNA
<213> ORGANISM: Zea mays

<400> SEQUENCE: 271
cagatcctcg ctgatc                                                   16

<210> SEQ ID NO 272
<211> LENGTH: 30
<212> TYPE: DNA
<213> ORGANISM: Zea mays

<400> SEQUENCE: 272
gatttacatg aggatggata tcaacacaca                                    30

<210> SEQ ID NO 273
<211> LENGTH: 26
<212> TYPE: DNA
<213> ORGANISM: Zea mays

<400> SEQUENCE: 273
cccctcttct cgtttatctt ctctct                                        26

<210> SEQ ID NO 274
<211> LENGTH: 158
<212> TYPE: DNA
<213> ORGANISM: Zea mays
<220> FEATURE:
<221> NAME/KEY: misc_feature
<222> LOCATION: (31)..(129)
<223> OTHER INFORMATION: n is a, c, g, or t
<220> FEATURE:
<220> FEATURE:
<221> NAME/KEY: misc_feature
<222> LOCATION: (65)..(65)
<223> OTHER INFORMATION: w is a or t

<400> SEQUENCE: 274
gatttacatg aggatggata tcaacacaca ntaangcttt tancgggggc taaccaaccc    60
attcwacccn agcacgacna tcccttccga gagaatatat ntgtaatcan ggtcancccg   120
aaaaagngna aagagagaa gataaacgag aagagggg                            158

<210> SEQ ID NO 275
<211> LENGTH: 15
<212> TYPE: DNA
<213> ORGANISM: Zea mays

<400> SEQUENCE: 275
caacccattc taccc                                                    15

<210> SEQ ID NO 276
<211> LENGTH: 15
<212> TYPE: DNA
<213> ORGANISM: Zea mays

<400> SEQUENCE: 276
caacccattc aaccc                                                    15

<210> SEQ ID NO 277
<211> LENGTH: 30
```

```
<212> TYPE: DNA
<213> ORGANISM: Zea mays

<400> SEQUENCE: 277
gatttacatg aggatggata tcaacacaca                                    30

<210> SEQ ID NO 278
<211> LENGTH: 26
<212> TYPE: DNA
<213> ORGANISM: Zea mays

<400> SEQUENCE: 278
cccctcttct cgtttatctt ctctct                                        26

<210> SEQ ID NO 279
<211> LENGTH: 158
<212> TYPE: DNA
<213> ORGANISM: Zea mays
<220> FEATURE:
<221> NAME/KEY: misc_feature
<222> LOCATION: (31)..(129)
<223> OTHER INFORMATION: n is a, c, g, or t
<220> FEATURE:
<220> FEATURE:
<221> NAME/KEY: misc_feature
<222> LOCATION: (79)..(79)
<223> OTHER INFORMATION: r is a or g

<400> SEQUENCE: 279
gatttacatg aggatggata tcaacacaca ntaangcttt tancgggggc taaccaaccc    60
attcnacccn agcacgacra tcccttccga gagaatatat ntgtaatcan ggtcancccg   120
aaaaagngna aagagagaa gataaacgag aagagggg                            158

<210> SEQ ID NO 280
<211> LENGTH: 13
<212> TYPE: DNA
<213> ORGANISM: Zea mays

<400> SEQUENCE: 280
cacgacgatc cct                                                      13

<210> SEQ ID NO 281
<211> LENGTH: 13
<212> TYPE: DNA
<213> ORGANISM: Zea mays

<400> SEQUENCE: 281
cacgacaatc cct                                                      13

<210> SEQ ID NO 282
<211> LENGTH: 15
<212> TYPE: DNA
<213> ORGANISM: Zea mays

<400> SEQUENCE: 282
gcagctgcgg ccaaa                                                    15

<210> SEQ ID NO 283
<211> LENGTH: 21
<212> TYPE: DNA
<213> ORGANISM: Zea mays

<400> SEQUENCE: 283
aagggatgtg ggcaagaaga g                                             21
```

<210> SEQ ID NO 284
<211> LENGTH: 60
<212> TYPE: DNA
<213> ORGANISM: Zea mays
<220> FEATURE:
<221> NAME/KEY: misc_feature
<222> LOCATION: (19)..(19)
<223> OTHER INFORMATION: s is c or g

<400> SEQUENCE: 284
gcagctgcgg ccaaaagasa gggagaggag gaggaggagc tcttcttgcc cacatcccctt    60

<210> SEQ ID NO 285
<211> LENGTH: 17
<212> TYPE: DNA
<213> ORGANISM: Zea mays

<400> SEQUENCE: 285
ctcctcctct ccctgtc    17

<210> SEQ ID NO 286
<211> LENGTH: 16
<212> TYPE: DNA
<213> ORGANISM: Zea mays

<400> SEQUENCE: 286
tcctcctctc cctctc    16

<210> SEQ ID NO 287
<211> LENGTH: 15
<212> TYPE: DNA
<213> ORGANISM: Zea mays

<400> SEQUENCE: 287
cggcgacgag agcgt    15

<210> SEQ ID NO 288
<211> LENGTH: 32
<212> TYPE: DNA
<213> ORGANISM: Zea mays

<400> SEQUENCE: 288
cgttaatttc aaatgtaaac gagtcaaaga ac    32

<210> SEQ ID NO 289
<211> LENGTH: 129
<212> TYPE: DNA
<213> ORGANISM: Zea mays
<220> FEATURE:
<221> NAME/KEY: misc_feature
<222> LOCATION: (16)..(81)
<223> OTHER INFORMATION: n is a, c, g, or t
<220> FEATURE:
<220> FEATURE:
<221> NAME/KEY: misc_feature
<222> LOCATION: (76)..(76)
<223> OTHER INFORMATION: w is a or t

<400> SEQUENCE: 289
cggcgacgag agcgtntnaa ggggaaaggg gaaantggta agcaggctgc aatttacggt    60
gccggatgag atacgwcaaa ntctaatcaa ataaatgtt ctttgactcg tttacatttg    120
aaattaacg    129

-continued

<210> SEQ ID NO 290
<211> LENGTH: 17
<212> TYPE: DNA
<213> ORGANISM: Zea mays

<400> SEQUENCE: 290
atgagatacg tcaaacc                                                    17

<210> SEQ ID NO 291
<211> LENGTH: 17
<212> TYPE: DNA
<213> ORGANISM: Zea mays

<400> SEQUENCE: 291
atgagatacg acaaacc                                                    17

<210> SEQ ID NO 292
<211> LENGTH: 19
<212> TYPE: DNA
<213> ORGANISM: Zea mays

<400> SEQUENCE: 292
gcttgcctca gtcgtttgc                                                  19

<210> SEQ ID NO 293
<211> LENGTH: 22
<212> TYPE: DNA
<213> ORGANISM: Zea mays

<400> SEQUENCE: 293 cccctcttc ttccttgttg ag                                               22

<210> SEQ ID NO 294
<211> LENGTH: 86
<212> TYPE: DNA
<213> ORGANISM: Zea mays
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (44)..(44)
<223> OTHER INFORMATION: s is c or g

<400> SEQUENCE: 294
gcttgcctca gtcgtttgcc cntttggtcc ctctccctcc cccstccgcc ctgcactctc     60
caagctcaac aaggaagaag aggggg                                          86

<210> SEQ ID NO 295
<211> LENGTH: 14
<212> TYPE: DNA
<213> ORGANISM: Zea mays

<400> SEQUENCE: 295
ctcccccctc cgcc                                                       14

<210> SEQ ID NO 296
<211> LENGTH: 13
<212> TYPE: DNA
<213> ORGANISM: Zea mays

<400> SEQUENCE: 296
tcccccgtcc gcc                                                        13

<210> SEQ ID NO 297
<211> LENGTH: 23
<212> TYPE: DNA
<213> ORGANISM: Zea mays

<400> SEQUENCE: 297
accaaggaca acgagtactc tga                                             23

<210> SEQ ID NO 298
<211> LENGTH: 21
<212> TYPE: DNA
<213> ORGANISM: Zea mays

<400> SEQUENCE: 298
gagacaagga accccagtgt t                                               21

<210> SEQ ID NO 299
<211> LENGTH: 74
<212> TYPE: DNA
<213> ORGANISM: Zea mays
<220> FEATURE:
<220> FEATURE:
<221> NAME/KEY: misc_feature
<222> LOCATION: (36)..(36)
<223> OTHER INFORMATION: m is a or c

<400> SEQUENCE: 299
accaaggaca acgagtactc tgaccttttc tatggmattc cctggtccca gggaacactg     60
gggttccttg tctc                                                       74

<210> SEQ ID NO 300
<211> LENGTH: 13
<212> TYPE: DNA
<213> ORGANISM: Zea mays

<400> SEQUENCE: 300
ctatggcatt ccc                                                        13

<210> SEQ ID NO 301
<211> LENGTH: 14
<212> TYPE: DNA
<213> ORGANISM: Zea mays

<400> SEQUENCE: 301
tctatggaat tccc                                                       14

<210> SEQ ID NO 302
<211> LENGTH: 25
<212> TYPE: DNA
<213> ORGANISM: Zea mays

<400> SEQUENCE: 302
tgatggatgt agtgtgtgtc tgtct                                           25

<210> SEQ ID NO 303
<211> LENGTH: 25
<212> TYPE: DNA
<213> ORGANISM: Zea mays

<400> SEQUENCE: 303
catagcaagt cccgaatcaa tctga                                           25

<210> SEQ ID NO 304

```
<211> LENGTH: 157
<212> TYPE: DNA
<213> ORGANISM: Zea mays
<220> FEATURE:
<221> NAME/KEY: misc_feature
<222> LOCATION: (28)..(132)
<223> OTHER INFORMATION: n is a, c, g, or t
<220> FEATURE:
<221> NAME/KEY: misc_feature
<222> LOCATION: (85)..(85)
<223> OTHER INFORMATION: y is c or t

<400> SEQUENCE: 304
tgatggatgt agtgtgtgtc tgtctaantc ntngtantna ctnttaaanc tngnggtcgn    60
tcggtcggtn gtcantcngt ntgtygntga ntccancntn tttttttattt taatattntn   120 taanggaatc tntcagattg attcgggact tgctatg                             157

<210> SEQ ID NO 305
<211> LENGTH: 17
<212> TYPE: DNA
<213> ORGANISM: Zea mays

<400> SEQUENCE: 305
ctggacatca acgacaa                                                    17

<210> SEQ ID NO 306
<211> LENGTH: 17
<212> TYPE: DNA
<213> ORGANISM: Zea mays

<400> SEQUENCE: 306
ctggacatca gcgacaa                                                    17

<210> SEQ ID NO 307
<211> LENGTH: 3927
<212> TYPE: DNA
<213> ORGANISM: Zea mays

<400> SEQUENCE: 307
taggataata gcccagtttc atttggattt tgaatttact tgcgggccat catcgattgg    60
ttgctggatc taattggcac gcacgtcacc cccaccggat gcatgccaca gatctgtgca   120
tgtgctcacc atgctgaggg aggtcaggat tggtgcctgc acgcatgggg ttcctacgcc   180
cagaccaaaa ggatctggtt gctatctttc gcccatacac ggatgctctt cttcagatct   240
ggttaagcgg gcaatgattg cattgcgggg gcaccagcac cagaaacaaa ctgtaggagg   300
ttgctgcggt ggtccctgtg gggttctact gctttaggat tattttctgg gatctgtttt   360
ttttccagcc cgagtatgca tgccgtcgag gttcaggttc ctcctctctt agcaaagttt   420
tatgaagctt cttttttggct tctggttgct gcctgcacaa ctttatcaag ctaccaaacg   480
tactagttgt actgcttcct ttggattata gaggagttac taaataaact gtgttgggtg   540
tgcatattct caaggctgtg gtcttaggaa ttgctttcag ttatgcaaga gatacttact   600
tggcatacaa ctactggcgc tccgaatgcc ctgccacccc cctggcctga tagattcttt   660
gatctggacc ttatatggtt agtttattca gtgttgctgc actgtctctc tacatgtttc   720
ctgaaacatc agtagattgt ggaatagcag tgtgatggtg tagctttatg gttacagcta   780
actcagctgt tggtgagata gctccttgca gttgcagata acaatgtgct tccttcagct   840
gtttcttcca tctagtgtac ttgtacaagt tcttccatga tatgataaat gtgtattttt   900
ttgttaactt cactgtttat ctaactctgc tgtgtcatgc tttttcaatt gtgttttttc   960
```

-continued

```
agtagcaacc accacccatg gcggacgtgc acgaaccttt ggtgcgccgt aagaggaaga    1020
aggttttggt ggactacttg gtgaagttcc gatggatcct cgtgatcttc gtggtccttc    1080
ctatttcaac tctgatctac ttcaacatct tcctgggcga catgtggtcc gccatgaagt    1140
cggagaagaa gcgccagaag cagcacgacg agaacgtgca aaggtcgtg aagcggctca     1200
agcagaggaa cccgaagaag gacggtcttg tttgcacggc caggaagccc tggatcgctg    1260
ttggcatgcg caacgtggac tacaagcgtg cgaggcattt cgaggtcgac ctttcttcct    1320
tcaggaacat ccttgagatc gacaaagaga ggatggttgc caaggtcgag ccccttgtca    1380
acatgggtca gataaccaga gctacctgcc caatgaacct tgcccttgcg gtcgtcgccg    1440
agctcgacga cctcactgtt ggtgggctga tcaacggtta cggcatcgag gggagctctc    1500
acctctatgg ccttttctcc gacacggttg tcgcgatgga ggttgttctc gcagatggcc    1560
gggtcgtcag agccaccaag gacaacgagt actctgacct tttctatggc attccctggt    1620
cccagggaac actggggttc cttgtctctg cggagatcaa gctgatcccc atcaaggagt    1680
acatgaagct cacctacact ccagtcaagg ggggtctaaa ggagatcgcg caggcctacg    1740
cggattcttt cgcgccgagg gacggtgacc cggcaaaggt ccctgacttt gttgaaggga    1800
tggtgtacac agagagcgag ggtgtcatga tgacgggcgt gtacgcttcc aaagaagagg    1860
cgaagaagaa gggcaacaag atcaactgcg tggggtggtg gtttaagccc tggttctacc    1920
agcacgctca gacggcgctg aagagggcg agtttgtgga gtacatcccg acgagggagt     1980
actaccaccg gcacacccgg tgcctgtact gggaggggaa gctgatcctg cccttcggcg    2040
accagttctg gttcaggttc ctgctgggct ggctgatgcc accgaaggtg tccctgctga    2100
aggcgaccca gggcgaggct atcaggaact actaccacga caaccatgtg atccaggaca    2160
tgctggtgcc gctgtacaag gttggggatg cgctggagtt cgtgcaccgc gagatggagg    2220
tacaatggct ggctggtgct ggtgctggtg ctgcttgctt tatgagtagt tgactggata    2280
tactaataat aattgaaatt cttttggtag gtgtatcctc tgtggctgtg ccctcaccgg    2340
ctgtacaagc tgccggtgaa gacgatggtg tacccggagc ctgggttcga gcaccagcac    2400
aggcagggcg acacgagcta cgcacagatg ttcacggacg tgggcgtgta ctacgccccc    2460
ggggcggtgc tgagggggga ggagttcaac ggcgcggagg ctgtgcacag gctggagcag    2520
tggctgatcg agaaccacag ctaccagccg cagtacgcgg tgtcggagct gaacgagaag    2580
gacttctggc gcatgttcga cgcgtcgcac tacgagcact gccgccaaaa gtacggggcg    2640
gtgggcacgt tcatgagcgt gtactacaag tccaagaagg ggcgcaagac ggagaaggag    2700
gtgcaggagg cggaggcggc catactggag ccggcctacg cggacgagga ggcctaaaag    2760
ctcgtggtcg ttttgcttag cccatttttaa ttagaacttg atggatgtag tgtgtgtctg    2820
tctcaagtca tttttaattag aactcttaaa gctcgtggtc ggtcggtcag tcagtcagtc    2880
attgtcgttg atgtccagcg ttgtgttttt tttatattct ctaatggaat ctctcagatt    2940
gattcgggac ttgctatggc tctgctcttt gttatgtttt tttttttaaag ttctccaggc    3000
gctgctgctg cgtcttgcaa ggagcccgga gctgatgact agcagcagca gcagcttgga    3060
acggtgggag gcagcaccac catggcacca tgtggctgag ctgggctggc aggcacagtg    3120
agaaaaagaa agacaccagc catctactcc ccagtccccc cacaagagca aaagcaaaga    3180
aagatgcatg tgcatgtgca gtgcagcaac tctgccatgc tgtcatgtgg acggcacgg     3240
gcaccagctg cactgcactg caccgccccca cagttatatt gtttactgct gctgtgccca    3300
```

```
ctccttgtat atttgcatca ctgcctgctt ctggaatcag gaaaggagat caccacttca    3360
ctcaagaagg caccctccct tgccactcct tttccttgag atgacgatga cgacgatgaa    3420
gaagcagcag cagctcctcc tcctcctttc tctcatgttt ctcgttgctg tgacagcagc    3480
cgctgttgct gccgatccac atccacagca ggtggtacta cgcctactct cctcttctcc    3540
tcggcatcat ccaaactgaa tcagattgaa gaatcatcag gtcattaaca tgttcagtgt    3600
gtgtccagca ggtgcaggtg cagcagcagc agcaagcaca gatgaggatt aacagggcca    3660
ccagatccct tcttcctcag ccgccgccga aactaggtac tactgaaaac tgtagacaac    3720
aagatacaag atctcatttc attgacgcct gtttctcacg caatacagac tgcccgtcca    3780
cctgctccgt gcgctgcggc aacaactgga agaaccagat gtgcaacaag atgtgcaacg    3840
tctgctgcaa caagtgcagc tgcgtgccgc cggggaccgg ccaggacacc cgccacctct    3900 gccccctgcta cgacaccatg ctcaatc                                       3927

<210> SEQ ID NO 308
<211> LENGTH: 86
<212> TYPE: DNA
<213> ORGANISM: Zea mays

<400> SEQUENCE: 308
gcgtgcgagg catttcgagg tcgacctttc ttccttcagg aacatccttg agatcgacaa     60
agagaggatg gttgccaagg tcgagc                                          86

<210> SEQ ID NO 309
<211> LENGTH: 4046
<212> TYPE: DNA
<213> ORGANISM: Zea mays

<400> SEQUENCE: 309
gacacatcca cgacacgaac gccgcgacgg gactgggcaa tgcaggtggt gtgggagtat     60
ttatcagcct cgccgtgtct tcttttttatg ttccagcacg taatgtaggg cgcgtagaat    120
ctagactatc aaatcgcgag gggcgagcga cgacgacggt gcggtgcagc tttctacagg    180
actagtcgtt ttcacgtcgt agcagagcac gctcgcttgg agcagccgac aaacaccaag    240
cgctagtaga ctaggactac agtgcagtgc gtctcgcaag tccacgggcc tcgcattgca    300
ttgcaaaaaa aaaaaaaaaa aacagttgcc gctatataac aggatccagc gcacggcaag    360
gcggcaggca acagcaacac ggagtcaagg agcacgagtt aggttggcaa ccctcgagag    420
tcgagagcat ggatcccaac gacgccttct cggcggcgca cccgttccgg tgggacctgg    480
gcccgccggc gcccgccgcg cccgcgcctc cgcccccacc gccgcccgcg ccgcagctgc    540
tgccccacgc gccgctgctg agcgcgccga gggagctgga ggacctggtg gccggctacg    600
gcgtgcgccc gtccacggtg gcgcggatct cggagctcgg gttcacggcc agcacgctcc    660
tcggcatgac ggagcgcgag ctcgacgaca tgatggccgc gctcgcgggg ctgttccgct    720
gggacgtgct cctcggcgag gcttccggcc tccgcgccgc gctgcgggcc gagcgcgggc    780
gtgtcatgtc cctcggcggc gcttccacag ccgggagcac attggacgcc gcgtcacaag    840
aaggtataca cagcatggtc aaattgtttg cctctgtggt cgtgcactcg tgcatgcatg    900
cggacagtgc ccatgattca gtcatgttga gttgagttct gcttgccggc ctgtgatgtt    960
atttgttctt gttcaatcat atcgcaactg gcagtgctgt ccgacgagcg cgacgccgcg   1020
gccagcggcg gcttgcgga aggcgaggcc gcaggaggga tggtgacggc cggcaagaag   1080
aagggcaaga aaggggttgg cgcgaggaag ggcaagaagg cgaggaggaa gaaggagctg   1140
```

-continued

```
aggccgttgg acgtgctgga cgacgagaac gacggagacg aggacggcgg cggcggcggg    1200
tcagactcga cggagtcttc cgctggcggc tccggcggcg gggagaggca gcgggagcac    1260
cccttcgtgg tcacagagcc cggcgaggtg gccagggcca agaagaacgg gcttgactac    1320
ctcttccatc tgtacgagca gtgccgcgtc ttcctgctgc aggtgcagtc ccttgctaag    1380
ctgggcggcc acaagtcccc taccaaggta cgcacactta ttattaattt agcagggcaa    1440
cgtttttata ttacatatgt ataaatccat ttggtggtgc atacggatag ctagattgaa    1500
tgtacgataa acaaacaaaa actgtagtgt taaaaaacgt aatgtaatga aacaaacttt    1560
ttaggtcgtt gacaagctag gtactgttta aatttgctc taaaacatgt gttatatatt    1620
ctcagacaca gttggagtca cacaagttaa gggtcagaac tctattaata atttaatacg    1680
aagacgtaat tctcaacttt gttagtagtg aaacggttta aggggttgact aaagttatat    1740 ataaaaatac taacatttat gatgttaaat aagcacattg ttagaataat aatgaagtat    1800
atctagttgg tatataatta ccaatactat ttgctatagt aaatttgatc aaagttagtc    1860
tagttcaact ttcacaaatc ctagaaatac agatactatt cattgtaata acatcatagt    1920
catagtaaaa aagatctagt ggcatgcaaa aggcccttca catcacctag aaggaagaag    1980
gaaatccttt gcagtggaat tctattatat tttgtgtacc gtaagtacgt ctacagtagc    2040
acatgtgcaa aagatggtct atatagtacg ccgtagtagt ctgtagtcaa gtacttctac    2100
gtacgtgtac tcaagtatat tttgctacag ccgcacacgc acgtagatga cctggaaaaa    2160
ggcgcgacgt gtcagtcatc ggtaggctgc caaagcctgt gcagcttgtg ttgtcttgtc    2220
cggccggccc caggcctcag atacagatag gcatgcatgg acgccctctc ctctcggagt    2280
ccgtggcctg tgtgctgttg ccaccggttt cgcgcgtacc agtacgagcc atgtgagctc    2340
gcttttggca gtttggccgg cgtacgagta gtcgcgactc gcgtgctcgc ccgcagtgaa    2400
atgaatgcac ggcctggcct gtccggattc cagggctgat tggatatgat gatagcttcc    2460
ctgacctgga cggctgcatc gatgcgctgc tcctgcgtcc gcgccaggcg cacccgacca    2520
caccggccag tttcacgaca ccggaaccaa tcgaccgtgg ctgatgaacc ttttttttt    2580 ttgcttgcac tgcaggtgac caaccaggtg ttccggtacg ccaagaagtg cggcgcgagc    2640
tacatcaaca agcccaagat gcggcactac gtgcactgct acgcgctgca ctgcctggac    2700
gaggaggcct ccaacgcgct cgccggggcg tacaaggccc gtggcgagaa cgtcggtgcc    2760
tggaggcagg cctgctacgc gccgctcgtc gagatcgccg cgcgccacgg cttcgacatc    2820
gacgccgtct tctccgcgca cccgcgcctc accatctggt acgtgcccac caggttgcgc    2880
cagctctgcc accaggcacg ggggagccac gcccacgccg ccgccggcct ccccccgccc    2940
ccgatgttct agctgcgtcg tcgatgtgtg cctgcaccgg cgcggcgccg tacgtctcac    3000
atcgcagttc aggctgttcc atggcgccat cgaaaagtgg aaggcggcct tcgtctgcct    3060
ctcatgttgt cgctttgttc gttgcgttgt ggttagtcag aagtgggctt agatttagaa    3120
tggggacgtc acttgttcgg ccgagcgggc cgggaaacaa tttactgttt cgatgggcca    3180
cttgttagtt tgttaccctcg cggccttact aagttgtatt gtatccctcg tgatagttgt    3240
cccccatcct ccaaaaaaaa aacccgacgg tgtaccgctc ctgtgatgat atatcctaag    3300
agtaaaatac attttcatta cttcaactta tatgacgtta tatgttaact cggtccataa    3360
acttttaaag tgtgtcagtc tggtcctaa ttgttgttcc ggtcttagtt aggtcgaaac    3420
gcgtcgtggt tgacatatga accccacatt ttagcctatg tatctatttt atctctcttt    3480
```

-continued

| | |
|---|---|
| cttggttctc tctcaccgta catgcggaaa agagagacaa aagagataca catgctcaca | 3540 |
| tgttgggggt ccatatgtca atcacaacct gtttggatct aactgagacc caaacaacaa | 3600 |
| ttaaatatcg gattgacaca ctttaaaagt ttgttaacca ggatgacata gggcgacaag | 3660 |
| tttcagaact gtaaatgtat tttaccctat atcctaatta tgctgtaaca gtagcaccat | 3720 |
| tttttttgctc cttcgtattc gctctaattg ttgaatggtt gggaatgact aatatgtctc | 3780 |
| tttgactttc ttataaggtt gtctctctta tacaccactc ttagctcatt cgtgattttc | 3840 |
| tttggttcat tctaatagtc aagttgtagg aaatgaaaac tatctctttg accctattct | 3900 |
| ctcttttacg atcatccctc tctccatgtt ctctctttttt tcaacctttc cttggtcacc | 3960 |
| ttacctaatt tgaaagctat aaaacttcca ttggtgcaag actactgatg ttaggttagt | 4020 |
| ccgcatatga atgttgcgac ttatcc | 4046 |

<210> SEQ ID NO 310
<211> LENGTH: 63
<212> TYPE: DNA
<213> ORGANISM: Zea mays

<400> SEQUENCE: 310

| | |
|---|---|
| ctcgcccgca gtgaaatgaa tgcacggcct ggcctgtccg gattccaggg ctgattggat | 60 |
| atg | 63 |

<210> SEQ ID NO 311
<211> LENGTH: 84
<212> TYPE: DNA
<213> ORGANISM: Zea mays

<400> SEQUENCE: 311

| | |
|---|---|
| ggcactacgt gcactgctac gcgctgcact gcctggacga ggaggcctcc aacgcgctgc | 60 |
| gccgggcgta caaggcccgt ggcg | 84 |

<210> SEQ ID NO 312
<211> LENGTH: 80
<212> TYPE: DNA
<213> ORGANISM: Zea mays

<400> SEQUENCE: 312

| | |
|---|---|
| gttgccgcta tataacagga tccagcgcac ggcaaggcgg caggcaacag caacacggag | 60 |
| tcaaggagca cgagttaggt | 80 |

<210> SEQ ID NO 313
<211> LENGTH: 4424
<212> TYPE: DNA
<213> ORGANISM: Zea mays

<400> SEQUENCE: 313

| | |
|---|---|
| cggcatgatg cacaggtcat ttatgtgttc ttcgttctaa ttatccactt ttaactagtg | 60 |
| ttgatcacat gtaatgaata ggagaggcca caaaccattg agattatcta tatcctctttt | 120 |
| attacatttt tgagtattac atgcataatg aagatcatgc cacgagtaat ataattacaa | 180 |
| gctaaaagca tatagagaac atgatttatc acaaggtttg gctataccac aaagtagtgt | 240 |
| ttacgtttca gttgtcgagt gaccacaaag gcctttagag tcttttttaaa cccccccctct | 300 |
| ttctcaagcg accaaaaaaa tcaagccatg atctctacta gaacaaatgg gtaatacaaa | 360 |
| cttttctaggc acccttttaca aacacaaatc aggagtgtcg ctagacaaca cctagccaac | 420 |
| taggattcaa agaccccaaa agtaataaaa tggaaaagaa atcaccgatg ggtgccacaa | 480 |

```
gtgctcaaga gatggatctt actctttgaa atcaagatct agtgaagagc tcactccaat    540
ctcactcaca agacgaaaat ctagcaaggg cgtgaggaag tatgagagag tgtaaagaga    600
gcttgctttt gtttcaaagt ggttttgtga attgaaatgg ctgacccaa gaaaacaaga     660 gggtgagaga aataaatccc cttgtcttag ctagagagcc attgctgagc aggaaggttc    720
cctctcaaaa atttcaacta gggaggcttg gaatttctga ggtggataag agaaacctcg    780
gtgcatccat agtcaaagag atttgaccca aggggcaccc cacctcaaat ttcgagggtt    840
cagaatttcc aaaggagagg aagataccat aaagcaaaac ttcgaagttt agaggtgtta    900
ctcaaatttt tccaaagggg ggtttgaaat tttccaaggg gagagaattt tttggggaaa    960
gaggaacatc agcagaaagc caaggttcaa agttaaggcg gtgtccagaa ttttttgtgg    1020
tgttgaaaac aggacgaata aaagaaagag aatacttgct cttttagagg ttttttaaga    1080
gaccttttta gagtattatt gggaatgtta ggagttaatg agtataatgt tttgagcata    1140
ttttgacacc tacaagtaat tttttctata tccttcttta tgatatacta tacttgaaag    1200
aagattgaat taaaactaaa atctctctct caagttgaat tgttgtgcca catctttcac    1260
taatttataa ttaaagggtc tcatattttt tgtactttt tataattata tttaattgta    1320
aatctcataa aatattgtta gctcgtgtca tcaaatcact aaaatccata aataggattg    1380
atgcacttag ctctttaaaa tgaaaaaggt acaaaaatat aaaaaaaatc gtgaaccccc    1440
caatcaattt ctaattgcat tgtgaaaact tcgacaacaa aaatataaga taccaccaaa    1500
ataaaatagt atcaaacaat atcatcctct atttcaaact tctttatgca agcagcgtca    1560
ttcacaattt cgcgtcctct attttacaca ctgtactgca gacaacctta acatctatgt    1620
tggttgtatc acatatttt gttgtagaaa atttccaaag cacatttaaa cttgattaaa    1680
atattttggg ggtttaacga tatttttta ttattctaga actaaatata ttttttaaagc   1740 ttatagatat atttttcgcgg gctctaaata ctttttttctc cggtcccaat ctatttctaa  1800 tattttgaa ctttttatat actttcaatg ttttaaataa acttttttccg attttcttag    1860 taaaagttg aaaccatcct aaaataaaaa ctatttctaa ccatggtaga gagctaattt     1920
aagcggcttt aagatttgaa gaagaaattg ccttatttta gagttcattc aagaaggaaa    1980
aaatggagtc ctagttgagg gaaaacacca cagattccac agccttcgcc tgttcgccac    2040
ctttcctcca aaatttgacc cacacgcggc gacgcccgag gccccgagcg accacatcct    2100
ccgcggccgc ggcgacgccc gaggcctgca aaaccctaac cactcaggtt ctgccggcca    2160
ccgccaccac caccaccagt ccaccaccat gctgacagcc actcccctac ccatcagct    2220 cctggccacc ttcctcctcg tcctggcgtc ggcgacccaa cctgcagtcc ctgcctccac    2280
cgaccgcgca gcgcttctcg ccttccgcgc gtccctgtcg ccgccctccc gcgccgcgct    2340
atcctcgtgg agcggcccgc tctcgccatc ctggctcggc gtgtcgctcc accccgccac    2400
ggcgccagcc ccttcggtca ccactccctc cgttgccgaa ctctcgctcc ggggcctcaa    2460
cctcacgggc gtgatccccg cggcgccgct cgcgctcctc cgacgtctcc ggacgctcga    2520
cctctccgcc aacgcgcttt cgggagagct tccctgctcc ctcccgcgct cgctcctcgc    2580
gctcgacctc tcccgcaacg cgctctcggg ggctgtcccc acctgcctgc cgtcctcgct    2640
ccccgcgctc cgcaccctca acctctccgc caacttcctc cgcctcccgc tctcccgcg    2700 tctctccttc cccgcgcgcc tcgctgccct tgatctctcc cgcaacgcca tctccggcgc    2760
cgtcccgccg cggatcgtcg ccgaccccga caactccgct ctcctcctcc tcgacctctc    2820
```

```
ccacaaccgc ttctccggcg agatccccgc cggtatcgca gccgtacgga gcctgcaggg      2880 gcttttctc gcggacaacc agctttccgg ggacattcct ccggggatag ggaacctgac      2940
ctatttgcag gtgctggatt tgtcgaataa ccgattgtcc ggttcagtgc ctgccggact      3000
tgcaggctgc ttccagcttc tgtacctgca gcttggggt aaccagctct ctggggcact      3060
ccgtccggag ctcgacgcac tagctagtct caaggttcta gatttgtcga ataacaagat      3120
atctggggag attccctgc cgctggctgg gtgcaggtct ttggaggtgg tggacttgtc      3180
aggaaatgag atctccggtg agctcagcag tgctgtagcg aaatggctga gcttgaagtt      3240
cttatcactg gctggtaacc agctctccgg ccacctacct gactggatgt tctcgttccc      3300
cctgctccag tggcttgatt tgtctagtaa taagtttgtg ggtttcatcc cagatggggg      3360
gttcaatgtc agtgaagtgc ttaacggtgg aggtggtcag gggactccat cagagagtgt      3420
gcttccaccc caattgtttg tgtcagcttc tgtggacacg gtgtcatggc agttggattt      3480
ggggtatgat gttcaggcaa ctactggtat agacctgtct gggaatgagc tctgtgggga      3540
gataccagaa gggttggttg acatgaaggg gttggagtat ttgaacctct cctgtaatta      3600
cttggctggg cagatccctg cggggcttgg gggcatgggg aggttgcata cgcttgactt      3660
ctcacataat gggctgtcag gggaggtgcc tcctggaatt gcagccatga cagtgcttga      3720
ggtgcttaac ctctcctaca atagcctgtc tgggcctttg ccaacaacga agttcccagg      3780
agcattagct ggaaacccag gaatttgcag tgggaaaggg tgctctgaga atgcaaggac      3840
tccagaaggg aaaatggaag gtagcaatca ccgcggttgg cttggtggct ggcatggaga      3900
gaatggatgg gtatctcttg gtgcatttg tatcagcaca atgactagct tctatgtatc      3960
attagcaacc ttactatgct cctctaatgc aagaaacttc gtgtttcggc ctgtgagggt      4020
tgaatattaa caagagggga gattgcaaaa tcaggttgtt ttgaagttcg agcgactctg      4080
gtctgcagct gattaacaag aaatatgagc atatgagatg gatatcttca gccaagagga      4140
agtgctgtct ctttttaatga tcaatcaagc tctcttgatt gtttcctaat attcttgatc      4200
ttgggatgtg tagatctagt tctaatattc ctactgttat agaatgcaat cacctgctgg      4260
tgcttggttg tagccctggc gtgttttggag gattggacac caaggatgca cataatttga      4320
agcgctggta ctgtgaacca cttcagatgt aaatattttc tttggttttt agttctgatc      4380
tagtttaaaa ctggacatgt atttagtgtt gttgagctac cttt              4424

<210> SEQ ID NO 314
<211> LENGTH: 67
<212> TYPE: DNA
<213> ORGANISM: Zea mays

<400> SEQUENCE: 314
ggcctgtgag ggttgaatat taacaagagg ggagattgca aaatcaggtt gttttgaagt      60
tcgagcg      67

<210> SEQ ID NO 315
<211> LENGTH: 67
<212> TYPE: DNA
<213> ORGANISM: Zea mays

<400> SEQUENCE: 315
ggcctgtgag ggttgaatat taacaagagg ggagattgca aaatcaggtt gttttgaagt      60
tcgagcg      67
```

```
<210> SEQ ID NO 316
<211> LENGTH: 105
<212> TYPE: DNA
<213> ORGANISM: Zea mays

<400> SEQUENCE: 316
ggcacccttt acaaacacaa atcaggagtg tcgctagaca acacctagcc aactaggatt      60
caaagacccc aaaagtaata aaatggaaaa gaaatcaccg atggg                    105

<210> SEQ ID NO 317
<211> LENGTH: 4343
<212> TYPE: DNA
<213> ORGANISM: Zea mays

<400> SEQUENCE: 317
gagctagctt aaatatggaa gccacactca ctcaccaagt catggatgag aggagagagt      60
gtggagagcc acacgcgcgc gcgcgctcgc tcgcctcgcc tcgcctggcc tggccgggcc     120
gggccggggc ggggcgaagg gcgcgggcgc acgacatgcg cgtgaatggt ccgccgaaat     180
ccggcccctc gccttgcgag ggcgcgacta cctttgccg tttgattttt tggtttcttg      240
gctgttacgc ttatcctaac cgatcgctac aaaatctcaa ctgattgcga gattttcgtg     300
ggcggataag cacgggggt cgcggactcg accctataaa aggagcccgg cagccagcct      360
ccaaatcatc ccagatccca gttcgctttc gcctctcttc atagctgagc cgccttttag     420
ttcccttcgt cccgaccgca gaggtgcatc tgcgatcagg agagcaggtc tccggaaccc     480
ttcgtcttct agatcctgca ccgggagagg gcgaataagg ttttgggaa gcgtcttcgc      540 gcgactgctc gtgatctgct gacctcgtca acccatctga tcctggcgcg cgccaacaat     600
cagtaagtct aatcagtacg catcatctga tttggctttt atttcagttc ttctgatttg     660
gtcatgattt atattcggaa tttaatttgg aatttgtcta attattcaac aggtgcaatc     720
tccggcctct actcactcca gatctattct tcgcttcgcc tgcaggcagc agtagcaccg     780
ttcaagttca accaacgcgg ccaacgcacc tgttgaagtt gaaccatgca tgaacccgcg     840
acgtgtttat cctccattat ccacggtgag ctctgaaatc cacgttgact cacatacata     900
cacggtacgc gcgtcaggga tttcactcgg aggcaagaat cgaaaagaa aaaggaagcc      960 acgcgtacga cgtgcaacgg ggacacacat ccacacggac gccgcgacgg gactgcacag    1020
tggcaatggc aacgcaggtg cagtggtggt ggtgttggag tgtttattat gcctcaccg     1080 tgtgcttctt tttttatgtt ccagagcaag cacgtaatgt agtaggggcg tagaatctag    1140
actatcaaat cgcgaggggc gacgacggtg ctcggtgcag tgcagctttg tacaggaaca    1200
ggactagtcg ttttcacgtc gtaacagagc acgctcccgc gtcgatagat cgctacgagc    1260
agtcgacaga cacggcagca taaatgcgcg cgcaaaagct agtagtagga ctaggcctac    1320
agtgcagtgc gtccccgaga ttcattcgtc aagttcaggt cgaccggccg gccttgccct    1380
tgcattggaa aacagttacc gctatataac aaacagccgc ggcgcacggc gagccaagcc    1440
cgtcaaggca cgaggactgc aggagcagaa agttggcaac cctttgagtt cctcactcac    1500
acgcgcgcga gccgagagag catggatccc aacgacgcct tctcggcggc gcacccgttc    1560
cggtgggacc tcggcccgcc ggcgcacgcc gcgcccgcgc ccgcgcctcc gcctccgccg    1620
ctagcaccgc tgctgctgcc gcctcacgcg ccgcgggagc tggaggacct ggtgggccgg    1680
ctacggcgtg cgcccgtcca cggtggcgcg gatctcggag ctcgggttca cggcgagcac    1740
gctcctcggc atgacggagc gcgagctgga cgacatgatg gccgcgctcg cggggctgtt    1800
```

-continued

```
ccgctgggac gtgctcctcg gcgagcgctt cggcctccgc gccgcgctgc gcgccgagcg    1860
cggccgcgtc atgtccctcg gcgcccgctg cttccacgcc gggagcacct tggatgccgc    1920
gtcacaagaa ggtacggcgt ataggagtat gtactcgtgt cacacacata cagacatact    1980
tgtatatatg ctcagttttc ttctgtagtt ctgtactagt tctgtgtgtt ttgcctctgc    2040
gagcaatgtg atgtgatgat gtggtcgctg gtcgatggtc gtgtgcatcg tgcctgcgtt    2100
aatgcatgca tgcatgcgga cagtgtccat gcatcagtct ttgttgggac tagagtcacg    2160
cgctctgctc tgctcgcctg tgatgttact tgctcttgtt cgatcatacc gcaaactcgc    2220
agcgctgtcc gacgagcgcg acgccgcggc cagcggcggc ggcatggcag aaggcgaggc    2280
cggcaggagg atggtgacga cgaccgccgg caagaagggc aagaaggggg tcgttggcac    2340
gaggaagggc aagaaggcga ggaggaagaa ggagctgagg ccgctgaacg tgctggacga    2400
cgagaacgac ggggacgagt acggcggcgg gtcggagtcg accgagtcgt ccgcgggagg    2460
ctccggggag aggcagcggg agcacccgtt cgtggtcacc gagcccggcg aggtggcgag    2520
ggccaagaag aacgggctcg actacctctt ccacctgtac gagcagtgcc gcgtcttcct    2580
gctccaggtg cagtccatcg ctaagctggg cggccacaaa tcccctacca aggtacgcgc    2640
gcgcacacac ttaggggggtg tttggttaca ccccgctaaa atttagctca tgtcccatcg    2700
aatgttttaaa cctccgttcc ggatattaaa tgtagtcgga ttataaaact aatttgtcag    2760
ccgaagatta aaagacgaga cgaatctagt ccagttgatt gggtctatat ttcatactcc    2820
tatttaaaag tcaaacgctt gatgtgaccc gagctaaact ttagcaggag caaccaaaca    2880
ccccctttatt catttagcag agtaacattt ttacatataa tatacaaacg gcagacgttt    2940
tctgtatacg aacaactgtc gtgaatgtac caatctttttt aggtcgttga caagctataa    3000
caatataatg gtaaagaaaa tatagtggca cgcaaagcgc caaagcccgc tctcattacc    3060
taggactagg aggaaggaag cagcaaaccc tttgtagtgg aattctatat ttcctgcgcc    3120
gttaagtcta tgctagtaca tgtactacat caccatagta tatgcgggtc ctcaattcaa    3180
gtactcgtaa tgatcgtgta gcacttgtac atacgtactg ctttaaagta tattttgctt    3240
gagacgcacc cgcactcgtg gataaagcga gtgacgtgtc atcagtcgtc ggtgccaaag    3300
cctggggtgg cttttgtgtcg tcttgtccgg ccctagggtc agacgggcat gcatggcatc    3360
gacactctct cggagtccgt ggctgtgtgc tgttgccacc ggtttcgcgc gtaccagtac    3420
gactgtacga gccacgtggg ctcgatttgt ggcagtttgg tggccggcgt acgagtagtc    3480
tcgtgctcgc ccccagtctt cagacggtgt gcgtcgaagt gaaatgaatg cacggtctgg    3540
cctggacgga ttccagggtg attggatatg atgatagctt ggtgacctac tgacctgacc    3600
cggacggccg catcgatgcg ctcctgcgtc tgcgtctgcg ccaggctagc ccacccagat    3660
ccagaccgag accggccagg cgcgcgcagc ttgttcgatc cgtgagcagc tgctgctgct    3720
gctgctgcgt gcgcacttgt gcgcgacgcg acacgacacg agcagcgagc tgctctgcac    3780
tgcactgcac gggaaccaac caaccatggc tgatgagcga catgttcgcg tggcgcgcgc    3840
gatcgtgctc gtgctttgct tgcaggtgac caaccaggtg ttccggtacg cgaacaagtg    3900
cggggcgagc tacatcaaca agcccaagat gcggcactac gtgcactgct acgcgctgca    3960
ctgcctggac gaggaggcct ccaacgcgct gcgccgggcg tacaagtccc gcggcgagaa    4020
cgtgggcgcc tggaggcagg cctgctacgc gccgctcgtc gagatcgccg cgcgccacgg    4080
cttcgacatt gacgccgtct tcgccgcgca cccgcgcctc gccgtctggt acgtgcccac    4140
caggctgcgc cagctctgcc accaggcgcg ggggagccac gcccacgctg ccgccggact    4200
```

```
cccgccgccc ccgatgttct agcgtgcgtc gtcgatgtgt gcctgcaccg tcgccgtacg    4260
tctcacagtt ccttttcctt ttagagtgtg aaccaccatg gaaaattgga ttccctctca    4320
tatgatgttg ccacttctca gtt                                            4343
```

<210> SEQ ID NO 318
<211> LENGTH: 87
<212> TYPE: DNA
<213> ORGANISM: Zea mays

<400> SEQUENCE: 318

```
acaactgtcg tgaatgtacc aatcttttta ggtcgttgac aagctataac aatataatgg    60
taaagaaaat atagtggcac gcaaagc                                        87
```

<210> SEQ ID NO 319
<211> LENGTH: 102
<212> TYPE: DNA
<213> ORGANISM: Zea mays

<400> SEQUENCE: 319

```
agtgtccatg catcagtctt tgttgggact agagtcacgc gctctgctct gctcgcctgt    60
gatgttactt gctcttgttc gatcataccg caaactcgca gc                       102
```

<210> SEQ ID NO 320
<211> LENGTH: 551
<212> TYPE: DNA
<213> ORGANISM: Zea mays

<400> SEQUENCE: 320

```
atgagataaa gaatctgcta gagatagtct aagtcatcca ctgcaggtat actcccaaca    60
atagcaagta ctcaattcat attgaaatcc accctgtgga attccatgga tggtggcatt    120
gtgctttcta tcaaccaaag cagatcactc ctggaacgga gtgaggtcga tcttgaatgg    180 cttcttttccc ttggtaactc gcttcacatg atggagaaaa gggggggataa acaaagggta    240 aatttactga tatttggctt gaatatattg aaggatatca aacttacagc aattgcaatt    300
aattcctcca acagctcttc cagattgcgc aacggctaag aatgaaaagg gtgcaaagaa    360
atagtatgtg ggttatatga taaacatgat caatgctaag taacgtggaa aaggctgcac    420
gaatggactg gattataccc attgagttgg gccatcgcat ggtgcattca aggggtcatc    480
atgtacctgt gggattatgc aataagatcc gtttaatgtt gagcataaca gcagattatg    540
ttaatatacc a                                                         551
```

<210> SEQ ID NO 321
<211> LENGTH: 151
<212> TYPE: DNA
<213> ORGANISM: Zea mays

<400> SEQUENCE: 321

```
tccaacagct cttccagatt gcgcaacggc taagaatgaa aagggtgcaa agaaatagta    60
tgtgggttat atgataaaca tgatcaatgc taagtaacgt ggaaaaggct gcacgaatgg    120
actggattat acccattgag ttgggccatc g                                   151
```

<210> SEQ ID NO 322
<211> LENGTH: 507
<212> TYPE: DNA
<213> ORGANISM: Zea mays

<400> SEQUENCE: 322

```
cgtcgtagtg gttgttgtgg tgcgcgcagc gcggcgcgtt gacgggcagc atcaggtagt      60
tgggacccag cctgtagcgc tgcgtgtcgg cgtaggcgaa cacccggcac tgcagcatct     120
tgtcgtccga gtagtagatc cctggcacca ccagccccgg gccgaacgcc agctgctcgt     180
tctcgttgaa gaagttgtcc acgttcctgt ccagcaccag cctccccacg gggcggagcg     240
gcagcaggtc ctccggccac gtcttggtgt cgtccagcgg gtcgaagtcg tactgctcct     300
ccgtgtccgg ctccatcacc tgcacgtaca gcgtccactc cgggaagctc ccgccgcga      360
tggagtcgta caggtcctgc gtcgcgtggc tgtggttccg tccccgacc agcgccgcct      420
cctcgtccgt caggatgcac cgcacgccgc acgtcggctt ccagtggaac ttgacgtact     480
gcgccttccc cgccgcgctc acgaacg                                         507
```

<210> SEQ ID NO 323
<211> LENGTH: 90
<212> TYPE: DNA
<213> ORGANISM: Zea mays

<400> SEQUENCE: 323

```
gcatcttgtc gtccgagtag tagatccctg gcaccaccag ccccgggccg aacgccagct      60
gctcgttctc gttgaagaag ttgtccacgt                                       90
```

<210> SEQ ID NO 324
<211> LENGTH: 75
<212> TYPE: DNA
<213> ORGANISM: Zea mays

<400> SEQUENCE: 324

```
gcgggtcgaa gtcgtactgc tcctccgtgt ccggctccat cacctgcacg tacagcgtcc      60
actccgggaa gctcc                                                       75
```

<210> SEQ ID NO 325
<211> LENGTH: 822
<212> TYPE: DNA
<213> ORGANISM: Zea mays

<400> SEQUENCE: 325

```
gatgttataa gtggatcaaa gaggtgctgc ttgcgattat gactgtaaat gcaaatatat      60
acatagatct gaaaccatg gaaaaaatat taatacatac accaaaaaac agtacagatt      120
atcaaaaagc tgatcaaaca taacatagag acacatgaaa ccccaatgaa tcaagccaaa     180
taaaaatata ggccggcatt tgtccacaaa cttaatccaa aacttgattt aacaaatcat     240
actaattaga agacttccct agcaataaca gaagtacata acttgaagac caaactgcat     300
catggttttc tagtacattc atccagttcc atatctatga ctgatgaaga cagtggagct     360
ggaaggggca gcacataatg caggttctac ctagaaccct tcaggacgaa ctaatcaagt     420
aattgcaaac tgacggcttt aaagaacgga tttgcaaatt aaaataaaaa tgataactgc     480
agtaaactga tgtttaagag caaccttata tagtacaagt aaatgcatcc ccgaactcaa     540
ctgaagctta tgaaatttaa ctagcactac aagcttgtta ctgccgcagc tggctaaca     600
acagttcatc agatcgaata gactacacca cgcatgccag attaaggta acgatcaat      660
cttctttgca gtcaagataa ccaaacgcta accctcacct tattgaactc aatctgcggc     720
gtccagtagt gaagcagacc gaagaagtag tcgaacatct cgacggatga ggagaactct     780
tttggcccca gcttcactgg cttgcgctcc gcctccactg tc                        822
```

<210> SEQ ID NO 326
<211> LENGTH: 83
<212> TYPE: DNA
<213> ORGANISM: Zea mays

<400> SEQUENCE: 326

| | | | | | |
|---|---|---|---|---|---|
| agaagacttc | cctagcaata | acagaagtac | ataacttgaa | gaccaaactg | catcatggtt | 60 |
| ttctagtaca | ttcatccagt | tcc | | | | 83 |

<210> SEQ ID NO 327
<211> LENGTH: 7136
<212> TYPE: DNA
<213> ORGANISM: Zea mays

<400> SEQUENCE: 327

| | | | | | |
|---|---|---|---|---|---|
| acgttgttgg | agagaaagta | gatataggag | atgaaatctt | ttagagaagc | ctgtaaagga | 60 |
| cggatataga | ggatgtatat | agaggacgtt | gctggagaca | gtctaaagag | ctattttag | 120 |
| agaagagttg | ctgtaacgtc | ggagtaggtc | tgtaggtgga | caagagcggg | cctagtggtt | 180 |
| taaaaaaaca | acagaggcta | ggacatagac | aatcctgtcg | tgtccagctc | accggatctc | 240 |
| ccccacgcaa | gacacacgga | cgaaaggaaa | aaaaataata | gaagaaactg | ggacgaccct | 300 |
| tttctgtcc | gtccgtggtc | ccttcaatct | ctctgcgcaa | tcaaactgcg | gtggccaacc | 360 |
| ccggaagcgg | cggcgggcaa | agcgcgcgac | gcagagaagc | gtaacttcag | gccgccggtc | 420 |
| gctctacgca | tcctgctccc | cgttctcgtc | ggagatccac | cggggcagcc | tttctttccc | 480 |
| cttcctcaat | caagtcggtg | agtaatccga | gctcgattgc | gtgggtggat | tgccttatct | 540 |
| cacccaatca | ttcaaccaga | tccaatttcg | cgcgcgggtc | gggctcgcct | tctcctccag | 600 |
| tctccacctc | caccagcgct | cgaggtcgac | ggacgctact | cgcagcagtt | cttctttgcg | 660 |
| gtgcggccga | gaagaagcta | aggctcaggc | atgagcttcc | gggaccagga | gagtggcggg | 720 |
| gaggatgggg | gcaggacgtc | ctccgcctcc | gacctgcgga | agccgctcat | caacaccggg | 780 |
| agctggtacc | gcatgccgcc | ggcgggtggc | gtgatgggct | cgcggcaatc | tagcctcatg | 840 |
| gagcgattgg | gctcctctgc | gttctctctc | cgcgacgtcg | ctatctcggc | gacgctctgc | 900 |
| acgctcattg | tcgcgctagg | tcccatccag | ttcggtttca | catgtggcta | ctcctcaccc | 960 |
| acgcaggacg | ccatcattgc | tgaccttggc | ctctccctct | ctgaggtgaa | cccctgttct | 1020 |
| tttatcattc | gttctttctt | tcttttaat | gcttacccttt | gcttgcttgc | tctttcttgg | 1080 |
| cggatgcatg | cagttctccc | tcttcggttc | attatctaat | gtagggggcga | tggtaggcgc | 1140 |
| catctccagt | gggcaacttg | cagagtatat | cggccgcaag | ggggtgagac | taccaccttta | 1200 |
| ctttgtcttt | gctagatcat | gaatcgcaat | gcaatacgac | tgacttaatc | attgtttaag | 1260 |
| tgtgcatagc | atccatacta | tataggaggc | ttcgctgctt | tgctaattgg | aaccttgaaa | 1320 |
| gatatgcctg | tgatgatttt | tcagaccgat | ggactgattg | aattatttgt | ttggccttgt | 1380 |
| agtctctcat | gatcgctgcg | attccaaaca | taattgggtg | gctcgcgata | tcatttgcaa | 1440 |
| aagtaagttc | aactaccatc | cttttttccat | gcttctgctg | ctgatttcct | ttgttcgtca | 1500 |
| atatatgata | taacctgtg | agtgtttttt | ttacttctgt | tgcggtgcat | attcaggatt | 1560 |
| cctcttttctt | gtttatgggt | cggctgctag | aaggatttgg | agttggtgta | atatcgtata | 1620 |
| cagtatgcct | cccctttctc | ctccctctta | gtaaaaacaa | attactctag | tggcatttttc | 1680 |
| atgttcatcc | gtcttccagc | tgttaaagat | tacaatcctt | tggtattttt | ttaatcgaaa | 1740 |

```
attctggttt tcacaattaa agtcttaaca agtccataca aacaaaaatc tgaagtcccg   1800
acatatttca aacaaaacaa tatgttctag tggaaaatgt aagcgtagta aggcatatag   1860
cttggaatga tgaaacaaaa ttaaataaca agtcgactaa aaaaagtgca gagtttgtag   1920
ctcttaaata caatgctact ttcttaggtt acattatctc aacaacaata aagtattta    1980 gtcataatca agtttgggta ggctagagtt gaaacccaac ggaaacagtc gaggttcaga   2040
cacatggata gctattttc gtgtgctcct attcaaggct aaatatttgg gtatattcca    2100
tccctgcatc ttcctatgtc aactcggtct ttccctgcct ctatttatat tcttatggac   2160
ttatggtgcc ttaagatctc actagcactg gtgcctctgg aggtctccgt tggacatgtc   2220
caaactatct caactagcgt tgaaaagttt ttcttctttc cataatacat aattgaatat   2280
taataatact agacaagaaa actcataaac caaggtcact gaccettgtt cagaataata   2340 gggtataatt atttcattgt caaatgagac tactagcact tagaagtgac tgaaatccta   2400
tgtcgaatac tgttgtagaa ttgactttct atatgcaagt tgtactatat aaagcaccat   2460
tttccacggt ttgcaccgtc gtcgtggtcc cccacattta aatggcaaaa ggctaaaatt   2520
atgtacaaat gaggattcga accatggttg ttggctctaa acccacactc acactcactt   2580
agccaacata acaaacatgt ctttatgttt tatactatat aattataaat ggtaaccgta   2640
gcaaagtacg ggcactttgc taatagtgca gtcaagtttc agttttctat aaaaccagga   2700
tgataatggg taaatttctt tgcatggcaa tagcatacct aggtaacctt tcaactccag   2760
tgtgccactt gctggtgcag ttttagcga tagggcgttt ctggttaaac aatgcagttt    2820
ttaataactt gttagcagct ctgttgctta tattttgatg tttttatgcc caatattact   2880
tttatgattg gaacttctat ttcatgtttc caggtaccgg tttatattgc agaaatcgct   2940
cctcaagatc agagggagc tcttggttct gtcaatcagg tagttttta atagtgaacg     3000 acaacatttt attaatgtta ttcatgtgta gtgtttcttc tgatctgtcg atgttgctac   3060
caatttcgaa ccaatccata atttcttctg cagctctccg tcacgattgg tatattgctt   3120
gcctatttgt ttggcatgtt tgttccctgg agaattcttg ctgttctagg tatgatgtaa   3180
aactttaatc cattggttta gtatatgaaa gaacaatgtt ctacatagca cccatcagat   3240
gactgttttg gttgttttat ttgtacagat catcttccta actactttc tgttacttct    3300 acatgttta ggcattttac cctgttcaat cctgattcct ggactgttct ttgtccctga    3360
atccccaagg tggttggtaa gtattccatg gtattatctt ttcatagctt taatgtcagg   3420
acctgaatac aacagattgt ttgtttcagg caaaaatggg gaagatggag gattttgaat   3480
attcattgca agttctgcga ggatttcaga cagatatcac agcagaagta aatgaaataa   3540
aggtaatcaa tagtggaaac tccagtttag ttaaaataga gatagagata tacagttttt   3600
ttcttggaca tgcaggagag ctgtgtactt acaaacatac ccacacaaca cactcagtcc   3660
aacattttag ttttaggaag ataaacacgc caatacataa taaaactcga tcatgaccta   3720
aactcaacta atagatgaag ggacataaga taagaaatac ttcaagctgc tggcatggga   3780
gatgccccat caaaaacaca ccagttacga tgagtcggtg acaccaaaag gtccaggcac   3840
caagagacat atatacttcg tcaatcttgc tcccagtggt atacactggt gcagctgcca   3900
atgcattgct ctctagtagc aaaagctgtt gtagaatctc ttaattttg cagtataatg     3960 tgccatagga gatgtgaatt acataattat cttcctttt ttacacagag atcattagca    4020
tcatcgagga ggaggacaac cataaggttc gctgatatca aacagaagag atacagtgtt   4080
ccccttgtgg ttggtgactt gctatttgtt tctctgttta catattgatg tttaaacttt   4140
```

```
tgtagttttg ctaattggct tgttttaga taggaatcgg tctccttgtc ctgcagcagc    4200
taagtggtgt caatggcatt ctattttatg ctgcgagcat cttcaaagct gctggtacat    4260
tcttcaaaac acgatcaatc tctgatgtag attctaatgc aattgagata tgctttgtgg    4320
cttgcgtatt cttgaacttg tccaggaaat gaaagttacc ttgttttggt tcgattcatg    4380
ctttgcatgg agacactgtg acaatgattc atttactatg taaaaaaagg gaagagttct    4440
agaacctagg cttcatcaaa gtctgatatc ttcctgaatt ctcttcctca acaggtatta    4500
caaacagtaa tctagcaaca tttggtttag gggctgttca ggtacatttg ttttaaagtt    4560
gttacatccc ttgtttctca gacaaatttt aggcagatgt gggcttggca ctgcatactt    4620
aatgggatct tgtcgtttca ggtgattgct actggagtga caacctggtt gactgacaaa    4680
gctggtcgaa ggcttcttct cattgttagt ttccaacttt ccatcacaat tgtttatcgg    4740
acatgctttt ccagttttgt taattgagct gtcttttcag atttccacca caggaatggt    4800
cattactctt gttattgttt ctgtgtcatt ttttgtgaag gtaatgtcac ttaaaagttt    4860
aatagtagca tgctattgtt tgcagcacac tcctattgaa ataatcatat gcttagagt     4920 ctatcgacat tgtcattcct ttctgaaata ctcttgcttc acttctggag caggacaaca    4980
tagctgctgg ttcgcactta tactctgtaa tgagtatgct ttcactggct ggacttgtgg    5040
ttagttccac tactattaca gattgtttgc cgcccttgtt gagataagct tgtttaatgc    5100
cttgtctttt gctattccag gcatttgtga ttgcattttc tcttggcttg ggagcgattc    5160
cgtggatcat tatgtctgag gtatagtttg ttcttgctt tttatattata cagagctttt    5220 aattcgctaa tgtgtctttg ctatcttatc tttatgtaat tattatgagt gccacttagc    5280
acttttgctc taagtcccca gctctgaatt tcacgcactc tgagacactg caaccccaaa    5340
tccacaacct ctcagcatag gggttgtttg gatacccacc ccacccccc tttttcttc     5400 tttttctgt cttggtctat ttttttggca gcttgtactg ggtctacttt agacctctat     5460 ctccttttc ttaatatata agatgcgcag ttctcctgcg cgttcgataa aaaagctata     5520
gcttctttaa aatcgcatgg gtctctagcc agaggacatc catgcctacc tcaaataact    5580
gaaattacct catccagtag ctattaattt aaccgcgaat gatagtgagc aacttatcta    5640
gtctagttgc ctagactaga taagttcagt gaaatgccta gaggtactgc atctgcaaac    5700
ttgcggggag atttatgcac ttacattgtg tttccttttca gatccttcct gttaacatca    5760
agagccttgc tggaagtgtt gcgaccctgg cgaactggct gacagcatgg gccattacaa    5820
tgacggcaag cctgatgttg aactggagca gtggaggtct cttcctttct ttttccattc    5880
tctccctccc ttcaagaacg tgtttcccat tgcgacgttg gatctaaccg tgtgtcttgg    5940
tttgaccagg aaccttttgct atctacgccg tcgtgtctac catggccctc attttcgtgt    6000
gcttgtgggt gcctgagacc aagggaagaa cgctagagga aatcgccttc tcattccgct    6060
gacacgtcgt catgatctag gtatgggaag ccacaccaca ccatgtgtca ttgagtcatg    6120
ccgcggtgcg ttcagttcat gaatcccgca gggatcttgc ggccattctg ttgcttggat    6180
gtaccaccat cttcagtgtt cataccaatg tacattgtac aatatgacga cgacgccata    6240
gcagaaaggc aagtgggttt atgtttgtac gatggactag tagcagaaag cactcgaacc    6300
cctgtacggg ttgcggagga gagcaattta tttgctgtat tttcctggtt caataccgga    6360
cacgttagaa ttttgaaaaa taaaaatctg agcaaattta tcaacggtgc tgccagctcc    6420
atgcgtttgc ctgcatgcgg tcatgaagta gaagacattg gagcctaaat atctaggaac    6480
```

```
ggttttgatt taggaaaaaa aaaagggaag gaatttatt ctgaaaccta ggggcatggt    6540
tgtgcagcgg caaacttgac tgctgaaggg gctgatcgga attaggtacc ttgtggtttt    6600
gaagcgttgt ttgaaatcgg cgtcagcctc gccccaccag cctcttctaa tcgtctgaaa    6660
cgggggctgc aagatctccg tggacctcgg ccgccgcgtc tgcctgccca tgcggcatta    6720
gcgccttcat gcgacgtcgg aggatcagga accgtggca tgtgagaagg atcatttcca    6780
tggacctcaa cggcggacgc cggatggcag gggcatcatc tgatgatcat ccgcctgccg    6840
cgtgcgccgc cggagatcag gaagccgtgc ccagtcaaca ctctgcaggc caccagccca    6900
ccaatttggg cacccggttg tggcagagcg agcgaatgcg aagcacggtc gacttcacta    6960
accctgctgc gactgtgaga aaaaaaggc ccttttggcc taacccaatg cctagtttgc    7020
tcggcccatc tgctggatat tttgtttctt ttttccttt gcgaaaaagt tggtacattt    7080
tgttgaactc aaaccgtgaa gacgcaaatc cttaaatttt ttattggttc acgcca        7136

<210> SEQ ID NO 328
<211> LENGTH: 143
<212> TYPE: DNA
<213> ORGANISM: Zea mays

<400> SEQUENCE: 328
gcgtattctt gaacttgtcc aggaaatgaa agttaccttg ttttggttcg attcatgctt      60
tgcatggaga cactgtgaca atgattcatt tactatgtaa aaaaagggaa gagttctaga    120
acctaggctt catcaaagtc tga                                            143

<210> SEQ ID NO 329
<211> LENGTH: 142
<212> TYPE: DNA
<213> ORGANISM: Zea mays

<400> SEQUENCE: 329
gcgtattctt gaacttgtcc aggaaatgaa agttaccttg ttttggttcg attcatgctt      60
tgcatggaga cactgtgaca atgattcatt tactatgtaa aaaaagggaa gagttctaga    120
acctaggctt catcaaagtc tg                                             142

<210> SEQ ID NO 330
<211> LENGTH: 1580
<212> TYPE: DNA
<213> ORGANISM: Zea mays

<400> SEQUENCE: 330
agcattgtca tgctccttgc ctatgtagcc tacctttct tccaactgaa aacccaccgc       60
caactatttg aaccccaacc ccaagaggtg tgtattgtaa tttgttgctg atcagtaacc    120
agcaggaact gctaacatag aaccagcttg ctaatttggg tatgtggtcc aaccaaatga    180
ttttgtaggt tgaagatgat ggtgatgatt cggtctctca agacgaggca gtactgggat    240
tttccagtgc aatgatttgg ctgggagtca tgaccctgat gacagcactc ctatcagagt    300 tgttgtgag cacaattgag gtatgcacca ctgagtacaa tgccatgttt atgttaccca    360
tttcagtcag cacatacact gtagtaagtt gtagtacagc taatggtttt atgacagaat    420
cttgttaaca cttaacaggc agcatcggaa tcttgggagc tatctgtcag tttcattagc    480
gtcatcttga ttccaatagt tggtaatgca gcagagcatg ctggtgcagt gatatttgcg    540
tttaaaaaca atctggtagg gaaatcgagg aggtcttaca cactcatcac gatgttatgg    600
tagcagatac taacataaca ttgttggctg aaacaggaca tcaccctcgg agtatctttg    660
```

```
gggtccgcta cgcagatttc catgtttgtg gtgtgtatta acttaaatgt agagatagtt      720
ccatgtgctt tttttgcatc ggtaaacttt aatggtggaa gcgaaatgtg ctaggtgcca      780
ttgagtgtcc ttgtagcatg gatcatggga gtcccgatgg atcttgattt caacttgctt      840
gagactggtt gtttgtttct tgcaatatta gtaacggcct tcacgctcca ggtattcttt      900
tgcaccctcc tcgatccggc ttgaacataa tcgataacac gcatggattt ttcattgaca      960
gaacatccat gaatcttgag tggttagttg tatgtgctga ttttgtttat taagaaaaga     1020
aatgtccact tgtgcggttc ggctgtgtcc ttgtttctaa ggatgcgggg ccataggagt     1080
tctgtcaata tcgtggtttt agcggtaaag agtgactgtt ctatgcgttt ttgcaggatg     1140
gatcatcaca ttatctgaag ggactgctgc ttgtgttttg ctacattgtc atctccttat     1200 gcttttttcgt tttgagacag catggaagta tggatttcta gtcttaacaa ccttcattca     1260
aaaaaaaacc tatagatgca ttattggttg acattttcta aataatctca ataacatgtt     1320
actgatgcta gatggaagca acgatgatca gctgggtgta gcaagcaagc catggaggat     1380
ttagggcgcc tgagctggca gtagtttctc aacaagtagc gtggactttg gtttgcacga     1440
ttttgcatgg aacactggag gggagacccg tgaagtttga ctaaagtatg tagactgcgg     1500
gaagatgctg ttcagctgat gtgtgaatgt aagtacatac aaagactata gatgaaaact     1560
gatgttgcgt gagagactat                                                 1580

<210> SEQ ID NO 331
<211> LENGTH: 69
<212> TYPE: DNA
<213> ORGANISM: Zea mays

<400> SEQUENCE: 331
agatgaaaac tgatgttgcg tgagagacta tttgtgtgtg ttttcttgt tctttccacc        60 aagcaatgg                                                              69

<210> SEQ ID NO 332
<211> LENGTH: 611
<212> TYPE: DNA
<213> ORGANISM: Zea mays

<400> SEQUENCE: 332
atttaactct ttcaagaaga ttgtaagatc catggggtat ggcgaggatg atctccctct        60
agtatcgtta cagtctgttt ccaaaggtaa atttatataa ccagctactt tatctgcctt       120
ttggccaagt aactggctta tccaaaacat tttgttgctg caaccaggat actatggaga       180
gtgtggtaaa agaggagggt acatggagat tactggcttc agtgctccag taagagagca       240
gatctacaag atagcttcag tgaacctatg ctccaatatc actggtcaaa tccttgcgag       300
cctcgtcatg aatccaccaa aggtctgcca tatggaattc tttaaattac gccctggttg       360
gaattaggaa atgccaaatc gtccagttaa aaatcattgc tttattctcc aggttggaga       420
cgaatcatat gcttcctaca aggcagagaa agatggaatc cttgagtctt tagctcgtcg       480
tgcaaaggtt agcctggttg catttccact acactcgagt gtcttcttta aaaatattca       540
agatttttct tttgttcgtt ttacaggcgt tggaggatgc attcaacaag cttgagggat       600
tttcatgtaa c                                                           611

<210> SEQ ID NO 333
<211> LENGTH: 93
<212> TYPE: DNA
```

```
<213> ORGANISM: Zea mays

<400> SEQUENCE: 333
ccctggttgg aattaggaaa tgccaaatcg tccagttaaa aatcattgct ttattctcca    60
ggttggagac gaatcatatg cttcctacaa ggc                                 93

<210> SEQ ID NO 334
<211> LENGTH: 147
<212> TYPE: DNA
<213> ORGANISM: Zea mays

<400> SEQUENCE: 334
tcatatgctt cctacaaggc agagaaagat ggaatccttg agtctttagc tcgtcgtgca    60
aaggttagcc tggttgcatt tccactacac tcgagtgtct tctttaaaaa tattcaagat   120
ttttcttttg ttcgttttac aggcgtt                                       147

<210> SEQ ID NO 335
<211> LENGTH: 130
<212> TYPE: DNA
<213> ORGANISM: Zea mays

<400> SEQUENCE: 335
ctccctctag tatcgttaca gtctgtttcc aaaggtaaat ttatataacc agctacttta    60
tctgcctttt ggccaagtaa ctggcttatc caaaacattt tgttgctgca accaggatac   120
tatggagagt                                                          130

<210> SEQ ID NO 336
<211> LENGTH: 5656
<212> TYPE: DNA
<213> ORGANISM: Zea mays

<400> SEQUENCE: 336
acatatcatc ttttgacagg atataatatg tgaaacaaaa aaagtcacct acgtgcggtg    60
tgggtagggg cggtacgtaa tggatcacga ttcatttgag tccttaataa attttagtat   120
aatattaaac aaaaataggg ctcgatctta atatggctcg atcctaaaat tttatagcgt   180
aaaattgaga acccagtacc atcataggtg tgggacatgt acatagaaca agatcagtgg   240
atactttggt tgttactgtg taactgtgtt acagcaccct tatatgcgag ttccacggg    300 agccattgat ttcgtcatag agaggcacac attgacctag gacgatgcga ttgtacttgc   360
acgaggagta aattgaccat caacggggaa taacataata ataagaaaaa gaaacacatc   420
tactatagaa tggaacaaaa agaaacacga cgcgtcccaa tatatacatt gactgcgatc   480
aaggtagccc atttatacag cgccaacaag gagtagaatt cacggtaggt acgtacacgt   540
acacgtacgg aatgtacgta tgtagtattt caacttgttt ttattacagt ggctttaatt   600
tgtgcatcct ggagaatctc aaagttacca atcttaaaat ttgcttaact tttaacaatg   660
tgtaccaggg agggcttgag caccgcagcc ctatgctatg cacctgcgct cccaatacta   720
gtcggagtag actagtagga gtagattttc tgtctctctc acacactctc tatgcctgcg   780
tgtttgactg cacctcagcc agcctagatg ctaggctact cacgctggac catcctccta   840
tagtcctagc tatagccccc cctccatgat aaaagctacc tacgcttgcg ttactgtgct   900
ctactgcgcc actgtgtggt aatttggcaa cagtaaaatc agagatcata cgagggtttt   960
tcttttagct agggcttgtc cgggagccac gggatcgagg tcagttagaa ttcctcgtta  1020
tttactccct ccagtttcct attagttgtc gttttggata aggttcgagt caaatttata  1080
```

```
aaatttttaac tacaaataac tattttatta tttagttttg gaacctaata tttatatgca    1140
tcaatttgtc ataaaaagta cttttataaa agtataaatg tattaagagt tcatttgtat    1200
tttaacaaaa aacattggtc aaagttatat tttgaagacc gtgtcgttgt cctaaacgac    1260
aactaatagg aaaccggagg gagtaaaatt caatagtgtg agattttaac ccctgatcaa    1320
tccactccat tacttttact ttaaacaagg gtttatagag aaagagggaa agaacacta     1380
agggctagtt tgacaactttt actttccaag tgattctatt ttttaaagag aaaaataaac   1440
taatttcttt tagaaaaata aaaatctctt gagaaaatag gctgcaaaac tagctctaaa    1500
taaataatta actaaacaaa tgaaaagaag gcggctaaaa gaaaggaaac aaaaggcagc    1560
cttattttcc cccttctctc tccttcccct gccttctgct actatatagc tcccctcac    1620
cttccgttct agagagagag aagggagagg cgagggagct caccaggaga gaggggcctg    1680
tgtgagcatt gagcaaagca aacgaagcag tacatacatc tctcgctcgc agaggcccgg   1740
ccggccggct ccatgcaaca agggacgacg agcggtggcg gtgggcgatg atgatgatga    1800
tggcggggga gcacgtgctg gccgctctgg ccaccctgct tctggcctcg ctcctgaccc    1860
tggtgctgaa ccacttcctg cccttgcttc tgaaccccaa ggcccccagg ggaagcttcg    1920
ggtggccgct cctcggcgag acgctcaggt tcctcacgcc gcacgcctcc aacacgctgg    1980
gcggcttcct cgaggatcac tgctccaggt acactgtgat actagtgccg tttgccgcgc    2040
gcgccggccg gcccggcggc cctttttttc cccctttctt ttttacccttt ttccaccgtc    2100
cgtgcccgtg ttccatgcac acggacggct cctagctgac tagccaaccg gccggccata   2160
tgagatggat ggatggatgg atggatggat cgatcgatcg gtcttgttac cgtgcaatta    2220
agtatcgcgc cattatttca tgtgacagca aaggtgacg cgctgcccgc cggccgctgt    2280
catgtctaag ctagcagcag cagccttttt tctcacggtt ttgttcttgg gtcgttccga    2340
gaccgggacg acagtagtct gatctgatct gagagagtag taaaaaaaga ggagaaagta    2400
aacaacggcg ctcgacgata gattttactt acatgcatgc atgcatgcat ggtcctacta    2460
gcagctagct agctaatggc agcatgcatt gttgatatgc aggtatgggc gggtgttcaa    2520
gtcccacctg ttctgcaccc cgacggtggt gtcctgcgac caggacctca accacttcat    2580
cctgcagaac gaggagcggc tgttccagtg cagctacccg aggccgatcc atggcatcct    2640
gggcaagtcc tccatgctcg tcgtcctggg cgaggaccac aagcgcctca ggaacctcgc    2700
cctcgccctc gtcacctcca ccaagctcaa gcccagctac ctaggcgaca tcgagaagat    2760
cgcgctgcac gtcgtcggcg catggcgacg gcacggcggc gtcagggtcg tcgcattctg    2820
cgaggaggca agaaaggttc gtcatgttgc ctctgcatca atctttttgc catggagact    2880
ctgtttgact taccaggatc gtttcgtttt cctttcctat ttcctctggg ccggccgcgc    2940
gtgtcctctg ctctgtcctt gagaaaagca cagttcgcat tcagtgtgat agtgaagcag    3000
gtgctgggc tgtcgccaga ggagccggtc actgcaagga tactcgagga cttcctggcc     3060
ttcatgaagg gcctcatctc cttcccctc tacatcccag ggaccccata tgccaaggct    3120
gtccgggtaa tcatccgcca ccatgtgtct ttagtagcac atgccatgct tgcttgcttg    3180
cttgcgttcg taaagagcat ccatgatcca tctcttcatt agtatatgcg tacaatacat    3240
acatagacac acactatgct tacatgtaca taaccgtggc tacgtttatt ttgttgcgta    3300
aatcccaacg gcaggcgaga gagaggatat ccagcactgt gaagggcatc atcaaggagc    3360
ggaggagcgc tgggtcatgg aacaagcagg gcgacttcct tgacgtgctg ctgtcaagca    3420
```

```
acgagctatc tgacgaggag aaagtgagct ttgtgctgga ctccctgctg ggagggtatg   3480
agaccacctc gctcctcatc tccatggtcg tttatttcct tggccagtct gctcaagatc   3540
tggacctggt taaggtaacg atagtaataa tcataatgtt taataataat atcactgtga   3600
aagcacagca cagcacaggc acatcttttt tttttgtgct ggtttggcat catcaataaa   3660
ttataagcta tccatgaaca tgcagaggga gcacgacagc ataagatcca acaaaggcaa   3720
ggaggagtgc ttgacttcag aagactacaa gaagatggaa tatacccaac aagtgagata   3780
gatgaccatt cattcaatca atatatacat gatgctagta gtattagaaa tggaagtagt   3840
aaatatgata aatttttatt tctgtgctgt aagtatgctg cagtatgtgg aatagaaatg   3900
ttgttgtcat tcatgcccct tcaccttcttg atcgcaggtc atcaacgagg cgctgagatg   3960
cggcaacatc gtcaagttcg tccaccggaa ggcgctgaaa gacgtcaaat acaaaggtga   4020
tgtagctaga tgagcccccc ggccccagtc ctgctcctgc atcgagagac tttcgctgca   4080
gattccatct gtgctcatca catgacagtg atcaggcag aggggatggc cgcgccttta   4140
agcctgattt ttaagcgatt gttttatgcc cagaataacc tcctatagct tttgctaaac   4200
gaagatgctc aaaaagcaag tggctctgcc ttttgctctg ttgcagagta tctgattcca   4260
tctggctgga aggtcctacc ggtcttcact gccgttcatc tgaaccccctc acttcatgga   4320 gacgcgcagc agtttcagcc ctgtaggtgg gaggtacgct gcgctccctt ctcaggagct   4380
cagactcctt cctcattact actgttctgc acttgccatc taactataac ggcaatgatc   4440
caatcatcca tgttccatga atagtgaagg ttacctttgt gataatatat atggtgctac   4500
ttaatcaaaa ctgaatgaaa taataggaat caaaggcaga gaacctatca aacaagctta   4560
tcagggcctt ttgctcttag ggaatcttct ttaaagtgtg cactctaact aattgctacc   4620
tttagttagt gtgtgtccat ctgtgacata gttactctca actgttctgg tatgttcaga   4680
tggcaagcat gctgcctgat gtagtgcttg ttggttgtta atggtcctaa ccatgattcc   4740
gttcgttgaa agccagccct ctgggctttg ctccgatttt tttttcttc ttcaatgatg   4800 ttcatggtct cattaatttt gtgtgactca tctgattgat gtataccagg cacaagcca   4860 agggacaagc aagaggttta caccgttcgg tggtggcccc cggctctgcc caggatcaga   4920
gctcgctaaa gtggagactg cttttcttcct ccatcacctt gtcctcaatt ataggtaaat   4980
aaacaaagga cggtgttatt agtcctaact gagttggtgg attttttggca aaccaaagca   5040 cggtacacct gaacatcatg caaaattcta accaaaccta aggaaatctt gtggcaggac   5100
agacagtgtt aatccacatg ctaggaagta atggcaacaa ggttatgaca gcactgttaa   5160
atggaaaata tattatgagg aaaaaatgaa caaggactca caatatcgag attgatagtg   5220
tccaactagt aagaaaaact atagcaagtg atggcaacaa ggttacgata caactggcc   5280 tctctaattt atgttttttgt caacagggac cacaggtctc aaaataaatg tttaactaat   5340
tttggatcca ggactgtaga gcatatatat cagaagatac catacagtac aaatatgggc   5400
agctttaggt tttcgacaag taggctatgc aagttgagtg ttatcataca agatatagaa   5460
ttctgaaata tgaccaaacc gccaaaatgt tgcccatgat aatcttaagc caactgaatg   5520
tttagtaata aggcgtttct ttcactgtta ttgttctttc agagtagtaa aactacttag   5580
ggcttgtttg ggaccaagtg aaacaaagag aattgagggg gctataatcc cttgttattc   5640
aaaattgaat agcaag                                                   5656

<210> SEQ ID NO 337
<211> LENGTH: 144
```

<212> TYPE: DNA
<213> ORGANISM: Zea mays

<400> SEQUENCE: 337

```
acgacagtag tctgatctga tctgagagag tagtaaaaaa agaggagaaa gtaaacaacg      60
gcgctcgacg atagatttta cttacatgca tgcatgcatg catggtccta ctagcagcta     120
gctagctaat ggcagcatgc attg                                            144
```

<210> SEQ ID NO 338
<211> LENGTH: 71
<212> TYPE: DNA
<213> ORGANISM: Zea mays

<400> SEQUENCE: 338

```
atcctgctcc tgcatcgaga gactttcgct gcagattcca tctgtgctca tcacatgaca      60
gtggatcagg c                                                           71
```

<210> SEQ ID NO 339
<211> LENGTH: 2885
<212> TYPE: DNA
<213> ORGANISM: Zea mays

<400> SEQUENCE: 339

```
catggaccat gccctagct tagctaggcc acccacacac aaactaccaa acaaaaactt       60
aacaacctat ccctctctct gcactagctt tcgtattttt gtttttctga tgggagatgt     120
gtgagtacca acaaaacgt tgacaggcta gtaggccagg agagatacac ctagaagcta      180
gtccctttag ctagctctcc gctcgtgtgc atcatatatt cagatatata gatagatgca     240
tggccgtagt gtggttgttg tgcgctgcat cgatcgtctg atgaaaacgt tggttgccgc     300
ctattttggg aagcaacaaa aatccgtgtg ccgcgcgcag acgactgcag agtcgacaca     360
tatattatac gcgcgcgcac gtacgggact agcagctgcc agctagggag agtagtatgt     420
agtcagagat acacgaacga agacgaagaa gacgacgacg acctaccttg agcgccttcc     480
agtaggccgt gcccgggaag ttgagcggcg ctgacacgac gcccttcatg aaggtgatgt     540
actccagccg cagccgctcc gtctcctcct cgccggggtc catgctcatt atgttcttcg     600
ccatcaggtt aaacgtgaac tgcactcgtc atccggccgg ccgcgcgccc atcaccggtt     660
gttatcccgg ccggggcacc ggttgttagc ggcgatcctt tgcatagatt cagccacata     720
tatagataga actgatctga tgtggcacgt acgtactacg cgtggagaca aattgaaggg     780
tcagaagaag gatggtgatg agtaccgtac cttcttggct tcgtgctggg cggagaaggt     840
gccgtcggag ggcggccacg agcggaggac cagcagggtg tggcgctcca cctcggggag     900
cagcacggcg cggaggcgga cggagctgag gaagttgagc gagatagcgc gcatctcgcg     960
gtgcgcgtcg cccacgagca ccagcatgga ccacttgccc aggatgccgc cgatgctgcg    1020
cgggtagctg cactcgaaca gccgcccctc gttctgcagg atgtagcggt tcagccccgc    1080
gtccgccgac accaccgtcc gctccccgaa caggctcgac cggtatatct tcccgtacct    1140
gcatgcacgc atggacgtcg ccgcgttagc aagcaagctc tcggtctcag agctaattct    1200
gattccatcg atgtcgcgcc atgcatgata ggtgcgcgct gctcgctgca ccgtgcatgc    1260
atgtcgtctg ctgtctgcac agaggtagag acagcggcgg cggcgacgca ccgtgcgaca    1320
tgccgctcca tgaagcggcc cacgaggtg gccgggtggg gcggaggta gccgaaagtt      1380
tcgccgacca agggccatcc gcgggcgccc gggggcaggt tgggccgctt cttcttctga    1440
```

```
cggcgccacg ggtgggtgcc gtggcatttg gcgacggtgg tggtgtacaa ggcgaggagg    1500
gccagcagga tgaagggaag gaagaagagg agctcgctgg ttatggaggc catcatggcg    1560
cccatgagct cctgctgatc agaggtctag ctttcttcaa atttatttcc tgcctgctgc    1620
ctctgcctga tcactcgccc gcttcgttgg ttttttatgtg tggagagaga ggacggatgg    1680
gttggagaga gaaagcagga gagggaatga atgaagcgcc tttatctctg gatttctctc    1740
tccctctctc tcagcaagtg caagctttgc gcaaggaaaa aaaaaactag taagaagcta    1800
ggcgccccac ttcgtccccc cttctgagct ctgtggtgct cttataggtt ttttcagagg    1860
tagctgtggg gtcctttaat ttaggtccta ttccaaactt ctaaaactaa caatttctaa    1920
caactaaaat ttatgagagg tatataacag gtccactaat ggaccggtta attgtgagct    1980
atattcttaa atagttatta ctagttgtta gctacctcca ctcagttaaa accgtaccag    2040
ctaatatgtg gtgctaacca aattgctctt ggtcgtttct acttattagc taatggttaa    2100
ctagcaaatt tagctatcaa cttattagtc aattaataat tagctctaga aatttaaaac    2160
aaaaacttag gctatgtttg attgcgctag agctaataat tagctgacga catctaaata    2220
gtctatctaa tagctaaact attatctagt tttagcaaat tagctaatag ttagctagct    2280
atttgttagc caactaattt cactatattt tttagcaaac taactattag ctatagtgca    2340
tttaaatgag ctttaataaa aaaattaatt ttagtcgaca caaggagtag gttagggtca    2400
ttcattaaaa catccaatgt ttagtatgta tcatataaga tgtttgaatg actattacga    2460
gtattaaata tagttaaatt ataaaactaa atacatagta ggtttattag attcatatta    2520
caccgtttag tgcatatctg catatctgta taattaattt taaaattaga ttttatttaa    2580
tacttataac taacatcaac atttgatttg atatagatta aaaattagga acgtgccacg    2640
cacgatttgg ctcgtcgaca gtcagcatcc aacccgatgg ggcgatggtt gctgcaggtt    2700
gagaatcatt gctcgagcca atcaaatatg ctggtcaggt tgaatctgtt aacagcttat    2760
aatcaggtac ggtgtaataa aaatacaaga aagcttagtt cacagaattt gctttggacc    2820
acccattatc tctaagttta ctccttatat atataccatc aaaaaataag tttgcttgcc    2880
tatat                                                              2885

<210> SEQ ID NO 340
<211> LENGTH: 133
<212> TYPE: DNA
<213> ORGANISM: Zea mays

<400> SEQUENCE: 340
gctgcttggc gcgttgttgc tctgcagcta gcaacagcag cggcagcaaa aaatattaaa     60
cacatgcgat gcgagagagc gcatgatcga tgagagaata taatagataa tccttgagga    120
gaaaaggagc gcg                                                      133

<210> SEQ ID NO 341
<211> LENGTH: 118
<212> TYPE: DNA
<213> ORGANISM: Zea mays

<400> SEQUENCE: 341
gagaaaagga gcgcgctttc gacgggctca tcgtctcatc agtgatcagt agtggaaaga     60
ggtcgatagc cactgacatg tgacattcac agcgatgccg atcgcctgaa cctagtac      118

<210> SEQ ID NO 342
<211> LENGTH: 6147
```

<212> TYPE: DNA
<213> ORGANISM: Zea mays

<400> SEQUENCE: 342

```
gaacggccgc ctcaagacgc tggacgtcac cagtaaccac ctcaccggca ccataccgcc      60
ggacctctgc gccggacgga acctgcagct gctcgtgctc atggacaacg gcttcttcgg     120
cagcatcccc gagtcgctcg gcgactgcaa gacgctcacg cgcgtccgcc tcggcaagaa     180
cttcctgacc ggccccgtcc cggccgggct cttcgacctt ccccaggcga acatgctcga     240
gctcaccgac aacatgctca ccggcgagct cccggacgtg atcgctggag acaagatcgg     300
catgctcatg ctggggaaca atcgcatcgg agggcgcatc cccgccgcta tcggcaacct     360
ccccgcgctg cagacgctgt ccctggagtc gaacaacttc tctggcccgc tgcctccgga     420
gatcggcagg ctcaggaacc tcaccaggct caacgccagc ggcaacgcgc tcacgggagg     480
catcccgagg gagctcatgg gctgcgcctc cctgggcgcc gtcgacctca gccggaacgg     540
cctcaccggc gagataccgg acaccgtgac gtcgctcaag atcctgtgca cgctcaacgt     600
gtcgaggaac aggctgtcgg gcgagctgcc ggcggcgatg ccaacatga cgagcctgac     660
gacgctggac gtgtcctaca accagctgtc gggccccgtg ccgatgcagg gccagttcct     720
ggtgttcaac gagagctcgt tcgtgggcaa cccggggctg tgcagcgcgt gcccccatc     780
gtccggcggc gcgcggtcgc ccttctcgct gcgccggtgg gactcgaaga agctgctggt     840
gtggctggtc gttctcctca ccctgctggt cctggcggtc ctgggcgcgc ggaaggcgca     900
cgaggcgtgg cgcgaggcgg cgcggcgcg tcgggggcc tggaagatga cggcgttcca     960
gaagctggac ttctcggcgg acgacgtggt ggagtgtctc aaggaggaca acatcatcgg    1020
caagggcggc gccgggatcg tgtaccacgg cgtgacccgc ggcggcgcgg agctggcgat    1080
caagcggctg gtggggagag ggtgcggcga ccacgaccgc gggttcaccg cagaggtcac    1140
cacgctgggc cgcatccggc accgcaacat cgtgcgcctg ctcggcttcg tctccaaccg    1200
ggaggccaac ctgctgctgt acgagtacat gcccaacggg tcgctaggcg agatgctgca    1260
cggcggcaag gggggccacc tcgggtggga ggcccgggcg cgcgttgcgg cggaggcggc    1320
gcgcgggctc tgctacctgc accacgactg cgcgccccgg atcatccacc gcgacgtcaa    1380
gtccaacaac atcctcctcg actccgcctt cgaggcgcac gtcgcggact ttggcctcgc    1440
caagttcctc ggcggcggcg cgccacgtc cgagtgcatg tctgccatcg ccggctccta    1500
cggctacatc gccccaggta acaaaactct cgccgcatag cagcataacc acgtgtttgt    1560
actccttta ataatatttt tttcactggc tcgcatgcag agtacgcgta cacccttcgc    1620
gtggacgaga agagtgacgt gtacagcttc ggcgtggtgc tgctggagct catcacgggg    1680
cggcgccccg tgggcagctt cggcgacggc gtggacatcg tgcactgggt gcgcaaggtg    1740
accgcggacg ccgccgccgc ggaggagccc gtcctgctgg tgcggaccg tcggctggcg    1800
ccggagccgg tgccgctgct ggcggacctc tacagggtgg ccatggcgtg cgtggaggag    1860
gccagcacgg cccggcccac catgcgcgag gtcgtgcaca tgctctccac ctccgccgcg    1920
gcccagcccg acgtccccca cgccttgtgc aaggtcgtcg attaatttgc cttatatatg    1980
acgattatgt atatgatccg ggcagggtta gcgcctgtga tctatttagc ggctgccttt    2040
ttggcgtcac tcgtctcgtg tgtgatgatg gctggatgga tgtgtaaaac aaataaccag    2100
caggtggcta ctcgtgaatg aaagttgccg gttcttattc tcatgcatat atattagcaa    2160
cacacaaagt gagatggcat atattcccttt tccctggcgt tgttgctttt gggttattcg    2220
```

```
tcttggcttc tcgcggaagg tctttctgct gttcttgaac gacaggatag tatagaggct    2280
tctatgagaa agatgcttca tgctgcgaaa gttgaaaatg gcagatgcac attgcgtatc    2340
cccacagggc aggacacttt gcgcatggcc tagtactaac acaatccatg gagcaaggaa    2400
cattactgcc cttggcctcc aagctgcttc cttaatcatc aaggatgaat taggaaaaaa    2460
aaggataaac ggaccgccat gaccagagcc agtgagggag ccacttcacc tgccgactgc    2520
aatcgacggc ccacccgtca gccagagaga acagtccac cgcggttgga ttggacgacg    2580
agatctcaac gtggggcggt ccgagccggg cgcacgcgca cacgcgcttc tcaactccca    2640
ccaatattac cctccatata tcaccgacag gtgggacatc aaccaagccg gtacccaaca    2700
acagcacaga aaacccaca ggtcatagac agcggagctc cctccagtct ccatccaata    2760
acacgagcta accaccgccc aaccgaaacc gggcccacc ggtctccccg tcgcacgta     2820 cgcggccgga gcgccctata caagcgccac gtcgatcgcc gactcgccgt cgccgcgtcc    2880
cccacggctc ttccttcatc ctccggcgag ctataaatcc ctcccgccga cgccacccc     2940 atggcatccc gcggttcccc ttcctcctac tcctcccga ggaccccgac gtcgtcgaag     3000
gctaaccctt ggcccgcgcc ctccgccccg ccgctgtacc cgacgctctc catggccgac    3060
ctcgcgcccg tcgagatagg gcccgcctcg tcgccgacgg cctcggatga ctacaacgcg    3120
cctccgccgt ctgaggacgt cctcctccgg gtccccggcg cgcggctcca cctcgtcgac    3180
cgcagccgca gccaccgct ggccgccggc gacctctccc tcctccgcat ccgctccggc     3240
gacacctccc tggccgccat cgcgctgctg ggcccggtcc agtggccgct cgcgcgcgac    3300
gtggccgccg tcaagctgga tccctgccac tacgccttct ccctcaccgt gccggcctcc    3360
gccgacgacc ccagccccga cccgctccac tacggcctca cgctctcccg ccccgatgtg    3420
cgcctcgacg gcgtcctcgc tgcctacacc agcttctccg tgcacgccgt ggtcggcgcc    3480
gggcagctgg aggccagggt gcgcgacgag gccgaggccg ccgcgtactg gacggccgtc    3540
gcgcccaacg tggaggcgta cggaggcgcg gtggccagga ccatcgccac gggcgccgag    3600
cacctcgcca aggggatact gtggtgcggg gaggtcacgg tggagaggct ccgttggggc    3660
aatgaggtcc tcaagaggag gatgcagcct ggcgacgcca acgccgaggt cagccccgag    3720
atgctcaggc gaatcaaaag gtattggccg tttccgctat ttctcttttt gttcctagta    3780
atatacattg gaaataaaaa ttactaaggt cggttattct aatgatatgt ggattgaagt    3840
gtattagaat gaagatttaa atcgactcaa taccactcaa tgcacatgta ttaacggtga    3900
aacaaacaag tcttagtctt atttggttat tatcaattca tgtggattgg tagagattgg    3960
caatttgtga tagattatga tagattttga cttgttatgg atttaaaccg actcaatgtc    4020
atccaatcta catggattgc cgtctaaaca aacatgccct gaagatgtaa tctactaatg    4080
tttgcttcat acaacattca gttatggtgt tgtgccttga ctctttgttt ttgccaattg    4140
ccatctagaa gagctgaagg ggctccctat ttctaaaaca tttctttagc gatgtccact    4200
gatattgaca gaggagtatg cactctgtga tcgatttcag agatggactg aactggattg    4260
gactgatgcc atgccacata gccatagata tatgcagatg tcaacttata atgagactgt    4320
tcgctgaggt ctgaggcgtc gttttctgaa cttgtgattg cttggctgag tagtatatgt    4380
ttggtgttaa gagattgttc agatgtctat gctaccatag cctgatatat gtcttcgtaa    4440
cctttttgtg tctgtgtgtg gacatttctg ttgccaataa catcgcattg tttctgcctc    4500
tagacgtcga atttacgtat ggtttgcctg actgttgatga ctcattttt gcctgactgt    4560 attgactcat ttttgggtat attggtttta cgtttttttg gtaatacaca agctttaaac    4620
```

-continued

```
tactatttaa acgattttgg acatagatag gtttggcata ttctgtgtga gtctgagata    4680
taggaaattc aggcaaatat ctgagttgct taacaacgtc cttgcttacg gttgctggca    4740
gggctaagag ggtgagccaa atatctgaga aagtggcgac tgggattttg tccggagtgg    4800
tgaaggtcac tggttacttc acaagctctc tggccaactc gaaagctggc aagaagttct    4860
tcaacatgtt gcctggagag atcgttcttg cttcgcttga cggatttggt acgttgctgt    4920
tactaacact tgtatcgtat aaggccaagt gcccgtgtgg cattactcgt ctgtcatttc    4980
actctagcgg cattgttaga tataatatta attgagatgt gcccctctgc cagccttgca    5040
taagtcaaca gacaactgtc tgtctgtgta tgttgtagta gtttctgtgt taatagagat    5100
gccttggatg ccctttatag agtctcgtat tgttttttgt tttattgaga tgataacttc    5160
tgtagttgtg gctttacgag gaaatttaga tagtgtttgg ttccggagcc actcgaggta    5220
gaatggttcc gtcccgagag cggctccgtc ctggagattt tgaggagtca gatgatttaa    5280
caattgagca tgacttttcca tttttagaat cactccattc tatatatgaa atcaatccaa    5340
acaacagtaa attaagagcg gagcgacctg ttggtttcag tacagccaca acaaaagtgc    5400
tgatgatcta tataagtcaa gtcaagtcgt caaagatttc tgaacatttg cgacttccat    5460
tccaccccat gctctgtgaa taggtggctg aatgctttgc actctgcttg ccaccgtggt    5520
ttatgcaccc aacttacgct gacatgtatg tcttccttcg ttgtcgccga cgccataaac    5580
agggaagatc tgcgacgccg tggaggtggc cggaaagaac gttttgtcca cgtcgtcaac    5640
tgtgacgacc gggctagtat ctcacaggta cggagacaaa gccgccgccg caacgaacga    5700
agggctggac gccgccgggc acgccatcgg gacggcatgg gccgtgttca agatccggca    5760
ggccttgaac cccaagagcg tcctcaaacc cacggcgctg gccacgtcca ccatcagggc    5820
caacgttgcc gagcttcgcg cgatgcacgg cagcagcaag tagctcgcgc ctgccgtccc    5880
tgtttcgtaa aaactctatt atctcgctct gtcacgacca acgatgcact cgctgcttcc    5940
agcagcagcg ttggctgttg cctgttggcc tgtaaattcg tgtggctgaa actgggaaag    6000
ccgggaactg aaaggcttac cgcttccgct ttgttagtga tgctggtgat gttctaagag    6060
cttttaccac tgctgtgctg ctgcgttggc ttgaactgtc acgagttgtt cggttttggc    6120
ctctgaagtc tgaaccaagt aaaaaaa                                        6147
```

<210> SEQ ID NO 343
<211> LENGTH: 101
<212> TYPE: DNA
<213> ORGANISM: Zea mays

<400> SEQUENCE: 343

```
tgtctcaagg aggacaacat catcggcaag ggcggcgccg ggatcgtgta ccacggcgtg      60
acccgcggcg gcgcggagct ggcgatcaag cggctggtgg g                        101
```

<210> SEQ ID NO 344
<211> LENGTH: 122
<212> TYPE: DNA
<213> ORGANISM: Zea mays

<400> SEQUENCE: 344

```
ccggccgggc tcttcgacct tccccaggcg aacatgctcg agctcaccga caacatgctc      60
accggcgagc tcccggacgt gatcgctgga gacaagatcg gcatgctcat gctggggaac     120
aa                                                                    122
```

<210> SEQ ID NO 345
<211> LENGTH: 96
<212> TYPE: DNA
<213> ORGANISM: Zea mays

<400> SEQUENCE: 345

| | | | | | |
|---|---|---|---|---|---|
| gacaagatcg | gcatgctcat | gctggggaac | aatcgcatcg | gagggcgcat | ccccgccgct | 60 |
| atcggcaacc | tccccgcgct | gcagacgctg | tccctg | | | 96 |

<210> SEQ ID NO 346
<211> LENGTH: 8507
<212> TYPE: DNA
<213> ORGANISM: Zea mays

<400> SEQUENCE: 346

| | | | | | |
|---|---|---|---|---|---|
| accaaacacc | cccttagtct | atataagcaa | ccaaacaaat | gtcttatatg | agctcaatcc | 60 |
| ggtgctactt | actcatcatg | gctggcctcg | gacaacctgg | cagcgctggc | aaccaaccag | 120 |
| acgtgtcatc | atgcctacac | catcgtctca | tataaagaca | gggcaaggca | tacggtgcga | 180 |
| agatatggaa | gaagatgagg | ggcatgtttc | atttgctgcg | tccgagttta | ttatttacaa | 240 |
| gatgcaccaa | caatccccaa | gccaagagtt | gccgcggctt | tgctcgccca | gcttattgca | 300 |
| ctgttcgcac | tactccacta | gatacatata | ttaataacat | cggaagagct | agctactgga | 360 |
| accgatgcga | ccgcaccaaa | ccatttctcg | tcgtccatgg | caacatccgg | caccaccagc | 420 |
| ccttcttcct | catgttcttg | tccctccgac | ggctcaagtc | aaggtcgggc | gcgcgcctca | 480 |
| aactaagtct | caactctcaa | gacgatgact | aacctgtaac | cttgcacgcc | atgcgtaagg | 540 |
| ccaaagttag | tctctatatg | acggtgccgt | ccttgatggt | tgcgttcttc | aggactacca | 600 |
| cgatcccaga | ccgatgtag | tatccttcgt | ccggccggtc | ggcttcttgg | acgccctggc | 660 |
| agagaacaca | cgatgcaagt | agagtcaatt | aggagcggtg | ttcttggtgg | tggtcatttc | 720 |
| ttcttttggg | agatagaaat | atttcggctc | ctcagaaact | taatatgttc | ctcccccact | 780 |
| tgctcacctc | tttgtttgtt | atggagacgt | tccttccaac | cctggcattc | atgtcgatga | 840 |
| tgcagttgct | gcaacgcatc | aatagaaggg | cttattaaac | catcgtgtta | tgacacacaa | 900 |
| tacttttctt | ttttgttcct | tcttccatca | aggttcaagc | caagcgctca | ccttatcttc | 960 |
| gtgttctccc | ctacgccaat | gggcaccttg | ccctctgcca | gtagccttga | gatctcgtct | 1020 |
| tcggtctcat | acaaatccgc | acccatcatc | atggtattct | gcaaagcacc | gttcgcgtca | 1080 |
| gtgtctgcgg | gcgctcaata | cagatacaag | actgagcagt | catcgacgat | gaacaagcaa | 1140 |
| gcgaaccttg | agctcgcatc | cagagtttag | gcgtgagcga | acaccaacaa | tagagtgctc | 1200 |
| gatggcacac | tcacgcaaga | agcagccgtg | tgaaatgatc | gcgtctttaa | tctgcacacg | 1260 |
| ttgaatccaa | aggtcaaata | ggcacaagct | catactacag | tttacaggtc | acaggcacca | 1320 |
| ttcattccat | gcataggaag | cgcgtaccct | gcacttatcc | gacttcgttg | gtggcaagta | 1380 |
| ccgagggaa | gtgaagaatg | gtgttttcgg | atcgtaaaac | tcgaactttg | gaggctgcga | 1440 |
| cggggcatac | gagatgaaaa | ctgtattagt | ctggatggaa | atctatcatt | tcaagatatt | 1500 |
| ttcagtctaa | atgcactgga | cagttaagag | cacattagac | cttggaaaga | gaaacagaa | 1560 |
| tatacctgct | cgcagagggc | catgtttgca | tcaaagaaag | atctgattgt | tccaatgtcc | 1620 |
| tcccagtagt | cagtgaaaac | atatgcctga | caaacgaagt | cacatgaact | gcctgtgcat | 1680 |
| ttggtgcgat | actgctctac | cctaatagag | attggactcg | tgcaaagctg | actgggcccg | 1740 |
| tgatttaccg | aataatggaa | gtgaatcaca | aaggaaactg | ttttacctgt | acattgtgct | 1800 |

```
catgcaaagc cttgggcaga atttcagaac caaagtcatg cagttcagca taccgtgacc    1860
tataagaatg ctccagttag aatgcagact atggggaact gtatggacca caagaaaaa    1920
aaaactctta ctttagaagg tctaacaaaa catctctctt aaaaacgtaa actcccattg    1980
aagcgatata gggatattca gctggggaat caatggcgaa attgaggaag ctggtatcca    2040
ctttctgcaa caagcagaag caacaacgta catttcagat agtgctagtt ttgtaaagta    2100
agttattctt ggaaggttcc aatatatatc tgagtccctg aggtaagatg atggctaacc    2160
atttcttcca aggcagcacc ctttggtttc tcagagaact gaattacacg gcctgaacta    2220
tcgaacttaa ctaatccata gtcagatgct cgacttccaa aacaaagaaa aaatcagcat    2280
gtgcaccggt tttctgatga caagtgctga aaaaaatca gaaacctgat gtaatgacat    2340
acctctctcc aacaggagcg catgataaag ttatgtctgc attgtcatcg acatgtttct    2400
gaaaatagta gatgtcaggg catcatcaga cagttaaact aagaacata tacacataca    2460
atacaatata caggagcgga tcaccaacct gcacaagctc catgtaatcc atacgataga    2520
gttgatctcc tgacaaaatc aaaatgtgtt ctatagcttt atgcttgtaa taatcctgaa    2580
aaagtacaca caacataaga tgcattgttc caggaatcaa aataagtcag caacatgta    2640
ccatcagcca ctagacataa ttattacctc aagtacccag ataaattttc taacggcgtc    2700
tgctgtgccc tggaaccaac cagcagcctc cccaggcatt tgtgttgcag ccagcaccta    2760
tttgttgcca aatttatatc agtaaatgca tgttctacgc tttaatgaga taagaaatt    2820
taaccaagct ccgagatggg aatcgtgaga ataatatttg caagctctct gagtaaagca    2880
atcaaacttg aggtgactta cctcaacaga tccatcagtg aagttgatcc ccccaccaag    2940
ataggtacga tgaatgtgac ggttaagaga agctgagttg aactgagtca taacaaatat    3000
cttgtttatg ccactgttga aacagttgct catggggata tcaataagcc tgtaacatcc    3060
tccaatagga acctaagtaa tgcaacaaaa ggaaagaaac aagattcaga ccactgattc    3120
aatgcaacaa aaggatggag atggacaaag tagtggaagg catcatgtgc ggtgggccc    3180
tgctaataat taataattaa taatttaaac atacggaaac ctcgctactg caggaattat    3240
ggtttaacta cctttataca aatcaattac catgtgaata tttctagcaa agccacagac    3300
ttttggtgcc ttctgcagta gaggtgtatc tacttgaaat aaaataaagc tggagattgc    3360
tagagatctc tagatcctgt ctacttaata agaccgaaga tgattattaa atcggtactt    3420
cttgcaacat gaagccaata aagtcaaagt gtgccatctt acagcagggg tggcccttgt    3480
gcttgtgaga gggaaaagct gagtcccggt accaccaccc aaaatgacgg cagcgacttc    3540
attaggatca gcataattcc tccgaaagga tgttcggacg acctgtaagt ttttgcatcc    3600
agaaattgat aattatagca gctaacatca agtcaaataa aaaatacaa agggctgtga    3660
tgaaacaccg acactattat cgacaggatg agacttacaa gagtgtctgg gccagcatct    3720
gatgtgagca cacactgcgt gctgctcaca gcacccttg cactgaaaca catcctcctc    3780
agtgccttgt tgcgcctgat gctgcagcag ttgatcctca tcctctcact cccataacct    3840
ccactgcctc tcctcactgg gctcatacac gcttttccct ctagggaag cacgctgctg    3900
aactgcatag ctgaagcaca cctgcacgat cacaaccatt aaccaccagg cagtcctgga    3960
aatctatttc actatgtact gaatcaagat gcagggcaag actatataaa aaaactgatt    4020
ttcttgccta gttcctgaca aatccccgca tcaatcaagg gaaagggag ccatactttt    4080
gcggaatcct tactgccgta aggagggatc atcaacgtac tcgcggaata acggactgga    4140
```

```
taataaagga ttaaagggtg gtggtgcaat ggtgtacaca acacaaggg agatttcgaa      4200 agcgaaggat ggaagcacac atcagactga ggaaagctat aaaaaggacc ttctgccttc      4260
ttttcgggag ttagacatgt gaatcacaac agctcagtcc cagttgggtt ggatcttttc      4320
ttccttgtac actctgaacc catatagaag caaagtgtac taggaaaact ttgcgataga      4380
aaattactcc acgatccaag gatgaaaagc aaccaggaga agaacatgag gttgaataac      4440
gaatagtcac aaccccaaat tagcaacccg gcccacctaa aatcaagtgc agctaaccaa      4500
aacgtatgca ggacagattc ataccagaaa tgggaggaga ttgcagaaag tgctcggaat      4560
caagtggaag cgtggagcca ctcgacgcga ggaggggggg aaaaggcagc acttttggag      4620
ttgtttaagg acaacaatga tgaaacgggg atgtccacaa gtcaaataca agtaataaaa      4680
ccaagagcgc aggatccaag aacgaaacgg aggacccatt tttgttgttg ggttgggaga      4740
cgaacacacg aaaagagaat aagagatagg tcgaagaaca cgtcgacttc ccgttccacc      4800
cgcgaggacc aagagacgta ctacaaccgt ctcgggaacg gcaaccaaga acgaaatctt      4860
gcggagagcc ggagactgta taagaactca aagtactatt tgctgcacca tcaattcagg      4920
caaaatataa ctggaaacag aaaaaaaatc gagagaaatc catgcaggag caggattacg      4980
atcctagccg acgtctccgt gctctggaga gtttgtaacg gatctccccc tcctccctcg      5040
cctcgcccga gggctgagcc cttattcacg gccacacact acccggcacc cacccacctg      5100
atccaccgcc cctcctgccg ccggcgccaa actcctacac aggtcacatg cacaactaat      5160
aacatcgcgc gcatacaccc gcggcaaaac ccaacgaacg aaggaaatgt tccagggaac      5220
cgaacgcgcg cccgcagcag cagcattcgc tgaggggcag cgtcgcaggc agaacgcgtc      5280
catcggaccg cccatgcgtt ccaggaacga cgagcgcacc cgggcgccgc tcagtcagag      5340
gcctctctcg ccttggacgc agaaatgcgg agacgacgcg caggcagcaa tcgacggcac      5400
gccaacgaag gagacaagag taacgaagat ggatgggttg gattacctag ggacggatgg      5460
atcgattgcg ctgggagccg gagcgatgcg atggacgaga gagaatgggt ggccgcgacg      5520
gtgcgagacg gtggcgatgt ggcgcgggcg gcggcctata aagcggggcg aggccgttgc      5580 gttgaatgg agtggagtgg ggaggaggaa ggcgagcgag gcaaatggaa atgagaatgg      5640
gaatggacgg acgaacggtg gagaaggcgt ggccgcggcc tcgcttggcg ctactacgcc      5700
gcgtgtgccc tgctccccgt gccgcgcctg cgcttgccca tgtggggag gagcccggcg      5760 cacggtaaac aaccacgagt gtaagagtaa cagacgccac tctatctcct ccttccaccg      5820
cgccaccgct cgccggtcgg tcccgtccgt ttctgtgttt tcccggatca aaacgcctcg      5880
tcgtcgcttg cattattggc tccatctgac gtgacgtgac ttgagatgga gattttttt       5940 tgccctcctc cttaaggaga aagaaaaaag gaaatatttt ttggcggttt cattgacaac      6000
aaaacggaaa atgaaaataa aaaatggctg tggccactcc ttagaatgcc gtgtcatctt      6060
tttaaagtct tggagcgctg cactgaaata caattttgac ggcttacgaa tgaaatggag      6120
ccaagtgcaa tccatagtga atgggaaacc gatcctaaaa caagaagcct aaaacgagct      6180
caaacgacag ctgagatgga gggtgagagg agtcttccgc caaaacatga gcatccaacg      6240
gctgcgaggg aaaatcatcg tcgaacggac ggttctaaat catccactag cagtagctag      6300
cacggtggag gagcggacaa aactgtgcag tgttccctcc cctgggccct ggccgcaaga      6360
gcaagtggcc cgtgcctgta acaattctcc cgtgggatgt caggcagagg catgcatagg      6420
ccgtaggagt gtggcctgtg gcctgtggga gtgggacaca cagccggggc aactgacggt      6480
tggaatcgcg cgccacggca gcgaacgtac ctgctccgca cgtcatgggc cccgcgccga      6540
```

```
ggatcttttg gtcgtcctcg ccacgcgcgg gcccacgtgg cgggcggatc tgcgccgggt    6600
gatcggacct cttgtccggg cccgggcgtc ctccctcctg cgtggtgggg tgggccatag    6660
acggacctct ccggcctgtc ctgtcccccg cgcgtcacac gtcagagcct gccactggcc    6720
actgctgggc ctggactctt ccttgaatgt ctcgaggaaa gggaatcaag tctggcccat    6780
gtaaaaggtg tgcatgccgc tgccatccaa caagctgtgt gttgcacgtg ccgatcccag    6840
tactatgtac tagcagcgac agcggcagcc agcagcgtcg tttaggcttt ggccgtggtt    6900
ggctgggaat tgggattatt tttggtaata gcatgtcatc actggctcct tttttttttc    6960
ttttagccat tagattgatg acgatgagcg cgggcggcca gggccggatt gaagccgagc    7020
tttacggagc acgggtcatg gatggctcca gatcaacagg tgctacggac cgtcgatggg    7080
gatctggcac ccggctaccc gcttaatttt gtccgcttgc gtcattaaac gcccatctcg    7140
tcgtgcaaag caaaccaatc gcttgacgac gcacggatcc gacgtcgccg tgggcccgga    7200
tcggacctcc gtccgcaact cacgcagcct tgcaaacctg cccgctcgct gggtgctggc    7260
cgctccagag tccagacccc atcaatcatg atacacagcg gtgtgggtgc gcgggcatcg    7320
ccgtcccgtc cggactcggg agcgacccca tgcgcgcgtg gcacccgcag cccgcgcacc    7380
acgtggtgtc tgctctgctc tctctgctgc tactgtggcc tgtgggtcgg gtacgtactg    7440
tactgtacgt tgccgcgacg cgaccgcctc ggtccgaccg tcgtctggtt ggttcgatgg    7500
cgtctccttt tcctgctgct acgactatgc tcgcgcggcc ggccgccggt gcgacgctgc    7560
gtgtccgatc gaggcatggc cgcagcgttc ggcctgatgt ttgtttattt agggcgcaaa    7620
acaaactagc tactgacacc ttacaggcca gcttggactg gcatggggggc agcacgacag    7680 cacaccagga ggcgaggcag gcagagaatg agaatgccac ttcccttctc ctcctgcagg    7740
ctgcagcata ccgataagat aaaataaaac tagggtctag gatctgttgt tattaagtcc    7800
tgttttctaa gcactctcct agttacttgt gctagttaat tatagtcatt aaagaccttg    7860
agcagctcaa caggtgtgtg cggctgccaa ggctcctatc tgattagcta agctctaatg    7920
agctgttatg taatcaatgt gactcatctc atctttctat ataatcaagc aatgatggct    7980
gaggttagta cctccggcaa aaccactctg tttacctcta acatttggta ccagagctta    8040
ggttagacac ctgagagtct caaggccgac tcctctcttc tctactcatg tcgacctctg    8100
ctgagcgcgc tgccaggctc aaggccaagg gaaccagcga aggagagctg ggcgacttct    8160
ccagccgggc tgcacgcctg aaggctgcag aggaagcagc ggcgctggca gtccaggcag    8220
cgaagcaggc agcggctgca gcagaggcag cggcaaggac ggcgcaggag ctgcgggccg    8280
aaatcgccgc cgagaaggga gaagatgagg aggactggga ggaggaagag gaaacagaga    8340
ggaacagacg gatgaggact ccaccgcgag ataggaggcg ctcgcagtca ccactgcggg    8400
accgaaggcg ctgccgtggc ggcgctcgct acgagtcgcc gcaaggaagg gtggtgtacc    8460
gcgactccgg cagcggcacg tcatggccaa tgctggacaa gacgaac           8507

<210> SEQ ID NO 347
<211> LENGTH: 107
<212> TYPE: DNA
<213> ORGANISM: Zea mays

<400> SEQUENCE: 347
aggctttggc cgtggttggc tgggaattgg gattattttt ggtaatagca tgtcatcact      60
ggctcctttt tttttctttt agccattag attgatgacg atgagcg                    107
```

<210> SEQ ID NO 348
<211> LENGTH: 163
<212> TYPE: DNA
<213> ORGANISM: Zea mays

<400> SEQUENCE: 348

| | | | | | |
|---|---|---|---|---|---|
| ttggcggttt | cattgacaac | aaaacggaaa | atgaaaataa | aaaatggctg | tggccactcc | 60 |
| ttagaatgcc | gtgtcatctt | tttaaagtct | tggagcgctg | cactgaaata | caattttgac | 120 |
| ggcttacgaa | tgaaatggag | ccaagtgcaa | tccatagtga | atg | | 163 |

<210> SEQ ID NO 349
<211> LENGTH: 2700
<212> TYPE: DNA
<213> ORGANISM: Zea mays

<400> SEQUENCE: 349

| | | | | | |
|---|---|---|---|---|---|
| aggagcatgg | agttgataaa | cacttacatt | atcaaagaca | cttggaagaa | ggtgcattat | 60 |
| attcgattgt | gtagtgctaa | ccggaaactg | gcatatgaca | caaacttttc | tgctatctgg | 120 |
| catagtgcga | tgcatgtaca | ataagtcatt | atagaggcac | tttaattttg | gacgacttg | 180 |
| tctaaatgca | tagacaaaaa | tgcacatatt | ttaacacaga | gggtattgat | gtcctttatt | 240 |
| ctagtcgaca | tggaaattct | aggagatcag | atcaaaatgt | ttttggacca | tactctattt | 300 |
| ctatttgatt | tttaactaaa | attaattaag | gtatcaaaca | aatcatgaaa | aaccaattg | 360 |
| aatcgtacgt | gatccattac | catccctacc | tacacccgag | atattttgaa | cgtgtcacaa | 420 |
| gaaaatttcc | agatgtttag | tttcacaact | agattaaatg | tgtttgtaag | aatcaggtga | 480 |
| aatatttctt | atccacatcg | attttttttag | ccaaactaat | tccaactaac | aattcacca | 540 |
| atttgaagta | tctatgtaga | aaaacaaaat | ggcttacaat | ttgaagtaaa | gatagtattt | 600 |
| atgaagagta | tagaggaaaa | ggtgtggcaa | agtagatttt | cacgagggta | taatatagca | 660 |
| aaattggttg | ttgtttacta | catcgatcga | tcaatccaca | tagtagtatg | gattccattc | 720 |
| cacgtgaact | tcgaaattct | atatttgttg | ttcaaatgct | acatcttctg | acgtacactt | 780 |
| ttcgtcttaa | attataagtc | acgctgtagt | ttttttttaga | gtcgaagtat | cttaagcttg | 840 |
| accaagtttg | tacaataaaa | taacaatatt | tataatatca | aataaatatt | gttatatttg | 900 |
| gtagtatatg | atgttacaat | tctttagttt | ttatacaatt | ttaattaaat | ttaagcttg | 960 |
| ttgatttttt | ttcaaatatt | gaaatgccct | gtaatccgga | acaaaggaag | tagcaagaat | 1020 |
| gtgattgtca | gctagcacat | gcatagtgta | ctcccatcag | cccacgaaag | actatagtag | 1080 |
| tcaagaaaaa | aaaagattcc | aatgtgggta | gcagtaagaa | cacacatctg | aattaaagta | 1140 |
| ctagttgctg | ctagctggct | atattttgcc | agtaattgat | agcttgattt | atgtacatat | 1200 |
| gattaagagg | gcgcacatag | aaatcagcaa | ttcagcacag | caatgacacg | ctacgatgag | 1260 |
| tagctagcta | gaattaatct | gccgacgacg | atggcatacc | ataccatcga | ttacatcagt | 1320 |
| ccatacaggc | taaaccactc | gaccacgctg | ctgtcagcgt | aggcatagtc | aggaacatag | 1380 |
| agcaggtcgt | cgtcccccag | gtgatcgccg | ccgccgccgc | ctcctccggg | ctgctggcag | 1440 |
| gtgccagtcg | agaacgatga | gctcgggctc | ccgctgcaga | cggcacgggc | catgacgtct | 1500 |
| ccgccgtcac | cggagaccgc | gtcattgccc | gcggatctga | atcgtgtcag | ctcctcctcg | 1560 |
| gcgagcacca | gcttgtcctt | cagcctcgtc | accttccagc | cgggcatgtg | cccacgaaag | 1620 |
| gcatgctcaa | tattatatat | gtactgcatc | gccgtaaatt | attcatggcg | catggggatg | 1680 |
| aacagagaag | aggattggag | cacaggcaaa | gagtgagagg | taggatgcat | gtccttcttt | 1740 |

```
ccaggttgcc atttgggaga aggggggcgtt ggtgccttgc tgaacctggc cgacttcttc    1800
ctcgagcagc tttctcttgg gcggggcgcg gcgtttcggg acccagacgg cgacctgctg    1860
ggggtcgagc ccgatctcgg cgcccaggtg caccttccgg ccggtctcca gcttccgctc    1920
ctcccggaag ctcagctcca gcatctctac ctgctcgtcg gtcagccgcc gcttcttgtg    1980
gtcccctcct ccgtccagct cgccaccgcc gccgccgcac ctcgctgctc gacgcctcct    2040
gcgccgcgct ctcggtctct cctcctgcgc agtgcctgca aaccgcacag aatacacatc    2100
aattgccatt catgtagcag gtgcatgtcc tgcaggtagc gggtaggccg gtactgatga    2160
tgagctgcgc agttgcagag acgaagtacc tacagctaca caactgtgag aaagagaatg    2220
tacgactact gcgcaccgtt ggcgttgggc accaggagga gggatgagga ggagtccacg    2280
taggcgggag gaaagagccc gtcgtattgt tccatccttc gcctgcgctc ccggccgggc    2340
gggcgcggat cagctgctgc aacgcctttc tctctccttg tcaagcgtga ccactgtgtc    2400
aggttatctg gagaggacca gggatagaga aagagagagg gaggctgctg gggagaggac    2460
caaggacaga gaaagagagg gaggctgggg agaggagacg tgctgtgcga ggaggagctg    2520
caggaggagt ggatcaagga gcgaggacca cagggcaagg caccagctgg ggtgttaagt    2580
aagctggggt gcgggtctcg agagagacct aggagtaata tatagggcta gcaaaggcgc    2640
gcaacgccgg aggcggtggg gttcgccggc cggctggccg gccgggtcgg ggggtggtgc    2700
```

<210> SEQ ID NO 350
<211> LENGTH: 72
<212> TYPE: DNA
<213> ORGANISM: Zea mays

<400> SEQUENCE: 350

```
gagaagagga ttggagcaca ggcaaagagt gagaggtagg atgcatgtcc ttcttttccag     60 gttgccattt gt                                                          72
```

<210> SEQ ID NO 351
<211> LENGTH: 92
<212> TYPE: DNA
<213> ORGANISM: Zea mays

<400> SEQUENCE: 351

```
gcccacgaaa ggcatgctca atattatata tgtactgcat cgccgtaaat tattcatggc     60
gcatggggat gaacagagaa gaggattgga gc                                    92
```

<210> SEQ ID NO 352
<211> LENGTH: 8309
<212> TYPE: DNA
<213> ORGANISM: Zea mays

<400> SEQUENCE: 352

```
taatcatccg ataaatatga gttgagggat tgaatattga tccttgttat gttatttgga     60
acgattcaga cttgtgaaca acttatgtta ctcaaagttc tattatgaat tcataaatat    120
ggtgtgcatg atttatgtga tgtgttgtga attgaattat gtgtgtgtat gagacgtggg    180
caaatatatg tatttgtgaa tgtatggaat atggttgaat atgtatgcgt tataattgag    240
ctagattgac taatttggtt ggatatgtat gtgtatggga tatagttgaa tatgtgtgtg    300
tatgggatgt ggataaatac atgtatttgt gaatttatgt gatgaggatt ggatatgtat    360
gactggacca cgaaaatcag agcaactaat ttccctgggc ggagcatagc cgacgaaaac    420
```

-continued

```
tagatggact aattcgtttg tcggcaaaaa tcagatagtt tttgtcattt aatctggtag    480
acccaagtat cgacaaaaat atatattatc aatgacaatt acttaatttc ataaacaata    540
taattttat aagtgaacat atcatgtgta ttcatgctaa ctaacttgtc caaccataca    600
tccagacatt taaaggcatc cgacatttaa tgacatccga tttgcatcca acgcacactg    660
gcagtggtat gtctttttg gcaaaattta cgttggatca ctattcacta gatactcatg    720
ctaacctgtc caaccataca gttttatgt aaaatgtact cacctatgat atgtgttgca    780
catgttttag cacgggggtg tgcatttaac cgatgaggtg gcatttaata aaaaaccaat    840
accatcaatt gtacaggtca tcttcagagg tacccactgg ttcaggttct ggagactcct    900
acaaaagtag gatgtacatc aacaaattat cgatgtgtgt caagctctag aaatggtggc    960
gatggaaatc tttgcgtttc atggatgacg atcaaatgca agacttgagt gtgcctagtg   1020
ttttcatag ccatgttatt tggtttcgtc gagttagttt tattttttaa agaactgttc   1080
attaagtcaa tatttgatat gtaatggctg tacgcatctg atgcgaaaag ccggaactct   1140
tgtttccatt ataaaaaaa gcatttaacc gatgaaaatt aacaagagac tactgttgca   1200
tgcagaatat ataaattggt acagataaat ggatgccaat gtttggtgtg tgagtgtgag   1260
gatcggatga gagatcctag cggaatatat atatgtgcgg tgaaatattc cggtccggcg   1320
gcagctagcg cagtgcattg agtgcccgat cggtacgcgc tcgatcggag acgagggccg   1380
agcgcgacgc gccggcgcaa gagggctcgc ggtgacggcg agcggtttgt ccccgccaac   1440
aacgggccaa acgcgccgtg tcgtccgcac caaatcccac gtagcgatcg tcattttccg   1500
tacgtccccc cctgtatatc ctactactac atactattcc tacggctacg gagtacgcgc   1560
aacacccatg gtccggtggg tggatatact acgccgtgca acagggtatc gatcgcgtcg   1620
gcgtcgctgc cggcaggaca tgcgttcgac cggcggccag ccgggcgcgc ctgctgcatg   1680
catgggacat gggtggctgc agaaaggatt cgattcgtgc gggtgacgca gggcgtccac   1740
atacgtaagc atcaccaccc tcgagcgcac gcacggcacg atccgtaacc gcctgcgaat   1800
gcgaatccta actaacggac ggtgaagcga atccaacgg acgcgcaacg agctggggtg   1860
gggccacggc ctagccacgt ttcgccagtg ccgcggcttt ctcagagcaa ctccaatagt   1920
tatgtaaatt ttagctctct aaatcacata tttaagaaat tgctaaatga cttttggagt   1980
aaaaaaatat gagttctcca atagttctct aaatataggt tgtaattttg ttttgtatct   2040
atccacataa aaaataagtc acaaaaacta tataatgcag tcaacatttt tgtttaggga   2100
gttgttaaat ggttgccaaa tgtagagaga aaatgaggtt agataacaag ttgttaaatt   2160
tagaaagttc atttagagaa ctgttggaaa atagttttca tgttaactac ctaaattatt   2220
gatttagaaa gttttagag aactactgga gttgctctca cccgcccgcg cgcctcctcc   2280
cttctccgtc cgtggcaacg gaagcccccc tataaccgcg gccgccgctg caactgcatg   2340
cacggcacga acctcccttc tttctcaaat tctctctccg cctccctgct ccgatgccgc   2400
ggtgacgcgt ggtgcatgcg tgcgcgcgcg ccttttcccc tgcctggatc cccgtcctc   2460
tctcgatcgg ttccagttaa cactcgcagc ctcgttctcg agtctcgact ctcgacttga   2520
gtcgccagtg gccacgcgcg ccgggacacg ggcgcgcttt ctcgctgccg cgccaaagca   2580
ggaaacagag caacggccag gaaggactca cgcgcgaggc gaaagcgaa gcgggtggga   2640
gaagcgtggg cgcctgggct agtgctcccg cagcgagcga tctacggtag agttccggcc   2700
gggcgcgcgg gagaggagga ggtcgggggg aggatccgat ggccgggaac gagtggatca   2760
atgggtacct ggaggcgatc ctcgacagcc acacctcgtc gcggggtgcc ggcggcggcg   2820
```

```
gcggcggcgg ggaccccagg tcgccgacga aggcggcgag cccccgcggc gcgcacatga    2880
acttcaaccc ctctcactac ttcgtcgagg aggtggtcaa gggcgtcgac gagagcgacc    2940
tccaccggac gtggatcaag gtcgtcgcca cccgcaacgc ccgcgagcgc agcaccaggc    3000
tcgagaacat gtgctggcgg atctggcacc tcgcgcgcaa aagaagcag gtcagggttt    3060 cgcgcccgcc tctttctcgg ttaaattctc tcgctgcatg ttctgttttt tttatttta    3120 cattctcgct cgtctctgaa ttagatgatt ttcaagtgtt ctctgtttgc tggacggatt    3180
aatgaagcgc acactgcaca gcgagtagaa tatcttataa atattttaat gttcccttt    3240 atgaacttgt ttctggttga tgttttaatg tttatgcccg atgatggtag atcagacatg    3300
catggttggt tgtggtgctt tctgaattca gaaccgcacg cttaactgga tgtcacgtct    3360
aaaaagaagc ttactagttg attgcagtgt tcactgttg ttcgtataaa ggtatctcat    3420
tcagtcgttc tagcatgtac tacctgtcag gacggatacg gtatactcgc ggatttagtt    3480
tgctttctcc tcgcctttt ttgaattgaa ataaactggt cacagcctgg atttacggtt    3540
ttgtccatgg caacagagaa ttccacatat tcgcgctgag attctcgccc tctgctgatg    3600
ctttctgaat tgtgttatga gcagctggag ctggagggca tccagagaat ctcggcaaga    3660
aggaaggaac aggagcaggt gcgtcgtgag gcgacggagg acctggccga ggatctgtca    3720
gaaggcgaga agggagacac catcggcgag cttgcgccgg ttgagacgac caagaagaag    3780
ttccagagga acttctctga ccttaccgtc tggtctgacg acaataagga gaagaagctt    3840
tacattgtgc tcatcaggtc tacccacttg cacattgttt tgttctatgt tgtgctaaat    3900
tggtaaacca tatatatata tatatatata tcgtaatgaa atgtctctag cctttttat    3960 ggctatagtt tttttattc tatcgtctaa taaaatccat ggaaagcttt tgccgtcgtt    4020
tctaaaaaaa agcctctagc cttagttttc tttgcacttt gcacatcgta ggagtagaaa    4080
ttttggtatt tttttcttat aaaaataatt tacagttaaa cttctggatt ttcacaagct    4140
gtttctttgt tgactgcctt tttgactgca gcgtgcatgg tcttgttcgt ggagaaaaca    4200
tggaactagg tcgtgattct gatacaggtg gccaggtaaa catcattggt cagttacttg    4260
ggagaagttc cttatgccga gtcaagtttt tcatggttga gcgcgattga tctttgaatc    4320
tcacaggtga aatatgtggt cgaacttgca agagcgatgt caatgatgcc tggagtgtac    4380
agggtggacc tcttcactcg tcaagtgtca tctcctgacg tggactggag ctacggtgag    4440
ccaaccgaga tgttatgcgc cggttccaat gatggagagg ggatgggtga gagtggcgga    4500
gcctacattg tgcgcatacc gtgtgggccg cgggataaat acctcaagaa ggaagcgttg    4560
tggccttacc tccaagagtt tgtcgatgga gcccttgcgc atatcctgaa catgtccaag    4620
gctctgggag agcaggttgg aaatggggag ccagtactgc cttacgtgat acatgggcac    4680
tatgccgatg ctggagatgt tgctgctctc ctttctggtg cgctgaatgt gccaatggtg    4740
ctcactggcc actcacttgg gaggaacaag ctggaacaac tgctgaagca agggcgcatg    4800
tccaaggagg agatcgattc gacatacaag atcatgaggc gtatcgaggg tgaggagctg    4860
gccctggatg cgtcagagct tgtaatcacg agcacaaggc aggagattga tgagcagtgg    4920
ggattgtacg atggatttga tgtcaagctt gagaaagtgc tgagggcacg ggcgaggcgc    4980
ggggttagct gccatggtcg ttacatgcct aggatggtgg taagtataaa aatctctgtt    5040
atccatgcca agtagtaagt gctgttcaac ataaataatt aaaatccatt aatccatata    5100
tgtattgatt agagaacttt gttggcaggt gattcctccg ggaatggatt tcagcaatgt    5160
```

```
tgtagttcat gaagacattg atggggatgg tgacgtcaaa gatgatatcg ttggtttgga    5220
gggtgcctca cccaagtcaa tgccccaat  ttgggccgaa gttggtgctt gatcccaaat   5280
tcctttgcag acctacaaca actgtcttca caagtgtcgt aaatcttaag gtcgctgcat    5340
gacaactttg tcgcaggtga tgcggttcct gaccaaccct cacaagccga tgatcctggc   5400
gttatcaaga ccagacccga agaagaacat cactaccctc gtcaaagcgt ttggagagtg   5460
tcgtccactc agggaacttg caaaccttgt aagaaacacc gaagtgcact catataattt    5520
cattgctact aatgtttata atttgtatgc ccaataact  agtgctacca tgaccacaat    5580
gcaggaatac ttttcttatc tctagcacac ctacatgaaa ccttctgatc ctgaacaatg    5640
cagtagctgc atgtattacc atgtgatgaa gtttcttct  gtttcagact ctgatcatgg   5700
gtaacagaga tgacatcgac gacatgtctg ctggcaatgc cagtgtcctc accacagttc   5760
tgaagctgat tgacaagtat gatctgtacg gaagcgtggc gttccctaag catcacaatc    5820
aggctgacgt cccggagatc tatcgcctcg cggccaaaat gaaggtctgc tgcataccac    5880
gacccttcat tgagctttga caagtcacac tcaaccataa ctgattgctc cctgcagggc    5940
gtcttcatca accctgctct cgttgagccg tttggtctca ccctgatcga ggtcagcttc    6000
ttctctagtt ctctaaccag ctgttgcctt tttttttaaa aaaatacat  tacattgcac    6060
tctgaaaaat gtgtggcttt caggctgcgg cacacggact cccgatagtc gctaccaaga   6120
atggtggtcc ggtcgacatt acaaatgtga gaaaccatat tttgaacatt caatttgtga   6180
aaaaacatct gcaattcact tgtgaaaaca gcggataatt atttgcgtgc atcatactgg   6240
caggcattaa acaacggact gctcgttgac ccacacgacc agaacgccat cgctgatgca   6300
ctgctgaagc ttgtggcaga caagaacctg tggcaggaat gccggagaaa cgggctgcgc   6360
aacatccacc tctactcatg gccggagcac tgccgcactt acctcaccag ggtggccggg    6420
tgccggttaa ggaacccgag gtggctgaag gacacaccag cagatgccgg agccgatgag   6480
gaggagttcc tggaggattc catggacgct caggacctgt cactccgtct gtccatcgac   6540
ggtgagaaga gctcgctgaa cactaacgat ccactgtggt tcgaccccca ggatcaagtg   6600
cagaagatca tgaacaacat caagcagtcg tcagcgcttc ctccgtccat gtcctcagtc    6660
gcagccgagg gcacaggcag caccatgaac aaatacccac tcctgcgccg gcgccggcgc    6720
ttgttcgtca tagctgtgga ctgctaccag gacgatggcc gtgctagcaa gaagatgctg    6780
caggtgatcc aggaagtttt cagagcagtc cgatcggact cccagatgtt caagatctca    6840
gggttcacgc tgtcgactgc catgccgttg tccgagacac tccagcttct gcagctcggc    6900
aagatcccag cgaccgactt cgacgccctc atctgtggca gcggcagcga ggtgtactat    6960
cctggcacgg cgaactgcat ggacgctgaa ggaaagctgc gcccagatca ggactatctg    7020
atgcacatca gccaccgctg gtcccatgac ggcgcgaggc agaccatagc gaagctcatg    7080
ggcgctcagg acggttcagg cgacgctgtc gagcaggacg tggcgtccag taatgcacac    7140
tgtgtcgcgt tcctcatcaa agaccccca  aaggttaggg aattctttaa taacacgtgt    7200
gcatccttaa ttcctccagt taaaaccagt tgctgtatga atctgaatta tgttttcctg   7260
cttaaggtga aaacggtcga tgagatgagg agcggctga  ggatgcgtgg tctccgctgc   7320
cacatcatgt actgcaggaa ctcgacaagg cttcaggttg tccctctgct agcatcaagg    7380
tcacaggcac tcaggtaaga acatacagaa tctatctaac ctgaaaagct ctcgtggaaa   7440
tttctgataa caaagttgc  gaatgtggat ctgtctgtaa taacaaataa aaaaaaaatt    7500
caattcagg  tatctttccg tgcgctgggg cgtatctgtg gggaacatgt atctgatcac   7560
```

```
cggggaacat ggcgacaccg atctagagga gatgctatcc gggctacaca agaccgtgat      7620
cgtccgtggc gtcaccgaga agggttcgga agcactggtg aggagcccag gaagctacaa      7680
gagggacgat gtcgtcccgt ctgagacccc cttggctgcg tacacgactg gtgagctgaa      7740
ggccgacgag atcatgcggg ctctgaagca agtctccaag acttccagcg gcatgtgaat      7800
ttgatgcttc ttttacattt tgtcctttc ttcactgcta tataaaataa gttgtgaaca       7860
gtaccgcggg tgtgtatata tatattgcag tgacaaataa aacaggacac tgctaactat      7920
actggtgaat atacgactgt caagattgta tgctaagtac tccatttctc aatgtatcaa      7980
tgtatataga agttaacgtg catgaggaga taatgatgac tcagaagtta ctaacgatta     8040
attcagtttt agttccggtc aatccagttt ggttttaagt ttcggttatt ttgccaggca      8100
tatccacatc tcacaatgat gccattgccc gttcattgcg atgtccataa ttgtttatgt      8160
atggacgtat ggtgagcact ttgaatctac aaatgaggaa gacgacgaca caatgttctt      8220
gtaaacggta ttgcaggtct ggttgctgat tcaaggcagt ctcgttgttg atcacgtgga      8280
accaggttat cctccaatac aagcacaaa                                        8309

<210> SEQ ID NO 353
<211> LENGTH: 127
<212> TYPE: DNA
<213> ORGANISM: Zea mays

<400> SEQUENCE: 353
tcagggaact tgcaaacctt gtaagaaaca ccgaagtgca ctcatatat ttcattgcta        60 ctaatgttta taatttgtat gcccaaataa ctagtgctac catgaccaca atggtttata     120
atttgta                                                                127

<210> SEQ ID NO 354
<211> LENGTH: 2362
<212> TYPE: DNA
<213> ORGANISM: Zea mays

<400> SEQUENCE: 354
gtgtatcttc gaaatgacga gctgagcagc gagtgccatg gcaaggggag cttgctagag       60
ttcaccagca ttcggcctga agagctcagc cggatgccaa gcaagaagct gtgcaacttc     120
actcgggtgt acatggggag cacagagtat accttcaata agaatggatc catgatattt     180
ctggatttgt catttaatca actcgactcg gagatcccaa aggagcttgg gaacatgtac     240
tacctcatga tcatgaatct tgggcacaac ttactgtctg gcgtcatccc accagaacta     300
gctggtgcca agaagcttgc ggtacttgac ctgtcacaca accagttaca agggcctatt     360
cccaactcct tctcaacgtt gtccttgtcg gagatcaacc tttcaaataa tcagctgaat     420
ggttcaattc cagagctggg ttcgctgttc acattcccga ggatttcata tgagaataac     480 tctggtctttt gtggcttccc actgttgcca tgtgggcaca atgctggctc aagttcttca     540
ggtgaccatc gatcccaccg gacccaggct tcgctcgcag gtagtgttgc tatgggactc     600
ttgttctcgc tgttctgtat agttggtatt gtcatcatag ccattgagtg caagaagcgg     660
aagcagatca atgaagaggc aagtacctcc cgtgacatat acattgatag ccggtcacat     720
tctgggacaa tgaattccaa ttggagactc tctggtacta atgctctcag cgtcaacctc     780
gctgcatttg agaagcgact gcagaagcta acttttaatg atcttattgt ggcaacgaat     840
ggcttccaca atgatagcca aatcgggtct ggtggttttg gggatgtcta taaggcccag     900
```

```
ctcaaggatg gaaaggttgt tgcaatcaag aagcttatac atgtgagtgg ccaaggtgac    960
cgggagttta cagcagaaat ggagaccatc gggaggatca acaccgcaa tcttgttccg    1020
ctccttggct actgcaagtg tggcgaggag cggctgttgg tttatgatta catgaggttt   1080
ggcagcttgg aagacgtgtt gcatgaccga aaaagatcg ggatcaagct aaattgggca    1140
gcaaggaaaa agatcgccat tggggctgca aggggattgg catacctcca ccacaactgt    1200
ataccgcaca tcatacaccg agacatgaag tcaagcaatg tgcttatcga tgagcagtta    1260
gaggcaaggg tatccgattt cggtatggca aggatgatga gcgtggtgga tacccacctg    1320
agcgtgtcca ctctcgccgg cactccaggc tacgtgccgc cagagtacta ccagagcttc    1380
agatgcacta ccaagggcga tgtgtatagc tatggcgttg tattgctcga gctgctcact    1440
gggaaaccgc ctacagattc aaccgacttc ggcgaggaca acaatctcgt aggatgggtc    1500
aaacaacact caaagtcgaa gctggcagat ctgtttgacc ctgtactact ggtggaggat    1560
ccggccttgg agctcgagct actagagcac ctgaaaatcg cctgtgcgtg cttggatgac    1620
cgaccatcca agcgcccgac gatgcttaaa gtcatggcga tgttcaagga gatgcaggcc    1680
agttcggctg tggactcgaa gacctcagca tgcacggtcg ccgtggatga tgcgtgtttt    1740
ggcgacgtgg agatgacgac cctgaaagaa gacaaggagg agaaggacta gagcaaggcc    1800
caccgacacg cgagaagctg cccttggttc ctgcccaggg ccgagcggca gctacacggt    1860
cagtcagatc tcagatgcaa aaaacaaaa tcaaaaaaac gcccgtagga atcagttggt    1920
caggacacca ttcgaagcat cttcttgagc ttagcattcc cttctgacgg tacaagacag    1980
aagttttttt ttcccttgta gcttcgcaaa gctgaagatg ttatgtacct atgggagtag    2040
gtcgattttc ttttctttc ttttaatcct taatcatctc ttctcgtcac actttagtaa    2100
gagctgtgta tgtacatata taaatggtgg tttttcctcg gtgccaaatc catttttcgtt    2160
tcattccttg tttgtcaaat tttaccttgc ttttgaccaa cgatgttgca aatcatacca    2220
tgaatgtaga tagaatacat ggttgcaggt gcagcaagca tgatggaaat ggggcgtcca    2280
aatctgagat gcaggcagtg tgaggcacca agggatgagg gggaggaagt gcaagagtac    2340
actggactgg tcaagcaaga tg                                            2362

<210> SEQ ID NO 355
<211> LENGTH: 73
<212> TYPE: DNA
<213> ORGANISM: Zea mays

<400> SEQUENCE: 355
ccgagacatg aagtcaagca atgtgcttat cgatgagcag ttagaggcaa gggtatccga    60
tttcggtatg gca                                                      73

<210> SEQ ID NO 356
<211> LENGTH: 75
<212> TYPE: DNA
<213> ORGANISM: Zea mays

<400> SEQUENCE: 356
atgatgagcg tggtggatac ccacctgagc gtgtccactc tcgccggcac tccaggctac    60
gtgccgccag agtac                                                    75

<210> SEQ ID NO 357
<211> LENGTH: 89
<212> TYPE: DNA
<213> ORGANISM: Zea mays
```

<400> SEQUENCE: 357

```
cgacttcggc gaggacaaca atctcgtagg atgggtcaaa caacactcaa agtcgaagct    60
ggcagatctg tttgaccctg tactactgg                                      89
```

<210> SEQ ID NO 358
<211> LENGTH: 2631
<212> TYPE: DNA
<213> ORGANISM: Zea mays

<400> SEQUENCE: 358

```
ctcaccgagt aagcccctat ctctctctct ctcttttcag cctttttaat taatttgcct    60
tatcttcttc aatcatgagt gtttttatgt tctctttgtc gttcgttcct gtgcaggcag   120
atcgcgatat acaccggccc caccggtaag tcacgggcgt cgtcagttct tcaagcctac   180
cacacggccg gctttttttcc aagcctaacg ctagcttctg ctgctgttct gctctgctgc   240
atggcgcgtt tgcagtgggc ggcctcctca acgcgacgtg cggcaacgcc acggagctca   300
tcatcgcgct cttcgcgctc atggagggcc agatcgaggt cgtcaagtgc tccctcctcg   360
gctccgtcct ctccaacctg ctgctcgtgc tcggcacgtc cctcttctgc ggcggcgtcg   420
tcaacctcgg ctccgaccag ccgtacgaca gggtgcgtgc gtacaaacaa cgaacgagcg   480
tcgtcaacct cttctccaca ctgcatgagc gccatcgatc agtaataatg tgtataatgc   540
atgcgcgtgc gtattattat atatatgcag acccaagcgg acgtcagcac gggcctcctc   600
atcctcggcg tgctgtgcca gtcgctgccg ctcatgctgc gctacgcggt gggcgccggc   660
gagcactccg tcgccgcggc caccacggtg ctcgacctct cccgcgcctg cagcgtcgtc   720
atgctgctcg cctacgtcgc ctacctcttc ttccagctca agacgcacgc gcagctgttc   780
gagccgcagg aggtggacga cggctgcgag gcggaagagg acgagcaggc cgtcatcggc   840
ttcgccagcg gactcttctg gctcgccttc aacaccgtgc tcatcgccat cctgtccgag   900
tacgtggtcg gcaccatcga ggtacagtac aatacagtac agtacatgca gtttatcttt   960
ctacttctac cacatcatca ttcgttcgtt ccctctgttc ttgttaatta attagttagt  1020
tagctaagct acccttgacc gtgccagcct acctccaagt cctggggttt gtccgtcagc  1080
ttcatcagca tcatacttct acccatcgtg gggaacgccg cggagcacgc cggagcaatc  1140
atttttgctc tcaagaacaa gctggtactg tacctagcct tcacacaccc agacccaggc  1200
caacccggat tattcctcct gtctcacatg ttcacgtact gttcatagcc aaccatgca   1260
tgtgaagttg ttaaattaac tcgctcctga atcctgatac gacacaggac attaccctcg  1320
gagtagcgtt ggggtcggcg acccagatct ccatgtttgt ggtgggtatt gcaatttaaa  1380
actgacgcgt acagatttca ttcgcttaaa ctattgaact accgaatcat gctggaataa  1440
tcgtacgact atgcttcctg tatacgccaa acgagacagg tgccgctgag tgtcattgta  1500
gcttggatcg cgggtattca aatggatctt gacttcaagc tcatagagac cggctctctc  1560
ttcgtctcag taatagtgac agcattcacc ctccaggtac acacacacac tacatactct  1620
ccattctcat cactgatgaa cattcaagct aataatcact tcgcggcctt tgcaggatgg  1680
ttcgtcacac tacctcaagg ggatccttct gctgctgtgc tacattgtga tcggtgcatg  1740
cttcttttgtt acgaggcaac ctgcaagtac gttggctcct tcacagaaac agactgggat  1800
ttacactctg tcttcggttg ttctgatttt tgccggcctg tgccattctc gtccatcatt  1860
tccatgatag gtaacaacaa tggcgctggg ctgtcgctgc caactggcac tttgagtgca  1920
```

```
caagctgcat gatgggtgag cctgcagaac cttgttttc cttgttcatc tatccactag    1980
taggttgtag tagtttaaaa aaggataata ggtgtttggt ttcgacctct gatggcagag    2040
atgatacgaa agcaactcct gttgtcttaa tcatgcaaaa tgcatgcccc cgttgctata    2100
gaatcatcct gaccttggga cagctggtgt gttcatcatc tgatctgatg agtagctcat    2160
gtgtcgtatt cataggttaa gtatatatag gtcctagtat ataattttgc cgcggcggtc    2220
acatgtcatg catggaactt acttaaatgt gtctcgattt atttgtcatc tctctgggcc    2280
gaatgcttgt tctcccacac agacacagca agaactattt ttcagtcagc ggcttctaac    2340
ttacctgtat caaataaaaa atgtgcccag tcgtttaaac tcaactgata gggatggtga    2400
ggtttgaccg ttccaatata tatccatttc acgttctggc cagcagatga ctgctctata    2460
tctctgcagt cctgtcagat ttattctgta attatcggaa agcaccttat gtgtttgatg    2520
tgtagccaat atgctatatt catcatggat ttaagtatgt gtgtgtctcc taatctgtac    2580
ttttagcaat gaaatatatg tccaactttt acattaatgt gttgtggccc a             2631
```

<210> SEQ ID NO 359
<211> LENGTH: 81
<212> TYPE: DNA
<213> ORGANISM: Zea mays

<400> SEQUENCE: 359

```
aggcaacctg caagtacgtt ggctcctttc acagaacaga ctgggattta cactctgtct    60
tcggttgttc tgattttgc c                                                81
```

<210> SEQ ID NO 360
<211> LENGTH: 136
<212> TYPE: DNA
<213> ORGANISM: Zea mays

<400> SEQUENCE: 360

```
gttctggcca gcagatgact gctctatatc tctgcagtcc tgtcagattt attctgtaat    60
tatcggaaag caccttatgt gtttgatgtg tagccaatat gctatattca tcatggattt   120
aagtatgtgt gtgtct                                                   136
```

<210> SEQ ID NO 361
<211> LENGTH: 66
<212> TYPE: DNA
<213> ORGANISM: Zea mays

<400> SEQUENCE: 361

```
tgctgtgcca gtcgctgccg ctcatgctgc gctacgcggt gggcgccggc gagcactccg    60
tcgccg                                                                66
```

<210> SEQ ID NO 362
<211> LENGTH: 2740
<212> TYPE: DNA
<213> ORGANISM: Zea mays

<400> SEQUENCE: 362

```
ccacaaagtc aacgcccag cattttaact ctattagccg aaacgaacaa aggcacaatg    60
tcaacgcatc agcgctgcga gagccagcat gcatgctgat ttatgactag ttattaaaga   120
cgtcgccgcc cctcgccggc cgggcgggcg gccggccggt gcagcgcgga cattaaccac   180
catgcaccac taataatact ataaataaat aaatatatga ttcgcattgt aggtaacgaa   240
tttcaatccg gctgattgaa cacggtgttg ccccgtggca agcaacagaa gtcgatgcag   300
```

-continued

```
gtgtactggc acgtaaaaaa aaaacaagct tttgcttgct tgctggtgtg gttgtgcaag      360
ggagggaaaa gtagtagtag gtgcacacgt accggtgata acgtccatct ccagcacgtt      420
agatatctgt gggccgtggc ggaacgcctg gccgctgatg cctgcgttgg acagcgtgcc      480
gccgacggtg aggtagaggt agtcggtcca ggagcgcggc gccacgccgc gcgccagcga      540
cgcgcgcaac acgtcgatcc acacctgctc gccgccggcg tccacgtagc ggccgtccgc      600
ggacacgttg atgcgcggcg gcgcggcggc gtcgcccagg acgccatgt tgacgacgac       660 gccgccgggg gcgaaggcct ggcccatgag ggagtggccg cggccgcgga acgcgatggt      720
gtagggccac cccggggtgg agttggccgc gctcagcagc gccaccaggt cgcccgtgga      780
cgatgggtac aggaccgccg ccgggagcgc cgacgtgatg ttgccgaagt ccgtcgaggc      840
cgccgccgtc gcgttgctgt cggtccggag cttgccgtcc aaggccagcg cggcgaggga      900
ggctggccag ggacggccgc gatcgtctcc gagcgcaggc gtgcctgccg ctagtgcatg      960
agagcaggcg atcagcccgg ccagcagcag gtaataaacc accgccatta gcgacgtcgt     1020
cgttcacggg agagagagag agctatacgt tatgtgtgag tgtttggtaa ctaggtgatt     1080 gcacccgta tatatatagg acggatacgg cggcacatac gtgtaggtgt agtgcgatta      1140
catacttctt caattacgta ctcgaacaca gagatgagct gctttccaag gaaaaaaata     1200
ttctgcatcc cgtctagttt tattctgttt gaccacagaa aaatatgcgc acaagtaagg     1260
tgcctagtta ccaacttcac catcctttca agaatttaca gaaaaaaaac tattatatat     1320
atagtcctgc ctagctaatt accccctgtt gccatgcaat gcaatatagc gtatttatac     1380
atttaaaaac ctgtaataat aaatataagc gatcaattct tgagaatgaa atagttttcg     1440
cactaaatag ttgtacaaat ttggtagcta taggtgtgtg ttgaccatat cgtttggtta     1500
tgaaataaaa tgaagccgtc ttttatgtta tcacttaatg tgtgtgcctg ctcaaaatcg     1560
tctctactag acagacagct gtactgcatt acgtacagga cgacgaagga agcaggctgt     1620
aattttggta ctacgacgag ccccggccca gctggttggt cgacttccaa aatacaccaa     1680
gctgaaggtt taatcaagct agccacgatt attctggcca tattatttga tttgctacca     1740
gaacctgcca acttctcata ttttgctatc aaaaatgtcg ctagccttcg ggatcttata     1800
tatatatata gagagagatt tcttgtcgct ttatctcacc ttaacagcca tgaatcaata     1860
taggattgat taagcaaatg gcaacatttt ggaaacaaac aatcgtccct agcttgattg     1920
ggacaattat attttttgttc ggtaagtcgc gtcaacatac gttactaact acacttacac    1980
gaccaaggta caaatgttag tgtttcagag aaggtgtcta gctagctgcc gcatgtcaac     2040
ttcagtggct ggctatagct agctagcgtc tgtacatatt tggggtccaa ttgttctctt     2100 gtttttcag cggttttcca tctgatgcca ttctctagta aaaagtaaaa cagatgttga      2160
tgaattcagt gtagaagcac acaccgtcta gttttgtcat ttctgatgtt ttcctcctca     2220
gctccacgaa caacgtacgg acttcggaat tcgccgtatg ctgatatata gaacaaatta     2280
gcacgcatga cttacacatg cattctaatt ttgagtcaat gactagtatt ctttccagta     2340
ccagtagtaa tacatagcag ccgttgtttc agctagctag taggtagaat ttctacgcac     2400
gaccacactg taattttggt tggtgatacg aaaatgacat cccatccaaa taatccatat     2460
atagatcata cttaagtta cagttttttt tccaatatat gactcgagca tgcgcagcct      2520
cctctcgtcg tcggagtctc gagatcggat gccgccaatt tttatgtttt ggccgcttgc     2580
cgcttgcagt gactccaggc agcgcataca gacgcgcgcg tgacggcggt gaaaccgacg     2640
```

```
atgcgtctgc atcgcgaccg atttttttc tattttagcc cttttcgtgt tttattttca     2700
caaataggtt cttttattt gaatttagaa tatggacctt                            2740
```

<210> SEQ ID NO 363
<211> LENGTH: 67
<212> TYPE: DNA
<213> ORGANISM: Zea mays

<400> SEQUENCE: 363

```
gcgggccgac gatgtcggtg ccctgcaaga tgcccttgaa gacgccgcgg tcgaagtcgg     60
cgatgcg                                                               67
```

<210> SEQ ID NO 364
<211> LENGTH: 81
<212> TYPE: DNA
<213> ORGANISM: Zea mays

<400> SEQUENCE: 364

```
tcagcagcgc caccaggtcg cccgtggacg atgggtacag gaccgccgcc gggagcgccg     60
acgtgatgtt gccgaagtcc g                                               81
```

<210> SEQ ID NO 365
<211> LENGTH: 97
<212> TYPE: DNA
<213> ORGANISM: Zea mays

<400> SEQUENCE: 365

```
aattagcacg catgacttac acatgcattc taattttgag tcaatgacta gtattctttc     60
cagtaccagt agtaatacat agcagccgtt gtttcag                              97
```

<210> SEQ ID NO 366
<211> LENGTH: 105
<212> TYPE: DNA
<213> ORGANISM: Zea mays

<400> SEQUENCE: 366

```
cggagcttgc cgtccaaggc cagcgcggcg agggaggctg gccagggacg gccgcgatcg     60
tctccgagcg caggcgtgcc tgccgctagt gcatgagagc aggcg                    105
```

<210> SEQ ID NO 367
<211> LENGTH: 5115
<212> TYPE: DNA
<213> ORGANISM: Zea mays

<400> SEQUENCE: 367

```
tgcgtttgca ggtgtccgtt gtagtcgacc gttgcgctgg tagtcgtgac tccgctggtg     60
caccagacag tccggtggca caccagacag tccggtgaat tatagcggag tggcgcttga    120
gaagcccgag ggtggctagt tcagagttgt acggtcctgg tgcaccggac attgtccggt    180
ggcacaccgg acagtccggt gcgccagacc agggtactct tcggtttctt ttgctccttt    240
cttttgaacc ctaactttga cattttattg gtttgtattg aacctttatg tacctgtaga    300
atatataatc tagagcaaac tagttagtcc aattatttgt gttgggcatt caaccaccaa    360
aattatttat aggaaaatgt taagccctat ttccccttc agcatgcaca atccctagag    420
gtacccataa taggctccaa cacaatacac gacccaacag cccaacagac ggtatcgcag    480
caccaaaaca gaatctaaac actgacttgt ttcgacaatt cccatgactc cggatgaatt    540
ttaaagtggt tacagttggg ttggaaagct tatatcctta tctttgcatt catataaaac    600
```

```
ccaacctaac cgaagttcgg atgcatcctg gtcgtctatt ttagtgcata ctggtcctag    660
agtccaaggt ggagacgaag ttgagtcaga cttggatttc tcttgctgtg aacgtcctag    720
cttctcctcc ctgacatctt ggtatttccc aagtccttga tggtactctc caaggttcct    780
agagattttg ttgtcgtgca tgtgctcgtg ttgttggccc atgcattatt tgtataggag    840
tgatgtcttc atcatcctcc ctcattcgaa ttggagttgt cttcgactca ggcgatggcc    900
aaggggatgg ccgaacaacc ctaagatgta caaggcatgt aggcccaaaa acatgtgtca    960
ttgatttctg gtagattctg gtcatcatct tgttatgacg attctcatca actccgagta   1020 tattttttacg tgggactagt tgggttggaa agcttatcac cttagcttcc caacagtatc   1080
tagaacgtca aaaatggagt atgtagcctg agcgtccgtt ttcgtgagac ccactcttgc   1140
agtccgaacc gaatttgcaa ataaactgga cttcaactcc ccttgagctt gagattctat   1200
gattgattga gccttgacca tatagttaac atccatgtac tcatgaagta atgtcgagcc   1260
acaaatgggt tatgttggtc atgcttatcc tgattggata ccatcctaa catcaggcta   1320 aatgggtcga ctataaagca gtcgtgctcg agccgctcga tggccttgca cacaagctca   1380
tgcatggtcc atgatgggcc tcgtgtcggc ctaggcacgg ttttgtcgaa atccctataa   1440
tgagtagcat ttgttgctgc caaataaacc aactttaaga tgggatacga tgctcgataa   1500
ggcatgaggt ttcagtatca taacagttta ctcgtagtaa cgccaacaaa tctcatctag   1560
aactctttgt gctttgataa catacatata tatgcgtttt tgtgctttga aaacccgttc   1620
gaattaaaaa atatcataat tattgttatt tttttatcgt aatattgttt agcacataat   1680
atactttata tttgagtttt catttatttt aaaaaataaa taaataggaa gatcggtcaa   1740
acgtgacaga aaaagtcaaa tgaattataa tttaggatga aggtgcaggc aatgccttat   1800
atccagtgga ccacggagaa acaatacac tgcactgtag tttgacggga aacagaggca   1860
ggcaccagta tttaccatag atattttttc tttataagaa gtatcgattt tgccacgttc   1920
atatttggct cccctcatcc cctgtacaga accgatcaca gcagccatgg cagagcacgc   1980
gattaacaac cccacatttg tacatgaacc aaccggagct aactaaacaa tcctgtatgg   2040
ttactgctgt agctagtacc tctaccttac actaaacgcg cctaataatt agtataagca   2100
gctggattac gttacgagtc ggccgcgagc gccggcgagc cgggcggcct gaagatgccc   2160
tgccccgccg ccaggatggc ccgcgggtcg aactcggcct tgagcctcgc gaaccggtcc   2220
cacctcgcgg cgccgaagtg ctccgcccac tcgtgccgcg ccttgtggcc cggcaggtac   2280
tgcttggcgc cgatgcccgc gcccgcgcag aagtcgagga tccgctggtt ctgccgcgcc   2340
agcgcctcca ggctctccgg cgcgcccggc agcgccgacc gcaggaacgc caccaggtag   2400
aacacctcct cgtccggggt caccgccgag ctcctcgggt cccacctgcg cgcacgaagc   2460
agcccgtcag ccacacggcc cagtccagat ctcagagctg cagtcgctaa tcgacgcgaa   2520
aagggtttgg gatactgcac gatactagta cagaatagag tacggaaaaa aataaataaa   2580
aaagcagcgg tttttagcag gatcgtctgg tgattctgat acgtcttttt tttaggttgg   2640
ttgtgtatgc gctgaagctg aaagcaacaa acaaattggt gccgtctagg cgtctacccg   2700
gcccactgac cccaatgcaa acaaagtact aaaaggcgag caggtctcag ctaaggaatt   2760
ccgattctga ccgctccgag ctcgttgcgc cctgtaaagc tctcgtcgcg gcgccggttt   2820
ataaatggca ggtcggcgtc accggccgca gttgcgtggc gtccattgca acagaataga   2880
gtaggccctg tcgcgcgagt gcgcggtttg tccacggcca ttctatctat cggggctcca   2940
```

```
gattcggctc gcgcagttgg gcaaataata atccgctgct acggatgggc tggctggtga    3000
tttgcgtgcg tggcgccaat aatgggcggc acaagtccat cgcaatcgca acacatgaca    3060
catgagcgag ccggcacctg cgctgcgcgt gcggtgccgt ccgcgtgtgg gcggcgcatg    3120
tgagggaggg tgctgtccgc ctgtccccgt gtcccgagcg ccgcatgtgg atggaatgga    3180
atggaaggtt ggttggttgg aagcgcgggg cggggcggg  dacggcgagg gcgacgcgcc    3240
gcgcctccgc gtgcgtggcg gcagatcgat gagcgcgcgc ggccttttggc ttgtggtccg    3300
tgtgtgcctt tgtgatttga cgacttactt gtgcttgttc atggggtaga tgaggacggg    3360
gccgccggcg ccggcggtgc ggccccccag cacgccacgg aagacgccgc ggtcgaagtc    3420
ggcgatgcgg gacgccggca cgaagaggtt gagccacggg tgcggcacct cccacatccc    3480
cttggcgcgc agcttcagct ccgccttgtg cacgcggtcc aggaagtcca cgtacggcag    3540
gtccgtagtg aacaccgtgc cagggaggaa gttcagctcg cccagcagcg tatccacgtc    3600
ctgaacggag agaagaagaa aaatattagc acacacagta cactgcctgc tactgttatc    3660
atacggctag taactgaaaa gcaaggctcc gagtccgagt acctacctgg tcgaccgacc    3720
ctgcggtttc gtcgtcgtag ttcttggtga cctcgaggca gtagaggacg ctggaatggt    3780
gcttgagcga ggtgagcttc acggggttct gcggcgagaa gaaggaggac ctccagttgt    3840
tgatgaggcc ctcggcggcg acgacgaagc cctccacgta gtcgaaccgg cgtccgccgc    3900
cgctgccgag ggagatgagg cgctcctggt ccgccgtgaa ctcgctgaag ttggagtaga    3960
gcgcccggat ccaccgaacc tgcaagcaac caccaccacc accaccaccc atgcattccg    4020
cccgtcaatt cttagctgct actaagatta caggccgatt aattagcaga ggaacaaaat    4080
cttgcgaaag atcccacgag ctaaacaaaa agaaaaggc ggactcgatg acgacgacac    4140
ggcggcggcg gctaatcgtt gagcaggggc accgtggacc atgcacctga ccggatgacg    4200
cgtacgtatg tgtcggactg gccatggctg gcccgggcgg ctgggggccc tgcttataga    4260
tagacccacg gatactacag tggcgattat caagacgtac acgtactacg cgtggatctt    4320
ttttcggacg ctacacatgt ggcagccgtt ttattagcgg acggcagagg ggcgcttttcc    4380
tcaacggatc agcagcgcgc tcgctcgcca cttgcatggc cggccggtgt gctgggtcgg    4440
tcattagttg gaaagcgagg ccggtgacac acgccacggg aggagatgca ctgcccgccc    4500
cgccctgtgt tccttttcccg gtgccacacg atcgagacac gactcacggg agggaaatta    4560
aaggctatct aatcggtgca ggtggtgatc catcagggcg cgcgcctgaa gggaggtcca    4620
gacacgacag agagcagaag ggagcgagga gaacgcagtt gtgggctgcc taagctgttt    4680
acttaccctc ttgggagcac gctccagggc gatgcgcgcc cgcgtgatga tgccgaactg    4740
gcccagcccg cccaggacgc cgaagaacag gtccgggttc tccgtctccg agcaggtcac    4800
cacctctccc ttccctgcca acgcacagcg cacgtgtgtc agtcagtcgg ttcattcgtc    4860
gatcggcccg ccagagacag cgccttgcat ctacgactcg tcggccggct cgatcgccta    4920
gctagctgct acgctacctg tgacgacgtc gagctcgtag acattgctga tctgtggccc    4980
gtggtggaac gcctgcccgc tgatgccggc gttggagagg gtgccgccca cggacaggta    5040
caggtagtcc gtccacgacc gcggcgccag cccgccgtgg dacagcgtcc agttgagcac    5100
gtccacccac agctc                                                    5115

<210> SEQ ID NO 368
<211> LENGTH: 90
<212> TYPE: DNA
<213> ORGANISM: Zea mays
```

<400> SEQUENCE: 368

```
cctcattcga attggagttg tcttcgactc aggcgatggc caaggggatg gccgaacaac     60
cctaagatgt acaaggcatg taggcccaaa                                      90
```

<210> SEQ ID NO 369
<211> LENGTH: 2114
<212> TYPE: DNA
<213> ORGANISM: Zea mays

<400> SEQUENCE: 369

```
tgattgacaa attattgctt cgcccgaccc gaggctagcg cacagtccat gtcatgtggg     60
cctggctgtg tggtttccgt cctgatgctg atgcctgaag ggacctgcgt gcgtgtgcgt    120
gcgtgcaggt gggaccccaa cacgtcggtg gcgctgccgg agggcgaggt cttctacctg    180
gtggcgctgc tgcggttctg ccggagcggc gggccggcgg tggacgagct ggtggcgcag    240
aacggcgcca tcctccgcgc ctgccgcgcc aacggctacg actacaaggc ctacttcccg    300
agctaccgcg gcgaggccga ctgggcgcgc cacttcggcg ccgccaggtg gaggcgcttc    360
gtggaccgca aggcccggta cgacccgctg gcgatcctcg cgccgggcca gaagatcttc    420
cctcgggtcc cggcgtccgt cgccgtgtag agcaagggggg aggaccagc cagctgccag    480
ccaagacagg aggaggagga ggaggggagg ctgatggatc gccgctgctg ttgccggtaa    540
tgatggcgat tacgctgctg atcctggtga tgatgatgga cgatcgagga agccgcaggg    600
ccgggcaatg atggcgatag gccaccgtt aggtgtgcat ccgggggcgc aaattaaagg     660
gattgctgtg tggagatctg cacgagtttt tgctccatgc atgcttgccg ttcgtgtccg    720
cgtgtccctc tccccttgt tattattcct tcgcccgccg aggccgagcg agcgggtggt    780
ggcgacgctg gatttgtctg ctctgctttg ctccgccgcc gtgccaccc cggtggcgtg    840
cgcccgcaag ctgttccttc cgcgcgcttc tgttccgttt cgttccgttc ctccgtggta    900
gcttccccc ctcgccgtcc tggtccccc cgcccggcac cccacgtggc acaccagccc     960
gatccaaacg ccgcgaccgc gacgcgcggg gccgttggtt cgcgttcccg ttccgtagta   1020
gcttggccgc agtacacgac gaccgcgaac aaagcgcggc caaaaccgac gggtctcgcc   1080
gccgccgccg cggacgcgcc cacgggacag gaggaatatc actctggggc catccgcgcg   1140
ggaccagaga actggtcggg tcgatcgata tcggcactgt gctggctggc gacggggacc   1200
gagcggcagg gacgtgacgg ttgttgccgc ccgagcgcga cggcgaccgt cgttcgtctc   1260
tgggccgggg cggcgcgggc ggcgttttcg tttggaaatt ttgtggactt ctacttgtat   1320
atataaaaaa aacgatcggt acgtatacaa ccagtcttcc tttccctgtc gtgcccagtc   1380
gcattccgtg atgcgagccg gatcgcgacg gaagcggctc gacagcgtc gtccctgctg    1440
caccctgcta gcatccgtcg cgacagatgg gcgctgcttc aaggacagga tgattggtta   1500
cacgccggcc tcgatctcgc ccagctgtgt gggttcatca ggacgcccca gcttgtctgg   1560
cacgtgcggc cacccatcgg cgagatgaga tccatcaatc cgatcacctc atcggtacgg   1620
aacggaacag attttttcgct gtcgactggt ccgaaacgag ccggcgacct cgaccgaccg   1680
accctctccc ccttcccccct ccccgcccg cccgccgacc catcgctgtt gcgctacagg   1740
ctgctggcaa cgacgctgtc gaggccgatg cgcagcaccg gtgatgaccc ggagcagaaa   1800
gggcgttagc tggttaatgt atcaagctgc agagacactt atccccgggg attaggtacg   1860
cgagggcgac actcctggat agatttacct cgtctccatg cctcgcagga attctaatga   1920
```

| | |
|---|---|
| atcttttctc cattgtttat caggacctgc cctgccagga taccagccgg agagctttca | 1980 |
| ggcgacaaaa gccgcggcga ggggatcagc gaggatctgc cgggccaccg ccaccgccgc | 2040 |
| cgccccgcgt tttatactgg agggtgggtg tgctccaagt ggtgcctttc tgacaacgcg | 2100 |
| atctaggcta tgag | 2114 |

<210> SEQ ID NO 370
<211> LENGTH: 63
<212> TYPE: DNA
<213> ORGANISM: Zea mays

<400> SEQUENCE: 370

| | |
|---|---|
| aggctgctgg caacgacgct gtcgaggccg atgcgcagca ccggtgatga cccggagcag | 60 |
| aaa | 63 |

<210> SEQ ID NO 371
<211> LENGTH: 101
<212> TYPE: DNA
<213> ORGANISM: Zea mays

<400> SEQUENCE: 371

| | |
|---|---|
| ggagagcttt caggcgacaa aagccgcggc gaggggatca gcgaggatct gccgggccac | 60 |
| cgccaccgcc gccgccccgc gttttatact ggagggtggg t | 101 |

<210> SEQ ID NO 372
<211> LENGTH: 2968
<212> TYPE: DNA
<213> ORGANISM: Zea mays

<400> SEQUENCE: 372

| | |
|---|---|
| ccactacgga taaaaaagct tctcgtatcc ataatgctgg ctaatacaaa tatttgaggt | 60 |
| aattagtttt gagtactgcc ataatggggc aatatctaat atatgtatca attatttgat | 120 |
| atatgttatg aaatcttatg gacgttcttg tactgcact atgggagttt gcttctgaca | 180 |
| aaagtgccag atgtgcagac acttttggag catgaattga caactatgtt ttctttcatt | 240 |
| tcatttgaat agcctatttc aggatatttg aaggtcgagt agctaaactg aaactatagt | 300 |
| ggatatgctc tgtttggttt aatgagtttt gtgtacagtt gtcctatttt tataaagtcg | 360 |
| atagtttcta atattgcat cgtgttccca gttttgtgct tgttacttct cagtgcttgc | 420 |
| atttgcatcc tgcaaacgac aaccgaccat tgacacccag ctaacgtaga cacctgagg | 480 |
| gctgggtcc agactcatca agggcaaatg acactgctat tacttatgaa caaccaatgc | 540 |
| gtaaccatac atagtatcaa ctgatatgat ctcaaggact tgtctgatct tagcaggcat | 600 |
| ctaagatgct cctaggcttc ccattataat acttaaaaaa tgcataaagg aaatgttttc | 660 |
| ataaaacagt taatggtaag attgatgaga tcttcagaa caccttttga aatcacttt | 720 |
| ttacttggat caaatccgaa caataatttt tgctttggaa tttatgtatt tgctaagtca | 780 |
| aagcaaactc tatatctgtt tcttatttgt ttcattacct tagcaggaac aaggacatct | 840 |
| agtaaatcct gtttgtggca gctacttttcc tgtaattgag ccaccatcac gtgaaaggca | 900 |
| ggcatttctt ccggctgctc ctctagaaat gcctcatcca ggtggatact cttgtgttgc | 960 |
| ggctttggct gagcaccagc caccaagcat ggatttctct tacatggctg gcagtagcac | 1020 |
| atacccagtc tttgacatga tccgccgacc gtgcaacatg tctagtggaa gcttgtgcag | 1080 |
| cgtcgagaac agttcactag acacctggag cgggatggca ccaaattgca gcagaggagt | 1140 |
| ggtaagagag gagggagagt gctcaaccga ccactggtcg gagggtgcgg aggcgggaac | 1200 |

```
aagctatgcc ggatcggaca tcatggtgga tgcaggggcc atgcaaccgc tgcctttcgc    1260
tgagaatttc accatggctc caagccactt ccgcccggag agcatcgagg agcagatgat    1320
gttttccatg gccgtgtcac tagcagaagg tcatcatggt aggacgcaag cgcaaggtct    1380
ggcatggttg taagttgtat aacactaatt ttgacgcctt gatccctgcc cctttctgtt    1440
ggttcgacct gcttcccctg cacctctgct ttttgccac tttgtttagc ttttgctcc     1500 ttttttttct tttctttctt ttttgcatgt gttgcttcat ggcttgatat agatcttgct    1560
atagtcctcc attgtcattg cttatatgta tgtaaaatgg aatatgtgga aataggaaag    1620
aaaatgggtc gaaagttctt ttgccggtag gatgcgcagt gtgttttcgc attgcaaagc    1680
attccaagat tttgcaaagt tgacctggaa caggcattct agctattctc tccgttgaca    1740
tgttcttggg gtgtaaagat gtttgattct atgggaaaaa acaactaga ctctggaccg     1800 gctgaggtta atttcagaca tgtttcgatc tatttgtgaa ttcttctgat ctgttgtaga    1860
actactttca gctgtagtgt atgacttgtc aggcagaggc aggcaacagc aacaccaata    1920
ttatccagcc tcacaagtat gttttttctta aggggggctc aagtacaggt attttggcat   1980
ggagcatgtc gatggaggat ggacagactg aggacaatgt acagagattt gttgcgttgc    2040
acacgattcc gcattccgaa ccgtgaggtt gacaaaagga gagaggatct cttcttggag    2100
aggaagcatc ctgtttctta acagcagtta gcaggtgagg tgagaaacct tggatgccga    2160
caccaatatg caaagctggc cggactgaaa cacgggaatt ccaagttttg tcttattttc    2220
cgcagaaact tacgcgaagc gaaggccaac aatggcttca aatgcgtttt gggggtaaga    2280
aatgaatgca gcttgtggct tgaaatgagg ccatgagcca ccgtgtggga agggcaaggg    2340
cttgcagtta ggatggtagg gcttgaaatg gtaatgaatt acgatctaaa tatttttttc    2400
ataatttatt taagctttta attaatttta gtttaaaaat aaatagaaat agacctcggt    2460
cataattcga ttcgatcctt aaattttgta gtgtaaaatt tagagctcat taccacctct    2520
atttgtagtt gcacgtgtgg acaactaggt gttgaaaatt aggttcggga tctagctcgg    2580
agcatcacaa gtatctctaa aattaggttc gggatctagc tcggagcatc acaagtatct    2640
ctcccacata gccgatagta atatacaaat atattccata taaaatcata ttagcttaat    2700
tgatctacgc ataaattaca attattagta tggaattcaa ttccaaggat ccgaacgggg    2760
ctaagaaaat aaaaaattta cattacttaa aaatacaata tacatatgtc aaattaaaat    2820
aaaaagttca caatgcataa aaaacaaaaa ttacatatct aatacaaata aaatttaatt    2880
cccatgtgca gatcctaaat atgctccatt aaattatttt ggagttgatc atgcaccgag    2940
cttgcatgga gtgcggtctc acgctgaa                                       2968
```

<210> SEQ ID NO 373
<211> LENGTH: 141
<212> TYPE: DNA
<213> ORGANISM: Zea mays

<400> SEQUENCE: 373

```
gatttacatg aggatggata tcaacacaca gtaaggcttt taccgggggc taaccaaccc      60
attctaccct agcacgacga tcccttccga gagaatatat ttgtaatcaa ggtcagcccg     120
aaaaagggga aagagagaa g                                                141
```

<210> SEQ ID NO 374
<211> LENGTH: 158
<212> TYPE: DNA

<213> ORGANISM: Zea mays

<400> SEQUENCE: 374

```
gatttacatg aggatggata tcaacacaca gtaaggcttt taccgggggc taaccaaccc      60
attctacccct agcacgacga tccccttccga gagaatatat ttgtaatcaa ggtcagcccg    120
aaaaagggga aagagagaa gataaacgag aagaggggg                              158
```

<210> SEQ ID NO 375
<211> LENGTH: 2260
<212> TYPE: DNA
<213> ORGANISM: Zea mays

<400> SEQUENCE: 375

```
gacccatgac tcctttagca aacttatgat gtgctgcaga ccatacagtg ccaatgcaaa      60
agaatgaaca cctcaaagaa acacagggta cttgtactga gatgtataaa gcagctgcgg    120
ccaaaagaca gggagaggag gaggaggagc tcttcttgcc cacatccctt tgtcaagaag    180
aatctctgat gcttgcttgt ttccatgtga cagggaagct tggtacttac tgctctcttt    240
acaaaaaaac aaaacaaaac aaaacaaaca accccccact ggcagaatag aattgaatag    300
aatagaatag cctttgtttc ccctccccca aaaagctaaa gttctcatca tgcttaaaac    360
cgtcttaaat agcagtgctt agaagaagat agggcaggcc acctcccct agttacaccc      420
agcatcccag ccagacccac caccccacga tgcacctctt gtctgttcct cttcctccat    480
gcaatgcaag tatgcaacgc aacgcatctt ctgtttgcta ccgccgctc ccaacacgtc     540
gctatcgccg gcctcttcgg gttcggaagc ttccacgcct cggcatgcgc gctcccgacg    600
tcatgctcgt cccggcgatc gtcctgactt gccggttcct ctgcaggatt tgaaaccggg    660
ttagaagctg aagctgaagc tgaagcaggg actgagacag cagcacagtc tttgtttcgg    720
caggtgatgc actgaaaccg ttaaggcttt cctgtagttt accatcatga tgaaccgtgg    780
gtgtggtgct gtgctgtgct ttgttttgac tgctttcatg gatgtagact aatgatttca    840
ggaatgatat gtgcatctac gttgctcact gggggaatag gacttgtgtg gttgcttttg    900
ctgaaagatt atagcatatc atcataggggg aatgtgggag tggtgaggga aaaagagcgc    960
atggcatctt ttgctcatat gcgtcgtctc cctttgtttt tcttccctc tccctgcgtt    1020
ttatccgtta tcatttattt tatattatta tgaaaagtat tgtttttct ttctttcttt    1080
cctgacctat cctacgtgaa aatatccaac aaaacatggt aaatgggagc atatggcaag    1140
acaaaatgat cacaacagac gcactgcaaa acattcacct ttgcatacca ccagtcagaa    1200
actggtgaaa caagaacatt cccttcattc cgtaacgcaa gcttaacaaa caaacaagcc    1260
atgcaaaaaa aaaacgtcaa gcgttggaat tctgctagtt caagttaggt gaaggctgca    1320
gcatttggcc tcatatcgta cgtagtaatt tttttttgaaa atcctaaagc ttctagtttc    1380
aagaaaccag tgcattgggt acaagggaa aaaaggggggg gccaactcaa acaccaaaac    1440
caaagcttgc agcgcagtaa gctgtacgta gatcaaagta cctgttgtgg ataggatcag    1500
ggccattggg caccccttctc ttgctgtcct ggaagggatc atgagccttg aaatcctcca    1560
gggtcctcag ccctccggcg cctccgccca gcatcatcct cctcccgccg atcgccgccg    1620
gcggagccgc tttcctgacg ccgtccacga cgaacgacac cagaaggagc gctccgaaca    1680
agatggccaa tgccgctggc gccgcccgcc tcacggacac ggccgacctt ctcatgacac    1740
ccaccgacca gtcgtccgtc gccgcgcagc gcagcgtcgt cttcttcttc cgtagagcgg    1800
cctcctcctc ctcctctcct ggcgagcgac aacgctggtc ttctaagagc ttcttctcat    1860
```

```
ggcatggggt ggcgctaagt gtgatgcaac ggctgcggct gcgcaacgtg actgcatatt   1920
ataatgtggg gaagaagtag cggcaggatt tgtgtcagtc gctgtcgcgc gggtattcct   1980
gcttcttgtt ctgttctggc cttctttcgc tttggcccga ttctgctgtg cttttgaagg   2040
atgccctgcc cctaatggag gggaggggggg gcagcagaga gtagaatcaa agcaagctga   2100
gccacgctcg cttttctttc ttttttttttt ttttgttgc gctttgcttt ttgagccatg   2160
ttgttttcct cctgcctttc cctttttttt aatcccccttt gttttttcttt cttctcgtga   2220 agagaagaag ggtaaaagac ggtggataaa taataaaaaa                         2260
```

<210> SEQ ID NO 376
<211> LENGTH: 60
<212> TYPE: DNA
<213> ORGANISM: Zea mays

<400> SEQUENCE: 376

```
gcagctgcgg ccaaaagaca gggagaggag gaggaggagc tcttcttgcc cacatccctt   60
```

<210> SEQ ID NO 377
<211> LENGTH: 2433
<212> TYPE: DNA
<213> ORGANISM: Zea mays

<400> SEQUENCE: 377

```
ccaaccggca atgccagcac aacacatgga tcctacaaaa atctcgggca catggcatcg   60
cggcgctgtc caaccggggg gtgtgcccgg cccggcgagc cgcttgcttt tattgtattt   120
atatttatac gagccccatg ggcgcttgcc tcagtcgttt gcccctttgg tccctctccc   180
tcccccgtcc gccctgcact ctccagctca acaaggaaga agaggggggcc ttcaccacac   240 cactcgattc ctcttttagag cacgacttac gaagtgtgcc caggccgtcg ccgccgacca   300
gcaaaagggc tggaaagccc ccctcttttg tgctgtgcgt gcaactcggc tcctgccctg   360
ccatcttgct ttccaagacc cctgcgcccc cagtcccata attagttagg attaggatca   420
ccaccatttc caaatccttg cagagctgcc gaagcgcgga tcacagatga agaggcaatc   480
caagaggccc accgccagcc gcgaatcccc agaaacaggt attgcgtccg tgatgtccgt   540
gacagaatac caaatggagt atagtagtta gtgaatagaa aagtacgtat gcgtgctttt   600
gacatctgat cagtgttgct tctgcctgca ttccattttt tgcatttggt tagcttgctg   660
ccacaaagct gcagaaagaa cgggtctccc cccttcattt tggggaatcc tccagtagct   720
aaccgcacgc gcgaattgca ggggagaagc agaagctggc gttcgcggag gaagaggccc   780
cgccggcgcg gaaggtggag cccgacgacg aggccgagat ggacgaggac gaggacgagc   840
tgggcccggg cctgggcggc gggcgcgcgg cgcggtcgcc gtgcgggctc ggggagaaga   900
agcggcgcct ggcgctggag caggtgcgcg cgctggagcg ctgcttcgag acggacaaca   960
agctggaccc ggaccgcaag gcccgcatcg cgcgcgacct cgcgctgcag ccgcgccagg   1020
tcgccgtctg gttccagaac cgccgcgccc gctggaagac caagacgctc gagcgcgact   1080
tcgcggcgct gcgcgcgcgc cacgacgccc tccgcgccga ctgcgacgcg ctccgccgcg   1140
acaaggacgc cctcgccgcc gaggtaatta accgactgct cttgctctgt catgtcatgt   1200
catgtcaccg ccggtcatgg tcagcaaccg tctacgtact ctccgcgtct tgtccggtgc   1260
cacttccaac ctgccgtcac tcactgatgt cgttttggcg cgcgcgcgcg cccgctcggc   1320
gcttcttatc agataaggga gctgaggcag aagctgctgc ccaagccgga agccacggtg   1380
```

-continued

```
aagctggagg cgacgacggg caatgacacg gcggaggagc gccgccaggc gacggccggc    1440
gcgccgcccg cggggggcctg caaggacggc tcctcggaca gcgactccag cgtggtcttc    1500
agcgacgtcg aggcgtcgcc ctactccggc ggcgcggcgt tcgagccgcc ggccttggcc    1560
gggctcggcg cgccgttcct ggacacgtcg gtggcgccga cgggctgctc gtctccccccc   1620 gttttcgtcg agaccaagtg gcagcagcac gggccgacac agtacccgtt cccattcgac    1680
tcgtacaagg cctgcgccgg ctatggcttc acggaggaat ggctcgccag ctcggacctc    1740
atcggcagcg acggcggcgc ggcggggttc ttctccgagg atcacgcctc cagcctcaac    1800
ttcaactggt gcccgagtgg catccagggc tgggagtgaa gaggggtttt tgatctgcac    1860
ggctagtgta aaaaaaccga tgttacggtg gcatttgtac atgcatggaa ctggagtcta    1920
gtgacctggc ctggcgagtg tggtgtggcc aaagctagag gacatccagc gcaaaaggcg    1980
ggaacaggag cagtagtagc ctgtaacaat aacggaataa cttgagccag gctagtaaaa    2040
aaagaggatg taaatgtaaa aagaggctgt cgcaccacta cggcactatc acttggatgc    2100
aacatgcaat gcagcaaatc ggcgacgaga gcgtctgaag gggaaactgg taagcaggct    2160
gcaatttacg gtgccggatg agatacgtca aacctctaat caaaataaat gttctttgac    2220
tcgtttacat ttgaaattaa cgtcttcaga aaaacaattt tagtgttaag gtaaaaccga    2280
agccgagcga cgaaggctat actacaagag ccctgcggag cggtttgctt tttccacttt    2340 tttttttcttc ctttccttttt cctaccactt cttcattctc cttttaaaaa ataaaaaaaa    2400
acggagggag ggcttaaaag gggagcacgg aag                                  2433

<210> SEQ ID NO 378
<211> LENGTH: 123
<212> TYPE: DNA
<213> ORGANISM: Zea mays

<400> SEQUENCE: 378
cggcgacgag agcgtctgaa ggggaaactg gtaagcaggc tgcaatttac ggtgccggat    60
gagatacgtc aaacctctaa tcaaaataaa tgttctttga ctcgtttaca tttgaaatta    120
acg                                                                  123

<210> SEQ ID NO 379
<211> LENGTH: 85
<212> TYPE: DNA
<213> ORGANISM: Zea mays

<400> SEQUENCE: 379
gcttgcctca gtcgtttgcc cctttggtcc ctctccctcc ccgtccgcc ctgcactctc     60 cagctcaaca aggaagaaga ggggg                                          85

<210> SEQ ID NO 380
<211> LENGTH: 3927
<212> TYPE: DNA
<213> ORGANISM: Zea mays

<400> SEQUENCE: 380
taggataata gcccagtttc atttggattt tgaatttact tgcgggccat catcgattgg    60
ttgctggatc taattggcac gcacgtcacc cccaccggat gcatgccaca gatctgtgca    120
tgtgctcacc atgctgaggg aggtcaggat tggtgcctgc acgcatgggg ttcctacgcc    180
```

```
cagaccaaaa ggatctggtt gctatctttc gcccatacac ggatgctctt cttcagatct    240
ggttaagcgg gcaatgattg cattgcgggg gcaccagcac cagaaacaaa ctgtaggagg    300
ttgctgcggt ggtccctgtg gggttctact gctttaggat tattttctgg gatctgtttt    360
ttttccagcc cgagtatgca tgccgtcgag gttcaggttc ctcctctctt agcaaagttt    420
tatgaagctt cttttttggct tctggttgct gcctgcacaa ctttatcaag ctaccaaacg    480
tactagttgt actgcttcct ttggattata gaggagttac taaataaact gtgttgggtg    540
tgcatattct caaggctgtg gtcttaggaa ttgctttcag ttatgcaaga gatacttact    600
tggcatacaa ctactggcgc tccgaatgcc ctgccacccc cctggcctga tagattcttt    660
gatctggacc ttatatggtt agtttattca gtgttgctgc actgtctctc tacatgtttc    720
ctgaaacatc agtagattgt ggaatagcag tgtgatggtg tagctttatg gttacagcta    780
actcagctgt tggtgagata gctccttgca gttgcagata acaatgtgct tccttcagct    840
gtttcttcca tctagtgtac ttgtacaagt tcttccatga tatgataaat gtgtatttt     900 ttgttaactt cactgtttat ctaactctgc tgtgtcatgc ttttttcaatt gtgttttttc    960 agtagcaacc accacccatg gcggacgtgc acgaaccttt ggtgcgccgt aagaggaaga   1020 aggtttttggt ggactacttg gtgaagttcc gatggatcct cgtgatcttc gtggtccttc   1080
ctatttcaac tctgatctac ttcaacatct tcctgggcga catgtggtcc gccatgaagt   1140
cggagaagaa gcgccagaag cagcacgacg agaacgtgca gaaggtcgtg aagcggctca   1200
agcagaggaa cccgaagaag gacggtcttg tttgcacggc caggaagccc tggatcgctg   1260
ttggcatgcg caacgtggac tacaagcgtg cgaggcattt cgaggtcgac cttcttcct     1320 tcaggaacat ccttgagatc gacaaagaga ggatggttgc caaggtcgag ccccttgtca   1380
acatgggtca gataaccaga gctacctgcc caatgaacct tgcccttgcg gtcgtcgccg   1440
agctcgacga cctcactgtt ggtgggctga tcaacggtta cggcatcgag gggagctctc   1500
acctctatgg ccttttctcc gacacggttg tcgcgatgga ggttgttctc gcagatggcc   1560
gggtcgtcag agccaccaag gacaacgagt actctgacct tttctatggc attccctggt   1620
cccagggaac actggggttc cttgtctctg cggagatcaa gctgatcccc atcaaggagt   1680
acatgaagct cacctacact ccagtcaagg ggggtctaaa ggagatcgcg caggcctacg   1740
cggattcttt cgcgccgagg gacggtgacc cggcaaaggt ccctgacttt gttgaaggga   1800
tggtgtacac agagagcgag ggtgtcatga tgacgggcgt gtacgcttcc aaagaagagg   1860
cgaagaagaa gggcaacaag atcaactgcg tgggtggtg gtttaagccc tggttctacc    1920
agcacgctca gacggcgctg aagaggggcg agtttgtgga gtacatcccg acgagggagt   1980
actaccaccg gcacacccgg tgcctgtact gggaggggaa gctgatcctg cccttcggcg   2040
accagttctg gttcaggttc ctgctgggct ggctgatgcc accgaaggtg tccctgctga   2100
aggcgaccca gggcgaggct atcaggaact actaccacga caaccatgtg atccaggaca   2160
tgctggtgcc gctgtacaag gttggggatg cgctggagtt cgtgcaccgc gagatggagg   2220
tacaatggct ggctggtgct ggtgctggtg ctgcttgctt tatgagtagt tgactggata   2280
tactaataat aattgaaatt cttttggtag gtgtatcctc tgtggctgtg ccctcaccgg   2340
ctgtacaagc tgccggtgaa gacgatggtg tacccggagc tgggttcga gcaccagcac    2400 aggcagggcg acacgagcta cgcacagatg ttcacggacg tgggcgtgta ctacgccccc   2460
```

```
ggggcggtgc tgagggggga ggagttcaac ggcgcggagg ctgtgcacag gctggagcag    2520
tggctgatcg agaaccacag ctaccagccg cagtacgcgg tgtcggagct gaacgagaag    2580
gacttctggc gcatgttcga cgcgtcgcac tacgagcact gccgccaaaa gtacggggcg    2640
gtgggcacgt tcatgagcgt gtactacaag tccaagaagg ggcgcaagac ggagaaggag    2700
gtgcaggagg cggaggcggc catactggag ccggcctacg cggacgagga ggcctaaaag    2760
ctcgtggtcg ttttgcttag cccatttaaa ttagaacttg atggatgtag tgtgtgtctg    2820
tctcaagtca ttttaattag aactcttaaa gctcgtggtc ggtcggtcag tcagtcagtc    2880
attgtcgttg atgtccagcg ttgtgttttt tttatattct ctaatggaat ctctcagatt    2940
gattcgggac ttgctatggc tctgctcttt gttatgtttt tttttaaag ttctccaggc     3000 gctgctgctg cgtcttgcaa ggagcccgga gctgatgact agcagcagca gcagcttgga    3060
acggtgggag gcagcaccac catggcacca tgtggctgag ctgggctggc aggcacagtg    3120
agaaaaagaa agacaccagc catctactcc ccagtccccc cacaagagca aaagcaaaga    3180
aagatgcatg tgcatgtgca gtgcagcaac tctgccatgc tgtcatgtgg gacggcacgg    3240
gcaccagctg cactgcactg caccgcccca cagttatatt gtttactgct gctgtgccca    3300
ctccttgtat atttgcatca ctgcctgctt ctggaatcag gaaggagat caccacttca     3360 ctcaagaagg caccctccct tgccactcct tttccttgag atgacgatga cgacgatgaa    3420
gaagcagcag cagctcctcc tcctcctttc tctcatgttt ctcgttgctg tgacagcagc    3480
cgctgttgct gccgatccac atccacagca ggtggtacta cgcctactct cctcttctcc    3540
tcggcatcat ccaaactgaa tcagattgaa gaatcatcag gtcattaaca tgttcagtgt    3600
gtgtccagca ggtgcaggtg cagcagcagc agcaagcaca gatgaggatt aacagggcca    3660
ccagatccct tcttcctcag ccgccgccga aactaggtac tactgaaaac tgtagacaac    3720
aagatacaag atctcatttc attgacgcct gtttctcacg caatacagac tgcccgtcca    3780
cctgctccgt gcgctgcggc aacaactgga agaaccagat gtgcaacaag atgtgcaacg    3840
tctgctgcaa caagtgcagc tgcgtgccgc cggggaccgg ccaggacacc cgccacctct    3900 gccccctgcta cgacaccatg ctcaatc                                       3927

<210> SEQ ID NO 381
<211> LENGTH: 74
<212> TYPE: DNA
<213> ORGANISM: Zea mays

<400> SEQUENCE: 381
accaaggaca acgagtactc tgaccttttc tatggcattc cctggtccca gggaacactg    60
gggttccttg tctc                                                      74

<210> SEQ ID NO 382
<211> LENGTH: 160
<212> TYPE: DNA
<213> ORGANISM: Zea mays

<400> SEQUENCE: 382
tgatggatgt agtgtgtgtc tgtctcaagt cattttaatt agaactctta aagctcgtgg    60
tcggtcggtc agtcagtcag tcattgtcgt tgatgtccag cgttgtgttt tttttatatt   120
ctctaatgga atctctcaga ttgattcggg acttgctatg                         160
```

YIELD TRAITS FOR MAIZE

RELATED APPLICATIONS

This application is a continuation of U.S. application Ser. No. 12/904,450 filed Oct. 14, 2010, which claims priority to U.S. Application Ser. No. 61/256,623, which is herein incorporated by reference in their entireties.

STATEMENT REGARDING SEQUENCE LISTING

A Sequence Listing in computer readable form (CRF) was submitted in parent application Ser. No. 12/904,450, filed Oct. 14, 2010. The CRF of the Sequence Listing in this continuation application is identical to the CRF of the Sequence Listing filed in the parent application. Pursuant to 37 C.F.R. §1.82(e) and MPEP §2422.05, applicants respectfully request that the CRF of the last filed Sequence Listing in the parent application be used as the CRF of the Sequence Listing in the present application. It is understood that the U.S. Patent and Trademark Office will make the necessary change in application number and filing date for the instant application.

TECHNICAL FIELD

The presently disclosed subject matter relates to maize, such as maize of the species Zea mays, and methods of breeding the same. More particularly, the presently disclosed subject matter relates to maize lines, such as Zea mays lines, with one or more improved yield traits, and methods for breeding the same, which methods involve in some embodiments genetic marker analysis and/or nucleic acid sequence analysis.

BACKGROUND

A goal of plant breeding is to combine, in a single plant, various desirable traits. For field crops such as corn, these traits can include greater yield and better agronomic quality. However, genetic loci that influence yield and agronomic quality are not always known, and even if known, their contributions to such traits are frequently unclear. Thus, new loci that can positively influence such desirable traits need to be identified and/or the abilities of known loci to do so need to be discovered.

Once discovered, these desirable loci can be selected for as part of a breeding program in order to generate plants that carry desirable traits. An exemplary embodiment of a method for generating such plants includes the transfer by introgression of nucleic acid sequences from plants that have desirable genetic information into plants that do not by crossing the plants using traditional breeding techniques.

Desirable loci can be introgressed into commercially available plant varieties using marker-assisted selection (MAS) or marker-assisted breeding (MAB). MAS and MAB involves the use of one or more of the molecular markers for the identification and selection of those progeny plants that contain one or more loci that encode the desired traits. Such identification and selection can be based on selection of informative markers that are associated with desired traits. MAB can also be used to develop near-isogenic lines (NIL) harboring loci of interest, allowing a more detailed study of the effect each locus can have on a desired trait, and is also an effective method for development of backcross inbred line (BIL) populations.

What are needed, then, are new methods and compositions for genetically analyzing Zea mays varieties and for employing the information obtained for producing new Zea mays plants that have improved traits.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

The presently disclosed subject matter provides methods for introgressing an allele of interest of a locus associated with a yield trait into Zea mays germplasm. In some embodiments, the methods comprise (a) selecting a Zea mays plant that comprises an allele of interest of a locus associated with a yield trait, identifiable by PCR amplification of a Zea mays nucleic acid with a pair of oligonucleotides primers selected from among primer pair 1 represented by a primer comprising SEQ ID NO: 52 and a primer comprising SEQ ID NO: 53; primer pair 2 represented by a primer comprising SEQ ID NO: 57 and a primer comprising SEQ ID NO: 58; primer pair 3 represented by a primer comprising SEQ ID NO: 62 and a primer comprising SEQ ID NO: 63; primer pair 4 represented by a primer comprising SEQ ID NO: 67 and a primer comprising SEQ ID NO: 68; primer pair 5 represented by a primer comprising SEQ ID NO: 72 and a primer comprising SEQ ID NO: 73; primer pair 6 represented by a primer comprising SEQ ID NO: 77 and a primer comprising SEQ ID NO: 78; primer pair 7 represented by a primer comprising SEQ ID NO: 82 and a primer comprising SEQ ID NO: 83; primer pair 8 by a primer comprising SEQ ID NO: 87 and a primer comprising SEQ ID NO: 88; primer pair 9 represented by a primer comprising SEQ ID NO: 92 and a primer comprising SEQ ID NO: 93; primer pair 10 represented by a primer comprising SEQ ID NO: 97 and a primer comprising SEQ ID NO: 98; primer pair 11 represented by a primer comprising SEQ ID NO: 102 and a primer comprising SEQ ID NO: 103; primer pair 12 by a primer comprising SEQ ID NO: 107 and a primer comprising SEQ ID NO: 108; primer pair 13 represented by a primer comprising SEQ ID NO: 112 and a primer comprising SEQ ID NO: 113; primer pair 14 represented by a primer comprising SEQ ID NO: 117 and a primer comprising SEQ ID NO: 118; primer pair 15 represented by a primer comprising SEQ ID NO: 122 and a primer comprising SEQ ID NO: 123; primer pair 16 represented by a primer comprising SEQ ID NO: 127 and a primer comprising SEQ ID NO: 128; primer pair 17 represented by a primer comprising SEQ ID NO: 132 and a primer comprising SEQ ID NO: 133; primer pair 18 represented by a primer comprising SEQ ID NO: 137 and a primer comprising SEQ ID NO: 138; primer pair 19 represented by a primer comprising SEQ ID NO: 142 and a primer comprising SEQ ID NO: 143; primer pair 20 represented by a primer comprising SEQ ID NO: 147 and a primer comprising SEQ ID NO: 148; primer pair 21 represented by a primer comprising SEQ ID NO: 152 and a primer comprising SEQ ID NO: 153; primer pair 22 by a primer comprising SEQ ID NO: 157 and a primer comprising SEQ ID NO: 158; primer pair 23 represented by a primer comprising SEQ ID NO: 162 and a primer comprising SEQ ID NO: 163; primer pair 24 represented by a primer comprising SEQ ID NO: 167 and a primer comprising SEQ ID NO: 168; primer pair 25 represented by a primer comprising SEQ ID NO: 172 and a primer comprising SEQ ID NO: 173; primer pair 26 represented by a primer comprising SEQ ID NO: 177 and a primer comprising SEQ ID NO: 178; primer pair 27 represented by a primer comprising SEQ ID NO: 182 and a primer comprising SEQ ID NO: 183; primer pair 28 represented by a primer comprising SEQ ID NO: 187 and a primer comprising SEQ ID NO: 188; primer pair 29 represented by a primer comprising SEQ ID NO: 192 and a primer comprising SEQ ID NO: 193; primer pair 30 represented by a primer comprising SEQ ID NO: 197 and a primer comprising SEQ ID NO: 198; primer pair 31 represented by a primer comprising SEQ ID NO: 202 and a primer comprising SEQ ID NO: 203; primer pair 32 by a primer comprising SEQ ID NO: 207 and a primer comprising SEQ ID NO: 208; primer pair 33 represented by a primer comprising SEQ ID NO: 212 and a primer comprising SEQ ID NO: 213; primer pair 34 represented by a primer comprising SEQ ID NO: 217 and a primer comprising SEQ ID NO: 218; primer pair 35 represented by a primer comprising SEQ ID NO: 222 and a primer comprising SEQ ID NO: 223; primer pair 36 represented by a primer comprising SEQ ID NO: 227 and a primer comprising SEQ ID NO: 228; primer pair 37 represented by a primer comprising SEQ ID NO: 232 and a primer comprising SEQ ID NO: 233; primer pair 38 represented by a primer comprising SEQ ID NO: 237 and a primer comprising SEQ ID NO: 238; primer pair 39 represented by a primer comprising SEQ ID NO: 242 and a primer comprising SEQ ID NO: 243; primer pair 40 represented by a primer comprising SEQ ID NO: 247 and a primer comprising SEQ ID NO: 248; primer pair 41 represented by a primer comprising SEQ ID NO: 252 and a primer comprising SEQ ID NO: 253; primer pair 42 by a primer comprising SEQ ID NO: 257 and a primer comprising SEQ ID NO: 258; primer pair 43 represented by a primer comprising SEQ ID NO: 262 and a primer comprising SEQ ID NO: 263; primer pair 44 represented by a primer comprising SEQ ID NO: 267 and a primer comprising SEQ ID NO: 268; primer pair 45 represented by a primer comprising SEQ ID NO: 272 and a primer comprising SEQ ID NO: 273; primer pair 46 represented by a primer comprising SEQ ID NO: 277 and a primer comprising SEQ ID NO: 278; primer pair 47 represented by a primer comprising SEQ ID NO: 282 and a primer comprising SEQ ID NO: 283; primer pair 48 represented by a primer comprising SEQ ID NO: 287 and a primer comprising SEQ ID NO: 288; primer pair 49 represented by a primer comprising SEQ ID NO: 292 and a primer comprising SEQ ID NO: 293; primer pair 50 represented by a primer comprising SEQ ID NO: 297 and a primer comprising SEQ ID NO: 298; and primer pair 51 represented by a primer comprising SEQ ID NO: 302 and a primer comprising SEQ ID NO: 303; and (b) introgressing the allele of interest into Zea mays germplasm that lacks the allele. In some embodiments, the allele of interest comprises any of SEQ ID NOs: 1-51, 54, 59, 64, 69, 74, 79, 84, 89, 94, 99, 104, 109, 114, 119, 124, 129, 134, 139, 144, 149, 154, 164, 169, 174, 179, 184, 189, 194, 199, 204, 209, 214, 219, 224, 229, 234, 239, 249, 254, 259, 264, 269, 274, 279, 284, 289, 294, 299, 304, and 307-382.

The presently disclosed subject matter also provides methods for identifying a Zea mays plant comprising at least one allele associated with improved yield. In some embodiments, the methods comprise (a) genotyping at least one Zea mays plant with at least one nucleic acid marker selected from among SEQ ID NOs: 1-51, 54, 59, 64, 69, 74, 79, 84, 89, 94, 99, 104, 109, 114, 119, 124, 129, 134, 139, 144, 149, 154, 159, 164, 174, 179, 184, 189, 194, 199, 204, 209, 214, 219, 224, 229, 234, 239, 244, 249, 259, 264, 269, 274, 279, 284, 289, 294, 299, 304, and 307-382; and (b) selecting at least one Zea mays plant comprising an allele of at least one of the at least one nucleic acid marker that is associated with improved yield. In some embodiments, the allele associated with improved yield comprises a nucleotide sequence at least 85% identical to the full length nucleotide sequence set forth in any of SEQ ID NOs: 1-51, 54, 59, 64, 69, 74, 79, 84, 89, 94, 99, 104, 109, 114, 119, 124, 129, 134, 139, 144, 149, 154, 159, 169, 174, 179, 184, 189, 194, 199, 204, 209, 214, 219, 224, 229, 234, 239, 244, 254, 259, 264, 269, 274, 279, 284, 289, 294, 299, 304, and 307-382. In some embodiments, the allele associated with improved yield is a favorable allele that positively correlates with an improved yield trait.

The presently disclosed subject matter also provides methods for producing inbred Zea mays plants adapted for conferring, in hybrid combination with a suitable second inbred, improved yield. In some embodiments, the methods comprise (a) selecting a first donor parental line possessing a desired yield trait and having at least one of improved yield loci selected from the Zea mays loci ZmDWF1, mapped by one or more of the markers SEQ ID NOs: 1, 50, 51, 54, 299, 304, 307, 308, and 380-382; ZmZfl2, mapped by one or more of the markers SEQ ID NOs: 2-4, 59, 64, 69, and 309-312; ZmFea2, mapped by one or more of the markers SEQ ID NOs: 5-7, 74, 79, 89, and 313-316; ZmZfl1, mapped by one or more of the markers SEQ ID NOs: 8, 9, 89, 94, and 317-319; M1_8138, mapped by one or more of the markers SEQ ID NOs: 10, 99, 320, and 321; ZmCat3, mapped by one or more of the markers SEQ ID NOs: 11, 12, 104, and 322-324; Zm013154, mapped by one or more of the markers SEQ ID NOs: 13, 325, and 326; ZmSTP1, mapped by one or more of the markers SEQ ID NOs: 14, 119, 124, and 327-329; ZmCaT, mapped by one or more of the markers SEQ ID NOs: 16, 129, 330, and 331; ZmAlaAT, mapped by one or more of the markers SEQ ID NOs: 17-19, 134, 139, 144, and 332-335; ZmD11/DWARF4L1, mapped by one or more of the markers SEQ ID NOs: 20, 21, 149, 154, and 336-338; ZmDWARF4, mapped by one or more of the markers SEQ ID NOs: 22, 23, 159, 164, and 339-341; ZmTD1, mapped by one or more of the markers SEQ ID NOs: 24-26, 169, 174, 179, and 342-345; ZmBT2, mapped by one or more of the markers SEQ ID NOs: 27, 28, 184, 189, and 346-348; ZmVrs1.1, mapped by one or more of the markers SEQ ID NOs: 29, 30, 194, and 349-351; ZmSPS1, mapped by one or more of the markers SEQ ID NOs: 31, 352, and 353; ZmBRl1, mapped by one or more of the markers SEQ ID NOs: 32-34, 209, 214, 219, and 354-357; ZmCaT2, mapped by one or more of the markers SEQ ID NOs: 35-37, 224, 229, 234, and 358-361; ZmCKX1, mapped by one or more of the markers SEQ ID NOs: 38-41, 239, 244, 249, 254, and 362-366; ZmCKX4, mapped by one or more of the markers SEQ ID NOs: 42, 259, 367, and 368; ZmCKX7, mapped by one or more of the markers SEQ ID NOs: 43, 44, 264, 269, and 369-371; ZmGW2-2, mapped by one or more of the markers SEQ ID NOs: 45, 46, 274, 279, and 372-374; ZmKRN1, mapped by one or more of the markers SEQ ID NOs: 47, 284, 375, and 376; and ZmVRS1-3, mapped by one or more of the markers SEQ ID NOs: 48, 49, 289, 294, and 377-379; (b) crossing the first donor parent line with a second parental line in hybrid combination to produce a segregating plant population; (c) screening the segregating plant population for presence of an allele associated with improved yield; and (d) selecting plants from the population having the allele for further screening until a line is obtained which is homozygous for improved yield at sufficient loci to give improved yield in hybrid combination.

The presently disclosed subject matter also provides methods for producing a Zea mays plant with improved yield. In some embodiments, the methods comprise (a) providing a Zea mays plant which contains one or more alleles that confer improved yield, wherein each of the one or more alleles that confer improved yield is selected from among Zea mays loci ZmDWF1, ZmZfl2, ZmFea2, ZmZfl1, M1_8138, ZmCat3, Zm013154, ZmSTP1, ZmCaT, ZmAlaAT, ZmD11/DWARF4L1, ZmDWARF4, ZmTD1, ZmBT2, ZmVrs1.1, ZmSPS1, ZmBRI1, ZmCaT2, ZmCKX1, ZmCKX4, ZmCKX7, ZmGW2-2, ZmKRN1, and ZmVRS1-3, and (b) crossing the Zea mays plant provided in step (a) with Zea mays breeding material to produce one or more progeny individuals, whereby one or more Zea mays plants with improved yield are produced. In some embodiments, ZmDWF1 maps to Zea mays chromosome 5 and comprises a nucleotide sequence at least 85% identical to one of SEQ ID NOs: 1, 50, 51, 54, 299, 304, 307, 308, and 380-382; ZmZfl2 maps to Zea mays chromosome 2 and comprises a nucleotide sequence at least 85% identical to one of SEQ ID NOs: 2-4, 59, 64, 69, and 309-312; ZmFea2 maps to Zea mays chromosome 4 and comprises a nucleotide sequence at least 85% identical to one of SEQ ID NOs: 5-7, 74, 79, 89, and 313-316; ZmZfl1 maps to Zea mays chromosome 10 and comprises a nucleotide sequence at least 85% identical to one of SEQ ID NOs: 8, 9, 89, 94, and 317-319; M1_8138 maps to Zea mays chromosome 3 and comprises a nucleotide sequence at least 85% identical to one of SEQ ID NOs: 10, 99, 320, and 321; ZmCat3 maps to Zea mays chromosome 4 and comprises a nucleotide sequence at least 85% identical to one of SEQ ID NOs: 11, 12, 109, and 322-324; Zm013154 maps to Zea mays chromosome 9 and comprises a nucleotide sequence at least 85% identical to one of SEQ ID NOs: 13, 114, 325, and 326; ZmSTP1 maps to Zea mays chromosome 8 and comprises a nucleotide sequence at least 85% identical to one of SEQ ID NOs: 14, 15, 119, 124, and 327-329; ZmCaT maps to Zea mays chromosome 8 and comprises a nucleotide sequence at least 85% identical to one of SEQ ID NOs: 16, 129, 330, and 331; ZmAlaAT maps to Zea mays chromosome 5 and comprises a nucleotide sequence at least 85% identical to one of SEQ ID NOs: 17-19, 134, 139, 144, and 332-335; ZmD11/DWARF4L1 maps to Zea mays chromosome 2 and comprises a nucleotide sequence at least 85% identical to one of SEQ ID NOs: 20, 21, 149, 154, and 336-338; ZmDWARF4 maps to Zea mays chromosome 1 and comprises a nucleotide sequence at least 85% identical to one of SEQ ID NOs: 22, 23, 159, 164, and 339-341; ZmTD1 maps to Zea mays chromosome 5 comprises a nucleotide sequence at least 85% identical to one of SEQ ID NOs: 24-26, 169, 174, 179, and 342-345; ZmBT2 maps to Zea mays chromosome 6 and comprises a nucleotide sequence at least 85% identical to one of SEQ ID NOs: 27, 28, 189, and 346-348; ZmVrs1.1 comprises a nucleotide sequence at least 85% identical to one of SEQ ID NOs: 29, 30, 194, 199, and 349-351; ZmSPS1 maps to Zea mays chromosome 8 and comprises a nucleotide sequence at least 85% identical to one of SEQ ID NOs: 31, 204, 352, and 353; ZmBRI1 maps to Zea mays chromosome 8 and comprises a nucleotide sequence at least 85% identical to one of SEQ ID NOs: 32-34, 209, 214, 219, and 354-357; ZmCaT2 maps to Zea mays chromosome 3 and comprises a nucleotide sequence at least 85% identical to one of SEQ ID NOs: 35-37, 224, 229, 234, and 358-361; ZmCKX1 maps to Zea mays chromosome 3 and comprises a nucleotide sequence at least 85% identical to one of SEQ ID NOs: 38-41, 239, 244, 249, 254, and 362-366; ZmCKX4 maps to Zea mays chromosome 3 and comprises a nucleotide sequence at least 85% identical to one of SEQ ID NOs: 42, 259, 367, and 368; ZmCKX7 comprises a nucleotide sequence at least 85% identical to one of SEQ ID NOs: 43, 44, 264, 269, and 369-371; ZmGW2-2 maps to Zea mays chromosome 5 and comprises a nucleotide sequence at least 85% identical to one of SEQ ID NOs: 45, 46, 279, and 372-374; ZmKRN1 maps to Zea mays chromosome 1 and comprises a nucleotide sequence at least 85% identical to one of SEQ ID NOs: 47, 284, 375, and 376; and ZmVRS1-3 maps to Zea mays chromosome 1 and comprises a nucleotide sequence at least 85% identical to one of SEQ ID NOs: 48, 49, 289, 294, and 377-379. In some embodiments, the methods further comprise (c) collecting the seeds resulting from the cross in step (b); (d) regenerating the seeds into plants; (e) evaluating the plants of step (d) for improved yield; and (f) identifying and selecting plants which have improved yield.

In some embodiments of the presently disclosed methods, the allele of interest is a favorable allele that positively correlates with an improved yield-associated trait. In some embodiments, the yield trait is grain yield at standard moisture percentage (YGSMN), and the favorable allele comprises a nucleotide sequence comprising a G at nucleotide position 2420 of SEQ ID NO: 2; a G at nucleotide position 2709 of SEQ ID NO: 3; a T at nucleotide position 368 of SEQ ID NO: 4; a C at nucleotide position 4038 SEQ ID NO: 5; a C at nucleotide position 4038 of SEQ ID NO: 6; an A at nucleotide position 402 of SEQ ID NO: 7; a T at nucleotide position 3050 of SEQ ID NO: 8; a C at nucleotide position 408 of SEQ ID NO: 10; a C at nucleotide position 160 of SEQ ID NO: 11; a C at nucleotide position 311 of SEQ ID NO: 12; an A at nucleotide position 338 of SEQ ID NO: 13; an A at nucleotide position 5356 of SEQ ID NO: 14; a C at nucleotide position 5371 of SEQ ID NO: 15; an A at nucleotide position 1587 of SEQ ID NO: 16; an A at nucleotide position 388 of SEQ ID NO: 17; a T at nucleotide position 494 of SEQ ID NO: 18; a T at nucleotide position 112 of SEQ ID NO: 19; a T at nucleotide position 2458 SEQ ID NO: 20; a T at nucleotide position 4037 of SEQ ID NO: 21; a T at nucleotide position 849 of SEQ ID NO: 22; a G at nucleotide position 1032 of SEQ ID NO: 24; an A at nucleotide position 286 of SEQ ID NO: 25; an A at nucleotide position 346 of SEQ ID NO: 26; an A at nucleotide position 6968 of SEQ ID NO: 27; an A at nucleotide position 6083 of SEQ ID NO: 28; an A at nucleotide position 1729 of SEQ ID NO: 29; a C at nucleotide position 1668 of SEQ ID NO: 30; a G at nucleotide position 1255 of SEQ ID NO: 32; a C at nucleotide position 1336 of SEQ ID NO: 33; a G at nucleotide position 1486 of SEQ ID NO: 34; an A at nucleotide position 1742 of SEQ ID NO: 35; a T at nucleotide position 631 of SEQ ID NO: 37; a T at nucleotide position 3860 of SEQ ID NO: 40; an A at nucleotide position 903 of SEQ ID NO: 42; an A at nucleotide position 1795 SEQ ID NO: 43; a T at nucleotide position 3597 of SEQ ID NO: 45; an A at nucleotide position 3611 of SEQ ID NO: 46; a C at nucleotide position 1603 of SEQ ID NO: 50; or an A at nucleotide position 2859 of SEQ ID NO: 51; the yield trait is grain moisture at harvest (GMSTP), and the favorable allele comprises a nucleotide sequence comprising a C at nucleotide position 2420 of SEQ ID NO: 2; a T at nucleotide position 2709 of SEQ ID NO: 3; a T at nucleotide position 368 of SEQ ID NO: 4; a T at nucleotide position 4038 of SEQ ID NO: 5; a T at nucleotide position 4038 of SEQ ID NO: 6; a G at nucleotide position 402 of SEQ ID NO: 7; a G at nucleotide position 3050 of SEQ ID NO: 8; a G at nucleotide position 2146 of SEQ ID NO: 9; a T at nucleotide position 408 of SEQ ID NO: 10; a G at nucleotide position 160 of SEQ ID NO: 11; a G at nucleotide position 338 of SEQ ID NO: 13; a G at nucleotide position 5356 of SEQ ID NO: 14; an A at nucleotide position 5371 of SEQ ID NO: 15; a G at nucleotide position 1587 of SEQ ID NO: 16; a G at nucleotide position 388 of SEQ ID NO: 17; a G at nucleotide position 112 SEQ ID NO: 19; an A at nucleotide position 2458 of SEQ ID NO: 20; a C at nucleotide position 1032 of SEQ ID NO: 24; a G at nucleotide position 286 of SEQ ID NO: 25; a T at nucleotide position 6968 of SEQ ID NO: 27; a G at nucleotide position 6083 of SEQ ID NO: 28; a G at nucleotide position 1729 of SEQ ID NO: 29; an A at nucleotide position 1668 of SEQ ID NO: 30; a G at nucleotide position 5516 of SEQ ID NO: 31; a G at nucleotide position 1255 of SEQ ID NO: 32; a G at nucleotide position 1486 of SEQ ID NO: 34; an A at nucleotide position 1742 of SEQ ID NO: 35; a C at nucleotide position 2457 of SEQ ID NO: 36; a G at nucleotide position 945 of SEQ ID NO: 38; an A at nucleotide position 2378 of SEQ ID NO: 39; an A at nucleotide position 3860 of SEQ ID NO: 40; a G at nucleotide position 2519 of SEQ ID NO: 41; a G at nucleotide position 903 of SEQ ID NO: 42; a T at nucleotide position 2040 of SEQ ID NO: 44; an A at nucleotide position 3597 of SEQ ID NO: 45; an A at nucleotide position 3611 of SEQ ID NO: 46; a G at nucleotide position 131 of SEQ ID NO: 47; an A at nucleotide position 2273 of SEQ ID NO: 48; a C at nucleotide position 187 of SEQ ID NO: 49; a C at nucleotide position 1603 of SEQ ID NO: 50; or an A at nucleotide position 2859 of SEQ ID NO: 51; and/or the yield trait is grain weight per plot (GWTPN), and the favorable allele comprises a nucleotide sequence comprising a G at nucleotide position 1333 of SEQ ID NO: 1; a T at nucleotide position 368 of SEQ ID NO: 4; a T at nucleotide position 4038 of SEQ ID NO: 5; a C at nucleotide position 408 of SEQ ID NO: 10; an A at nucleotide position 338 of SEQ ID NO: 13; a G at nucleotide position 966 of SEQ ID NO: 23; or an A at nucleotide position 286 of SEQ ID NO: 25.

The presently disclosed subject matter also provides improved *Zea mays* plants produced by the presently disclosed methods, or parts, seeds, progeny, or tissue cultures thereof.

The presently disclosed subject matter also provides *Zea mays* plants, optionally inbred *Zea mays* plants, that comprise one or more of the alleles associated with a desired yield-associated trait. In some embodiments, the yield trait is grain yield at standard moisture percentage (YGSMN), and at least one of the alleles of interest is selected from a nucleotide sequence comprising a G at nucleotide position 2420 of SEQ ID NO: 2; a G at nucleotide position 2709 of SEQ ID NO: 3; a T at nucleotide position 368 of SEQ ID NO: 4; a C at nucleotide position 4038 of SEQ ID NO: 5; a C at nucleotide position 4038 of SEQ ID NO: 6; an A at nucleotide position 402 of SEQ ID NO: 7; a T at nucleotide position 3050 of SEQ ID NO: 8; a C at nucleotide position 408 of SEQ ID NO: 10; a C at nucleotide position 160 of SEQ ID NO: 11; a C at nucleotide position 311 of SEQ ID NO: 12; an A at nucleotide position 338 of SEQ ID NO: 13; an A at nucleotide position 5356 of SEQ ID NO: 14; a C at nucleotide position 5371 of SEQ ID NO: 15; an A at nucleotide position 1587 of SEQ ID NO: 16; an A at nucleotide position 388 of SEQ ID NO: 17; a T at nucleotide position 494 of SEQ ID NO: 18; a T at nucleotide position 112 of SEQ ID NO: 19; a T at nucleotide position 2458 of SEQ ID NO: 20; a T at nucleotide position 4037 of SEQ ID NO: 21; a T at nucleotide position 849 of SEQ ID NO: 22; a G at nucleotide position 1032 of SEQ ID NO: 24; an A at nucleotide position 286 of SEQ ID NO: 25; an A at nucleotide position 346 of SEQ ID NO: 26; an A at nucleotide position 6968 of SEQ ID NO: 27; an A at nucleotide position 6083 of SEQ ID NO: 28; an A at nucleotide position 1729 of SEQ ID NO: 29; a C at nucleotide position 1668 of SEQ ID NO: 30; a G at nucleotide position 1255 of SEQ ID NO: 32; a C at nucleotide position 1336 of SEQ ID NO: 33; a G at nucleotide position 1486 of SEQ ID NO: 34; an A at nucleotide position 1742 of SEQ ID NO: 35; a T at nucleotide position 631 of SEQ ID NO: 37; a T at nucleotide position 3860 of SEQ ID NO: 40; an A at nucleotide position 903 of SEQ ID NO: 42; an A at nucleotide position 1795 of SEQ ID NO: 43; a T at nucleotide position 3597 of SEQ ID NO: 45; an A at nucleotide position 3611 of SEQ ID NO: 46; a C at nucleotide position 1603 of SEQ ID NO: 50; and an A at nucleotide position 2859 of SEQ ID NO: 51. In some embodiments, the yield trait is grain moisture at harvest (GMSTP), and at least one of the alleles of interest is selected from a nucleotide sequence comprising a C at nucleotide position 2420 of SEQ ID NO: 2; a T at nucleotide position 2709 of SEQ ID NO: 3; a T at nucleotide position 368 of SEQ ID NO: 4; a T at nucleotide position 4038 of SEQ ID NO: 5; a T at nucleotide position 4038 of SEQ ID NO: 6; a G at nucleotide position 402 of SEQ ID NO: 7; a G at nucleotide position 3050 of SEQ ID NO: 8; a G at nucleotide position 2146 of SEQ ID NO: 9; a T at nucleotide position 408 of SEQ ID NO: 10; a G at nucleotide position 160 SEQ ID NO: 11; a G at nucleotide position 338 of SEQ ID NO: 13; a G at nucleotide position 5356 of SEQ ID NO: 14; an A at nucleotide position 5371 of SEQ ID NO: 15; a G at nucleotide position 1587 of SEQ ID NO: 16; a G at nucleotide position 388 of SEQ ID NO: 17; a G at nucleotide position 112 of SEQ ID NO: 19; an A at nucleotide position 2458 of SEQ ID NO: 20; a C at nucleotide position 1032 of SEQ ID NO: 24; a G at nucleotide position 286 of SEQ ID NO: 25; a T at nucleotide position 6968 of SEQ ID NO: 27; a G at nucleotide position 6083 of SEQ ID NO: 28; a G at nucleotide position 1729 of SEQ ID NO: 29; an A at nucleotide position 1668 of SEQ ID NO: 30; a G at nucleotide position 5516 of SEQ ID NO: 31; a G at nucleotide position 1255 of SEQ ID NO: 32; a G at nucleotide position 1486 of SEQ ID NO: 34; an A at nucleotide position 1742 of SEQ ID NO: 35; a C at nucleotide position 2457 of SEQ ID NO: 36; a G at nucleotide position 945 of SEQ ID NO: 38; an A at nucleotide position 2378 of SEQ ID NO: 39; an A at nucleotide position 3860 of SEQ ID NO: 40; a G at nucleotide position 2519 of SEQ ID NO: 41; a G at nucleotide position 903 of SEQ ID NO: 42; a T at nucleotide position 2040 of SEQ ID NO: 44; an A at nucleotide position 3597 of SEQ ID NO: 45; an A at nucleotide position 3611 of SEQ ID NO: 46; a G at nucleotide position 131 of SEQ ID NO: 47; an A at nucleotide position 2273 of SEQ ID NO: 48; a C at nucleotide position 187 of SEQ ID NO: 49; a C at nucleotide position 1603 of SEQ ID NO: 50; and an A at nucleotide position 2859 of SEQ ID NO: 51. In some embodiments, the yield trait is grain weight per plot (GWTPN), and at least one of the alleles of interest is selected from a nucleotide sequence comprising a G at nucleotide position 1333 of SEQ ID NO: 1; a T at nucleotide position 368 of SEQ ID NO: 4; a T at nucleotide position 4038 of SEQ ID NO: 5; a C at nucleotide position 408 of SEQ ID NO: 10; an A at nucleotide position 338 SEQ ID NO: 13; a G at nucleotide position 966 of SEQ ID NO: 23; or an A at nucleotide position 286 of SEQ ID NO: 25. In some embodiments, the *Zea mays* plant comprises a plurality of alleles of interest disclosed herein, including, but not limited to 2, 4, 5, 6, 7, 8, 9, 10, 15, 20, or more of the alleles of interest disclosed herein.

The presently disclosed subject matter also provides elite *Zea mays* plants produced from the disclosed improved *Zea mays* plants.

The presently disclosed subject matter also provides biomass produced from the disclosed improved *Zea mays* plants, or from a progeny plant thereof, or from a part, seed, or tissue culture thereof.

The presently disclosed subject matter also provides isolated and purified genetic markers associated with yield traits in *Zea mays*. In some embodiments, the isolated and purified genetic marker (a) comprise a nucleotide sequence as set forth in any of SEQ ID NOs: 1-382, or the reverse complement thereof, or an informative fragment thereof; and/or (b) comprise a nucleotide sequence of an amplification product or an informative fragment thereof from a nucleic acid sample isolated from a *Zea mays* plant, wherein the amplification product is produced by amplifying a *Zea mays* nucleic acid using a pair of oligonucleotide primers selected from among SEQ ID NOs: 52 and 53, SEQ ID NOs: 57 and 58, SEQ ID NOs: 62 and 63, SEQ ID NOs: 67 and 68, SEQ ID NOs: 72 and 73, SEQ ID NOs: 77 and 78, SEQ ID NOs: 82 and 83, SEQ ID NOs: 87 and 88, SEQ ID NOs: 92 and 93, SEQ ID NOs: 97 and 98, SEQ ID NOs: 102 and 103, SEQ ID NOs: 107 and 108, SEQ ID NOs: 112 and 113, SEQ ID NOs: 117 and 118, SEQ ID NOs: 122 and 123, SEQ ID NOs: 127 and 128, SEQ ID NOs: 132 and 133, SEQ ID NOs: 137 and 138, SEQ ID NOs: 142 and 143, SEQ ID NOs: 147 and 148, SEQ ID NOs: 152 and 153, SEQ ID NOs: 157 and 158, SEQ ID NOs: 162 and 163, SEQ ID NOs: 167 and 168, SEQ ID NOs: 172 and 173, SEQ ID NOs: 177 and 178, SEQ ID NOs: 182 and 183, SEQ ID NOs: 187 and 188, SEQ ID NOs: 192 and 193, SEQ ID NOs: 197 and 198, SEQ ID NOs: 202 and 203, SEQ ID NOs: 207 and 208, SEQ ID NOs: 212 and 213, SEQ ID NOs: 217 and 218, SEQ ID NOs: 222 and 223, SEQ ID NOs: 227 and 228, SEQ ID NOs: 232 and 233, SEQ ID NOs: 237 and 238, SEQ ID NOs: 242 and 243, SEQ ID NOs: 247 and 248, SEQ ID NOs: 252 and 253, SEQ ID NOs: 257 and 258, SEQ ID NOs: 262 and 263, SEQ ID NOs: 267 and 268, SEQ ID NOs: 272 and 273, SEQ ID NOs: 277 and 278, SEQ ID NOs: 282 and 283, SEQ ID NOs: 287 and 288, SEQ ID NOs: 292 and 293, SEQ ID NOs: 297 and 298; and SEQ ID NOs: 302 and 303. In some embodiments, the isolated and purified genetic markers permit identification of a nucleotide in the genome of a *Zea mays* plant that corresponds to the nucleotide present at any of nucleotide position 1333 of SEQ ID NO: 1, nucleotide position 2420 of SEQ ID NO: 2, nucleotide position 2709 of SEQ ID NO: 3, nucleotide position 368 of SEQ ID NO: 4, nucleotide position 4038 of SEQ ID NO: 5, nucleotide position 4038 of SEQ ID NO: 6, nucleotide position 402 of SEQ ID NO: 7, nucleotide position 3050 of SEQ ID NO: 8, nucleotide position 2146 of SEQ ID NO: 9, nucleotide position 408 of SEQ ID NO: 10, nucleotide position 160 of SEQ ID NO: 11, nucleotide position 311 of SEQ ID NO: 12, nucleotide position 338 of SEQ ID NO: 13, nucleotide position 5356 of SEQ ID NO: 14, nucleotide position 5371 of SEQ ID NO: 15, nucleotide position 1587 of SEQ ID NO: 16, nucleotide position 388 of SEQ ID NO: 17, nucleotide position 494 of SEQ ID NO: 18, nucleotide position 112 of SEQ ID NO: 19, nucleotide position 2458 of SEQ ID NO: 20, nucleotide position 4037 of SEQ ID NO: 21, nucleotide position 849 of SEQ ID NO: 22, nucleotide position 966 of SEQ ID NO: 23; nucleotide position 1032 of SEQ ID NO: 24, nucleotide position 286 of SEQ ID NO: 25, nucleotide position 346 of SEQ ID NO: 26, nucleotide position 6968 of SEQ ID NO: 27, nucleotide position 6083 of SEQ ID NO: 28, nucleotide position 1729 of SEQ ID NO: 29, nucleotide position 1668 of SEQ ID NO: 30, nucleotide position 5516 of SEQ ID NO: 31, nucleotide position 1255 of SEQ ID NO: 32, nucleotide position 1336 of SEQ ID NO: 33, nucleotide position 1486 of SEQ ID NO: 34, nucleotide position 1742 of SEQ ID NO: 35, nucleotide position 2457 of SEQ ID NO: 36, nucleotide position 631 of SEQ ID NO: 37, nucleotide position 945 of SEQ ID NO: 38, nucleotide position 2378 of SEQ ID NO: 39, nucleotide position 3860 of SEQ ID NO: 40, nucleotide position 2519 of SEQ ID NO: 41, nucleotide position 903 of SEQ ID NO: 42, nucleotide position 1795 of SEQ ID NO: 43, nucleotide position 2040 of SEQ ID NO: 44, nucleotide position 3597 of SEQ ID NO: 45, nucleotide position 3611 of SEQ ID NO: 46, nucleotide position 131 of SEQ ID NO: 47, nucleotide position 2273 of SEQ ID NO: 48, nucleotide position 187 of SEQ ID NO: 49, nucleotide position 1603 of SEQ ID NO: 50; and nucleotide position 2859 of SEQ ID NO: 51. In some embodiments, the isolated and purified genetic markers further comprise a detectable moiety.

The presently disclosed subject matter also provides compositions comprising one or more amplification primer pairs capable of amplifying a *Zea mays* nucleic acid to generate a *Zea mays* marker amplicon. In some embodiments, the *Zea mays* marker amplicon corresponds to any of SEQ ID NOs: 1-51, 54, 59, 64, 69, 74, 79, 84, 89, 94, 99, 104, 109, 114, 119, 124, 129, 134, 139, 144, 149, 154, 159, 164, 169, 174, 179, 184, 194, 199, 204, 209, 214, 219, 224, 229, 234, 239, 244, 249, 254, 259, 264, 269, 279, 284, 289, 294, 299, 304, and 307-382.

Thus, it is an object of the presently disclosed subject matter to provide methods for conveying one or more yield traits into maize germplasm.

An object of the presently disclosed subject matter having been stated hereinabove, and which is achieved in whole or in part by the presently disclosed subject matter, other objects will become evident as the description proceeds when taken in connection with the accompanying Figures as best described herein below.

BRIEF DESCRIPTION OF THE SEQUENCE LISTING

SEQ ID NO: 1 is a nucleotide sequence that is associated with the yield locus ZmDWF1, subsequences of which can be amplified from chromosome 5 of the *Zea mays* genome using the polymerase chain reaction with amplification primers as set forth in Table 1 below.

SEQ ID NOs: 2-4 are nucleotide sequences that are associated with the yield locus ZmZfl2, subsequences of which can be amplified from chromosome 2 of the *Zea mays* genome using the polymerase chain reaction with amplification primers as set forth in Table 1 below.

SEQ ID NOs: 5-7 are nucleotide sequences that are associated with the yield locus ZmFea2, subsequences of which can be amplified from chromosome 4 of the *Zea mays* genome using the polymerase chain reaction with amplification primers as set forth in Table 1 below.

SEQ ID NOs: 8 and 9 are nucleotide sequences that are associated with the yield locus ZmZfl1, subsequences of which can be amplified from chromosome 10 of the *Zea mays* genome using the polymerase chain reaction with amplification primers as set forth in Table 1 below.

SEQ ID NO: 10 is a nucleotide sequence that is associated with the yield locus M1_8138, a subsequence of which can be amplified from chromosome 3 of the *Zea mays* genome using the polymerase chain reaction with amplification primers as set forth in Table 1 below.

SEQ ID NOs: 11 and 12 are nucleotide sequences that are associated with the yield locus ZmCat3, subsequences of which can be amplified from chromosome 4 of the *Zea mays* genome using the polymerase chain reaction with amplification primers as set forth in Table 1 below.

SEQ ID NO: 13 is a nucleotide sequence that is associated with the yield locus Zm013154, a subsequence of which can be amplified from chromosome 9 of the *Zea mays* genome using the polymerase chain reaction with amplification primers as set forth in Table 1 below.

SEQ ID NOs: 14 and 15 are nucleotide sequences that are associated with the yield locus ZmSTP1, subsequences of which can be amplified from chromosome 8 of the *Zea mays* genome using the polymerase chain reaction with amplification primers as set forth in Table 1 below.

SEQ ID NO: 16 is a nucleotide sequence that is associated with the yield locus ZmCaT, a subsequence of which can be amplified from chromosome 8 of the *Zea mays* genome using the polymerase chain reaction with amplification primers as set forth in Table 1 below.

SEQ ID NOs: 17-19 are nucleotide sequences that are associated with the yield locus ZmAlaAT, subsequences of which can be amplified from chromosome 5 of the *Zea mays* genome using the polymerase chain reaction with amplification primers as set forth in Table 1 below.

SEQ ID NOs: 20 and 21 are nucleotide sequences that are associated with the yield locus ZmD11/DWARF4L1, subsequences of which can be amplified from chromosome 2 of the *Zea mays* genome using the polymerase chain reaction with amplification primers as set forth in Table 1 below.

SEQ ID NOs: 22 and 23 are nucleotide sequences that are associated with the yield locus ZmDWARF4, subsequences of which can be amplified from chromosome 1 the *Zea mays* genome using the polymerase chain reaction with amplification primers as set forth in Table 1 below.

SEQ ID NOs: 24-26 are nucleotide sequences that are associated with the yield locus ZmTD1, subsequences of which can be amplified from chromosome 5 of the *Zea mays* genome using the polymerase chain reaction with amplification primers as set forth in Table 1 below.

SEQ ID NOs: 27 and 28 are nucleotide sequences that are associated with the yield locus ZmBT2, subsequences of which can be amplified from chromosome 6 of the *Zea mays* genome using the polymerase chain reaction with amplification primers as set forth in Table 1 below.

SEQ ID NOs: 29 and 30 are nucleotide sequences that are associated with the yield locus ZmVrs1-1, subsequences of which can be amplified from the *Zea mays* genome using the polymerase chain reaction with amplification primers as set forth in Table 1 below.

SEQ ID NO: 31 is a nucleotide sequence that is associated with the yield locus ZmSPS1, a subsequence of which can be amplified from chromosome 8 of the *Zea mays* genome using the polymerase chain reaction with amplification primers as set forth in Table 1 below.

SEQ ID NOs: 32-34 are nucleotide sequences that are associated with the yield locus ZmBRI1, subsequences of which can be amplified from chromosome 8 of the *Zea mays* genome using the polymerase chain reaction with amplification primers as set forth in Table 1 below.

SEQ ID NOs: 35-37 are nucleotide sequences that are associated with the yield locus ZmCaT2, subsequences of which can be amplified from chromosome 3 of the *Zea mays* genome using the polymerase chain reaction with amplification primers as set forth in Table 1 below.

SEQ ID NOs: 38-41 are nucleotide sequences that are associated with the yield locus ZmCKX1, subsequences of which can be amplified from chromosome 3 of the *Zea mays* genome using the polymerase chain reaction with amplification primers as set forth in Table 1 below.

SEQ ID NO: 42 is a nucleotide sequence that is associated with the yield locus ZmCKX4, a subsequence of which can be amplified from chromosome 3 of the *Zea mays* genome using the polymerase chain reaction with amplification primers as set forth in Table 1 below.

SEQ ID NOs: 43 and 44 are nucleotide sequences that are associated with the yield locus ZmCKX7, subsequences of which can be amplified from the *Zea mays* genome using the polymerase chain reaction with amplification primers as set forth in Table 1 below.

SEQ ID NOs: 45 and 46 are nucleotide sequences that are associated with the yield locus ZmGW2.2, subsequences of which can be amplified from chromosome 5 of the *Zea mays* genome using the polymerase chain reaction with amplification primers as set forth in Table 1 below.

SEQ ID NO: 47 is a nucleotide sequence that is associated with the yield locus ZmKRN1, a subsequence of which can be amplified from chromosome 1 of the *Zea mays* genome using the polymerase chain reaction with amplification primers as set forth in Table 1 below.

SEQ ID NOs: 48 and 49 are nucleotide sequences that are associated with the yield locus ZmVRS1-3, subsequences of which can be amplified from chromosome 1 of the *Zea mays* genome using the polymerase chain reaction with amplification primers as set forth in Table 1 below.

SEQ ID NOs: 50 and 51 are nucleotide sequences that are associated with the yield locus ZmDWF1, subsequences of which can be amplified from chromosome 5 of the *Zea mays* genome using the polymerase chain reaction with amplification primers as set forth in Table 1 below.

Table 1 lists SEQ ID NOs. for oligonucleotides that can be employed to amplify *Zea mays* nucleic acids derived from the loci that correspond to SEQ ID NOs: 1-51 and exemplary amplicons produced thereby. Table 1 also lists the nucleotide position in each locus sequence of SEQ ID NOs 1-51 of an SNP that is associated with a yield trait, as well as the corresponding nucleotide position for the SNP in each amplicon.

TABLE 1

SEQ ID NOs. for Oligonucleotides that can be Employed to Amplify *Zea mays* Loci Corresponding to SEQ ID NOs: 1-51

| Locus SEQ ID NO. and Position of SNP (nucleotide) | Amplification Primer 1 SEQ ID NO. | Amplification Primer 2 SEQ ID NO. | Amplicon SEQ ID NO. and Position of SNP (nucleotide) |
|---|---|---|---|
| 1 (1333) | 52 | 53 | 54 (55) |
| 2 (2420) | 57 | 58 | 59 (26) |
| 3 (2709) | 62 | 63 | 64 (44) |
| 4 (368) | 67 | 68 | 69 (49) |
| 5 (4038) | 72 | 73 | 74 (34) |
| 6 (4038) | 77 | 78 | 79 (34) |
| 7 (402) | 82 | 83 | 84 (35) |
| 8 (3050) | 87 | 88 | 89 (56) |
| 9 (2146) | 92 | 93 | 94 (39) |
| 10 (408) | 97 | 98 | 99 (93) |
| 11 (160) | 102 | 103 | 104 (47) |
| 12 (311) | 107 | 108 | 109 (35) |
| 13 (338) | 112 | 113 | 114 (37) |

TABLE 1-continued

SEQ ID NOs. for Oligonucleotides that can be Employed to Amplify
Zea mays Loci Corresponding to SEQ ID NOs: 1-51

| Locus SEQ ID NO. and Position of SNP (nucleotide) | Amplification Primer 1 SEQ ID NO. | Amplification Primer 2 SEQ ID NO. | Amplicon SEQ ID NO. and Position of SNP (nucleotide) |
|---|---|---|---|
| 14 (5356) | 117 | 118 | 119 (58) |
| 15 (5371) | 122 | 123 | 124 (63) |
| 16 (1587) | 127 | 128 | 129 (32) |
| 17 (388) | 132 | 133 | 134 (34) |
| 18 (494) | 137 | 138 | 139 (67) |
| 19 (112) | 142 | 143 | 144 (57) |
| 20 (2458) | 147 | 148 | 149 (74) |
| 21 (4037) | 152 | 153 | 154 (30) |
| 22 (849) | 157 | 158 | 159 (70) |
| 23 (966) | 162 | 163 | 164 (58) |
| 24 (1032) | 167 | 168 | 169 (39) |
| 25 (286) | 172 | 173 | 174 (87) |
| 26 (346) | 177 | 178 | 179 (57) |
| 27 (6968) | 182 | 183 | 184 (38) |
| 28 (6083) | 187 | 188 | 189 (79) |
| 29 (1729) | 192 | 193 | 194 (35) |
| 30 (1668) | 197 | 198 | 199 (58) |
| 31 (5516) | 202 | 203 | 204 (44) |
| 32 (1255) | 207 | 208 | 209 (40) |
| 33 (1336) | 212 | 213 | 214 (45) |
| 34 (1486) | 217 | 218 | 219 (25) |
| 35 (1742) | 222 | 223 | 224 (28) |
| 36 (2457) | 227 | 228 | 229 (58) |
| 37 (631) | 232 | 233 | 234 (24) |
| 38 (945) | 237 | 238 | 239 (28) |
| 39 (2378) | 242 | 243 | 244 (32) |
| 40 (3860) | 247 | 248 | 249 (77) |
| 41 (2519) | 252 | 253 | 254 (60) |
| 42 (903) | 257 | 258 | 259 (54) |
| 43 (1795) | 262 | 263 | 264 (35) |
| 44 (2040) | 267 | 268 | 269 (44) |
| 45 (3597) | 272 | 273 | 274 (65) |
| 46 (3611) | 277 | 278 | 279 (79) |
| 47 (131) | 282 | 283 | 284 (19) |
| 48 (2273) | 287 | 288 | 289 (76) |
| 49 (187) | 292 | 293 | 294 (44) |
| 50 (1603) | 297 | 298 | 299 (36) |
| 51 (2859) | 302 | 303 | 304 (85) |

Table 2 lists SEQ ID NOs. for exemplary oligonucleotides that can be used to assay Zea mays nucleic acid sequences to identify nucleotides that are present at the SNP positions identified in Table 1.

TABLE 2

SEQ ID NOs. for Assay Oligonucleotides

| SEQ ID NO: of Locus Assayed* | SEQ ID NO: of Amplicon Assayed* | Nucleotide Assayed (SEQ ID NO:)[1] | SEQ ID NO: of Locus Assayed* | SEQ ID NO: of Amplicon Assayed* | Nucleotide Assayed (SEQ ID NO:)[1] |
|---|---|---|---|---|---|
| 1 | 54 | T (55) C (56) | 2 | 59 | G (60) C (61) |
| 3 | 64 | T (65) G (66) | 4 | 69 | G (70) T (71) |
| 5 | 74 | A (75) G (76) | 6 | 79 | G (80) A (81) |
| 7 | 84 | T (85) C (86) | 8 | 89 | G (90) T (91) |
| 9 | 94 | C (95) T (96) | 10 | 99 | G (100) A (101) |
| 11 | 104 | C (105) G (106) | 12 | 109 | C (110) G (111) |
| 13 | 114 | T (115) C (116) | 14 | 119 | T (120) C (121) |
| 15 | 124 | T (125) G (126) | 16 | 129 | T (130) C (131) |
| 17 | 134 | A (135) G (136) | 18 | 139 | A (140) C (141) |
| 19 | 144 | T (145) G (146) | 20 | 149 | T (150) A (151) |
| 21 | 154 | T (155) G (156) | 22 | 159 | C (160) T (161) |
| 23 | 164 | A (165) G (166) | 24 | 169 | C (170) G (171) |
| 25 | 174 | C (175) T (176) | 26 | 179 | C (180) A (181) |
| 27 | 184 | T (185) A (186) | 28 | 189 | C (190) T (191) |
| 29 | 194 | G (195) A (196) | 30 | 199 | C (200) A (201) |
| 31 | 204 | A (205) G (206) | 32 | 209 | G (210) A (211) |
| 33 | 214 | C (215) G (216) | 34 | 219 | T (220) C (221) |
| 35 | 224 | T (225) C (226) | 36 | 229 | C (230) A (231) |
| 37 | 234 | T (235) A (236) | 38 | 239 | G (240) A (241) |
| 39 | 244 | T (245) C (246) | 40 | 249 | T (250) A (251) |
| 41 | 254 | T (255) G (256) | 42 | 259 | G (260) A (261) |
| 43 | 264 | G (265) A (266) | 44 | 269 | G (270) A (271) |
| 45 | 274 | T (275) A (276) | 46 | 279 | G (280) A (281) |
| 47 | 284 | C (285) G (286) | 48 | 289 | T (290) A (291) |
| 49 | 294 | C (295) G (296) | 50 | 299 | C (300) A (301) |
| 51 | 304 | T (305) C (306) | | | |

[1]numbers in these columns refer to SEQ ID NOs. for oligonucleotides that can be employed to assay for the listed nucleotide at the listed SNP position.

Table 3 lists SEQ ID NOs 307-382, which are Zea mays genomic sequences present in the GENBANK® database that correspond to SEQ ID NOs: 1-51 as well as amplicons that can be amplified from the corresponding GENBANK® sequences and/or assayed using the oligonucleotides listed in Table 1.

TABLE 3

GENBANK® Database Sequences that Correspond to SEQ ID NOs: 1-51

| SEQ ID NO. | GENBANK® Accession No. | Corresponding Nucleotides* | SEQ ID NO. of Corresponding Nucleotides | GENBANK® Amplicon SEQ ID NO. |
|---|---|---|---|---|
| 1 | AC212758.3 | 120,519-124,445 | 307 | 308 |
| 2 | AC194054.3 | 112,287-116,332 | 309 | 310 |
| 3 | | | | 311 |

TABLE 3-continued

GENBANK ® Database Sequences that Correspond to SEQ ID NOs: 1-51

| SEQ ID NO. | GENBANK ® Accession No. | Corresponding Nucleotides* | SEQ ID NO. of Corresponding Nucleotides | GENBANK ® Amplicon SEQ ID NO. |
|---|---|---|---|---|
| 4 | | | | 312 |
| 5 | AC193511.3 | 75,839-80,262 | 313 | 314 |
| 6 | | | | 315 |
| 7 | | | | 316 |
| 8 | AC203811.3 | 71,468-75,810 | 317 | 318 |
| 9 | | | | 319 |
| 10 | AC183783.4 | 72,844-73,394 | 320 | 321 |
| 11 | AC194475.4 | 7,792-7,286 | 322 | 323 |
| 12 | | | | 324 |
| 13 | AC191304.3 | 144,760-145,581 | 325 | 326 |
| 14 | AC203908.3 | 76,203-83,388 | 327 | 328 |
| 15 | | | | 329 |
| 16 | AC203862.4 | 44,222-42,385 | 330 | 331 |
| 17 | AC214133.3 | 75,523-74,913 | 332 | 333 |
| 18 | | | | 334 |
| 19 | | | | 335 |
| 20 | AC213693.3 | 103,642-109,297 | 336 | 337 |
| 21 | | | | 338 |
| 22 | AC217909.3 | 146,835-143,989 | 339 | 340 |
| 23 | | | | 341 |
| 24 | AC209026.3 | 35,122-41,268 | 342 | 343 |
| 25 | | | | 344 |
| 26 | | | | 345 |
| 27 | AC190718.3 | 107,472-98,966 | 346 | 347 |
| 28 | | | | 348 |
| 29 | AC187394.3 | 73,707-76,406 | 349 | 350 |
| 30 | | | | 351 |
| 31 | AC193939.3 | 107,773-116,081 | 352 | 353 |
| 32 | AC199011.4 | 140,199-137,838 | 354 | 355 |
| 33 | | | | 356 |
| 34 | | | | 357 |
| 35 | AC216861.3 | 128,894-131,524 | 358 | 359 |
| 36 | | | | 360 |
| 37 | | | | 361 |
| 38 | AC225703.1 | 25,980-28,719 | 362 | 363 |
| 39 | | | | 364 |
| 40 | | | | 365 |
| 41 | | | | 366 |
| 42 | AC203958.4 | 84,395-79,281 | 367 | 368 |
| 43 | AC197220.4 | 39,028-36,915 | 369 | 370 |
| 44 | | | | 371 |
| 45 | AC211190.4 | 195,470-192,503 | 372 | 373 |
| 46 | | | | 374 |
| 47 | AC177932.3 | 5,838-3,574 | 375 | 375 |
| 48 | AC197760.3 | 120,435-118,003 | 377 | 378 |
| 49 | | | | 379 |
| 50 | AC212758.3 | 120,519-124,445 | 380 | 381 |
| 51 | | | | 382 |

*Numbers in this column that are listed from lower to higher indicate that the GENBANK ® database entry corresponds to the nucleotide sequence from the same strand as in the corresponding sequence disclosed in SEQ ID NOs: 1-51. For those entries in which the numbers in this column are listed from higher to lower, the nucleotide sequence disclosed in the GENBANK ® database entry is the reverse complement of the nucleotide sequence of the corresponding sequence in SEQ ID NOs: 1-51.

SEQ ID NOs: 307, 309, 313, 317, 320, 322, 325, 327, 330, 332, 336, 339, 342, 349, 352, 354, 358, 362, 367, 369, 372, 375, 377, and 380 have been added to the GENBANK® database by the Genome Sequencing Center, Washington University School of Medicine, St. Louis, Mo., United States of America. As set forth in the annotations to these database entries, the sequences were part of an effort by The Maize Sequencing Consortium to sequence the genome of *Zea mays*. Currently, the sequencing effort has not been completed, and various portions of the *Zea mays* genome remain unsequenced and/or the sequences have not been ordered in the database.

As can be seen in Tables 1-3, certain of the sequences of SEQ ID NOs: 1-382 are related to each other. By way of example, SEQ ID NO: 1 is a nucleotide sequence from *Zea mays* that has been mapped to the *Zea mays* ZMDWF1 locus on chromosome 5. A subsequence of SEQ ID NO: 1 can be amplified in an amplification reaction (e.g., a PCR) using oligonucleotides having the sequences set forth in SEQ ID NOs: 52 and 53 yield an amplicon that in some embodiments has a nucleotide sequence as set forth in SEQ ID NO: 54. At position 1333 of SEQ ID NO: 1 there is an SNP, and the specific nucleotide that is present in any nucleic acid sample at this position can be determined using oligonucleotides that have the sequences set forth in SEQ ID NOs: 55 and 56.

Additionally, GENBANK® Accession No. AC212758.3 includes a subsequence (i.e., nucleotides 120,519-124,445; SEQ ID NO: 307) that itself is highly similar to SEQ ID NO: 1 (i.e., 3727/3941 nucleotides identical; 94%) and thus is present at the same locus from which SEQ ID NO: 1 is derived. The differences between the two sequences (which can be identified using a BLAST algorithm, a ClustalX algorithm, or any other appropriate method of analysis) can be attributable to normal variation within *Zea mays* populations. A subsequence of SEQ ID NO: 307 can also be amplified in an amplification reaction (e.g., a PCR) using oligonucleotides having the sequences set forth in SEQ ID NOs: 52 and 53 to yield an amplicon which in some embodiments has a nucleotide sequence as set forth in SEQ ID NO: 308, which has a size of 86 basepairs (bp) and is 100% identical to one embodiment of SEQ ID NO: 54. Oligonucleotides with the sequences set forth in SEQ ID NOs: 55 and 56 can also be used to assay the base that is present at the position that corresponds to position 1333 of SEQ ID NO: 1, which in this case is position 1340 of SEQ ID NO: 307 and is position 55 of SEQ ID NO: 308.

For SEQ ID NOs: 2-306, similar interrelationships exist with SEQ ID NOs: 307-382 as are described hereinabove, and would be identifiable by one of ordinary skill in the art using routine sequence analysis techniques. It is noted that with respect to certain of SEQ ID NOs: 1-51, the complete nucleotide sequence of a genomic clone that includes the full length sequence that corresponds to these sequences has not been yet been added to the GENBANK® database by The Maize Sequencing Consortium.

DETAILED DESCRIPTION

I. Definitions

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. For example, the phrase "a marker" refers to one or more markers. Similarly, the phrase "at least one", when employed herein to refer to an entity, refers to, for example, 1, 2, 3, 4, 5, 6, 7, 8, 9, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods. Accordingly, unless indicated to the contrary, the numerical parameters set forth in this specification and attached claims are approximations that can vary depending upon the desired properties sought to be obtained by the presently disclosed subject matter.

As used herein, the term "allele" refers to a variant or an alternative sequence form at a genetic locus. In diploids, a single allele is inherited by a progeny individual separately from each parent at each locus. The two alleles of a given locus present in a diploid organism occupy corresponding places on a pair of homologous chromosomes, although one of ordinary skill in the art understands that the alleles in any particular individual do not necessarily represent all of the alleles that are present in the species.

As used herein, the phrase "associated with" refers to a recognizable and/or assayable relationship between two entities. For example, the phrase "associated with a yield trait" refers to a trait, locus, gene, allele, marker, phenotype, etc., or the expression thereof, the presence or absence of which can influence an extent, degree, and/or rate at which a plant or a part of interest thereof that has the yield trait grows.

As used herein, the term "backcross", and grammatical variants thereof, refers to a process in which a breeder crosses a progeny individual back to one of its parents: for example, a first generation F1 with one of the parental genotypes of the F1 individual. In some embodiments, a backcross is performed repeatedly, with a progeny individual of each successive backcross generation being itself backcrossed to the same parental genotype.

As used herein, the term "chromosome" is used in its art-recognized meaning of the self-replicating genetic structure in the cellular nucleus containing the cellular DNA and bearing in its nucleotide sequence the linear array of genes. The *Zea mays* chromosome numbers disclosed herein refer to those as set forth in Perin et al., 2002, which relates to a reference nomenclature system adopted by L'institut National da la Recherché Agronomique (INRA; Paris, France).

As used herein, the phrase "consensus sequence" refers to a sequence of DNA built to identify nucleotide differences (e.g., SNP and Indel polymorphisms) in alleles at a locus. A consensus sequence can be either strand of DNA at the locus and states the nucleotide(s) at one or more positions (e.g., at one or more SNPs and/or at one or more Indels) in the locus. In some embodiments, a consensus sequence is used to design oligonucleotides and probes for detecting polymorphisms in the locus.

As used herein, the terms "cultivar" and "variety" refer to a group of similar plants that by structural or genetic features and/or performance can be distinguished from other varieties within the same species.

As used herein, the phrase "elite line" refers to any line that is substantially homozygous and has resulted from breeding and selection for superior agronomic performance.

As used herein, the term "gene" refers to a hereditary unit including a sequence of DNA that occupies a specific location on a chromosome and that contains the genetic instruction for a particular characteristic or trait in an organism.

As used herein, the phrase "genetic map" refers to the ordered list of loci usually relevant to position on a chromosome.

As used herein, the phrase "genetic marker" refers to a nucleic acid sequence (e.g., a polymorphic nucleic acid sequence) that has been identified as associated with a locus or allele of interest and that is indicative of the presence or absence of the locus or allele of interest in a cell or organism. Examples of genetic markers include, but are not limited to genes, DNA or RNA-derived sequences, promoters, any untranslated regions of a gene, microRNAs, siRNAs, QTLs, transgenes, mRNAs, ds RNAs, transcriptional profiles, and methylation patterns.

As used herein, the term "genotype" refers to the genetic component of a phenotype of interest, a plurality of phenotypes of interest, or an entire cell or organism. Genotypes can be indirectly characterized using markers and/or directly characterized by nucleic acid sequencing.

As used herein, the term "heterozygous" refers to a genetic condition that exists in a cell or an organism when different alleles reside at corresponding loci on homologous chromosomes. As used herein, the term "homozygous" refers to a genetic condition existing when identical alleles reside at corresponding loci on homologous chromosomes. It is noted that both of these terms can refer to single nucleotide positions, multiple nucleotide positions, whether contiguous or not, or entire loci on homologous chromosomes.

As used herein, the term "hybrid" refers to a seed and the plant the seed develops into that result from crossing at least two genetically different plant parents.

As used herein, the term "hybrid" when used in the context of nucleic acids, refers to a double-stranded nucleic acid molecule, or duplex, formed by hydrogen bonding between complementary nucleotide bases. The terms "hybridize" and "anneal" refer to the process by which single strands of nucleic acid sequences form double-helical segments through hydrogen bonding between complementary bases.

As used herein, the phrase "ILLUMINA® GOLDEN-GATE® Assay" refers to a high throughput genotyping assay sold by Illumina Inc. of San Diego, Calif., United States of America that can generate SNP-specific PCR products. This assay is described in detail at the website of Illumina Inc. and in Fan et al., 2006.

As used herein, the term "improved", and grammatical variants thereof, refers to a plant or a part, progeny, or tissue culture thereof, that as a consequence of having (or lacking) a particular yield associated allele (such as, but not limited to those yield associated alleles disclosed herein) is characterized by a higher or lower content of a yield associated trait, depending on whether the higher or lower content is desired for a particular purpose.

As used herein, the term "inbred" refers to a substantially homozygous individual or line. It is noted that the term can refer to individuals or lines that are substantially homozygous throughout their entire genomes or that are substantially homozygous with respect to subsequences of their genomes that are of particular interest.

As used herein, the phrase "immediately adjacent", when used to describe a nucleic acid molecule that hybridizes to DNA containing a polymorphism, refers to a nucleic acid that hybridizes to a DNA sequence that directly abuts the polymorphic nucleotide base position. For example, a nucleic acid molecule that can be used in a single base extension assay is "immediately adjacent" to the polymorphism.

As used herein, the phrase "interrogation position" refers to a physical position on a solid support that can be queried to obtain genotyping data for one or more predetermined genomic polymorphisms.

As used herein, the terms "introgression", "introgressed", and "introgressing" refer to both a natural and artificial process whereby genomic regions of one species, variety, or cultivar are moved into the genome of another species, variety, or cultivar by crossing those species. Exemplary methods for introgressing a trait of interest include, but are not limited to breeding an individual that has the trait of interest to an individual that does not, and backcrossing an individual that has the trait of interest to a recurrent parent.

As used herein, the term "isolated" refers to a nucleotide sequence (e.g., a genetic marker) that is free of sequences that normally flank one or both sides of the nucleotide sequence in a plant genome. As such, the phrase "isolated and purified genetic marker associated with a yield trait in *Zea mays*" can be, for example, a recombinant DNA molecule, provided one of the nucleic acid sequences normally found flanking that recombinant DNA molecule in a naturally-occurring genome is removed or absent. Thus, isolated nucleic acids include, without limitation, a recombinant DNA that exists as a separate molecule (including, but not limited to genomic DNA fragments produced by PCR or restriction endonuclease treatment) with no flanking sequences present, as well as a recombinant DNA that is incorporated into a vector, an autonomously replicating plasmid, or into the genomic DNA of a plant as part of a hybrid or fusion nucleic acid molecule.

As used herein, the term "linkage" refers to a phenomenon wherein alleles on the same chromosome tend to be transmitted together more often than expected by chance if their transmission were independent. Thus, two alleles on the same chromosome are said to be "linked" when they segregate from each other in the next generation in some embodiments less than 50% of the time, in some embodiments less than 25% of the time, in some embodiments less than 20% of the time, in some embodiments less than 15% of the time, in some embodiments less than 10% of the time, in some embodiments less than 9% of the time, in some embodiments less than 8% of the time, in some embodiments less than 7% of the time, in some embodiments less than 6% of the time, in some embodiments less than 5% of the time, in some embodiments less than 4% of the time, in some embodiments less than 3% of the time, in some embodiments less than 2% of the time, and in some embodiments less than 1% of the time.

As such, "linkage" typically implies and can also refer to physical proximity on a chromosome. Thus, two loci are linked if they are within in some embodiments 20 (cM), in some embodiments 15 cM, in some embodiments 12 cM, in some embodiments 10 cM, in some embodiments 9 cM, in some embodiments 8 cM, in some embodiments 7 cM, in some embodiments 6 cM, in some embodiments 5 cM, in some embodiments 4 cM, in some embodiments 3 cM, in some embodiments 2 cM, and in some embodiments 1 cM of each other. Similarly, a yield locus of the presently disclosed subject matter is linked to a marker (e.g., a genetic marker) if it is in some embodiments within 20, 15, 12, 10, 9, 8, 7, 6, 5, 4, 3, 2, or 1 cM of the marker.

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, in the present context, the term "linkage group" is synonymous with the physical entity of a chromosome, although one of ordinary skill in the art will understand that a linkage group can also be defined as corresponding to a region of (i.e., less than the entirety) of a given chromosome.

As used herein, the phrase "linkage disequilibrium" is defined as change from the expected relative frequency of gamete types in a population of many individuals in a single generation such that two or more loci act as genetically linked loci. If the frequency in a population of allele S is x, s is x', B is y, and b is y', then the expected frequency of genotype SB is xy, that of Sb is xy', that of sB is x'y, and that of sb is x'y', and any deviation from these frequencies is an example of disequilibrium.

As used herein, the term "locus" refers to an established position on a chromosome of a species, and which may encompass a single nucleotide, several nucleotides, or more in a genomic region.

As used herein, the term "maize" refers to a plant, or a part thereof, of the species Zea mays, also referred to herein as Zea mays L.

As used herein, the terms "marker" and "molecular marker" are used interchangeably to refer to an identifiable position on a chromosome the inheritance of which can be monitored and/or a reagent that is used in methods for visualizing differences in nucleic acid sequences present at such identifiable positions on chromosomes. Thus, in some embodiments a marker comprises a known or detectable nucleic acid sequence. Examples of markers include, but are not limited to genetic markers, protein composition, peptide levels, protein levels, oil composition, oil levels, carbohydrate composition, carbohydrate levels, fatty acid composition, fatty acid levels, amino acid composition, amino acid levels, biopolymers, starch composition, starch levels, fermentable starch, fermentation yield, fermentation efficiency (e.g., captured as digestibility at 24, 48, and/or 72 hours), energy yield, secondary compounds, metabolites, morphological characteristics, and agronomic characteristics. Molecular markers include, but are not limited to restriction fragment length polymorphisms (RFLPs), random amplified polymorphic DNA (RAPD), amplified fragment length polymorphisms (AFLPs), single strand conformation polymorphism (SSCPs), single nucleotide polymorphisms (SNPs), insertion/deletion mutations (Indels), simple sequence repeats (SSRs), microsatellite repeats, sequence-characterized amplified regions (SCARs), cleaved amplified polymorphic sequence (CAPS) markers, and isozyme markers, microarray-based technologies, TAQMAN® markers, ILLUMINA® GOLDENGATE® Assay markers, nucleic acid sequences, or combinations of the markers described herein, which define a specific genetic and chromosomal location. The phrase a "molecular marker linked to an MTL" as defined herein can thus refer in some embodiments to SNPs, Indels, AFLP markers, or any other type of marker used in the field.

In some embodiments, a marker corresponds to an amplification product generated by amplifying a Zea mays nucleic acid with one or more oligonucleotides, for example, by the polymerase chain reaction (PCR). As used herein, the phrase "corresponds to an amplification product" in the context of a marker refers to a marker that has a nucleotide sequence that is the same (allowing for mutations introduced by the amplification reaction itself and/or naturally occurring and/or artificial allelic differences) as an amplification product that is generated by amplifying Zea mays genomic DNA with a particular set of oligonucleotides. In some embodiments, the amplifying is by PCR, and the oligonucleotides are PCR primers that are designed to hybridize to opposite strands of the Zea mays genomic DNA in order to amplify a Zea mays genomic DNA sequence present between the sequences to which the PCR primers hybridize in the Zea mays genomic DNA. The amplified fragment that results from one or more rounds of amplification using such an arrangement of primers is a double stranded nucleic acid, one strand of which has a nucleotide sequence that comprises, in 5' to 3' order, the sequence of one of the primers, the sequence of the Zea mays genomic DNA located between the primers, and the reverse-complement of the second primer. Typically, the "forward" primer is assigned to be the primer that has the same sequence as a subsequence of the (arbitrarily assigned) "top" strand of a double-stranded nucleic acid to be amplified, such that the "top" strand of the amplified fragment includes a nucleotide sequence that is, in 5' to 3' direction, equal to the sequence of the forward primer—the sequence located between the forward and reverse primers of the top strand of the genomic fragment—the reverse-complement of the reverse primer. Accordingly, a marker that "corresponds to" an amplified fragment is a marker that has the same sequence of one of the strands of the amplified fragment.

As used herein, the phrase "marker assay" refers to a method for detecting a polymorphism at a particular locus using a particular method such as but not limited to measurement of at least one phenotype (such as seed color, oil content, or a visually detectable trait); nucleic acid-based assays including, but not limited to restriction fragment length polymorphism (RFLP), single base extension, electrophoresis, sequence alignment, allelic specific oligonucleotide hybridization (ASO), random amplified polymorphic DNA (RAPD), microarray-based technologies, TAQMAN® Assays, ILLUMINA® GOLDENGATE® Assay analysis, nucleic acid sequencing technologies; peptide and/or polypeptide analyses; or any other technique that can be employed to detect a polymorphism in an organism at a locus of interest.

As used herein, the terms "ZmDWF1", "ZmZfl2", "ZmFea2", "ZmZfl1", "M1_8138", "ZmCat3", "Zm013154", "ZmSTP1", "ZmCaT", "ZmAlaAT", "ZmD11/DWARF4L1", "ZmDWARF4", "ZmTD1", "ZmBT2", "ZmVrs1.1", "ZmSPS1", "ZmBRI1", "ZmCaT2", "ZmCKX1", "ZmCKX4", "ZmCKX7", "ZmGW2-2", "ZmKRN1", and "ZmVRS1-3" refer to genomic regions and/or genetic loci that are linked to yield associated traits present on Zea mays chromosomes and as described in more detail hereinbelow. Exemplary genomic nucleotide sequences that are derived from these loci are summarized in Table 3 below.

The term "ZmDWF1" refers to a locus on Zea mays chromosome 5 that encodes a brassinosteroid biosynthesis-like protein (Tao et al., 2005). Exemplary gene products derived from the ZmDWF1 locus can be found in GEN-BANK® Accession Nos. NM_001112090 and NP_001105560.

The term "ZmZfl2" refers to a locus on Zea mays chromosome 2 that encodes an ortholog of the FLORICAULA (FLO)/LEAFY(LFY) transcription factor of Antirrhinum and Arabidopsis (Bomblies & Doebley, 2006). Exemplary gene products derived from the ZmZfl2 locus can be found in GENBANK® Accession Nos. NM_001111731 and NP_001105201.

The term "ZmFea2" refers to a locus on Zea mays chromosome 4 that was cloned from a maize mutant fasciated ear2 (Taguchi-Shiobara et al., 2001). Exemplary gene products derived from the ZmFea2 locus can be found in GENBANK® Accession Nos. NM_001112192 and NP_001105662.

The term "ZmZfl1" refers to a locus on *Zea mays* chromosome 10 that like ZmZfl2 encodes an ortholog of the FLORICAULA(FLO)/LEAFY(LFY) transcription factor of *Antirrhinum* and *Arabidopsis* (Bomblies & Doebley, 2005). Exemplary gene products derived from the ZmZfl1 locus can be found in GENBANK® Accession Nos. NM_001111731 and NP_001105201.

The term "M1_8138" refers to a locus on *Zea mays* chromosome 3 that in some embodiments comprises nucleotides 72,844-73,394 of GENBANK® Accession No. AC183783.4.

The term "ZmCat3" refers to a locus on *Zea mays* chromosome 4 that in some embodiments comprises nucleotides 7,286-7,792 of GENBANK® Accession No. AC194475.4.

The term "Zm013154" refers to a locus on *Zea mays* chromosome 9 that in some embodiments comprises nucleotides 144,760-145,581 of GENBANK® Accession No. AC191304.3.

The term "ZmSTP1" refers to a locus on *Zea mays* chromosome 8 that encodes the *Zea mays* sucrose transporter 1 (Sauer, 2007).

The term "ZmCaT" refers to a locus on *Zea mays* chromosome 8 that encodes a calcium transporter.

The term "ZmAlaAT" refers to a locus on *Zea mays* chromosome 5 that encodes an alanine amino transferase involved in nitrogen assimilation.

The term "ZmD11/DWARF4L1" refers to a locus on *Zea mays* chromosome 2 encodes a Cytochrome P450 (C22-hydroxylase; Tanabe et al., 2005).

The term "ZmDWARF4" refers to a locus on *Zea mays* chromosome 1 that encodes a Cytochrome P450 involved in brassinosteroid biosynthesis.

The term "ZmTD1" refers to a locus on *Zea mays* chromosome 5 that encodes a leucine-rich repeat receptor-like kinase (LRR-RLK) that is an ortholog of *Arabidopsis* CLAVATA1, which functions in the clavata pathway regulating meristem development (Bommert et al., 2005).

The term "ZmBT2" refers to a locus on *Zea mays* chromosome 6 that encodes an enzyme involved in starch synthesis (Greene & Hannah, 1998; Hannah et al., 2001). In plants, ADP-glucose pyrophosphorylases (AGP) are heterotetrameric enzymes composed of two large and two small subunits. ZmBT2 encodes the small subunit in *Zea mays*.

The term "ZmVrs1.1" refers to a locus in *Zea mays* that encodes the ortholog of a barley homeodomain-leucine zipper I-class homeobox transcription factor that was isolated from barley through positional cloning and proved to be responsible for mutation from two-rowed to six-rowed barley (Komatsuda et al., 2007).

The term "ZmSPS1" refers to a locus on *Zea mays* chromosome 8 that encodes a sucrose phosphate synthase 1. Sucrose phosphate synthase (SPS; EC2.4.1.14), a key enzyme in the sucrose biosynthetic pathway, catalyzes the formation of sucrose-phosphate from UDP-glucose and fructose 6-phosphate.

The term "ZmBRI1" refers to a locus on *Zea mays* chromosome 8 that encodes an ortholog of the rice Brassinosteroid Insensitive-1 (OsBRI1) gene (Morinaka et al., 2006).

The term "ZmCaT2" refers to a locus on *Zea mays* chromosome 3 that in some embodiments comprises nucleotides 128,894-131,524 of GENBANK® Accession No. AC216861.3.

The term "ZmCKX1" refers to a locus on *Zea mays* chromosome 3 that encodes a cytokinin oxidase/dehydrogenase 2.

The term "ZmGW2-2" refers to a locus on *Zea mays* chromosome 5 that encodes a RING-type protein with E3 ubiquitin ligase activity.

The term "ZmKRN1" refers to a locus on *Zea mays* chromosome 1 that in some embodiments comprises nucleotides 3,574-5,838 of GENBANK® Accession No. AC177932.3.

The term "ZmVRS1-3" refers to a locus on *Zea mays* chromosome 1 that in some embodiments comprises nucleotides 118,003-120,435 of GENBANK® Accession No. AC197760.3.

As used herein, the phrase "native trait" refers to any existing monogenic or oligogenic trait in a certain crop's germplasm. When identified through molecular marker(s), the information obtained can be used for the improvement of germplasm through marker assisted breeding of the yield associated traits disclosed herein.

As used herein, the phrases "nucleotide sequence identity" refers to the presence of identical nucleotides at corresponding positions of two polynucleotides. Polynucleotides have "identical" sequences if the sequence of nucleotides in the two polynucleotides is the same when aligned for maximum correspondence. Sequence comparison between two or more polynucleotides is generally performed by comparing portions of the two sequences over a comparison window to identify and compare local regions of sequence similarity, The comparison window is generally from about 20 to 200 contiguous nucleotides. The "percentage of sequence identity" for polynucleotides, such as 50, 55, 60, 65, 70, 75, 80, 85, 90, 95, 98, 99 or 100 percent sequence identity, can be determined by comparing two optimally aligned sequences over a comparison window, wherein the portion of the polynucleotide sequence in the comparison window can include additions or deletions (i.e., gaps) as compared to the reference sequence for optimal alignment of the two sequences. The percentage is calculated by: (a) determining the number of positions at which the identical nucleic acid base occurs in both sequences to yield the number of matched positions; (b) dividing the number of matched positions by the total number of positions in the window of comparison; and (c) multiplying the result by 100 to yield the percentage of sequence identity. Optimal alignment of sequences for comparison can also be conducted by computerized implementations of known algorithms, or by visual inspection. Readily available sequence comparison and multiple sequence alignment algorithms are, respectively, the Basic Local Alignment Search Tool (BLAST; Altschul et al., 1990; Altschul et al., 1997) and ClustalW programs, both available on the internet. Other suitable programs include, but are not limited to, GAP, BestFit, Plot Similarity, and FASTA, which are part of the Accelrys GCG Package available from Accelrys, Inc. of San Diego, Calif., United States of America. In some embodiments, a percentage of sequence identity refers to sequence identity over the full length of one of the sequences being compared. In some embodiments, a calculation to determine a percentage of sequence identity does not include in the calculation any nucleotide positions in which either of the compared nucleic acids includes an "n" (i.e., where any nucleotide could be present at that position).

As used herein, the phrases "progeny plant" refers to any plant resulting as progeny from a vegetative or sexual reproduction from one or more parent plants or descendants thereof. For instance, a progeny plant can be obtained by cloning or selfing of a parent plant or by crossing two parental plants and include selfings as well as the F1 F2 or still further generations. An F1 is a first-generation progeny produced from parents at least one of which is used for the first time as donor of a trait, while progeny of second generation (F2) or subsequent generations (F3, F4, and the like) are specimens produced from selfings, intercrosses, backcrosses, or other crosses of F1s, F2s, and the like. An F1 can thus be (and in some embodiments is) a hybrid resulting from a cross between two true breeding parents (i.e., parents that are true-breeding are each homozygous for a trait of interest or an allele thereof), while an F2 can be (and in some embodiments is) a progeny resulting from self-pollination of the F1 hybrids.

As used herein, the phrase "phenotypic marker" refers to a marker that can be used to discriminate between different phenotypes.

As used herein, the term "plant" refers to an entire plant, its organs (i.e., leaves, stems, roots, flowers etc.), seeds, plant cells, and progeny of the same. The term "plant cell" includes without limitation cells within seeds, suspension cultures, embryos, meristematic regions, callus tissue, leaves, shoots, gametophytes, sporophytes, pollen, and microspores. The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "polymorphism" refers to the presence of one or more variations of a nucleic acid sequence at a locus in a population of one or more individuals. The sequence variation can be a base or bases that are different, inserted, or deleted. Polymorphisms can be, for example, single nucleotide polymorphisms (SNPs), simple sequence repeats (SSRs), and Indels, which are insertions and deletions. Additionally, the variation can be in a transcriptional profile or a methylation pattern. The polymorphic sites of a nucleic acid sequence can be determined by comparing the nucleic acid sequences at one or more loci in two or more germplasm entries.

As used herein, the term "population" refers to a genetically heterogeneous collection of plants sharing a common genetic derivation.

As used herein, the term "primer" refers to an oligonucleotide which is capable of annealing to a nucleic acid target (in some embodiments, annealing specifically to a nucleic acid target) allowing a DNA polymerase to attach, thereby serving as a point of initiation of DNA synthesis when placed under conditions in which synthesis of a primer extension product is induced (e.g., in the presence of nucleotides and an agent for polymerization such as DNA polymerase and at a suitable temperature and pH). In some embodiments, a plurality of primers are employed to amplify *Zea mays* nucleic acids (e.g., using the polymerase chain reaction; PCR).

As used herein, the term "probe" refers to a nucleic acid (e.g., a single stranded nucleic acid or a strand of a double stranded or higher order nucleic acid, or a subsequence thereof) that can form a hydrogen-bonded duplex with a complementary sequence in a target nucleic acid sequence. Typically, a probe is of sufficient length to form a stable and sequence-specific duplex molecule with its complement, and as such can be employed in some embodiments to detect a sequence of interest present in a plurality of nucleic acids.

As used herein, the term "progeny" refers to any plant that results from a natural or assisted breeding of one or more plants. For example, progeny plants can be generated by crossing two plants (including, but not limited to crossing two unrelated plants, backcrossing a plant to a parental plant, intercrossing two plants, etc.), but can also be generated by selfing a plant, creating a double haploid, or other techniques that would be known to one of ordinary skill in the art.

As used herein, the phrase "quantitative trait locus" (QTL; quantitative trait loci—QTLs) refers to a genetic locus (or loci) that control to some degree a numerically representable trait that, in some embodiments, is continuously distributed. In some embodiments, a QTL comprises a yield associated locus. As used herein, the phrase "yield associated locus" is used herein to refer to a chromosomal region containing alleles (e.g., in the form of genes or regulatory sequences) associated with the expression of a yield associated trait. Thus, a locus "associated with" a yield trait refers to one or more regions located on one or more chromosomes that includes at least one gene the expression of which influences yield and/or at least one regulatory region that controls the expression of one or more genes involved in one or more yield traits. The loci can be defined by indicating their genetic location in the genome of a given *Zea mays* plant using one or more molecular genomic markers. One or more markers, in turn, indicate a specific locus. Distances between loci are usually measured by the frequency of crossovers between loci on the same chromosome. The farther apart two loci are, the more likely that a crossover will occur between them. Conversely, if two loci are close together, a crossover is less likely to occur between them. Typically, one centiMorgan (cM) is equal to 1% recombination between loci. When a QTL can be indicated by multiple markers, the genetic distance between the end-point markers is indicative of the size of the QTL.

As used herein, the phrase "recombination" refers to an exchange of DNA fragments between two DNA molecules or chromatids of paired chromosomes (a "crossover") over in a region of similar or identical nucleotide sequences. A "recombination event" is herein understood to refer to a meiotic crossover.

As used herein, the term "regenerate", and grammatical variants thereof, refers to the production of a plant from tissue culture.

As used herein, the phrases "selected allele", "desired allele", and "allele of interest" are used interchangeably to refer to a nucleic acid sequence that includes a polymorphic allele associated with a desired trait. It is noted that a "selected allele", "desired allele", and/or "allele of interest" can be associated with either an increase in a desired trait or a decrease in a desired trait, depending on the nature of the phenotype sought to be generated in an introgressed plant.

As used herein, the phrase "single nucleotide polymorphism", or "SNP", refers to a polymorphism that constitutes a single base pair difference between two nucleotide sequences. As used herein, the term "SNP" also refers to differences between two nucleotide sequences that result from simple alterations of one sequence in view of the other that occurs at a single site in the sequence. For example, the term "SNP" is intended to refer not just to sequences that differ in a single nucleotide as a result of a nucleic acid substitution in one versus the other, but is also intended to refer to sequences that differ in 1, 2, 3, or more nucleotides as a result of a deletion of 1, 2, 3, or more nucleotides at a single site in one of the sequences versus the other. It would be understood that in the case of two sequences that differ from each other only by virtue of a deletion of 1, 2, 3, or more nucleotides at a single site in one of the sequences versus the other, this same scenario can be considered an addition of 1, 2, 3, or more nucleotides at a single site in one of the sequences versus the other, depending on which of the two sequences is considered the reference sequence. Single site insertions and/or deletions are thus also considered to be encompassed by the term "SNP".

As used herein, the phrase "stringent hybridization conditions" refers to conditions under which a polynucleotide hybridizes to its target subsequence, typically in a complex mixture of nucleic acids, but to essentially no other sequences. Stringent conditions are sequence-dependent and can be different under different circumstances.

Longer sequences typically hybridize specifically at higher temperatures. An extensive guide to the hybridization of nucleic acids is found in Tijssen, 1993. Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Exemplary stringent conditions are those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

Stringent conditions can also be achieved with the addition of destabilizing agents such as formamide. Additional exemplary stringent hybridization conditions include 50% formamide, 5×SSC, and 1% SDS incubating at 42<C; or SSC, 1% SDS, incubating at 65° C.; with one or more washes in 0.2×SSC and 0.1% SDS at 65° C. For PCR, a temperature of about 36° C. is typical for low stringency amplification, although annealing temperatures can vary between about 32° C. and 48° C. (or higher) depending on primer length. Additional guidelines for determining hybridization parameters are provided in numerous references (see e.g., Ausubel et al., 1999).

As used herein, the phrase "TAQMAN® Assay" refers to real-time sequence detection using PCR based on the TAQMAN® Assay sold by Applied Biosystems, Inc. of Foster City, Calif., United States of America. For an identified marker a TAQMAN® Assay can be developed for the application in the breeding program.

As used herein, the term "tester" refers to a line used in a testcross with one or more other lines wherein the tester and the line(s) tested are genetically dissimilar. A tester can be an isogenic line to the crossed line.

As used herein, the term "trait" refers to a phenotype of interest, a gene that contributes to a phenotype of interest, as well as a nucleic acid sequence associated with a gene that contributes to a phenotype of interest. For example, a "yield trait" refers to a yield phenotype as well as a gene that contributes to a yield phenotype and a nucleic acid sequence (e.g., an SNP or other marker) that is associated with a yield phenotype.

As used herein, the term "transgene" refers to a nucleic acid molecule introduced into an organism or its ancestors by some form of artificial transfer technique. The artificial transfer technique thus creates a "transgenic organism" or a "transgenic cell". It is understood that the artificial transfer technique can occur in an ancestor organism (or a cell therein and/or that can develop into the ancestor organism) and yet any progeny individual that has the artificially transferred nucleic acid molecule or a fragment thereof is still considered transgenic even if one or more natural and/or assisted breedings result in the artificially transferred nucleic acid molecule being present in the progeny individual.

As used herein, the term "yield" refers to any measure of a plant, its parts, or its structure that can be measured and/or quantitated in order to assess an extent of or a rate of plant growth and development. As such, a "yield trait" is any trait that can be shown to influence yield in a plant under any set of growth conditions.

Similarly, "yield" can be considered a "phenotype", which as used herein refers to a detectable, observable, and/or measurable characteristic of a cell or organism. In some embodiments, a phenotype is based at least in part on the genetic make up of the cell or the organism (referred to herein as the cell or the organism's "genotype"). Exemplary yield phenotypes are grain yield at standard moisture percentage (YGSMN), grain moisture at harvest (GMSTP), and grain weight per plot (GWTPN). It is noted that as used herein, the term "phenotype" takes into account how the environment (e.g., environmental conditions) might affect yield such that the yield effect is real and reproducible.

II. Molecular Markers, Yield Associated Loci, and Compositions for Assaying Nucleic Acid Sequences Molecular markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., STS, SSR/microsatellites, AFLP, and the like.). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson, 1993; Zietkiewicz et al., 1994. The recombination frequencies of molecular markers on different chromosomes are generally 50%. Between molecular markers located on the same chromosome, the recombination frequency generally depends on the distance between the markers. A low recombination frequency typically corresponds to a small genetic distance between markers on a chromosome. Comparing all recombination frequencies results in the most logical order of the molecular markers on the chromosomes. This most logical order can be depicted in a linkage map (Paterson, 1996). A group of adjacent or contiguous markers on the linkage map that is associated with increased yield can provide the position of an MTL associated with increased yield.

The presently disclosed subject matter provides markers associated with improved yield traits. In some embodiments, the one or more alleles are characterized by one or more loci selected from, but not limited to, the loci represented by SEQ ID NOs: 1-51 or 1-382, which are located on at least nine (9) different chromosomes as follows:

(i) SEQ ID NO: 1 is derived from the *Zea mays* ZmDWF1 locus, and is defined by a first oligonucleotide and a second oligonucleotide, wherein said oligonucleotides can be emploued to amplify a subsequence of SEQ ID NO: 1 generated by amplifying a *Zea mays* nucleic acid with a first oligonucleotide comprising a nucleotide sequence as set forth in SEQ ID NO: 52 and a second oligonucleotide comprising a nucleotide sequence as set forth in SEQ ID NO: 52; and further wherein this locus comprises alleles of a yield-associated trait wherein the alleles are characterized by a single nucleic polymorphism at nucleotide position 1333 of SEQ ID NO: 1 (nucleotide position 55 of SEQ ID NO: 54; nucleotide position 1340 of SEQ ID NO: 307) and comprises any part of a DNA sequence associated within 1, 2, 3, 4, 5, 6, 7, 8, 9, 10, 15, 20, of 25 cM of SEQ ID NO: 1 on Zea mays chromosome 5 that confers an improved yield-associated trait;

(ii) SEQ ID NO: 2 is derived from the Zea mays ZmZfl2 locus, and is defined by a first oligonucleotide and a second oligonucleotide, wherein said oligonucleotides can be emploued to amplify a subsequence of SEQ ID NO: 2 generated by amplifying a Zea mays nucleic acid with a first oligonucleotide comprising a nucleotide sequence as set forth in SEQ ID NO: 57 and a second oligonucleotide comprising a nucleotide sequence as set forth in SEQ ID NO: 58; and further wherein this locus comprises alleles of a yield-associated trait wherein the alleles are characterized by a single nucleic polymorphism at nucleotide position 2420 of SEQ ID NO: 2 (nucleotide position 26 of SEQ ID NO: 59; nucleotide position 2411 of SEQ ID NO: 309) and the locus comprises any part of a DNA sequence associated within 1, 2, 3, 4, 5, 6, 7, 8, 9, 10, 15, 20, of 25 of SEQ ID NO: 2 on Zea mays chromosome 2 that confers an improved yield-associated trait;

(iii) SEQ ID NO: 3 is derived from the Zea mays ZmZfl2 locus, and is defined by a first oligonucleotide and a second oligonucleotide, wherein said oligonucleotides can be emploued to amplify a subsequence of SEQ ID NO: 3 generated by amplifying a Zea mays nucleic acid with a first oligonucleotide comprising a nucleotide sequence as set forth in SEQ ID NO: 62 and a second oligonucleotide comprising a nucleotide sequence as set forth in SEQ ID NO: 63; and further wherein this locus comprises alleles of a yield-associated trait wherein the alleles are characterized by a single nucleic polymorphism at nucleotide position 2709 of SEQ ID NO: 3 (nucleotide position 44 of SEQ ID NO: 64; nucleotide position 2706 of SEQ ID NO: 359) and comprises any part of a DNA sequence associated within 1, 2, 3, 4, 5, 6, 7, 8, 9, 10, 15, 20, of 25 cM of SEQ ID NO: 3 on Zea mays chromosome 2 that confers an improved yield-associated trait;

(iv) SEQ ID NO: 4 is derived from the Zea mays ZmZfl2 locus, and is defined by a first oligonucleotide and a second oligonucleotide, wherein said oligonucleotides can be emploued to amplify a subsequence of SEQ ID NO: 4 generated by amplifying a Zea mays nucleic acid with a first oligonucleotide comprising a nucleotide sequence as set forth in SEQ ID NO: 67 and a second oligonucleotide comprising a nucleotide sequence as set forth in SEQ ID NO: 68; further wherein this locus comprises alleles of a yield-associated trait wherein the alleles are characterized by a single nucleic polymorphism at nucleotide position 368 of SEQ ID NO: 4 (nucleotide position 49 of SEQ ID NO: 69; nucleotide position 374 of SEQ ID NO: 309) and comprises any part of a DNA sequence associated within 1, 2, 3, 4, 5, 6, 7, 8, 9, 10, 15, 20, of 25 cM of SEQ ID NO: 4 on Zea mays chromosome 2 that confers an improved yield-associated trait;

(v) SEQ ID NO: 5 is derived from the Zea mays ZmFea2 locus, and is defined by a first oligonucleotide and a second oligonucleotide, wherein said oligonucleotides can be emploued to amplify a subsequence of SEQ ID NO: 5 generated by amplifying a Zea mays nucleic acid with a first oligonucleotide comprising a nucleotide sequence as set forth in SEQ ID NO: 72 and a second oligonucleotide comprising a nucleotide sequence as set forth in SEQ ID NO: 73; and further wherein this locus comprises alleles of a yield-associated trait wherein the alleles are characterized by a single nucleic polymorphism at nucleotide position 4038 of SEQ ID NO: 5 (nucleotide position 34 of SEQ ID NO: 74; nucleotide position 4041 of SEQ ID NO: 313) and comprises any part of a DNA sequence associated within 1, 2, 3, 4, 5, 6, 7, 8, 9, 10, 15, 20, of 25 cM of SEQ ID NO: 5 on Zea mays chromosome 4 that confers an improved yield-associated trait;

(vi) SEQ ID NO: 6 is derived from the Zea mays ZmFea2 locus, and is defined by a first oligonucleotide and a second oligonucleotide, wherein said oligonucleotides can be emploued to amplify a subsequence of SEQ ID NO: 6 generated by amplifying a Zea mays nucleic acid with a first oligonucleotide comprising a nucleotide sequence as set forth in SEQ ID NO: 77 and a second oligonucleotide comprising a nucleotide sequence as set forth in SEQ ID NO: 78; and further wherein this locus comprises alleles of a yield-associated trait wherein the alleles are characterized by a single nucleic polymorphism at nucleotide position 4038 of SEQ ID NO: 6 (nucleotide position 34 of SEQ ID NO: 79; nucleotide position 4041 of SEQ ID NO: 313) and comprises any part of a DNA sequence associated within 1, 2, 3, 4, 5, 6, 7, 8, 9, 10, 15, 20, of 25 cM of SEQ ID NO: 6 on Zea mays chromosome 4 that confers an improved yield-associated trait;

(vii) SEQ ID NO: 7 is derived from the Zea mays ZmFea2 locus, and is defined by a first oligonucleotide and a second oligonucleotide, wherein said oligonucleotides can be emploued to amplify a subsequence of SEQ ID NO: 7 generated by amplifying a Zea mays nucleic acid with a first oligonucleotide comprising a nucleotide sequence as set forth in SEQ ID NO: 82 and a second oligonucleotide comprising a nucleotide sequence as set forth in SEQ ID NO: 83; and further wherein this locus comprises alleles of a yield-associated trait wherein the alleles are characterized by a single nucleic polymorphism at nucleotide position 402 of SEQ ID NO: 7 (nucleotide position 35 of SEQ ID NO: 84; nucleotide position 402 of SEQ ID NO: 313) and comprises any part of a DNA sequence associated within 1, 2, 3, 4, 5, 6, 7, 8, 9, 10, 15, 20, of 25 cM of SEQ ID NO: 7 on Zea mays chromosome 4 that confers an improved yield-associated trait;

(viii) SEQ ID NO: 8 is derived from the Zea mays ZmZfl1 locus, and is defined by a first oligonucleotide and a second oligonucleotide, wherein said oligonucleotides can be emploued to amplify a subsequence of SEQ ID NO: 8 generated by amplifying a Zea mays nucleic acid with a first oligonucleotide comprising a nucleotide sequence as set forth in SEQ ID NO: 87 and a second oligonucleotide comprising a nucleotide sequence as set forth in SEQ ID NO: 88; and further wherein this locus comprises alleles of a yield-associated trait wherein the alleles are characterized by a single nucleic polymorphism at nucleotide position 3050 of SEQ ID NO: 8 (nucleotide position 56 of SEQ ID NO: 89; nucleotide position 3007 of SEQ ID NO: 317) and comprises any part of a DNA sequence associated within 1, 2, 3, 4, 5, 6, 7, 8, 9, 10, 15, 20, of 25 cM of SEQ ID NO: 8 on Zea mays chromosome 10 that confers an improved yield-associated trait;

(ix) SEQ ID NO: 9 is derived from the Zea mays ZmZfl1 locus, and is defined by a first oligonucleotide and a second oligonucleotide, wherein said oligonucleotides can be emploued to amplify a subsequence of SEQ ID NO: 9 generated by amplifying a Zea mays nucleic acid with a first oligonucleotide comprising a nucleotide sequence as set forth in SEQ ID NO: 92 and a second oligonucleotide comprising a nucleotide sequence as set forth in SEQ ID NO: 93; and further wherein this locus comprises alleles of a yield-associated trait wherein the alleles are characterized by a single nucleic polymorphism at nucleotide position 2146 of SEQ ID NO: 9 (nucleotide position 39 of SEQ ID NO: 94; nucleotide position 2161 of SEQ ID NO: 317) and comprises any part of a DNA sequence associated within 1, 2, 3, 4, 5, 6, 7, 8, 9, 10, 15, 20, of 25 cM of SEQ ID NO: 9 on *Zea mays* chromosome 10 that confers an improved yield-associated trait;

(x) SEQ ID NO: 10 is derived from the *Zea mays* M18138 locus, and is defined by a first oligonucleotide and a second oligonucleotide, wherein said oligonucleotides can be emploued to amplify a subsequence of SEQ ID NO: 10 by amplifying a *Zea mays* nucleic acid with a first oligonucleotide comprising a nucleotide sequence as set forth in SEQ ID NO: 97 and a second oligonucleotide comprising a nucleotide sequence as set forth in SEQ ID NO: 98; and further wherein this locus comprises alleles of a yield-associated trait wherein the alleles are characterized by a single nucleic polymorphism at nucleotide position 408 of SEQ ID NO: 10 (nucleotide position 93 of SEQ ID NO: 99; nucleotide position 399 of SEQ ID NO: 320) and comprises any part of a DNA sequence associated within 1, 2, 3, 4, 5, 6, 7, 8, 9, 10, 20, of 25 cM of SEQ ID NO: 10 on *Zea mays* chromosome 3 that confers an improved yield-associated trait;

(xi) SEQ ID NO: 11 is derived from the *Zea mays* ZmCat3 locus, and is defined by a first oligonucleotide and a second oligonucleotide, wherein said oligonucleotides can be emploued to amplify a subsequence of SEQ ID NO: 11 can generated by amplifying a *Zea mays* nucleic acid with a first oligonucleotide comprising a nucleotide sequence as set forth in SEQ ID NO: 102 and a second oligonucleotide comprising a nucleotide sequence as set forth in SEQ ID NO: 103; and further wherein this locus comprises alleles of a yield-associated trait wherein the alleles are characterized by a single nucleic polymorphism at nucleotide position 160 of SEQ ID NO: 11 (nucleotide position 47 of SEQ ID NO: 104; nucleotide position 161 of SEQ ID NO: 322) and comprises any part of a DNA sequence associated within 1, 2, 3, 4, 5, 6, 7, 8, 9, 10, 15, 20, of 25 cM of SEQ ID NO: 11 on *Zea mays* chromosome 4 that confers an improved yield-associated trait;

(xii) SEQ ID NO: 12 is derived from the *Zea mays* ZmCat3 locus, and is defined by a first oligonucleotide and a second oligonucleotide, wherein said oligonucleotides can be emploued to amplify a subsequence of SEQ ID NO: 12 generated by amplifying a *Zea mays* nucleic acid with a first oligonucleotide comprising a nucleotide sequence as set forth in SEQ ID NO: 107 and a second oligonucleotide comprising a nucleotide sequence as set forth in SEQ ID NO: 108; and further wherein this locus comprises alleles of a yield-associated trait wherein the alleles are characterized by a single nucleic polymorphism at nucleotide position 311 of SEQ ID NO: 12 (nucleotide position 35 of SEQ ID NO: 109; nucleotide position 311 of SEQ ID NO: 322) and comprises any part of a DNA sequence associated within 1, 2, 3, 4, 5, 6, 7, 8, 9, 10, 15, 20, of 25 cM of SEQ ID NO: 12 on *Zea mays* chromosome 4 that confers an improved yield-associated trait;

(xiii) SEQ ID NO: 13 is derived from the *Zea mays* Zm013154 locus, and is defined by a first oligonucleotide and a second oligonucleotide, wherein said oligonucleotides can be emploued to amplify a subsequence of SEQ ID NO: 13 by amplifying a *Zea mays* nucleic acid with a first oligonucleotide comprising a nucleotide sequence as set forth in SEQ ID NO: 112 and a second oligonucleotide comprising a nucleotide sequence as set forth in SEQ ID NO: 113; and further wherein this locus comprises alleles of a yield-associated trait wherein the alleles are characterized by a single nucleic polymorphism at nucleotide position 338 of SEQ ID NO: 13 (nucleotide position 37 of SEQ ID NO: 114; nucleotide position 284 of SEQ ID NO: 325) and comprises any part of a DNA sequence associated within 1, 2, 3, 4, 5, 6, 7, 8, 9, 15, 20, of 25 cM of SEQ ID NO: 13 on *Zea mays* chromosome 9 that confers an improved yield-associated trait;

(xiv) SEQ ID NO: 14 is derived from the *Zea mays* ZmSTP1 locus, and is defined by a first oligonucleotide and a second oligonucleotide, wherein said oligonucleotides can be emploued to amplify a subsequence of SEQ ID NO: 14 by amplifying a *Zea mays* nucleic acid with a first oligonucleotide comprising a nucleotide sequence as set forth in SEQ ID NO: 117 and a second oligonucleotide comprising a nucleotide sequence as set forth in SEQ ID NO: 118; and further wherein this locus comprises alleles of a yield-associated trait wherein the alleles are characterized by a single nucleic polymorphism at nucleotide position 5356 of SEQ ID NO: 14 (nucleotide position 58 of SEQ ID NO: 119; nucleotide position 4372 of SEQ ID NO: 327) and comprises any part of a DNA sequence associated within 1, 2, 3, 4, 5, 6, 7, 9, 10, 15, 20, of 25 cM of SEQ ID NO: 14 on *Zea mays* chromosome 8 that confers an improved yield-associated trait;

(xv) SEQ ID NO: 15 is derived from the *Zea mays* ZmSTP1 locus, and is defined by a first oligonucleotide and a second oligonucleotide, wherein said oligonucleotides can be emploued to amplify a subsequence of SEQ ID NO: 15 by amplifying a *Zea mays* nucleic acid with a first oligonucleotide comprising a nucleotide sequence as set forth in SEQ ID NO: 122 and a second oligonucleotide comprising a nucleotide sequence as set forth in SEQ ID NO: 123; and further wherein this locus comprises alleles of a yield-associated trait wherein the alleles are characterized by a single nucleic polymorphism at nucleotide position 5371 of SEQ ID NO: 15 (nucleotide position 63 of SEQ ID NO: 124; nucleotide position 4389 of SEQ ID NO: 327) and comprises any part of a DNA sequence associated within 1, 2, 3, 4, 5, 6, 7, 9, 10, 15, 20, of 25 cM of SEQ ID NO: 15 on *Zea mays* chromosome 8 that confers an improved yield-associated trait;

(xvi) SEQ ID NO: 16 is derived from the *Zea mays* ZmCaT locus, and is defined by a first oligonucleotide and a second oligonucleotide, wherein said oligonucleotides can be emploued to amplify a subsequence of SEQ ID NO: 16 generated by amplifying a *Zea mays* nucleic acid with a first oligonucleotide comprising a nucleotide sequence as set forth in SEQ ID NO: 127 and a second oligonucleotide comprising a nucleotide sequence as set forth in SEQ ID NO: 128; and further wherein this locus comprises alleles of a yield-associated trait wherein the alleles are characterized by a single nucleic polymorphism at nucleotide position 1587 of SEQ ID NO: 16 (nucleotide position 32 of SEQ ID NO: 129; nucleotide position 1582 of SEQ ID NO: 330) and comprises any part of a DNA sequence associated within 1, 2, 3, 4, 5, 6, 7, 8, 9, 10, 15, 20, of 25 cM of SEQ ID NO: 16 on *Zea mays* chromosome 8 that confers an improved yield-associated trait;

(xvii) SEQ ID NO: 17 is derived from the *Zea mays* ZmAlaAT locus, and is defined by a first oligonucleotide and a second oligonucleotide, wherein said oligonucleotides can be emploued to amplify a subsequence of SEQ ID NO: 17 by amplifying a *Zea mays* nucleic acid with a first oligonucleotide comprising a nucleotide sequence as set forth in SEQ ID NO: 132 and a second oligonucleotide comprising a nucleotide sequence as set forth in SEQ ID NO: 133; and further wherein this locus comprises alleles of a yield-associated trait wherein the alleles are characterized by a single nucleic polymorphism at nucleotide position 388 of SEQ ID NO: 17 (nucleotide position 63 of SEQ ID NO: 134; nucleotide position 385 of SEQ ID NO: 332) and comprises any part of a DNA sequence associated within 1, 2, 3, 4, 5, 6, 7, 8, 9, 15, 20, of 25 cM of SEQ ID NO: 17 on *Zea mays* chromosome 5 that confers an improved yield-associated trait;

(xviii) SEQ ID NO: 18 is derived from the *Zea mays* ZmAlaAT locus, and is defined by a first oligonucleotide and a second oligonucleotide, wherein said oligonucleotides can be emploued to amplify a subsequence of SEQ ID NO: 18 by amplifying a *Zea mays* nucleic acid with a first oligonucleotide comprising a nucleotide sequence as set forth in SEQ ID NO: 137 and a second oligonucleotide comprising a nucleotide sequence as set forth in SEQ ID NO: 138; and further wherein this locus comprises alleles of a yield-associated trait wherein the alleles are characterized by a single nucleic polymorphism at nucleotide position 494 of SEQ ID NO: 18 (nucleotide position 67 of SEQ ID NO: 139; nucleotide position 491 of SEQ ID NO: 332) and comprises any part of a DNA sequence associated within 1, 2, 3, 4, 5, 6, 7, 8, 9, 15, 20, of 25 cM of SEQ ID NO: 18 on *Zea mays* chromosome 5 that confers an improved yield-associated trait;

(xix) SEQ ID NO: 19 is derived from the *Zea mays* ZmAlaAT locus, and is defined by a first oligonucleotide and a second oligonucleotide, wherein said oligonucleotides can be emploued to amplify a subsequence of SEQ ID NO: 19 by amplifying a *Zea mays* nucleic acid with a first oligonucleotide comprising a nucleotide sequence as set forth in SEQ ID NO: 142 and a second oligonucleotide comprising a nucleotide sequence as set forth in SEQ ID NO: 143; and further wherein this locus comprises alleles of a yield-associated trait wherein the alleles are characterized by a single nucleic polymorphism at nucleotide position 112 of SEQ ID NO: 19 (nucleotide position 57 of SEQ ID NO: 144; nucleotide position 109 of SEQ ID NO: 332) and comprises any part of a DNA sequence associated within 1, 2, 3, 4, 5, 6, 7, 8, 9, 15, 20, of 25 cM of SEQ ID NO: 19 on *Zea mays* chromosome 5 that confers an improved yield-associated trait;

(xx) SEQ ID NO: 20 is derived from the *Zea mays* ZmD11/DWARF4L1 locus, and is defined by a first oligonucleotide and a second oligonucleotide, wherein said oligonucleotides can be emploued to amplify a subsequence of SEQ ID NO: 20 by amplifying a *Zea mays* nucleic acid with a first oligonucleotide comprising a nucleotide sequence as set forth in SEQ ID NO: 147 and a second oligonucleotide comprising a nucleotide sequence as set forth in SEQ ID NO: 148; and further wherein this locus comprises alleles of a yield-associated trait wherein the alleles are characterized by a single nucleic polymorphism at nucleotide position 2458 of SEQ ID NO: 20 (nucleotide position 74 of SEQ ID NO: 149; nucleotide position 2419 of SEQ ID NO: 336) and comprises any part of a DNA sequence associated within 1, 2, 3, 4, 5, 6, 7, 9, 10, 15, 20, of 25 cM of SEQ ID NO: 20 on *Zea mays* chromosome 2 that confers an improved yield-associated trait;

(xxi) SEQ ID NO: 21 is derived from the *Zea mays* ZmD11/DWARF4L1 locus, and is defined by a first oligonucleotide and a second oligonucleotide, wherein said oligonucleotides can be emploued to amplify a subsequence of SEQ ID NO: 21 by amplifying a *Zea mays* nucleic acid with a first oligonucleotide comprising a nucleotide sequence as set forth in SEQ ID NO: 152 and a second oligonucleotide comprising a nucleotide sequence as set forth in SEQ ID NO: 153; and further wherein this locus comprises alleles of a yield-associated trait wherein the alleles are characterized by a single nucleic polymorphism at nucleotide position 4037 of SEQ ID NO: 21 (nucleotide position 30 of SEQ ID NO: 154; nucleotide position 4077 of SEQ ID NO: 336) and comprises any part of a DNA sequence associated within 1, 2, 3, 4, 5, 6, 7, 9, 10, 15, 20, of 25 cM of SEQ ID NO: 21 on *Zea mays* chromosome 2 that confers an improved yield-associated trait;

(xxii) SEQ ID NO: 22 is derived from the *Zea mays* ZmDWARF4 locus, and is defined by a first oligonucleotide and a second oligonucleotide, wherein said oligonucleotides can be emploued to amplify a subsequence of SEQ ID NO: 22 by amplifying a *Zea mays* nucleic acid with a first oligonucleotide comprising a nucleotide sequence as set forth in SEQ ID NO: 157 and a second oligonucleotide comprising a nucleotide sequence as set forth in SEQ ID NO: 158; and further wherein this locus comprises alleles of a yield-associated trait wherein the alleles are characterized by a single nucleic polymorphism at nucleotide position 849 of SEQ ID NO: 22 (nucleotide position 70 of SEQ ID NO: 159; nucleotide position 378 of SEQ ID NO: 389) and comprises any part of a DNA sequence associated within 1, 2, 3, 4, 5, 6, 7, 8, 9, 15, 20, of 25 cM of SEQ ID NO: 22 on *Zea mays* chromosome 1 that confers an improved yield-associated trait;

(xxiii) SEQ ID NO: 23 is derived from the *Zea mays* ZmDWARF4 locus, and is defined by a first oligonucleotide and a second oligonucleotide, wherein said oligonucleotides can be emploued to amplify a subsequence of SEQ ID NO: 23 by amplifying a *Zea mays* nucleic acid with a first oligonucleotide comprising a nucleotide sequence as set forth in SEQ ID NO: 162 and a second oligonucleotide comprising a nucleotide sequence as set forth in SEQ ID NO: 163; and further wherein this locus comprises alleles of a yield-associated trait wherein the alleles are characterized by a single nucleic polymorphism at nucleotide position 966 of SEQ ID NO: 23 (nucleotide position 58 of SEQ ID NO: 164; nucleotide position 499 of SEQ ID NO: 339) and comprises any part of a DNA sequence associated within 1, 2, 3, 4, 5, 6, 7, 8, 9, 15, 20, of 25 cM of SEQ ID NO: 23 on *Zea mays* chromosome 1 that confers an improved yield-associated trait;

(xxiv) SEQ ID NO: 25 is derived from the *Zea mays* ZmTD1 locus, and is defined by a first oligonucleotide and a second oligonucleotide, wherein said oligonucleotides can be emploued to amplify a subsequence of SEQ ID NO: 25 generated by amplifying a *Zea mays* nucleic acid with a first oligonucleotide comprising a nucleotide sequence as set forth in SEQ ID NO: 167 and a second oligonucleotide comprising a nucleotide sequence as set forth in SEQ ID NO: 168; and further wherein this locus comprises alleles of a yield-associated trait wherein the alleles are characterized by a single nucleic polymorphism at nucleotide position 1032 of SEQ ID NO: 24 (nucleotide position 39 of SEQ ID NO: 169; nucleotide position 1033 of SEQ ID NO: 342) and comprises any part of a DNA sequence associated within 1, 2, 3, 4, 5, 6, 7, 8, 9, 10, 15, 20, of 25 cM of SEQ ID NO: 24 on *Zea mays* chromosome 5 that confers an improved yield-associated trait;

(xxv) SEQ ID NO: 25 is derived from the *Zea mays* ZmTD1 locus, and is defined by a first oligonucleotide and a second oligonucleotide, wherein said oligonucleotides can be emploued to amplify a subsequence of SEQ ID NO: 25 generated by amplifying a *Zea mays* nucleic acid with a first oligonucleotide comprising a nucleotide sequence as set forth in SEQ ID NO: 172 and a second oligonucleotide comprising a nucleotide sequence as set forth in SEQ ID NO: 173; and further wherein this locus comprises alleles of a yield-associated trait wherein the alleles are characterized by a single nucleic polymorphism at nucleotide position 286 of SEQ ID NO: 25 (nucleotide position 87 of SEQ ID NO: 174; nucleotide position 286 of SEQ ID NO: 392) and comprises any part of a DNA sequence associated within 1, 2, 3, 4, 5, 6, 7, 8, 9, 10, 15, 20, of 25 cM of SEQ ID NO: 25 on *Zea mays* chromosome 5 that confers an improved yield-associated trait;

(xxvi) SEQ ID NO: 26 is derived from the *Zea mays* ZmTD1 locus, and is defined by a first oligonucleotide and a second oligonucleotide, wherein said oligonucleotides can be emploued to amplify a subsequence of SEQ ID NO: 26 generated by amplifying a *Zea mays* nucleic acid with a first oligonucleotide comprising a nucleotide sequence as set forth in SEQ ID NO: 177 and a second oligonucleotide comprising a nucleotide sequence as set forth in SEQ ID NO: 178; and further wherein this locus comprises alleles of a yield-associated trait wherein the alleles are characterized by a single nucleic polymorphism at nucleotide position 346 of SEQ ID NO: 26 (nucleotide position 57 of SEQ ID NO: 179; nucleotide position 346 of SEQ ID NO: 342) and comprises any part of a DNA sequence associated within 1, 2, 3, 4, 5, 6, 7, 8, 9, 10, 15, 20, of 25 cM of SEQ ID NO: 26 on *Zea mays* chromosome 5 that confers an improved yield-associated trait;

(xxvii) SEQ ID NO: 27 is derived from the *Zea mays* ZmBT2 locus, and is defined by a first oligonucleotide and a second oligonucleotide, wherein said oligonucleotides can be emploued to amplify a subsequence of SEQ ID NO: 27 by amplifying a *Zea mays* nucleic acid with a first oligonucleotide comprising a nucleotide sequence as set forth in SEQ ID NO: 182 and a second oligonucleotide comprising a nucleotide sequence as set forth in SEQ ID NO: 183; and further wherein this locus comprises alleles of a yield-associated trait wherein the alleles are characterized by a single nucleic polymorphism at nucleotide position 6968 of SEQ ID NO: 27 (nucleotide position 38 of SEQ ID NO: 184; nucleotide position 6921 of SEQ ID NO: 346) and comprises any part of a DNA sequence associated within 1, 2, 3, 4, 5, 6, 7, 9, 10, 15, 20, of 25 cM of SEQ ID NO: 27 on *Zea mays* chromosome 6 that confers an improved yield-associated trait;

(xxviii) SEQ ID NO: 28 is derived from the *Zea mays* ZmBT2 locus, and is defined by a first oligonucleotide and a second oligonucleotide, wherein said oligonucleotides can be emploued to amplify a subsequence of SEQ ID NO: 28 by amplifying a *Zea mays* nucleic acid with a first oligonucleotide comprising a nucleotide sequence as set forth in SEQ ID NO: 187 and a second oligonucleotide comprising a nucleotide sequence as set forth in SEQ ID NO: 188; and further wherein this locus comprises alleles of a yield-associated trait wherein the alleles are characterized by a single nucleic polymorphism at nucleotide position 6083 of SEQ ID NO: 28 (nucleotide position 79 of SEQ ID NO: 189; nucleotide position 6057 of SEQ ID NO: 346) and comprises any part of a DNA sequence associated within 1, 2, 3, 4, 5, 6, 7, 9, 10, 15, 20, of 25 cM of SEQ ID NO: 28 on *Zea mays* chromosome 6 that confers an improved yield-associated trait;

(xxix) SEQ ID NO: 29 is derived from the *Zea mays* ZmVrs1.1 locus, and is defined by a first oligonucleotide and a second oligonucleotide, wherein said oligonucleotides can be emploued to amplify a subsequence of SEQ ID NO: 29 by amplifying a *Zea mays* nucleic acid with a first oligonucleotide comprising a nucleotide sequence as set forth in SEQ ID NO: 192 and a second oligonucleotide comprising a nucleotide sequence as set forth in SEQ ID NO: 193; and further wherein this locus comprises alleles of a yield-associated trait wherein the alleles are characterized by a single nucleic polymorphism at nucleotide position 1729 of SEQ ID NO: 29 (nucleotide position 35 of SEQ ID NO: 194; nucleotide position 1719 of SEQ ID NO: 349) and comprises any part of a DNA sequence associated within 1, 2, 3, 4, 5, 6, 7, 9, 10, 15, 20, of 25 cM of SEQ ID NO: 29 on a *Zea mays* chromosome that confers an improved yield-associated trait;

(xxx) SEQ ID NO: 30 is derived from the *Zea mays* ZmVrs1.1 locus, and is defined by a first oligonucleotide and a second oligonucleotide, wherein said oligonucleotides can be emploued to amplify a subsequence of SEQ ID NO: 30 by amplifying a *Zea mays* nucleic acid with a first oligonucleotide comprising a nucleotide sequence as set forth in SEQ ID NO: 197 and a second oligonucleotide comprising a nucleotide sequence as set forth in SEQ ID NO: 198; and further wherein this locus comprises alleles of a yield-associated trait wherein the alleles are characterized by a single nucleic polymorphism at nucleotide position 1668 of SEQ ID NO: 30 (nucleotide position 58 of SEQ ID NO: 199; nucleotide position 1657 of SEQ ID NO: 349) and comprises any part of a DNA sequence associated within 1, 2, 3, 4, 5, 6, 7, 8, 9, 10, 15, 20, of 25 cM of SEQ ID NO: 30 on a *Zea mays* chromosome that confers an improved yield-associated trait;

(xxxi) SEQ ID NO: 31 is derived from the *Zea mays* ZmSPS1 locus, and is defined by a first oligonucleotide and a second oligonucleotide, wherein said oligonucleotides can be emploued to amplify a subsequence of SEQ ID NO: 31 by amplifying a *Zea mays* nucleic acid with a first oligonucleotide comprising a nucleotide sequence as set forth in SEQ ID NO: 202 and a second oligonucleotide comprising a nucleotide sequence as set forth in SEQ ID NO: 203; and further wherein this locus comprises alleles of a yield-associated trait wherein the alleles are characterized by a single nucleic polymorphism at nucleotide position 5516 of SEQ ID NO: 31 (nucleotide position 44 of SEQ ID NO: 204; nucleotide position 5512 of SEQ ID NO: 352) and comprises any part of a DNA sequence associated within 1, 2, 3, 4, 5, 6, 7, 9, 10, 15, 20, of 25 cM of SEQ ID NO: 31 on *Zea mays* chromosome 8 that confers an improved yield-associated trait;

(xxxii) SEQ ID NO: 32 is derived from the *Zea mays* ZmBRI1 locus, and is defined by a first oligonucleotide and a second oligonucleotide, wherein said oligonucleotides can be emploued to amplify a subsequence of SEQ ID NO: 32 by amplifying a *Zea mays* nucleic acid with a first oligonucleotide comprising a nucleotide sequence as set forth in SEQ ID NO: 207 and a second oligonucleotide comprising a nucleotide sequence as set forth in SEQ ID NO: 208; and further wherein this locus comprises alleles of a yield-associated trait wherein the alleles are characterized by a single nucleic polymorphism at nucleotide position 1255 of SEQ ID NO: 32 (nucleotide position 40 of SEQ ID NO: 209; nucleotide position 1257 of SEQ ID NO: 354) and comprises any part of a DNA sequence associated within 1, 2, 3, 4, 5, 6, 7, 9, 10, 15, 20, of 25 cM of SEQ ID NO: 32 on *Zea mays* chromosome 8 that confers an improved yield-associated trait;

(xxxiii) SEQ ID NO: 33 is derived from the *Zea mays* ZmBRI1 locus, and is defined by a first oligonucleotide and a second oligonucleotide, wherein said oligonucleotides can be emploued to amplify a subsequence of SEQ ID NO: 33 by amplifying a *Zea mays* nucleic acid with a first oligonucleotide comprising a nucleotide sequence as set forth in SEQ ID NO: 212 and a second oligonucleotide comprising a nucleotide sequence as set forth in SEQ ID NO: 213; and further wherein this locus comprises alleles of a yield-associated trait wherein the alleles are characterized by a single nucleic polymorphism at nucleotide position 1336 of SEQ ID NO: 33 (nucleotide position 45 of SEQ ID NO: 214; nucleotide position 1338 of SEQ ID NO: 354) and comprises any part of a DNA sequence associated within 1, 2, 3, 4, 5, 6, 7, 9, 10, 15, 20, of 25 cM of SEQ ID NO: 33 on *Zea mays* chromosome 8 that confers an improved yield-associated trait;

(xxxiv) SEQ ID NO: 34 is derived from the *Zea mays* ZmBRI1 locus, and is defined by a first oligonucleotide and a second oligonucleotide, wherein said oligonucleotides can be emploued to amplify a subsequence of SEQ ID NO: 34 by amplifying a *Zea mays* nucleic acid with a first oligonucleotide comprising a nucleotide sequence as set forth in SEQ ID NO: 217 and a second oligonucleotide comprising a nucleotide sequence as set forth in SEQ ID NO: 218; and further wherein this locus comprises alleles of a yield-associated trait wherein the alleles are characterized by a single nucleic polymorphism at nucleotide position 1486 of SEQ ID NO: 34 (nucleotide position 25 of SEQ ID NO: 219; nucleotide position 1488 of SEQ ID NO: 354) and comprises any part of a DNA sequence associated within 1, 2, 3, 4, 5, 6, 7, 9, 10, 15, 20, of 25 cM of SEQ ID NO: 34 on *Zea mays* chromosome 8 that confers an improved yield-associated trait;

(xxxv) SEQ ID NO: 35 is derived from the *Zea mays* ZmCaT2 locus, and is defined by a first oligonucleotide and a second oligonucleotide, wherein said oligonucleotides can be emploued to amplify a subsequence of SEQ ID NO: 35 by amplifying a *Zea mays* nucleic acid with a first oligonucleotide comprising a nucleotide sequence as set forth in SEQ ID NO: 222 and a second oligonucleotide comprising a nucleotide sequence as set forth in SEQ ID NO: 223; and further wherein this locus comprises alleles of a yield-associated trait wherein the alleles are characterized by a single nucleic polymorphism at nucleotide position 1742 of SEQ ID NO: 35 (nucleotide position 28 of SEQ ID NO: 224) and comprises any part of a DNA sequence associated within 1, 2, 3, 4, 5, 6, 7, 8, 9, 10, 15, 20, of 25 cM of SEQ ID NO: 35 on *Zea mays* chromosome 3 that confers an improved yield-associated trait;

(xxxvi) SEQ ID NO: 36 is derived from the *Zea mays* ZmCaT2 locus, and is defined by a first oligonucleotide and a second oligonucleotide, wherein said oligonucleotides can be emploued to amplify a subsequence of SEQ ID NO: 36 by amplifying a *Zea mays* nucleic acid with a first oligonucleotide comprising a nucleotide sequence as set forth in SEQ ID NO: 227 and a second oligonucleotide comprising a nucleotide sequence as set forth in SEQ ID NO: 228; and further wherein this locus comprises alleles of a yield-associated trait wherein the alleles are characterized by a single nucleic polymorphism at nucleotide position 2457 of SEQ ID NO: 36 (nucleotide position 58 of SEQ ID NO: 229; nucleotide position 2488 of SEQ ID NO: 358) and comprises any part of a DNA sequence associated within 1, 2, 3, 4, 5, 6, 7, 9, 10, 15, 20, of 25 cM of SEQ ID NO: 36 on *Zea mays* chromosome 3 that confers an improved yield-associated trait;

(xxxvii) SEQ ID NO: 37 is derived from the *Zea mays* ZmCaT2 locus, and is defined by a first oligonucleotide and a second oligonucleotide, wherein said oligonucleotides can be emploued to amplify a subsequence of SEQ ID NO: 37 by amplifying a *Zea mays* nucleic acid with a first oligonucleotide comprising a nucleotide sequence as set forth in SEQ ID NO: 232 and a second oligonucleotide comprising a nucleotide sequence as set forth in SEQ ID NO: 233; and further wherein this locus comprises alleles of a yield-associated trait wherein the alleles are characterized by a single nucleic polymorphism at nucleotide position 631 of SEQ ID NO: 37 (nucleotide position 24 of SEQ ID NO: 234; nucleotide position 634 of SEQ ID NO: 358) and comprises any part of a DNA sequence associated within 1, 2, 3, 4, 5, 6, 7, 8, 9, 15, 20, of 25 cM of SEQ ID NO: 37 on *Zea mays* chromosome 3 that confers an improved yield-associated trait;

(xxxviii) SEQ ID NO: 38 is derived from the *Zea mays* ZmCKX1 locus, and is defined by a first oligonucleotide and a second oligonucleotide, wherein said oligonucleotides can be emploued to amplify a subsequence of SEQ ID NO: 38 by amplifying a *Zea mays* nucleic acid with a first oligonucleotide comprising a nucleotide sequence as set forth in SEQ ID NO: 237 and a second oligonucleotide comprising a nucleotide sequence as set forth in SEQ ID NO: 238; and further wherein this locus comprises alleles of a yield-associated trait wherein the alleles are characterized by a single nucleic polymorphism at nucleotide position 945 of SEQ ID NO: 38 (nucleotide position 28 of SEQ ID NO: 239) and comprises any part of a DNA sequence associated within 1, 2, 3, 4, 5, 6, 7, 8, 9, 10, 15, 20, of 25 cM of SEQ ID NO: 38 on *Zea mays* chromosome 3 that confers an improved yield-associated trait;

(xxxix) SEQ ID NO: 39 is derived from the *Zea mays* ZmCKX1 locus, and is defined by a first oligonucleotide and a second oligonucleotide, wherein said oligonucleotides can be emploued to amplify a subsequence of SEQ ID NO: 39 by amplifying a *Zea mays* nucleic acid with a first oligonucleotide comprising a nucleotide sequence as set forth in SEQ ID NO: 242 and a second oligonucleotide comprising a nucleotide sequence as set forth in SEQ ID NO: 243; and further wherein this locus comprises alleles of a yield-associated trait wherein the alleles are characterized by a single nucleic polymorphism at nucleotide position 2378 of SEQ ID NO: 39 (nucleotide position 32 of SEQ ID NO: 244; nucleotide position 784 of SEQ ID NO: 363) and comprises any part of a DNA sequence associated within 1, 2, 3, 4, 5, 6, 7, 9, 10, 15, 20, of 25 cM of SEQ ID NO: 39 on *Zea mays* chromosome 3 that confers an improved yield-associated trait;

(xl) SEQ ID NO: 40 is derived from the *Zea mays* ZmCKX1 locus, and is defined by a first oligonucleotide and a second oligonucleotide, wherein said oligonucleotides can be emploued to amplify a subsequence of SEQ ID NO: 40 by amplifying a *Zea mays* nucleic acid with a first oligonucleotide comprising a nucleotide sequence as set forth in SEQ ID NO: 247 and a second oligonucleotide comprising a nucleotide sequence as set forth in SEQ ID NO: 248; and further wherein this locus comprises alleles of a yield-associated trait wherein the alleles are characterized by a single nucleic polymorphism at nucleotide position 3860 of SEQ ID NO: 40 (nucleotide position 77 of SEQ ID NO: 249; nucleotide position 2349 of SEQ ID NO: 363) and comprises any part of a DNA sequence associated within 1, 2, 3, 4, 5, 6, 7, 9, 10, 15, 20, of 25 cM of SEQ ID NO: 40 on *Zea mays* chromosome 3 that confers an improved yield-associated trait;

(xli) SEQ ID NO: 41 is derived from the *Zea mays* ZmCKX1 locus, and is defined by a first oligonucleotide and a second oligonucleotide, wherein said oligonucleotides can be emploued to amplify a subsequence of SEQ ID NO: 41 by amplifying a *Zea mays* nucleic acid with a first oligonucleotide comprising a nucleotide sequence as set forth in SEQ ID NO: 252 and a second oligonucleotide comprising a nucleotide sequence as set forth in SEQ ID NO: 253; and further wherein this locus comprises alleles of a yield-associated trait wherein the alleles are characterized by a single nucleic polymorphism at nucleotide position 2519 of SEQ ID NO: 41 (nucleotide position 60 of SEQ ID NO: 254; nucleotide position 925 of SEQ ID NO: 363) and comprises any part of a DNA sequence associated within 1, 2, 3, 4, 5, 6, 7, 9, 10, 15, 20, of 25 cM of SEQ ID NO: 41 on *Zea mays* chromosome 3 that confers an improved yield-associated trait;

(xlii) SEQ ID NO: 42 is derived from the *Zea mays* ZmCKX4 locus, and is defined by a first oligonucleotide and a second oligonucleotide, wherein said oligonucleotides can be emploued to amplify a subsequence of SEQ ID NO: 42 by amplifying a *Zea mays* nucleic acid with a first oligonucleotide comprising a nucleotide sequence as set forth in SEQ ID NO: 257 and a second oligonucleotide comprising a nucleotide sequence as set forth in SEQ ID NO: 258; and further wherein this locus comprises alleles of a yield-associated trait wherein the alleles are characterized by a single nucleic polymorphism at nucleotide position 903 of SEQ ID NO: 42 (nucleotide position 54 of SEQ ID NO: 259; nucleotide position 913 of SEQ ID NO: 368) and comprises any part of a DNA sequence associated within 1, 2, 3, 4, 5, 6, 7, 8, 9, 15, 20, of 25 cM of SEQ ID NO: 42 on *Zea mays* chromosome 3 that confers an improved yield-associated trait;

(xliii) SEQ ID NO: 43 is derived from the *Zea mays* ZmCKX7 locus, and is defined by a first oligonucleotide and a second oligonucleotide, wherein said oligonucleotides can be emploued to amplify a subsequence of SEQ ID NO: 43 by amplifying a *Zea mays* nucleic acid with a first oligonucleotide comprising a nucleotide sequence as set forth in SEQ ID NO: 262 and a second oligonucleotide comprising a nucleotide sequence as set forth in SEQ ID NO: 263; and further wherein this locus comprises alleles of a yield-associated trait wherein the alleles are characterized by a single nucleic polymorphism at nucleotide position 1795 of SEQ ID NO: 43 (nucleotide position 35 of SEQ ID NO: 264; nucleotide position 1772 of SEQ ID NO: 370) and comprises any part of a DNA sequence associated within 1, 2, 3, 4, 5, 6, 7, 9, 10, 15, 20, of 25 cM of SEQ ID NO: 43 on a *Zea mays* chromosome that confers an improved yield-associated trait;

(xliv) SEQ ID NO: 44 is derived from the *Zea mays* ZmCKX7 locus, and is defined by a first oligonucleotide and a second oligonucleotide, wherein said oligonucleotides can be emploued to amplify a subsequence of SEQ ID NO: 44 by amplifying a *Zea mays* nucleic acid with a first oligonucleotide comprising a nucleotide sequence as set forth in SEQ ID NO: 267 and a second oligonucleotide comprising a nucleotide sequence as set forth in SEQ ID NO: 268; and further wherein this locus comprises alleles of a yield-associated trait wherein the alleles are characterized by a single nucleic polymorphism at nucleotide position 2040 of SEQ ID NO: 44 (nucleotide position 44 of SEQ ID NO: 269; nucleotide position 2012 of SEQ ID NO: 370) and comprises any part of a DNA sequence associated within 1, 2, 3, 4, 5, 6, 7, 9, 10, 15, 20, of 25 cM of SEQ ID NO: 44 on a *Zea mays* chromosome that confers an improved yield-associated trait;

(xlv) SEQ ID NO: 45 is derived from the *Zea mays* ZmGW2-2 locus, and is defined by a first oligonucleotide and a second oligonucleotide, wherein said oligonucleotides can be emploued to amplify a subsequence of SEQ ID NO: 45 by amplifying a *Zea mays* nucleic acid with a first oligonucleotide comprising a nucleotide sequence as set forth in SEQ ID NO: 272 and a second oligonucleotide comprising a nucleotide sequence as set forth in SEQ ID NO: 273; and further wherein this locus comprises alleles of a yield-associated trait wherein the alleles are characterized by a single nucleic polymorphism at nucleotide position 3597 of SEQ ID NO: 45 (nucleotide position 65 of SEQ ID NO: 274) and comprises any part of a DNA sequence associated within 1, 2, 3, 4, 5, 6, 7, 8, 9, 10, 15, 20, of 25 cM of SEQ ID NO: 45 on *Zea mays* chromosome 5 that confers an improved yield-associated trait;

(xlvi) SEQ ID NO: 46 is derived from the *Zea mays* ZmGW2-2 locus, and is defined by a first oligonucleotide and a second oligonucleotide, wherein said oligonucleotides can be emploued to amplify a subsequence of SEQ ID NO: 46 by amplifying a *Zea mays* nucleic acid with a first oligonucleotide comprising a nucleotide sequence as set forth in SEQ ID NO: 277 and a second oligonucleotide comprising a nucleotide sequence as set forth in SEQ ID NO: 278; and further wherein this locus comprises alleles of a yield-associated trait wherein the alleles are characterized by a single nucleic polymorphism at nucleotide position 3611 of SEQ ID NO: 46 (nucleotide position 79 of SEQ ID NO: 279) and comprises any part of a DNA sequence associated within 1, 2, 3, 4, 5, 6, 7, 8, 9, 10, 15, 20, of 25 cM of SEQ ID NO: 46 on *Zea mays* chromosome 5 that confers an improved yield-associated trait;

(xlvii) SEQ ID NO: 47 is derived from the *Zea mays* ZmKRN1 locus, and is defined by a first oligonucleotide and a second oligonucleotide, wherein said oligonucleotides can be emploued to amplify a subsequence of SEQ ID NO: 47 by amplifying a *Zea mays* nucleic acid with a first oligonucleotide comprising a nucleotide sequence as set forth in SEQ ID NO: 282 and a second oligonucleotide comprising a nucleotide sequence as set forth in SEQ ID NO: 283; and further wherein this locus comprises alleles of a yield-associated trait wherein the alleles are characterized by a single nucleic polymorphism at nucleotide position 131 of SEQ ID NO: 47 (nucleotide position 19 of SEQ ID NO: 284; nucleotide position 129 of SEQ ID NO: 375) and comprises any part of a DNA sequence associated within 1, 2, 3, 4, 5, 6, 7, 8, 9, 15, 20, of 25 cM of SEQ ID NO: 47 on *Zea mays* chromosome 1 that confers an improved yield-associated trait;

(xlviii) SEQ ID NO: 48 is derived from the *Zea mays* ZmVRS1-3 locus, and is defined by a first oligonucleotide and a second oligonucleotide, wherein said oligonucleotides can be emploued to amplify a subsequence of SEQ ID NO: 48 by amplifying a *Zea mays* nucleic acid with a first oligonucleotide comprising a nucleotide sequence as set forth in SEQ ID NO: 287 and a second oligonucleotide comprising a nucleotide sequence as set forth in SEQ ID NO: 288; and further wherein this locus comprises alleles of a yield-associated trait wherein the alleles are characterized by a single nucleic polymorphism at nucleotide position 2273 of SEQ ID NO: 48 (nucleotide position 76 of SEQ ID NO: 289; nucleotide position 2188 of SEQ ID NO: 377) and comprises any part of a DNA sequence associated within 1, 2, 3, 4, 5, 6, 7, 9, 10, 15, 20, of 25 cM of SEQ ID NO: 48 on *Zea mays* chromosome 1 that confers an improved yield-associated trait;

(xlix) SEQ ID NO: 49 is derived from the *Zea mays* ZmVRS1-3 locus, and is defined by a first oligonucleotide and a second oligonucleotide, wherein said oligonucleotides can be emploued to amplify a subsequence of SEQ ID NO: 49 by amplifying a *Zea mays* nucleic acid with a first oligonucleotide comprising a nucleotide sequence as set forth in SEQ ID NO: 292 and a second oligonucleotide comprising a nucleotide sequence as set forth in SEQ ID NO: 293; and further wherein this locus comprises alleles of a yield-associated trait wherein the alleles are characterized by a single nucleic polymorphism at nucleotide position 187 of SEQ ID NO: 49 (nucleotide position 44 of SEQ ID NO: 294; nucleotide position 187 of SEQ ID NO: 377) and comprises any part of a DNA sequence associated within 1, 2, 3, 4, 5, 6, 7, 8, 9, 15, 20, of 25 cM of SEQ ID NO: 49 on *Zea mays* chromosome 1 that confers an improved yield-associated trait;

(l) SEQ ID NO: 50 is derived from the *Zea mays* ZmDWF1 locus, and is defined by a first oligonucleotide and a second oligonucleotide, wherein said oligonucleotides can be emploued to amplify a subsequence of SEQ ID NO: 50 by amplifying a *Zea mays* nucleic acid with a first oligonucleotide comprising a nucleotide sequence as set forth in SEQ ID NO: 297 and a second oligonucleotide comprising a nucleotide sequence as set forth in SEQ ID NO: 298; and further wherein this locus comprises alleles of a yield-associated trait wherein the alleles are characterized by a single nucleic polymorphism at nucleotide position 1603 of SEQ ID NO: 50 (nucleotide position 36 of SEQ ID NO: 299; nucleotide position 1610 of SEQ ID NO: 380) and comprises any part of a DNA sequence associated within 1, 2, 3, 4, 5, 6, 7, 9, 10, 15, 20, of 25 cM of SEQ ID NO: 50 on *Zea mays* chromosome 5 that confers an improved yield-associated trait; and (li) SEQ ID NO: 51 is derived from the *Zea mays* ZmDWF1 locus, and is defined by a first oligonucleotide and a second oligonucleotide, wherein said oligonucleotides can be emploued to amplify a subsequence of SEQ ID NO: 51 by amplifying a *Zea mays* nucleic acid with a first oligonucleotide comprising a nucleotide sequence as set forth in SEQ ID NO: 302 and a second oligonucleotide comprising a nucleotide sequence as set forth in SEQ ID NO: 303; and further wherein this locus comprises alleles of a yield-associated trait wherein the alleles are characterized by a single nucleic polymorphism at nucleotide position 2859 of SEQ ID NO: 51 (nucleotide position 85 of SEQ ID NO: 304; nucleotide position 2886 of SEQ ID NO: 380) and comprises any part of a DNA sequence associated within 1, 2, 3, 4, 5, 6, 7, 9, 10, 15, 20, of 25 cM of SEQ ID NO: 51 on *Zea mays* chromosome 5 that confers an improved yield-associated trait.

In some embodiments, a DNA sequence associated within 1, 2, 3, 4, 5, 6, 7, 8, 9, 15, 20, or 25 cM of a marker of the presently disclosed subject matter displays a genetic recombination frequency of less than about 25%, 20%, 15%, 10%, 9%, 8%, 7%, 6%, 5%, 4%, 3%, 2%, or 1% with the marker of the presently disclosed subject matter. In some embodiments, the germplasm is a *Zea mays* line or variety.

The presently disclosed subject matter thus provides in some embodiments isolated and purified genetic markers associated with improved yield traits in *Zea mays*. In some embodiments, the markers comprise a nucleotide sequence that comprises the full length sequence of any of SEQ ID NOs: 1-382, the complement of any of SEQ ID NOs: 1-382, or informative fragments thereof; or comprise a nucleotide sequence of at least 10, 15, 20, 25, or more contiguous nucleotides up to the full length of an amplification product from a DNA sample isolated from a maize, wherein the amplification product is produced by an amplification reaction using pairs of oligonucleotide primers comprising the following nucleotide sequences: SEQ ID NOs: 52 and 53; SEQ ID NOs: 57 and 58; SEQ ID NOs: 62 and 63; SEQ ID NOs: 67 and 68; SEQ ID NOs: 72 and 73; SEQ ID NOs: 77 and 78; SEQ ID NOs: 82 and 83; SEQ ID NOs: 87 and 88; SEQ ID NOs: 92 and 93; SEQ ID NOs: 97 and 98; SEQ ID NOs: 102 and 103; SEQ ID NOs: 107 and 108; SEQ ID NOs: 112 and 113; SEQ ID NOs: 117 and 118; SEQ ID NOs: 122 and 123; SEQ ID NOs: 127 and 128; SEQ ID NOs: 132 and 133; SEQ ID NOs: 137 and 138; SEQ ID NOs: 142 and 143; SEQ ID NOs: 147 and 148; SEQ ID NOs: 152 and 153; SEQ ID NOs: 157 and 158; SEQ ID NOs: 162 and 163; SEQ ID NOs: 167 and 168; SEQ ID NOs: 172 and 173; SEQ ID NOs: 177 and 178; SEQ ID NOs: 182 and 183; SEQ ID NOs: 187 and 188; SEQ ID NOs: 192 and 193; SEQ ID NOs: 197 and 198; SEQ ID NOs: 202 and 203; SEQ ID NOs: 207 and 208; SEQ ID NOs: 212 and 213; SEQ ID NOs: 217 and 218; SEQ ID NOs: 222 and 223; SEQ ID NOs: 227 and 228; SEQ ID NOs: 232 and 233; SEQ ID NOs: 237 and 238; SEQ ID NOs: 242 and 243; SEQ ID NOs: 247 and 248; SEQ ID NOs: 252 and 253; SEQ ID NOs: 257 and 258; SEQ ID NOs: 262 and 263; SEQ ID NOs: 267 and 268; SEQ ID NOs: 272 and 273; SEQ ID NOs: 277 and 278; SEQ ID NOs: 282 and 283; SEQ ID NOs: 287 and 288; SEQ ID NOs: 292 and 293; SEQ ID NOs: 297 and 298; and SEQ ID NOs: 302 and 303. In some embodiments, the probe comprises an isolated and purified genetic marker as disclosed herein and a detectable moiety.

The markers identified herein can be used is various aspects of the presently disclosed subject matter as set forth herein. Aspects of the presently disclosed subject matter are not to be limited to the use of the markers identified herein, however. It is stressed that the aspects can also make use of markers not explicitly disclosed herein or even yet to be identified.

DNA fragments associated with the presence of a yield associated trait including, but not limited to SEQ ID NOs: 1-51, 54, 59, 64, 69, 74, 79, 84, 89, 94, 99, 104, 109, 114, 119, 124, 129, 134, 139, 144, 149, 154, 159, 164, 169, 174, 179, 184, 189, 194, 199, 209, 214, 219, 224, 229, 234, 239, 244, 249, 254, 259, 264, 269, 274, 279, 284, 294, 299, 304, and 307-382, are also provided. In some embodiments, the DNA fragments associated with the presence of a yield associated trait have a predicted length and/or nucleic acid sequence, and detecting a DNA fragment having the predicted length and/or the predicted nucleic acid sequence is performed such that the amplified DNA fragment has a length that corresponds (plus or minus a few bases; e.g., a length of one, two or three bases more or less) to the predicted length. In some embodiments, a DNA fragment is an amplified fragment and the amplified fragment has a predicted length and/or nucleic acid sequence as does an amplified fragment produced by a similar reaction with the same primers with the DNA from the plant in which the marker was first detected or the nucleic acid sequence that corresponds (i.e., as a nucleotide sequence identity of more than 80%, 81%, 82%, 83%, 84%, 85%, 86%, 87%, 88%, 89%, 90%, 91%, 92%, 93%, 94%, 95%, 96%, 97%, 98%, or 99%) to the expected sequence as based on the sequence of the marker associated with that yield associated trait in the plant in which the marker was first detected. Upon a review of the instant disclosure, one of ordinary skill in the art would appreciate that markers that are absent in plants while they were present in at least one parent plant (so-called trans-markers), can also be useful in assays for detecting a desired trait in an progeny plant, although testing for the absence of a marker to detect the presence of a specific trait is not optimal. The detecting of an amplified DNA fragment having the predicted length or the predicted nucleic acid sequence can be performed by any of a number of techniques, including but not limited to standard gel electrophoresis techniques and/or by using automated DNA sequencers. The methods are not described here in detail as they are well known to the skilled person.

The primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum lengths of the primers can depend on many factors, including but not limited to temperature and composition (A/T vs. G/C content) of the primer.

In the context of an amplification primer, these are typically provided as one or more sets of bidirectional primers that include one or more forward and one or more reverse primers as commonly used in the art of DNA amplification such as in PCR amplification, As such, it will be understood that the term "primer", as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing. Primers can be prepared by any suitable method. Methods for preparing oligonucleotides of specific sequence are known in the art, and include, for example, cloning, and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,068.

Primers can be labeled, if desired, by incorporating detectable moieties by for instance spectroscopic, fluorescence, photochemical, biochemical, immunochemical, or chemical moieties.

Template-dependent extension of an oligonucleotide primer is catalyzed by a polymerizing agent in the presence of adequate amounts of the four deoxyribonucleotides triphosphates (dATP, dGTP, dCTP and dTTP; i.e., dNTPs) or analogues, in a reaction medium that comprises appropriate salts, metal cations, and a pH buffering system. Suitable polymerizing agents are enzymes known to catalyze primer- and template-dependent DNA synthesis. Known DNA polymerases include, for example, E. coli DNA polymerase or its Klenow fragment, T4 DNA polymerase, and Taq DNA polymerase, as well as various modified versions thereof. The reaction conditions for catalyzing DNA synthesis with these DNA polymerases are known in the art. The products of the synthesis are duplex molecules consisting of the template strands and the primer extension strands, which include the target sequence. These products, in turn, can serve as template for another round of replication. In the second round of replication, the primer extension strand of the first cycle is annealed with its complementary primer; synthesis yields a "short" product which is bound on both the 5'- and the 3'-ends by primer sequences or their complements. Repeated cycles of denaturation, primer annealing, and extension can result in the exponential accumulation of the target region defined by the primers. Sufficient cycles are run to achieve the desired amount of polynucleotide containing the target region of nucleic acid. The desired amount can vary, and is determined by the function which the product polynucleotide is to serve.

The PCR method is well described in handbooks and known to the skilled person. After amplification by PCR, the target polynucleotides can be detected by hybridization with a probe polynucleotide which forms a stable hybrid with that of the target sequence under stringent to moderately stringent hybridization and wash conditions. If it is expected that the probes will be essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell, 2001. Generally, lower salt concentration and higher temperature increase the stringency of hybridization conditions.

In order to detect the presence of two yield associated alleles on a single chromosome in a plant, chromosome painting methods can also be used. In such methods at least a first yield associated allele and at least a second yield associated allele can be detected in the same chromosome by in situ hybridization or in situ PCR techniques. More conveniently, the fact that two yield associated alleles are present on a single chromosome can be confirmed by determining that they are in coupling phase: i.e., that the traits show reduced segregation when compared to genes residing on separate chromosomes.

The yield associated alleles identified herein are located on a number of different chromosomes or linkage groups and their locations can be characterized by a number of otherwise arbitrary markers. In the present investigations, single nucleotide polymorphisms (SNPs), were used, although restriction fragment length polymorphism (RFLP) markers, amplified fragment length polymorphism (AFLP) markers, microsatellite markers (e.g., SSRs), insertion mutation markers, sequence-characterized amplified region (SCAR) markers, cleaved amplified polymorphic sequence (CAPS) markers, isozyme markers, microarray-based technologies, TAQMAN® Assays, ILLUMINA® GOLDENGATE® Assay analysis, nucleic acid sequencing technologies, or combinations of these markers might also have been used, and indeed can be used.

In general, providing complete sequence information for a yield associated allele is unnecessary, as the way in which the yield associated allele is first detected—through an observed correlation between the presence of a single nucleotide polymorphism and the presence of a particular phenotypic trait—allows one to trace among a population of progeny plants those plants that have the genetic potential for exhibiting a particular phenotypic trait. By providing a non-limiting list of markers, the presently disclosed subject matter thus provides for the effective use of the presently disclosed yield associated alleles in a breeding program. In some embodiments, a marker is specific for a particular line of descent. Thus, a specific trait can be associated with a particular marker.

The markers as disclosed herein not only indicate the location of the yield associated allele, they also correlate with the presence of the specific phenotypic trait in a plant. It is noted that a single nucleotide polymorphism that indicates where a yield associated allele is present in the genome is non-limiting. In general, the location of a yield associated allele is indicated by a single nucleotide polymorphism that exhibit statistical correlation to the phenotypic trait. Once a marker is found outside a single nucleotide polymorphism (i.e., one that has a LOD-score below a certain threshold, indicating that the marker is so remote that recombination in the region between that marker and the yield associated allele occurs so frequently that the presence of the marker does not correlate in a statistically significant manner to the presence of the phenotype), the boundaries of the yield associated allele can be considered set. Thus, it is also possible to indicate the location of the yield associated allele by other markers located within that specified region. It is further noted that a single nucleotide polymorphism can also be used to indicate the presence of the yield associated allele (and thus of the phenotype) in an individual plant, which in some embodiments means that it can be used in marker-assisted selection (MAS) procedures.

In principle, the number of potentially useful markers can be very large. Any marker that is linked to a yield associated allele (e.g., falling within the physically boundaries of the genomic region spanned by the markers having established LOD scores above a certain threshold thereby indicating that no or very little recombination between the marker and the yield associated allele occurs in crosses, as well as any marker in linkage disequilibrium to the yield associated allele, as well as markers that represent the actual causal mutations within the yield associated allele) can be used in the presently disclosed methods and compositions, and are within the scope of the presently disclosed subject matter. This means that the markers identified in the application as associated with the yield associated allele (e.g., markers that are present in or comprise any of SEQ ID NOs: 1-382) are non-limiting examples of markers suitable for use in the presently disclosed methods and compositions. Moreover, when a yield associated allele, or the specific trait-conferring part thereof, is introgressed into another genetic background (i.e., into the genome of another maize or another plant species), then some markers might no longer be found in the progeny although the trait is present therein, indicating that such markers are outside the genomic region that represents the specific trait-conferring part of the yield associated allele in the original parent line only and that the new genetic background has a different genomic organization. Such markers of which the absence indicates the successful introduction of the genetic element in the progeny are called "trans markers" and can be equally suitable with respect to the presently disclosed subject matter.

Upon the identification of a yield associated allele, the yield associated allele effect (e.g., the trait) can for instance be confirmed by assessing trait in progeny segregating for the yield associated alleles under investigation. The assessment of the trait can suitably be performed by using phenotypic assessment as known in the art for yield traits. For example, (field) trials under natural and/or irrigated conditions can be conducted to assess the traits of hybrid and/or inbred maize.

The markers provided by the presently disclosed subject matter can be used for detecting the presence of one or more yield trait alleles at loci of the presently disclosed subject matter in a suspected yield trait introgressed maize plant, and can therefore be used in methods involving marker-assisted breeding and selection of such yield trait bearing maize plants. In some embodiments, detecting the presence of a yield associated allele of the presently disclosed subject matter is performed with at least one of the markers for a yield associated allele as defined herein. The presently disclosed subject matter therefore relates in another aspect to a method for detecting the presence of a yield associated allele for at least one of the presently disclosed yield traits, comprising detecting the presence of a nucleic acid sequence of the yield associated allele in a trait bearing maize plant, which presence can be detected by the use of the disclosed markers.

In some embodiments, the detecting comprises determining the nucleotide sequence of a *Zea mays* nucleic acid associated with yield associated trait. The nucleotide sequence of a yield associated allele of the presently disclosed subject matter can for instance be resolved by determining the nucleotide sequence of one or more markers associated with the yield associated allele and designing internal primers for the marker sequences that can then be used to further determine the sequence of the yield associated allele outside of the marker sequences. For instance, the nucleotide sequence of the SNP markers disclosed herein can be obtained by isolating the markers from the electrophoresis gel used in the determination of the presence of the markers in the genome of a subject plant, and determining the nucleotide sequence of the markers by, for example, dideoxy chain termination sequencing methods, which are well known in the art. In some embodiments of such methods for detecting the presence of a yield associated allele in a trait bearing maize plant, the method can also comprise providing a oligonucleotide or polynucleotide capable of hybridizing under stringent hybridization conditions to a nucleic acid sequence of a marker linked to the yield associated allele, in some embodiments selected from the markers disclosed herein, contacting the oligonucleotide or polynucleotide with digested genomic nucleic acid of a trait bearing maize plant, and determining the presence of specific hybridization of the oligonucleotide or polynucleotide to the digested genomic nucleic acid. In some embodiments, the method is performed on a nucleic acid sample obtained from the trait-bearing maize plant, although in situ hybridization methods can also be employed. Alternatively, one of ordinary skill in the art can, once the nucleotide sequence of the yield associated allele has been determined, design specific hybridization probes or oligonucleotides capable of hybridizing under stringent hybridization conditions to the nucleic acid sequence of the yield associated allele and can use such hybridization probes in methods for detecting the presence of a yield associated allele disclosed herein in a trait bearing maize plant.

The presently disclosed subject matter also provides compositions comprising amplification primer pairs capable of initiating polymerization by a nucleic acid polymerase on *Zea mays* nucleic acid templates to generate *Zea mays* marker amplicons. In some embodiments, the *Zea mays* marker amplicons correspond to SEQ ID NOs: 1-51 or 307-380, and/or informative fragments thereof. As used herein, the phrase "informative fragment" refers to a nucleotide sequence of any length that is present within any of SEQ ID NOs: 1-382 (e.g., at least 10, 15, 20, 25, or more nucleotides up to and including the full length of any of SEQ ID NOs: 1-382) that is indicative of the presence or absence of a genetic marker associated with improved yield traits in *Zea mays*. In some embodiments, an informative fragment comprises an SNP selected from among nucleotide position 1333 of SEQ ID NO: 1; nucleotide position 2420 of SEQ ID NO: 2; nucleotide position 2709 of SEQ ID NO: 3; nucleotide position 368 of SEQ ID NO: 4; nucleotide position 4038 of SEQ ID NO: 5; nucleotide position 4038 of SEQ ID NO: 6; nucleotide position 402 of SEQ ID NO: 7; nucleotide position 3050 of SEQ ID NO: 8; nucleotide position 2146 of SEQ ID NO: 9; nucleotide position 408 of SEQ ID NO: 10; nucleotide position 160 of SEQ ID NO: 11; nucleotide position 311 of SEQ ID NO: 12; nucleotide position 338 of SEQ ID NO: 13; nucleotide position 5356 of SEQ ID NO: 14; nucleotide position 5371 of SEQ ID NO: 15; nucleotide position 1587 of SEQ ID NO: 16; nucleotide position 388 of SEQ ID NO: 17; nucleotide position 494 of SEQ ID NO: 18; nucleotide position 112 of SEQ ID NO: 19; nucleotide position 2458 of SEQ ID NO: 20; nucleotide position 4037 of SEQ ID NO: 21; nucleotide position 849 of SEQ ID NO: 22; nucleotide position 966 of SEQ ID NO: 23; nucleotide position 1032 of SEQ ID NO: 24; nucleotide position 286 of SEQ ID NO: 25; nucleotide position 346 of SEQ ID NO: 26; nucleotide position 6968 of SEQ ID NO: 27; nucleotide position 6083 of SEQ ID NO: 28; nucleotide position 1729 of SEQ ID NO: 29; nucleotide position 1668 of SEQ ID NO: 30; nucleotide position 5516 of SEQ ID NO: 31; nucleotide position 1255 of SEQ ID NO: 32; nucleotide position 1336 of SEQ ID NO: 33; nucleotide position 1486 of SEQ ID NO: 34; nucleotide position 1742 of SEQ ID NO: 35; nucleotide position 2457 of SEQ ID NO: 36; nucleotide position 631 of SEQ ID NO: 37; nucleotide position 945 of SEQ ID NO: 38; nucleotide position 2378 of SEQ ID NO: 39; nucleotide position 3860 of SEQ ID NO: 40; nucleotide position 2519 of SEQ ID NO: 41; nucleotide position 903 of SEQ ID NO: 42; nucleotide position 1795 of SEQ ID NO: 43; nucleotide position 2040 of SEQ ID NO: 44; nucleotide position 3597 of SEQ ID NO: 45; nucleotide position 3611 of SEQ ID NO: 46; nucleotide position 131 of SEQ ID NO: 47; nucleotide position 2273 of SEQ ID NO: 48; nucleotide position 187 of SEQ ID NO: 49; nucleotide position 1603 of SEQ ID NO: 50; and nucleotide position 2859 of SEQ ID NO: 51.

III. Methods for Employing Markers and MTLs to Produce Improved Maize Plants by Marker Assisted Selection and Marker Assisted Breeding The presently disclosed subject matter provides methods for conveying selected yield traits into maize germplasm. In some embodiments, the methods comprise introgressing yield traits into maize using one or more nucleic acid markers for marker-assisted selection among maize lines to be used in a maize breeding program, wherein the markers are linked to yield traits. In some embodiments, the one or more nucleic acid markers are selected from the group of markers listed in SEQ ID NOs: 1-382. In some embodiments, the marker-assisted selection comprises the use of an analysis technique selected from the group including, but not limited to, single nucleotide polymorphism (SNP) analysis, random amplified polymorphic DNA (RAPD) analysis, restriction fragment-length polymorphism (RFLP) analysis, microsatellite analysis, amplified fragment length polymorphism (AFLP) analysis, TAQMAN® Assay analysis (Applied Biosystems, Inc., Foster City, Calif., United States of America), and ILLUMINA® GOLDENGATE® Genotyping Assay analysis (Illumina Inc., San Diego, Calif., United States of America). In some embodiments, the methods further comprise screening an introgressed maize plant for an introgressed phenotypic trait.

The presently disclosed subject matter also provides methods for reliably and predictably introgressing yield traits into maize germplasm. In some embodiments, the methods comprise using one or more nucleic acid markers for marker-assisted selection among maize lines to be used in a maize breeding program, wherein the nucleic acid markers are selected from the group including, but not limited to, SEQ ID NOs: 1-382, and introgressing the desired trait into the non-trait carrying maize germplasm. In some embodiments, the one or more nucleic acid markers are selected from the group including, but not limited to, markers for positive or negative alleles of yield traits. In some embodiments, the marker-assisted selection comprises the use of an analysis technique selected from the group including, but not limited to, SNP analysis, RAPD analysis, RFLP analysis, microsatellite analysis, AFLP analysis, TAQMAN® Assay analysis, and ILLUMINA® GOLDENGATE® Genotyping Assay analysis.

The presently disclosed subject matter also provides methods for the production of an inbred maize plant adapted for conferring improved yield traits in hybrid combination with a suitable second inbred. In some embodiments, the methods comprise (a) selecting a first donor parental line possessing a desired yield trait and having at least one of improved yield loci selected from Zea mays loci ZmDWF1, mapped by one or more of the markers SEQ ID NOs: 1, 50, 51, 54, 299, 304, 307, 308, and 380-382; ZmZfl2, mapped by one or more of the markers SEQ ID NOs: 2-4, 59, 64, 69, and 309-312; ZmFea2, mapped by one or more of the markers SEQ ID NOs: 5-7, 74, 79, 89, and 313-316; ZmZfl1, mapped by one or more of the markers SEQ ID NOs: 8, 9, 94, and 317-319; M1_8138, mapped by one or more of the markers SEQ ID NOs: 10, 320, and 321; ZmCat3, mapped by one or more of the markers SEQ ID NOs: 11, 12, 109, and 322-324; Zm013154, mapped by one or more of the markers SEQ ID NOs: 13, 114, 325, and 326; ZmSTP1, mapped by one or more of the markers SEQ ID NOs: 14, 15, 119, 124, and 327-329; ZmCaT, mapped by one or more of the markers SEQ ID NOs: 16, 129, 330, and 331; ZmAlaAT, mapped by one or more of the markers SEQ ID NOs: 17-19, 134, 139, 144, and 332-335; ZmD11/DWARF4L1, mapped by one or more of the markers SEQ ID NOs: 20, 21, 149, 154, and 336-338; ZmDWARF4, mapped by one or more of the markers SEQ ID NOs: 22, 23, 159, 164, and 339-341; ZmTD1, mapped by one or more of the markers SEQ ID NOs: 24-26, 169, 174, 179, and 342-345; ZmBT2, mapped by one or more of the markers SEQ ID NOs: 27, 28, 184, 189, and 346-348; ZmVrs1.1, mapped by one or more of the markers SEQ ID NOs: 29, 30, 194, and 349-351; ZmSPS1, mapped by one or more of the markers SEQ ID NOs: 31, 352, and 353; ZmBRI1, mapped by one or more of the markers SEQ ID NOs: 32-34, 209, 214, 219, and 354-357; ZmCaT2, mapped by one or more of the markers SEQ ID NOs: 35-37, 224, 229, 234, and 358-361; ZmCKX1, mapped by one or more of the markers SEQ ID NOs: 38-41, 239, 244, 249, 254, and 362-366; ZmCKX4, mapped by one or more of the markers SEQ ID NOs: 42, 259, 367, and 368; ZmCKX7, mapped by one or more of the markers SEQ ID NOs: 43, 44, 264, 269, and 369-371; ZmGW2-2, mapped by one or more of the markers SEQ ID NOs: 45, 46, 274, 279, and 372-374; ZmKRN1, mapped by one or more of the markers SEQ ID NOs: 47, 284, 375, and 376; and ZmVRS1-3 mapped by one or more of the markers SEQ ID NOs: 48, 49, 289, 294, and 377-379; (b) crossing the first donor parent line with a second parental line in hybrid combination to produce a segregating plant population; (c) screening the segregating plant population for presence of an allele associated with improved yield; and (d) selecting plants from the population having the allele for further screening until a line is obtained which is homozygous for improved yield at sufficient loci to give improved yield in hybrid combination.

In some embodiments, the methods comprise (a) selecting a first donor parental line possessing a desired inbred allele for a first yield trait and also possessing an inbred allele for a second yield trait; (b) crossing the first donor parent line with a second parental line in hybrid combination to produce an F1 generation, and producing an F2 from the F1 generation, wherein the F2 generation comprises a segregating plant population; (c) screening one or more members of the segregating plant population for presence of desired chromosomal loci associated with the first yield trait and with the second yield trait; (d) identifying a plant in the F2 generation, or a selfed and/or double haploid progeny of a plant from the F2 generation, that is homozygous for at least the first yield trait at sufficient loci to produce improved yield in hybrid combination; and (e) establishing from the homozygous plant identified in step (d) an inbred maize plant adapted for conferring, in hybrid combination with a suitable second inbred, a yield trait. In some embodiments, the methods further comprise screening the plants of the line that is homozygous for improved yield traits at sufficient loci to give improved yield in hybrid combination.

In some embodiments, the methods comprise (a) providing a *Zea mays* plant which contains one or more alleles that confer improved yield, wherein each of the one or more alleles that confer improved yield is selected from among *Zea mays* loci ZmDWF1, ZmZfl2, ZmFea2, ZmZfl1, M1_8138, ZmCat3, Zm013154, ZmSTP1, ZmCaT, ZmAlaAT, ZmD11/DWARF4L1, ZmDWARF4, ZmTD1, ZmBT2, ZmVrs1.1, ZmSPS1, ZmBRI1, ZmCaT2, ZmCKX1, ZmCKX4, ZmCKX7, ZmGW2-2, ZmKRN1, and ZmVRS1-3, and further wherein ZmDWF1 maps to *Zea mays* chromosome 5 and comprises a nucleotide sequence at least 85% identical to one of SEQ ID NOs: 1, 50, 51, 54, 299, 307, 308, and 380-382; ZmZfl2 maps to *Zea mays* chromosome 2 and comprises a nucleotide sequence at least 85% identical to one of SEQ ID NOs: 2-4, 59, 64, 69, and 309-312; ZmFea2 maps to *Zea mays* chromosome 4 and comprises a nucleotide sequence at least 85% identical to one of SEQ ID NOs: 5-7, 74, 79, 89, and 313-316; ZmZfl1 maps to *Zea mays* chromosome 10 and comprises a nucleotide sequence at least 85% identical to one of SEQ ID NOs: 8, 9, 89, 94, and 317-319; M1_8138 maps to *Zea mays* chromosome 3 and comprises a nucleotide sequence at least 85% identical to one of SEQ ID NOs: 10, 99, 320, and 321; ZmCat3 maps to *Zea mays* chromosome 4 comprises a nucleotide sequence at least 85% identical to one of SEQ ID NOs: 11, 104, 109, and 322-324; Zm013154 maps to *Zea mays* chromosome 9 and comprises a nucleotide sequence at least 85% identical to one of SEQ ID NOs: 13, 114, 325, and 326; ZmSTP1 maps to *Zea mays* chromosome 8 and comprises a nucleotide sequence at least 85% identical to one of SEQ ID NOs: 14, 15, 119, 124, and 327-329; ZmCaT maps to *Zea mays* chromosome 8 and comprises a nucleotide sequence at least 85% identical to one of SEQ ID NOs: 16, 129, 330, and 331; ZmAlaAT maps to *Zea mays* chromosome 5 and comprises a nucleotide sequence at least 85% identical to one of SEQ ID NOs: 17-19, 134, 139, 144, and 332-335; ZmD11/DWARF4L1 maps to *Zea mays* chromosome 2 and comprises a nucleotide sequence at least 85% identical to one of SEQ ID NOs: 20, 21, 149, 154, and 336-338; ZmDWARF4 maps to *Zea mays* chromosome 1 and comprises a nucleotide sequence at least 85% identical to one of SEQ ID NOs: 22, 23, 159, 164, and 339-341; ZmTD1 maps to *Zea mays* chromosome 5 comprises a nucleotide sequence at least 85% identical to one of SEQ ID NOs: 24-26, 169, 174, 179, and 342-345; ZmBT2 maps to *Zea mays* chromosome 6 and comprises a nucleotide sequence at least 85% identical to one of SEQ ID NOs: 27, 28, 189, and 346-348; ZmVrs1.1 comprises a nucleotide sequence at least 85% identical to one of SEQ ID NOs: 29, 30, 194, 199, and 349-351; ZmSPS1 maps to *Zea mays* chromosome 8 and comprises a nucleotide sequence at least 85% identical to one of SEQ ID NOs: 31, 204, 352, and 353; ZmBRI1 maps to *Zea mays* chromosome 8 and comprises a nucleotide sequence at least 85% identical to one of SEQ ID NOs: 32-34, 209, 214, 219, and 354-357; ZmCaT2 maps to *Zea mays* chromosome 3 and comprises a nucleotide sequence at least 85% identical to one of SEQ ID NOs: 35-37, 224, 229, 234, and 358-361; ZmCKX1 maps to *Zea mays* chromosome 3 and comprises a nucleotide sequence at least 85% identical to one of SEQ ID NOs: 38-41, 239, 244, 249, 254, and 362-366; ZmCKX4 maps to *Zea mays* chromosome 3 and comprises a nucleotide sequence at least 85% identical to one of SEQ ID NOs: 42, 259, 367, and 368; ZmCKX7 comprises a nucleotide sequence at least 85% identical to one of SEQ ID NOs: 43, 44, 264, 269, and 369-371; ZmGW2-2 maps to *Zea mays* chromosome 5 and comprises a nucleotide sequence at least 85% identical to one of SEQ ID NOs: 45, 46, 279, and 372-374; ZmKRN1 maps to *Zea mays* chromosome 1 and comprises a nucleotide sequence at least 85% identical to one of SEQ ID NOs: 47, 284, 375, and 376; and ZmVRS1-3 maps to *Zea mays* chromosome 1 and comprises a nucleotide sequence at least 85% identical to one of SEQ ID NOs: 48, 49, 289, 294, and 377-379; and (b) crossing the *Zea mays* plant provided in step (a) with *Zea mays* breeding material to produce one or more progeny individuals, whereby one or more *Zea mays* plants with improved yield are produced. In some embodiments, the methods further comprise (c) collecting the seeds resulting from the cross in step (b); (d) regenerating the seeds into plants; (e) evaluating the plants of step (d) for improved yield; and (f) identifying and selecting plants which have improved yield.

In some embodiments, the detecting of the desired trait comprises detecting at least one allelic form of a polymorphic simple sequence repeat (SSR) or a single nucleotide polymorphism (SNP). In some embodiments, the detecting comprises amplifying the marker locus or a portion of the marker locus and detecting the resulting amplified marker amplicon. In some embodiments, the amplifying comprises: (a) admixing an amplification primer or amplification primer pair with a nucleic acid isolated from the first *Zea mays* plant or germplasm, wherein the primer or primer pair is complementary or partially complementary to at least a portion of the marker locus, and is capable of initiating DNA polymerization by a DNA polymerase using the maize nucleic acid as a template; and (b) extending the primer or primer pair in a DNA polymerization reaction comprising a DNA polymerase and a template nucleic acid to generate at least one amplicon. In some embodiments, the nucleic acid is selected from DNA and RNA. In some embodiments, the at least one allele is an SNP allele and the method comprises detecting the SNP using allele specific hybridization (ASH) analysis. In some embodiments, the amplifying comprises employing a polymerase chain reaction (PCR) or ligase chain reaction (LCR) using a nucleic acid isolated from the first maize plant or germplasm as a template in the PCR or LCR.

As used herein, the term "favorable allele" refers to an allele the presence of which is desirable in a plant in order to achieve a desired goal. For example, a favorable allele can be an allele that is associated with higher or lower yield, depending on whether higher or lower yield is desired under specific circumstances. As such, a "favorable" allele for increased yield is in some embodiments an unfavorable allele for decreased yield, and vice versa.

Table 4 discloses exemplary SNPs that are associated with increases and decreases of various yield traits (e.g., YGSMN, GMSTP, and/or GWTPN). With respect to Table 4, the phrase "favorable allele" refers to an allele that when present results in a quantitatively higher yield versus the case when the "unfavorable allele" is present. It is noted, however, then in the case where a lower yield is desirable, the alleles listed in Table 4 as "unfavorable" would in fact be the favorable alleles. As such, in Table 4 "favorable" and "unfavorable" are employed in the context of increased yield, and would be reversed in the context of decreased yield.

TABLE 4

Summary of Favorable and Unfavorable Alleles for Increased Yield

| SEQ ID NO. | SNP Position | Both | | | TASSEL | | | QIPDT2 | | |
|---|---|---|---|---|---|---|---|---|---|---|
| | | F | U | Trait | F | U | Trait | F | U | Trait |
| 1 | 1333 | | | | | | | G | A | GWTPN |
| 2 | 2420 | | | | C | G | GMSTP | G | C | YGSMN |
| 3 | 2709 | | | | G | T | YGSMN | | | |
| | | | | | T | G | GMSTP | | | |
| 4 | 368 | T | G | YGSMN | T | G | YGSMN | | | |
| | | | | | T | G | GMSTP | | | |
| | | | | | | | | T | G | GWTPN |
| 5 | 4038 | T | C | GMSTP | C | T | YGSMN | | | |
| | | | | | T | C | GMSTP | T | C | GMSTP |
| 6 | 4038 | | | | C | T | YGSMN | | | |
| | | | | | T | C | GMSTP | | | |
| 7 | 402 | | | | A | G | YGSMN | | | |
| | | | | | G | A | GMSTP | | | |
| 8 | 3050 | | | | T | G | YGSMN | | | |
| | | | | | G | T | GMSTP | | | |
| 9 | 2146 | | | | G | A | GMSTP | | | |
| 10 | 408 | C | T | YGSMN | | | | | | |
| | | | | | T | C | GMSTP | | | |
| | | | | | | | | C | T | GWTPN |
| 11 | 160 | | | | C | G | YGSMN | | | |
| | | | | | G | C | GMSTP | | | |
| 12 | 311 | | | | C | G | YGSMN | | | |
| 13 | 338 | A | G | YGSMN | A | G | YGSMN | | | |
| | | | | | G | A | GMSTP | | | |
| | | | | | | | | A | G | GWTPN |
| 14 | 5356 | A | G | GMSTP | A | G | YGSMN | | | |
| | | | | | G | A | GMSTP | A | G | GMSTP |
| 15 | 5371 | | | | C | A | YGSMN | | | |
| | | | | | A | C | GMSTP | | | |
| 16 | 1587 | | | | A | G | YGSMN | | | |
| | | | | | G | A | GMSTP | | | |
| 17 | 388 | | | | A | G | YGSMN | | | |
| | | | | | G | A | GMSTP | | | |
| 18 | 494 | | | | T | G | YGSMN | | | |
| 19 | 112 | | | | T | G | YGSMN | | | |
| | | | | | G | T | GMSTP | | | |
| 20 | 2458 | | | | T | A | YGSMN | | | |
| | | | | | A | T | GMSTP | | | |
| 21 | 4037 | | | | T | G | YGSMN | | | |
| 22 | 849 | | | | T | C | YGSMN | | | |
| 23 | 966 | | | | G | A | GWTPN | | | |

TABLE 4-continued

Summary of Favorable and Unfavorable Alleles for Increased Yield

| SEQ ID NO. | SNP Position | Both F | Both U | Both Trait | TASSEL F | TASSEL U | TASSEL Trait | QIPDT2 F | QIPDT2 U | QIPDT2 Trait |
|---|---|---|---|---|---|---|---|---|---|---|
| 24 | 1032 | | | | G | C | YGSMN | | | |
|    |      | | | | C | G | GMSTP | | | |
| 25 | 286  | A | G | YGSMN | A | G | YGSMN | | | |
|    |      | | | | G | A | GMSTP | | | |
|    |      | | | | | | | A | G | GWTPN |
| 26 | 346  | | | | A | C | YGSMN | | | |
| 27 | 6968 | | | | A | T | YGSMN | | | |
|    |      | | | | T | A | GMSTP | | | |
| 28 | 6083 | | | | A | G | YGSMN | | | |
|    |      | | | | G | A | GMSTP | | | |
| 29 | 1729 | | | | A | G | YGSMN | | | |
|    |      | | | | G | A | GMSTP | | | |
| 30 | 1668 | | | | C | A | YGSMN | | | |
|    |      | | | | A | C | GMSTP | | | |
| 31 | 5516 | | | | G | A | GMSTP | | | |
| 32 | 1255 | | | | | | | G | A | YGSMN |
|    |      | | | | G | A | GMSTP | | | |
| 33 | 1336 | | | | | | | C | G | YGSMN |
| 34 | 1486 | | | | | | | G | A | YGSMN |
|    |      | | | | G | A | GMSTP | | | |
| 35 | 1742 | A | G | YGSMN | A | G | YGSMN | | | |
|    |      | A | G | GMSTP | | | | A | G | GMSTP |
| 36 | 2457 | C | A | GMSTP | | | | | | |
| 37 | 631  | T | A | YGSMN | | | | T | A | YGSMN |
| 38 | 945  | G | A | GMSTP | G | A | GMSTP | | | |
| 39 | 2378 | A | G | GMSTP | A | G | GMSTP | | | |
| 40 | 2860 | T | A | YGSMN | T | A | YGSMN | T | A | YGSMN |
|    |      | A | T | GMSTP | | | | A | T | GMSTP |
| 41 | 2519 | G | T | GMSTP | G | T | GMSTP | G | T | GMSTP |
| 42 | 903  | | | | A | G | YGSMN | | | |
|    |      | | | | | | | G | T | GMSTP |
| 43 | 1795 | | | | A | G | YGSMN | | | |
| 44 | 2040 | | | | T | C | GMSTP | | | |
| 45 | 3597 | T | A | YGSMN | T | A | YGSMN | | | |
|    |      | A | T | GMSTP | A | T | GMSTP | | | |
| 46 | 3611 | A | G | YGSMN | | | | A | G | YGSMN |
|    |      | A | G | GMSTP | | | | | | |
| 47 | 131  | | | | | | | G | C | GMSTP |
| 48 | 2273 | | | | | | | A | T | GMSTP |
| 49 | 187  | | | | | | | C | G | GMSTP |
| 50 | 1603 | C | A | YGSMN | C | A | YGSMN | C | A | YGSMN |
|    |      | | | | | | | C | A | GMSTP |
| 51 | 2859 | A | G | YGSMN | A | G | YGSMN | A | G | YGSMN |
|    |      | | | | | | | A | G | GMSTP |

In some embodiments, the yield trait is YGSMN and the favorable allele (i.e., the allele associated with higher YGSMN) comprises a nucleotide sequence comprising a G at nucleotide position 2420 of SEQ ID NO: 2; a G at nucleotide position 2709 of SEQ ID NO: 3; a T at nucleotide position 368 of SEQ ID NO: 4; a C at nucleotide position 4038 of SEQ ID NO: 5; a C at nucleotide position 4038 of SEQ ID NO: 6; an A at nucleotide position 402 of SEQ ID NO: 7; a T at nucleotide position 3050 of SEQ ID NO: 8; a C at nucleotide position 408 of SEQ ID NO: 10; a C at nucleotide position 160 of SEQ ID NO: 11; a C at nucleotide position 311 of SEQ ID NO: 12; an A at nucleotide position 338 of SEQ ID NO: 13; an A at nucleotide position 5356 of SEQ ID NO: 14; a C at nucleotide position 5371 of SEQ ID NO: 15; an A at nucleotide position 1587 of SEQ ID NO: 16; an A at nucleotide position 388 of SEQ ID NO: 17; a T at nucleotide position 494 of SEQ ID NO: 18; a T at nucleotide position 112 of SEQ ID NO: 19; a T at nucleotide position 2458 of SEQ ID NO: 20; a T at nucleotide position 4037 of SEQ ID NO: 21; a T at nucleotide position 849 of SEQ ID NO: 22; a G at nucleotide position 1032 of SEQ ID NO: 24; an A at nucleotide position 286 of SEQ ID NO: 25; an A at nucleotide position 346 of SEQ ID NO: 26; an A at nucleotide position 6968 of SEQ ID NO: 27; an A at nucleotide position 6083 of SEQ ID NO: 28; an A at nucleotide position 1729 of SEQ ID NO: 29; a C at nucleotide position 1668 of SEQ ID NO: 30; a G at nucleotide position 1255 of SEQ ID NO: 32; a C at nucleotide position 1336 of SEQ ID NO: 33; a G at nucleotide position 1486 of SEQ ID NO: 34; an A at nucleotide position 1742 of SEQ ID NO: 35; a T at nucleotide position 631 of SEQ ID NO: 37; a T at nucleotide position 3860 of SEQ ID NO: 40; an A at nucleotide position 903 of SEQ ID NO: 42; an A at nucleotide position 1795 of SEQ ID NO: 43; a T at nucleotide position 3597 of SEQ ID NO: 45; an A at nucleotide position 3611 of SEQ ID NO: 46; a C at nucleotide position 1603 of SEQ ID NO: 50; or an A at nucleotide position 2859 of SEQ ID NO: 51. In some embodiments, the yield trait is GMSTP, and the favorable allele (i.e., the allele associated with higher GMSTP) comprises a nucleotide sequence comprising a C at nucleotide position 2420 of SEQ ID NO: 2; a T at nucleotide position 2709 of SEQ ID NO: 3; a T at nucleotide position 368 of SEQ ID NO: 4; a T at nucleotide position 4038 of SEQ ID NO: 5; a T at nucleotide position 4038 of SEQ ID NO: 6; a G at nucleotide position 402 of SEQ ID NO: 7; a G at nucleotide position 3050 of SEQ ID NO: 8; a G at nucleotide position 2146 of SEQ ID NO: 9; a T at nucleotide position 408 of SEQ ID NO: 10; a G at nucleotide position 160 of SEQ ID NO: 11; a G at nucleotide position 338 of SEQ ID NO: 13; a G at nucleotide position 5356 of SEQ ID NO: 14; an A at nucleotide position 5371 of SEQ ID NO: 15; a G at nucleotide position 1587 of SEQ ID NO: 16; a G at nucleotide position 388 of SEQ ID NO: 17; a G at nucleotide position 112 of SEQ ID NO: 19; an A at nucleotide position 2458 of SEQ ID NO: 20; a C at nucleotide position 1032 of SEQ ID NO: 24; a G at nucleotide position 286 of SEQ ID NO: 25; a T at nucleotide position 6968 of SEQ ID NO: 27; a G at nucleotide position 6083 of SEQ ID NO: 28; a G at nucleotide position 1729 of SEQ ID NO: 29; an A at nucleotide position 1668 of SEQ ID NO: 30; a G at nucleotide position 5516 of SEQ ID NO: 31; a G at nucleotide position 1255 of SEQ ID NO: 32; a G at nucleotide position 1486 of SEQ ID NO: 34; an A at nucleotide position 1742 of SEQ ID NO: 35; a C at nucleotide position 2457 of SEQ ID NO: 36; a G at nucleotide position 945 of SEQ ID NO: 38; an A at nucleotide position 2378 of SEQ ID NO: 39; an A at nucleotide position 3860 of SEQ ID NO: 40; a G at nucleotide position 2519 of SEQ ID NO: 41; a G at nucleotide position 903 of SEQ ID NO: 42; a T at nucleotide position 2040 of SEQ ID NO: 44; an A at nucleotide position 3597 of SEQ ID NO: 45; an A at nucleotide position 3611 of SEQ ID NO: 46; a G at nucleotide position 131 of SEQ ID NO: 47; an A at nucleotide position 2273 of SEQ ID NO: 48; a C at nucleotide position 187 of SEQ ID NO: 49; a C at nucleotide position 1603 of SEQ ID NO: 50; or an A at nucleotide position 2859 of SEQ ID NO: 51. In some embodiments, the yield trait is GWTPN, and the favorable allele (i.e., the allele associated with higher GWTPN) comprises a nucleotide sequence comprising a G at nucleotide position 1333 of SEQ ID NO: 1; a T at nucleotide position 368 of SEQ ID NO: 4; a T at nucleotide position 4038 of SEQ ID NO: 5; a C at nucleotide position 408 of SEQ ID NO: 10; an A at nucleotide position 338 SEQ ID NO: 13; a G at nucleotide position 966 of SEQ ID NO: 23; or an A at nucleotide position 286 of SEQ ID NO: 25.

Knowledge of the nucleotides present at these positions allows one of skill to determine whether or not the plant carries an allele of interest. If so, the plant can be chosen for further breeding. Thus, one of ordinary skill in the art would understand that plants can be affirmatively chosen for further use based on identifying favorable alleles at specific genomic sites (e.g., those listed hereinabove). However, it is also noted that the absence of a favorable allele at a specific site can also be used to affirmatively reject a certain plant as a candidate for further breeding.

For example, increased yield in *Zea mays* is associated with markers that comprise SEQ ID NO: 4 and informative fragments thereof. As set forth in Table 4, a T nucleotide at position 368 of SEQ ID NO: 4 is associated with increased grain yield at standard moisture percentage (YGSMN). Thus, identification of the nucleotide at position 368 of SEQ ID NO: 4 in a plant can be employed to determine whether or not the plant is likely to carry an increased YGSMN allele associated with the locus represented by SEQ ID NO: 4. If the plant has a T nucleotide at position 368 of SEQ ID NO: 4 in one or both of its chromosome 2s, it is a candidate for further breeding in those instances in which increased YGSMN is desirable.

However, as set forth in Table 4, having a G at nucleotide 368 of SEQ ID NO: 4 have the opposite effect of having a T at this position. Thus, Table 4 also indicates that if decreased YGSMN is desired, plants can be screened for what nucleotide is present at position 368 of SEQ ID NO: 4, and those that have a G at this position in one or both of its chromosome 2s can be chosen under these circumstances, and those that have a T at this position in one or both of its chromosome 2s can be rejected. Thus, with respect to the alleles disclosed in Table 4, the "favorable" allele and the "unfavorable" allele can be considered to have opposite effects, and depending on the trait that is of interest, either can in fact be a favorable allele (affirmatively chosen) or an unfavorable allele (affirmatively rejected).

Similarly, Table 4 discloses that a T nucleotide at position 368 of SEQ ID NO: 4 associated with increased grain moisture at harvest (GMSTP) and increased grain weight per plot (GWTPN), whereas a G nucleotide at this position is associated with decreased grain moisture at harvest (GMSTP) and increased grain weight per plot (GWTPN). Note, however, that for several of the alleles disclosed in Table 4, YGSMN, GMSTP, and GWTPN do not have the same allele being associated with increases in these phenotypes. For example, for the locus that is represented by SEQ ID NO: 10, a C at nucleotide position 408 of SEQ ID NO: 10 is associated with increased YGSMN and GWTPN, but is also associated with decreased GMSTP, and vice versa (i.e., a T at nucleotide position 408 of SEQ ID NO: 10 is associated with decreased YGSMN and GWTPN, and is also associated with increased GMSTP). See also the locus associated with SEQ ID NO: 13, in which an A at nucleotide position 338 of SEQ ID NO: 13 is associated with increased YGSMN and GWTPN, but with decreased GMSTP, while a G at nucleotide position 338 of SEQ ID NO: 13 is associated with decreased YGSMN and GWTPN and with increased GMSTP.

In some embodiments, the at least one allele is correlated with at least one improved yield trait, the method comprising introgressing the allele in the first Zea mays plant or germplasm into a second Zea mays plant or germplasm to produce an introgressed Zea mays plant or germplasm. In some embodiments, the second Zea mays plant or germplasm displays more improved yield traits as compared to the first Zea mays plant or germplasm, and wherein the introgressed Zea mays plant or germplasm displays an increased improved yield trait as compared to the second Zea mays plant or germplasm.

The presently disclosed subject matter also provides methods for producing maize plants which carry improved yield traits. In some embodiments, the methods comprise providing a Zea mays plant which contains one or more alleles that confer improved yield, the alleles being characterized by one or more sets of loci. These alleles can be employed individually or in combinations. Combinations of yield traits selected for increase or decrease of yield can be employed to alter yield, and combinations of these yield traits can be introgressed into a single plant (i.e., "stacked"), if desired.

In some embodiments, a marker locus associated with an improved yield trait displays a genetic recombination frequency of less than about 50%, 25%, 20%, 15%, 10%, 9%, 8%, 7%, 6%, 5%, 4%, 3%, 2%, or 1% with a genetic locus encoding a yield trait. In some embodiments, the marker locus associated with improved yield is selected from, but not limited to, marker loci localizing within the chromosome intervals of 20 cM. In some embodiments, the germplasm is a Zea mays line or variety.

In some embodiments, the detecting of the desired trait comprises detecting at least one allelic form of a polymorphic simple sequence repeat (SSR) or a single nucleotide polymorphism (SNP). In some embodiments, the detecting comprises amplifying the marker locus or a portion of the marker locus and detecting the resulting amplified marker amplicon. In some embodiments, the amplifying comprises (a) admixing an amplification primer or amplification primer pair with a nucleic acid isolated from the first Zea mays plant or germplasm, wherein the primer or primer pair is complementary or partially complementary to at least a portion of the marker locus and is capable of initiating DNA polymerization by a DNA polymerase using the maize nucleic acid as a template; and (b) extending the primer or primer pair in a DNA polymerization reaction comprising a DNA polymerase and a template nucleic acid to generate at least one amplicon. In some embodiments, the nucleic acid is selected from DNA and RNA. In some embodiments, the at least one allele is an SNP allele and the methods comprise detecting the SNP using allele specific hybridization (ASH) analysis, TAQMAN® Assay Analysis (Applied Biosystems, Inc., Foster City, Calif., United States of America), and/or the ILLUMINA® GOLDENGATE® Genotyping Assay analysis (Illumina Inc., San Diego, Calif., United States of America). In some embodiments, the amplifying comprises employing a polymerase chain reaction (PCR) or ligase chain reaction (LCR) using a nucleic acid isolated from the first maize plant or germplasm as a template in the PCR or LCR.

In some embodiments, the at least one allele is a favorable allele that positively correlates with an improved yield trait. In some embodiments, the at least one allele is a favorable allele that negatively correlates with an improved yield trait. In some embodiments, the at least one allele comprises two or more alleles. In some embodiments, the at least one allele is correlated with an improved yield trait and the methods comprise introgressing the allele in the first Zea mays plant or germplasm into a second Zea mays plant or germplasm to produce an introgressed Zea mays plant or germplasm. In some embodiments, the second Zea mays plant or germplasm is characterized by more improved yield traits as compared to the first Zea mays plant or germplasm, and wherein the introgressed Zea mays plant or germplasm displays an increase in the number of improved yield traits as compared to the second Zea mays plant or germplasm.

The presently disclosed subject matter also provides methods for introgressing an allele associated with a pre-selected yield trait into Zea mays germplasm. In some embodiments, the methods comprise (a) selecting from a population of Zea mays plants at least one Zea mays plant that comprises an allele of a yield locus associated with a pre-selected yield trait, wherein the yield locus is genetically linked to at least one marker locus that co-segregates with the yield associated trait, and further wherein the yield locus comprises a nucleotide sequence at least 85% identical to a Zea mays genomic sequence selected from the group including, but not limited to, nucleotides 120,519-124,445 of AC212758.3; nucleotides 112,287-116,332 of AC194054.3; nucleotides 75,839-80,262 of AC193511.3; nucleotides 71,468-75,810 of AC203811.3; nucleotides 72,844-73,394 of AC183783.4; nucleotides 7,792-7,286 of AC194475.4; nucleotides 144,760-145,581 of AC191304.3; nucleotides 76,203-83,388 of AC203908.3; nucleotides 44,222-42,385 of AC203862.4; nucleotides 75,523-74,913 of AC214133.3; nucleotides 103,642-109,297 of AC213693.3; nucleotides 146,835-143,989 of AC217909.3; nucleotides 35,122-41,268 of AC209026.3; nucleotides 107,472-98,966 of AC190718.3; nucleotides 73,707-76,406 of AC187394.3; nucleotides 107,773-116,081of AC193939.3; nucleotides 140,199-137,838 of AC199011.4; nucleotides 128,894-131,524 of AC216861.3; nucleotides 25,980-28,719 of AC225703.1; nucleotides 84,395-79,281 of AC203958.4; nucleotides 39,028-36,915 of AC197220.4; nucleotides 195,470-192,503 of AC211190.4; nucleotides 5,838-3,574 of AC177932.3; nucleotides 120,435-118,003 of AC197760.3; nucleotides 120,519-124,445 of AC212758.3; and (b) introgressing the allele of the yield locus associated with the pre-selected yield trait into Zea mays germplasm that lacks the allele.

The presently disclosed subject matter also provides methods for introgressing an allele associated with a pre-selected yield trait into Zea mays germplasm. In some embodiments, the methods comprise (a) selecting from a population of Zea mays plants at least one Zea mays plant comprising at least one allele associated with a pre-selected yield trait, wherein the allele comprises a nucleotide sequence selected from the group including, but not limited to, SEQ ID NOs: 55, 56, 60, 61, 65, 66, 70, 71, 75, 76, 80, 81, 86, 90, 91, 95, 96, 100, 101, 105, 106, 110, 111, 115, 116, 120, 121, 125, 126, 130, 135, 136, 140, 141, 145, 146, 150, 151, 155, 156, 160, 161, 165, 166, 170, 171, 176, 180, 181, 185, 186, 190, 191, 195, 196, 200, 201, 205, 206, 210, 211, 215, 220, 221, 225, 226, 230, 231, 235, 236, 240, 241, 245, 246, 250, 251, 255, 256, 261, 265, 266, 270, 271, 275, 276, 280, 281, 285, 286, 290, 291, 295, 296, 300, 305, and 306; and (b) introgressing the allele associated with the pre-selected yield trait into *Zea mays* germplasm that lacks the allele.

The presently disclosed subject matter also provides methods for introgressing an allele associated with a pre-selected yield trait into *Zea mays* germplasm. In some embodiments, the methods comprise (a) selecting from a population of *Zea mays* plants at least one *Zea mays* plant that comprises an allele of a yield locus associated with a pre-selected yield trait, wherein the yield locus is selected from the group including, but not limited to, *Zea mays* loci ZmDWF1, ZmZfl2, ZmFea2, ZmZfl1, M1_8138, ZmCat3, Zm013154, ZmSTP1, ZmCaT, ZmAlaAT, ZmD11/DWARF4L1, ZmDWARF4, ZmTD1, ZmBT2, ZmVrs1.1, ZmSPS1, ZmBRI1, ZmCaT2, ZmCKX1, ZmCKX4, ZmCKX7, ZmGW2-2, ZmKRN1, and ZmVRS1-3, and further wherein: (1) ZmDWF1 maps to *Zea mays* chromosome 5 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 1, 50, 51, 54, 299, 304, 307, 308, and 380-382; (2) ZmZfl2 maps to *Zea mays* chromosome 2 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 2-4, 59, 64, 69, and 309-312; (3) ZmFea2 maps to *Zea mays* chromosome 4 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 5-7, 74, and 313-316; (4) ZmZfl1 maps to *Zea mays* chromosome 10 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 8, 9, 89, 94, and 317-319; (5) M1_8138 to *Zea mays* chromosome 3 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 10, 99, 320, and 321; (6) ZmCat3 maps to *Zea mays* chromosome 4 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 11, 12, 104, and 322-324; (7) Zm013154 maps to *Zea mays* chromosome 9 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 13, 114, 325, and 326; (8) ZmSTP1 maps to *Zea mays* chromosome 8 comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 14, 15, 119, 124, and 327-329; (9) ZmCaT maps to *Zea mays* chromosome 8 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 16, 129, 330, and 331; (10) ZmAlaAT maps to *Zea mays* chromosome 5 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 17-19, 134, 139, 144, and 332-335; (11) ZmD11/DWARF4L1 maps to *Zea mays* chromosome 2 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 20, 21, 149, 154, and 336-338; (12) ZmDWARF4 maps to *Zea mays* chromosome 1 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 22, 23, 159, 164, and 339-341; (13) ZmTD1 maps to *Zea mays* chromosome 5 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 24-26, 169, 174, 179, and 342-345; (14) ZmBT2 maps to *Zea mays* chromosome 6 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 27, 28, 184, 189, and 346-348; (15) ZmVrs1.1 maps to a *Zea mays* chromosome and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 29, 30, 194, 199, and 349-351; (16) ZmSPS1 maps to *Zea mays* chromosome 8 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 31, 204, 352, and 353; (17) ZmBRI1 maps to *Zea mays* chromosome 8 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 32-34, 209, 214, 219, and 354-357; (18) ZmCaT2 maps to *Zea mays* chromosome 3 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 35-37, 224, 229, 234, and 358-361; (19) ZmCKX1 maps to *Zea mays* chromosome 3 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 38-41, 239, 244, 249, 254, and 362-366; (20) ZmCKX4 maps to *Zea mays* chromosome 3 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 42, 259, 367, and 368; (21) ZmCKX7 maps to a *Zea mays* chromosome and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 43, 44, 264, 269, and 369-371; (22) ZmGW2-2 maps to *Zea mays* chromosome 5 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 45, 46, 274, 279, and 372-374; (23) ZmKRN1 maps to *Zea mays* chromosome 1 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 47, 284, 375, and 375; and (24) ZmVRS1-3 maps to *Zea mays* chromosome 1 and comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID NOs: 5448, 49, 294, and 377-379; and (b) introgressing the allele of the yield locus into Zea mays germplasm that lacks the allele, whereby an allele associated with a pre-selected yield trait is introgressed into Zea mays germplasm. In some embodiments, the percent identity is over at least 25, 50, 75, or 100 nucleotides of the indicated SEQ ID NO. In some embodiments, the percent identity is over the full length of the indicated SEQ ID NO. In some embodiments, the percent identity excludes consideration of any position at which the indicated SEQ ID NO. includes an "n" nucleotide from the percent identity calculation.

IV. Production of Improved Trait Carrying Maize Plants by Transgenic Methods

The use of SNPs as defined or trait-conferring parts, for producing a trait carrying maize plant, which by introducing a nucleic acid sequence comprising the trait-associated allele of the SNP into a recipient plant.

A donor plant, with the nucleic acid sequence that comprises a yield trait allele can be transferred to the recipient plant lacking the allele. The nucleic acid sequence can be transferred by crossing a yield trait carrying donor plant with a non-trait carrying recipient plant (i.e., by introgression), by transformation, by protoplast transformation or fusion, by a doubled haploid technique, by embryo rescue, or by any other nucleic acid transfer system. Then if desired optionally of progeny plants comprising one or more of the presently disclosed yield trait alleles can be selected. A nucleic acid sequence comprising an yield trait allele can be isolated from the donor plant using methods known in the art, and the this isolated nucleic acid sequence can transform the recipient plant by transgenic methods. This can occur with a vector, in a gamete, or other suitable transfer element, such as a ballistic particle coated with the nucleic acid sequence.

Plant transformation generally involves the construction of an expression vector that will function in plant cells and includes nucleic acid sequence that comprises an allele associated with the yield trait, which vector can comprise a yield trait-conferring gene. This gene usually is controlled or operatively linked to one or more regulatory element, such as a promoter. The expression vector can contain one or more such operably linked gene/regulatory element combinations, provided that at least one of the genes contained in the combinations encodes yield trait. The vector(s) can be in the form of a plasmid, and can be used, alone or in combination with other plasmids, to provide transgenic plants that are better yield plants, using transformation methods known in the art, such as the *Agrobacterium* transformation system.

Transformed cells often contain a marker allow transformation identification. The marker is adapted to be recovered by negative selection (by inhibiting the growth of cells that do not contain the selectable marker gene), or by positive selection (by screening for the product encoded by the marker gene). Many commonly used selectable marker genes for plant transformation are known in the art, and include, for example, genes that code for enzymes that metabolically detoxify a selective chemical agent that can be an antibiotic or a herbicide, or genes that encode an altered target which is insensitive to the inhibitor. Several positive selection methods are known in the art, such as mannose selection. Alternatively, marker-less transformation can be used to obtain plants without the aforementioned marker genes, the techniques for which are also known in the art.

V. Improved Plants, and Plant Parts, Seeds, Tissue Cultures, and Biomass Derived Therefrom The presently disclosed subject matter also provides improved maize plants, parts, seeds, progeny, and tissue cultures produced by any of the presently disclosed methods.

In some embodiments, the presently disclosed subject matter provides improved maize plants or a part, seed, progeny, and/or tissue culture thereof, which evidences a selected yield trait (e.g., a trait associated with YGSMN, GMSTP, and/or GWTPN), a genome homozygous with respect to one or more genetic alleles which are present in a first parent and not present in a second parent of the improved maize plant, in some embodiments, (a) the second parent evidences a more improved yield trait (e.g., a more improved a trait associated with YGSMN, GMSTP, and/or GWTPN trait) than the first parent; and (b) the improved plant comprises one or more alleles from the first parent that evidence an improved yield trait in hybrid combination in at least one locus selected from (i) a YGSMN locus with a desired YGSMN allele; (ii) a GMSTP locus with a desired GMSTP allele; and/or (iii) a GWTPN locus with a desired a trait associated with YGSMN, GMSTP, and/or GWTPN allele; and the desired trait is not significantly less than that of the first parent in the same hybrid combination and yield characteristics which are not significantly different than those of the second parent in the same hybrid combination.

In some embodiments, the improved maize plants, or parts, seeds, progeny, and tissue cultures thereof, comprise progeny of a cross between first and second inbred or hybrid lines, wherein one or more alleles conferring selected yield traits (e.g., YGSMN, GMSTP, and/or GWTPN traits) are present in a homozygous state in the genome of one or the other or both of the first and second inbred or hybrid lines, such that the genome of the first and second inbreds or hybrids together donate to the improved maize plant or part thereof a complement of alleles sufficient to confer the improved yield trait(s). The presently disclosed subject matter also provides hybrids, or a part thereof, formed with the presently disclosed improved maize plants.

The presently disclosed subject matter also provides maize plants, or parts, seeds, and tissue cultures thereof, formed by selfing the presently disclosed improved yield traited hybrid(s).

The presently disclosed subject matter also provides maize plants, or parts, seeds, progeny, and tissue cultures thereof, that have one or more desired yield traits produced by the presently disclosed methods. In some embodiments, the maize plants that have one or more improved yield traits are hybrid maize. The presently disclosed subject matter also provides biomass and seed produced by the presently disclosed maize plants.

As such, the presently disclosed subject matter provides improved maize plants, or parts, seeds, progeny, tissue cultures, and biomass derived thereof, which evidence a selected yield trait, optionally wherein the genome of the improved maize plant, or the part, seed, progeny, or tissue culture thereof is homozygous with respect to one or more genetic alleles associated with the selected trait.

In some embodiments, the improved maize plant, or the part, seed, progeny, or tissue culture thereof comprises a genome that is homozygous with respect to one or more genetic alleles that are present in a first parent and not present in a second parent of the improved maize plant. In some embodiments, the second parent evidences more improved yield traits than the first parent, and the improved plant comprises one or more alleles from the first parent that evidence improved yield traits in hybrid combination in at least one locus selected from, but not limited to, a YGSMN locus with a desired YGSMN allele, a GMSTP locus with a desired GMSTP allele, and/or a GWTPN locus with a desired GWTPN allele, and the desired trait is not significantly less than that of the first parent in the same hybrid combination and yield characteristics which are not significantly different than those of the second parent in the same hybrid combination.

In some embodiments, the improved maize plants or parts thereof comprise progeny of a cross between first and second inbred or hybrid lines, wherein one or more alleles conferring selected yield traits are present in a homozygous state in the genome of one or the other or both of the first and second inbred or hybrid lines, such that the genome of the first and second inbreds or hybrids together donate to the improved maize plant or part thereof a complement of alleles sufficient to confer the improved yield trait(s). The presently disclosed subject matter also provides hybrids, or a part thereof, formed with the presently disclosed improved maize plants.

The presently disclosed subject matter also provides maize plants, or a part thereof, formed by selfing the presently disclosed improved yield traited hybrids.

The presently disclosed subject matter also provides maize plants that have desired yield traits occurring in maize produced by the presently disclosed methods. In some embodiments, the maize plants that have improved yield traits are hybrid maize. The presently disclosed subject matter also provides biomass and seed produced by the presently disclosed maize plants.

The presently disclosed subject matter also provides *Zea mays* plants having one or more improved yield traits associated with the presence of an allele comprising a nucleotide sequence as set forth in any of SEQ ID NOs. 1-51, 54, 59, 64, 69, 74, 79, 84, 89, 94, 99, 104, 109, 114, 119, 124, 129, 134, 139, 144, 149, 154, 159, 164, 169, 174, 184, 189, 194, 199, 204, 209, 214, 219, 224, 229, 234, 239, 244, 249, 254, 259, 269, 274, 279, 284, 289, 294, 299, 304, and 307-382 in a homozygous genetic background.

The presently disclosed subject matter also provides parts of the plants defined herein. In some embodiments, the plant part is pollen, ovule, leaf, embryo, root, root tip, anther, flower, fruit, stem, shoot, seed; cell, rootstock, protoplast, or callus.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Assessment of the Phenotypic Data

In order to identify alleles that were associated with high yield, hybrids were grown in different stages at multiple locations and evaluated for yield. In this analysis, three traits were tested in stage 2-3: YGSMN (grain yield at standard moisture %), GMSTP (grain moisture at harvest), and GWTPN (grain weight per plot). The distribution of the phenotypic data of hybrids of the lines across locations and testers for YGSMN, GMSTP, and GWTPN, was determined. The mean values were 201.68 bushels/acre, 18.95%, and 25.29 bushels/plot respectively. The phenotypic data for the selected trials included information from 69 locations. The number of observations in these locations ranged from 1 to 725. A total of 890 inbreds were evaluated in crosses with 33 different inbred testers. The number of observations for inbred lines crossed to a particular tester ranged from 4 to 2167 across all locations. An empirical threshold of a minimum of ~300 was set to select 10 subsets of lines with each subset crossed to a particular tester, and 10 subsets of lines with each subset were evaluated in a particular location.

The testing for associations between potential markers and these three traits employed two analytical approaches: a Mixed Linear Models—(TASSEL) and a Quantitative Inbred Pedigree Disequilibrium Test (referred to herein as "QIPDT2"). As set forth in more detail hereinbelow, significant associations using Bonferroni thresholds were identified for 59 alleles at 24 different loci.

Example 2

Phenotypic Adjustments

The use of stage 2-3 data for association mapping is not a traditional approach, and there are several aspects of its analysis that needed to be considered. Moreover, hybrids with various testers, instead of the lines perse, were employed for phenotyping, while both of the statistical approaches (TASSEL and QIPDT2) were designed for data on inbred lines which require a unique trait value for each line. To obtain a unique trait value for each inbred line that could be compared against its genotype, it was necessary to make phenotypic adjustments that help to control the effect of tester and/or location. Additional factors (e.g., maturity group) were not considered to avoid the further reduction of degrees of freedom or subsets sample sizes.

To do the phenotypic adjustments, mixed linear model analyses were performed in two different statistical packages, SAS/JMP and R, which were intended to ensure that the mixed-model approaches for the large data set were implemented correctly. Since approaches gave very close results, the SAS/JMP results were used for the downstream data analysis.

The "full model" analysis included effects of both locations and testers in the model as follows:

Phenotype=Location effect (random)+Line effect (random)+Tester effect (fixed)+error term The "by Location" model was used for each of the 10 selected locations as follows:

Phenotype=Line effect (random)+Tester effect (fixed)+error term

The "by Tester" model was used for each of the 10 selected subsets of lines crossed to a particular tester as follows:

Phenotype=Location effect (random)+Line effect (random)+error term

The 21 models per trait (1 full model, 10 by-location models and 10 by-tester models) were evaluated for convergence, estimation of covariance estimates, significance of fixed effects, etc. Best linear unbiased predictors (BLUPs)

for line effects were used as adjusted genotypes. In some cases, the proposed mixed models did not converge or there was a problem with the estimation of line effects due to the lack of replications. For each such case, the effect of the line was removed from the model and the residuals were used as a rough method to capture line effects (additional replication was obtained later in the association analysis where each biallelic locus was represented by the total number of inbred lines of each group).

The solution for the lines random effects (BLUPs) were obtained from the mixed models that converged.

Example 3

Genotypic Data

A total of 890 lines for which phenotypic data was collected in any of the selected trials were also genotyped. A total of 61 SNPs corresponding to 17 candidate genes were scored in the inbred lines. After eliminating monomorphic assays and SNPs with allele frequencies less than 0.01, 46 candidate SNPs were tested for association in TASSEL. Besides, 299 random SNPs were genotyped in the inbred lines. After filtering, 259 random SNPs were also analyzed for association in TASSEL as anonymous candidates.

Example 4

Methodologies for Association Analysis

Kinship Analysis.

The method implemented in TASSEL uses a kinship matrix in the mixed-model approach for controlling genetic correlations among lines. Kinship analysis was done using genotypic data on the 299 random SNP assays. A method to estimate kinship relationships based on Zhao et al., 2007 was adopted. Scripts were created to calculate Kinship coefficients that were defined simply as the proportion of shared alleles for each pair of individuals (K pShared). Zhao et al. used the proportion of shared haplotypes as their kinship coefficients. The matrix of K coefficients was included for some association models in TASSEL to assess the control for spurious associations due to close interrelatedness of the lines in the panel.

Kinship Coefficient Matrix Calculator.

The K matrix was calculated for a set of inbred lines. The kinship coefficient kij was calculated as proportion of shared alleles for all loci between two lines i and j, and kij=kji, kii=1.

Population Structure Analysis.

Analysis with the software program Structure (Pritchard et al., 2000) was done using genotypic data of the 299 random SNP assays.

A linkage model that incorporated population admixture and linkage between the markers was employed. The likelihoods of population structures ranging from k=1 to 15 subpopulations were determined using a burnin period of 50,000 followed by 50,000 MCMC reps. Four replications were run for each value of k. The estimated log probability of data Pr(X|K) for each value of k was plotted to choose an appropriate number of subpopulations to include in the covariance matrix.

The probability for a determinate k increased along with the number of k tested until it reached k=6, and then started to decrease, k=6 was used as the number of subpopulations for association analysis. The inferred ancestry table containing the fraction of each subpopulation contributing to the ancestry of each inbred was used as a series of covariates in the association testing model.

Principal Component Analysis.

Principal Component Analysis (PCA) or "Eigen analysis" was used as an alternative to Structure for inferring population structure from genotypic data. PCA has some advantages over Structure such as the ability to handle large datasets in much shorter periods of time, and avoiding the need of selecting a specific number of sub-populations. PCA was performed using the software SMARTPCA that is part of Eigenstrat (Price et al., 2006). Ten Eigenvectors and their corresponding Eigenvalues for each of the lines were used as another covariate series for the association models of TASSEL.

Example 5

Association Analysis Using TASSEL

Association Models in TASSEL.

The different models employed in TASSEL are shown in the Table 5. For the YGSMN and GMSTP phenotypes adjusted across locations and testers, the six (6) models were run and compared. Only Model 4 was run for all the sub-sets by location and by tester.

TABLE 5

Association Models Employed in TASSEL

General Lineal Models

1) Adj. Phenotype = Marker
2) Adj. Phenotype = Marker + Q (Structure)
3) Adj. Phenotype = Marker + PCA (Eigenvalues)

Mixed Lineal Models

4) Adj. Phenotype = Marker + K (pshared)*
5) Adj. Phenotype = Marker + K (pshared) + Q (Structure)
6) Adj. Phenotype = Marker + K (pshared) + PCA (Eigenvalues)

The GLM procedure in TASSEL employed an option to perform permutations to find out the experiment-wise error rate that corrected for accumulation of false positives when doing multiple comparisons. A total of 10,000 permutations were used for the yield data. The MLM procedure did not include correction for multiple testing. The Bonferroni correction was used a posteriori to avoid accumulation of false positives.

Example 6

Association Analysis using QIPDT2

QIPDT2 (Quantitative inbred Pedigree Disequilibrium Test 2) was used for association mapping that takes advantage of inbred pedigree information, which may give higher statistical power and lower false positive rates with a better control of population structure issue (Stich et al. 2006, TAG 113:1121-1130). This is an extension of QIPDT originally developed for mapping human disease genes (Zhang et al, 2001. Genetic Epidemiol 21:370-375—see reference in Stich et al 2006). An advantage of QIPDT2 is that this method can be more easily applied to materials from early breeding stages (e.g., stage 2 and 3) because phenotypic data on these materials have been collected for breeding purposes. Generally speaking, the materials from early breeding stages are similar to the lines in the well-known nested association populations (NAM), which was designed to use both linkage and linkage disequilibrium for mapping QTL.

The original QIPDT is a test statistic, T, which is calculated in the following way (Stich et al. 2006):

$$T = \frac{\sum_{k=1}^{p} D_k}{\sqrt{\sum_{k=1}^{p} D_k^2}}, \text{ following } N(0, 1) \text{ under } H_0$$

$$D_k = \sum_{i=1}^{n_k} U_{jk}, E\left(\sum_{k=1}^{p} D_k\right) = 0 \text{ under } H_0$$

$$U_{jk} = \sum_{i=1}^{t_{jk}} (Y_{ijk} - \overline{Y_k}) X_{ijk}$$

$\overline{Y_k}$—mean trait value for extended pedigree k
$X_{ijk}$—marker value (−1, 0, 1)

In the general approach, a T value is calculated for each SNP, and its p value is found from standard normal distribution. While this approach is useful for testing the statistical significance of association, it does not provide an estimate of the magnitude of the SNP genetic effect, nor the relative genetic contribution to the total phenotypic variance.

Thus, the general QIPDT approach was improved using a regression model, which is referred to herein as "QIPDT2"; the original method is then called QIPDT1. The model for QIPDT2 can be written as:

$$y_{ki} = \beta_0 + \beta_1 x_{ki} + e_{ki},$$

where $y_{ki}$ is adjusted phenotypic value for individual i in pedigree k; $x_{ki}$ is coded marker genotypic value; $\beta_0$ is intercept; $\beta_1$ is regression coefficient, or genetic effect, of the SNP in question. Note that the methods for adjusting phenotypic values and coding marker genotypes are the same as used by Stich et al., 2006. With this model, both the genetic effect and $R^2$ for each SNP can be estimated. It is important to note that the phenotypic data were pre-adjusted for excluding effects from testers and/or locations before being further adjusted for pedigree structure; this adjustment was necessary to implement the complex model in QIPDT2. The methods for pre-adjustment were the same as described previously for the TASSEL analysis.

Association Models in QIPDT2.

Association results from both QIPDT1 and QIPDT2 for the whole data set and split subsets for locations and testers were generated. Like the analysis with TASSEL, the phenotypic data were adjusted for locations and/or testers, depending on which subset was used. This resulted in one adjusted phenotypic value (either BLUP line values or model residuals) for each inbred, which contains a combination of all genetic effects for the inbred and random residual only.

Before QIPDT analysis, all inbreds were grouped into different nuclear families, according to their parental lines. The use of nuclear families was expected to give better control of population structure than extended pedigrees that were used in Stich et al (2006). For QIPDT1, a test statistic (Z value) and corresponding p value were estimated for each SNP; for QIPDT2, a test statistic (T value) and corresponding p value were derived from the simple regression model, along with R square, for each SNP. QIPDT2 more powerful than QIPDT1, in terms of p values. Since QIPDT2 also gave estimates ($R^2$) for relative contribution for each SNP, QIPDT2 was used for reporting association results from the QIPDT approach.

Example 7

Significance and Contributions of Favorable Alleles to Yield Phenotypes

P values and contributions that each favorable allele was observed to have on the yield phenotypes YGSMN, GMSTP, and GWTPN were calculated. These values are summarized in Tables 6-8. In Tables 6-8, the term "contribution" refers to the contribution that the favorable allele was calculated to have with respect to the phenotype observed in view of the mean values of 201.68 bushels/acre, 18.95%, and 25.29 bushels/plot for YGSMN, GMSTP, and GWTPN, respectively. In Tables 6-8, the "contribution" is expressed in bushels/acre, percent, and bushels/plot for YGSMN, GMSTP, and GWTPN, respectively.

TABLE 6

Contributions of Favorable Alleles to Increased Yield Identified by Both TASSEL and QIPDT2

| SEQ ID NO. | SNP Position | F | U | Trait | Contribution | P-Value |
|---|---|---|---|---|---|---|
| 4 | 368 | T | G | YGSMN | 2.871241 | 0.000723 |
| 5 | 4038 | T | C | GMSTP | 0.026291 | 0.000855 |
| 10 | 408 | C | T | YGSMN | 11.66073 | 0.000001 |
| 13 | 338 | A | G | YGSMN | 4.880021 | 0.000053 |
| 14 | 5356 | A | G | GMSTP | 1.186592 | 0.000885 |
| 25 | 286 | A | G | YGSMN | 4.501456 | 0.000405 |
| 35 | 1742 | A | G | YGSMN | 1.12357 | 0 |
|  |  | A | G | GMSTP | 0.2108 | 0 |
| 36 | 2457 | C | A | GMSTP | 0.1034 | 0 |
| 37 | 631 | T | A | YGSMN | 2.87987 | 0.0014214 |
| 38 | 945 | G | A | GMSTP | 0.059 | 0 |

TABLE 6-continued

Contributions of Favorable Alleles to Increased Yield Identified by Both TASSEL and QIPDT2

| SEQ ID NO. | SNP Position | F U Trait | Contribution | P-Value |
|---|---|---|---|---|
| 39 | 2378 | A G GMSTP | 0.1306 | 0 |
| 40 | 2860 | T A YGSMN | 0.62154 | 0.0040265 |
|  |  | A T GMSTP | 0.0571 | 0.0029 |
| 41 | 2519 | G T GMSTP | 0.6192 | 0.0005 |
| 45 | 3597 | T A YGSMN | 1.0261 | 0 |
|  |  | A T GMSTP | 0.0387 | 0 |
| 46 | 3611 | A G YGSMN | 4.29316 | 0 |
|  |  | A G GMSTP | 0.082 | 0.0007 |
| 50 | 1603 | C A YGSMN | 18.9078 | 0.0002639 |
| 51 | 2859 | A G YGSMN | 18.9078 | 0.0002639 |

TABLE 7

Contributions of Favorable Alleles to Increased Yield Identified by TASSEL

| SEQ ID NO. | SNP Position | F U Trait | Contribution | P-Value |
|---|---|---|---|---|
| 2 | 2420 | G C YGSMN | 5.8825 | 0.001683 |
|  |  | C G GMSTP | 0.0094 | $2.2 \times 10^{-5}$ |
| 3 | 2709 | G T YGSMN | 6.5807 | 0.000102 |
|  |  | T G GMSTP | 0.3236 | $5.86 \times 10^{-8}$ |
| 4 | 368 | T G YGSMN | 5.07 | 0.000259 |
|  |  | T G GMSTP | 0.1978 | $1.53 \times 10^{-5}$ |
| 5 | 4038 | C T YGSMN | 1.6219 | 0.000368 |
|  |  | T C GMSTP | 0.1087 | $4.5 \times 10^{-5}$ |
| 6 | 4038 | C T YGSMN | 1.6249 | 0.000244 |
|  |  | T C GMSTP | 0.1125 | 0.001377 |
| 7 | 402 | A G YGSMN | 1.6249 | 0.0004 |
|  |  | G A GMSTP | 0.116 | 0.004012 |
| 8 | 3050 | T G YGSMN | 9.1894 | 0.00018 |
|  |  | G T GMSTP | 0.2085 | 1.000107 |
| 9 | 2146 | G A GMSTP | 0.144 | 0.00108 |
| 10 | 408 | T C GMSTP | 0.0069 | 0.000124 |
| 11 | 160 | C G YGSMN | 3.0277 | 0.000733 |
|  |  | G C GMSTP | 0.1451 | $7.81 \times 10^{-5}$ |
| 12 | 311 | C G YGSMN | 3.8175 | $4.74 \times 10^{-5}$ |
| 13 | 338 | A G YGSMN | 3.0277 | 0.0016 |
|  |  | G A GMSTP | 0.0295 | 0.000772 |
| 14 | 5356 | A G YGSMN | 2.1002 | 0.0028 |
|  |  | G A GMSTP | 0.247 | 0.000211 |
| 15 | 5371 | C A YGSMN | 0.4474 | 0.0015 |
|  |  | A C GMSTP | 0.386 | $5.55 \times 10^{-5}$ |
| 16 | 1587 | A G YGSMN | 0.4237 | 0.0024 |
|  |  | G A GMSTP | 0.3405 | $8.48 \times 10^{-5}$ |
| 17 | 388 | A G YGSMN | 6.1114 | 0.000278 |
|  |  | G A GMSTP | 0.2688 | 0.000825 |

TABLE 7-continued

Contributions of Favorable Alleles to Increased Yield Identified by TASSEL

| SEQ ID NO. | SNP Position | F U Trait | Contribution | P-Value |
|---|---|---|---|---|
| 18 | 494 | T G YGSMN | 7.2079 | $2.04 \times 10^{-5}$ |
| 19 | 112 | T G YGSMN | 5.92 | 0.000459 |
|  |  | G T GMSTP | 0.4324 | 0.000325 |
| 20 | 2458 | T A YGSMN | 7.9072 | 0.000184 |
|  |  | A T GMSTP | 0.3375 | 0.00014 |
| 21 | 4037 | T G YGSMN | 9.1091 | 0.00021 |
| 22 | 849 | T C YGSMN | 1.9133 | $8.51 \times 10^{-7}$ |
| 24 | 1032 | G C YGSMN | 9.9887 | $2.22 \times 10^{-5}$ |
|  |  | C G GMSTP | 0.0651 | $1.64 \times 10^{-12}$ |
| 25 | 286 | A G YGSMN | 10.4903 | $8.54 \times 10^{-6}$ |
|  |  | G A GMSTP | 0.0309 | 0.0026 |
| 26 | 346 | A C YGSMN | 2.2564 | 0.000133 |
| 27 | 6968 | A T YGSMN | 4.2075 | $2.63 \times 10^{-5}$ |
|  |  | T A GMSTP | 0.0307 | $2.22 \times 10^{-8}$ |
| 28 | 6083 | A G YGSMN | 5.882 | 0.000321 |
|  |  | G A GMSTP | 0.3085 | $6.83 \times 10^{-8}$ |
| 29 | 1729 | A G YGSMN | 6.28 | 0.000289 |
|  |  | G A GMSTP | 0.2284 | 0.000889 |
| 30 | 1668 | C A YGSMN | 6.3213 | $6.19 \times 10^{-5}$ |
|  |  | A C GMSTP | 0.2382 | 0.0011 |
| 31 | 5516 | G A GMSTP | 0.0968 | 0.000222 |
| 32 | 1255 | G A GMSTP | 0.3077 | 0.005 |
| 34 | 1486 | G A GMSTP | 0.2485 | 0.004 |
| 35 | 1742 | A G YGSMN | 0.0786 | 0.0012 |
| 38 | 945 | G A GMSTP | 0.2248 | $4 \times 10^{-5}$ |
| 39 | 2378 | A G GMSTP | 0.0824 | $3 \times 10^{-4}$ |
| 40 | 2860 | T A YGSMN | 1.2678 | 0.0021 |
| 41 | 2519 | G T GMSTP | 0.7182 | 0.006 |
| 42 | 903 | A G YGSMN | 1.0029 | 0.0026 |
| 43 | 1795 | A G YGSMN | 4.7106 | 0.0037 |
| 44 | 2040 | T C GMSTP | 0.113 | 0.003 |
| 45 | 3597 | T A YGSMN | 0.6016 | 0.0042 |
|  |  | A T GMSTP | 0.0258 | 0.001 |
| 50 | 1603 | C A YGSMN | 15.8079 | 0.0007 |
| 51 | 2859 | A G YGSMN | 15.8967 | 0.002 |

TABLE 8

Contributions of Favorable Alleles to Increased Yield Identified by QIPDT2

| SEQ ID NO. | SNP Position | F | U | Trait | Contribution | P-Value |
|---|---|---|---|---|---|---|
| 1  | 1333 | G | A | GWTPN | 2.21646  | 0.000023 |
| 4  | 368  | T | G | GWTPN | 0.34528  | 0.000873 |
| 5  | 4038 | T | C | GMSTP | 0.026291 | 0.000855 |
| 10 | 408  | C | T | GWTPN | 1.512896 | 0        |
| 13 | 338  | A | G | GWTPN | 0.59517  | 0.000054 |
| 14 | 5356 | A | G | GMSTP | 1.186583 | 0.000885 |
| 23 | 966  | G | A | GWTPN | 0.212929 | 0.001004 |
| 25 | 286  | A | G | GWTPN | 0.583598 | 0.000332 |
| 32 | 1255 | G | A | YGSMN | 6.986932 | 0.002462 |
| 33 | 1336 | C | G | YGSMN | 6.950575 | 0.002519 |
| 34 | 1486 | G | A | YGSMN | 6.271452 | 0.00353  |
| 35 | 1742 | A | G | GMSTP | 0.962058 | 0.001557 |
| 37 | 631  | T | A | YGSMN | 2.879866 | 0.001421 |
| 40 | 2860 | T | A | YGSMN | 0.621539 | 0.004026 |
|    |      | A | T | GMSTP | 0.057075 | 0.002945 |
| 41 | 2519 | G | T | GMSTP | 0.619242 | 0.000528 |
| 42 | 903  | G | T | GMSTP | 0.101635 | 0.001662 |
| 46 | 3611 | A | G | YGSMN | 18.7052  | 0.000128 |
| 47 | 131  | G | C | GMSTP | 0.138321 | 0.002778 |
| 48 | 2273 | A | T | GMSTP | 0.279381 | 0.001871 |
| 49 | 187  | C | G | GMSTP | 0.255931 | 0.003415 |
| 50 | 1603 | C | A | YGSMN | 18.90784 | 0.000264 |
|    |      | C | A | GMSTP | 0.962058 | 0.001557 |
| 51 | 2859 | A | G | YGSMN | 18.90784 | 0.000264 |
|    |      | A | G | GMSTP | 0.962058 | 0.001557 |

REFERENCES

All references listed below, as well as all references cited in the instant disclosure, including but not limited to all patents, patent applications and publications thereof, scientific journal articles, and database entries (e.g., GEN-BANK® database entries and all annotations available therein) are incorporated herein by reference in their entireties to the extent that they supplement, explain, provide a background for, or teach methodology, techniques, and/or compositions employed herein.

Altschul et al. (1990) Basic local alignment search tool. *J Mol Biol* 215:403-410.

Altschul et al. (1997) Gapped BLAST and PSI-BLAST: a new generation of protein database search programs. *Nucleic Acids Res* 25:3389-3402.

Ausubel et al. (eds.) (1999) *Short Protocols in Molecular Biology* Wiley, New York, N.Y., United States of America.

Bomblies & Doebley (2005) Molecular evolution of FLORICAULA/LEAFY orthologs in the Andropogoneae (Poaceae). *Mol Biol Evol* 22:1082-1094.

Bomblies & Doebley (2006) Pleiotropic effects of the duplicate maize FLORICAULA/LEAFY genes zfl1 and zfl2 on traits under selection during maize domestication. *Genetics* 172:519-531.

Bommert et al. (2005) thick tassel dwarf1 encodes a putative maize ortholog of the *Arabidopsis* CLAVATA1 leucine-rich repeat receptor-like kinase. *Development* 132:1235-1245.

Bradbury et al. (2007) TASSEL: software for association mapping of complex traits in diverse samples. *Bioinformatics* 23:2633-2635.

Camus-Kulandaivelu et al. (2007) Evaluating the Reliability of Structure Outputs in Case of Relatedness between Individuals, *Crop Science* 47:887-890.

Evanno et al. (2005) Detecting the number of clusters of individuals using the software STRUCTURE: a simulation study. *Molecular Ecology* 14:2611-2620.

Falush et al. (2003) Inference of Population Structure Using Multilocus Genotype Data: Linked Loci and Correlated Allele Frequencies. *Genetics* 164:1567-1587.

Fan et al. (2006) Highly parallel genomic assays. *Nature Reviews. Genetics* 7:632-644.

Glick & Thompson (1993) *Methods in Plant Molecular Biology and Biotechnology*, CRC Press, Boca Raton. Fla., United States of America.

Greene & Hannah (1998) Enhanced stability of maize endosperm ADP-glucose pyrophosphorylase is gained through mutants that alter subunit interactions. *Proc Natl Acad Sci USA* 95:13342-13347.

Hannah et al. (2001) Maize genes encoding the small subunit of ADP-glucose pyrophosphorylase. *Plant Physiol* 127:173-183.

Hardy & Vekemans (2002) SPAGeDi: a versatile computer program to analyse spatial genetic structure at the individual or population levels. *Molecular Ecology Notes* 2:618-620.

Jannink & B. Walsh (2002) Association mapping in plant populations, in *Quantitative Genetics, Genomics and Plant Breeding*. Kang (ed.) CAB International Publishing, New York, N.Y., United States of America, pp. 59-68.

Komatsuda et al. (2007) Six-rowed barley originated from a mutation in a homeodomain-leucine zipper I-class homeobox gene. *Proc Natl Acad Sci USA* 104:1424-1429.

Liu & Muse (2005) PowerMarker: an integrated analysis environment for genetic marker analysis. *Bioinformatics* 21:2128-2129.

Loiselle et al. (2005) Spatial genetic structure of a tropical understory shrub, *Psychotria officinalis* (Rubiaceae). *American Journal of Botany* 82:1420-1425.

Morinaka et al. (2006) Morphological alteration caused by brassinosteroid insensitivity increases the biomass and grain production of rice. *Plant Physiol* 141:924-931.

Paterson (1996) in Paterson (ed.) *Genome Mapping in Plants*. R. G. Landes Company, Georgetown, Tex., United States of America, pages 41-54.

Patterson et al. (2006) Population Structure and Eigenanalysis. *PLoS Genetics* 2:e190.

Perin et al. (2002) A reference map of *Cucumis melo* based on two recombinant inbred line populations. *Theor Appl Genet* 104:1017-1034.

Price et al. (2006) Principal components analysis corrects for stratification in genome-wide association studies. *Nature Genetics* 38:904-909.

Pritchard et al. (2000) Inference of Population Structure Using Multilocus Genotype Data. *Genetics* 155:945-959.

Ritland (1996) Estimators for pairwise relatedness and individual inbreeding coefficients. *Genetics Research* 67:175-186.

Sambrook & Russell (2001). *Molecular Cloning: A Laboratory Manual., Third Edition*, Cold Spring Harbor Laboratory Press, Cold Spring Harbor, N.Y., United States of America.

Sauer (2007) Molecular physiology of higher plant sucrose transporters. *FEBS Lett* 581:2309-2317.

Stich et al. (2006) A new test for family-based association mapping with inbred lines from plant breeding programs. *Theoretical and Applied Genetics* 113:1121-1130.

Storey (2002) A direct approach to false discovery rates. *Journal of the Royal Statistical Society: Series B* 64:479-498.

Taguchi-Shiobara et al. (2001) The fasciated ear2 gene encodes a leucine-rich repeat receptor-like protein that regulates shoot meristem proliferation in maize. *Genes Dev* 15:2755-2766.

Tanabe et al. (2005) A novel cytochrome P450 is implicated in brassinosteroid biosynthesis via the characterization of a rice dwarf mutant, dwarf11, with reduced seed length. *Plant Cell* 17:776-790.

Tao et al. (2004) Functional analysis of ZmDWF1, a maize homolog of the *Arabidopsis* brassinosteroids biosynthetic DWF1/DIM gene. *Plant Sci* 167:743-751.

Tijssen (1993) in *Laboratory Techniques in Biochemistry and Molecular Biology*, Elsevier, New York, N.Y., United States of America.

U.S. Pat. No. 4,458,068.

Zhao et al. (2007) An *Arabidopsis* Example of Association Mapping in Structured Samples. *PLoS Genetics* 3:e4.

Zietkiewicz et al. (1994) Genome fingerprinting by simple sequence repeat (SSR)-anchored polymerase chain reaction amplification. *Genomics* 20:176-183.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of producing a *Zea mays* plant having increased grain yield at standard moisture percentage (YGSMN), the method comprising:
   (a) isolating a nucleic acid molecule from a *Zea mays* plant or plant part;
   (b) detecting in the nucleic acid of a) a molecular marker associated with increased YGSMN, wherein said molecular marker is associated with yield locus ZmZfl2 on maize chromosome 2 and further wherein said yield locus comprises the following alleles corresponding to a G at nucleotide position 2420 of SEQ ID NO: 2; a G at nucleotide position 2709 of SEQ ID NO: 3; and a T at nucleotide position 368 of SEQ ID NO: 4;
   (c) selecting a first *Zea mays* plant based on the detection of the molecular marker of b);
   (d) crossing the first *Zea mays* plant of (c) with a second *Zea mays* plant not comprising in its genome the molecular marker of (b); and
   (e) producing a progeny plant from the cross of (d) wherein said progeny plant has in its genome the molecular marker of (b) thereby producing a *Zea mays* plant with increased YGSMN;
   wherein said molecular marker is any one of the following alleles corresponding to a G at nucleotide position 2420 of SEQ ID NO: 2; a G at nucleotide position 2709 of SEQ ID NO: 3; or a T at nucleotide position 368 of SEQ ID NO: 4.

2. The method of claim 1, wherein the molecular marker further associates with increased grain moisture at harvest (GMSTP).

3. The method of claim 1, wherein the progeny plant is a hybrid maize plant.

4. The method of claim 1, wherein either the first *Zea mays* plant or second *Zea mays* plant is a maize inbred.

5. The method of claim 1, wherein detecting in (b) is carried out by PCR amplification or by nuclear probes.

6. The method of claim 5, wherein an amplification primer is utilized the PCR amplification of claim 5, and the amplicon comprises and one of SEQ ID Nos: 57, 58, 62, 63, 67 or 68 and a corresponding primer that when amplified produce an amplicon diagnostic for YGSMN.

7. The method of claim 6, wherein the amplicon comprises any one of SEQ ID Nos: 59, 64 or 69.

8. The method of claim 6, wherein the amplification primer pairs consists of SEQ ID Nos: 57 and 58; SEQ ID Nos: 62 and 63; or SEQ ID Nos: 67 and 68.

9. The method of claim 8, wherein the amplicon consists of SEQ ID Nos: 59, 64, or 69.

* * * * *